US012582713B2

(12) United States Patent
Huang et al.

(10) Patent No.: US 12,582,713 B2
(45) **Date of Patent: \*Mar. 24, 2026**

(54) METHODS OF TREATING TUMORS

(71) Applicants: Bristol-Myers Squibb Company,
Princeton, NJ (US); Halozyme, Inc.,
San Diego, CA (US)

(72) Inventors: Masano Huang, Princeton, NJ (US);
Thomas Arthur Haby, Lincroft, NJ
(US); Mehrnaz Khossravi, West
Windsor, NJ (US); Scott Aaron Hart,
Hillsborough, NJ (US); **Rao
Venkatramana Mantri,** Pennington, NJ
(US); Heather Elizabeth Vezina,
Upper Holland, PA (US); Amit Roy,
Woodbury, CT (US); **Bindu Purnima
Murthy, Robbinsville, NJ (US); Urvi
Ashish Aras,** Kendall Park, NJ (US);
Kinjal Sanghavi, Princeton, NJ (US);
Xiaochen Zhao, Pennington, NJ (US);
Akintunde Bello, Princeton Junction,
NJ (US)

(73) Assignees: Bristol-Myers Squibb Company,
Princeton, NJ (US); Halozyme, Inc.,
San Diego, CA (US)

( \* ) Notice: Subject to any disclaimer, the term of this
patent is extended or adjusted under 35
U.S.C. 154(b) by 0 days.

This patent is subject to a terminal dis-
claimer.

(21) Appl. No.: 18/423,089

(22) Filed: Jan. 25, 2024

(65) Prior Publication Data

US 2024/0252629 A1      Aug. 1, 2024

Related U.S. Application Data

(63) Continuation of application No. 17/562,958, filed on
Dec. 27, 2021, now abandoned.

(60) Provisional application No. 63/184,082, filed on May
4, 2021, provisional application No. 63/150,420, filed
on Feb. 17, 2021, provisional application No.
63/131,240, filed on Dec. 28, 2020.

(51) Int. Cl.
| | |
|---|---|
| *A61K 39/395* | (2006.01) |
| *A61K 9/00* | (2006.01) |
| *A61K 38/47* | (2006.01) |
| *A61K 47/18* | (2017.01) |
| *A61K 47/22* | (2006.01) |
| *A61K 47/26* | (2006.01) |
| *A61P 35/00* | (2006.01) |
| *A61K 39/00* | (2006.01) |

(52) U.S. Cl.
CPC ........ *A61K 39/3955* (2013.01); *A61K 9/0019*
(2013.01); *A61K 38/47* (2013.01); *A61K
47/183* (2013.01); *A61K 47/22* (2013.01);
*A61K 47/26* (2013.01); *A61K 2039/545*
(2013.01)

(58) Field of Classification Search
CPC .............. A61K 39/3955; A61K 9/0019; A61K
38/47; A61K 2039/505; A61P 35/00
See application file for complete search history.

(56) References Cited

U.S. PATENT DOCUMENTS

| | | | |
|---|---|---|---|
| 5,821,337 | A | 10/1998 | Carter et al. |
| 5,977,318 | A | 11/1999 | Linsley et al. |
| 6,051,227 | A | 4/2000 | Allison et al. |
| 6,210,669 | B1 | 4/2001 | Aruffo et al. |
| 6,303,121 | B1 | 10/2001 | Kwon |
| 6,355,476 | B1 | 3/2002 | Kwon et al. |
| 6,362,325 | B1 | 3/2002 | Kwon |
| 6,569,997 | B1 | 5/2003 | Kwon |
| 6,682,736 | B1 | 1/2004 | Hanson et al. |
| 6,808,710 | B1 | 10/2004 | Wood et al. |
| 6,887,673 | B2 | 5/2005 | Kunkel et al. |
| 6,905,685 | B2 | 6/2005 | Kwon |
| 6,974,863 | B2 | 12/2005 | Kwon |
| 6,984,720 | B1 | 1/2006 | Korman et al. |
| 7,034,121 | B2 | 4/2006 | Carreno et al. |
| 7,045,615 | B2 | 5/2006 | Tamatani et al. |
| 7,112,655 | B1 | 9/2006 | Tamatani et al. |
| 7,214,493 | B2 | 5/2007 | Kunkel et al. |

(Continued)

FOREIGN PATENT DOCUMENTS

| | | |
|---|---|---|
| AU | 2013202020 B2 | 11/2014 |
| CA | 3131052 A1 | 10/2020 |

(Continued)

OTHER PUBLICATIONS

Zhao X et al. Assessment of nivolumab benefit-risk profile of a
240-mg flat dose relative to a 3-mg/kg dosing regimen in patients
with advanced tumors. Ann Oncol. Aug. 1, 2017;28(8):2002-2008.
(Year: 2017).\*
Bergerot P, Lamb P, Wang E, Pal SK. Cabozantinib in Combination
with Immunotherapy for Advanced Renal Cell Carcinoma and
Urothelial Carcinoma: Rationale and Clinical Evidence. Mol Can-
cer Ther. Dec. 2019;18(12):2185-2193. (Year: 2019).\*
Almagro, J.C., and Fransson, J., "Humanization of antibodies,"
Front Biosci 13:1619-1633, Frontiers in Bioscience, Singapore (Jan.
2008).

(Continued)

*Primary Examiner* — Aurora M Fontainhas
*Assistant Examiner* — Jennifer A Benavides
(74) *Attorney, Agent, or Firm* — Sterne, Kessler,
Goldstein & Fox P.L.L.C.

(57) ABSTRACT

The disclosure provides pharmaceutical compositions com-
prising an anti-PD-1 antibody or an anti-PD-L1 antibody. In
some aspects, the pharmaceutical compositions are formu-
lated for subcutaneous delivery. In some aspects, the phar-
maceutical compositions further comprise an endoglycosi-
dase hydrolase enzyme. Other aspects of the present
disclosure are directed to methods of subcutaneously deliv-
ering a pharmaceutical composition comprising an anti-
PD-1 antibody or an anti-PD-L1 antibody.

30 Claims, 31 Drawing Sheets
Specification includes a Sequence Listing.

(56) References Cited

U.S. PATENT DOCUMENTS

| | | | |
|---|---|---|---|
| 7,259,247 | B1 | 8/2007 | Kroczek |
| 7,288,638 | B2 | 10/2007 | Jure-Kunkel et al. |
| 7,488,802 | B2 | 2/2009 | Collins et al. |
| 7,722,872 | B2 | 5/2010 | Kroczek |
| 7,767,429 | B2 | 8/2010 | Bookbinder et al. |
| 7,812,135 | B2 | 10/2010 | Smith et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,206,709 | B2 | 6/2012 | Spee et al. |
| 8,217,149 | B2 | 7/2012 | Irving et al. |
| 8,252,275 | B2 | 8/2012 | Bentley et al. |
| 8,354,509 | B2 | 1/2013 | Carven et al. |
| 8,388,967 | B2 | 3/2013 | Smith et al. |
| 8,389,690 | B2 | 3/2013 | Tamatani et al. |
| 8,399,623 | B2 | 3/2013 | Terrett et al. |
| 8,709,424 | B2 | 4/2014 | Schebye et al. |
| 8,779,105 | B2 | 7/2014 | Korman et al. |
| 8,796,427 | B2 | 8/2014 | Spee et al. |
| 8,900,587 | B2 | 12/2014 | Carven et al. |
| 8,901,283 | B2 | 12/2014 | Spee et al. |
| 8,927,249 | B2 | 1/2015 | Wei et al. |
| 8,993,319 | B2 | 3/2015 | Moretta et al. |
| 9,169,325 | B2 | 10/2015 | Keler et al. |
| 9,212,495 | B2 | 12/2015 | Nakamura et al. |
| 9,284,543 | B2 | 3/2016 | Wei et al. |
| 9,422,368 | B2 | 8/2016 | Spee et al. |
| 9,447,185 | B2 | 9/2016 | Romagne et al. |
| 9,447,401 | B2 | 9/2016 | Wei et al. |
| 9,556,270 | B2 | 1/2017 | Takayanagi et al. |
| 9,580,507 | B2 | 2/2017 | Korman et al. |
| 9,683,041 | B2 | 6/2017 | Spee et al. |
| 9,738,718 | B2 | 8/2017 | Liu et al. |
| 9,771,424 | B2 | 9/2017 | Liu et al. |
| 9,993,529 | B2 | 6/2018 | Yang et al. |
| 10,066,013 | B2 | 9/2018 | Chen et al. |
| 10,188,730 | B2 | 1/2019 | Liang et al. |
| 10,280,227 | B2 | 5/2019 | Adler et al. |
| 10,328,130 | B2 | 6/2019 | Frost et al. |
| 10,344,090 | B2 | 7/2019 | Yuan et al. |
| 10,358,495 | B2 | 7/2019 | Ullman et al. |
| 10,588,983 | B2 | 3/2020 | Bookbinder et al. |
| 10,624,974 | B2 | 4/2020 | Xu et al. |
| 10,711,060 | B2 | 7/2020 | Triebel et al. |
| 10,865,400 | B2 | 12/2020 | Wei et al. |
| 11,041,149 | B2 | 6/2021 | Wei et al. |
| 11,066,656 | B2 | 7/2021 | Wei et al. |
| 2005/0095244 | A1 | 5/2005 | Jure-Kunkel et al. |
| 2006/0171763 | A1 | 8/2006 | Dieudonat et al. |
| 2009/0136494 | A1 | 5/2009 | Ponath et al. |
| 2011/0007023 | A1 | 1/2011 | Abrahamsson et al. |
| 2011/0150892 | A1 | 6/2011 | Thudium et al. |
| 2012/0128683 | A1 | 5/2012 | Shantha |
| 2012/0301460 | A1* | 11/2012 | Bao ..................... A61K 38/47 |
| | | | 424/133.1 |
| 2013/0183321 | A1 | 7/2013 | Smith et al. |
| 2014/0065152 | A1 | 3/2014 | Kwon |
| 2014/0072565 | A1 | 3/2014 | Kwon |
| 2014/0072566 | A1 | 3/2014 | Kwon |
| 2014/0093511 | A1 | 4/2014 | Lonberg et al. |
| 2014/0220002 | A1 | 8/2014 | Ponte et al. |
| 2014/0322208 | A1 | 10/2014 | Kuhne et al. |
| 2014/0348841 | A1 | 11/2014 | Schebye et al. |
| 2015/0079109 | A1 | 3/2015 | Li et al. |
| 2016/0272708 | A1 | 9/2016 | Chen |
| 2017/0121417 | A1 | 5/2017 | Jansson et al. |
| 2017/0260271 | A1 | 9/2017 | Igawa et al. |
| 2018/0044419 | A9* | 2/2018 | Rosengren ............. A61K 38/47 |
| 2018/0263898 | A1 | 9/2018 | Chen et al. |
| 2018/0296470 | A1* | 10/2018 | Eng-Wong ............. C07K 16/32 |
| 2018/0296471 | A1 | 10/2018 | Goren et al. |
| 2018/0326058 | A1 | 11/2018 | Tsunenari et al. |
| 2018/0333493 | A1* | 11/2018 | Shenoy .................. C07K 16/06 |
| 2019/0077872 | A1 | 3/2019 | Igawa et al. |
| 2019/0233533 | A1* | 8/2019 | Otten ................. C07K 16/2896 |
| 2019/0330363 | A1 | 10/2019 | Jansson et al. |
| 2020/0055938 | A1 | 2/2020 | Desai et al. |
| 2020/0172617 | A1 | 6/2020 | Stein et al. |
| 2020/0199226 | A1 | 6/2020 | Bezman et al. |
| 2020/0330593 | A1* | 10/2020 | Bandekar ............. A61K 9/0053 |
| 2020/0354453 | A1 | 11/2020 | De et al. |
| 2021/0155913 | A1 | 5/2021 | Park et al. |
| 2021/0363270 | A1 | 11/2021 | Park et al. |
| 2022/0089738 | A1 | 3/2022 | Yogita et al. |
| 2022/0233689 | A1 | 7/2022 | Huang et al. |
| 2022/0233693 | A1 | 7/2022 | Huang et al. |
| 2024/0000934 | A1 | 1/2024 | Huang et al. |
| 2024/0024471 | A1 | 1/2024 | Huang et al. |
| 2025/0057948 | A1 | 2/2025 | Huang et al. |
| 2025/0205334 | A1 | 6/2025 | Huang et al. |

FOREIGN PATENT DOCUMENTS

| | | |
|---|---|---|
| EP | 2482849 B1 | 6/2018 |
| EP | 3147297 B1 | 12/2018 |
| EP | 3636752 A1 | 4/2020 |
| EP | 3785701 A1 | 3/2021 |
| JP | 2008278814 A | 11/2008 |
| JP | 2020518599 A | 6/2020 |
| JP | 2020518600 A | 6/2020 |
| WO | WO-9512673 A1 | 5/1995 |
| WO | WO-9838216 A1 | 9/1998 |
| WO | WO-9915553 A2 | 4/1999 |
| WO | WO-9942585 A1 | 8/1999 |
| WO | WO-0037504 A2 | 6/2000 |
| WO | WO-0100244 A2 | 1/2001 |
| WO | WO-03106498 A2 | 12/2003 |
| WO | WO-2004007520 A2 | 1/2004 |
| WO | WO-2004078140 A2 | 9/2004 |
| WO | WO-2005003168 A2 | 1/2005 |
| WO | WO-2005009465 A1 | 2/2005 |
| WO | WO-2006003179 A2 | 1/2006 |
| WO | WO-2006070286 A2 | 7/2006 |
| WO | WO-2006072625 A2 | 7/2006 |
| WO | WO-2006072626 A1 | 7/2006 |
| WO | WO-2006105021 A2 | 10/2006 |
| WO | WO-2007042573 A2 | 4/2007 |
| WO | WO-2007113648 A2 | 10/2007 |
| WO | WO-2008009545 A1 | 1/2008 |
| WO | WO-2008084106 A1 | 7/2008 |
| WO | WO-2008137915 A2 | 11/2008 |
| WO | WO-2008156712 A1 | 12/2008 |
| WO | WO-2009009116 A2 | 1/2009 |
| WO | WO-2009044273 A2 | 4/2009 |
| WO | WO-2009073533 A2 | 6/2009 |
| WO | WO-2009092805 A1 | 7/2009 |
| WO | WO-2009117085 A1 | 9/2009 |
| WO | WO-2009128917 A2 | 10/2009 |
| WO | WO-2010065939 A1 | 6/2010 |
| WO | WO-2010077297 A1 | 7/2010 |
| WO | WO-2011028683 A1 | 3/2011 |
| WO | WO-2011041613 A2 | 4/2011 |
| WO | WO-2011066389 A1 | 6/2011 |
| WO | WO-2011155607 A1 | 12/2011 |
| WO | WO-2011159877 A2 | 12/2011 |
| WO | WO-2012027328 A2 | 3/2012 |
| WO | WO-2012065086 A1 | 5/2012 |
| WO | WO-2012071411 A2 | 5/2012 |
| WO | WO-2012122444 A1 | 9/2012 |
| WO | WO-2012131004 A2 | 10/2012 |
| WO | WO-2012145493 A1 | 10/2012 |
| WO | WO-2012160448 A2 | 11/2012 |
| WO | WO-2012174478 A2 | 12/2012 |
| WO | WO-2012174480 A2 | 12/2012 |
| WO | WO-2013006490 A2 | 1/2013 |
| WO | WO-2013027328 A1 | 2/2013 |
| WO | WO-2013028231 A1 | 2/2013 |
| WO | WO-2013038191 A2 | 3/2013 |
| WO | WO-2013039954 A1 | 3/2013 |
| WO | WO-2013079174 A1 | 6/2013 |
| WO | WO-2013102144 A2 | 7/2013 |
| WO | WO-2013173223 A1 | 11/2013 |
| WO | WO-2013181634 A2 | 12/2013 |
| WO | WO-2014008218 A1 | 1/2014 |

(56) References Cited

FOREIGN PATENT DOCUMENTS

| | | |
|---|---|---|
| WO | WO-2014055648 A1 | 4/2014 |
| WO | WO-2014140180 A1 | 9/2014 |
| WO | WO-2014148895 A1 | 9/2014 |
| WO | WO-2014179664 A2 | 11/2014 |
| WO | WO-2014194302 A2 | 12/2014 |
| WO | WO-2014206107 A1 | 12/2014 |
| WO | WO-2015003167 A1 | 1/2015 |
| WO | WO-2015026684 A1 | 2/2015 |
| WO | WO-2015031667 A2 | 3/2015 |
| WO | WO-2015035606 A1 | 3/2015 |
| WO | WO-2015042246 A1 | 3/2015 |
| WO | WO-2015085847 A1 | 6/2015 |
| WO | WO-2015112800 A1 | 7/2015 |
| WO | WO-2015112900 A1 | 7/2015 |
| WO | WO-2015117002 A1 | 8/2015 |
| WO | WO-2015125159 A1 | 8/2015 |
| WO | WO-2015153513 A1 | 10/2015 |
| WO | WO-2015153514 A1 | 10/2015 |
| WO | WO-2015184099 A1 | 12/2015 |
| WO | WO-2015187835 A2 | 12/2015 |
| WO | WO-2015200119 A1 | 12/2015 |
| WO | WO-2016028672 A1 | 2/2016 |
| WO | WO-2016032334 A1 | 3/2016 |
| WO | WO-2016033555 A1 | 3/2016 |
| WO | WO-2016041945 A1 | 3/2016 |
| WO | WO-2016041947 A1 | 3/2016 |
| WO | WO-2016057667 A1 | 4/2016 |
| WO | WO-2016068802 A1 | 5/2016 |
| WO | WO-2016068803 A1 | 5/2016 |
| WO | WO-2016071448 A1 | 5/2016 |
| WO | WO-2016106159 A1 | 6/2016 |
| WO | WO-2016106302 A1 | 6/2016 |
| WO | WO-2016111947 A2 | 7/2016 |
| WO | WO-2016126858 A2 | 8/2016 |
| WO | WO-2016134371 A2 | 8/2016 |
| WO | WO-2016144803 A2 | 9/2016 |
| WO | WO-2016149201 A2 | 9/2016 |
| WO | WO-2016154177 A2 | 9/2016 |
| WO | WO-2016161270 A1 | 10/2016 |
| WO | WO-2016168716 A1 | 10/2016 |
| WO | WO-2016196228 A1 | 12/2016 |
| WO | WO-2016196237 A1 | 12/2016 |
| WO | WO-2016197367 A1 | 12/2016 |
| WO | WO-2016200782 A1 | 12/2016 |
| WO | WO-2016200836 A1 | 12/2016 |
| WO | WO-2017015560 A2 | 1/2017 |
| WO | WO-2017019846 A1 | 2/2017 |
| WO | WO-2017019894 A1 | 2/2017 |
| WO | WO-2017020291 A1 | 2/2017 |
| WO | WO-2017020858 A1 | 2/2017 |
| WO | WO-2017024465 A1 | 2/2017 |
| WO | WO-2017024515 A1 | 2/2017 |
| WO | WO-2017025016 A1 | 2/2017 |
| WO | WO-2017025051 A1 | 2/2017 |
| WO | WO-2017025498 A1 | 2/2017 |
| WO | WO-2017031242 A1 | 2/2017 |
| WO | WO-2017034916 A1 | 3/2017 |
| WO | WO-2017040790 A1 | 3/2017 |
| WO | WO-2017053748 A2 | 3/2017 |
| WO | WO-2017055399 A1 | 4/2017 |
| WO | WO-2017055404 A1 | 4/2017 |
| WO | WO-2017062888 A1 | 4/2017 |
| WO | WO-2017063162 A1 | 4/2017 |
| WO | WO-2017079112 A1 | 5/2017 |
| WO | WO-2017079115 A1 | 5/2017 |
| WO | WO-2017079116 A2 | 5/2017 |
| WO | WO-2017086367 A1 | 5/2017 |
| WO | WO-2017086419 A1 | 5/2017 |
| WO | WO-2017087589 A2 | 5/2017 |
| WO | WO-2017087901 A2 | 5/2017 |
| WO | WO-2017096179 A1 | 6/2017 |
| WO | WO-2017096182 A1 | 6/2017 |
| WO | WO-2017096281 A1 | 6/2017 |
| WO | WO-2017106061 A1 | 6/2017 |
| WO | WO-2017106129 A1 | 6/2017 |
| WO | WO-2017123557 A1 | 7/2017 |
| WO | WO-2017132825 A1 | 8/2017 |
| WO | WO-2017132827 A1 | 8/2017 |
| WO | WO-2017133540 A1 | 8/2017 |
| WO | WO-2017134292 A1 | 8/2017 |
| WO | WO-2017149143 A1 | 9/2017 |
| WO | WO-2017178493 A1 | 10/2017 |
| WO | WO-2017198741 A1 | 11/2017 |
| WO | WO-2017205721 A1 | 11/2017 |
| WO | WO-2017219995 A1 | 12/2017 |
| WO | WO-2017220555 A1 | 12/2017 |
| WO | WO-2017220569 A1 | 12/2017 |
| WO | WO-2017220988 A1 | 12/2017 |
| WO | WO-2018013818 A2 | 1/2018 |
| WO | WO-2018034227 A1 | 2/2018 |
| WO | WO-2018036561 A1 | 3/2018 |
| WO | WO-2018039020 A1 | 3/2018 |
| WO | WO-2018069500 A2 | 4/2018 |
| WO | WO-2018071500 A1 | 4/2018 |
| WO | WO-2018083087 A2 | 5/2018 |
| WO | WO-2018136412 A2 | 7/2018 |
| WO | WO-2018160536 A1 | 9/2018 |
| WO | WO-2018185043 A1 | 10/2018 |
| WO | WO-2018185046 A1 | 10/2018 |
| WO | WO-2018201096 A1 | 11/2018 |
| WO | WO-2018204368 A1 | 11/2018 |
| WO | WO-2018204374 A1 | 11/2018 |
| WO | WO-2018208868 A1 | 11/2018 |
| WO | WO-2018217940 A2 | 11/2018 |
| WO | WO-2018222722 A2 | 12/2018 |
| WO | WO-2019011306 A1 | 1/2019 |
| WO | WO-2019018730 A1 | 1/2019 |
| WO | WO-2019183551 A1 | 9/2019 |
| WO | WO-2020022791 A1 | 1/2020 |
| WO | WO-2020092546 A1 | 5/2020 |
| WO | WO-2020097141 A1 | 5/2020 |
| WO | WO-2020197230 A1 | 10/2020 |
| WO | WO-2021150079 A1 | 7/2021 |
| WO | WO-2022031093 A1 | 2/2022 |
| WO | WO-2022146947 A1 | 7/2022 |
| WO | WO-2022146948 A1 | 7/2022 |

OTHER PUBLICATIONS

Edwards, B.M., et al., "The remarkable flexibility of the human antibody repertoire; isolation of over one thousand different antibodies to a single protein, BLyS," J Mol Biol 334(1):103-118, Elsevier, Netherlands (Nov. 2003).

Kussie, P.H., et al., "A single engineered amino acid substitution changes antibody fine specificity," J Immunol 152(1):146-152, American Association of Immunologists, United States (Jan. 1994).

Non-final Office Action mailed in U.S. Appl. No. 18/453,265 to Huang et al. on Feb. 28. 2024.

Final Office Action mailed in U.S. Appl. No. 17/562,961 to Huang et al. on Apr. 24, 2024.

Final Office Action mailed in U.S. Appl. No. 18/453,258 to Huang et al. on Feb. 14, 2024.

NCT03656718, "A Study of Subcutaneous Nivolumab Monotherapy With or Without Recombinant Human Hyaluronidase PH20 (rHuPH20)," ClinicalTrials.gov, accessed at https://clinicaltrials.gov/ct2/show/NCT03656718, Feb. 7, 2020, 16 pages.

Ryman, J., and Melbohm, B., "Pharmacokinetics of Monoclonal Antibodies," CPT Pharm Syst Pharmacol 6(9):576-588, Wiley, United States (Sep. 2017).

Zhang, J., et al., "Model-Based Population Pharmacokinetic Analysis of Nivolumab in Chinese Patients with Previously Treated Advanced Solid Tumors, Including Non-Small Cell Lung Cancer," J Clin Pharm 59(10):1415-1424, Wiley, United States (Oct. 2019).

Yarbrough, M., et al., "Edetate Disodium as a Polysorbate Degradation and Monoclonal Antibody Oxidation Stabilizer," J Pharm Sci 108(4):1631-1635, Elsevier, Inc., Netherlands (Apr. 2019).

Wang, G. and Tomasella, F. P., "Ion-pairing HPLC methods to determine EDTA and DTPA in small molecule and biological pharmaceutical formulations," J Pharm Anal 6(3):150-156, Xi'an Jiaotong University, China (Jun. 2016).

(56) References Cited

OTHER PUBLICATIONS

Hamuro, L., et al., "Perspectives on Subcutaneous Route of Administration as an Immunogenicity Risk Factor for Therapeutic Proteins," J Pharm Sci 106(10):2946-2954, Elsevier Inc., Netherlands (Oct. 2017).

Zhao, Y., et al., "Model-Based Dose Selection of Subcutaneous Nivolumab in Patients with Advanced Solid Tumors," Clin Pharmacol & Ther 115(3):488-497, Wiley, United States (Mar. 2024).

Richter, W.F., et al., "Mechanistic Determinants of Biotherapeutics Absorption Following SC Administration," The AAPS J 14:559-570, Springer Nature, Germany (May 2012).

Porter, C.J.H., and Charman, S.A., "Lymphatic Transport of Proteins After Subcutaneous Administration," J Pharm Sci 89(3):297-310, Elsevier, Inc., Netherlands (Mar. 2000).

McDonald, T.A., et al., "Subcutaneous administration of biotherapeutics: current experience in animal models," Current Opinion in Mol Ther 12(4):461-470, Thomson Reuters, Canada (Aug. 2010).

McLennan, D.N., et al., "Subcutaneous drug delivery and the role of the lymphatics," Drug Discoveries Today: Technologies 2(1):89-96, Elsevier, Inc., Netherlands (Mar. 2005).

Reply to Office Action for U.S. Appl. No. 15/444,151, dated Apr. 15, 2020, 26 pages.

Co-pending U.S. Appl. No. 18/812,813, Masano Huang et al., filed on Aug. 22, 2024 (Not Published).

Angulo, J ., et al., "Ligand-Receptor Binding Affinities from Saturation Transfer Difference (STD) NMR Spectroscopy: The Binding Isotherm of STD Initial Growth Rates," Chemistry Eur. J. 16(26):7803-7812, Wiley-VCH, Germany (2010).

A Study of Subcutaneous Nivolumab Monotherapy With or Without Recombinant Human Hyaluronidase PH20 (rHuPH20), ClinicalTrials. gov, accessed at https://clinicaltrials.gov/ct2/show/NCT03656718, Sep. 4, 2018, 10 pages.

Bird, R.E., et al., "Single-Chain Antigen-Binding Proteins," Science 242(4877):423-426, Association for the Advancement of Science, United States (Oct. 1988).

Bittner, B., et al., "Development of a Subcutaneous Formulation for Trastuzumab—Nonclinical and Clinical Bridging Approach to the Approved Intravenous Dosing Regimen," Arzneimittelforschung 62(9):401-409, Thieme Medical Publishers, Germany (2012).

Burova, E., et al., "A Novel Anti-human LAG-3 Antibody in Combination With Anti-human PD-1 (REGN2810) Shows Enhanced Anti-tumor Activity in PD-1 x LAG-3 Dual-dehumanized Mice and Favorable Pharmacokinetic and Safety Profiles in Cynomolgus Monkeys," Journal for Immunotherapy of Cancer 4(1):P195, BMJ Journals, United Kingdom (2016).

Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).

Co-pending U.S. Appl. No. 17/562,961, Masano Huang et al., filed on Dec. 27, 2021, (Not Published).

Desai, A., et al., "Phase II Trial of Pembrolizumab (P) in Patients (pts) with Previously-treated Mesothelioma (MM)," Journal of Clinical Oncology 36(15_suppl):8565-8565, American Society of Clinical Oncology, United States of America (May 2018).

Dong, W., et al., "rHuPH20-facilitated subcutaneous administration of monoclonal antibodies in cancer therapy," Immunotherapy 13(1):79-88, Future Medicine, United Kingdom (2021).

Genbank, "Human hPD-1 (hPD-1) mRNA, complete cds," Accession No. U64863.1, accessed at https://www.ncbi.nlm.nih.gov/nuccore/U64863 on May 11, 2022, 3 pages.

Genbank, "Programmed Cell Death 1 Ligand 1," Accession No. Q9NZQ7, accessed at https://www.ncbi.nlm.nih.gov/protein/Q9NZQ7, accessed on Nov. 3, 2020, 5 pages.

Gorelik, L., et al., "Abstract 4606: Preclinical Characterization of a Novel Fully Human IgG1 Anti-PD-L1 mAb CK-301," Proceedings of 2017 AACR Annual Meeting 77(13):4606, American Association for Cancer Research, United States (Jul. 2017).

Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).

Hamid, O. and Carvajal, R.D., "Anti-programmed Death-1 and Anti-programmed Death-ligand 1 Antibodies in Cancer Therapy," Expert Opinion on Biological Therapy 13(6):847-861, Taylor & Francis, United Kingdom (Jun. 2013).

Herbst, R. S., et al., "A Study of MPDL3280A, an Engineered PD-L1 Antibody in Patients with Locally Advanced or Metastatic Tumors," Journal of Clinical Oncology 31(Suppl):3000, American Society of Clinical Oncology, United States (2013).

Huston, J.S., et al., "Protein Engineering of Antibody Binding Sites: Recovery of Specific Activity in an Anti-digoxin Single-chain Fv Analogue Produced in Escherichia coli," Proceedings of the National Academy of Sciences of the United States of America 85(16):5879-5883, , United States (Aug. 1988).

International Search Report and Written Opinion for International Application No. PCT/US2021/065255, mailed on Apr. 7, 2022, 16 pages.

International Search Report and Written Opinion for International Application No. PCT/US2021/065254, mailed on Jun. 20, 2022, 19 pages.

Johnson, M.L., et al., "Assessment of Subcutaneous vs Intravenous Administration of Anti-PD-1 Antibody PF-06801591 in Patients With Advanced Solid Tumors: A Phase 1 Dose-Escalation Trial," JAMA Oncol. 5(7):999-1007, American Medical Association, United States (2019).

Kamerzell, T.J., et al., "Protein-excipient Interactions: Mechanisms and Biophysical Characterization Applied to Protein Formulation Development," Advanced Drug Delivery Reviews 63(13):1118-1159, Elsevier Science Publishers, Netherlands (2011).

Kaplon, H. and Reichert, J.M., "Antibodies to Watch in 2018," mAbs 10(2):183-203, Taylor & Francis, United States (Feb./Mar. 2018).

Lonardi, S., et al., "CheckMate 8KX: Phase 1/2 multitumor preliminary analyses of a subcutaneous formulation of nivolumab (± rHuPH20)," J. Clin. Onc. (2021 ASCO Annual Meeting I) 39(15): Abstract 2575, United States (2021). Accessed at on Jun. 27, 2022.

Liu, S.-Y., and Wu, Y.-L., "Ongoing clinical trials of PD-1 and PD-L1 inhibitors for lung cancer in China," J Hematol Oncol 10(1):136, BioMed Central, United Kingdom (Jul. 2017).

McCabe, K.E. and Wu, A.M., "Positive Progress in ImmunoPET—Not Just a Coincidence," Cancer Biotherapy & Radiopharmaceuticals 25(3):253-261, Mary Ann Liebert, Inc, United States (Jun. 2010).

McDermott, D. F., and Atkins, M. B., "PD-1 as a Potential Target in Cancer Therapy," Cancer Medicine 2(5):662-673, John Wiley & Sons Ltd., United States (Oct. 2013).

NCBI, "CD274 CD274 molecule [ Homo sapiens (human) ]," ncbi.nlm.nih.gov, Accession No. 29126, accessed at URL:[https://ncbi.nlm.nih.gov, www.ncbi.nlm.nih.gov/gene/?term=29126] on Apr. 6, 2022, 8 pages.

Olafsen, T., et al., "ImmunoPET Imaging of B-Cell Lymphoma Using $^{124}$I-Anti-CD20 scFv Dimers (Diabodies)," Protein Engineering, Design & Selection 23(4):243-249, Oxford University Press, United Kingdom (Apr. 2010).

"Opdivo- Assessment Report," European Medicines Agency, Apr. 23, 2015, 130 pages.

Phillips, J.C., et al., "Scalable Molecular Dynamics With NAMD," Journal of Computational Chemistry 26(16):1781-1802, Wiley, United States (Dec. 2004).

Ribas, A., "Anti-CTLA4 Antibody Clinical Trials in Melanoma," Update on Cancer Therapeutics 2(3):133-139, Elsevier, Ltd., United Kingdom (Sep. 2007).

Rosengren, S., et al., "Clinical Immunogenicity of rHuPH20, a Hyaluronidase Enabling Subcutaneous Drug Administration," AAPS J. 17(5):1144-1156, Springer Science+Business Media, Germany (2015).

Sahin, I.H., et al., "Immune checkpoint inhibitors for the treatment of MSI-H/MMR-D colorectal cancer and a perspective on resistance mechanisms" Br. J. Cancer. 121(10):809-818, Nature Portfolio, Germany (2019).

(56)          References Cited

OTHER PUBLICATIONS

Schaer, D.A., et al., "Modulation of GITR for Cancer Immunotherapy," Current Opinion in Immunology 24(2):217-224, Elsevier Ltd., United Kingdom (Apr. 2012).

Shpilberg, O., et al., "Subcutaneous administration of rituximab (MabThera) and trastuzumab (Herceptin) using hyaluronidase," Br. J. Cancer. 109(6):1556-1561, Nature Portfolio, Germany (2013).

Sjöblom, T., et al., "The Consensus Coding Sequences of Human Breast and Colorectal Cancers," Science 314(5797):268-274, American Association for the Advancement of Science, United States (Oct. 2006).

Taube, J.M., et al., "Colocalization of Inflammatory Response with B7-H1 Expression in Human Melanocytic Lesions Supports an Adaptive Resistance Mechanism of Immune Escape," Science Translational Medicine 4(127):127ra37, American Association for the Advancement of Science, United States (Mar. 2012).

Topalian, S.L., et al., "Targeting the PD-1/B7-H1(PD-L1) Pathway to Activate Anti-tumor Immunity," Current Opinion in Immunology 24(2):207-212, Elsevier, United Kingdom (Apr. 2012).

Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).

Topalian, S.L., et al., "Survival, Durable Tumor Remission, and Long-term Safety in Patients with Advanced Melanoma Receiving Nivolumab," Journal of Clinical Oncology 32(10):1020-1030, American Society of Clinical Oncology, United States (Apr. 2014).

Wang, C., et al., "In Vitro Characterization of the Anti-PD-1 Antibody Nivolumab, BMS-936558, and In Vivo Toxicology in Non-human Primates," Cancer Immunology Research 2(9):846-856, American Association for Cancer Research, United States (Sep. 2014).

Ward, E.S., et al., "Binding Activities of a Repertoire of Single Immunoglobulin Variable Domains Secreted from Escherichia coli," Nature 341(6242):544-546, Nature Publishing Group, United Kingdom (Oct. 1989).

Zhang, F., et al., "Structural basis of a novel PD-L1 nanobody for immune checkpoint blockade," Cell Discov 3:17004, Nature Publishing Group, United Kingdom (Mar. 2017).

Anonymous, "Biopharmaceutical Composition Ed—Darl Kuhn", IP.com, IP.com Inc., West Henrietta, New York, United States, published Jul. 12, 2019, 735 pages.

Non-final Office Action mailed in U.S. Appl. No. 17/562,958 to Huang et al. on Jun. 8, 2023.

Non-final Office Action mailed in U.S. Appl. No. 17/562,961 to Huang et al. on Jun. 22, 2023.

Walpole, S.C., et al., "The weight of nations: an estimation of adult human biomass," BMC Public Health 12:439, BioMed Central, United Kingdom (Jun. 2012).

Motzer, R.J., et al., "Nivolumab versus Everolimus in Advanced Renal-Cell Carcinoma," N Engl J Med 373(19):1803-1813, Massachusetts Medical Society, United States (Nov. 2015).

Wang, W., et al., "Antibody Structure, Instability, and Formulation," J Pharm Sci 96(1):1-26, 8-11, Elsevier, Netherlands (Jan. 2007).

Andrews, J.M., and Roberts, C.J., "A Lumry-Eyring Nucleated Polymerization Model of Protein Aggregation Kinetics: 1. Aggregation with Pre-Equilibrated Unfolding," J Phys Chem B 111:7897-7913, American Chemical Society, United States (Jul. 2007).

Roberts, C.J., "Therapeutic Protein Aggregation: Mechanisms, Design, and Control," Trends Biotechnol 32(7):372-380, Cell Press, United States (Jul. 2014).

Chi, E.Y., et al., "Physical Stability of Proteins in Aqueous Solution: Mechanism and Driving Forces in Nonnative Protein Aggregation," Pharm Res 20(9):1325-1336, 1328, Springer Nature, Germany (Sep. 2003).

Zapadka, K.L., et al., "Factors affecting the physical stability (aggregation) of peptide therapeutics," Interface Focus 7(6):20170030, Royal Society, United Kingdom (Dec. 2017).

Zhou, S., et al., "Comparative evaluation of disodium edetate and diethylenetriaminepentaacetic acid as iron chelators to prevent metal-catalyzed destabilization of a therapeutic monoclonal antibody," J Pharm Sci 99(10):4239-4250, Elsevier, Netherlands (Oct. 2010).

Final Office Action mailed in U.S. Appl. No. 17/562,961 to Huang et al. on Oct. 25, 2023.

Non-final Office Action mailed in U.S. Appl. No. 18/453,258 to Huang et al. on Oct. 25, 2023.

Advisory Action mailed in U.S. Appl. No. 17/562,961 to Huang et al. on Jan. 24, 2024.

Final Office Action mailed in U.S. Appl. No. 17/562,958 to Huang et al. on Dec. 7, 2023.

Agrawal, S., "Clinical pharmacokinetics (PK) of BMS-936558, a fully human anti-PD-1 monoclonal antibody," J Clin Oncol 30(Suppl 15): Abstract TPS2622, American Society of Clinical Oncology, United States (May 2012).

Agrawal, S., et al., "Nivolumab dose selection: challenges, opportunities, and lessons learned for cancer immunotherapy," J Immunother Cancer 4:72, BMJ, United States (Nov. 2016).

Bajaj, G., et al., "Exposure-Response Analysis of Nivolumab in Patients With Previously Treated or Untreated Advanced Melanoma," J Clin Pharmacol 57(12):1527-1533, Wiley, United States (Dec. 2017).

Center for Drug Evaluation and Research, "Application No. 761064Orig1s000, Clincal Pharmacology and Biopharmaceutics Review(s)," pp. 1-38, U.S. Food and Drug Administration, United States (May 2017).

Feng, Y., et al., "Nivolumab Exposure-Response Analyses of Efficacy and Safety in Previously Treated Squamous or Nonsquamous Non-Small Cell Lung Cancer," Clin Cancer Res 23(18):5394-5405, American Association for Cancer Research, United States (Sep. 2017).

Lonardi, S., et al., "Checkmate 8KX: Phase 1/2 multi-tumor preliminary analyses of a subcutaneous formulation of nivolumab (+-rHuPH20)," 2021 ASCO Annual Meeting—Online (Jun. 4-8, 2021), Poster 2575, American Society of Clinical Oncology, United States (Jun. 2021).

Lonardi, S., et al., "Checkmate 8KX: Phase 1/2 multi-tumor preliminary analyses of a subcutaneous formulation of nivolumab (+-rHuPH20)," 2021 ASCO Annual Meeting—Online (Jun. 4-8, 2021), Presentation No. 2575, slides 1-8, American Society of Clinical Oncology, United States (Jun. 2021).

Topalian, S., et al., "Five-Year Survival and Correlates Among Patients With Advanced Melanoma, Renal Cell Carcinoma, or Non-Small Cell Lung Cancer Treated With Nivolumab," JAMA Oncology 5(10):1411-20 (Jul. 25, 2019).

Topalian, S., et al., "Five-Year Survival and Correlates Among Patients With Advanced Melanoma, Renal Cell Carcinoma, or Non-Small Cell Lung Cancer Treated With Nivolumab: Supplement 2: Online Content" JAMA Oncology 5(10):1411-20 (Jul. 25, 2019).

U.S. Department of Health and Human Services, "Guidance for Industry: Providing Clinical Evidence of Effectiveness for Human Drug and Biological Products," pp. 1-23, U.S. Food and Drug Administration, Rockville, United States (May 1998).

U.S. Food and Drug Administration, Press Release on Dec. 27, 2024, "FDA approves nivolumab and hyaluronidase-nvhy for subcutaneous injection," accessed at https://www.fda.gov/drugs/resources-information-approved-drugs/fda-approves-nivolumab-and-hyaluronidase-nvhy-subcutaneous-injection, accessed on Aug. 5, 2025, 2 pages.

Wang, X., et al., "Quantitative Characterization of the Exposure-Response Relationship for Cancer Immunotherapy: A Case Study of Nivolumab in Patients With Advanced Melanoma," CPT Pharmacometrics Syst Pharmacol 6(1):40-48, Wiley, United States (Jan. 2017).

Zhao, Y., et al., "Novel MIDD Approach to Support Clinical Pharmacology Profiling of Subcutaneous (SC) Nivolumab in Renal-Cell Carcinoma and Bridging to Alternative SC Dosing Regimens and Solid Tumor Indications," J Immunother Cancer 12(Suppl 2):Abstract 524, BMJ, United States (Nov. 2024).

Zhao, Y., et al., "Novel MIDD Approach to Support Clinical Pharmacology Profiling of Subcutaneous (SC) Nivolumab in Renal-Cell Carcinoma (RCC) and Bridging to Alternative SC Dosing Regimens and Solid Tumor Indications," Society for Immunotherapy

(56)         References Cited

OTHER PUBLICATIONS

*of Cancer (SITC) 39th Annual Meeting 2024*—Houston, TX (Nov. 6-10, 2024), Poster 524, Society for Immunotherapy of Cancer, United States (Nov. 2024).

Uniprot, "HYALP_HUMAN," Accession No. P38567, accessed at https://www.uniprot.org/uniprotkb/P38567/entry#P38567-1, accessed on Jun. 18, 2025, 9 pages.

Genbank, "RecName: Full=Programmed cell death I ligand 1; Short-PD-L1; Short=PDCDI ligand 1;Short=Programmed death ligand 1; Short=hPD-L1; AltName: Full=B7 homolog 1; Short=B7-H1; AltName: CD _antigen=CD274; Flags: Precursor," Accession No. Q9NZQ7.1, accessed at https://www.ncbi.nlm.nih.gov/protein/Q9NZQ7, accessed on Feb. 7, 2023, 9 pages.

Locke, K.W., et al., "ENHANZE® drug delivery technology: a novel approach to subcutaneous administration using recombinant human hyaluronidase PH20," Drug Deliv 26(1):98-106, Taylor & Francis, United Kingdom (Dec. 2019).

"FDA Approves Opdivo," Drugs.com (Dec. 22, 2014) available at https://www.drugs.com/newdrugs/fda-approves-opdivo-nivolumab-advanced-melanoma-4133.html.

Opdivo Package Insert, updated Apr. 2019, available at https://www.accessdata.fda.gov/drugsatfda_docs/label/2019/125554s070lbl.pdf.

Motzer et al., "Nivolumab for metastatic renal cell carcinoma: results of a randomized phase II trial," *JCO* 33(13):1430-37 (Dec. 1, 2014).

Bittner et al., "Subcutaneous Administration of Biotherapeutics: An Overview of Current Challenges and Opportunities," *BioDrugs* 32:425-440 (2018).

Collins et al., "Accelerating the development of novel technologies and tools for the subcutaneous delivery of biotherapeutics," *J. Controlled Release 321*:475-82 (Feb. 2020).

Richter et al., "Mechanistic Determinants of Biotherapeutics Absorption Following SC Administration," *The AAPS Journal 14*(3):559-70 (Sep. 2012).

Yervoy Package Insert, revised Jan. 2025, available at https://packageinserts.bms.com/pi/pi_yervoy.pdf.

Press Release, Dec. 27, 2024, available at https://news.bms.com/news/corporate-financial/2024/US-Food-and-Drug-Administration-Approves-Opdivo-Qvantig-nivolumab-and-hyaluronidase-nvhy-Injection-for-Subcutaneous-Use-in-Most-Previously-Approved-Adult-Solid-Tumor-Opdivo-nivolumab-Indications12/default.aspx.

Albiges, L. et al., "Subcutaneous versus intravenous nivolumab for renal cell carcinoma," *European Society for Medical Oncology 36*(1):99-107 (Jan. 2025).

Richter and Jacobsen, "Subcutaneous Absorption of Biotherapeutics: Knowns and Unknowns," *Drug Metabolism and Disposition 42*:1881-89 (Nov. 2014).

Desai et al., "Monoclonal antibody and protein therapeutic formulations for subcutaneous delivery: high-concentration, low-vol. vs. low-concentration, high-volume," *MABS 15*(1):1-19 (Nov. 27, 2023).

George et al., "Subcutaneous nivolumab (NIVO SC) vs intravenous nivolumab (NIVO IV) in patients with previously treated advanced or metastatic clear cell renal cell carcinoma (ccRCC): Pharmacokinetics (PK), efficacy, and safety results from CheckMate 67T," ASCO Oral Abstract: LBA360 (May 2024).

BMS press release. Bristol-Myers Squibb and Halozyme Enter Global Collaboration and License Agreement for ENHANZE Technology. Sep. 14, 2017. Accessed at: https://news.bms.com/news/detai 1s/2017/Bristol-Myers-Squibb-and-Halozyme-Enter-GlobalCollaboration-and-License-Agreement-for-ENHANZE-Technology/default.aspx.

Bookbinder et al., "A recombinant human enzyme for enhanced interstitial transport of therapeutics," Journal of Controlled Release 114:230-241 (Aug. 2006).

Declaration of Dr. Michael Adler, filed in Opposition to EP Patent EP2459167, dated Aug. 19, 2015.

Doshi et al., "A Comprehensive Assessment of All-Oleate Polysorbate 80: Free Fatty Acid Particle Formation, Interfacial Protection and Oxidative Degradation," Pharm Res. 38(3):531-548 (Mar. 2021).

Falconer, "Advances in liquid formulations of parenteral therapeutic proteins," Biotechnol. Adv. 37(7): 107412 (Jun. 2019).

FDA label of Darzalex, Highlights of Prescribing Information, FDA.gov (dated Aug. 2020).

FDA label of Darzalex Faspro, Highlights of Prescribing Information, FDA.gov (dated May 2020).

FDA label of Darzalex Faspro (daratuzumab and hyaluronidase-fihj) injection, for subcutaneous use Highlights of Prescribing Information, FDA.gov (dated Jul. 2024).

FDA label of Herceptin, Highlights of Prescribing Information, FDA.gov (dated Nov. 2018).

FDA label of Herceptin Hylecta (trastuzumab and hyaluronidase-oysk) injection, for subcutaneous use, Highlights of Prescribing Information, FDA.gov (dated Feb. 2019).

FDA label of Herceptin Hylecta (trastuzumab and hyaluronidase-oysk) injection, for subcutaneous use, Highlights of Prescribing Information, FDA.gov (dated Jun. 2024).

FDA label of Perjeta, Highlights of Prescribing Information, FDA.gov (dated Jan. 2020).

FDA label of Phesgo, Highlights of Prescribing Information, FDA.gov (dated Jun. 2020).

FDA label of Rituxan, Highlights of Prescribing Information, FDA.gov (dated Aug. 2020).

FDA label of Rituxan Hycela (rituximab and hyaluronidase human) injection, for subcutaneous use, Highlights of Prescribing Information, FDA.gov (dated Jun. 2021).

FDA label of Rituxan Hycela, Highlights of Prescribing Information, FDA.gov (dated Dec. 2019).

FDA Label of Opdivo, Highlights of Prescribing Information, FDA.gov (dated Nov. 2020).

Frost, "Recombinant human hyaluronidase ((HuPH20): an enabling platform for subcutaneous drug and fluid administration," Expert Opin. Drug Deliv. 4(4):427-40 (Aug. 2007).

Garidel P., et al., "High-concentration protein formulations: How high is high?" Eur. J. Pharm. Biopharm. 119:353-360 (Oct. 2017).

Guo, J., et al., "An industry perspective on hyaluronidase co-formulated biopharmaceutics," J. Control. Release 381:113573 (Feb. 2025).

Hada, S., et al., "Evaluation of antioxidants in protein formulation against oxidative stress using various biophysical methods," Int J Biol Macromol. 82:192-200 (Jan. 2016).

Holstein, M., "Strategies for high-concentration drug substance manufacturing to facilitate subcutaneous administration: A review," Biotechnol. Bioeng. 117(11):3591-3606 (Nov. 2020).

Kang, J., et al., "Rapid Formulation Development for Monoclonal Antibodies," BioProcess International (Apr. 12, 2016); available at: https://www.bioprocessintl.com/formulation/rapidformulation-development-for-monoclonal-antibodies.

Liu, L., "Pharmacokinetics of monoclonal antibodies and Fc-fusion proteins," Protein Cell 9(1):15-32 (Jan. 2018).

NCT03656718, A Study of Subcutaneous Nivolumab Monotherapy With or Without Recombinant Human Hyaluronidase PH20 (rHuPH20), Bristol-Myers Squibb, clinicaltrials.gov, last updated Nov. 12, 2025.

Sadineni V, et al., "Implications of Trace Levels of Redox-Active Metals in Drug-Product Formulation," BioPharm International 27(4) (Apr. 2014), available at https://www.biopharminternational.com/view/implications-trace-levels-redox-active-metalsdrug-product-formulation.

The Dow Chemical Company, "Chelation Chemistry General Concepts of the Chemistry of Chelation," (May 2018), available at: https://chemistry.beloit.edu/classes/Chem220/SlideShow/pdf/113-01388-01-chelationchemistry-general-concepts-of-the-chemistry-of-chelation.pdf.

Usach, I., et al., "Subcutaneous Injection of Drugs: Literature Review of Factors Influencing Pain Sensation at the Injection Site," Adv. Ther. 36(11):2986-2996 (Nov. 2019).

Zhang, Y., et al., "Formulation strategies in immunotherapeutic pharmaceutical products," World J. Clin. Oneal. 11(5):275-282 (May 2020).

Zhou, S., et al., "Biotherapeutic formulation factors affecting metal leachables from stainless steel studied by design of experiments," AAPS PharmSciTech. 13(1):284-94 (Mar. 2012).

(56) References Cited

OTHER PUBLICATIONS

Communication of Notice of Opposition against EP4267105, filed by Camulon Ltd., mailed on Jan. 7, 2026.
Communication of Notice of Opposition against EP4267105, filed by Pajaro Limited, mailed on Jan. 7, 2026.

* cited by examiner

Cavg

Ctau

Cmax

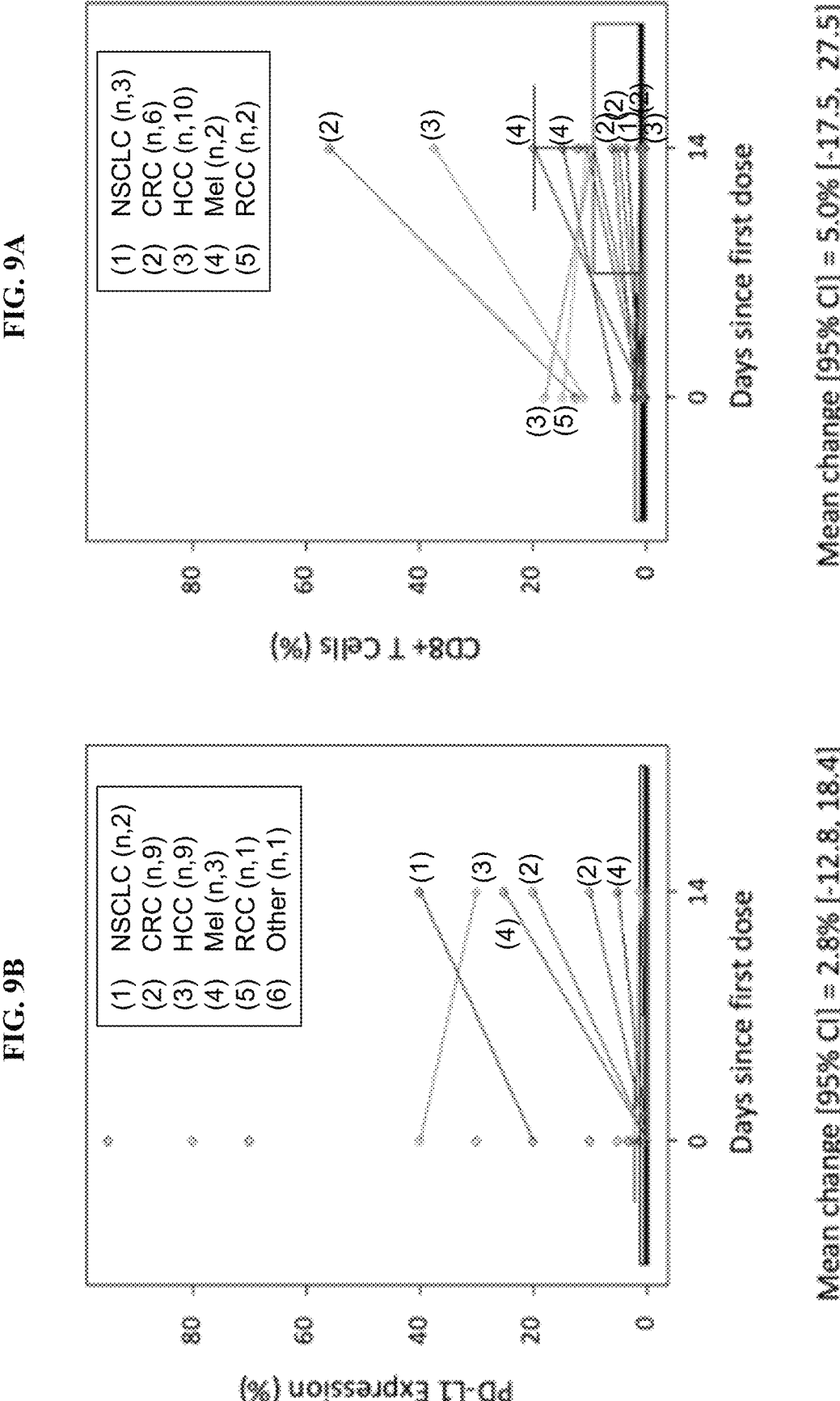

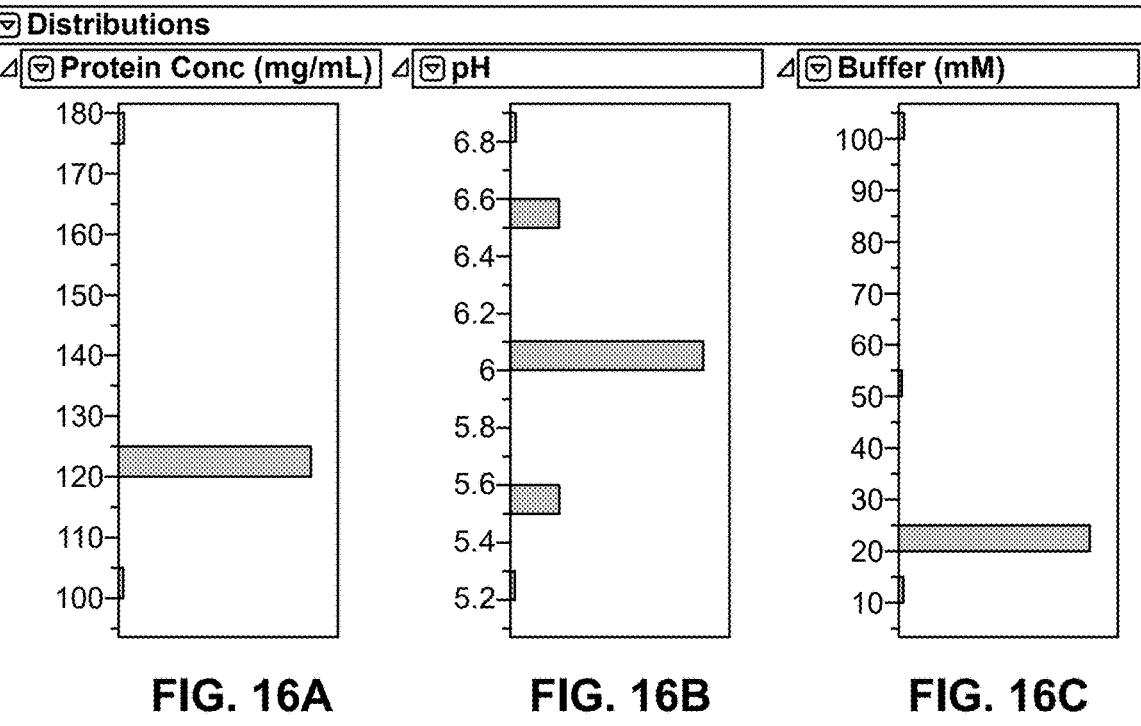
FIG. 16A          FIG. 16B          FIG. 16C
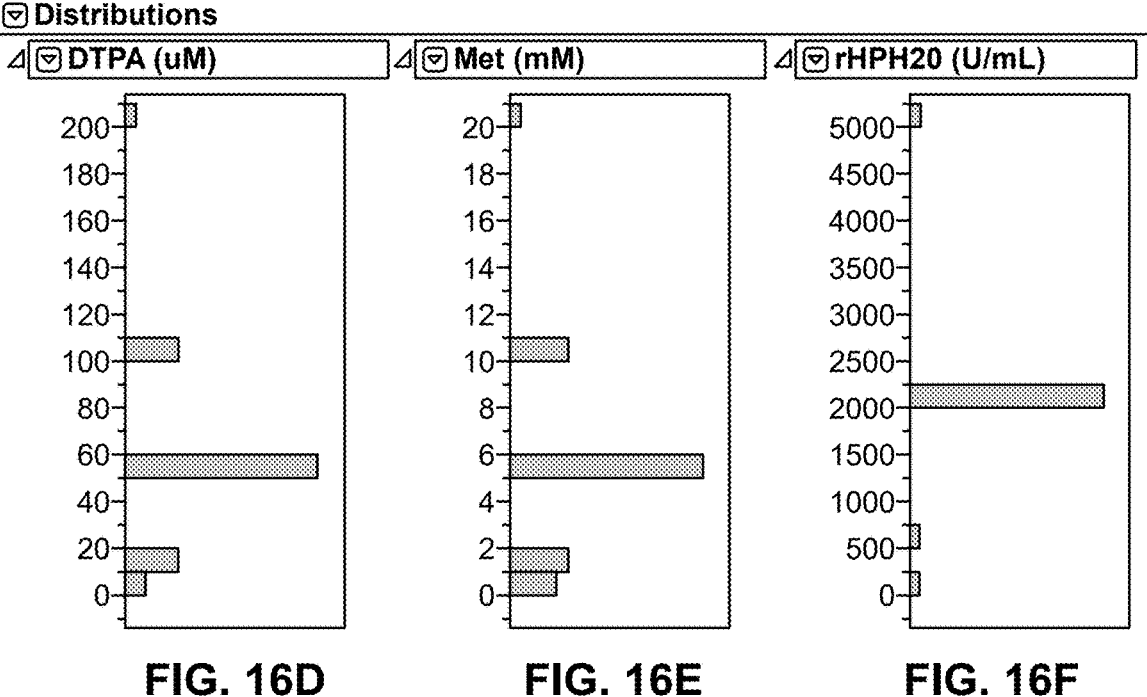
FIG. 16D          FIG. 16E          FIG. 16F

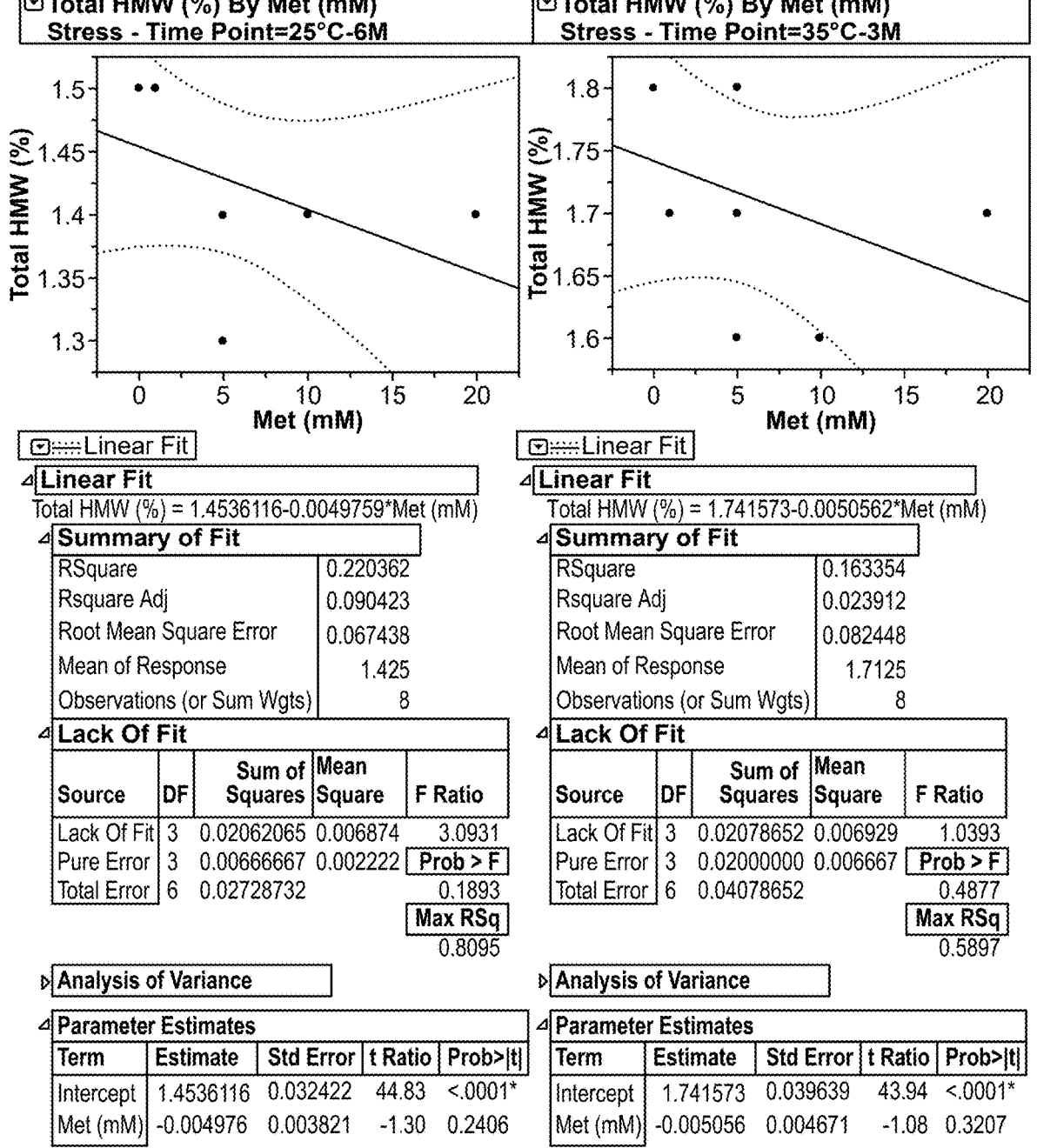

Total HMW (%) By Met (mM)
Stress - Time Point=25°C-6M

Linear Fit

Linear Fit
Total HMW (%) = 1.4536116-0.0049759*Met (mM)

Summary of Fit

| | |
|---|---|
| RSquare | 0.220362 |
| Rsquare Adj | 0.090423 |
| Root Mean Square Error | 0.067438 |
| Mean of Response | 1.425 |
| Observations (or Sum Wgts) | 8 |

Lack Of Fit

| Source | DF | Sum of Squares | Mean Square | F Ratio |
|---|---|---|---|---|
| Lack Of Fit | 3 | 0.02062065 | 0.006874 | 3.0931 |
| Pure Error | 3 | 0.00666667 | 0.002222 | Prob > F |
| Total Error | 6 | 0.02728732 | | 0.1893 |
| | | | | Max RSq |
| | | | | 0.8095 |

▷ Analysis of Variance

Parameter Estimates

| Term | Estimate | Std Error | t Ratio | Prob>|t| |
|---|---|---|---|---|
| Intercept | 1.4536116 | 0.032422 | 44.83 | <.0001* |
| Met (mM) | -0.004976 | 0.003821 | -1.30 | 0.2406 |

Total HMW (%) By Met (mM)
Stress - Time Point=35°C-3M

Linear Fit

Linear Fit
Total HMW (%) = 1.741573-0.0050562*Met (mM)

Summary of Fit

| | |
|---|---|
| RSquare | 0.163354 |
| Rsquare Adj | 0.023912 |
| Root Mean Square Error | 0.082448 |
| Mean of Response | 1.7125 |
| Observations (or Sum Wgts) | 8 |

Lack Of Fit

| Source | DF | Sum of Squares | Mean Square | F Ratio |
|---|---|---|---|---|
| Lack Of Fit | 3 | 0.02078652 | 0.006929 | 1.0393 |
| Pure Error | 3 | 0.02000000 | 0.006667 | Prob > F |
| Total Error | 6 | 0.04078652 | | 0.4877 |
| | | | | Max RSq |
| | | | | 0.5897 |

▷ Analysis of Variance

Parameter Estimates

| Term | Estimate | Std Error | t Ratio | Prob>|t| |
|---|---|---|---|---|
| Intercept | 1.741573 | 0.039639 | 43.94 | <.0001* |
| Met (mM) | -0.005056 | 0.004671 | -1.08 | 0.3207 |

FIG. 21C

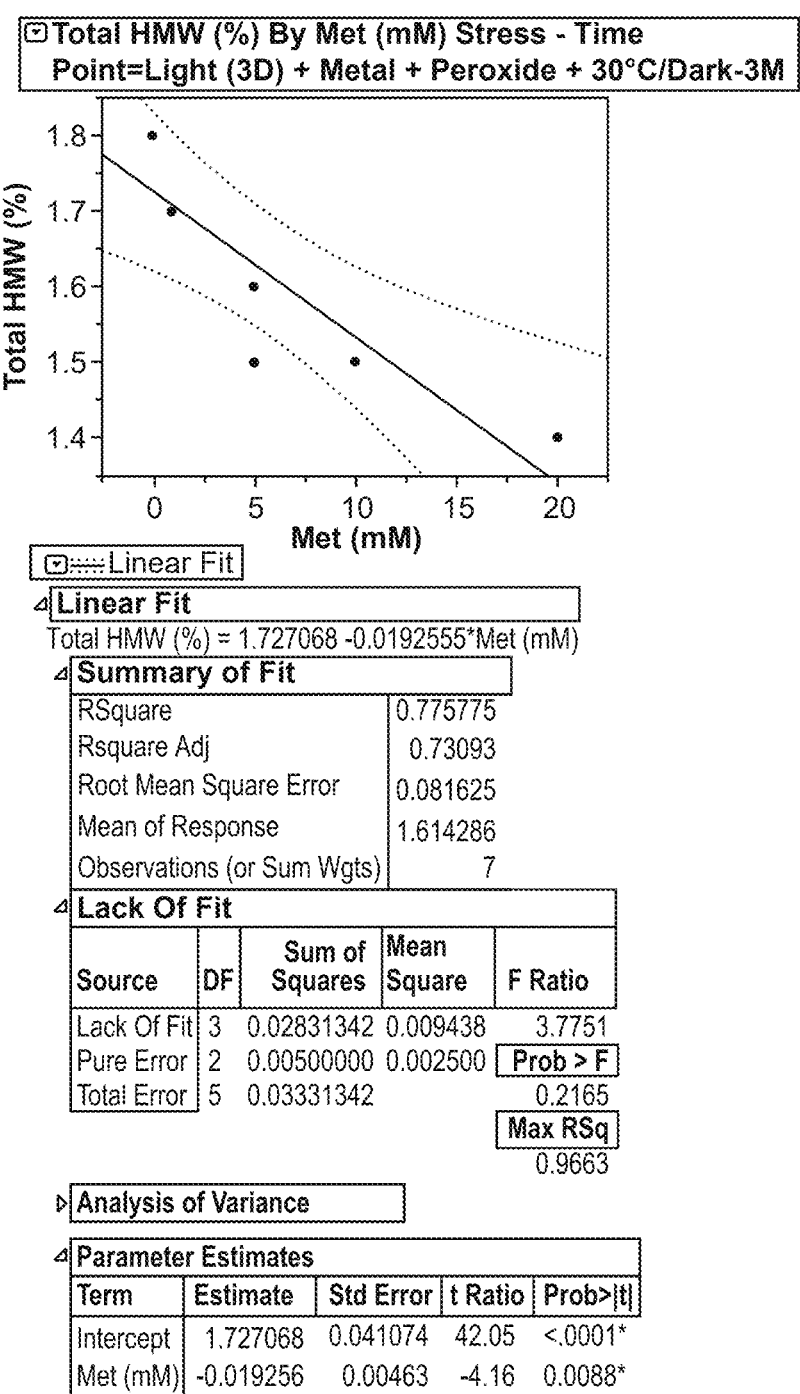

| ⊡Total HMW (%) By Met (mM) Stress - Time Point=Light (3D) + Metal + Peroxide + 30°C/Dark-3M |

⊡┈Linear Fit

◢ Linear Fit

Total HMW (%) = 1.727068 -0.0192555*Met (mM)

◢ Summary of Fit

| | |
|---|---|
| RSquare | 0.775775 |
| Rsquare Adj | 0.73093 |
| Root Mean Square Error | 0.081625 |
| Mean of Response | 1.614286 |
| Observations (or Sum Wgts) | 7 |

◢ Lack Of Fit

| Source | DF | Sum of Squares | Mean Square | F Ratio |
|---|---|---|---|---|
| Lack Of Fit | 3 | 0.02831342 | 0.009438 | 3.7751 |
| Pure Error | 2 | 0.00500000 | 0.002500 | Prob > F |
| Total Error | 5 | 0.03331342 | | 0.2165 |
| | | | | Max RSq |
| | | | | 0.9663 |

▷ Analysis of Variance

◢ Parameter Estimates

| Term | Estimate | Std Error | t Ratio | Prob>|t| |
|---|---|---|---|---|
| Intercept | 1.727068 | 0.041074 | 42.05 | <.0001* |
| Met (mM) | -0.019256 | 0.00463 | -4.16 | 0.0088* |

Glycine

Sorbitol

Mannitol

Sucrose

Trehalose

METHODS OF TREATING TUMORS

CROSS-REFERENCE TO RELATED APPLICATIONS

This application is a continuation application of U.S. patent application Ser. No. 17/562,958, filed on Dec. 27, 2021, which claims priority to and benefit of U.S. Provisional Application Nos. U.S. 63/131,240, filed on Dec. 28, 2020; U.S. 63/150,420, filed on Feb. 17, 2021; and U.S. 63/184,082, filed on May 4, 2021; each of which is hereby incorporated by reference herein in its entirety.

REFERENCE TO SEQUENCE LISTING SUBMITTED ELECTRONICALLY VIA EFS-WEB

The content of the electronically submitted sequence listing (Name: 3338_2250006_SequenceListing_ST26.xml; Size: 443,997 bytes; and Date of Creation: Jan. 25, 2024) is herein incorporated by reference in its entirety.

FIELD OF THE DISCLOSURE

The present disclosure provides a method for treating a subject afflicted with a tumor using a checkpoint inhibitor, e.g., an immunotherapy.

BACKGROUND OF THE DISCLOSURE

Human cancers harbor numerous genetic and epigenetic alterations, generating neoantigens potentially recognizable by the immune system (Sjoblom et al., Science (2006)314 (5797):268-274). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of antibodies such as nivolumab and pembrolizumab (formerly lambrolizumab; USAN Council Statement, 2013) that bind specifically to the Programmed Death-1 (PD-1) receptor and block the inhibitory PD-1/PD-1 ligand pathway (Topalian et al., 2012a, b; Topalian et al., 2014; Hamid et al., 2013; Hamid and Carvajal, 2013; McDermott and Atkins, 2013).

Current methods of delivering anti-PD-1 and/or anti-PD-L1 antibodies use periodic intravenous administration, administered by a clinician, often in a clinic or hospital. The inconvenience and invasiveness of the treatment can negatively impact the patient's experience. Subcutaneous delivery, such as through the use of an auto injector or a wearable pump could greatly improve patient compliance. However, there remains a need in the art for formulations comprising anti-PD-1 or anti-PD-L1 antibodies that are suitable for subcutaneous delivery to patients.

SUMMARY OF THE DISCLOSURE

Certain aspects of the present disclosure are directed to a method of treating a subject in need thereof, comprising subcutaneously administering to the subject a dose of a pharmaceutical composition comprising (i) an antibody that specifically binds PD-1 or PD-L1 and inhibits the interaction of PD-1 and PD-L1 ("an anti-PD-1 antibody" or "an anti-PD-L1 antibody", respectively) and (ii) an endoglycosidase hydrolase enzyme; wherein the dose comprises one or more subcutaneous unit doses; and wherein the dose comprises at least about 300 mg to at least about 2400 mg of the anti-PD-1 antibody or the anti-PD-L1 antibody.

In some aspects, the dose comprises two or more subcutaneous unit doses, wherein the two or more subcutaneous unit doses are administered concurrently or subsequently. In some aspects, the two or more subcutaneous unit doses are administered subsequently, wherein each of the two or more subcutaneous unit doses is administered within an interval of about 5 minutes, about 10 minutes, about 15 minutes, about 20 minutes, about 30 minutes, about 45 minutes, about one hour, about two hours, about three hours, about four hours, about five hours, about six hours, about nine hours, about twelve hours, about eighteen hours, or about twenty-four hours between the subcutaneous unit doses. In some aspects, the dose is administered about every one, two, three, four, six, eight weeks.

In some aspects, the antibody comprises an anti-PD-1 antibody. In some aspects, the dose of the antibody is about 250 mg to about 600 mg administered about every week. In some aspects, the dose of the antibody is about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg administered about every week. In some aspects, the dose of the antibody is about 300 mg administered about every week. In some aspects, the dose of the antibody comprises a single subcutaneous unit dose of about 300 mg. In some aspects, the dose of the antibody comprises a single subcutaneous unit dose of about 300 mg in a total administered volume of about 2 mL.

In some aspects, the dose of the antibody comprises (i) two subcutaneous unit doses, wherein each of the two subcutaneous unit doses comprises about 150 mg of the antibody; or (ii) three subcutaneous unit doses, wherein each of the three subcutaneous unit doses comprises about 100 mg of the antibody. In some aspects, (i) the two subcutaneous unit doses are administered to the subject at the same bodily location or (ii) at least two of the three subcutaneous unit doses are administered to the subject at the same bodily location.

In some aspects, the dose of the antibody is about 300 mg to about 900 mg administered about every two weeks. In some aspects, the dose of the antibody is about 300 mg, about 350 mg, about 400 mg, about 450 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, or about 900 mg administered about every two weeks. In some aspects, the dose of the antibody is about 600 mg administered about every two weeks. In some aspects, the dose of the antibody comprises a single subcutaneous unit dose.

In some aspects, the dose of the antibody comprises two, three, or at least four subcutaneous unit doses. In some aspects, the dose of the antibody comprises two subcutaneous unit doses, wherein each of the two subcutaneous unit doses comprises about 300 mg of the antibody. In some aspects, at least one of the two subcutaneous unit doses comprises about 300 mg of the antibody in a total volume of greater than about 2 mL. In some aspects, at least two of the subcutaneous unit doses are administered to the subject the same bodily location.

In some aspects, the dose of the antibody is about 900 mg to about 1500 mg administered about every four weeks. In some aspects, the dose of the antibody is about 900, about 950, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, or about 1500 mg administered about every four weeks. In some aspects, the dose of the antibody is about 1200 mg administered about every four weeks. In some aspects, the dose of the antibody comprises a single subcutaneous unit dose.

In some aspects, the dose of the antibody comprises two, three, four, six, or at least eight subcutaneous unit doses. In some aspects, the dose of the antibody comprises four subcutaneous unit doses, wherein each of the four subcutaneous unit doses comprises about 300 mg of the antibody. In some aspects, at least one of the four subcutaneous unit doses comprises about 300 mg of the antibody in a total volume of greater than 2 mL. In some aspects, at least two of the subcutaneous unit doses are administered to the subject at the same bodily location. In some aspects, the two, three, four, six, or at least eight subcutaneous unit doses are administered on the same day.

In some aspects, the antibody comprises an anti-PD-L1 antibody. In some aspects, the dose of the antibody is about 900 mg to about 1800 mg of the antibody administered about every two weeks. In some aspects, the dose of the antibody is about 900, about 950, about 1000, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, about 1500 mg administered about every two weeks. In some aspects, the dose of the antibody is about 1200 mg about every two weeks. In some aspects, the dose comprises a single subcutaneous unit dose of about 1200 mg in a total administered volume of greater than about 5 mL.

In some aspects, the dose comprises two, three, four, six, or at least eight subcutaneous unit doses. In some aspects, the dose of the antibody comprises four subcutaneous unit doses, wherein each of the four subcutaneous unit doses comprises about 300 mg of the antibody. In some aspects, at least one of the four subcutaneous unit doses comprises about 300 mg of the antibody in a total volume of greater than about 2 mL. In some aspects, at least two of the subcutaneous unit doses are administered to the subject at the same bodily location. In some aspects, the two, three, four, six, or at least eight subcutaneous unit doses are administered on the same day.

In some aspects, the anti-PD-1 antibody or anti-PD-L1 antibody and the endoglycosidase hydrolase enzyme are administered together. In some aspects, the anti-PD-1 antibody or anti-PD-L1 antibody and the endoglycosidase hydrolase enzyme are administered concurrently. In some aspects, the anti-PD-1 antibody or anti-PD-L1 antibody and the endoglycosidase hydrolase enzyme are administered sequentially.

In some aspects, the pharmaceutical composition is administered at a dose of at least about 1,000 units to at least about 30,000 units of the endoglycosidase hydrolase enzyme. In some aspects, the pharmaceutical composition is administered at a dose of at least about 1000 units, at least about 1500 units, at least about 2000 units, at least about 2500 units, at least about 3000 units, at least about 3500 units, at least about 4000 units, at least about 4500 units, at least about 5000 units, at least about 6000 units, at least about 7000 units, at least about 8000 units, at least about 9000 units, at least about 10,000 units, at least about 11,000 units, at least about 12,000 units, at least about 13,000 units, at least about 14,000 units, at least about 15,000 units, at least about 16,000 units, at least about 17,000 units, at least about 18,000 units, at least about 19,000 units, at least about 20,000 units, at least about 21,000 units, at least about 22,000 units, at least about 23,000 units, at least about 24,000 units, at least about 25,000 units, at least about 26,000 units, at least about 27,000 units, at least about 28,000 units, at least about 29,000 units, or at least about 30,000 units of the endoglycosidase hydrolase enzyme. In some aspects, the pharmaceutical composition is administered at a dose of about 4000 units of the endoglycosidase hydrolase enzyme.

In some aspects, the pharmaceutical composition is administered at a dose of (i) about 300 mg of the antibody and (ii) about 4000 units of the endoglycosidase hydrolase enzyme, once about every week. In some aspects, the pharmaceutical composition is administered at a dose of (i) about 600 mg of the antibody and (ii) about 8000 units of the endoglycosidase hydrolase enzyme, once about every two weeks. In some aspects, the pharmaceutical composition is administered at a dose of (i) about 1200 mg of the antibody and (ii) about 20,000 units of the endoglycosidase hydrolase enzyme, once about every four weeks. In some aspects, the pharmaceutical composition is administered at a dose of (i) about 1200 mg of the antibody and (ii) about 8000 units of the endoglycosidase hydrolase enzyme, once about every two weeks. In some aspects, the pharmaceutical composition is administered at a dose of (i) about 1800 mg of the antibody and (ii) about 12,000 units of the endoglycosidase hydrolase enzyme, once about every three weeks.

In some aspects, the endoglycosidase hydrolase enzyme cleaves hyaluronic acid at a hexosaminidic β (1-4) or (1-3) linkage. In some aspects, the endoglycosidase hydrolase enzyme comprises a catalytic domain of hyaluronidase PH-20 (HuPH20), HYAL1, HYAL2, HYAL3, HYAL4, or HYALPS1. In some aspects, the endoglycosidase hydrolase enzyme comprises an amino acid sequence having at least about 70%, at least about 75%, at least about 80%, at least about 85%, at least about 90%, at least about 95%, at least about 96%, at least about 97%, at least about 98%, at least about 99%, or about 100% sequence identity to amino acids 36-490 of SEQ ID NO: 1. In some aspects, the endoglycosidase hydrolase enzyme comprises a hyaluronidase. In some aspects, the endoglycosidase hydrolase enzyme comprises a hyaluronidase selected from the group consisting of HuPH20, HYAL1, HYAL2, HYAL3, HYAL4, any variant, and any isoform thereof. In some aspects, the endoglycosidase hydrolase enzyme comprises rHuPH20 or a fragment thereof.

In some aspects, the endoglycosidase hydrolase enzyme comprises a modified hyaluronidase comprising one or more amino acid substitutions relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase comprising one or more amino acid substitution in an alpha-helix region relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase comprising one or more amino acid substitution in linker region relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase, wherein one or more N-terminal and/or C-terminal amino acids are deleted relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified rHuPH20, wherein the modified rHuPH20 comprises: i. one or more amino acid substitution in an alpha-helix region, a linker region, or both an alpha-helix region and a linker region relative to wild-type rHuPH20; ii. deletion of one or more N-terminal amino acid, one or more C-terminal amino acid, or one or more N-terminal amino acid and one or more C-terminal amino acid relative to wild-type rHuPH20; or iii. both (i) and (ii).

In some aspects, the anti-PD-1 antibody comprises an antibody selected from the group consisting of nivolumab, pembrolizumab, PDR001, MEDI-0680, cemiplimab, toripalimab, tislelizumab, INCSHR1210, TSR-042, GLS-010, AM-0001, STI-1110, AGEN2034, MGA012, BCD-100, IBI308, and any combination thereof. In some aspects, the anti-PD-1 antibody cross-competes with nivolumab for binding to human PD-1. In some aspects, the anti-PD-1 antibody comprises nivolumab. In some aspects, the anti-PD-1 antibody comprises pembrolizumab.

In some aspects, the anti-PD-L1 antibody comprises an antibody selected from the group consisting of BMS-936559, atezolizumab, durvalumab, avelumab, STI-1014, CX-072, KN035, LY3300054, BGB-A333, CK-301, and any combination thereof.

In some aspects, the subject is afflicted with a cancer. In some aspects, the cancer is selected from the group consisting of squamous cell carcinoma, small-cell lung cancer (SCLC), non-small cell lung cancer (NSCLC), squamous NSCLC, nonsquamous NSCLC, glioma, gastrointestinal cancer, renal cancer, clear cell carcinoma, ovarian cancer, liver cancer, colorectal cancer, endometrial cancer, kidney cancer, renal cell carcinoma (RCC), prostate cancer, hormone refractory prostate adenocarcinoma, thyroid cancer, neuroblastoma, pancreatic cancer, glioblastoma, glioblastoma multiforme, cervical cancer, stomach cancer, bladder cancer, hepatoma, breast cancer, colon carcinoma, head and neck cancer, gastric cancer, germ cell tumor, pediatric sarcoma, sinonasal natural killer, melanoma, bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, rectal cancer, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, environmentally-induced cancers including those induced by asbestos, virus-related cancers or cancers of viral origin (e.g., human papilloma virus (HPV-related or -originating tumors)), and any combination thereof.

In some aspects, the pharmaceutical composition is administered using an auto-injector. In some aspects, the pharmaceutical composition is administered using a wearable pump.

In some aspects, the pharmaceutical composition is administered to the subject by subcutaneous infusion for less than about 10 minutes. In some aspects, the pharmaceutical composition is administered to the subject by subcutaneous infusion for less than about 5 minutes.

In some aspects, the pharmaceutical compositions further comprises at least two antioxidants. In some aspects, the at least two antioxidants are selected from methionine, tryptophan, histidine, cysteine, ascorbic acid, glycine, DTPA, and EDTA. In some aspects, the at least two antioxidants comprise (i) methionine and EDTA or (ii) methionine and DTPA. In some aspects, the at least two antioxidants comprise at least about 1 to about 20 mM methionine. In some aspects, the at least two antioxidants comprise at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, at least about 10 mM, at least about 11 mM, at least about 12 mM, at least about 13 mM, at least about 14 mM, at least about 15 mM, at least about 16 mM, at least about 17 mM, at least about 18 mM, at least about 19 mM, or at least about 20 mM methionine. In some aspects, the at least two antioxidants comprise about 5 mM methionine.

In some aspects, the at least two antioxidants comprise at least about 10 μM to about 200 μM DTPA. In some aspects, the at least two antioxidants comprise at least about 10 M, at least about 15 μM, at least about 20 μM, at least about 25 μM, at least about 30 μM, at least about 35 μM, at least about 40 µM, at least about 45 µM, at least about 50 µM, at least about 55 µM, at least about 60 µM, at least about 65 µM, at least about 70 µM, at least about 75 µM, at least about 80 µM, at least about 85 µM, at least about 90 µM, at least about 95 µM, at least about 100 µM, at least about 110 µM, at least about 120 µM, at least about 130 µM, at least about 140 µM, at least about 150 µM, at least about 160 µM, at least about 170 µM, at least about 180 µM, at least about 190 µM, or at least about 200 µM DTPA. In some aspects, the at least two antioxidants comprise about 50 µM DTPA.

In some aspects, the pharmaceutical compositions further comprises a tonicity modifier and/or stabilizer. In some aspects, the tonicity modifier and/or stabilizer comprises a sugar, an amino acid, a polyol, a salt, or a combination thereof. In some aspects, the tonicity modifier and/or stabilizer is selected from the group consisting of sucrose, sorbitol, trehalose, mannitol, glycerol, glycine, leucine, isoleucine, sodium chloride, proline, arginine, histidine, and any combination thereof. In some aspects, the tonicity modifier comprises sucrose. In some aspects, the pharmaceutical composition comprises at least about 10 mM to at least about 500 mM sucrose. In some aspects, the pharmaceutical composition comprises at least about 10 mM, at least about 20 mM, at least about 30 mM, at least about 40 mM, at least about 50 mM, at least about 60 mM, at least about 70 mM, at least about 80 mM, at least about 90 mM, at least about 100 mM, at least about 110 mM, at least about 120 mM, at least about 130 mM, at least about 140 mM, at least about 150 mM, at least about 160 mM, at least about 170 mM, at least about 180 mM, at least about 190 mM, at least about 200 mM, at least about 210 mM, at least about 220 mM, at least about 230 mM, at least about 240 mM, at least about 250 mM, at least about 260 mM, at least about 270 mM, at least about 280 mM, at least about 290 mM, at least about 300 mM, at least about 310 mM, at least about 320 mM, at least about 330 mM, at least about 340 mM, at least about 350 mM, at least about 360 mM, at least about 370 mM, at least about 380 mM, at least about 390 mM, at least about 400 mM, at least about 410 mM, at least about 420 mM, at least about 430 mM, at least about 440 mM, at least about 450 mM, at least about 460 mM, at least about 470 mM, at least about 480 mM, at least about 490 mM, or at least about 500 mM sucrose. In some aspects, the pharmaceutical composition comprises about 250 mM sucrose.

In some aspects, the pharmaceutical composition further comprises a buffering agent. In some aspects, the buffering agent is selected from histidine, succinate, tromethamine, sodium phosphate, sodium acetate, and sodium citrate. In some aspects, the buffering agent comprises histidine. In some aspects, the pharmaceutical composition comprises at least about 5 mM to at least about 100 mM histidine. In some aspects, the pharmaceutical composition comprises at least about 5 mM, at least about 10 mM, at least about 15 mM, at least about 20 mM, at least about 25 mM, at least about 30 mM, at least about 35 mM, at least about 40 mM, at least about 45 mM, at least about 50 mM, at least about 60 mM, at least about 70 mM, at least about 80 mM, at least about 90 mM, or at least about 100 mM histidine. In some aspects, the pharmaceutical composition comprises about 20 mM histidine.

In some aspects, the pharmaceutical composition further comprises a surfactant. In some aspects, the surfactant is selected from the group consisting of polysorbate 20, polysorbate 80, and poloxamer 188. In some aspects, the surfactant comprises polysorbate 80. In some aspects, the pharmaceutical composition comprises at least about 0.01% w/v to at least about 0.1% w/v polysorbate 80. In some aspects, the pharmaceutical composition comprises at least about 0.01% w/v, at least about 0.02% w/v, at least about 0.03% w/v, at least about 0.04% w/v, at least about 0.05% w/v, at least about 0.06% w/v, at least about 0.07% w/v, at least about 0.08% w/v, at least about 0.09% w/v, or at least about 0.1% w/v polysorbate 80. In some aspects, the pharmaceutical composition comprises about 0.05% w/v polysorbate 80.

In some aspects, the pharmaceutical composition comprises: (a) about 120 mg/mL of the anti-PD-1 antibody; (b) about 20 mM L-histidine; (c) about 250 mM sucrose; (d) about 0.05% w/v polysorbate 80; (e) about 50 µM pentetic acid; (f) about 5 mM methionine; and (g) about 0.0182 mg/mL rHuPH20.

In some aspects, the pharmaceutical composition comprises: (a) about 120 mg/mL of the anti-PD-1 antibody; (b) about 20 mM L-histidine; (c) about 250 mM sucrose; (d) about 0.05% w/v polysorbate 80; (e) about 50 µM pentetic acid; (f) about 5 mM methionine; and (g) about 2000 U/mL rHuPH20.

In some aspects, the pharmaceutical composition comprises: (a) about 150 mg/mL of the anti-PD-1 antibody; (b) about 20 mM L-histidine; (c) about 250 mM sucrose; (d) about 0.05% w/v polysorbate 80; (e) about 50 µM pentetic acid; (f) about 5 mM methionine; and (g) about 0.0182 mg/mL rHuPH20.

In some aspects, the pharmaceutical composition comprises: (a) about 150 mg/mL of the anti-PD-1 antibody; (b) about 20 mM L-histidine; (c) about 250 mM sucrose; (d) about 0.05% w/v polysorbate 80; (e) about 50 µM pentetic acid; (f) about 5 mM methionine; and (g) about 2000 U/mL rHuPH20.

In some aspects, the pharmaceutical composition comprises a pH of about 5.2 to about 6.8. In some aspects, the pharmaceutical composition comprises a pH of about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, or about 6.8. In some aspects, the pharmaceutical composition comprises a pH of about 6.0.

Certain aspects of the present disclosure are directed to a pharmaceutical composition for use in any method disclosed herein. Certain aspects of the present disclosure are directed to a pharmaceutical composition comprising (i) an antibody that specifically binds PD-1 ("anti-PD-1 antibody"), (ii) an endoglycosidase hydrolase enzyme, and (iii) at least two antioxidants.

In some aspects, the pharmaceutical composition comprises at least about 50 U/mL to at least about 5000 U/mL of the endoglycosidase hydrolase enzyme. In some aspects, the pharmaceutical composition comprises at least about 50 U/mL, at least about 100 U/mL, at least about 150 U/mL, at least about 200 U/mL, at least about 250 U/mL, at least about 300 U/mL, at least about 350 U/mL, at least about 400 U/mL, at least about 450 U/mL, at least about 500 U/mL, at least about 750 U/mL, at least about 1000 U/mL, at least about 1500 U/mL, at least about 2000 U/mL, at least about 2500 U/mL, at least about 3000 U/mL, at least about 3500 U/mL, at least about 4000 U/mL, at least about 4500 U/mL, at least about 5000 U/mL, at least about 5500 U/mL, at least about 6000 U/mL, at least about 6500 U/mL, at least about 7000 U/mL, at least about 7500 U/mL, at least about 8000 U/mL, at least about 8500 U/mL, at least about 9000 U/mL, at least about 9500 U/mL, at least about 10,000 U/mL of the endoglycosidase hydrolase enzyme. In some aspects, the pharmaceutical composition comprises at least about 500 U/mL of the endoglycosidase hydrolase enzyme. In some aspects, the pharmaceutical composition comprises at least about 1000 U/mL of the endoglycosidase hydrolase enzyme. In some aspects, the pharmaceutical composition comprises at least about 2000 U/mL of the endoglycosidase hydrolase enzyme.

In some aspects, the endoglycosidase hydrolase enzyme cleaves hyaluronic acid at a hexosaminidic β (1-4) or (1-3) linkage. In some aspects, the endoglycosidase hydrolase enzyme comprises a catalytic domain of hyaluronidase PH-20 (HuPH20), HYAL1, HYAL2, HYAL3, HYAL4, or HYALPS1. In some aspects, the endoglycosidase hydrolase enzyme comprises an amino acid sequence having at least about 70%, at least about 75%, at least about 80%, at least about 85%, at least about 90%, at least about 95%, at least about 96%, at least about 97%, at least about 98%, at least about 99%, or about 100% sequence identity to amino acids 36-490 of SEQ ID NO: 1. In some aspects, the endoglycosidase hydrolase enzyme comprises a hyaluronidase. In some aspects, the endoglycosidase hydrolase enzyme comprises a hyaluronidase selected from the group consisting of HuPH20, HYAL1, HYAL2, HYAL3, HYAL4, any variant, and any isoform thereof. In some aspects, the endoglycosidase hydrolase enzyme comprises rHuPH20 or a fragment thereof.

In some aspects, the endoglycosidase hydrolase enzyme comprises a modified hyaluronidase comprising one or more amino acid substitutions relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase comprising one or more amino acid substitution in an alpha-helix region relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase comprising one or more amino acid substitution in linker region relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase, wherein one or more N-terminal and/or C-terminal amino acids are deleted relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified rHuPH20, wherein the modified rHuPH20 comprises: (i) one or more amino acid substitution in an alpha-helix region, a linker region, or both an alpha-helix region and a linker region relative to wild-type rHuPH20; (ii) deletion of one or more N-terminal amino acid, one or more C-terminal amino acid, or one or more N-terminal amino acid and one or more C-terminal amino acid relative to wild-type rHuPH20; or (iii) both (i) and (ii).

In some aspects, the at least two antioxidants are selected from methionine, tryptophan, histidine, cysteine, ascorbic acid, glycine, DTPA, and EDTA. In some aspects, the at least two antioxidants comprise (i) methionine and EDTA or (ii) methionine and DTPA. In some aspects, the at least two antioxidants comprise at least about 1 to about 20 mM methionine. In some aspects, the at least two antioxidants comprise at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, at least about 10 mM, at least about 11 mM, at least about 12 mM, at least about 13 mM, at least about 14 mM, at least about 15 mM, at least about 16 mM, at least about 17 mM, at least about 18 mM, at least about 19 mM, or at least about 20 mM methionine. In some aspects, the at least two antioxidants comprise about 5 mM methionine.

In some aspects, the at least two antioxidants comprise at least about 10 μM to about 200 μM DTPA. In some aspects, the at least two antioxidants comprise at least about 10 μM, at least about 15 μM, at least about 20 μM, at least about 25 μM, at least about 30 μM, at least about 35 μM, at least about 40 μM, at least about 45 μM, at least about 50 μM, at least about 55 μM, at least about 60 μM, at least about 65 μM, at least about 70 μM, at least about 75 μM, at least about 80 μM, at least about 85 μM, at least about 90 μM, at least about 95 μM, at least about 100 μM, at least about 110 μM, at least about 120 μM, at least about 130 μM, at least about 140 μM, at least about 150 μM, at least about 160 μM, at least about 170 μM, at least about 180 μM, at least about 190 μM, or at least about 200 μM DTPA. In some aspects, the at least two antioxidants comprise about 50 μM DTPA.

In some aspects, the pharmaceutical composition comprises at least about 20 mg/mL to at least about 200 mg/mL of the anti-PD-1 antibody. In some aspects, the pharmaceutical composition comprises at least about 135 mg/mL to at least about 180 mg/mL of the anti-PD-1 antibody. In some aspects, the pharmaceutical composition comprises at least about 108 mg/mL to at least about 132 mg/mL of the anti-PD-1 antibody. In some aspects, the pharmaceutical composition comprises at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, at least about 100 mg/mL, at least about 110 mg/mL, at least about 120 mg/mL, at least about 130 mg/mL, at least about 140 mg/mL, at least about 150 mg/mL, at least about 160 mg/mL, at least about 170 mg/mL, at least about 180 mg/mL, at least about 190 mg/mL, or at least about 200 mg/mL of the anti-PD-1 antibody. In some aspects, the pharmaceutical composition comprises about 120 mg/mL of the anti-PD-1 antibody. In some aspects, the pharmaceutical composition comprises about 150 mg/mL of the anti-PD-1 antibody.

In some aspects, the pharmaceutical composition further comprises a tonicity modifier and/or stabilizer. In some aspects, the tonicity modifier and/or stabilizer comprises a sugar, an amino acid, a polyol, a salt, or a combination thereof. In some aspects, the tonicity modifier and/or stabilizer is selected from the group consisting of sucrose, sorbitol, trehalose, mannitol, glycerol, glycine, leucine, isoleucine, sodium chloride, proline, arginine, histidine, and any combination thereof. In some aspects, the tonicity modifier comprises sucrose. In some aspects, the pharmaceutical composition comprises at least about 10 mM to at least about 500 mM sucrose. In some aspects, the pharmaceutical composition comprises at least about 10 mM, at least about 20 mM, at least about 30 mM, at least about 40 mM, at least about 50 mM, at least about 60 mM, at least about 70 mM, at least about 80 mM, at least about 90 mM, at least about 100 mM, at least about 110 mM, at least about 120 mM, at least about 130 mM, at least about 140 mM, at least about 150 mM, at least about 160 mM, at least about 170 mM, at least about 180 mM, at least about 190 mM, at least about 200 mM, at least about 210 mM, at least about 220 mM, at least about 230 mM, at least about 240 mM, at least about 250 mM, at least about 260 mM, at least about 270 mM, at least about 280 mM, at least about 290 mM, at least about 300 mM, at least about 310 mM, at least about 320 mM, at least about 330 mM, at least about 340 mM, at least about 350 mM, at least about 360 mM, at least about 370 mM, at least about 380 mM, at least about 390 mM, at least about 400 mM, at least about 410 mM, at least about 420 mM, at least about 430 mM, at least about 440 mM, at least about 450 mM, at least about 460 mM, at least about 470 mM, at least about 480 mM, at least about 490 mM, or at least about 500 mM sucrose. In some aspects, the pharmaceutical composition comprises about 250 mM sucrose.

In some aspects, the pharmaceutical composition further comprises a buffering agent. In some aspects, the buffering agent is selected from histidine, succinate, tromethamine, sodium phosphate, sodium acetate, and sodium citrate. In some aspects, the buffering agent comprises histidine. In some aspects, the pharmaceutical composition comprises at least about 5 mM to at least about 100 mM histidine. In some aspects, the pharmaceutical composition comprises at least about 5 mM, at least about 10 mM, at least about 15 mM, at least about 20 mM, at least about 25 mM, at least about 30 mM, at least about 35 mM, at least about 40 mM, at least about 45 mM, at least about 50 mM, at least about 60 mM, at least about 70 mM, at least about 80 mM, at least about 90 mM, or at least about 100 mM histidine. In some aspects, the pharmaceutical composition comprises about 20 mM histidine.

In some aspects, the pharmaceutical composition further comprises a surfactant. In some aspects, the surfactant is selected from the group consisting of polysorbate 20, polysorbate 80, and poloxamer 188. In some aspects, the surfactant comprises polysorbate 80. In some aspects, the pharmaceutical composition comprises at least about 0.01% w/v to at least about 0.1% w/v polysorbate 80. In some aspects, the pharmaceutical composition comprises at least about 0.0100 w/v, at least about 0.02% w/v, at least about 0.03% w/v, at least about 0.04% w/v, at least about 0.05% w/v, at least about 0.06% w/v, at least about 0.07% w/v, at least about 0.08% w/v, at least about 0.09% w/v, or at least about 0.1% w/v polysorbate 80. In some aspects, the pharmaceutical composition comprises about 0.05% w/v polysorbate 80.

In some aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In some aspects, the pharmaceutical composition comprises: (a) about 120 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In some aspects, the pharmaceutical composition comprises a pH of about 5.2 to about 6.8. In some aspects, the pharmaceutical composition comprises a pH of about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, or about 6.8. In some aspects, the pharmaceutical composition comprises a pH of about 6.0.

Certain aspects of the present disclosure are directed to a unit dose comprising any pharmaceutical composition disclosed herein.

Certain aspects of the present disclosure are directed to a unit dose comprising: (a) about 120 mg/mL of the anti-PD-1 antibody; (b) about 20 mM L-histidine; (c) about 250 mM sucrose; (d) about 0.05% w/v polysorbate 80; (e) about 50 μM pentetic acid; (f) about 5 mM methionine; and (g) about 2000 U/mL rHuPH20.

Certain aspects of the present disclosure are directed to a unit dose comprising: (a) about 150 mg/mL of the anti-PD-1 antibody; (b) about 20 mM L-histidine; (c) about 250 mM sucrose; (d) about 0.05% w/v polysorbate 80; (e) about 50 μM pentetic acid; (f) about 5 mM methionine; and (g) about 2000 U/mL rHuPH20.

In some aspects, the pharmaceutical composition further comprises a second therapeutic agent. In some aspects, the second therapeutic agent is an antibody. In some aspects, the second therapeutic agent is a checkpoint inhibitor. In some aspects, the checkpoint inhibitor is an anti-CTLA-4 antibody, an anti-LAG-3 antibody, an anti-TIM3 antibody, an anti-TIGIT antibody, an anti-TIM3 antibody, an anti-NKG2a antibody, an anti-OX40 antibody, an anti-ICOS antibody, an anti-MICA antibody, an anti-CD137 antibody, an anti-KIR antibody, an anti-TGFβ antibody, an anti-IL-10 antibody, an anti-IL-8 antibody, an anti-B7-H4 antibody, an anti-Fas ligand antibody, an anti-CXCR4 antibody, an anti-mesothelin antibody, an anti-CD27 antibody, an anti-GITR, or any combination thereof. In some aspects, the pharmaceutical composition further comprises a third therapeutical agent. In some aspects, the second therapeutic agent, the third therapeutic agent, or both comprises an IL-2 (e.g., bempegaldesleukin) or an IL12-Fc (e.g., BMS-986415).

Certain aspects of the present disclosure are directed to a vial comprising any pharmaceutical composition disclosed herein or any unit dose disclosed herein.

In some aspects, the vial is an autoinjector. Certain aspects of the present disclosure are directed to an autoinjector comprising any pharmaceutical composition disclosed herein or any unit dose disclosed herein.

In some aspects, the vial is a wearable pump. Certain aspects of the present disclosure are directed to a wearable pump comprising any pharmaceutical composition disclosed herein or any unit dose disclosed herein.

BRIEF DESCRIPTION OF THE DRAWINGS

FIGS. 9A-9B show tumor infiltrating lymphocyte CD8 expression (FIG. 9A) and PD-L1 tumor expression (FIG. 9B) 14 days after a first subcutaneous dose of nivolumab and rHuPH20 (Parts A, B, and D) for subjects afflicted with non-small cell lung cancer (NSCLC), renal cell carcinoma (RCC), melanoma (Mel), hepatocellular carcinoma (HCC), and microsatellite instability-high/mismatch repair deficient colorectal cancer (MSI-H/dMMR CRC).

FIGS. 16A-16F are graphical representations of the distribution of the formulations of Study 2. Formulations ranged at max and min of the excipient with all other factors at the target composition of 120 mg/mL Nivo (FIG. 16A), 20 mM Histidine (FIG. 16C), 250 mM Sucrose, 50 μM DTPA (FIG. 16D), 5 mM Met (FIG. 16E), 2,000 U/mL rHPH20 (FIG. 16F), 0.05% w/v PS80 at pH 6.0 (FIG. 16B).

FIGS. 21A-21C are graphical representations of linear regression models for the % total HMW after 6 months at 25° C. 6 month (FIG. 21A), 3 months at 35° C. (FIG. 21B), and 3 months with MPL stress (FIG. 21C) as a function of Met levels with fit performance for formulations containing 120 mg/mL Nivo, 20 mM Histidine, 250 mM Sucrose, 50 μM DTPA, 0.05% w/v PS80, 2000 U/mL rHuPH20 at pH 6.0.

Figure 22A:
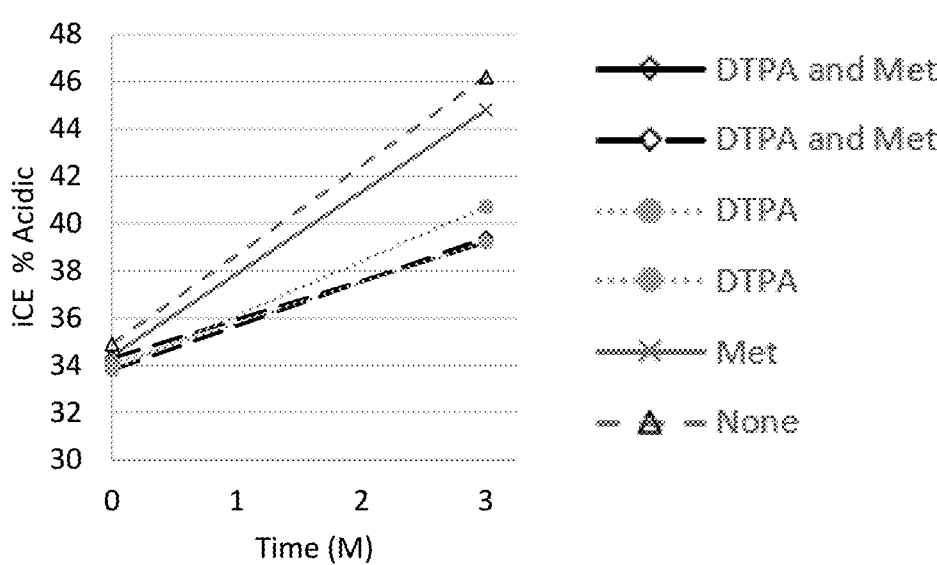
Figure 22B:
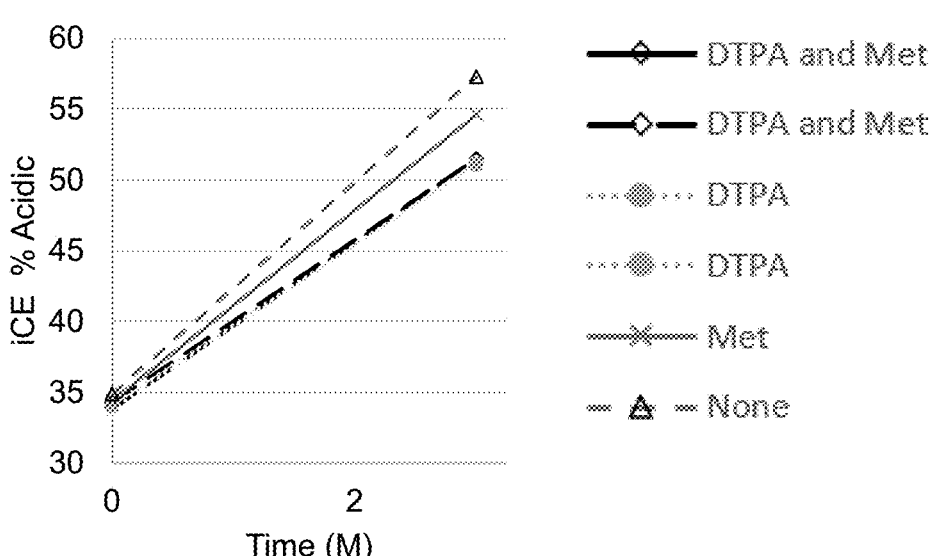

FIGS. 22A-22B are graphical representations of acidic species as a function of time under MPL condition (FIG. 22A) and 35° C. stress (FIG. 22B). Duplicate samples for formulations with DTPA and Met as well as for DTPA alone. DTPA at 50 μM and 5 mM Met concentrations. The formulation is at 120 mg/mL Nivo, 20 mM Histidine, 250 mM Sucrose, 0.05% w/v PS80, 2,000 U/mLrHuPH20 at pH 6.0.

Figure 23A:
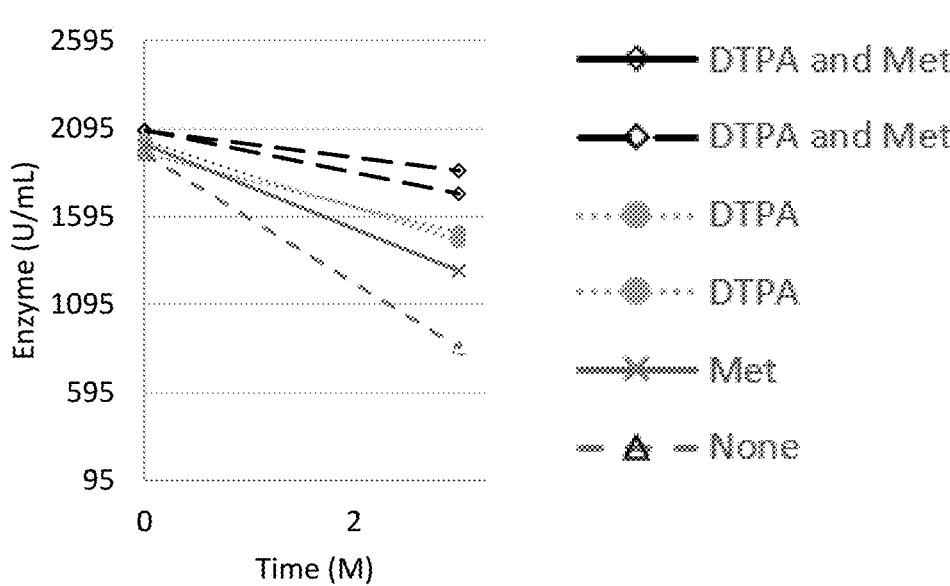
Figure 23B:
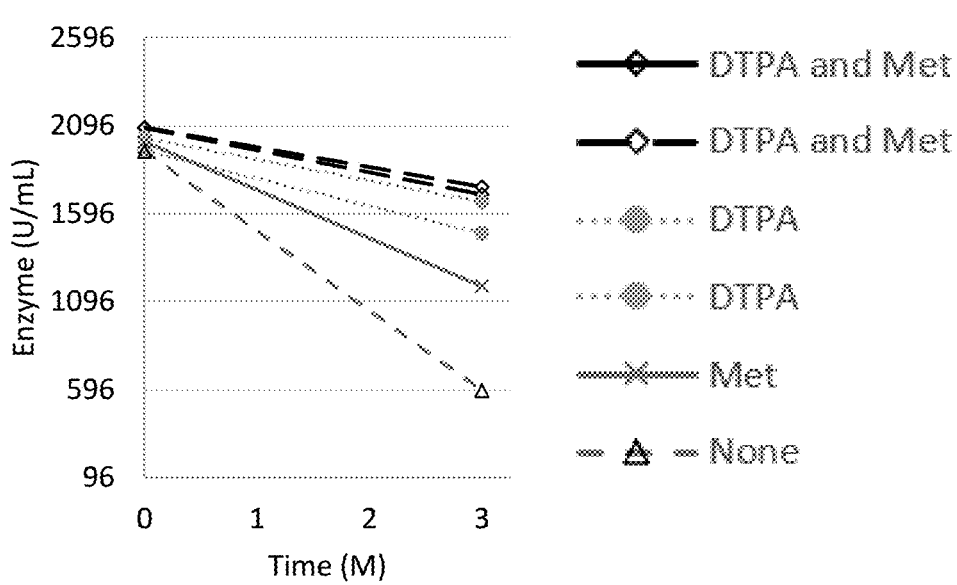

FIGS. 23A-23B are graphical representations of enzyme activity as a function of time under MPL condition (FIG. 23A) and 35° C. stress (FIG. 23B). Duplicate samples for formulations with DTPA and Met as well as for DTPA alone. DTPA at 50 μM and 5 mM Met concentrations. The formulation is at 120 mg/mL Nivo, 20 mM Histidine, 250 mM Sucrose, 0.05% w/v PS80, 2,000 U/mLrHuPH20 at pH 6.0.

Figure 24A:
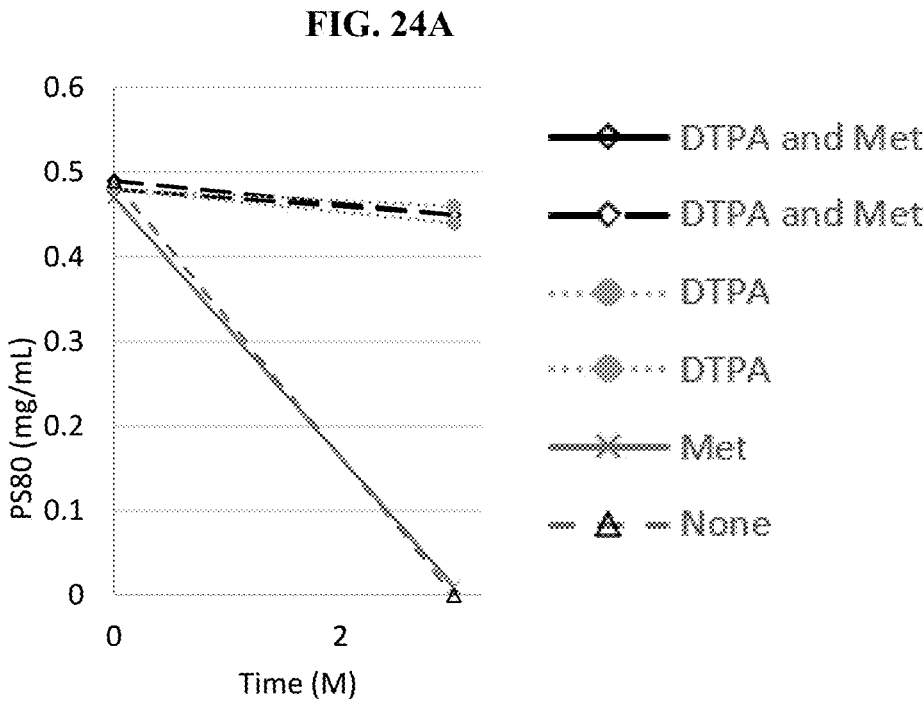
Figure 24B:
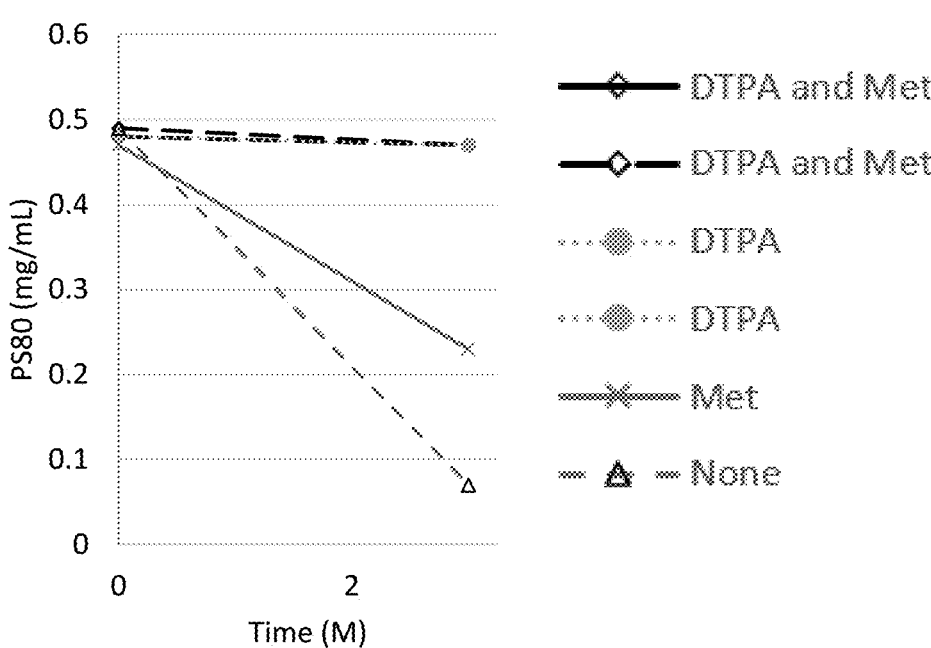

FIGS. 24A-24B are graphical representations of PS80 levels as a function of time under MPL condition (FIG. 24A) and 35° C. stress (FIG. 24B). Duplicate samples for formulations with DTPA and Met as well as for DTPA alone. DTPA at 50 μM and 5 mM Met concentrations. The formulation is at 120 mg/mL Nivo, 20 mM histidine, 250 mM sucrose, 0.05% w/v PS80, 2,000 U/mLrHuPH20 at pH 6.0.

Figure 25A:
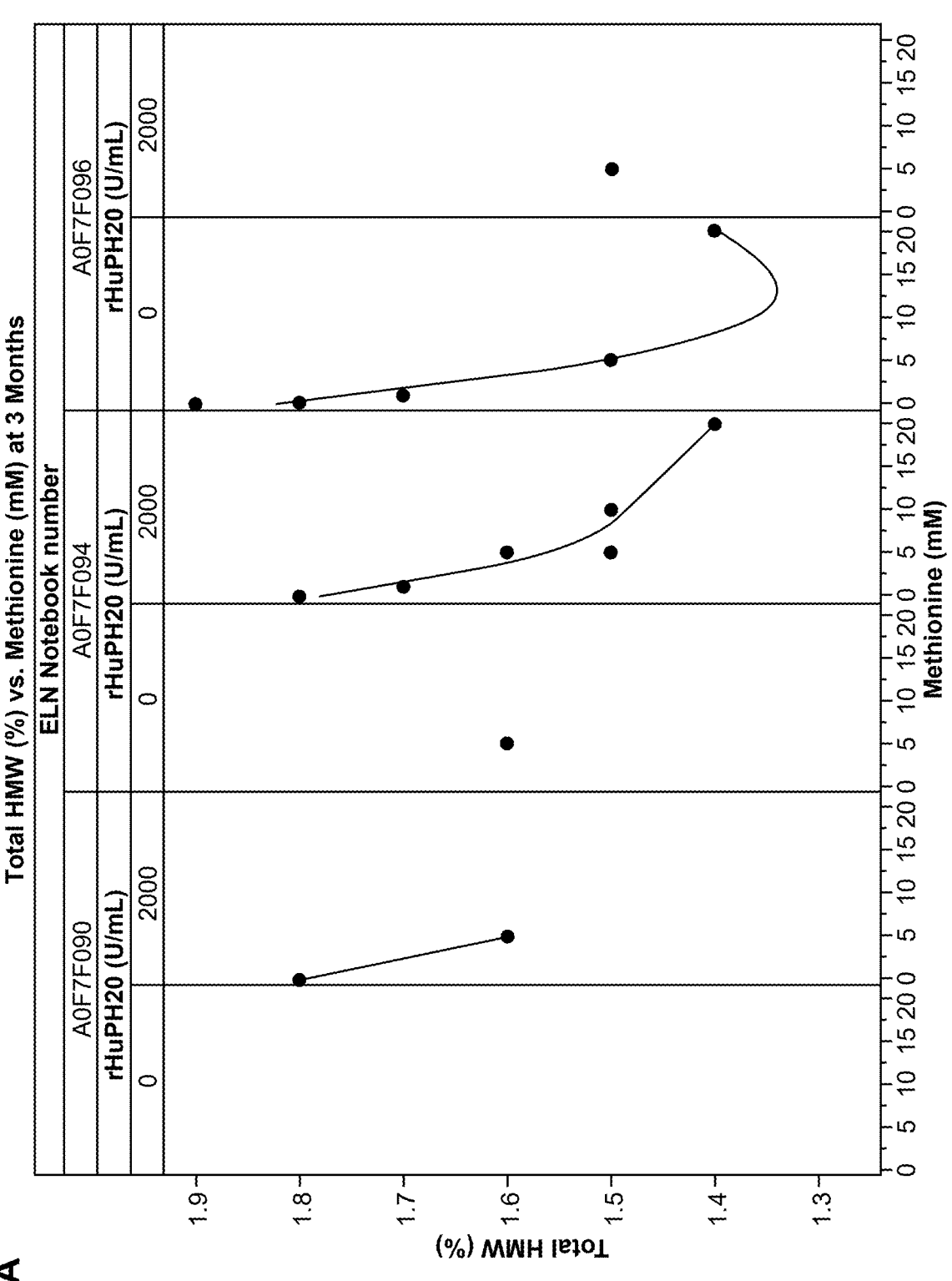
Figure 25B:
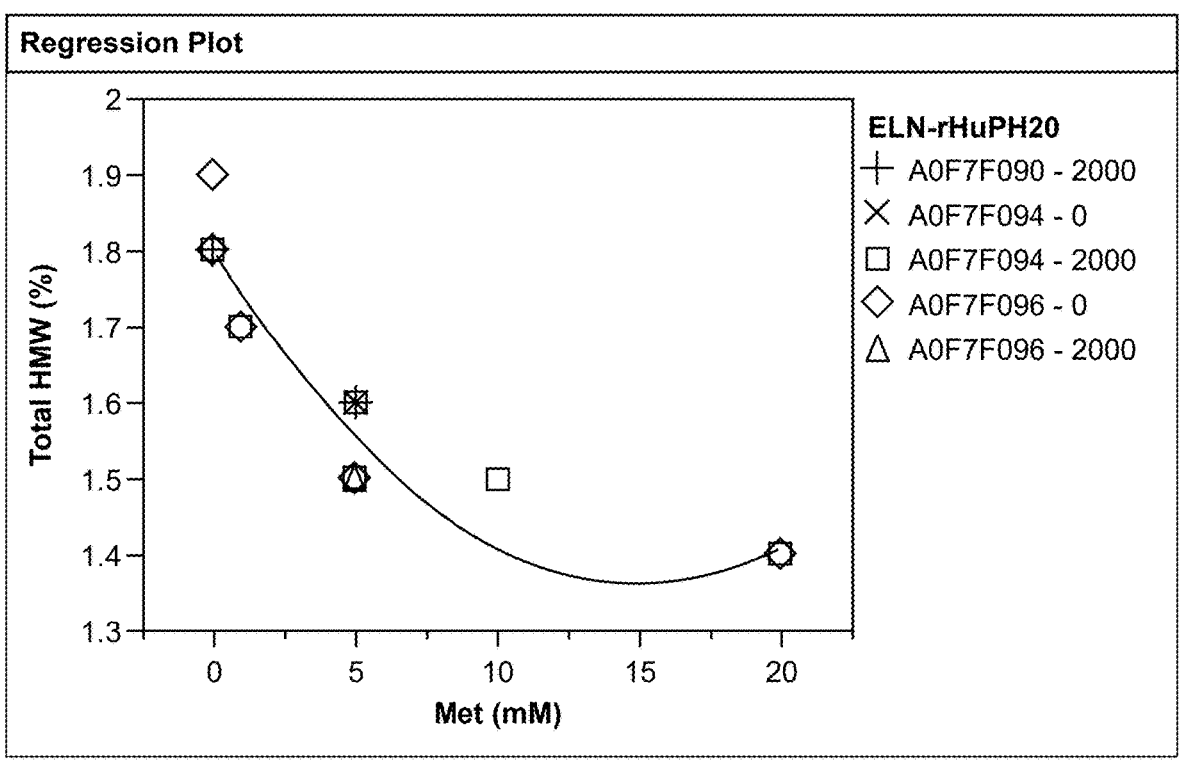

FIG. 25A is a graphical representation illustrating a comparison across study 1, study 2, and study 3 at the high molecular weight species, by SEC at the 3-month timepoint for the MPL condition, separated by with and w/out 2,000 U/mL of rHuPH20 enzyme at various Met levels. FIG. 25B is a regression plot with study 1, study 2, and study 3 for the high molecular weight species by SEC at the 3 month timepoint for the MPL condition as a function of Met. Composition includes 120 mg/mL Nivo, 20 mM Histidine, 250 mM Sucrose, 50 μM DTPA, 0.05% w/v PS80, 2000 U/mL rHuPH20 at pH 6.0 (FIGS. 25A-25B).

Figure 26:
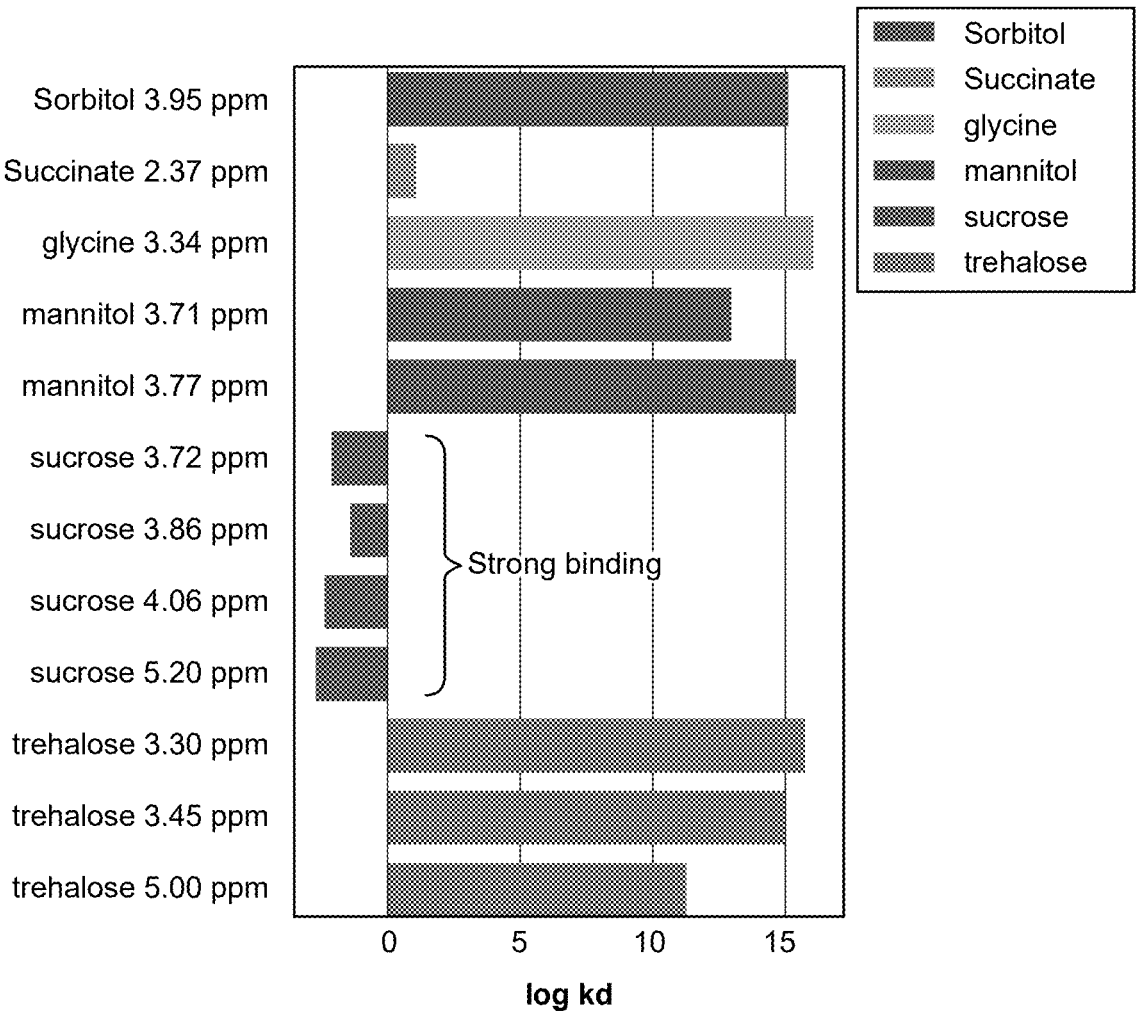

FIG. 26 is a bar graph providing a comparison of $\log_{10}$ (kd) for glycine, mannitol, sucrose, trehalose, and succinate, as indicated.

Figure 27:
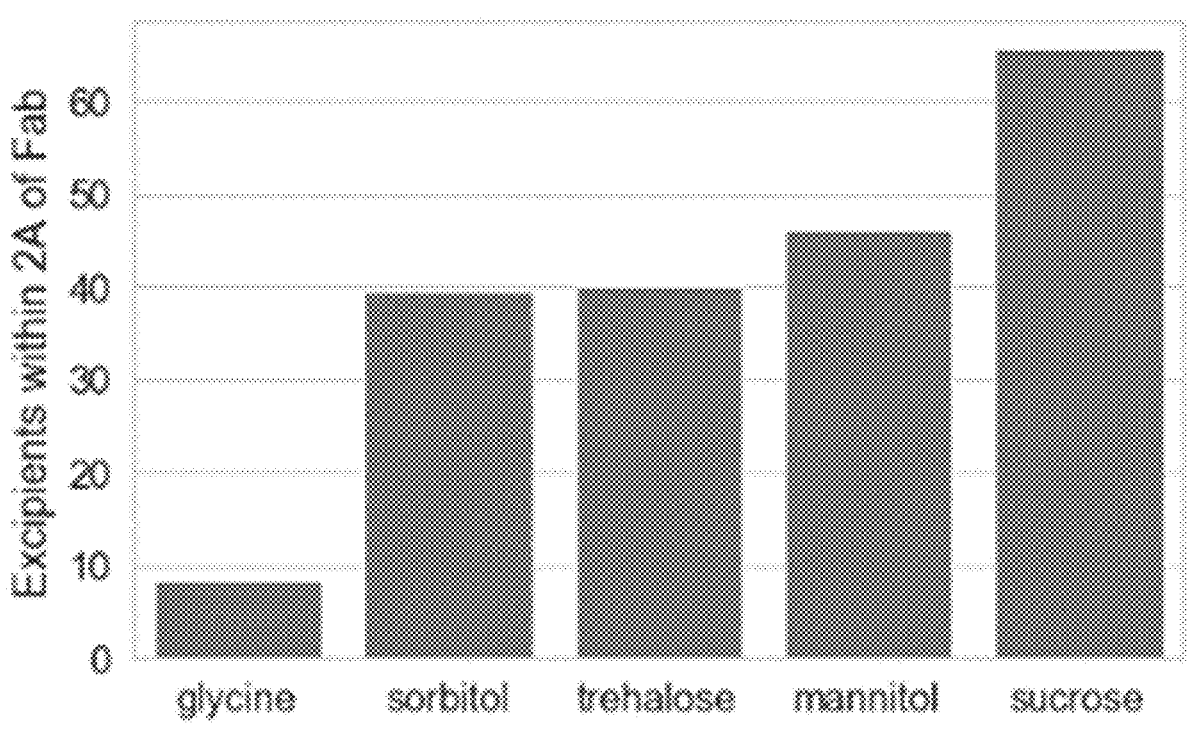

FIG. 27 is a bar graph showing the average count of the number of excipient molecules interacting with the Nivolumab Fab group during the last 8 ns of the MD simulations for glycine, sorbitol, trehalose, mannitol, and sucrose, as indicated.

FIGS. 28A-28E are illustrations of the binding poses found for each of glycine (FIG. 28A), sorbitol (FIG. 28B), mannitol (FIG. 28C), sucrose (FIG. 28D), and trehalose (FIG. 28E) on the Nivolumab Fab. The Fab group is displayed as a ribbon, lightly-binding poses are shown in ball and stick representation, and the tightly bound poses are shown in space filling representation.

Figure 29A:
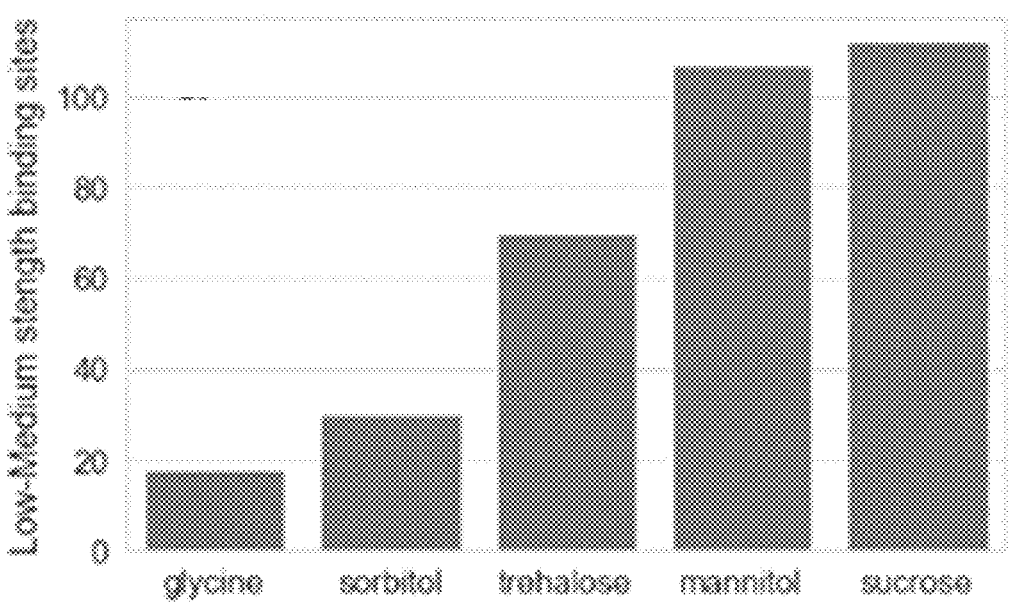
Figure 29B:
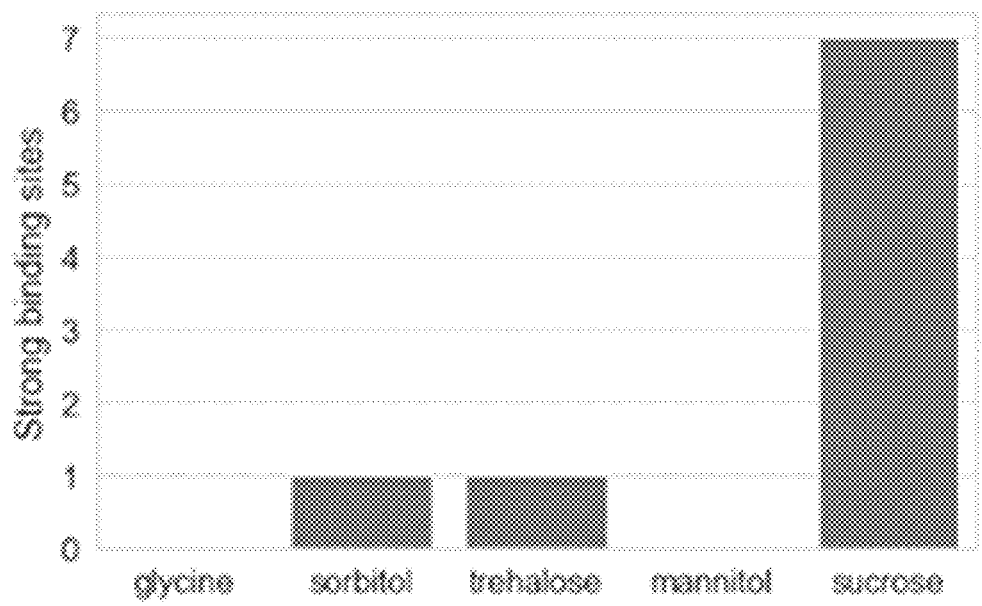

FIGS. 29A-29B are bar graphs illustrating the number of unique binding poses found for each excipient (glycine, sorbitol, trehalose, mannitol, and sucrose) in the MD simulations for medium strength interactions (FIG. 29A) and strongly bound interactions (FIG. 29B).

DETAILED DESCRIPTION OF THE DISCLOSURE

Current methods of delivering anti-PD-1 and/or anti-PD-L1 antibodies require periodic intravenous administration, administered by a clinician, often in a clinic or hospital. This regimen often creates significant inconvenience for the patient, and the nature of the treatment itself can negatively impact the patient's experience. Subcutaneous delivery, such as through the use of an auto injector or a wearable pump could greatly improve patient compliance, possibly allowing for a patient to receive this potentially life-saving therapy in the comfort of their own home. The present disclosure provides a method of treating a subject in need thereof, comprising subcutaneously administering to the subject a dose of a pharmaceutical composition comprising (i) an antibody that specifically binds PD-1 or PD-L1 and inhibits the interaction of PD-1 and PD-L1 ("an anti-PD-1 antibody" or "an anti-PD-L1 antibody", respectively). In some aspects, the pharmaceutical composition further comprises (ii) an endoglycosidase hydrolase enzyme. In some aspects, the dose comprises one or more subcutaneous unit doses.

In some aspects, the pharmaceutical composition does not comprise an endoglycosidase hydrolase enzyme. In some aspects, at least one of the subcutaneous unit doses has a total volume of less than about 5 mL (e.g., less than about 4.5 mL, less than about 4.0 mL, less than about 3.5 mL, less than about 3.0 mL, less than about 3 mL, or less than about 2.5 mL). In certain aspects, the dose comprises at least about 250 mg to at least about 2400 mg of the antibody.

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a composition comprising a therapeutic agent to a subject, using any of the various methods and delivery systems known to those skilled in the art. Administration can refer to any form of administration for the immunotherapy, e.g., the anti-PD-1 antibody or the anti-PD-L1 antibody, include intravenous, intramuscular, subcutaneous, intraperitoneal, spinal or other parenteral routes of administration, for example by injection or infusion. The phrases "subcutaneous administration" and "subcutaneous injection" are used interchangeably and refer to modes of administration wherein a substance, e.g., a composition comprising an antibody that specifically binds PD-1 or PD-L1 and inhibits the interaction of PD-1 and PD-L1 is delivered to a subject under the skin, between the dermis and, e.g., the muscle.

Subcutaneous administration can be achieved using any methods. In some aspects, subcutaneous administration is achieved using a short needle or a plurality of short needles. In some aspects, the needle or at least one of the plurality of needles are less than about 1 inch, less than about ⅞ inches, less than about ⅚ inches, less than about ⅝ inches, are less than about ½ inches. In some aspects, the needle or at least one of the plurality of needles is about ⅝ inches in length.

Administering can be performed, for example, once, a plurality of times, and/or over one or more extended periods. Thus, as used herein, administering can refer to a single unit dose or more than one unit dose.

As used herein, the term "dose" or "dosage" is defined as an amount of a therapeutic agent that can be administered at a given point. The dose or dosage can be an amount sufficient to achieve or at least partially achieve a desired effect, but such a desired effect may not be visible or detectable. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, an increase in overall survival (the length of time from either the date of diagnosis or the start of treatment for a disease, such as cancer, that patients diagnosed with the disease are still alive), or a prevention of impairment or disability due to the disease affliction. An amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods available to the skilled practitioner, such as in human subjects during clinical trials, in animal model systems predictive of efficacy in humans, or by assaying the activity of the agent in in vitro assays. A "dose" can comprise a single unit dose or multiple unit doses. In some aspects, the dose comprises a single unit dose. In some aspects, the dose comprises multiple unit doses.

As used herein, a subcutaneous "unit dose" refers to a single amount of a substance delivered by a subcutaneous injection, e.g., from a single vial, a single auto-injector, and/or a single syringe. In some aspects, multiple subcutaneous doses are administered to achieve a therapeutically effective dose. When multiple unit doses are administered, individual unit doses can be administered at the same time or sequentially. In some aspects, each unit dose of a therapeutically effective dose is administered on the same day. Each unit dose can be administered at the same bodily location or at different bodily locations. In some aspects, a first unit dose is administered at a first bodily location, and a second unit dose is administered at a second bodily location. Any bodily locations known in the art to be suitable for subcutaneous delivery can be used in the methods disclosed herein. In some aspects, at least one subcutaneous unit dose of the dose is administered to a bodily location selected from the arm (e.g., the side or back of an upper arm), the abdomen, and the front of the thigh.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Therefore, the term "anti-PD-1 antibody" includes a full antibody having two heavy chains and two light chains that specifically binds to PD-1 and antigen-binding portions of the full antibody. Non-limiting examples of the antigen-binding portions are shown elsewhere herein.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

In some aspects, an "antibody" of the present disclosure is capable of binding to more than one antigen, e.g., a "multispecific" antibody. As used herein, a "bispecific" antibody is an antibody that is capable of specifically binding two antigens, wherein the first and second antigen are the same or different. As used herein, a "multispecific" antibody is capable of specifically binding more than one antigen, e.g., at least two (i.e., a "bispecific" antibody), at least three (i.e., a "trispecific" antibody), at least four, at least five, or at least six antigens. Various multispecific antibodies are known and can be used in the compositions and/or methods disclosed herein, including but not limited to bispecific antibodies that bind PD-1 and a second target and bispecific antibodies that bind PD-L1 and a second target. In some aspects, the multispecific antibody is a T-cell dependent bispecific antibody. In some aspects, the multispecific antibody is an anti-FcRH5/CD3 bispecific antibody that targets the B cell lineage marker, FcRH5, and CD3, e.g., for use in the treatment of multiple myeloma.

In some aspects, an "antibody" of the present disclosure is engineered to be activated at a target site, e.g., a "probody." In some aspects, the antibody, e.g., probody, is proteolytically cleaved at a target tissue (e.g., a tumor).

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 may, however, have cross-reactivity to other antigens, such as PD-1 molecules from different species. Moreover, an isolated antibody can be substantially free of other cellular material and/or chemicals.

The term "monoclonal antibody" (mAb) refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. Monoclonal antibodies can be produced by hybridoma, recombinant, transgenic or other techniques known to those skilled in the art.

A "human antibody" (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibody" and "fully human antibody" and are used synonymously.

A "humanized antibody" refers to an antibody in which some, most or all of the amino acids outside the CDRs of a non-human antibody are replaced with corresponding amino acids derived from human immunoglobulins. In one aspect of a humanized form of an antibody, some, most or all of the amino acids outside the CDRs have been replaced with amino acids from human immunoglobulins, whereas some, most or all amino acids within one or more CDRs are unchanged. Small additions, deletions, insertions, substitutions or modifications of amino acids are permissible as long as they do not abrogate the ability of the antibody to bind to a particular antigen. A "humanized antibody" retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen antibody" refers to an antibody that binds specifically to the antigen. For example, an anti-PD-1 antibody binds specifically to PD-1, and an anti-PD-L1 antibody binds specifically to PD-L1.

An "antigen-binding portion" of an antibody (also called an "antigen-binding fragment") refers to one or more fragments of an antibody that retain the ability to bind specifically to the antigen bound by the whole antibody. It has been shown that the antigen-binding function of an antibody can be performed by fragments of a full-length antibody. Examples of binding fragments encompassed within the term "antigen-binding portion" of an antibody, e.g., an anti-PD-1 antibody or an anti-PD-L1 antibody described herein, include (i) a Fab fragment (fragment from papain cleavage) or a similar monovalent fragment consisting of the $V_L$, $V_H$, LC and CH1 domains; (ii) a F(ab')2 fragment (fragment from pepsin cleavage) or a similar bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR) and (vii) a combination of two or more isolated CDRs which can optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "cancer" refers a broad group of various diseases characterized by the uncontrolled growth of abnormal cells in the body. Unregulated cell division and growth divide and grow results in the formation of malignant tumors that invade neighboring tissues and can also metastasize to distant parts of the body through the lymphatic system or bloodstream.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, seventy or recurrence of a symptom, complication or condition, or biochemical indicia associated with a disease.

"Programmed Death-1" (PD-1) refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1" (PD-L1) is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7. The human PD-L1 protein is encoded by the human CD274 gene (NCBI Gene ID: 29126).

"Hyaluronidase," as used herein, refers to an enzyme capable of catalyzing the cleavage of hyaluronan. Hyaluronan is a repeating polymer of N-acetyl-glucosamine and glucuronic acid, which is present in the subcutaneous space and contributes to the soluble gel-like component of the extracellular matrix of the skin and is restored by rapid turnover (resynthesis). In some aspects, the hyaluronidase comprises rHuPH20, which is a glycosylated 447-amino acid single chain polypeptide that depolymerizes hyaluronan in the subcutaneous space locally at the site of injection in the skin. Depolymerization of hyaluronan by hyaluronidase is accomplished by hydrolysis of the polysaccharide polymer. Depolymerization of hyaluronan results in a transient reduction in the viscosity of the gel-like phase of the extracellular matrix and increased hydraulic conductance that facilitates the dispersion and absorption of the coadministered therapeutic agent. Thus, a hyaluronidase, e.g., rHuPH20, can improve the speed and ease of subcutaneous delivery of injectable biologics and drugs by acting as a permeation enhancer. In certain aspects, the hyaluronidase comprises ENHANZE™.

A "subject" includes any human or nonhuman animal. The term "nonhuman animal" includes, but is not limited to, vertebrates such as nonhuman primates, sheep, dogs, and rodents such as mice, rats and guinea pigs. In preferred aspects, the subject is a human. The terms, "subject" and "patient" are used interchangeably herein.

The use of the term "flat dose" with regard to the methods and dosages of the disclosure means a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of an antibody (e.g., 240 mg of an anti-PD-1 antibody).

The term "weight-based dose" as referred to herein means that a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

By way of example, an "anti-cancer agent" promotes cancer regression in a subject. In some aspects, a therapeutically effective amount of the drug promotes cancer regression to the point of eliminating the cancer. "Promoting cancer regression" means that administering a therapeutically effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent preferably inhibits cell growth or tumor growth by at least about 20%, more preferably by at least about 40%, even more preferably by at least about 60%, and still more preferably by at least about 80% relative to untreated subjects. In other preferred aspects of the disclosure, tumor regression can be observed and continue for a period of at least about 20 days, more preferably at least about 40 days, or even more preferably at least about 60 days. Notwithstanding these ultimate measurements of therapeutic effectiveness, evaluation of immunotherapeutic drugs must also make allowance for immune-related response patterns.

An "immune response" is as understood in the art, and generally refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4$^+$ cell, a CD8$^+$ T cell, or a Treg cell, or activation or inhibition of any other cell of the immune system, e.g., NK cell.

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

As used herein, the term "stable," in reference to a formulation or drug product, is one in which an antibody, antibodies, or molecules therein essentially retain their physical and chemical stability and integrity upon storage. Stability of a formulation herein can be measured at selected temperatures after selected time periods. For example, an increase in aggregate formation or low molecular weight species are indicators of instability. Retention of original clarity and/or color throughout shelf-life are also indicators utilized to monitor stability. In some aspects, a "stable" drug product is one wherein an increase in aggregation, as measured by an increase in the percentage of high molecular weight species (% HMW), is less than about 5%, and preferably less than about 3%, when the formulation is stored at 2-8° C. for at least about one year.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease or enhancing overall survival. Treatment can be of a subject having a disease or a subject who does not have a disease (e.g., for prophylaxis).

The terms "about every week," "about every two weeks," or any other similar dosing interval terms as used herein mean approximate numbers. "About every week" can include every seven days±one day, i.e., every six days to every eight days. "About every two weeks" can include every fourteen days±three days, i.e., every eleven days to every seventeen days. Similar approximations apply, for example, to about every three weeks, about every four weeks, about every five weeks, about every six weeks, and about every twelve weeks. In some aspects, a dosing interval of about every six weeks or about every twelve weeks means that the first dose can be administered any day in the first week, and then the next dose can be administered any day in the sixth or twelfth week, respectively. In other aspects, a dosing interval of about every six weeks or about every twelve weeks means that the first dose is administered on a particular day of the first week (e.g., Monday) and then the next dose is administered on the same day of the sixth or twelfth weeks (i.e., Monday), respectively. When multiple subcutaneous unit doses are administered to reach a dose, the dosing interval refers to the period of time between administration of the first subcutaneous unit dose of the first effective dose and the first subcutaneous unit dose of the second effective dose. For example, where the method comprises administering a dose of about 600 mg administered about every two weeks, wherein the dose of the antibody comprises two subcutaneous unit doses, wherein each of the two subcutaneous unit doses comprises about 300 mg of the antibody, a first subcutaneous unit dose of about 300 mg of the first effective dose of the antibody is administered on day 1 and a first subcutaneous unit dose of about 300 mg of the second effective dose of the antibody is administered on about day 14. In this example, the second unit dose of about 300 mg of the first effective dose of the antibody can be administered on day 1 or at any other time before the administration of the first subcutaneous unit dose of about 300 mg of the second effective dose of the antibody.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. Methods of the Disclosure

Some aspects of the present disclosure are directed to methods of treating a subject in need thereof, comprising subcutaneously administering to the subject a dose of a pharmaceutical composition comprising (i) an antibody that specifically binds PD-1 or PD-L1 and inhibits the interaction of PD-1 and PD-L1 ("an anti-PD-1 antibody" or "an anti-PD-L1 antibody", respectively). In some aspects, the pharmaceutical composition comprises (ii) an endoglycosidase hydrolase enzyme. In some aspects, the dose can be a therapeutically effective dose. In some aspects, the dose comprises one or more subcutaneous unit doses. In some aspects, the dose comprises at least about 300 mg to at least about 2400 mg of the anti-PD-1 antibody or the anti-PD-L1 antibody.

In some aspects, the pharmaceutical composition does not comprise an endoglycosidase hydrolase enzyme. In some aspects, at least one of the subcutaneous unit doses has a total volume of less than about 5 mL (e.g., less than about 4.5 mL, less than about 4.0 mL, less than about 3.5 mL, less than about 3.0 mL, less than about 3 mL, or less than about 2.5 mL. In certain aspects, the therapeutically effective dose comprises at least about 250 mg to at least about 2400 mg of the antibody. In some aspects, the pharmaceutical composition does not comprise an enzyme that facilitates subcutaneous delivery. In certain aspects, the pharmaceutical composition does not comprise a hyaluronidase.

II.A. Dosing

In some aspects, a therapeutically effective dose of the antibody comprises a single subcutaneous unit dose, e.g., the entire dose is administered as a single unit dose. In some aspects, a therapeutically effective dose of the antibody comprises two or more subcutaneous unit doses, e.g., the effective unit dose is divided into two or more subcutaneous unit doses. In some aspects, the therapeutically effective dose of the antibody comprises at least two subcutaneous unit doses. In some aspects, the therapeutically effective dose of the antibody comprises at least three subcutaneous unit doses. In some aspects, the therapeutically effective dose of the antibody comprises at least four subcutaneous unit doses. In some aspects, the therapeutically effective dose of the antibody comprises at least five subcutaneous unit doses. In some aspects, the therapeutically effective dose of the antibody comprises at least six subcutaneous unit doses. In some aspects, the therapeutically effective dose of the antibody comprises at least seven subcutaneous unit doses. In some aspects, the therapeutically effective dose of the antibody comprises at least eight subcutaneous unit doses. In some aspects, the therapeutically effective dose of the antibody comprises at least nine subcutaneous unit doses. In some aspects, the therapeutically effective dose of the antibody comprises ten or more subcutaneous unit doses.

In some aspects, each subcutaneous unit dose is administered on the same day. In some aspects, one or more subcutaneous unit doses are administered on a first day, and one or more subcutaneous unit doses of the same therapeutically effective dose are administered on a second day. In some aspects, a first subcutaneous unit dose and a second subcutaneous unit dose are administered sequentially. In some aspects, a first subcutaneous unit dose and a second subcutaneous unit dose of the same effective dose are administered sequentially, wherein the second subcutaneous unit dose is administered less than about 5 minutes, less than about 10 minutes, less than about 15 minutes, less than about 20 minutes, less than about 25 minutes, less than about 30 minutes, less than about 45 minutes, less than about 60 minutes, less than about 75 minutes, less than about 90 minutes, less than about 2 hours, less than about 2.5 hours, less than about 3 hours, less than about 3.5 hours, less than about 4 hours, less than about 4.5 hours, less than about 5 hours, less than about 5.5 hours, less than about 6 hours, less than about 7 hours, less than about 8 hours, less than about 9 hours, less than about 12 hours, less than about 18 hours, or less than about 24 hours after the first subcutaneous unit dose. In some aspects, the two or more subcutaneous unit doses are administered subsequently, wherein each of the two or more subcutaneous unit doses is administered within an interval of less than about 10 minutes, less than about 15 minutes, less than about 20 minutes, less than about 25 minutes, less than about 30 minutes, less than about 45 minutes, less than about 1 hour, less than about 2 hours, less than about 3 hours, less than about 4 hours, less than about 5 hours, less than about 6 hours, less than about 7 hours, less than about 8 hours, less than about 9 hours, less than about 10 hours, less than about 11 hours, less than about 12 hours, less than about 15 hours, less than about 18 hours, less than about 21 hours, or less than about 24 hours between the subcutaneous unit doses.

In some aspects, the one or more subcutaneous unit doses are administered at one or more bodily location. In some aspects, a first subcutaneous unit dose and a second subcutaneous unit dose are administered at the same bodily location. In some aspects, a first subcutaneous unit dose and a second subcutaneous unit dose are administered at a first bodily location and a second bodily location, wherein the first bodily location is not the same as the second bodily location. In some aspects, a first subcutaneous unit dose and a second subcutaneous unit dose are administered at a first bodily location, and a third subcutaneous unit dose is administered at a second bodily location, wherein the first bodily location is not the same as the second bodily location. In some aspects, a first subcutaneous unit dose and a second subcutaneous unit dose are administered at a first bodily location, and a third subcutaneous unit dose and a fourth subcutaneous dose is administered at a second bodily location, wherein the first bodily location is not the same as the second bodily location. In some aspects, a first subcutaneous unit dose is administered at a first bodily location, a second subcutaneous unit dose is administered at a second bodily location, and a third subcutaneous unit dose is administered at a third bodily location, wherein the first bodily location, the second bodily location, and the third bodily location are different. In some aspects, a first subcutaneous unit dose is administered at a first bodily location, a second subcutaneous unit dose is administered at a second bodily location, a third subcutaneous unit dose is administered at a third bodily location, and a fourth subcutaneous unit dose is administered at a fourth bodily location, wherein the first bodily location, the second bodily location, the third bodily location, and the fourth bodily location are different.

As used herein, where at least two subcutaneous unit doses are administered at the same bodily location, the two subcutaneous doses can be administered at the exact same injection site or at a nearby injection site within the same bodily location. For example, two subcutaneous doses administered to a singly bodily location can both be administered to the subject's right arm. In this example, so long as both subcutaneous doses are administered to, e.g., the right arm, then both subcutaneous unit doses are administered to the same "bodily location," as used herein.

The therapeutically effective dose and/or the subcutaneous dose can be administered subcutaneously as disclosed herein using any methods or devices. In some aspects, the therapeutically effective dose and/or the subcutaneous dose is administered using a syringe. In some aspects, the therapeutically effective dose and/or the subcutaneous dose is administered using an autoinjector. In some aspects, the therapeutically effective dose and/or the subcutaneous dose is administered using an injector pen. In some aspects, the therapeutically effective dose and/or the subcutaneous dose is administered using a wearable pump.

In some aspects, the therapeutically effective dose and/or the subcutaneous unit dose are administered by subcutaneous infusion for less than about 30 minutes, less than about 25 minutes, less than about 20 minutes, less than about 15 minutes, less than about 14 minutes, less than about 13 minutes, less than about 12 minutes, less than about 11 minutes, less than about 10 minutes, less than about 9 minutes, less than about 8 minutes, less than about 7 minutes, less than about 6 minutes, less than about 5 minutes, less than about 4 minutes, less than about 3 minutes, or less than about 2 minutes. In some aspects, the therapeutically effective dose and/or the subcutaneous unit dose are administered by subcutaneous infusion for less than about 90 seconds, less than about 75 seconds, less than about 60 seconds, less than about 45 seconds, less than about 30 seconds, less than about 15 seconds, or less than about 10 seconds. In some aspects, the therapeutically effective dose and/or the subcutaneous unit dose are administered by subcutaneous infusion for less than about 15 minutes. In some aspects, the therapeutically effective dose and/or the subcutaneous unit dose are administered by subcutaneous infusion for less than about 10 minutes. In some aspects, the therapeutically effective dose and/or the subcutaneous unit dose are administered by subcutaneous infusion for less than about 5 minutes. In some aspects, the therapeutically dose and/or the subcutaneous dose are administered by subcutaneous infusion for less than about 4 minutes. In some aspects, the therapeutically effective dose and/or the subcutaneous dose are administered by subcutaneous infusion for less than about 3 minutes. In some aspects, the therapeutically effective dose and/or the subcutaneous unit dose are administered by subcutaneous infusion for less than about 2 minutes.

II.A.1. Anti-PD-1 Antibody Dosing

In certain aspects of the present disclosure, the antibody comprises an anti-PD-1 antibody. Any anti-PD-1 antibody can be used in the methods disclosed herein. In some aspects, the anti-PD-1 antibody comprises nivolumab. In some aspects, the anti-PD-1 antibody comprises pembrolizumab.

In some aspects, the dose of the antibody, e.g., the anti-PD-1 antibody (e.g., nivolumab), is about 250 mg to about 600 mg of the antibody administered about every week. In some aspects, the dose of the antibody, e.g., the anti-PD-1 antibody (e.g., nivolumab), is about 250 mg to about 550 mg, about 250 mg to about 500 mg, about 250 mg to about 450 mg, about 250 mg to about 400 mg, about 250 mg to about 350 mg, about 250 mg to about 300 mg, about 275 mg to about 400 mg, about 275 mg to about 375 mg, about 275 mg to about 350 mg, about 275 mg to about 325 mg, about 275 mg to about 300 mg, about 300 mg to about 600 mg, about 300 mg to about 550 mg, about 300 mg to about 400 mg, about 300 mg to about 450 mg, about 300 mg to about 400 mg, about 300 mg to about 350 mg, or about 300 mg to about 325 mg of the antibody administered about every week. In some aspects, the dose of the antibody, e.g., the anti-PD-1 antibody (e.g., nivolumab), is about 250 mg to about 400 mg of the antibody administered about every week. In some aspects, the dose of the antibody, e.g., the anti-PD-1 antibody (e.g., nivolumab), is about 250 mg to about 350 mg of the antibody administered about every week. In some aspects, the dose of the antibody, e.g., the anti-PD-1 antibody (e.g., nivolumab), is about 275 mg to about 325 mg of the antibody administered about every week.

In some aspects, the dose of the antibody is about 250 mg, about 260 mg, about 270 mg, about 275 mg, about 280 mg, about 290 mg, about 300 mg, about 310 mg, about 320 mg, about 325 mg, about 330 mg, about 340 mg, about 350 mg, about 360 mg, about 370 mg, about 375 mg, about 380 mg, about 390 mg, about 400 mg, about 410 mg, about 420 mg, about 425 mg, about 430 mg, about 440 mg, about 450 mg, about 460 mg, about 470 mg, about 475 mg, about 480 mg, about 490 mg, about 500 mg, about 510 mg, about 520 mg, about 525 mg, about 530 mg, about 540 mg, about 550 mg, about 560 mg, about 570 mg, about 575 mg, about 580 mg, about 590 mg, or about 600 mg administered about every week. In certain aspects, the dose of the antibody is about 250 mg administered about every week. In certain aspects, the dose of the antibody is about 275 mg administered about every week. In certain aspects, the dose of the antibody is about 300 mg administered about every week. In certain aspects, the dose of the antibody is about 325 mg administered about every week. In certain aspects, the dose of the antibody is about 350 mg administered about every week.

In some aspects, the dose of the antibody comprises a single subcutaneous unit dose of about 300 mg. In some aspects, the dose of the antibody comprises a single subcutaneous unit dose of about 300 mg in a total administered volume of about 2 mL. In some aspects, the dose of the antibody comprises a single subcutaneous unit dose of about 300 mg in a total administered volume of greater than about 2 mL. In some aspects, the dose of the antibody comprises two subcutaneous unit doses, wherein each of the two subcutaneous unit doses comprises about 150 mg of the antibody. In some aspects, at least one of the two subcutaneous unit doses comprises about 150 mg of the antibody in a total volume of less than about 5 mL (e.g., less than about 4.5 mL, less than about 4.0 mL, less than about 3.5 mL, less than about 3.0 mL, less than about 2.5 mL, or less than about 2.0 mL). In some aspects, the two subcutaneous unit doses are administered to the subject at two different bodily locations.

In some aspects, the dose comprises three subcutaneous unit doses, wherein each of the three subcutaneous unit doses comprises about 100 mg of the antibody. In some aspects, at least one of the three subcutaneous unit doses comprises about 100 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the three subcutaneous unit doses are administered to the subject at least two different bodily locations. In some aspects, the first subcutaneous unit dose and the second subcutaneous unit dose are administered at a first bodily location, and the third subcutaneous unit dose is administered at a second bodily location. In some aspects, the first subcutaneous unit dose is administered at a first bodily location, the second subcutaneous unit dose is administered at a second bodily location, and the third subcutaneous unit dose is administered at a third bodily location.

In some aspects, the dose of the antibody, e.g., the anti-PD-1 antibody (e.g., nivolumab), is about 300 mg to about 900 mg of the antibody administered about every two weeks. In some aspects, the dose of the antibody, e.g., the anti-PD-1 antibody (e.g., nivolumab), is about 300 mg to about 850 mg, about 300 mg to about 800 mg, about 300 mg to about 750 mg, about 300 mg to about 700 mg, about 300 mg to about 650 mg, about 300 mg to about 600 mg, about 350 mg to about 900 mg, about 350 mg to about 850 mg, about 350 mg to about 800 mg, about 350 mg to about 750 mg, about 350 mg to about 700 mg, about 350 mg to about 650 mg, about 350 mg to about 600 mg, about 400 mg to about 900 mg, about 400 mg to about 850 mg, about 400 mg to about 800 mg, about 400 mg to about 750 mg, about 400 mg to about 700 mg, about 400 mg to about 650 mg, about 400 mg to about 600 mg, about 450 to about 900 mg, about 450 to about 850 mg, about 450 to about 800 mg, about 450 mg to about 750 mg, about 450 mg to about 700 mg, about 450 mg to about 650 mg, about 450 mg to about 600 mg, about 500 mg to about 900 mg, about 500 mg to about 850 mg, about 500 mg to about 800 mg, about 500 mg to about 700 mg, about 500 mg to about 650 mg, about 500 mg to about 600 mg, about 550 mg to about 900 mg, about 550 mg to about 850 mg, about 550 mg to about 800 mg, about 550 mg to about 750 mg, about 550 mg to about 700 mg, about 550 mg to about 650 mg, about 550 mg to about 600 mg, about 600 mg to about 900 mg, about 600 mg to about 850 mg, about 600 mg to about 800 mg, about 600 mg to about 750 mg, about 600 mg to about 700 mg, about 600 mg to about 650 mg, about 575 mg to about 625 mg, about 575 mg to about 600 mg, or about 600 mg to about 625 mg of the antibody administered about every two weeks. In some aspects, the dose of the antibody, e.g., the anti-PD-1 antibody (e.g., nivolumab), is about 400 mg to about 800 mg of the antibody administered about every two weeks. In some aspects, the dose of the antibody, e.g., the anti-PD-1 antibody (e.g., nivolumab), is about 500 mg to about 700 mg of the antibody administered about every two weeks. In some aspects, the dose of the antibody, e.g., the anti-PD-1 antibody (e.g., nivolumab), is about 550 mg to about 650 mg of the antibody administered about every two weeks. In some aspects, the dose of the antibody, e.g., the anti-PD-1 antibody (e.g., nivolumab), is about 575 mg to about 625 mg of the antibody administered about every two weeks.

In some aspects, the dose of the antibody is about 300 mg, about 350 mg, about 400 mg, about 450 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, or about 900 mg administered about every two weeks. In some aspects, the dose of the antibody is about 500 mg administered about every two weeks. In some aspects, the dose of the antibody is about 550 mg administered about every two weeks. In some aspects, the dose of the antibody is about 575 mg administered about every two weeks. In some aspects, the dose of the antibody is about 600 mg administered about every two weeks. In some aspects, the dose of the antibody is about 625 mg administered about every two weeks. In some aspects, the dose of the antibody is about 650 mg administered about every two weeks. In some aspects, the dose of the antibody is about 700 mg administered about every two weeks.

In some aspects, the dose of the antibody comprises a single subcutaneous unit dose of about 600 mg. In some aspects, the dose of the antibody comprises a single subcutaneous unit dose of about 600 mg in a total administered volume of about 2 mL. In some aspects, the dose of the antibody comprises a single subcutaneous unit dose of about 600 mg in a total administered volume of greater than about 2 mL. In some aspects, the dose of the antibody comprises a single subcutaneous unit dose of about 600 mg in a total administered volume of greater than about 5 mL.

In some aspects, the dose of the antibody comprises a single subcutaneous unit dose of about 600 mg in a total administered volume of less than about 5 mL (e.g., less than about 4.5 mL, less than about 4.0 mL, less than about 3.5 mL, less than about 3.0 mL, less than about 2.5 mL, or less than about 2.0 mL).

In some aspects, the dose of the antibody comprises two subcutaneous unit doses, wherein each of the two subcutaneous unit doses comprises about 300 mg of the antibody. In some aspects, at least one of the two subcutaneous unit doses comprises about 300 mg of the antibody in a total volume of about 2 mL. In some aspects, at least one of the two subcutaneous unit doses comprises about 300 mg of the antibody in a total volume of greater than about 2 mL. In some aspects, at least one of the two subcutaneous unit doses comprises about 300 mg of the antibody in a total volume of greater than about 5 mL. In some aspects, at least one of the two subcutaneous unit doses comprises about 300 mg of the antibody in a total volume of less than about 5 mL (e.g., less than about 4.5 mL, less than about 4.0 mL, less than about 3.5 mL, less than about 3.0 mL, less than about 2.5 mL, or less than about 2.0 mL). In certain aspects, at least one of the two subcutaneous unit doses comprises about 300 mg of the antibody in a total volume of less than about 2 mL. In some aspects, the two subcutaneous unit doses are administered to the subject at a single bodily location. In some aspects, the two subcutaneous unit doses are administered to the subject at two different bodily locations.

In some aspects, the dose of about 600 mg of the antibody comprises three subcutaneous unit doses. In some aspects, at least one of the three subcutaneous unit doses comprises about 200 mg of the antibody. In some aspects, each of the three subcutaneous unit doses comprises about 200 mg of the antibody. In some aspects, at least one of the three subcutaneous unit doses comprises about 200 mg of the antibody in a total volume of about 2 mL. In some aspects, at least one of the three subcutaneous unit doses comprises about 200 mg of the antibody in a total volume of greater than about 2 mL. In some aspects, at least one of the three subcutaneous unit doses comprises about 200 mg of the antibody in a total volume of greater than about 5 mL. In some aspects, at least one of the three subcutaneous unit doses comprises about 200 mg of the antibody in a total volume of less than about 5 mL (e.g., less than about 4.5 mL, less than about 4.0 mL, less than about 3.5 mL, less than about 3.0 mL, less than about 2.5 mL, or less than about 2.0 mL). In some aspects, at least two of the three subcutaneous unit doses are administered to the subject at least two different bodily locations. In some aspects, the first subcutaneous unit dose and the second subcutaneous unit dose are administered at a first bodily location, and the third subcutaneous unit dose is administered at a second bodily location. In some aspects, the first subcutaneous unit dose is administered at a first bodily location, the second subcutaneous unit dose is administered at a second bodily location, and the third subcutaneous unit dose is administered at a third bodily location.

In some aspects, the dose of about 600 mg of the antibody comprises at least four subcutaneous unit doses. In some aspects, at least one of the four subcutaneous unit doses comprises about 150 mg of the antibody. In some aspects, at least one of the four subcutaneous unit doses comprises about 150 mg of the antibody in a total volume of about 2 mL. In some aspects, at least one of the four subcutaneous unit doses comprises about 150 mg of the antibody in a total volume of greater than about 2 mL. In some aspects, at least one of the four subcutaneous unit doses comprises about 150 mg of the antibody in a total volume of greater than about 5 mL. In some aspects, at least one of the four subcutaneous unit doses comprises about 150 mg of the antibody in a total volume of less than about 5 mL (e.g., less than about 4.5 mL, less than about 4.0 mL, less than about 3.5 mL, less than about 3.0 mL, less than about 2.5 mL, or less than about 2.0 mL). In some aspects, at least two of the four subcutaneous unit doses are administered to the subject at at least two different bodily locations. In some aspects, the first subcutaneous unit dose and the second subcutaneous unit dose are administered at a first bodily location, and the third subcutaneous unit dose and the fourth subcutaneous unit dose are administered at a second bodily location. In some aspects, the first subcutaneous unit dose is administered at a first bodily location, the second subcutaneous unit dose is administered at a second bodily location, the third subcutaneous unit dose is administered at a third bodily location, and the fourth subcutaneous unit dose is administered at a fourth bodily location.

In some aspects, the dose of the antibody, e.g., the anti-PD-1 antibody (e.g., nivolumab), is about 900 mg to about 1500 mg of the antibody administered about every four weeks. In some aspects, the dose of the antibody, e.g., the anti-PD-1 antibody (e.g., nivolumab), is about 900 mg to about 1450 mg, about 900 mg to about 1400 mg, about 900 mg to about 1350 mg, about 900 mg to about 1300 mg, about 900 mg to about 1250 mg, about 900 mg to about 1200 mg, about 950 mg to about 1500 mg, about 950 mg to about 1450 mg, about 950 mg to about 1400 mg, about 950 mg to about 1350 mg, about 950 mg to about 1300 mg, about 950 mg to about 1250 mg, about 950 mg to about 1200 mg, about 1000 mg to about 1500 mg, about 1000 mg to about 1450 mg, about 1000 mg to about 1400 mg, about 1000 mg to about 1350 mg, about 1000 mg to about 1300 mg, about 1000 mg to about 1250 mg, about 1000 mg to about 1200 mg, about 1050 to about 1500 mg, about 1050 to about 1450 mg, about 1050 to about 1400 mg, about 1050 mg to about 1350 mg, about 1050 mg to about 1300 mg, about 1050 mg to about 1250 mg, about 1050 mg to about 1200 mg, about 1100 mg to about 1500 mg, about 1100 mg to about 1450 mg, about 1100 mg to about 1400 mg, about 1100 mg to about 1350 mg, about 1100 mg to about 1300 mg, about 1100 mg to about 1250 mg, about 1100 mg to about 1200 mg, about 1150 mg to about 1500 mg, about 1150 mg to about 1450 mg, about 1150 mg to about 1400 mg, about 1150 mg to about 1350 mg, about 1150 mg to about 1300 mg, about 1150 mg to about 1250 mg, about 1150 mg to about 1200 mg, about 1200 mg to about 1500 mg, about 1200 mg to about 1450 mg, about 1200 mg to about 1400 mg, about 1200 mg to about 1350 mg, about 1200 mg to about 1300 mg, about 1200 mg to about 1250 mg, about 1175 mg to about 1225 mg, about 1175 mg to about 1200 mg, or about 1200 mg to about 1225 mg of the antibody administered about every four weeks. In some aspects, the dose of the antibody, e.g., the anti-PD-1 antibody (e.g., nivolumab), is about 1000 mg to about 1400 mg of the antibody administered about every four weeks. In some aspects, the dose of the antibody, e.g., the anti-PD-1 antibody (e.g., nivolumab), is about 1100 mg to about 1300 mg of the antibody administered about every four weeks. In some aspects, the dose of the antibody, e.g., the anti-PD-1 antibody, is about 1150 mg to about 1250 mg of the antibody administered about every four weeks. In some aspects, the dose of the antibody, e.g., the anti-PD-1 antibody (e.g., nivolumab), is about 1175 mg to about 1225 mg of the antibody administered about every four weeks.

In some aspects, the dose of the antibody is about 900 mg, about 950 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, or about 1500 mg administered about every four weeks. In some aspects, the dose of the antibody is about 1100 mg administered about every four weeks. In some aspects, the dose of the antibody is about 1150 mg administered about every four weeks. In some aspects, the dose of the antibody is about 1175 mg administered about every four weeks. In some aspects, the dose of the antibody is about 1200 mg administered about every four weeks. In some aspects, the dose of the antibody is about 1225 mg administered about every four weeks. In some aspects, the dose of the antibody is about 1250 mg administered about every four weeks. In some aspects, the dose of the antibody is about 1300 mg administered about every four weeks.

In some aspects, the dose of the antibody comprises a single subcutaneous unit dose of about 1200 mg. In some aspects, the dose of the antibody comprises a single subcutaneous unit dose of about 1200 mg in a total administered volume of about 2 mL. In some aspects, the dose of the antibody comprises a single subcutaneous unit dose of about 1200 mg in a total administered volume of greater than about 2 mL. In some aspects, the dose of the antibody comprises a single subcutaneous unit dose of about 1200 mg in a total administered volume of greater than about 5 mL.

In some aspects, the dose of the antibody comprises a single subcutaneous unit dose of about 1200 mg in a total administered volume of less than about 5 mL (e.g., less than about 4.5 mL, less than about 4.0 mL, less than about 3.5 mL, less than about 3.0 mL, less than about 2.5 mL, or less than about 2.0 mL).

In some aspects, the dose of the antibody comprises two, three, four, six, or at least eight subcutaneous unit doses. In some aspects, the dose of the antibody comprises two subcutaneous unit doses, wherein each of the two subcutaneous unit doses comprises about 600 mg of the antibody. In some aspects, at least one of the two subcutaneous unit doses comprises about 600 mg of the antibody in a total volume of about 2 mL. In some aspects, at least one of the two subcutaneous unit doses comprises about 600 mg of the antibody in a total volume of greater than about 2 mL. In some aspects, at least one of the two subcutaneous unit doses comprises about 600 mg of the antibody in a total volume of greater than about 5 mL. In some aspects, at least one of the two subcutaneous unit doses comprises about 600 mg of the antibody in a total volume of less than about 5 mL (e.g., less than about 4.5 mL, less than about 4.0 mL, less than about 3.5 mL, less than about 3.0 mL, less than about 2.5 mL, or less than about 2.0 mL). In certain aspects, at least one of the two subcutaneous unit doses comprises about 600 mg of the antibody in a total volume of less than about 2 mL. In some aspects, the two subcutaneous unit doses are administered to the subject at a single bodily location. In some aspects, the two subcutaneous unit doses are administered to the subject at two different bodily locations.

In some aspects, the dose of about 1200 mg of the antibody comprises three subcutaneous unit doses. In some aspects, at least one of the three subcutaneous unit doses comprises about 400 mg of the antibody. In some aspects, each of the three subcutaneous unit doses comprises about 400 mg of the antibody. In some aspects, at least one of the three subcutaneous unit doses comprises about 400 mg of the antibody in a total volume of about 2 mL. In some aspects, at least one of the three subcutaneous unit doses comprises about 400 mg of the antibody in a total volume of greater than about 2 mL. In some aspects, at least one of the three subcutaneous unit doses comprises about 400 mg of the antibody in a total volume of greater than about 5 mL. In some aspects, at least one of the three subcutaneous unit doses comprises about 400 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the three subcutaneous unit doses are administered to the subject at at least two different bodily locations. In some aspects, the first subcutaneous unit dose and the second subcutaneous unit dose are administered at a first bodily location, and the third subcutaneous unit dose is administered at a second bodily location. In some aspects, the first subcutaneous unit dose is administered at a first bodily location, the second subcutaneous unit dose is administered at a second bodily location, and the third subcutaneous unit dose is administered at a third bodily location.

In some aspects, the dose of about 1200 mg of the antibody comprises four subcutaneous unit doses. In some aspects, at least one of the four subcutaneous unit doses comprises about 300 mg of the antibody. In some aspects, at least one of the four subcutaneous unit doses comprises about 300 mg of the antibody in a total volume of about 2 mL. In some aspects, at least one of the four subcutaneous unit doses comprises about 300 mg of the antibody in a total volume of greater than about 2 mL. In some aspects, at least one of the four subcutaneous unit doses comprises about 300 mg of the antibody in a total volume of greater than about 5 mL. In some aspects, at least one of the four subcutaneous unit doses comprises about 300 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the four subcutaneous unit doses are administered to the subject at at least two different bodily locations. In some aspects, the first subcutaneous unit dose and the second subcutaneous unit dose are administered at a first bodily location, and the third subcutaneous unit dose and the fourth subcutaneous unit dose are administered at a second bodily location. In some aspects, the first subcutaneous unit dose is administered at a first bodily location, the second subcutaneous unit dose is administered at a second bodily location, the third subcutaneous unit dose is administered at a third bodily location, and the fourth subcutaneous unit dose is administered at a fourth bodily location.

In some aspects, the dose of about 1200 mg of the antibody comprises six subcutaneous unit doses. In some aspects, at least one of the six subcutaneous unit doses comprises about 200 mg of the antibody. In some aspects, at least one of the six subcutaneous unit doses comprises about 200 mg of the antibody in a total volume of about 2 mL. In some aspects, at least one of the six subcutaneous unit doses comprises about 200 mg of the antibody in a total volume of greater than about 2 mL. In some aspects, at least one of the six subcutaneous unit doses comprises about 200 mg of the antibody in a total volume of greater than about 5 mL. In some aspects, at least one of the six subcutaneous unit doses comprises about 200 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the six subcutaneous unit doses are administered to the subject at at least two different bodily locations. In some aspects, the first subcutaneous unit dose and the second subcutaneous unit dose are administered at a first bodily location, the third subcutaneous unit dose and the fourth subcutaneous unit dose are administered at a second bodily location, and the fifth subcutaneous unit dose and the sixth subcutaneous unit dose are administered at a third bodily location. In some aspects, the first subcutaneous unit dose is administered at a first bodily location, the second subcutaneous unit dose is administered at a second bodily location, the third subcutaneous unit dose is administered at a third bodily location, the fourth subcutaneous unit dose is administered at a fourth bodily location, the fifth subcutaneous unit dose is administered at a fifth bodily location, and the sixth subcutaneous unit dose is administered at a sixth bodily location.

In some aspects, the dose of about 1200 mg of the antibody comprises at least eight subcutaneous unit doses. In some aspects, at least one of the eight subcutaneous unit doses comprises about 150 mg of the antibody. In some aspects, at least one of the eight subcutaneous unit doses comprises about 150 mg of the antibody in a total volume of about 2 mL. In some aspects, at least one of the eight subcutaneous unit doses comprises about 150 mg of the antibody in a total volume of greater than about 2 mL. In some aspects, at least one of the eight subcutaneous unit doses comprises about 150 mg of the antibody in a total volume of greater than about 5 mL. In some aspects, at least one of the eight subcutaneous unit doses comprises about 150 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the eight subcutaneous unit doses are administered to the subject at at least two different bodily locations. In some aspects, the first subcutaneous unit dose and the second subcutaneous unit dose are administered at a first bodily location, the third subcutaneous unit dose and the fourth subcutaneous unit dose are administered at a second bodily location, the fifth subcutaneous unit dose and the sixth subcutaneous unit dose are administered at a third bodily location, and the seventh subcutaneous unit dose and the eighth subcutaneous unit dose are administered at a fourth bodily location.

In some aspects, the dose of the antibody, e.g., the anti-PD-1 antibody (e.g., nivolumab), is about 1800 mg to about 3000 mg of the antibody administered about every eight weeks. In some aspects, the dose of the antibody, e.g., the anti-PD-1 antibody (e.g., nivolumab), is about 1800 mg to about 3000 mg of the antibody administered about every eight weeks. In some aspects, the dose of the antibody is about 1900 mg, about 1950 mg, about 2000 mg, about 2010 mg, about 2020 mg, about 2030 mg, about 2040 mg, about 2050 mg, about 2060 mg, about 2070 mg, about 2080 mg, about 2090 mg, about 2100 mg, about 2110 mg, about 2120 mg, about 2130 mg, about 2140 mg, about 2150 mg, about 2160 mg, about 2170 mg, about 2180 mg, about 2190 mg, about 2200 mg, about 2210 mg, about 2220 mg, about 2230 mg, about 2240 mg, about 2250 mg, about 2260 mg, about 2270 mg, about 2280 mg, about 2290 mg, about 2300 mg, about 2310 mg, about 2320 mg, about 2330 mg, about 2340 mg, about 2350 mg, about 2360 mg, about 2370 mg, about 2380 mg, about 2390 mg, about 2400 mg, about 2410 mg, about 2420 mg, about 2430 mg, about 2440 mg, about 2450 mg, about 2460 mg, about 2470 mg, about 2480 mg, about 2490 mg, about 2500 mg, about 2510 mg, about 2520 mg, about 2530 mg, about 2540 mg, about 2550 mg, about 2560 mg, about 2570 mg, about 2580 mg, about 2590 mg, or about 2600 mg administered about every four weeks. In some aspects, the dose of the antibody is about 2300 mg administered about every four weeks. In some aspects, the dose of the antibody is about 2350 mg administered about every four weeks. In some aspects, the dose of the antibody is about 2375 mg administered about every four weeks. In some aspects, the dose of the antibody is about 2400 mg administered about every four weeks. In some aspects, the dose of the antibody is about 2425 mg administered about every four weeks. In some aspects, the dose of the antibody is about 2450 mg administered about every four weeks. In some aspects, the dose of the antibody is about 2475 mg administered about every four weeks. In some aspects, the dose of the antibody is about 2500 mg administered about every four weeks.

In some aspects, the dose of the antibody comprises a single subcutaneous unit dose of about 2400 mg. In some aspects, the dose of the antibody comprises a single subcutaneous unit dose of about 2400 mg in a total administered volume of greater than about 5 mL. In some aspects, the dose of the antibody comprises a single subcutaneous unit dose of about 2400 mg in a total administered volume of about 5 mL. In some aspects, the dose of the antibody comprises a single subcutaneous unit dose of about 2400 mg in a total administered volume of less than about 5 mL (e.g., less than about 4.5 mL, less than about 4.0 mL, less than about 3.5 mL, less than about 3.0 mL, less than about 2.5 mL, or less than about 2.0 mL).

In some aspects, the dose of about 2400 mg of the antibody comprises four subcutaneous unit doses. In some aspects, at least one of the four subcutaneous unit doses comprises about 600 mg of the antibody. In some aspects, at least one of the four subcutaneous unit doses comprises about 600 mg of the antibody in a total volume of about 2 mL. In some aspects, at least one of the four subcutaneous unit doses comprises about 600 mg of the antibody in a total volume of greater than about 2 mL. In some aspects, at least one of the four subcutaneous unit doses comprises about 600 mg of the antibody in a total volume of greater than about 5 mL. In some aspects, at least one of the four subcutaneous unit doses comprises about 600 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the four subcutaneous unit doses are administered to the subject at at least two different bodily locations. In some aspects, the first subcutaneous unit dose and the second subcutaneous unit dose are administered at a first bodily location, and the third subcutaneous unit dose and the fourth subcutaneous unit dose are administered at a second bodily location. In some aspects, the first subcutaneous unit dose is administered at a first bodily location, the second subcutaneous unit dose is administered at a second bodily location, the third subcutaneous unit dose is administered at a third bodily location, and the fourth subcutaneous unit dose is administered at a fourth bodily location.

In some aspects, the dose of about 2400 mg of the antibody comprises six subcutaneous unit doses. In some aspects, at least one of the six subcutaneous unit doses comprises about 400 mg of the antibody. In some aspects, at least one of the six subcutaneous unit doses comprises about 400 mg of the antibody in a total volume of about 2 mL. In some aspects, at least one of the six subcutaneous unit doses comprises about 400 mg of the antibody in a total volume of greater than about 2 mL. In some aspects, at least one of the six subcutaneous unit doses comprises about 400 mg of the antibody in a total volume of greater than about 5 mL. In some aspects, at least one of the six subcutaneous unit doses comprises about 400 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the six subcutaneous unit doses are administered to the subject at at least two different bodily locations. In some aspects, the first subcutaneous unit dose and the second subcutaneous unit dose are administered at a first bodily location, the third subcutaneous unit dose and the fourth subcutaneous unit dose are administered at a second bodily location, and the fifth subcutaneous unit dose and the sixth subcutaneous unit dose are administered at a third bodily location. In some aspects, the first subcutaneous unit dose is administered at a first bodily location, the second subcutaneous unit dose is administered at a second bodily location, the third subcutaneous unit dose is administered at a third bodily location, the fourth subcutaneous unit dose is administered at a fourth bodily location, the fifth subcutaneous unit dose is administered at a fifth bodily location, and the sixth subcutaneous unit dose is administered at a sixth bodily location.

In some aspects, the dose of about 2400 mg of the antibody comprises at least eight subcutaneous unit doses. In some aspects, at least one of the eight subcutaneous unit doses comprises about 300 mg of the antibody. In some aspects, at least one of the eight subcutaneous unit doses comprises about 300 mg of the antibody in a total volume of about 2 mL. In some aspects, at least one of the eight subcutaneous unit doses comprises about 300 mg of the antibody in a total volume of greater than about 2 mL. In some aspects, at least one of the eight subcutaneous unit doses comprises about 300 mg of the antibody in a total volume of greater than about 5 mL. In some aspects, at least one of the eight subcutaneous unit doses comprises about 300 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the eight subcutaneous unit doses are administered to the subject at at least two different bodily locations. In some aspects, the first subcutaneous unit dose and the second subcutaneous unit dose are administered at a first bodily location, the third subcutaneous unit dose and the fourth subcutaneous unit dose are administered at a second bodily location, the fifth subcutaneous unit dose and the sixth subcutaneous unit dose are administered at a third bodily location, and the seventh subcutaneous unit dose and the eighth subcutaneous unit dose are administered at a fourth bodily location.

In some aspects, the anti-PD-1 antibody comprises pembrolizumab, which is administered subcutaneously once about every week, once about every two weeks, once about every three weeks, or once about every four weeks. In some aspects, about 100 mg to about 300 mg pembrolizumab is administered subcutaneously once about every two weeks. In some aspects, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg pembrolizumab is administered subcutaneously once about every two weeks. In some aspects, at least about 150 mg pembrolizumab is administered subcutaneously once about every two weeks. In some aspects, at least about 200 mg pembrolizumab is administered subcutaneously once about every two weeks. In some aspects, at least about 300 mg pembrolizumab is administered subcutaneously once about every four weeks. In some aspects, at least about 400 mg pembrolizumab is administered subcutaneously once about every four weeks. In some aspects, the dose of pembrolizumab is administered in a volume of at least about 2 mL to at least about 4 mL.

In some aspects, the anti-PD-1 antibody comprises sasanlimab, which is administered subcutaneously once about every week, once about every two weeks, once about every three weeks, or once about every four weeks. In some aspects, about 200 mg to about 400 mg sasanlimab is administered subcutaneously once about every four weeks. In some aspects, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg sasanlimab is administered subcutaneously once about every four weeks. In some aspects, at least about 250 mg sasanlimab is administered subcutaneously once about every four weeks. In some aspects, at least about 200 mg sasanlimab is administered subcutaneously once about every four weeks. In some aspects, at least about 250 mg sasanlimab is administered subcutaneously once about every four weeks. In some aspects, at least about 300 mg sasanlimab is administered subcutaneously once about every four weeks. In some aspects, the dose of sasanlimab is administered in a volume of at least about 2 mL in a single injection. In some aspects, the dose of sasanlimab is administered in a volume of at least about 6 mL in at least three injections.

In some aspects, the anti-PD-1 antibody comprises KN035, which is administered subcutaneously once about every week, once about every two weeks, once about every three weeks, or once about every four weeks. In some aspects, about 100 mg to about 200 mg KN035 is administered subcutaneously once about every week. In some aspects, about 100 mg, about 110 mg, about 120 mg, about 130 mg, about 140 mg, about 150 mg, about 160 mg, about 170 mg, about 180 mg, about 190 mg, or about 200 mg KN035 is administered subcutaneously once about every week. In some aspects, at least about 150 mg KN035 is administered subcutaneously once about every week. In some aspects, about 2.5 mg/kg KN035 is administered subcutaneously once about every week. In some aspects, about 200 mg to about 400 mg KN035 is administered subcutaneously once about every three weeks. In some aspects, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg KN035 is administered subcutaneously once about every three weeks. In some aspects, at least about 300 mg KN035 is administered subcutaneously once about every three weeks. In some aspects, at least about 300 mg KN035 is administered subcutaneously once about every four weeks. In some aspects, at least about 400 mg KN035 is administered subcutaneously once about every four weeks. In some aspects, the dose of KN035 is administered in a volume of less than about 1 mL.

II.A.2. Anti-PD-L1 Antibody Dosing

In some aspects of the present disclosure, the antibody comprises an anti-PD-L1 antibody. Any anti-PD-L1 antibody known in the art and/or disclosed herein can be used in the methods disclosed herein. In certain aspects, the anti-PD-L1 antibody comprises atezolizumab. In certain aspects, the anti-PD-L1 antibody comprises durvalumab. In certain aspects, the anti-PD-L1 antibody comprises avelumab.

In some aspects, the dose of the antibody, e.g., the anti-PD-L1 antibody, is about 300 mg to about 900 mg of the antibody administered about every week. In some aspects, the dose of the antibody, e.g., the anti-PD-L1 antibody, is about 300 mg to about 850 mg, about 300 mg to about 800 mg, about 300 mg to about 750 mg, about 300 mg to about 700 mg, about 300 mg to about 650 mg, about 300 mg to about 600 mg, about 350 mg to about 900 mg, about 350 mg to about 850 mg, about 350 mg to about 800 mg, about 350 mg to about 750 mg, about 350 mg to about 700 mg, about 350 mg to about 650 mg, about 350 mg to about 600 mg, about 400 mg to about 900 mg, about 400 mg to about 850 mg, about 400 mg to about 800 mg, about 400 mg to about 750 mg, about 400 mg to about 700 mg, about 400 mg to about 650 mg, about 400 mg to about 600 mg, about 450 to about 900 mg, about 450 to about 850 mg, about 450 to about 800 mg, about 450 mg to about 750 mg, about 450 mg to about 700 mg, about 450 mg to about 650 mg, about 450 mg to about 600 mg, about 500 mg to about 900 mg, about 500 mg to about 850 mg, about 500 mg to about 800 mg, about 500 mg to about 700 mg, about 500 mg to about 650 mg, about 500 mg to about 600 mg, about 550 mg to about 900 mg, about 550 mg to about 850 mg, about 550 mg to about 800 mg, about 550 mg to about 750 mg, about 550 mg to about 700 mg, about 550 mg to about 650 mg, about 550 mg to about 600 mg, about 600 mg to about 900 mg, about 600 mg to about 850 mg, about 600 mg to about 800 mg, about 600 mg to about 750 mg, about 600 mg to about 700 mg, about 600 mg to about 650 mg, about 575 mg to about 625 mg, about 575 mg to about 600 mg, or about 600 mg to about 625 mg of the antibody administered about every week. In some aspects, the dose of the antibody, e.g., the anti-PD-L1 antibody, is about 400 mg to about 800 mg of the antibody administered about every week. In some aspects, the dose of the antibody, e.g., the anti-PD-L1 antibody, is about 500 mg to about 700 mg of the antibody administered about every week. In some aspects, the dose of the antibody, e.g., the anti-PD-L1 antibody, is about 550 mg to about 650 mg of the antibody administered about every week. In some aspects, the dose of the antibody, e.g., the anti-PD-L1 antibody, is about 575 mg to about 625 mg of the antibody administered about every week.

In some aspects, the dose of the antibody is about 300 mg, about 350 mg, about 400 mg, about 450 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, or about 900 mg administered about every week. In some aspects, the dose of the antibody is about 500 mg administered about every week. In some aspects, the dose of the antibody is about 550 mg administered about every week. In some aspects, the dose of the antibody is about 575 mg administered about every week. In some aspects, the dose of the antibody is about 600 mg administered about every week. In some aspects, the dose of the antibody is about 625 mg administered about every week. In some aspects, the dose of the antibody is about 650 mg administered about every week. In some aspects, the dose of the antibody is about 700 mg administered about every week.

In some aspects, the dose of the antibody comprises a single subcutaneous unit dose of about 600 mg. In some aspects, the dose of the antibody comprises a single subcutaneous unit dose of about 600 mg in a total administered volume of less than about 5 mL (e.g., less than about 4.5 mL, less than about 4.0 mL, less than about 3.5 mL, less than about 3.0 mL, less than about 2.5 mL, or less than about 2.0 mL). In some aspects, the dose of the antibody comprises a single subcutaneous unit dose of about 600 mg in a total administered volume of about 2 mL. In some aspects, the dose of the antibody comprises a single subcutaneous unit dose of about 600 mg in a total administered volume of about 5 mL. In some aspects, the dose of the antibody comprises a single subcutaneous unit dose of about 600 mg in a total administered volume of greater than about 5 mL.

In some aspects, the dose of the antibody comprises two subcutaneous unit doses, wherein each of the two subcutaneous unit doses comprises about 300 mg of the antibody. In some aspects, at least one of the two subcutaneous unit doses comprises about 300 mg of the antibody in a total volume of about 2 mL. In some aspects, at least one of the two subcutaneous unit doses comprises about 300 mg of the antibody in a total volume of greater than about 2 mL. In some aspects, at least one of the two subcutaneous unit doses comprises about 300 mg of the antibody in a total volume of greater than about 5 mL. In some aspects, at least one of the two subcutaneous unit doses comprises about 300 mg of the antibody in a total volume of less than about 5 mL (e.g., less than about 4.5 mL, less than about 4.0 mL, less than about 3.5 mL, less than about 3.0 mL, less than about 2.5 mL, or less than about 2.0 mL). In certain aspects, at least one of the two subcutaneous unit doses comprises about 300 mg of the antibody in a total volume of less than about 2 mL. In some aspects, the two subcutaneous unit doses are administered to the subject at a single bodily location. In some aspects, the two subcutaneous unit doses are administered to the subject at two different bodily locations.

In some aspects, the dose of about 600 mg of the antibody comprises three subcutaneous unit doses. In some aspects, at least one of the three subcutaneous unit doses comprises about 200 mg of the antibody. In some aspects, each of the three subcutaneous unit doses comprises about 200 mg of the antibody. In some aspects, at least one of the three subcutaneous unit doses comprises about 200 mg of the antibody in a total volume of about 2 mL. In some aspects, at least one of the three subcutaneous unit doses comprises about 200 mg of the antibody in a total volume of greater than about 2 mL. In some aspects, at least one of the three subcutaneous unit doses comprises about 200 mg of the antibody in a total volume of greater than about 5 mL. In some aspects, at least one of the three subcutaneous unit doses comprises about 200 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the three subcutaneous unit doses are administered to the subject at least two different bodily locations. In some aspects, the first subcutaneous unit dose and the second subcutaneous unit dose are administered at a first bodily location, and the third subcutaneous unit dose is administered at a second bodily location. In some aspects, the first subcutaneous unit dose is administered at a first bodily location, the second subcutaneous unit dose is administered at a second bodily location, and the third subcutaneous unit dose is administered at a third bodily location.

In some aspects, the dose of about 600 mg of the antibody comprises at least four subcutaneous unit doses. In some aspects, at least one of the four subcutaneous unit doses comprises about 150 mg of the antibody. In some aspects, at least one of the four subcutaneous unit doses comprises about 150 mg of the antibody in a total volume of about 2 mL. In some aspects, at least one of the four subcutaneous unit doses comprises about 150 mg of the antibody in a total volume of greater than about 2 mL. In some aspects, at least one of the four subcutaneous unit doses comprises about 150 mg of the antibody in a total volume of greater than about 5 mL. In some aspects, at least one of the four subcutaneous unit doses comprises about 150 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the four subcutaneous unit doses are administered to the subject at at least two different bodily locations. In some aspects, the first subcutaneous unit dose and the second subcutaneous unit dose are administered at a first bodily location, and the third subcutaneous unit dose and the fourth subcutaneous unit dose are administered at a second bodily location. In some aspects, the first subcutaneous unit dose is administered at a first bodily location, the second subcutaneous unit dose is administered at a second bodily location, the third subcutaneous unit dose is administered at a third bodily location, and the fourth subcutaneous unit dose is administered at a fourth bodily location.

In some aspects, the dose of the antibody, e.g., the anti-PD-L1 antibody, is about 900 mg to about 1800 mg of the antibody administered about every two weeks. In some aspects, the dose of the antibody, e.g., the anti-PD-L1 antibody, is about 900 mg to about 1750 mg, about 900 mg to about 1700 mg, about 900 mg to about 1650 mg, about 900 mg to about 1600 mg, about 900 mg to about 1550 mg, about 900 mg to about 1500 mg, about 900 mg to about 1450 mg, about 900 mg to about 1400 mg, about 900 mg to about 1350 mg, about 900 mg to about 1300 mg, about 900 mg to about 1250 mg, about 900 mg to about 1200 mg, about 950 mg to about 1500 mg, about 950 mg to about 1450 mg, about 950 mg to about 1400 mg, about 950 mg to about 1350 mg, about 950 mg to about 1300 mg, about 950 mg to about 1250 mg, about 950 mg to about 1200 mg, about 1000 mg to about 1500 mg, about 1000 mg to about 1450 mg, about 1000 mg to about 1400 mg, about 1000 mg to about 1350 mg, about 1000 mg to about 1300 mg, about 1000 mg to about 1250 mg, about 1000 mg to about 1200 mg, about 1050 to about 1500 mg, about 1050 to about 1450 mg, about 1050 to about 1400 mg, about 1050 mg to about 1350 mg, about 1050 mg to about 1300 mg, about 1050 mg to about 1250 mg, about 1050 mg to about 1200 mg, about 1100 mg to about 1500 mg, about 1100 mg to about 1450 mg, about 1100 mg to about 1400 mg, about 1100 mg to about 1350 mg, about 1100 mg to about 1300 mg, about 1100 mg to about 1250 mg, about 1100 mg to about 1200 mg, about 1150 mg to about 1500 mg, about 1150 mg to about 1450 mg, about 1150 mg to about 1400 mg, about 1150 mg to about 1350 mg, about 1150 mg to about 1300 mg, about 1150 mg to about 1250 mg, about 1150 mg to about 1200 mg, about 1200 mg to about 1500 mg, about 1200 mg to about 1450 mg, about 1200 mg to about 1400 mg, about 1200 mg to about 1350 mg, about 1200 mg to about 1300 mg, about 1200 mg to about 1250 mg, about 1175 mg to about 1225 mg, about 1175 mg to about 1200 mg, or about 1200 mg to about 1225 mg of the antibody administered about every two weeks. In some aspects, the dose of the antibody, e.g., the anti-PD-L1 antibody, is about 1000 mg to about 1400 mg of the antibody administered about every two weeks. In some aspects, the dose of the antibody, e.g., the anti-PD-L1 antibody, is about 1100 mg to about 1300 mg of the antibody administered about every two weeks. In some aspects, the dose of the antibody, e.g., the anti-PD-L1 antibody, is about 1150 mg to about 1250 mg of the antibody administered about every two weeks. In some aspects, the dose of the antibody, e.g., the anti-PD-L1 antibody, is about 1175 mg to about 1225 mg of the antibody administered about every two weeks.

In some aspects, the dose of the antibody is about 900 mg, about 950 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, about 1500 mg, about 1550 mg, about 1600 mg, about 1650 mg, about 1700 mg, about 1750 mg, or about 1800 mg administered about every two weeks. In some aspects, the dose of the antibody is about 1100 mg administered about every two weeks. In some aspects, the dose of the antibody is about 1150 mg administered about every two weeks. In some aspects, the dose of the antibody is about 1175 mg administered about every two weeks. In some aspects, the dose of the antibody is about 1200 mg administered about every two weeks. In some aspects, the dose of the antibody is about 1225 mg administered about every two weeks. In some aspects, the dose of the antibody is about 1250 mg administered about every two weeks. In some aspects, the dose of the antibody is about 1300 mg administered about every two weeks.

In some aspects, the dose of the antibody comprises a single subcutaneous unit dose of about 1200 mg. In some aspects, the dose of the antibody comprises a single subcutaneous unit dose of about 1200 mg in a total administered volume of less than about 5 mL (e.g., less than about 4.5 mL, less than about 4.0 mL, less than about 3.5 mL, less than about 3.0 mL, less than about 2.5 mL, or less than about 2.0 mL). In some aspects, the dose of the antibody comprises a single subcutaneous unit dose of about 1200 mg in a total administered volume of about 2 mL. In some aspects, the dose of the antibody comprises a single subcutaneous unit dose of about 1200 mg in a total administered volume of about 5 mL. In some aspects, the dose of the antibody comprises a single subcutaneous unit dose of about 1200 mg in a total administered volume of greater than about 5 mL.

In some aspects, the dose of the antibody comprises two, three, four, six, or at least eight subcutaneous unit doses. In some aspects, the dose of the antibody comprises two subcutaneous unit doses, wherein each of the two subcutaneous unit doses comprises about 600 mg of the antibody. In some aspects, at least one of the two subcutaneous unit doses comprises about 600 mg of the antibody in a total volume of about 2 mL. In some aspects, at least one of the two subcutaneous unit doses comprises about 600 mg of the antibody in a total volume of greater than about 2 mL. In some aspects, at least one of the two subcutaneous unit doses comprises about 600 mg of the antibody in a total volume of greater than about 5 mL. In some aspects, at least one of the two subcutaneous unit doses comprises about 600 mg of the antibody in a total volume of less than about 5 mL (e.g., less than about 4.5 mL, less than about 4.0 mL, less than about 3.5 mL, less than about 3.0 mL, less than about 2.5 mL, or less than about 2.0 mL). In certain aspects, at least one of the two subcutaneous unit doses comprises about 600 mg of the antibody in a total volume of less than about 2 mL. In some aspects, the two subcutaneous unit doses are administered to the subject at a single bodily location. In some aspects, the two subcutaneous unit doses are administered to the subject at two different bodily locations.

In some aspects, the dose of about 1200 mg of the antibody comprises three subcutaneous unit doses. In some aspects, at least one of the three subcutaneous unit doses comprises about 400 mg of the antibody. In some aspects, each of the three subcutaneous unit doses comprises about 400 mg of the antibody. In some aspects, at least one of the three subcutaneous unit doses comprises about 400 mg of the antibody in a total volume of about 2 mL. In some aspects, at least one of the three subcutaneous unit doses comprises about 400 mg of the antibody in a total volume of greater than about 2 mL. In some aspects, at least one of the three subcutaneous unit doses comprises about 400 mg of the antibody in a total volume of greater than about 5 mL.

In some aspects, at least one of the three subcutaneous unit doses comprises about 400 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the three subcutaneous unit doses are administered to the subject at least two different bodily locations. In some aspects, the first subcutaneous unit dose and the second subcutaneous unit dose are administered at a first bodily location, and the third subcutaneous unit dose is administered at a second bodily location. In some aspects, the first subcutaneous unit dose is administered at a first bodily location, the second subcutaneous unit dose is administered at a second bodily location, and the third subcutaneous unit dose is administered at a third bodily location.

In some aspects, the dose of about 1200 mg of the antibody comprises four subcutaneous unit doses. In some aspects, at least one of the four subcutaneous unit doses comprises about 300 mg of the antibody. In some aspects, at least one of the four subcutaneous unit doses comprises about 300 mg of the antibody in a total volume of about 2 mL. In some aspects, at least one of the four subcutaneous unit doses comprises about 300 mg of the antibody in a total volume of greater than about 2 mL. In some aspects, at least one of the four subcutaneous unit doses comprises about 300 mg of the antibody in a total volume of greater than about 5 mL. In some aspects, at least one of the four subcutaneous unit doses comprises about 300 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the four subcutaneous unit doses are administered to the subject at at least two different bodily locations. In some aspects, the first subcutaneous unit dose and the second subcutaneous unit dose are administered at a first bodily location, and the third subcutaneous unit dose and the fourth subcutaneous unit dose are administered at a second bodily location. In some aspects, the first subcutaneous unit dose is administered at a first bodily location, the second subcutaneous unit dose is administered at a second bodily location, the third subcutaneous unit dose is administered at a third bodily location, and the fourth subcutaneous unit dose is administered at a fourth bodily location.

In some aspects, the dose of about 1200 mg of the antibody comprises six subcutaneous unit doses. In some aspects, at least one of the six subcutaneous unit doses comprises about 200 mg of the antibody. In some aspects, at least one of the six subcutaneous unit doses comprises about 200 mg of the antibody in a total volume of about 2 mL. In some aspects, at least one of the six subcutaneous unit doses comprises about 200 mg of the antibody in a total volume of greater than about 2 mL. In some aspects, at least one of the six subcutaneous unit doses comprises about 200 mg of the antibody in a total volume of greater than about 5 mL. In some aspects, at least one of the six subcutaneous unit doses comprises about 200 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the six subcutaneous unit doses are administered to the subject at least two different bodily locations. In some aspects, the first subcutaneous unit dose and the second subcutaneous unit dose are administered at a first bodily location, the third subcutaneous unit dose and the fourth subcutaneous unit dose are administered at a second bodily location, and the fifth subcutaneous unit dose and the sixth subcutaneous unit dose are administered at a third bodily location. In some aspects, the first subcutaneous unit dose is administered at a first bodily location, the second subcutaneous unit dose is administered at a second bodily location, the third subcutaneous unit dose is administered at a third bodily location, the fourth subcutaneous unit dose is administered at a fourth bodily location, the fifth subcutaneous unit dose is administered at a fifth bodily location, and the sixth subcutaneous unit dose is administered at a sixth bodily location.

In some aspects, the dose of about 1200 mg of the antibody comprises at least eight subcutaneous unit doses. In some aspects, at least one of the eight subcutaneous unit doses comprises about 150 mg of the antibody. In some aspects, at least one of the eight subcutaneous unit doses comprises about 150 mg of the antibody in a total volume of about 2 mL. In some aspects, at least one of the eight subcutaneous unit doses comprises about 150 mg of the antibody in a total volume of greater than about 2 mL. In some aspects, at least one of the eight subcutaneous unit doses comprises about 150 mg of the antibody in a total volume of greater than about 5 mL. In some aspects, at least one of the eight subcutaneous unit doses comprises about 150 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the eight subcutaneous unit doses are administered to the subject at at least two different bodily locations. In some aspects, the first subcutaneous unit dose and the second subcutaneous unit dose are administered at a first bodily location, the third subcutaneous unit dose and the fourth subcutaneous unit dose are administered at a second bodily location, the fifth subcutaneous unit dose and the sixth subcutaneous unit dose are administered at a third bodily location, and the seventh subcutaneous unit dose and the eighth subcutaneous unit dose are administered at a fourth bodily location.

In some aspects, the two, three, four, six, or at least eight subcutaneous unit doses are administered on the same day.

In some aspects, the dose of the antibody, e.g., the anti-PD-L1 antibody, is about 2100 mg to about 2700 mg of the antibody administered about every four weeks. In some aspects, the dose of the antibody, e.g., the anti-PD-L1 antibody, is about 2100 mg to about 2650 mg, about 2100 mg to about 2600 mg, about 2100 mg to about 2550 mg, about 2100 mg to about 2500 mg, about 2100 mg to about 2450 mg, about 2100 mg to about 2400 mg, about 2200 mg to about 2700 mg, about 2200 mg to about 2650 mg, about 2200 mg to about 2600 mg, about 2200 mg to about 2550 mg, about 2200 mg to about 2500 mg, about 2200 mg to about 2450 mg, about 2200 mg to about 2400 mg, about 2300 mg to about 2700 mg, about 2300 mg to about 2650 mg, about 2300 mg to about 2600 mg, about 2300 mg to about 2550 mg, about 2300 mg to about 2500 mg, about 2300 mg to about 2450 mg, about 2300 mg to about 2400 mg, about 2350 mg to about mg, about 2350 mg to about 2700 mg, about 2350 mg to about 2650 mg, about 2350 mg to about 2600 mg, about 2350 mg to about 2550 mg, about 2350 mg to about 2500 mg, about 2350 mg to about 2450 mg, about 2350 mg to about 2400 mg, about 2400 mg to about 2700 mg, about 2400 mg to about 2650 mg, about 2400 mg to about 2600 mg, about 2400 mg to about 2550 mg, about 2400 mg to about 2500 mg, about 2400 mg to about 2450 mg, about 2400 mg to about 2425 mg, about 2375 mg to about 2425 mg, or about 2375 mg to about 2400 mg of the antibody administered about every four weeks. In some aspects, the dose of the antibody, e.g., the anti-PD-L1 antibody, is about 2200 mg to about 2600 mg of the antibody administered about every four weeks. In some aspects, the dose of the antibody, e.g., the anti-PD-L1 antibody, is about 2300 mg to about 2500 mg of the antibody administered about every four weeks. In some aspects, the dose of the antibody, e.g., the anti-PD-L1 antibody, is about 2350 mg to about 2450 mg of the antibody administered about every four weeks. In some aspects, the dose of the antibody, e.g., the anti-PD-L1 antibody, is about 2375 mg to about 2425 mg of the antibody administered about every four weeks.

In some aspects, the dose of the antibody is about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, or about 2700 mg administered about every four weeks. In some aspects, the dose of the antibody is about 2300 mg administered about every four weeks. In some aspects, the dose of the antibody is about 2350 mg administered about every four weeks. In some aspects, the dose of the antibody is about 2400 mg administered about every four weeks. In some aspects, the dose of the antibody is about 2450 mg administered about every four weeks. In some aspects, the dose of the antibody is about 2500 mg administered about every four weeks.

In some aspects, the dose of the antibody comprises a single subcutaneous dose comprising about 2400 mg of the antibody. In some aspects, the single subcutaneous dose of the antibody comprises about 2400 mg of the antibody in a total volume of greater than about 2 mL. In some aspects, the single subcutaneous unit dose comprises about 2400 mg of the antibody in a total volume of greater than about 5 mL.

In some aspects, the dose of the antibody comprises two, three, four, six, or at least eight subcutaneous unit doses. In some aspects, the dose of the antibody comprises two subcutaneous unit doses, wherein each of the two subcutaneous unit doses comprises about 1200 mg of the antibody. In some aspects, at least one of the two subcutaneous unit doses comprises about 1200 mg of the antibody in a total volume of about 2 mL. In some aspects, at least one of the two subcutaneous unit doses comprises about 1200 mg of the antibody in a total volume of greater than about 2 mL. In some aspects, at least one of the two subcutaneous unit doses comprises about 1200 mg of the antibody in a total volume of greater than about 5 mL. In some aspects, at least one of the two subcutaneous unit doses comprises about 1200 mg of the antibody in a total volume of less than about 5 mL (e.g., less than about 4.5 mL, less than about 4.0 mL, less than about 3.5 mL, less than about 3.0 mL, less than about 2.5 mL, or less than about 2.0 mL). In certain aspects, at least one of the two subcutaneous unit doses comprises about 1200 mg of the antibody in a total volume of less than about 2 mL. In some aspects, the two subcutaneous unit doses are administered to the subject at a single bodily location. In some aspects, the two subcutaneous unit doses are administered to the subject at two different bodily locations.

In some aspects, the dose of about 2400 mg of the antibody comprises three subcutaneous unit doses. In some aspects, at least one of the three subcutaneous unit doses comprises about 800 mg of the antibody. In some aspects, each of the three subcutaneous unit doses comprises about 800 mg of the antibody. In some aspects, at least one of the three subcutaneous unit doses comprises about 800 mg of the antibody in a total volume of about 2 mL. In some aspects, at least one of the three subcutaneous unit doses comprises about 800 mg of the antibody in a total volume of greater than about 2 mL. In some aspects, at least one of the three subcutaneous unit doses comprises about 800 mg of the antibody in a total volume of greater than about 5 mL. In some aspects, at least one of the three subcutaneous unit doses comprises about 800 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the three subcutaneous unit doses are administered to the subject at at least two different bodily locations. In some aspects, the first subcutaneous unit dose and the second subcutaneous unit dose are administered at a first bodily location, and the third subcutaneous unit dose is administered at a second bodily location. In some aspects, the first subcutaneous unit dose is administered at a first bodily location, the second subcutaneous unit dose is administered at a second bodily location, and the third subcutaneous unit dose is administered at a third bodily location.

In some aspects, the dose of about 2400 mg of the antibody comprises four subcutaneous unit doses. In some aspects, at least one of the four subcutaneous unit doses comprises about 600 mg of the antibody. In some aspects, at least one of the four subcutaneous unit doses comprises about 600 mg of the antibody in a total volume of about 2 mL. In some aspects, at least one of the four subcutaneous unit doses comprises about 600 mg of the antibody in a total volume of greater than about 2 mL. In some aspects, at least one of the four subcutaneous unit doses comprises about 600 mg of the antibody in a total volume of greater than about 5 mL. In some aspects, at least one of the four subcutaneous unit doses comprises about 600 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the four subcutaneous unit doses are administered to the subject at at least two different bodily locations. In some aspects, the first subcutaneous unit dose and the second subcutaneous unit dose are administered at a first bodily location, and the third subcutaneous unit dose and the fourth subcutaneous unit dose are administered at a second bodily location. In some aspects, the first subcutaneous unit dose is administered at a first bodily location, the second subcutaneous unit dose is administered at a second bodily location, the third subcutaneous unit dose is administered at a third bodily location, and the fourth subcutaneous unit dose is administered at a fourth bodily location.

In some aspects, the dose of about 2400 mg of the antibody comprises six subcutaneous unit doses. In some aspects, at least one of the six subcutaneous unit doses comprises about 400 mg of the antibody. In some aspects, at least one of the six subcutaneous unit doses comprises about 400 mg of the antibody in a total volume of about 2 mL. In some aspects, at least one of the six subcutaneous unit doses comprises about 400 mg of the antibody in a total volume of greater than about 2 mL. In some aspects, at least one of the six subcutaneous unit doses comprises about 400 mg of the antibody in a total volume of greater than about 5 mL. In some aspects, at least one of the six subcutaneous unit doses comprises about 400 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the six subcutaneous unit doses are administered to the subject at at least two different bodily locations. In some aspects, the first subcutaneous unit dose and the second subcutaneous unit dose are administered at a first bodily location, the third subcutaneous unit dose and the fourth subcutaneous unit dose are administered at a second bodily location, and the fifth subcutaneous unit dose and the sixth subcutaneous unit dose are administered at a third bodily location. In some aspects, the first subcutaneous unit dose is administered at a first bodily location, the second subcutaneous unit dose is administered at a second bodily location, the third subcutaneous unit dose is administered at a third bodily location, the fourth subcutaneous unit dose is administered at a fourth bodily location, the fifth subcutaneous unit dose is administered at a fifth bodily location, and the sixth subcutaneous unit dose is administered at a sixth bodily location.

In some aspects, the dose of about 2400 mg of the antibody comprises at least eight subcutaneous unit doses. In some aspects, at least one of the eight subcutaneous unit doses comprises about 300 mg of the antibody. In some aspects, at least one of the eight subcutaneous unit doses comprises about 300 mg of the antibody in a total volume of about 2 mL. In some aspects, at least one of the eight subcutaneous unit doses comprises about 300 mg of the antibody in a total volume of greater than about 2 mL. In some aspects, at least one of the eight subcutaneous unit doses comprises about 300 mg of the antibody in a total volume of greater than about 5 mL. In some aspects, at least one of the eight subcutaneous unit doses comprises about 300 mg of the antibody in a total volume of about 5 mL (e.g., less than about 4.5 mL, less than about 4.0 mL, less than about 3.5 mL, less than about 3.0 mL, less than about 2.5 mL, or less than about 2.0 mL). In some aspects, at least two of the eight subcutaneous unit doses are administered to the subject at at least two different bodily locations. In some aspects, the first subcutaneous unit dose and the second subcutaneous unit dose are administered at a first bodily location, the third subcutaneous unit dose and the fourth subcutaneous unit dose are administered at a second bodily location, the fifth subcutaneous unit dose and the sixth subcutaneous unit dose are administered at a third bodily location, and the seventh subcutaneous unit dose and the eighth subcutaneous unit dose are administered at a fourth bodily location.

In some aspects, the two, three, four, six, or at least eight subcutaneous unit doses are administered on the same day.

In some aspects, the anti-PD-L1 antibody comprises atezolizumab, which is administered subcutaneously once about every week, once about every two weeks, once about every three weeks, or once about every four weeks. In some aspects, about 1000 mg to about 1400 mg atezolizumab is administered subcutaneously once about every two weeks. In some aspects, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, or about 1300 mg atezolizumab is administered subcutaneously once about every two weeks. In some aspects, at least about 1200 mg atezolizumab is administered subcutaneously once about every two weeks. In some aspects, about 1700 mg to about 1900 mg atezolizumab is administered subcutaneously once about every three weeks. In some aspects, about 1700 mg, about 1710 mg, about 1720 mg, about 1730 mg, about 1740 mg, about 1750 mg, about 1760 mg, about 1770 mg, about 1780 mg, about 1790 mg, about 1800 mg, about 1810 mg, about 1820 mg, about 1830 mg, about 1840 mg, about 1850 mg, about 1860 mg, about 1870 mg, about 1880 mg, about 1890 mg, or about 1900 mg atezolizumab is administered subcutaneously once about every three weeks. In some aspects, at least about 1800 mg atezolizumab is administered subcutaneously once about every three weeks. In some aspects, the dose of atezolizumab is administered in a volume of at least about 2 mL to at least about 20 mL.

II.A.3. Endoglycosidase Hydrolase Enzyme Dosing

In some aspects, the pharmaceutical composition comprises an endoglycosidase hydrolase enzyme. Any endoglycosidase hydrolase enzyme can be used in the pharmaceutical compositions disclosed herein. In some aspects, the endoglycosidase hydrolase enzyme cleaves hyaluronic acid at a hexosaminidic β (1-4) or (1-3) linkage. In some aspects, the endoglycosidase hydrolase enzyme comprises a catalytic domain of hyaluronidase PH-20 (HuPH20), HYAL1, HYAL2, HYAL3, HYAL4, or HYALPS1.

In some aspects, the endoglycosidase hydrolase enzyme comprises a hyaluronidase. In some aspects, the endoglycosidase hydrolase enzyme comprises a hyaluronidase selected from the group consisting of HuPH20, HYAL1, HYAL2, HYAL3, HYAL4, any variant, and any isoform thereof. In some aspects, the endoglycosidase hydrolase enzyme comprises rHuPH20 or a fragment thereof. In some aspects, the endoglycosidase hydrolase enzyme comprises an amino acid sequence having at least about 70%, at least about 75%, at least about 80%, at least about 85%, at least about 90%, at least about 95%, at least about 96%, at least about 97%, at least about 98%, at least about 99%, or about 100% sequence identity to amino acids 36-490 of SEQ ID NO: 1. In some aspects, the endoglycosidase hydrolase enzyme comprises the catalytic domain of rHuPH20 (Uni-Prot ID No. P38567-1). In some aspects, the endoglycosidase hydrolase enzyme comprises the rHuPH20 mature peptide (amino acids 36-490 of SEQ ID NO: 1A).

TABLE 1A

Amino Acid Sequence of rHuPH20

MGVLKFKHIFFRSFVKSSGVSQIVFTFLLIPCCLTLNFRAPPVIPNVP
FLWAWNAPSEFCLGKFDEPLDMSLFSFIGSPRINATGQGVTIFYVDRL
GYYPYIDSITGVTVNGGIPQKISLQDHLDKAKKDITFYMPVDNLGMAV
IDWEEWRPTWARNWKPKDVYKNRSIELVQQQNVQLSLTEATEKAKQEF
EKAGKDFLVETIKLGKLLRPNHLWGYYLFPDCYNHHYKKPGYNGSCFN
VEIKRNDDLSWLWNESTALYPSIYLNTQQSPVAATLYVRNRVREAIRV
SKIPDAKSPLPVFAYTRIVFTDQVLKFLSQDELVYTFGETVALGASGI
VIWGTLSIMRSMKSCLLLDNYMETILNPYIINVTLAAKMCSQVLCQEQ
GVCIRKNWNSSDYLHLNPDNFAIQLEKGGKFTVRGKPTLEDLEQFSEK
FYCSCYSTLSCKEKADVKDTDAVDVCIADGVCIDAFLKPPMETEEPQI
FYNASPSTLS*ATMFIVSILFLIISSVASL* (SEQ ID NO: 1)

Signal peptide: underlined; mature protein: bold; propeptide: italics.

Signal peptide: underlined; mature protein: bold; propeptide: italics.

In some aspects, the subcutaneous injection is based on Halozyme Therapeutics' ENHANZE® drug-delivery technology (see U.S. Pat. No. 7,767,429, which is incorporated by reference herein in its entirety). ENHANZE® uses a co-formulation of an antibody with recombinant human hyaluronidase enzyme (rHuPH20), which removes traditional limitations on the volume of biologics and drugs that can be delivered subcutaneously due to the extracellular matrix (see U.S. Pat. No. 7,767,429). In some aspects, the pharmaceutical composition for the present disclosure can further comprise recombinant human hyaluronidase enzyme, e.g., rHuPH20.

Recombinant human hyaluronidase PH20 (rHuPH20, Halozyme Therapeutics Inc.) is a glycosylated 447-amino acid single-chain recombinant human polypeptide that depolymerizes hyaluronan in the subcutaneous (SC) space locally at the site of injection. Hyaluronan is a repeating polymer of N-acetyl-glucosamine and glucuronic acid that contributes to the soluble gel-like component of the extracellular matrix of the skin. Depolymerization of hyaluronan by rHuPH20 results in a transient reduction in the viscosity of the gel-like phase of the extracellular matrix and increased hydraulic conductance that facilitates the dispersion and absorption of injected drugs (see rHuPH20 IB). Use of rHuPH20 enables the delivery of large volumes for rapid SC injections (for example, approximately 2 mL to 20 mL), which may shorten dose administration times, reduce administration frequency, and enable potential improvements to the PK profiles of coadministered drugs, including improved absorption, increased bioavailability, accelerated time to maximum concentration (Tmax), increased maximum concentration (Cmax), and decreased PK variability.

The half-life of rHuPH20 in skin is <30 minutes, and the local permeability barrier in these tissues is restored to pre-injection levels within 24 hours to 48 hours after injection of hyaluronidase. A study showed that rHuPH20 was not detectable systemically in healthy volunteers and patients following SC administration at doses of 10,000 U and 30,000 U. Another study of the PK of rHuPH20 (Halozyme Study HALO-104-104) demonstrated that plasma concentrations of rHuPH20 rapidly declined, with a very short $t\frac{1}{2}$ (≤10.4 min) and the plasma concentration became undetectable (<0.03 ng/mL) within 1.5 hours after the end of the IV infusion at for IV doses of 10,000 or 30,000 units of rHuPH20.

Subcutaneous injection of rHuPH20 is generally well-tolerated in healthy participants, dehydrated pediatric participants, hospice and palliative care participants, participants with type 1 and 2 diabetes, and participants with rheumatoid arthritis. Subcutaneous injections of rHuPH20 either alone or coadministered with lactated Ringer's, normal saline, co-injected drugs (morphine, ceftriaxone, insulin and insulin analogues) or biologic products (immunoglobulin G [IgG] and adalimumab) has been well-tolerated.

In some aspects, the endoglycosidase hydrolase enzyme comprises a modified hyaluronidase comprising one or more amino acid substitutions relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase comprising one or more amino acid substitution in an alpha-helix region relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase comprising one or more amino acid substitution in linker region relative to a wild-type hyaluronidase selected from the group consisting of HuPH20, HYAL1, HYAL2, HYAL3, HYAL4, HYALPS1, or a fragment thereof. In some aspects, the endoglycosidase hydrolase enzyme comprises a modified hyaluronidase, wherein one or more N-terminal and/or C-terminal amino acids are deleted relative to a wild-type hyaluronidase selected from the group consisting of HuPH20, HYAL1, HYAL2, HYAL3, HYAL4, HYALPS1, or a fragment thereof.

In some aspects, the endoglycosidase hydrolase enzyme comprises a modified rHuPH20, wherein the modified rHuPH20 comprises one or more amino acid substitution in an alpha-helix region, a linker region, or both an alpha-helix region and a linker region relative to wild-type rHuPH20. In some aspects, the endoglycosidase hydrolase enzyme comprises a modified rHuPH20, wherein the modified rHuPH20 comprises deletion of one or more N-terminal amino acid, one or more C-terminal amino acid, or one or more N-terminal amino acid and one or more C-terminal amino acid relative to wild-type rHuPH20. In some aspects, the endoglycosidase hydrolase enzyme comprises a modified rHuPH20, wherein the modified rHuPH20 comprises one or more amino acid substitution in an alpha-helix region, a linker region, or both an alpha-helix region and a linker region relative to wild-type rHuPH20; and wherein the modified rHuPH20 comprises deletion of one or more N-terminal amino acid, one or more C-terminal amino acid, or one or more N-terminal amino acid and one or more C-terminal amino acid relative to wild-type rHuPH20

Additional, non-limiting examples of endoglycosidase hydrolase enzymes are found in EP3636752, which is incorporated by reference herein in its entirety.

In some aspects, the endoglycosidase hydrolase enzyme is any polypeptide having endoglycosidase hydrolase enzyme activity disclosed in U.S. Pat. Nos. 9,447,401; 10,865,400; 11,041,149; 11,066,656; 8,927,249; 9,284,543; 10,588,983; U.S. Ser. No. 10/328,130; and/or U.S. Pat. No. 9,993,529, each of which is incorporated by reference herein in its entirety. In some aspects, the endoglycosidase hydrolase enzyme is any polypeptide having endoglycosidase hydrolase enzyme activity disclosed in International Publication No. WO/13/102144, WO/10/077297, WO/15/003167, WO/04/078140 WO/09/128917, WO/12/174478, and/or WO/12/174480, each of which is incorporated by reference herein in its entirety. In some aspects, the endoglycosidase hydrolase enzyme comprises an amino acid sequence at least about 70%, at least about 75%, at least about 80%, at least about 85%, at least about 90%, at least about 95%, at least about 96%, at least about 97%, at least about 98%, at least about 99%, or about 100% identical to an amino acid sequence selected from the amino acid sequences set forth in SEQ ID NOs: 5-52. In some aspects, the endoglycosidase hydrolase enzyme comprises an amino acid sequence selected from the amino acid sequences set forth in SEQ ID NOs: 5-52.

In some aspects, the endoglycosidase hydrolase enzyme is any polypeptide having endoglycosidase hydrolase enzyme activity disclosed in US Patent Application Publication No. US2021155913A1 and/or US2021363270A1; and/or International Publication Nos. WO/20/022791, WO/20/197230 and/or WO/21/150079; each of which is incorporated by reference herein in its entirety. In some aspects, the endoglycosidase hydrolase enzyme comprises an amino acid sequence at least about 70%, at least about 75%, at least about 80%, at least about 85%, at least about 90%, at least about 95%, at least about 96%, at least about 97%, at least about 98%, at least about 99%, or about 100% identical to an amino acid sequence selected from the amino acid sequences set forth in SEQ ID NOs: 53-263. In some aspects, the endoglycosidase hydrolase enzyme comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence set forth in SEQ ID NO: 92. In some aspects, the endoglycosidase hydrolase enzyme comprises an amino acid sequence selected from the amino acid sequences set forth in SEQ ID NOs: 53-263. In some aspects, the endoglycosidase hydrolase enzyme comprises the amino acid sequence set forth in SEQ ID NO: 92. In some aspects, the endoglycosidase hydrolase enzyme is HP46 (SEQ ID NO: 44 of Int'l Publication No. WO/20/197230).

In certain aspects, a pharmaceutical composition disclosed herein comprises a hyaluronidase. In some aspects, the pharmaceutical composition comprises a sufficient concentration of a hyaluronidase for administration of at least about 20,000 units of the hyaluronidase. In some aspects, the hyaluronidase is rHuPH20. In other aspects, the pharmaceutical composition does not comprise a hyaluronidase.

In some aspects, the anti-PD-1 antibody or the anti-PD-L1 antibody and the endoglycosidase hydrolase enzyme (e.g., rHuPH20) are administered together. In some aspects, the anti-PD-1 antibody or the anti-PD-L1 antibody and the endoglycosidase hydrolase enzyme (e.g., rHuPH20) are administered concurrently. In some aspects, the anti-PD-1 antibody or the anti-PD-L1 antibody and the endoglycosidase hydrolase enzyme (e.g., rHuPH20) are administered sequentially.

In some aspects, the anti-PD-1 antibody or the anti-PD-L1 antibody and the endoglycosidase hydrolase enzyme (e.g., rHuPH20) are present in a single pharmaceutical composition.

In some aspects, the dose comprises at least about 5000 units to at least about 100,000 units of an endoglycosidase hydrolase enzyme (e.g., rHuPH20). In some aspects, the dose comprises at least about 5000 units, at least about 10,000 units, at least about 15,000 units, at least about 20,000 units, at least about 25,000 units, at least about 30,000 units, at least about 35,000 units, at least about 40,000 units, at least about 45,000 units, at least about 50,000 units, at least about 55,000 units, at least about 60,000 units, at least about 65,000 units, at least about 70,000 units, at least about 75,000 units, at least about 80,000 units, at least about 85,000 units, at least about 90,000 units, at least about 95,000 units, or at least about 100,000 units of an endoglycosidase hydrolase enzyme (e.g., rHuPH20). In some aspects, the dose comprises at least about 20,000 units of an endoglycosidase hydrolase enzyme (e.g., rHuPH20). In some aspects, the dose comprises at least about 30,000 units of an endoglycosidase hydrolase enzyme (e.g., rHuPH20). In some aspects, the dose comprises at least about 40,000 units of an endoglycosidase hydrolase enzyme (e.g., rHuPH20). In some aspects, the dose comprises at least about 50,000 units of an endoglycosidase hydrolase enzyme (e.g., rHuPH20). In some aspects, the dose comprises at least about 60,000 units of an endoglycosidase hydrolase enzyme (e.g., rHuPH20). In some aspects, the dose comprises at least about 70,000 units of an endoglycosidase hydrolase enzyme (e.g., rHuPH20). In some aspects, the dose comprises at least about 80,000 units of an endoglycosidase hydrolase enzyme (e.g., rHuPH20). In some aspects, the dose comprises at least about 90,000 units of an endoglycosidase hydrolase enzyme (e.g., rHuPH20). In some aspects, the dose comprises at least about 100,000 units of an endoglycosidase hydrolase enzyme (e.g., rHuPH20).

It would be readily apparent to a person of ordinary skill in the art that the amount of the endoglycosidase hydrolase enzyme (e.g., rHuPH20) can be expressed in terms of units or the amount of the endoglycosidase hydrolase enzyme (e.g., rHuPH20) can be expressed in terms mg (or in other weight-based units). For example, in some aspects, the dose comprises an amount of an endoglycosidase hydrolase enzyme (e.g., rHuPH20) expressed as at least about 500 U or at least about 0.00455 mg. In another example, in some aspects, the dose comprises an amount of an endoglycosidase hydrolase enzyme (e.g., rHuPH20) expressed as at least about 2000 U or at least about 0.0182 mg.

II.B. Anti-PD-1 Antibodies Useful for the Disclosure

Anti-PD-1 antibodies that are known in the art can be used in the presently described compositions and methods. Various human monoclonal antibodies that bind specifically to PD-1 with high affinity have been disclosed in U.S. Pat. No. 8,008,449. Anti-PD-1 human antibodies disclosed in U.S. Pat. No. 8,008,449 have been demonstrated to exhibit one or more of the following characteristics: (a) bind to human PD-1 with a $K_D$ of $1 \times 10^{-7}$ M or less, as determined by surface plasmon resonance using a Biacore biosensor system; (b) do not substantially bind to human CD28, CTLA-4 or ICOS; (c) increase T-cell proliferation in a Mixed Lymphocyte Reaction (MLR) assay; (d) increase interferon-γ production in an MLR assay; (e) increase IL-2 secretion in an MLR assay; (f) bind to human PD-1 and cynomolgus monkey PD-1; (g) inhibit the binding of PD-L1 and/or PD-L2 to PD-1; (h) stimulate antigen-specific memory responses; (i) stimulate antibody responses; and (j) inhibit tumor cell growth in vivo. Anti-PD-1 antibodies usable in the present disclosure include monoclonal antibodies that bind specifically to human PD-1 and exhibit at least one, in some aspects, at least five, of the preceding characteristics.

Other anti-PD-1 monoclonal antibodies have been described in, for example, U.S. Pat. Nos. 6,808,710, 7,488, 802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

In some aspects, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; also known as toripalimab; see Si-Yang Liu et al., *J Hematol. Oncol.* 10:136 (2017)), BGB-A317 (Beigene; also known as Tislelizumab; see WO 2015/35606 and US 2015/0079109), INCSHR1210 (Jiangsu Hengrui Medicine; also known as SHR-1210; see WO 2015/085847; Si-Yang Liu et al., *J Hematol. Oncol.* 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), BCD-100 (Biocad; Kaplon et al., *mAbs* 10(2):183-203 (2018), IBI308 (Innovent; see WO 2017/024465, WO 2017/025016, WO 2017/132825, and WO 2017/133540); and sasanlimab (PF-06801591).

In one aspect, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56). The heavy chain variable and light chain variable regions for nivolumab are shown in Table 1B (SEQ ID NOs: 2 and 3). In some aspects, the anti-PD-1 antibody comprises a heavy chain variable region comprising the amino acid sequence set forth in SEQ ID NO: 2, and a light chain variable region comprising the amino acid sequence set forth in SEQ ID NO: 3. In some aspects, the antibody comprises heavy chain complementarity determining region (CDR) 1, CDR2, and CDR3 sequences comprising the amino acid sequences of the heavy chain CDR1, CDR2, and CDR3 of SEQ ID NO: 2. In some aspects, the antibody comprises light chain CDR1, CDR2, and CDR3 sequences comprising the amino acid sequences of the light chain CDR1, CDR2, and CDR3 of SEQ ID NO: 3.

TABLE 1B

Anti-PD-1 Antibody Sequences

| | |
|---|---|
| Anti-PD-1 Antibody Heavy Chain Variable Region | QVQLVESGGG VVQPGRSLRL DCKASGITFS NSGMHWVRQA PGKGLEWVAV IWYDGSKRYY ADSVKGRFTI SRDNSKNTLF LQMNSLRAED TAVYYCATND DYWGQGTLVT VSS (SEQ ID NO: 2) |
| Anti-PD-1 Antibody Light Chain Variable Region | EIVLTQSPAT LSLSPGERAT LSCRASQSVS SYLAWYQQKP GQAPRLLIYD ASNRATGIPA RFSGSGSGTD FTLTISSLEP EDFAVYYCQQ SSNWPRTFGQ GTKVEIK (SEQ ID NO: 3) |

In another aspect, the anti-PD-1 antibody is pembrolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

Anti-PD-1 antibodies usable in the disclosed compositions and methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some aspects, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain aspects, the antibodies that cross-compete for binding to human PD-1 with, or bind to the same epitope region of human PD-1 antibody, nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies usable in the compositions and methods of the disclosed disclosure also include antigen-binding portions of the above antibodies. It has been amply demonstrated that the antigen-binding function of an antibody can be performed by fragments of a full-length antibody.

Anti-PD-1 antibodies suitable for use in the disclosed compositions and methods are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain aspects, the anti-PD-1 antibody or antigen-binding portion thereof cross-competes with nivolumab for binding to human PD-1.

In some aspects, the anti-PD-1 antibody is administered at a dose ranging from 0.1 mg/kg to 20.0 mg/kg body weight once every 2, 3, 4, 5, 6, 7, or 8 weeks, e.g., 0.1 mg/kg to 10.0 mg/kg body weight once every 2, 3, or 4 weeks. In other aspects, the anti-PD-1 antibody is administered at a dose of about 2 mg/kg, about 3 mg/kg, about 4 mg/kg, about 5 mg/kg, about 6 mg/kg, about 7 mg/kg, about 8 mg/kg, about 9 mg/kg, or 10 mg/kg body weight once every 2 weeks. In other aspects, the anti-PD-1 antibody is administered at a dose of about 2 mg/kg, about 3 mg/kg, about 4 mg/kg, about 5 mg/kg, about 6 mg/kg, about 7 mg/kg, about 8 mg/kg, about 9 mg/kg, or 10 mg/kg body weight once every 3 weeks. In one aspect, the anti-PD-1 antibody is administered at a dose of about 5 mg/kg body weight about once every 3 weeks. In another aspect, the anti-PD-1 antibody, e.g., nivolumab, is administered at a dose of about 3 mg/kg body weight about once every 2 weeks. In other aspects, the anti-PD-1 antibody, e.g., pembrolizumab, is administered at a dose of about 2 mg/kg body weight about once every 3 weeks.

The anti-PD-1 antibody useful for the present disclosure can be administered as a flat dose. In some aspects, the anti-PD-1 antibody is administered at a flat dose of from about 100 to about 1000 mg, from about 100 mg to about 900 mg, from about 100 mg to about 800 mg, from about 100 mg to about 700 mg, from about 100 mg to about 600 mg, from about 100 mg to about 500 mg, from about 200 mg to about 1000 mg, from about 200 mg to about 900 mg, from about 200 mg to about 800 mg, from about 200 mg to about 700 mg, from about 200 mg to about 600 mg, from about 200 mg to about 500 mg, from about 200 mg to about 480 mg, or from about 240 mg to about 480 mg, In one aspect, the anti-PD-1 antibody is administered as a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 520 mg, at least about 540 mg, at least about 550 mg, at least about 560 mg, at least about 580 mg, at least about 600 mg, at least about 620 mg, at least about 640 mg, at least about 660 mg, at least about 680 mg, at least about 700 mg, or at least about 720 mg at a dosing interval of about 1, 2, 3, 4, 5, 6, 7, 8, 9, or 10 weeks. In another aspects, the anti-PD-1 antibody is administered as a flat dose of about 200 mg to about 800 mg, about 200 mg to about 700 mg, about 200 mg to about 600 mg, about 200 mg to about 500 mg, at a dosing interval of about 1, 2, 3, or 4 weeks.

In some aspects, the anti-PD-1 antibody is administered as a flat dose of about 200 mg at about once every 3 weeks. In other aspects, the anti-PD-1 antibody is administered as a flat dose of about 200 mg at about once every 2 weeks. In other aspects, the anti-PD-1 antibody is administered as a flat dose of about 240 mg at about once every 2 weeks. In certain aspects, the anti-PD-1 antibody is administered as a flat dose of about 480 mg at about once every 4 weeks.

In some aspects, nivolumab is administered at a flat dose of about 240 mg once about every 2 weeks. In some aspects, nivolumab is administered at a flat dose of about 240 mg once about every 3 weeks. In some aspects, nivolumab is administered at a flat dose of about 360 mg once about every 3 weeks. In some aspects, nivolumab is administered at a flat dose of about 480 mg once about every 4 weeks. In some aspects, nivolumab is administered at a flat dose of about 720 mg once about every 6 weeks. In some aspects, nivolumab is administered at a flat dose of about 960 mg once about every 8 weeks.

In some aspects, pembrolizumab is administered at a flat dose of about 200 mg once about every 2 weeks. In some aspects, pembrolizumab is administered at a flat dose of about 200 mg once about every 3 weeks. In some aspects, pembrolizumab is administered at a flat dose of about 400 mg once about every 4 weeks.

In some aspects, the pharmaceutical composition comprises a bispecific antibody or a multispecific antibody comprising a first antigen binding moiety and a second antigen binding moiety, wherein the first antigen binding moiety comprises an anti-PD-1 antigen binding portion (e.g., scFv of nivolumab). In some aspects, the second antigen binding moiety is an antigen binding portion of any one of the antibodies disclosed herein. In some aspects, the second antigen binding moiety is an antigen binding portion of an anti-LAG-3 antibody, e.g., relatlimab.

In some aspects, the pharmaceutical composition comprises a multispecific antibody comprising a first antigen binding moiety, a second antigen binding moiety, and at least a third antigen binding moiety, wherein the first antigen binding moiety comprises an anti-PD-1 antigen binding portion (e.g., scFv of nivolumab).

II.C. Anti-PD-L1 Antibodies Useful for the Disclosure

In certain aspects, an anti-PD-L1 antibody is substituted for the anti-PD-1 antibody in any of the methods disclosed herein. Any anti-PD-L1 antibodies can be used in the compositions and methods of the present disclosure. Examples of anti-PD-L1 antibodies useful in the compositions and methods of the present disclosure include the antibodies disclosed in U.S. Pat. No. 9,580,507. Anti-PD-L1 human monoclonal antibodies disclosed in U.S. Pat. No. 9,580,507 have been demonstrated to exhibit one or more of the following characteristics: (a) bind to human PD-L1 with a $K_D$ of $1 \times 10^{-7}$ M or less, as determined by surface plasmon resonance using a Biacore biosensor system; (b) increase T-cell proliferation in a Mixed Lymphocyte Reaction (MLR) assay; (c) increase interferon-$\gamma$ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present disclosure include monoclonal antibodies that bind specifically to human PD-L1 and exhibit at least one, in some aspects, at least five, of the preceding characteristics.

In certain aspects, the anti-PD-L1 antibody is selected from the group consisting of BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) *J Clin Oncol* 31(suppl):3000), durvalumab (AstraZeneca; also known as IMFINZI™, MEDI-4736; see WO 2011/066389), avelumab (Pfizer; also known as BAVENCIO®, MSB-0010718C; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g., WO 2017/034916), BGB-A333 (BeiGene; see Desai et al., *JCO* 36 (15*suppl*):TPS3113 (2018)), and CK-301 (Checkpoint Therapeutics; see Gorelik et al., AACR:Abstract 4606 (April 2016)).

In certain aspects, the PD-L1 antibody is atezolizumab (TECENTRIQ®). Atezolizumab is a fully humanized IgG1 monoclonal anti-PD-L1 antibody.

In certain aspects, the PD-L1 antibody is durvalumab (IMFINZI™). Durvalumab is a human IgG1 kappa monoclonal anti-PD-L1 antibody.

In certain aspects, the PD-L1 antibody is avelumab (BAVENCIO®). Avelumab is a human IgG1 lambda monoclonal anti-PD-L1 antibody.

Anti-PD-L1 antibodies usable in the disclosed compositions and methods also include isolated antibodies that bind specifically to human PD-L1 and cross-compete for binding to human PD-L1 with any anti-PD-L1 antibody disclosed herein, e.g., atezolizumab, durvalumab, and/or avelumab. In some aspects, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain aspects, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the compositions and methods of the disclosed disclosure also include antigen-binding portions of the above antibodies. It has been amply demonstrated that the antigen-binding function of an antibody can be performed by fragments of a full-length antibody.

Anti-PD-L1 antibodies suitable for use in the disclosed compositions and methods are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain aspects, the anti-PD-L1 antibody or antigen-binding portion thereof cross-competes with atezolizumab, durvalumab, and/or avelumab for binding to human PD-L1.

The anti-PD-L1 antibody useful for the present disclosure can be any PD-L1 antibody that specifically binds to PD-L1, e.g., antibodies that cross-compete with durvalumab, avelumab, or atezolizumab for binding to human PD-1, e.g., an antibody that binds to the same epitope as durvalumab, avelumab, or atezolizumab. In a particular aspect, the anti-PD-L1 antibody is durvalumab. In other aspects, the anti-PD-L1 antibody is avelumab. In some aspects, the anti-PD-L1 antibody is atezolizumab.

In some aspects, the anti-PD-L1 antibody is administered at a dose ranging from about 0.1 mg/kg to about 20.0 mg/kg body weight, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg, about once every 2, 3, 4, 5, 6, 7, or 8 weeks.

In some aspects, the anti-PD-L1 antibody is administered at a dose of about 15 mg/kg body weight at about once every 3 weeks. In other aspects, the anti-PD-L1 antibody is administered at a dose of about 10 mg/kg body weight at about once every 2 weeks.

In other aspects, the anti-PD-L1 antibody useful for the present disclosure is a flat dose. In some aspects, the anti-PD-L1 antibody is administered as a flat dose of from about 200 mg to about 1600 mg, about 200 mg to about 1500 mg, about 200 mg to about 1400 mg, about 200 mg to about 1300 mg, about 200 mg to about 1200 mg, about 200 mg to about 1100 mg, about 200 mg to about 1000 mg, about 200 mg to about 900 mg, about 200 mg to about 800 mg, about 200 mg to about 700 mg, about 200 mg to about 600 mg, about 700 mg to about 1300 mg, about 800 mg to about 1200 mg, about 700 mg to about 900 mg, or about 1100 mg to about 1300 mg. In some aspects, the anti-PD-L1 antibody is administered as a flat dose of at least about 240 mg, at least about 300 mg, at least about 320 mg, at least about 400 mg, at least about 480 mg, at least about 500 mg, at least about 560 mg, at least about 600 mg, at least about 640 mg, at least about 700 mg, at least about 720 mg, at least about 800 mg, at least about 840 mg, at least about 880 mg, at least about 900 mg, at least about 960 mg, at least about 1000 mg, at least about 1040 mg, at least about 1100 mg, at least about 1120 mg, at least about 1200 mg, at least about 1280 mg, at least about 1300 mg, at least about 1360 mg, or at least about 1400 mg, at a dosing interval of about 1, 2, 3, or 4 weeks. In some aspects, the anti-PD-L1 antibody is administered as a flat dose of about 1200 mg at about once every 3 weeks. In other aspects, the anti-PD-L1 antibody is administered as a flat dose of about 800 mg at about once every 2 weeks. In other aspects, the anti-PD-L1 antibody is administered as a flat dose of about 840 mg at about once every 2 weeks.

In some aspects, atezolizumab is administered as a flat dose of about 1200 mg once about every 3 weeks. In some aspects, atezolizumab is administered as a flat dose of about 800 mg once about every 2 weeks. In some aspects, atezolizumab is administered as a flat dose of about 840 mg once about every 2 weeks.

In some aspects, avelumab is administered as a flat dose of about 800 mg once about every 2 weeks.

In some aspects, durvalumab is administered at a dose of about 10 mg/kg once about every 2 weeks. In some aspects, durvalumab is administered as a flat dose of about 800 mg/kg once about every 2 weeks. In some aspects, dur-valumab is administered as a flat dose of about 1200 mg/kg once about every 3 weeks.

In some aspects, the antibody is a multispecific antibody, e.g., a bispecific antibody, that specifically (i) PD-L1 and (ii) a second antigen. In some aspects, the antibody is a multi-specific antibody, e.g., a bispecific antibody, that specifically (i) PD-L1 and (ii) CD3.

II.D. Combination Therapies

In some aspects of the present disclosure, the methods disclosed herein comprise administering an anti-PD-1 anti-body (or an anti-PD-L1 antibody) in combination with an additional anticancer therapy. The additional anticancer therapy can comprise any therapy for the treatment of a tumor in a subject and/or any standard-of-care therapy, as disclosed herein. In some aspects, the additional anticancer therapy comprises a surgery, a radiation therapy, a chemo-therapy, an immunotherapy, or any combination thereof. In some aspects, the additional anticancer therapy comprises a chemotherapy, including any chemotherapy disclosed herein. In some aspect, the additional anticancer therapy comprises an immunotherapy. In some aspects, the addi-tional anticancer therapy comprises administration of an antibody or antigen-binding portion thereof that specifically binds CTLA-4, LAG-3, TIGIT, TIM3, NKG2a, OX40, ICOS, MICA, CD137, KIR, TGFβ, IL-10, IL-8, B7-H4, Fas ligand, CXCR4, mesothelin, CD27, GITR, or any combi-nation thereof. In some aspects, the additional anticancer therapy comprises administering an IL-2 (e.g., a modified IL-2, e.g., pegylated IL-2, e.g., bempegaldesleukin). In some aspects, the second therapeutic agent, the third therapeutic agent, or both comprises IL12-Fc (e.g., BMS-986415).

In some aspects, the anti-PD-1 antibody or the anti-PD-L1 antibody is administered subcutaneously according to any method disclosed herein, and the additional anti-cancer therapy is administered by any suitable route known in the art. In some aspects, the anti-PD-1 antibody or the anti-PD-L1 antibody is administered subcutaneously according to any method disclosed herein, and the additional anti-cancer therapy is administered subcutaneously. In some aspects, the anti-PD-1 antibody or the anti-PD-L1 antibody is adminis-tered subcutaneously according to any method disclosed herein, and the additional anti-cancer therapy is adminis-tered intravenously. In some aspects, the anti-PD-1 antibody or the anti-PD-L1 antibody and the additional anticancer therapy are administered concurrently. In some aspects, the anti-PD-1 antibody or the anti-PD-L1 antibody and the additional anticancer therapy are administered sequentially. In some aspects, the anti-PD-1 antibody or the anti-PD-L1 antibody and the additional anticancer therapy are adminis-tered on the same day. In some aspects, the anti-PD-1 antibody or the anti-PD-L1 antibody and the additional anticancer therapy are administered on different days.

In some aspects, the anti-PD-1 antibody or the anti-PD-L1 antibody and the additional anticancer therapy, e.g., a check-point inhibitor, are combined in a single formulation.

In some aspects, the method comprises administering a therapeutically effective amount of an anti-PD-1 antibody and an anti-CTLA-4 antibody, e.g., ipilimumab. In other aspects, the method comprises administering a therapeuti-cally effective amount of a composition comprising an anti-PD-1 antibody and an anti-CTLA-4 antibody. Human monoclonal antibodies that bind specifically to CTLA-4 with high affinity have been disclosed in U.S. Pat. No. 6,984,720. Other anti-CTLA-4 monoclonal antibodies have been described in, for example, U.S. Pat. Nos. 5,977,318, 6,051,227, 6,682,736, and 7,034,121 and International Publication Nos. WO 2012/122444, WO 2007/113648, WO 2016/196237, and WO 2000/037504, each of which is incorporated by reference herein in its entirety. In certain aspects, the CTLA-4 antibody is selected from the group consisting of ipilimumab (also known as YERVOY®, MDX-010, 10D1; see U.S. Pat. No. 6,984,720), MK-1308 (Merck), AGEN-1884 (Agenus Inc.; see WO 2016/196237), and tremelimumab (AstraZeneca; also known as ticilim-umab, CP-675,206; see WO 2000/037504 and Ribas, *Update Cancer Ther.* 2(3): 133-39 (2007)). In particular aspects, the anti-CTLA-4 antibody is ipilimumab. In par-ticular aspects, the CTLA-4 antibody is tremelimumab. In particular aspects, the CTLA-4 antibody is MK-1308. In particular aspects, the CTLA-4 antibody is AGEN-1884.

In some aspects, the method comprises administering a therapeutically effective amount of an anti-PD-1 antibody and an anti-LAG-3 antibody. In other aspects, the method comprises administering a therapeutically effective amount of a single formulation comprising an anti-PD-1 antibody and an anti-LAG-3 antibody, e.g., relatlimab. In some aspects, the anti-LAG-3 antibody is relatlimab, e.g., BMS-986016 as described in PCT/US13/48999, the teachings of which are hereby incorporated by reference. In some aspects, the anti-LAG-3 antibody cross-competes with relatlimab for binding to human LAG-3. In some aspects, the anti-LAG-3 antibody binds to the same epitope as relatlimab. In some aspects, the anti-LAG-3 antibody is a biosimilar of relatlimab. In some aspects, the anti-LAG-3 antibody is LAG-525, MK-4280, REGN3767, TSR-033, TSR-075, Sym022, FS-118, or any combination thereof.

In some aspects, the method comprises administering a therapeutically effective amount of an anti-PD-1 antibody or an anti-PD-L1 antibody according to any method disclosed herein and a chemotherapy. In some aspects, the chemo-therapy comprises a platinum-based therapy. In some aspects, the platinum-based therapy comprises a platinum-based antineoplastic selected from the group consisting of cisplatin, carboplatin, oxaliplatin, nedaplatin, triplatin tet-ranitrate, phenanthriplatin, picoplatin, satraplatin, and any combination thereof. In certain aspects, the platinum-based therapy comprises cisplatin. In one particular aspect, the platinum-based therapy comprises carboplatin. In some aspects, the chemotherapy comprises an anticancer agent selected from the group consisting of a platinum agent (e.g., cisplatin, carboplatin), a taxanes agent (e.g., paclitaxel, albumin-bound paclitaxel, docetaxel), vinorelbine, vinblas-tine, etoposide, pemetrexed, gemcitabine, bevacizumab (AVASTIN®), erlotinib (TARCEVA®), crizotinib (XALKORI®), cetuximab (ERBITUX®), and any combi-nation thereof. In certain aspects, the chemotherapy com-prises a platinum-based doublet chemotherapy.

II.E. Tumors

Certain aspects of the present disclosure are directed to methods of treating a subject in need thereof, comprising subcutaneously delivering an anti-PD-1 antibody or an anti-PD-L1 antibody. In some aspects, the subject is afflicted with a cancer (e.g., a tumor derived from a cancer). In some aspects, the tumor is derived from a cancer selected from the group consisting of squamous cell carcinoma, small-cell lung cancer (SCLC), non-small cell lung cancer (NSCLC), squamous NSCLC, nonsquamous NSCLC, glioma, gastro-intestinal cancer, renal cancer, clear cell carcinoma, ovarian cancer, liver cancer, colorectal cancer, endometrial cancer, kidney cancer, renal cell carcinoma (RCC), prostate cancer, hormone refractory prostate adenocarcinoma, thyroid can-cer, neuroblastoma, pancreatic cancer, glioblastoma, glio-blastoma multiforme, cervical cancer, stomach cancer, bladder cancer, hepatoma, breast cancer, colon carcinoma, head and neck cancer, gastric cancer, germ cell tumor, pediatric sarcoma, sinonasal natural killer, melanoma, bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, rectal cancer, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, environmentally-induced cancers including those induced by asbestos, virus-related cancers or cancers of viral origin (e.g., human papilloma virus (HPV-related or -originating tumors)), and any combination thereof. In certain aspects, the subject has received one, two, three, four, five or more prior cancer treatments. In other aspects, the subject is treatment-naïve. In some aspects, the subject has progressed on other cancer treatments. In certain aspects, the prior cancer treatment comprised an immunotherapy. In other aspects, the prior cancer treatment comprised a chemotherapy. In some aspects, the tumor has reoccurred. In some aspects, the tumor is metastatic. In other aspects, the tumor is not metastatic. In some aspects, the tumor is locally advanced.

In some aspects, the subject has received a prior therapy to treat the tumor and the tumor is relapsed or refractory. In certain aspects, the at least one prior therapy comprises a standard-of-care therapy. In some aspects, the at least one prior therapy comprises a surgery, a radiation therapy, a chemotherapy, an immunotherapy, or any combination thereof. In some aspects, the at least one prior therapy comprises a chemotherapy. In some aspects, the subject has received a prior immuno-oncology (I-O) therapy to treat the tumor and the tumor is relapsed or refractory. In some aspects, the subject has received more than one prior therapy to treat the tumor and the subject is relapsed or refractory. In other aspects, the subject has received either an anti-PD-1 or an anti-PD-L1 antibody therapy.

In some aspects, the previous line of therapy comprises a chemotherapy. In some aspects, the chemotherapy comprises a platinum-based therapy. In some aspects, the platinum-based therapy comprises a platinum-based antineoplastic selected from the group consisting of cisplatin, carboplatin, oxaliplatin, nedaplatin, triplatin tetranitrate, phenanthriplatin, picoplatin, satraplatin, and any combination thereof. In certain aspects, the platinum-based therapy comprises cisplatin. In one particular aspect, the platinum-based therapy comprises carboplatin.

In some aspects, the at least one prior therapy is selected from a therapy comprising administration of an anticancer agent selected from the group consisting of a platinum agent (e.g., cisplatin, carboplatin), a taxanes agent (e.g., paclitaxel, albumin-bound paclitaxel, docetaxel), vinorelbine, vinblastine, etoposide, pemetrexed, gemcitabine, bevacizumab (AVASTIN®), erlotinib (TARCEVA®), crizotinib (XALKORI®), cetuximab (ERBITUX®), and any combination thereof. In certain aspects, the at least one prior therapy comprises a platinum-based doublet chemotherapy.

In some aspects, the subject has experienced disease progression after the at least one prior therapy. In certain aspects, the subject has received at least two prior therapies, at least three prior therapies, at least four prior therapies, or at least five prior therapies. In certain aspects, the subject has received at least two prior therapies. In one aspect, the subject has experienced disease progression after the at least two prior therapies. In certain aspects, the at least two prior therapies comprises a first prior therapy and a second prior therapy, wherein the subject has experienced disease progression after the first prior therapy and/or the second prior therapy, and wherein the first prior therapy comprises a surgery, a radiation therapy, a chemotherapy, an immunotherapy, or any combination thereof; and wherein the second prior therapy comprises a surgery, a radiation therapy, a chemotherapy, an immunotherapy, or any combination thereof. In some aspects, the first prior therapy comprises a platinum-based doublet chemotherapy, and the second prior therapy comprises a single-agent chemotherapy. In certain aspects, the single-agent chemotherapy comprises docetaxel.

In certain aspects, the tumor that is a PD-L1 positive tumor. "PD-L1 positive" as used herein can be interchangeably used with "PD-L1 expression of at least about 1%." PD-L1 expression can be measured by any methods known in the art. In some aspects, PD-L1 expression is measured by an automated IHC. PD-L1 positive tumors can thus have at least about 1%, at least about 2%, at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of the tumor cells expressing PD-L1 as measured by an automated IHC. In certain aspects, "PD-L1 positive" means that there are at least 100 cells that express PD-L1 on the surface of the cells.

In order to assess the PD-L1 expression, in one aspect, a test tissue sample is obtained from a patient who is in need of a therapy disclosed herein. In another aspect, the assessment of PD-L1 expression is achieved without obtaining a test tissue sample. In some aspects, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain aspects the "measuring" or "assessing" step to identify, or determine the number or proportion of, cells in the test tissue sample that express PD-L1 (e.g., the expression of PD-L1 on the cell surface) is performed by a transformative method of assaying for PD-L1 expression, for example by performing a reverse transcriptase-polymerase chain reaction (RT-PCR) assay or an IHC assay. In certain other aspects, no transformative step is involved and PD-L1 expression is assessed by, for example, reviewing a report of test results from a laboratory. In certain aspects, the steps of the methods up to, and including, assessing PD-L1 expression provides an intermediate result that may be provided to a physician or other healthcare provider for use in selecting a suitable candidate for the anti-PD-1 antibody or anti-PD-L1 antibody therapy. In certain aspects, the steps that provide the intermediate result is performed by a medical practitioner or someone acting under the direction of a medical practitioner. In other aspects, these steps are performed by an independent laboratory or by an independent person such as a laboratory technician.

In certain aspects of any of the present methods, the proportion of cells that express PD-L1 is assessed by performing an assay to determine the presence of PD-L1 RNA. In further aspects, the presence of PD-L1 RNA is determined by RT-PCR, in situ hybridization or RNase protection. In other aspects, the proportion of cells that express PD-L1 is assessed by performing an assay to determine the presence of PD-L1 polypeptide. In further aspects, the presence of PD-L1 polypeptide is determined by immunohistochemistry (IHC), enzyme-linked immunosorbent assay (ELISA), in vivo imaging, or flow cytometry. In some aspects, PD-L1 expression is assayed by IHC. In other aspects of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM), and multiphoton microscopy (MPM) will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2(12):a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25(3):253-61 (2010); Olafsen et al., "ImmunoPET imaging of B-cell lymphoma using 124I-anti-CD20 scFv dimers (diabodies)," *Protein Eng. Des. Sel.* 23(4):243-9 (2010)). In certain aspects of any of the present methods, PD-L1 expression is assayed by immunoPET imaging. In certain aspects of any of the present methods, the proportion of cells in a test tissue sample that express PD-L1 is assessed by performing an assay to determine the presence of PD-L1 polypeptide on the surface of cells in the test tissue sample. In certain aspects, the test tissue sample is a FFPE tissue sample. In other aspects, the presence of PD-L1 polypeptide is determined by IHC assay. In further aspects, the IHC assay is performed using an automated process. In some aspects, the IHC assay is performed using an anti-PD-L1 monoclonal antibody to bind to the PD-L1 polypeptide.

In one aspect of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a monoclonal antibody that specifically binds to human PD-L1, under conditions that allow for formation of a complex between the antibody or portion thereof and human PD-L1. In certain aspects, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular aspect, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary antibody; incubating with a postprimary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1$^{++}$ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one aspect, the threshold number of cells that needs to be PD-L1 positive is at least about 100, at least about 125, at least about 150, at least about 175, or at least about 200 cells. In certain aspects, the threshold number of cells that need to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain aspects of these scoring methods, the samples are scored by two pathologists operating independently, and the scores are subsequently consolidated. In certain other aspects, the identification of positive and negative cells is scored using appropriate software.

A histoscore (also described as H-score) is used as a more quantitative measure of the IHC data. The histoscore is calculated as follows:

Histoscore=[(% tumor×1 (low intensity))+(%
tumor×2 (medium intensity))+(% tumor×3 (high
intensity)]

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-hi expression in human melanocytic lesions supports an adaptive resistance mechanism of immune escape," *Sci. Transl. Med.* 4(127):127ra37 (2012)).

III. Compositions of the Disclosure

Also within the scope of the present disclosure are pharmaceutical compositions comprising an anti-PD-1 antibody or an anti-PD-L1 antibody. In some aspects, the pharmaceutical compositions are formulated for subcutaneous administration according to a method disclosed herein. In some aspects, the pharmaceutical compositions are formulated such that they exhibit improved properties compared to the compositions without two antioxidants or at least one antioxidant. Therapeutic agents of the present disclosure can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier for a composition containing an antibody is suitable for intravenous, intramuscular, subcutaneous, parenteral, spinal or epidermal administration (e.g., by injection or infusion), whereas the carrier for a composition containing an antibody and/or a cytokine is suitable for non-parenteral, e.g. oral, administration. In certain aspects, the pharmaceutical composition does not comprise a hyaluronidase.

In some aspects, the pharmaceutical composition comprises at least about 10 mg/mL to at least about 500 mg/mL of the anti-PD-1 antibody or the anti-PD-L1 antibody. In some aspects, the pharmaceutical composition comprises at least about 10 mg/mL to at least about 500 mg/mL, at least about 10 mg/mL to at least about 400 mg/mL, at least about 10 mg/mL to at least about 300 mg/mL, at least about 10 mg/mL to at least about 250 mg/mL, at least about 10 mg/mL to at least about 200 mg/mL, at least about 10 mg/mL to at least about 190 mg/mL, at least about 10 mg/mL to at least about 180 mg/mL, at least about 10 mg/mL to at least about 170 mg/mL, at least about 10 mg/mL to at least about 160 mg/mL, at least about 10 mg/mL to at least about 150 mg/mL, at least about 20 mg/mL to at least about 500 mg/mL, at least about 20 mg/mL to at least about 400 mg/mL, at least about 20 mg/mL to at least about 300 mg/mL, at least about 20 mg/mL to at least about 250 mg/mL, at least about 20 mg/mL to at least about 200 mg/mL, at least about 20 mg/mL to at least about 190 mg/mL, at least about 20 mg/mL to at least about 180 mg/mL, at least about 20 mg/mL to at least about 170 mg/mL, at least about 20 mg/mL to at least about 160 mg/mL, at least about 20 mg/mL to at least about 150 mg/mL, at least about 50 mg/mL to at least about 200 mg/mL, at least about 100 mg/mL to at least about 200 mg/mL, at least about 150 mg/mL to at least about 200 mg/mL, at least about 135 mg/mL to at least about 180 mg/mL, at least about 100 mg/mL to at least about 200 mg/mL, at least about 150 mg/mL to at least about 200 mg/mL, at least about 100 mg/mL to at least about 130 mg/mL, or at least about 108 mg/mL to at least about 132 mg/mL of the anti-PD-1 antibody or the anti-PD-L1 antibody. In some aspects, the pharmaceutical composition comprises at least about 50 mg/mL of the anti-PD-1 antibody or the anti-PD-L1 antibody. In some aspects, the pharmaceutical composition comprises at least about 60 mg/mL of the anti-PD-1 antibody or the anti-PD-L1 antibody. In some aspects, the pharmaceutical composition comprises at least about 70 mg/mL of the anti-PD-1 antibody or the anti-PD-L1 antibody. In some aspects, the pharmaceutical composition comprises at least about 75 mg/mL of the anti-PD-1 antibody or the anti-PD-L1 antibody. In some aspects, the pharmaceutical composition comprises at least about 80 mg/mL of the anti-PD-1 antibody or the anti-PD-L1 antibody. In some aspects, the pharmaceutical composition comprises at least about 90 mg/mL of the anti-PD-1 antibody or the anti-PD-L1 antibody. In some aspects, the pharmaceutical composition comprises at least about 100 mg/mL of the anti-PD-1 antibody or the anti-PD-L1 antibody. In some aspects, the pharmaceutical composition comprises at least about 108 mg/mL of the anti-PD-1 antibody or the anti-PD-L1 antibody. In some aspects, the pharmaceutical composition comprises at least about 110 mg/mL of the anti-PD-1 antibody or the anti-PD-L1 antibody. In some aspects, the pharmaceutical composition comprises at least about 120 mg/mL of the anti-PD-1 antibody or the anti-PD-L1 antibody. In some aspects, the pharmaceutical composition comprises at least about 130 mg/mL of the anti-PD-1 antibody or the anti-PD-L1 antibody. In some aspects, the pharmaceutical composition comprises at least about 132 mg/mL of the anti-PD-1 antibody or the anti-PD-L1 antibody. In some aspects, the pharmaceutical composition comprises at least about 135 mg/mL of the anti-PD-1 antibody or the anti-PD-L1 antibody. In some aspects, the pharmaceutical composition comprises at least about 140 mg/mL of the anti-PD-1 antibody or the anti-PD-L1 antibody. In some aspects, the pharmaceutical composition comprises at least about 150 mg/mL of the anti-PD-1 antibody or the anti-PD-L1 antibody. In some aspects, the pharmaceutical composition comprises at least about 160 mg/mL of the anti-PD-1 antibody or the anti-PD-L1 antibody. In some aspects, the pharmaceutical composition comprises at least about 170 mg/mL of the anti-PD-1 antibody or the anti-PD-L1 antibody. In some aspects, the pharmaceutical composition comprises at least about 175 mg/mL of the anti-PD-1 antibody or the anti-PD-L1 antibody. In some aspects, the pharmaceutical composition comprises at least about 180 mg/mL of the anti-PD-1 antibody or the anti-PD-L1 antibody. In some aspects, the pharmaceutical composition comprises at least about 190 mg/mL of the anti-PD-1 antibody or the anti-PD-L1 antibody. In some aspects, the pharmaceutical composition comprises at least about 200 mg/mL of the anti-PD-1 antibody or the anti-PD-L1 antibody.

III.A. Endoglycosidase Hydrolase Enzyme

In some aspects, the pharmaceutical composition comprises an endoglycosidase hydrolase enzyme. In some aspects, the pharmaceutical composition comprises at least about 50 U/mL to at least about 48000 units of an endogly-cosidase hydrolase enzyme (e.g., rHuPH20). In some aspects, the pharmaceutical composition comprises at least about 50 U/mL to at least about 5000 U/mL of an endogly-cosidase hydrolase enzyme (e.g., rHuPH20). In some aspects, the pharmaceutical composition comprises at least about 50 U/mL, at least about 100 U/mL, at least about 150 U/mL, at least about 200 U/mL, at least about 250 U/mL, at least about 300 U/mL, at least about 350 U/mL, at least about 400 U/mL, at least about 450 U/mL, at least about 500 U/mL, at least about 750 U/mL, at least about 1000 U/mL, at least about 1500 U/mL, at least about 2000 U/mL, at least about 2500 U/mL, at least about 3000 U/mL, at least about 3500 U/mL, at least about 4000 U/mL, at least about 4500 U/mL, at least about 5000 U/mL, at least about 5500 U/mL, at least about 6000 U/mL, at least about 6500 U/mL, at least about 7000 U/mL, at least about 7500 U/mL, at least about 8000 U/mL, at least about 8500 U/mL, at least about 9000 U/mL, at least about 9500 U/mL, at least about 10,000 U/mL of an endoglycosidase hydrolase enzyme (e.g., rHuPH20). In some aspects, the pharmaceutical composition comprises at least about 500 U/mL of an endoglycosidase hydrolase enzyme (e.g., rHuPH20). In some aspects, the pharmaceutical composition comprises at least about 1000 U/mL of an endoglycosidase hydrolase enzyme (e.g., rHuPH20). In some aspects, the pharmaceutical composition comprises at least about 2000 U/mL of an endoglycosidase hydrolase enzyme (e.g., rHuPH20). In some aspects, the pharmaceutical composition comprises at least about 2500 U/mL of an endoglycosidase hydrolase enzyme (e.g., rHuPH20). In some aspects, the pharmaceutical composition comprises at least about 3000 U/mL of an endoglycosidase hydrolase enzyme (e.g., rHuPH20). In some aspects, the pharmaceutical composition comprises at least about 3500 U/mL of an endoglycosidase hydrolase enzyme (e.g., rHuPH20). In some aspects, the pharmaceutical composition comprises at least about 4000 U/mL of an endoglycosidase hydrolase enzyme (e.g., rHuPH20). In some aspects, the pharmaceutical composition comprises at least about 4500 U/mL of an endoglycosidase hydrolase enzyme (e.g., rHuPH20). In some aspects, the pharmaceutical composition comprises at least about 5000 U/mL of an endoglycosidase hydrolase enzyme (e.g., rHuPH20). In some aspects, the pharmaceutical composition comprises at least about 6000 U/mL of an endoglycosidase hydrolase enzyme (e.g., rHuPH20). In some aspects, the pharmaceutical composition comprises at least about 7000 U/mL of an endoglycosidase hydrolase enzyme (e.g., rHuPH20). In some aspects, the pharmaceutical composition comprises at least about 8000 U/mL of an endoglycosidase hydrolase enzyme (e.g., rHuPH20). In some aspects, the pharmaceutical composition comprises at least about 9000 U/mL of an endoglycosidase hydrolase enzyme (e.g., rHuPH20). In some aspects, the pharmaceutical composition comprises at least about 10,000 U/mL of an endoglycosidase hydrolase enzyme (e.g., rHuPH20).

In some aspects, the pharmaceutical composition comprises at least about 50 units to at least about 100,000 units of an endoglycosidase hydrolase enzyme (e.g., rHuPH20). In some aspects, the pharmaceutical composition comprises at least about 50 units, at least about 100 units, at least about 150 units, at least about 200 units, at least about 250 units, at least about 300 units, at least about 400 units, at least about 500 units, at least about 600 units, at least about 700 units, at least about 800 units, at least about 900 units, at least about 1000 units, at least about 1500 units, at least about 2000 units, at least about 2500 units, at least about 3000 units, at least about 4000 units, at least about 5000 units, at least about 10,000 units, at least about 15,000 units, at least about 20,000 units, at least about 25,000 units, at least about 30,000 units, at least about 35,000 units, at least about 40,000 units, at least about 45,000 units, at least about 48,000 units, at least about 50,000 units, at least about 55,000 units, at least about 60,000 units, at least about 65,000 units, at least about 70,000 units, at least about 75,000 units, at least about 80,000 units, at least about 85,000 units, at least about 90,000 units, at least about 95,000 units, or at least about 100,000 units of an endogly-cosidase hydrolase enzyme (e.g., rHuPH20). In some aspects, the pharmaceutical composition comprises at least about 20,000 units of an endoglycosidase hydrolase enzyme (e.g., rHuPH20). In some aspects, the pharmaceutical com-position comprises at least about 30,000 units of an endo-glycosidase hydrolase enzyme (e.g., rHuPH20). In some aspects, the pharmaceutical composition comprises at least about 40,000 units of an endoglycosidase hydrolase enzyme (e.g., rHuPH20). In some aspects, the pharmaceutical com-position comprises at least about 50,000 units of an endo-glycosidase hydrolase enzyme (e.g., rHuPH20). In some aspects, the pharmaceutical composition comprises at least about 60,000 units of an endoglycosidase hydrolase enzyme (e.g., rHuPH20). In some aspects, the pharmaceutical com-position comprises at least about 70,000 units of an endo-glycosidase hydrolase enzyme (e.g., rHuPH20). In some aspects, the pharmaceutical composition comprises at least about 80,000 units of an endoglycosidase hydrolase enzyme (e.g., rHuPH20). In some aspects, the pharmaceutical com-position comprises at least about 90,000 units of an endo-glycosidase hydrolase enzyme (e.g., rHuPH20). In some aspects, the pharmaceutical composition comprises at least about 100,000 units of an endoglycosidase hydrolase enzyme (e.g., rHuPH20).

It would be readily apparent to a person of ordinary skill in the art that the amount of the endoglycosidase hydrolase enzyme (e.g., rHuPH20) can be expressed in terms of units or U/mL or the amount of the endoglycosidase hydrolase enzyme (e.g., rHuPH20) can be expressed in terms mg/mL (or in other weight-based units). For example, in some aspects, the pharmaceutical composition comprises an amount of an endoglycosidase hydrolase enzyme (e.g., rHuPH20) expressed as at least about 500 U/mL or at least about 0.00455 mg/mL. In another example, in some aspects, the pharmaceutical composition comprises an amount of an endoglycosidase hydrolase enzyme (e.g., rHuPH20) expressed as at least about 2000 U/mL or at least about 0.0182 mg/mL.

In certain aspects, the pharmaceutical composition com-prises: (a) about 120 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine, and (g) about 2000 U/mL rHuPH20. In certain aspects, the pharmaceutical composi-tion comprises: (a) about 120 mg/mL of nivolumab; (b) about 20 mM histidine; (c) about 250 mM sucrose; (d) about 0.05% w/v polysorbate 80; (e) about 50 μM pentetic acid; (f) about 5 mM methionine, and (g) about 2000 U/mL rHuPH20. In certain aspects, the pharmaceutical composi-tion comprises: (a) about 120 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine, and (g) about 0.0182 mg/mL rHuPH20. In certain aspects, the pharma-ceutical composition comprises: (a) about 120 mg/mL of nivolumab; (b) about 20 mM histidine; (c) about 250 mM sucrose; (d) about 0.05% w/v polysorbate 80; (e) about 50 µM pentetic acid; (f) about 5 mM methionine, and (g) about 0.0182 mg/mL rHuPH20.

In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine, and (g) about 2000 U/mL rHuPH20. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine, and (g) about 2000 U/mL rHuPH20. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 nM methionine, and (g) about 0.0182 mg/mL rHuPH20. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine, and (g) about 0.0182 mg/mL rHuPH20.

In certain aspects, a unit dose described herein comprises: (a) about 120 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine, and (g) about 2000 U/mL rHuPH20. In certain aspects, a unit dose described herein comprises: (a) about 120 mg/mL of nivolumab; (b) about 20 mM histidine; (c) about 250 mM sucrose; (d) about 0.05% w/v polysorbate 80; (e) about 50 µM pentetic acid; (f) about 5 mM methionine, and (g) about 2000 U/mL rHuPH20. In certain aspects, a unit dose described herein comprises: (a) about 120 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine, and (g) about 0.0182 mg/mL rHuPH20. In certain aspects, a unit dose described herein comprises: (a) about 120 mg/mL of nivolumab; (b) about 20 mM histidine; (c) about 250 mM sucrose; (d) about 0.05% w/v polysorbate 80; (e) about 50 µM pentetic acid; (f) about 5 mM methionine, and (g) about 0.0182 mg/mL rHuPH20.

In certain aspects, a unit dose described herein comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine, and (g) about 2000 U/mL rHuPH20. In certain aspects, a unit dose described herein comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine, and (g) about 2000 U/mL rHuPH20. In certain aspects, a unit dose described herein comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine, and (g) about 0.0182 mg/mL rHuPH20. In certain aspects, a unit dose described herein comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine, and (g) about 0.0182 mg/mL rHuPH20.

In certain aspects, the pharmaceutical composition comprises (a) about 672 mg nivolumab; (b) about 8.68 mg L-histidine; (c) about 11.8 mg histidine HCl H20; (d) about 479 mg sucrose; (e) about 2.80 mg polysorbate 80; (f) about 0.110 mg pentetic acid; (g) about 4.18 mg methionine; (h) about 0.102 mg rHuPH20; wherein (a)-(h) are reconstituted in water to a final volume of at least about 5.6 mL.

III.B. Antioxidants

In some aspects, the pharmaceutical composition further comprises an antioxidant. Any antioxidant can be used in the pharmaceutical compositions disclosed herein. In some aspects, the antioxidant is selected from methionine, tryptophan, and histidine, cysteine, ascorbic acid, glycine, pentetic acid (DTPA), and EDTA. In certain aspects, the pharmaceutical composition comprises methionine. In some aspects, the pharmaceutical composition comprises at least two antioxidants. In some aspects, more than one antioxidants, e.g., two antioxidants, prevents oxidation of the formulation components and/or improves stability of the antibody. In some aspects, the at least two antioxidants comprise (i) methionine and EDTA or (ii) methionine and pentetic acid (DTPA).

In some aspects, the pharmaceutical composition comprises the anti-PD-1 antibody, methionine, and pentetic acid (DTPA). In some aspects, the pharmaceutical composition comprises from at least about 0.1 mM to at least about 100 mM methionine. In some aspects, the pharmaceutical compositions comprises at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, or at least about 10 mM, at least about 11 mM, at least about 12 mM, at least about 13 mM, at least about 14 m, at least about 15 mM, at least about 16 mM, at least about 17 mM, at least about 18 mM, at least about 19 mM, or at least about 20 mM methionine. In certain aspects, the pharmaceutical composition comprises at least about 10 mM methionine. In certain aspects, the pharmaceutical composition comprises at least about 9 mM methionine. In certain aspects, the pharmaceutical composition comprises at least about 8 mM methionine. In certain aspects, the pharmaceutical composition comprises at least about 7 mM methionine. In certain aspects, the pharmaceutical composition comprises at least about 6 mM methionine. In certain aspects, the pharmaceutical composition comprises at least about 4 mM methionine. In certain aspects, the pharmaceutical composition comprises at least about 4 mM methionine. In certain aspects, the pharmaceutical composition comprises at least about 3 mM methionine. In certain aspects, the pharmaceutical composition comprises at least about 2 mM methionine. In certain aspects, the pharmaceutical composition comprises at least about 1 mM methionine.

In some aspects, the pharmaceutical composition comprises from at least about 1 mM to at least about 250 mM pentetic acid (DTPA). In some aspects, the pharmaceutical composition comprises at least about 1 µM, at least about 5 µM, at least about 10 µM, at least about 15 µM, at least about 20 µM, at least about 25 µM, at least about 30 µM, at least about 35 µM, at least about 40 µM, at least about 45 µM, at least about 50 µM, at least about 55 µM, at least about 60 µM, at least about 65 µM, at least about 70 µM, at least about 75 µM, at least about 80 µM, at least about 85 µM, at least about 90 µM, at least about 95 µM, or at least about 100 µM, at least about 110 µM, at least about 120 µM, at least about 130 µM, at least about 140 µM, at least about 150 µM, at least about 160 µM, at least about 170 µM, at least about 180

µM, at least about 190 µM, or at least about 200 µM DTPA. In certain aspects, the pharmaceutical composition comprises at least about 75 µM pentetic acid (DTPA).In certain aspects, the pharmaceutical composition comprises at least about 70 µM pentetic acid (DTPA).In certain aspects, the pharmaceutical composition comprises at least about 65 µM pentetic acid (DTPA).In certain aspects, the pharmaceutical composition comprises at least about 60 µM pentetic acid (DTPA).In certain aspects, the pharmaceutical composition comprises at least about 55 µM pentetic acid (DTPA).In certain aspects, the pharmaceutical composition comprises at least about 50 µM pentetic acid (DTPA). In certain aspects, the pharmaceutical composition comprises at least about 45 µM pentetic acid (DTPA). In certain aspects, the pharmaceutical composition comprises at least about 40 µM pentetic acid (DTPA). In certain aspects, the pharmaceutical composition comprises at least about 35 µM pentetic acid (DTPA). In certain aspects, the pharmaceutical composition comprises at least about 30 µM pentetic acid (DTPA). In certain aspects, the pharmaceutical composition comprises at least about 25 µM pentetic acid (DTPA).

III.C. Tonicity Modifiers/Stabilizers

In some aspects, the pharmaceutical composition further comprises a tonicity modifier and/or stabilizer. Any tonicity modifier and/or any stabilizer can be used in the pharmaceutical compositions disclosed herein. In some aspects, the tonicity modifier and/or stabilizer comprises a sugar, an amino acid, a polyol, a salt, or any combination thereof. In some aspects, the tonicity modifier and/or stabilizer is selected from the group consisting of sucrose, sorbitol, trehalose, mannitol, glycerol, glycine, leucine, isoleucine, sodium chloride, proline, arginine, polyols, amino acids, and salts.

In certain aspects, the pharmaceutical composition comprises sucrose. In some aspects, the pharmaceutical composition comprises from at least about 1 mM to at least about 500 mM sucrose. In some aspects, the pharmaceutical compositions comprises from at least about 10 mM to at least about 400 mM, at least about 50 mM to at least about 400 mM, at least about 100 mM to at least about 400 mM, at least about 150 mM to at least about 400 mM, at least about 200 mM to at least about 400 mM, at least about 250 mM to at least about 400 mM, at least about 300 mM to at least about 400 mM, at least about 350 mM to at least about 400 mM, at least about 50 mM to at least about 350 mM, at least about 100 mM to at least about 300 mM, at least about 100 mM to at least about 250 mM, at least about 100 mM to at least about 200 mM, at least about 100 mM to at least about 150 mM, at least about 200 mM to at least about 400 mM, at least about 200 mM to at least about 300 mM sucrose, or at least about 200 mM to at least about 250 mM. In some aspects, the pharmaceutical compositions comprises at least about 10 mM, at least about 20 mM, at least about 30 mM, at least about 40 mM, at least about 50 mM, at least about 60 mM, at least about 70 mM, at least about 80 mM, at least about 90 mM, at least about 100 mM, at least about 110 mM, at least about 120 mM, at least about 130 mM, at least about 140 mM, at least about 150 mM, at least about 160 mM, at least about 170 mM, at least about 180 mM, at least about 190 mM, at least about 200 mM, at least about 210 mM, at least about 220 mM, at least about 230 mM, at least about 240 mM, at least about 250 mM, at least about 260 mM, at least about 270 mM, at least about 280 mM, at least about 290 mM, at least about 300 mM, at least about 310 mM, at least about 320 mM, at least about 330 mM, at least about 340 mM, at least about 350 mM, at least about 360 mM, at least about 370 mM, at least about 380 mM, at least about 390 mM, at least about 400 mM, at least about 410 mM, at least about 420 mM, at least about 430 mM, at least about 440 mM, at least about 450 mM, at least about 460 mM, at least about 470 mM, at least about 480 mM, at least about 490 mM, or at least about 500 mM sucrose. In certain aspects, the pharmaceutical composition comprises at least about 200 mM sucrose. In certain aspects, the pharmaceutical composition comprises at least about 210 mM sucrose. In certain aspects, the pharmaceutical composition comprises at least about 220 mM sucrose. In certain aspects, the pharmaceutical composition comprises at least about 230 mM sucrose. In certain aspects, the pharmaceutical composition comprises at least about 240 mM sucrose. In certain aspects, the pharmaceutical composition comprises at least about 250 mM sucrose. In certain aspects, the pharmaceutical composition comprises at least about 260 mM sucrose. In certain aspects, the pharmaceutical composition comprises at least about 270 mM sucrose. In certain aspects, the pharmaceutical composition comprises at least about 280 mM sucrose. In certain aspects, the pharmaceutical composition comprises at least about 290 mM sucrose. In certain aspects, the pharmaceutical composition comprises at least about 300 mM sucrose.

III.D. Buffering Agents

In some aspects, the pharmaceutical composition further comprises a buffering agent. In some aspects, the buffering agent is selected from histidine, succinate, tromethamine, sodium phosphate, sodium acetate, and sodium citrate. In certain aspects, the pharmaceutical composition comprises histidine. In certain aspects, the pharmaceutical composition comprises citrate. In some aspects, the pharmaceutical composition comprises from at least about 1 mM to at least about 100 mM histidine. In some aspects, the pharmaceutical composition comprises from at least about 5 mM to at least about 100 mM, at least about 10 mM to at least about 100 mM, at least about 15 mM to at least about 100 mM, at least about 20 mM to at least about 100 mM, at least about 25 mM to at least about 100 mM, at least about 30 mM to at least about 100 mM, at least about 35 mM to at least about 100 mM, at least about 40 mM to at least about 100 mM, at least about 45 mM to at least about 100 mM, at least about 50 mM to at least about 100 mM, at least about 10 mM to at least about 75 mM, at least about 10 mM to at least about 50 mM, at least about 10 mM to at least about 40 mM, at least about 10 mM to at least about 30 mM, at least about 15 mM to at least about 30 mM, at least about 10 mM to at least about 25 mM, or at least about 15 mM to at least about 25 mM, histidine.

In some aspects, the pharmaceutical composition comprises at least about 5 mM, at least about 10 mM, at least about 15 mM, at least about 20 mM, at least about 25 mM, at least about 30 mM, at least about 35 mM, at least about 40 mM, at least about 45 mM, at least about 50 mM, at least about 60 mM, at least about 70 mM, at least about 80 mM, at least about 90 mM, or at least about 100 mM histidine. In certain aspects, the pharmaceutical composition comprises at least about 10 mM histidine. In certain aspects, the pharmaceutical composition comprises at least about 15 mM histidine. In certain aspects, the pharmaceutical composition comprises at least about 20 mM histidine. In certain aspects, the pharmaceutical composition comprises at least about 25 mM histidine. In certain aspects, the pharmaceutical composition comprises at least about 30 mM histidine. In certain aspects, the pharmaceutical composition comprises at least about 35 mM histidine. In certain aspects, the pharmaceutical composition comprises at least about 40 mM histidine. In certain aspects, the pharmaceutical composition comprises at least about 45 mM histidine. In certain aspects, the pharmaceutical composition comprises at least about 50 mM histidine.

In some aspects, the pharmaceutical composition comprises a pH of about 5.2 to about 6.8. In some aspects, the pH of the pharmaceutical composition is about 5.2. In some aspects, the pH of the pharmaceutical composition is about 5.3. In some aspects, the pH of the pharmaceutical composition is about 5.4. In some aspects, the pH of the pharmaceutical composition is about 5.5. In some aspects, the pH of the pharmaceutical composition is about 5.6. In some aspects, the pH of the pharmaceutical composition is about 5.7. In some aspects, the pH of the pharmaceutical composition is about 5.8. In some aspects, the pH of the pharmaceutical composition is about 5.9. In some aspects, the pH of the pharmaceutical composition is about 6.0. In some aspects, the pH of the pharmaceutical composition is about 6.1. In some aspects, the pH of the pharmaceutical composition is about 6.2. In some aspects, the pH of the pharmaceutical composition is about 6.3. In some aspects, the pH of the pharmaceutical composition is about 6.4. In some aspects, the pH of the pharmaceutical composition is about 6.5. In some aspects, the pH of the pharmaceutical composition is about 6.6. In some aspects, the pH of the pharmaceutical composition is about 6.7. In some aspects, the pH of the pharmaceutical composition is about 6.8.

III.E. Surfactants

In some aspects, the pharmaceutical composition further comprises a surfactant. Any surfactant can be used in the pharmaceutical compositions disclosed herein. In some aspects, the surfactant is selected from the group consisting of polysorbate 20, polysorbate 80, and poloxamer 188. In certain aspects, the pharmaceutical composition comprises polysorbate 80. In some aspects, the pharmaceutical composition comprises from at least about 0.001% to at least about 1% w/v polysorbate 80. In some aspects, the pharmaceutical compositions comprises at least about 0.01% to at least about 0.1%, at least about 0.02% to at least about 0.1%, at least about 0.03% to at least about 0.1%, at least about 0.4% to at least about 0.1%, at least about 0.0% to at least about 0.1, at least about 0.01% to at least about 0.09%, at least about 0.01% to at least about 0.8%, at least about 0.01% to at least about 0.7%, at least about 0.02% to at least about 0.6%, at least about 0.0% to at least about 0.5%, at least about 0.02% to at least about 0.09%, at least about 0.03% to at least about 0.08%, at least about 0.04% to at least about 0.07%, or at least about 0.04% to at least about 0.06% w/v polysorbate 80. In some aspects, the pharmaceutical compositions comprises at least about 0.01% to at least about 0.1% w/v polysorbate 80.

In some aspects, the pharmaceutical composition comprises at least about 0.01% w/v, at least about 0.02% w/v, at least about 0.03% w/v, at least about 0.04% w/v, at least about 0.05% w/v, at least about 0.06% w/v, at least about 0.07% w/v, at least about 0.08% w/v, at least about 0.09% w/v, or at least about 0.1% w/v polysorbate 80. In certain aspects, the pharmaceutical composition comprises at least about 0.03% w/v polysorbate 80. In certain aspects, the pharmaceutical composition comprises at least about 0.04% w/v polysorbate 80. In certain aspects, the pharmaceutical composition comprises at least about 0.05% w/v polysorbate 80. In certain aspects, the pharmaceutical composition comprises at least about 0.06% w/v polysorbate 80. In certain aspects, the pharmaceutical composition comprises at least about 0.07% w/v polysorbate 80.

In certain aspects, the pharmaceutical composition comprises: (a) about 120 mg/mL of the anti-PD-1 antibody; (b) about 20 mM histidine; (c) about 250 mM sucrose; (d) about 0.05% w/v polysorbate 80; (e) about 50 μM pentetic acid; and (f) about 5 mM methionine. In certain aspects, the pharmaceutical composition comprises: (a) about 120 mg/mL of nivolumab; (b) about 20 mM histidine; (c) about 250 mM sucrose; (d) about 0.05% w/v polysorbate 80; (e) about 50 μM pentetic acid; and (f) about 5 mM methionine.

In some aspects, the pharmaceutical composition comprises: (a) an anti-PD-1 antibody, e.g., nivolumab; (b) a checkpoint inhibitor, e.g., an anti-CTLA-4 antibody; (c) about 20 mM histidine; (d) about 250 mM sucrose; (e) about 0.05% w/v polysorbate 80; (f) about 50 μM pentetic acid; and (g) about 5 mM methionine. In some aspects, the pharmaceutical composition comprises: (a) an anti-PD-1 antibody, e.g., nivolumab; (b) a checkpoint inhibitor, e.g., an anti-CTLA-4 antibody; (c) about 20 mM histidine; (d) about 250 mM sucrose; (e) about 0.05% w/v polysorbate 80; (f) about 50 μM pentetic acid; (g) about 5 mM methionine; and (h) about 2000 U/mL rHuPH20.

In some aspects, the pharmaceutical composition comprises: (a) an anti-PD-1 antibody, e.g., nivolumab; (b) a checkpoint inhibitor, e.g., an anti-LAG-3 antibody; (c) about 20 mM histidine; (d) about 250 mM sucrose; (e) about 0.05% w/v polysorbate 80; (f) about 50 μM pentetic acid; and (g) about 5 mM methionine. In some aspects, the pharmaceutical composition comprises: (a) an anti-PD-1 antibody, e.g., nivolumab; (b) a checkpoint inhibitor, e.g., an anti-LAG-3 antibody; (c) about 20 mM histidine; (d) about 250 mM sucrose; (e) about 0.05% w/v polysorbate 80; (f) about 50 μM pentetic acid; (g) about 5 mM methionine; and (h) about 2000 U/mL rHuPH20.

In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; and (f) about 5 mM methionine. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; and (f) about 5 mM methionine. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In certain aspects, a unit dose described herein comprises: (a) about 120 mg/mL of the anti-PD-1 antibody; (b) about 20 mM histidine; (c) about 250 mM sucrose; (d) about 0.05% w/v polysorbate 80; (e) about 50 μM pentetic acid; and (f) about 5 mM methionine. In certain aspects, a unit dose described herein comprises: (a) about 120 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20. In certain aspects, a unit dose described herein comprises: (a) about 120 mg/mL of nivolumab; (b) about 20 mM histidine; (c) about 250 mM sucrose; (d) about 0.05% w/v polysorbate 80; (e) about 50 μM pentetic acid; and (f) about 5 mM methionine. In certain aspects, a unit dose described herein comprises: (a) about 120 mg/mL of nivolumab; (b) about 20 mM histidine; (c)

about 250 mM sucrose; (d) about 0.05% w/v polysorbate 80; (e) about 50 μM pentetic acid; (f) about 5 mM methionine; and (g) about 2000 U/mL rHuPH20.

In certain aspects, a unit dose described herein comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; and (f) about 5 mM methionine. In certain aspects, a unit dose described herein comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20. In certain aspects, a unit dose described herein comprises: (a) about 150 mg/mL of nivolumab; (b) about 20 mM histidine; (c) about 250 mM sucrose; (d) about 0.05% w/v polysorbate 80; (e) about 50 μM pentetic acid; and (f) about 5 mM methionine. In certain aspects, a unit dose described herein comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In certain aspects, the pharmaceutical composition comprises (a) about 672 mg nivolumab; (b) about 8.68 mg L-histidine; (c) about 11.8 mg histidine HCl H20; (d) about 479 mg sucrose; (e) about 2.80 mg polysorbate 80; (f) about 0.110 mg pentetic acid; (g) about 4.18 mg methionine; wherein (a)-(g) are reconstituted in water (e.g., sterile water for injection, SWFI) to a final volume of at least about 5.6 mL.

III.F. Containers and Delivery Devices

Some aspects of the present disclosure are directed to a vial comprising a pharmaceutical composition disclosed herein. In some aspects, the vial comprises a unit dose of the pharmaceutical composition. In some aspects, the vial comprises (a) about 150 mg/mL of the anti-PD-1 antibody; (b) about 20 mM L-histidine; (c) about 250 mM sucrose; (d) about 0.05% w/v polysorbate 80; (e) about 50 μM pentetic acid; and (f) about 5 mM methionine. In some aspects, the vial does not comprise a hyaluronidase.

In some aspects, the vial is a syringe. Any syringe can be used in the compositions and methods disclosed herein. In some aspects, the syringe comprises one or more mechanical element that improves subcutaneous administration.

In some aspects, the vial is an autoinjector. Typically, an autoinjector works by the patient actuating the needle and subsequent flow of medication solely through the application of pressure on the injection site. The pressure causes the actuation of a needle shield, which engages the needle and causes the device to inject the drug. Accordingly, some aspects of the present disclosure are directed to an autoinjector comprising (a) about 150 mg/mL of the anti-PD-1 antibody; (b) about 20 mM L-histidine; (c) about 250 mM sucrose; (d) about 0.05% w/v polysorbate 80; (e) about 50 μM pentetic acid; and (f) about 5 mM methionine. In some aspects, the autoinjector does not comprise a hyaluronidase.

In some aspects, the vial is a pen injector. Standard pen injectors require the patient to activate a push-button, which actuates the needle into the targeted injection site. Accordingly, some aspects of the present disclosure are directed to an injection pen comprising (a) about 150 mg/mL of the anti-PD-1 antibody; (b) about 20 mM L-histidine; (c) about 250 mM sucrose; (d) about 0.05% w/v polysorbate 80; (e) about 50 μM pentetic acid; and (f) about 5 mM methionine. In some aspects, the injection pen does not comprise a hyaluronidase.

In some aspects, the vial is a wearable pump or a wearable device. In some aspects, the wearable pump is a patch pump. Accordingly, some aspects of the present disclosure are directed to a wearable pump comprising (a) about 150 mg/mL of the anti-PD-1 antibody; (b) about 20 mM L-histidine; (c) about 250 mM sucrose; (d) about 0.05% w/v polysorbate 80; (e) about 50 μM pentetic acid; and (f) about 5 mM methionine. In some aspects, the wearable pump does not comprise a hyaluronidase.

Some aspects of the present disclosure are directed to an autoinjector comprising (a) about 150 mg/mL of the anti-PD-1 antibody; (b) about 20 mM L-histidine; (c) about 250 mM sucrose; (d) about 0.05% w/v polysorbate 80; (e) about 50 μM pentetic acid; (f) about 5 mM methionine; and (g) about 0.0182 mg/mL rHuPH20.

In some aspects, the vial is a pen injector. Standard pen injectors require the patient to activate a push-button, which actuates the needle into the targeted injection site. Accordingly, some aspects of the present disclosure are directed to an injection pen comprising (a) about 150 mg/mL of the anti-PD-1 antibody; (b) about 20 mM L-histidine; (c) about 250 mM sucrose; (d) about 0.05% w/v polysorbate 80; (e) about 50 μM pentetic acid; (f) about 5 mM methionine; and (g) about 0.0182 mg/mL rHuPH20.

In some aspects, the vial is a wearable pump or a wearable device. In some aspects, the wearable pump is a patch pump. Accordingly, some aspects of the present disclosure are directed to a wearable pump comprising (a) about 150 mg/mL of the anti-PD-1 antibody; (b) about 20 mM L-histidine; (c) about 250 mM sucrose; (d) about 0.05% w/v polysorbate 80; (e) about 50 μM pentetic acid; (f) about 5 mM methionine; and (g) about 0.0182 mg/mL rHuPH20.

III.G. Additional Therapeutic Agents

In some aspects, the pharmaceutical composition further comprises a second therapeutic agent (e.g., an anti-PD-1 antibody and an additional therapeutic agent, or an anti-PD-L1 antibody and an additional therapeutic agent). In some aspects, the pharmaceutical composition further comprises a third therapeutical agent. The additional therapeutic agent can comprise any therapy for the treatment of a tumor in a subject and/or any standard-of-care therapy, as disclosed herein. In some aspects, the additional therapeutic agent comprises a second antibody. In some aspects, the additional therapeutic agent comprises an antibody or antigen-binding portion thereof that specifically binds CTLA-4, LAG-3, TIGIT, TIM3, NKG2a, OX40, ICOS, MICA, CD137, KIR, TGFβ, IL-10, IL-8, B7-H4, Fas ligand, CXCR4, mesothelin, CD27, GITR, or any combination thereof. In some aspects, the second therapeutic agent, the third therapeutic agent, or both comprises IL-2 (e.g., bempegaldesleukin). In some aspects, the second therapeutic agent, the third therapeutic agent, or both comprises IL12-Fc (e.g., BMS-986415).

In some aspects, the antibody is a multispecific antibody. In some aspects, the antibody is a bispecific antibody. In some aspects, the antibody is a trispecific antibody. In some aspects, the antibody specifically binds (i) PD-1 and (ii) a second antigen. In some aspects, the antibody specifically binds (i) PD-1, (ii) a second antigen, and (iii) a third antigen. In some aspects, the antibody specifically binds (i) PD-L1 and (ii) a second antigen. In some aspects, the antibody specifically binds (i) PD-L1 (ii) a second antigen, and (iii) a third antigen. In some aspects, the second antigen and third antigen are the same. In some aspects, the second antigen and third antigen are different. In some aspects, the second antigen is CD3.

In some aspects, the antibody specifically binds (i) TIGIT and (ii) an inhibitory receptor expressed on T cells, NK cells, or both. In some aspects, the antibody specifically binds (i) CD40 and (ii) CD20.

In some aspects, the second antibody comprises an anti-CTLA-4 antibody. The anti-CTLA-4 antibody can be any antibody or an antigen-binding portion thereof that binds CTLA-4 and inhibits its activity. In some aspects, the anti-CTLA-4 antibody is any anti-CTLA-4 antibody disclosed herein. In some aspects, the second antibody comprises tremelimumab. In some aspects, the second antibody comprises ipilimumab.

In some aspects, the second antibody comprises an anti-LAG3 antibody. The anti-LAG3 antibody can be any antibody or an antigen-binding portion thereof that binds LAG-3 and inhibits its activity. In some aspects, the anti-LAG3 antibody comprises any anti-LAG3 antibody disclosed herein. In some aspects, the second antibody comprises 25F7.

In some aspects, the second antibody comprises an anti-CD137 antibody. The anti-CD137 antibody can be any antibody or an antigen-binding portion thereof that binds CD137 and inhibits its activity. In some aspects, the anti-CD137 antibody comprises any anti-CD137 antibody disclosed herein. In some aspects, the second antibody comprises urelumab.

In some aspects, the second antibody comprises an anti-KIR antibody. The anti-KIR antibody comprises any antibody or an antigen-binding portion thereof that binds KIR and inhibits its activity. In some aspects, the anti-KIR antibody comprises any anti-KIR antibody disclosed herein. In some aspects, the second antibody comprises lirilumab.

In some aspects, the second antibody comprises an anti-GITR antibody. The anti-GITR antibody can be any antibody or an antigen-binding portion thereof that binds GITR and inhibits its activity. In some aspects, the anti-GITR antibody comprises any anti-GITR antibody disclosed herein. In some aspects, the second antibody comprises MK4166. In some aspects, the second antibody comprises TRX518.

In some aspects, the second antibody comprises an anti-CD96 antibody. In some aspects, the second antibody comprises an anti-TIM3 antibody. In some aspects, the second antibody comprises an anti-VISTA antibody. In some aspects, the second antibody comprises an anti-NKG2a antibody. In some aspects, the second antibody comprises an anti-ICOS antibody. In some aspects, the second antibody comprises an anti-OX40 antibody. In some aspects, the second antibody comprises an anti-IL8 antibody, such as HuMax®-IL8 (BMS-986253).

III.G.1. Anti-CTLA-4 Antibodies

In some aspects, the second antibody comprises an anti-CTLA-4 antibody. Anti-CTLA-4 antibodies that are known in the art can be used in the compositions and methods of the present disclosure. Anti-CTLA-4 antibodies of the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. No. 6,984,720. Other anti-CTLA-4 monoclonal antibodies have been described in, for example, U.S. Pat. Nos. 5,977, 318, 6,051,227, 6,682,736, and 7,034,121 and International Publication Nos. WO 2012/122444, WO 2007/113648, WO 2016/196237, and WO 2000/037504, each of which is incorporated by reference herein in its entirety. The anti-CTLA-4 human monoclonal antibodies disclosed in U.S. Pat. No. 6,984,720 have been demonstrated to exhibit one or more of the following characteristics: (a) binds specifically to human CTLA-4 with a binding affinity reflected by an equilibrium association constant ($K_a$) of at least about $10^7$ $M^{-1}$, or about 109 $M^{-1}$, or about $10^{10}$ $M^{-1}$ to $10^{11}$ $M^{-1}$ or higher, as determined by Biacore analysis; (b) a kinetic association constant (ka) of at least about $10^3$, about $10^4$, or about $10^5$ $m^{-1}$ $s^{-1}$; (c) a kinetic disassociation constant (kd) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies useful for the present invention include monoclonal antibodies that bind specifically to human CTLA-4 and exhibit at least one, at least two, or at least three of the preceding characteristics.

In certain aspects, the CTLA-4 antibody is selected from the group consisting of ipilimumab (also known as YER-VOY®, MDX-010, 10D1; see U.S. Pat. No. 6,984,720), MK-1308 (Merck), AGEN-1884 (Agenus Inc.; see WO 2016/196237), and tremelimumab (AstraZeneca; also known as ticilimumab, CP-675,206; see WO 2000/037504 and Ribas, *Update Cancer Ther.* 2(3): 133-39 (2007)). In particular aspects, the anti-CTLA-4 antibody is ipilimumab.

In particular aspects, the CTLA-4 antibody is ipilimumab for use in the compositions and methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

In particular aspects, the CTLA-4 antibody is tremelimumab. In particular aspects, the CTLA-4 antibody is MK-1308. In particular aspects, the CTLA-4 antibody is AGEN-1884.

In some aspects, the CTLA-4 antibody is nonfucosylated or hypofucosylated. In some aspects, the CTLA-4 antibody exhibits enhanced ADCC and/or ADCP activity. In some aspects, the CTLA-4 antibody is BMS-986218, as described in PCT/US18/19868.

Anti-CTLA-4 antibodies usable in the disclosed compositions and methods also include isolated antibodies that bind specifically to human CTLA-4 and cross-compete for binding to human CTLA-4 with any anti-CTLA-4 antibody disclosed herein, e.g., ipilimumab and/or tremelimumab. In some aspects, the anti-CTLA-4 antibody binds the same epitope as any of the anti-CTLA-4 antibodies described herein, e.g., ipilimumab and/or tremelimumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., ipilimumab and/or tremelimumab, by virtue of their binding to the same epitope region of CTLA-4. Cross-competing antibodies can be readily identified based on their ability to cross-compete with ipilimumab and/or tremelimumab in standard CTLA-4 binding assays such as Biacore analysis, ELISA assays or flow cytometry (see, e.g., WO 2013/173223).

In certain aspects, the antibodies that cross-compete for binding to human CTLA-4 with, or bind to the same epitope region of human CTLA-4 antibody as, ipilimumab and/or tremelimumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-CTLA-4 antibodies usable in the compositions and methods of the disclosed invention also include antigen-binding portions of the above antibodies. It has been amply demonstrated that the antigen-binding function of an antibody can be performed by fragments of a full-length antibody.

In some aspects, an anti-CTLA-4 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-CTLA-4 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-CTLA-4 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-CTLA-4 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-CTLA-4 antibody; and (h) about 2000 U/mL rHuPH20.

Anti-CTLA-4 antibodies suitable for use in the disclosed methods or compositions are antibodies that bind to CTLA-4 with high specificity and affinity, block the activity of CTLA-4, and disrupt the interaction of CTLA-4 with a human B7 receptor. In any of the compositions or methods disclosed herein, an anti-CTLA-4 "antibody" includes an antigen-binding portion or fragment that binds to CTLA-4 and exhibits the functional properties similar to those of whole antibodies in inhibiting the interaction of CTLA-4 with a human B7 receptor and up-regulating the immune system. In certain aspects, the anti-CTLA-4 antibody or antigen-binding portion thereof cross-competes with ipilimumab and/or tremelimumab for binding to human CTLA-4.

In some aspects, the antibody is a multispecific antibody, e.g., a bispecific antibody, that specifically (i) CTLA-4 and (ii) a second antigen. In some aspects, the antibody is a multispecific antibody, e.g., a bispecific antibody, that specifically (i) CTLA-4 and (ii) CD3.

III.G.2. Anti-LAG-3 Antibodies

In some aspects, the second antibody comprises an anti-LAG-3 antibody, e.g., relatlimab. Anti-LAG-3 antibodies of the instant disclosure bind to human LAG-3. Antibodies that bind to LAG-3 have been disclosed in Int'l Publ. No. WO/2015/042246 and U.S. Publ. Nos. 2014/0093511 and 2011/0150892, each of which is incorporated by reference herein in its entirety.

An exemplary LAG-3 antibody useful in the present disclosure is 25F7 (described in U.S. Publ. No. 2011/0150892). An additional exemplary LAG-3 antibody useful in the present disclosure is BMS-986016 (relatlimab). In some aspects, an anti-LAG-3 antibody useful in the present disclosure cross-competes with 25F7 or BMS-986016. In some aspects, an anti-LAG-3 antibody useful in the present disclosure binds to the same epitope as 25F7 or BMS-986016. In some aspects, an anti-LAG-3 antibody comprises six CDRs of 25F7 or BMS-986016.

Other art-recognized anti-LAG-3 antibodies that can be used in the methods and/or compositions of the disclosure include IMP731 (H5L7BW) described in US 2011/007023, MK-4280 (28G-10, favezelimab) described in WO2016028672 and U.S. Publication No. 2020/0055938, REGN3767 (fianlimab) described in Burova E, et al., J. Immunother. Cancer (2016); 4(Supp. 1):P195 and U.S. Pat. No. 10,358,495, humanized BAP050 described in WO2017/019894, GSK2831781, IMP-701 (LAG525; ieramilimab) described in U.S. Pat. No. 10,711,060 and U.S. Publ. No. 2020/0172617, aLAG3(0414), aLAG3(0416), Sym022, TSR-033, TSR-075, XmAb841 (previously XmAb22841), MGD013 (tebotelimab), B1754111, FS118, P 13B02-30, AVA-017, AGEN1746, R07247669, INCAGN02385, IBI-110, EMB-02, IBI-323, LBL-007, and ABL501. These and other anti-LAG-3 antibodies useful in the claimed invention can be found in, for example: U.S. Pat. No. 10,188,730, WO 2016/028672, WO 2017/106129, WO2017/062888, WO2009/044273, WO2018/069500, WO2016/126858, WO2014/179664, WO2016/200782, WO2015/200119, WO2017/019846, WO2017/198741, WO2017/220555, WO2017/220569, WO2018/071500, WO2017/015560, WO2017/025498, WO2017/087589, WO2017/087901, WO2018/083087, WO2017/149143, WO2017/219995, US2017/0260271, WO2017/086367, WO2017/086419, WO2018/034227, WO2018/185046, WO2018/185043, WO2018/217940, WO19/011306, WO2018/208868, WO2014/140180, WO2018/201096, WO2018/204374, and WO2019/018730. The contents of each of these references are incorporated by reference in their entirety.

Anti-LAG-3 antibodies that can be used in the methods and/or compositions of the disclosure also include isolated antibodies that bind specifically to human LAG-3 and cross-compete for binding to human LAG-3 with any anti-LAG-3 antibody disclosed herein, e.g., relatlimab. In some aspects, the anti-LAG-3 antibody binds the same epitope as any of the anti-LAG-3 antibodies described herein, e.g., relatlimab.

In some aspects, the antibodies that cross-compete for binding to human LAG-3 with, or bind to the same epitope region as, any anti-LAG-3 antibody disclosed herein, e.g., relatlimab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

The ability of antibodies to cross-compete for binding to an antigen indicates that the antibodies bind to the same epitope region of the antigen and sterically hinder the binding of other cross-competing antibodies to that particular epitope region. These cross-competing antibodies are expected to have functional properties very similar those of the reference antibody, e.g., relatlimab, by virtue of their binding to the same epitope region. Cross-competing antibodies can be readily identified based on their ability to cross-compete in standard binding assays such as Biacore analysis, ELISA assays or flow cytometry (see, e.g., WO 2013/173223).

Anti-LAG-3 antibodies that can be used in the methods and/or compositions of the disclosure also include antigen-binding portions of any of the above full-length antibodies.

It has been amply demonstrated that the antigen-binding function of an antibody can be performed by fragments of a full-length antibody.

In some aspects, the anti-LAG-3 antibody is a full-length antibody.

In some aspects, the anti-LAG-3 antibody is a monoclonal, human, humanized, chimeric, or multispecific antibody. In some aspects, the multispecific antibody is a dual-affinity re-targeting antibody (DART), a DVD-Ig, or bispecific antibody.

In some aspects, the anti-LAG-3 antibody is a F(ab')2 fragment, a Fab' fragment, a Fab fragment, a Fv fragment, a scFv fragment, a dsFv fragment, a dAb fragment, or a single chain binding polypeptide.

In some aspects, the anti-LAG-3 antibody is BMS-986016 (relatlimab), IMP731 (H5L7BW), MK4280 (28G-10, favezelimab), REGN3767 (fianlimab), GSK2831781, humanized BAP050, IMP-701 (LAG525, ieramilimab), aLAG3(0414), aLAG3(0416), Sym022, TSR-033, TSR-075, XmAb841 (XmAb22841), MGD013 (tebotelimab), BI754111, FS118, P 13B02-30, AVA-017, 25F7, AGEN1746, R07247669, INCAGN02385, IBI-110, EMB-02, IBI-323, LBL-007, ABL501, or comprises an antigen binding portion thereof.

In some aspects, the anti-LAG-3 antibody is relatlimab.

In some aspects, the anti-LAG-3 antibody is MGD013 (tebotelimab), which is a bispecific PD-1×LAG-3 DART.

In some aspects, the anti-LAG-3 antibody is REGN3767 (fianlimab).

In some aspects, the anti-LAG-3 antibody is LAG525 (ieramilimab).

In some aspects, the anti-LAG-3 antibody is MK4280 (favezelimab).

In some aspects, an anti-LAG-3 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-LAG-3 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) relatlimab. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-LAG-3 antibody; and (h) about 2000 U/mL rHuPH20. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) relatlimab; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-LAG-3 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) relatlimab. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-LAG-3 antibody; and (h) about 2000 U/mL rHuPH20. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) relatlimab; and (h) about 2000 U/mL rHuPH20.

An exemplary LAG-3 antibody useful in the present disclosure is 25F7 (described in U.S. Publ. No. 2011/0150892). An additional exemplary LAG-3 antibody useful in the present disclosure is BMS-986016. In one aspect, an anti-LAG-3 antibody useful for the composition cross-competes with 25F7 or BMS-986016. In another aspect, an anti-LAG-3 antibody useful for the composition binds to the same epitope as 25F7 or BMS-986016. In other aspects, an anti-LAG-3 antibody comprises six CDRs of 25F7 or BMS-986016.

In some aspects, the antibody is a multispecific antibody, e.g., a bispecific antibody, that specifically (i) LAG-3 and (ii) a second antigen. In some aspects, the antibody is a multispecific antibody, e.g., a bispecific antibody, that specifically (i) LAG-3 and (ii) CD3.

III.G.3. Anti-CD137 Antibodies

In some aspects, the second antibody comprises an anti-CD137 antibody. Anti-CD137 antibodies specifically bind to and activate CD137-expressing immune cells, stimulating an immune response, in particular a cytotoxic T cell response, against tumor cells. Antibodies that bind to CD137 have been disclosed in U.S. Publ. No. 2005/0095244 and U.S. Pat. Nos. 7,288,638, 6,887,673, 7,214,493, 6,303,121, 6,569,997, 6,905,685, 6,355,476, 6,362,325, 6,974,863, and 6,210,669.

In some aspects, an anti-CD137 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-CD137 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-CD137 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-CD137 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-CD137 antibody; and (h) about 2000 U/mL rHuPH20.

In some aspects, the anti-CD137 antibody is urelumab (BMS-663513), described in U.S. Pat. No. 7,288,638 (20H4.9-IgG4 [10C7 or BMS-663513]). In some aspects, the anti-CD137 antibody is BMS-663031 (20H4.9-IgG1), described in U.S. Pat. No. 7,288,638. In some aspects, the anti-CD137 antibody is 4E9 or BMS-554271, described in U.S. Pat. No. 6,887,673. In some aspects, the anti-CD137 antibody is an antibody disclosed in U.S. Pat. Nos. 7,214, 493; 6,303,121; 6,569,997; 6,905,685; or 6,355,476. In some aspects, the anti-CD137 antibody is 1D8 or BMS-469492; 3H3 or BMS-469497; or 3E1, described in U.S. Pat. No. 6,362,325. In some aspects, the anti-CD137 antibody is an antibody disclosed in issued U.S. Pat. No. 6,974,863 (such as 53A2). In some aspects, the anti-CD137 antibody is an antibody disclosed in issued U.S. Pat. No. 6,210,669 (such as 1D8, 3B8, or 3E1). In some aspects, the antibody is Pfizer's PF-05082566 (PF-2566). In other aspects, an anti-CD137 antibody useful for the invention cross-competes with the anti-CD137 antibodies disclosed herein. In some aspects, an anti-CD137 antibody binds to the same epitope as the anti-CD137 antibody disclosed herein. In other aspects, an anti-CD137 antibody useful in the disclosure comprises six CDRs of the anti-CD137 antibodies disclosed herein.

In some aspects, the antibody is a multispecific antibody, e.g., a bispecific antibody, that specifically (i) CD137 and (ii) a second antigen. In some aspects, the antibody is a multispecific antibody, e.g., a bispecific antibody, that specifically (i) CD137 and (ii) CD3.

III.G.4. Anti-KIR Antibodies

In some aspects, the second antibody comprises an anti-KIR3 antibody. Antibodies that bind specifically to KIR block the interaction between Killer-cell immunoglobulin-like receptors (KIR) on NK cells with their ligands. Blocking these receptors facilitates activation of NK cells and, potentially, destruction of tumor cells by the latter. Examples of anti-KIR antibodies have been disclosed in Int'l Publ. Nos. WO/2014/055648, WO 2005/003168, WO 2005/009465, WO 2006/072625, WO 2006/072626, WO 2007/042573, WO 2008/084106, WO 2010/065939, WO 2012/071411 and WO/2012/160448.

In some aspects, an anti-KIR antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) an anti-KIR antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; (g) an anti-KIR antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) an anti-KIR antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; (g) an anti-KIR antibody; and (h) about 2000 U/mL rHuPH20.

One anti-KIR antibody useful in the present disclosure is lirilumab (also referred to as BMS-986015, IPH2102, or the S241P variant of 1-7F9), first described in Int'l Publ. No. WO 2008/084106. An additional anti-KIR antibody useful in the present disclosure is 1-7F9 (also referred to as IPH2101), described in Int'l Publ. No. WO 2006/003179. In one aspect, an anti-KIR antibody for the present composition cross competes for binding to KIR with lirilumab or I-7F9. In another aspect, an anti-KIR antibody binds to the same epitope as lirilumab or I-7F9. In other aspects, an anti-KIR antibody comprises six CDRs of lirilumab or I-7F9.

In some aspects, the antibody is a multispecific antibody, e.g., a bispecific antibody, that specifically (i) KIR and (ii) a second antigen. In some aspects, the antibody is a multispecific antibody, e.g., a bispecific antibody, that specifically (i) KIR and (ii) CD3.

III.G.5. Anti-GITR antibodies

In some aspects, the second antibody comprises an anti-GITR antibody. Anti-GITR antibodies comprises any anti-GITR antibody that binds specifically to human GITR target and activates the glucocorticoid-induced tumor necrosis factor receptor (GITR). GITR is a member of the TNF receptor superfamily that is expressed on the surface of multiple types of immune cells, including regulatory T cells, effector T cells, B cells, natural killer (NK) cells, and activated dendritic cells ("anti-GITR agonist antibodies"). Specifically, GITR activation increases the proliferation and function of effector T cells, as well as abrogating the suppression induced by activated T regulatory cells. In addition, GITR stimulation promotes anti-tumor immunity by increasing the activity of other immune cells such as NK cells, antigen presenting cells, and B cells. Examples of anti-GITR antibodies have been disclosed in Int'l Publ. Nos. WO/2015/031667, WO2015/184,099, WO2015/026,684, WO11/028683 and WO/2006/105021, U.S. Pat. Nos. 7,812, 135 and 8,388,967 and U.S. Publ. Nos. 2009/0136494, 2014/0220002, 2013/0183321 and 2014/0348841.

In some aspects, an anti-GITR antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) an anti-GITR antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; (g) an anti-GITR antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) an anti-GITR antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; (g) an anti-GITR antibody; and (h) about 2000 U/mL rHuPH20.

In one aspect, an anti-GITR antibody useful in the present disclosure is TRX518 (described in, for example, Schaer et al. Curr Opin Immunol. (2012) April; 24(2): 217-224, and WO/2006/105021). In another aspect, the anti-GITR antibody is selected from MK4166, MK1248, and antibodies described in WO11/028683 and U.S. Pat. No. 8,709,424, and comprising, e.g., a VH chain comprising SEQ ID NO: 104 and a VL chain comprising SEQ ID NO: 105 (wherein the SEQ ID NOs are from WO11/028683 or U.S. Pat. No. 8,709,424). In certain aspects, an anti-GITR antibody is an anti-GITR antibody that is disclosed in WO2015/031667, e.g., an antibody comprising VH CDRs 1-3 comprising SEQ ID NOs: 31, 71 and 63 of WO2015/031667, respectively, and VL CDRs 1-3 comprising SEQ ID NOs: 5, 14 and 30 of WO2015/031667. In certain aspects, an anti-GITR antibody is an anti-GITR antibody that is disclosed in WO2015/184099, e.g., antibody Hum231 #1 or Hum231 #2, or the CDRs thereof, or a derivative thereof (e.g., pab1967, pab1975 or pab1979). In certain aspects, an anti-GITR antibody is an anti-GITR antibody that is disclosed in JP2008278814, WO09/009116, WO2013/039954, US20140072566, US20140072565, US20140065152, or WO2015/026684, or is INBRX-110 (INHIBRx), LKZ-145 (Novartis), or MEDI-1873 (MedImmune). In certain aspects, an anti-GITR antibody is an anti-GITR antibody that is described in PCT/US2015/033991 (e.g., an antibody comprising the variable regions of 28F3, 18E10 or 19D3).

In certain aspects, the anti-GITR antibody cross-competes with an anti-GITR antibody described herein, e.g., TRX518, MK4166 or an antibody comprising a VH domain and a VL domain amino acid sequence described herein. In some aspects, the anti-GITR antibody binds the same epitope as that of an anti-GITR antibody described herein, e.g., TRX518, MK4166 or an antibody comprising a VH domain and a VL domain amino acid sequence described herein. In certain aspects, the anti-GITR antibody comprises the six CDRs of TRX518, MK4166 or those of an antibody comprising a VH domain and a VL domain amino acid sequence described herein.

In some aspects, the antibody is a multispecific antibody, e.g., a bispecific antibody, that specifically (i) GITR and (ii) a second antigen. In some aspects, the antibody is a multispecific antibody, e.g., a bispecific antibody, that specifically (i) GITR and (ii) CD3.

III.G.6. Anti-TIM3 Antibodies

In some aspects, the second antibody comprises an anti-TIM3 antibody. In some aspects, the anti-TIM3 antibody comprises selected from the anti-TIM3 antibodies disclosed in Int'l Publ. Nos. WO2018013818, WO/2015/117002 (e.g., MGB453, Novartis), WO/2016/161270 (e.g., TSR-022, Tesaro/AnaptysBio), WO2011155607, WO2016/144803 (e.g., STI-600, Sorrento Therapeutics), WO2016/071448, WO17055399; WO17055404, WO17178493, WO18036561, WO18039020 (e.g., Ly-3221367, Eli Lilly), WO2017205721, WO17079112; WO17178115; WO17079116, WO11159877, WO13006490, WO2016068802, WO2016068803, WO2016/111947, WO/2017/031242.

In some aspects, an anti-TIM3 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-TIM3 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-TIM3 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-TIM3 antibody. In certain aspects, the pharmaceutical composition comprises: (a)

about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-TIM3 antibody; and (h) about 2000 U/mL rHuPH20.

In some aspects, the antibody is a multispecific antibody, e.g., a bispecific antibody, that specifically (i) TIM-3 and (ii) a second antigen. In some aspects, the antibody is a multispecific antibody, e.g., a bispecific antibody, that specifically (i) TIM-3 and (ii) CD3.

III.G.7. Anti-OX40 Antibodies

In some aspects, the second antibody comprises an anti-OX40 (also known as CD134, TNFRSF4, ACT35 and/or TXGP1L) antibody. In some aspects, the anti-OX40 antibody comprises BMS-986178 (Bristol-Myers Squibb Company), described in Int'l Publ. No. WO20160196228. In some aspects, the anti-OX40 antibody comprises selected from the anti-OX40 antibodies described in Int'l Publ. Nos. WO95012673, WO199942585, WO14148895, WO15153513, WO15153514, WO13038191, WO16057667, WO03106498, WO12027328, WO13028231, WO16200836, WO 17063162, WO17134292, WO 17096179, WO 17096281, and WO 17096182.

In some aspects, an anti-OX40 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-OX40 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-OX40 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-OX40 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-OX40 antibody; and (h) about 2000 U/mL rHuPH20.

In some aspects, the antibody is a multispecific antibody, e.g., a bispecific antibody, that specifically (i) OX40 and (ii) a second antigen. In some aspects, the antibody is a multispecific antibody, e.g., a bispecific antibody, that specifically (i) OX40 and (ii) CD3.

III.G.8. Anti-NKG2A Antibodies

In some aspects, the second antibody comprises an anti-NKG2A antibody. NKG2A is a member of the C-type lectin receptor family that is expressed on natural killer (NK) cells and a subset of T lymphocytes. Specifically, NKG2A primarily expressed on tumor infiltrating innate immune effector NK cells, as well as on some CD8$^+$ T cells. Its natural ligand human leukocyte antigen E (HLA-E) is expressed on solid and hematologic tumors. NKG2A is an inhibitory receptor that blinds HLA-E.

In some aspects, an anti-NKG2A antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-NKG2A antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-NKG2A antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-NKG2A antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-NKG2A antibody; and (h) about 2000 U/mL rHuPH20.

In some aspects, the anti-NKG2A antibody comprises BMS-986315, a human monoclonal antibody that blocks the interaction of NKG2A to its ligand HLA-E, thus allowing activation of an anti-tumor immune response. In some aspects, the anti-NKG2A antibody comprises a checkpoint inhibitor that activates T cells, NK cells, and/or tumor-infiltrating immune cells. In some aspects, the anti-NKG2A antibody comprises selected from the anti-NKG2A antibodies described in, for example, WO 2006/070286 (Innate Pharma S.A.; University of Genova); U.S. Pat. No. 8,993,319 (Innate Pharma S.A.; University of Genova); WO 2007/042573 (Innate Pharma S/A; Novo Nordisk A/S; University of Genova); U.S. Pat. No. 9,447,185 (Innate Pharma S/A; Novo Nordisk A/S; University of Genova); WO 2008/009545 (Novo Nordisk A/S); U.S. Pat. Nos. 8,206,709; 8,901,283; 9,683,041 (Novo Nordisk A/S); WO 2009/092805 (Novo Nordisk A/S); U.S. Pat. Nos. 8,796,427 and 9,422,368 (Novo Nordisk A/S); WO 2016/134371 (Ohio State Innovation Foundation); WO 2016/032334 (Janssen); WO 2016/041947 (Innate); WO 2016/041945 (Academisch Ziekenhuis Leiden H.O.D.N. LUMC); WO 2016/041947 (Innate Pharma); and WO 2016/041945 (Innate Pharma).

In some aspects, the antibody is a multispecific antibody, e.g., a bispecific antibody, that specifically (i) NKG2A and (ii) a second antigen. In some aspects, the antibody is a multispecific antibody, e.g., a bispecific antibody, that specifically (i) NKG2A and (ii) CD3.

III.G.9. Anti-ICOS Antibodies

In some aspects, the second antibody comprises an anti-ICOS antibody. ICOS is an immune checkpoint protein that is a member of the CD28-superfamily. ICOS is a 55-60 kDa type I transmembrane protein that is expressed on T cells after T cell activation and co-stimulates T-cell activation after binding its ligand, ICOS-L (B7H2). ICOS is also known as inducible T-cell co-stimulator, CVID1, AILIM, inducible costimulator, CD278, activation-inducible lymphocyte immunomediatory molecule, and CD278 antigen.

In some aspects, an anti-ICOS antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-ICOS antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-ICOS antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-ICOS antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-ICOS antibody; and (h) about 2000 U/mL rHuPH20.

In some aspects, the anti-ICOS antibody comprises BMS-986226, a humanized IgG monoclonal antibody that binds to and stimulates human ICOS. In some aspects, the anti-ICOS antibody comprises selected from anti-ICOS antibodies described in, for example, WO 2016/154177 (Jounce Therapeutics, Inc.), WO 2008/137915 (MedImmune), WO 2012/131004 (INSERM, French National Institute of Health and Medical Research), EP3147297 (INSERM, French National Institute of Health and Medical Research), WO 2011/041613 (Memorial Sloan Kettering Cancer Center), EP 2482849 (Memorial Sloan Kettering Cancer Center), WO 1999/15553 (Robert Koch Institute), U.S. Pat. Nos. 7,259,247 and 7,722,872 (Robert Kotch Institute); WO 1998/038216 (Japan Tobacco Inc.), U.S. Pat. Nos. 7,045,615; 7,112,655, and 8,389,690 (Japan Tobacco Inc.), U.S. Pat. Nos. 9,738,718 and 9,771,424 (GlaxoSmithKline), and WO 2017/220988 (Kymab Limited).

In some aspects, the antibody is a multispecific antibody, e.g., a bispecific antibody, that specifically (i) ICOS and (ii) a second antigen. In some aspects, the antibody is a multispecific antibody, e.g., a bispecific antibody, that specifically (i) ICOS and (ii) CD3.

III.G.10. Anti-TIGIT Antibodies

In some aspects, the second antibody comprises an anti-TIGIT antibody. In some aspects, the anti-TIGIT antibody comprises BMS-986207. In some aspects, the anti-TIGIT antibody comprises clone 22G2, as described in WO 2016/106302. In some aspects, the anti-TIGIT antibody comprises MTIG7192A/RG6058/RO7092284, or clone 4.1D3, as described in WO 2017/053748. In some aspects, the anti-TIGIT antibody comprises selected from the anti-TIGIT antibodies described in, for example, WO 2016/106302 (Bristol-Myers Squibb Company) and WO 2017/053748 (Genentech).

In some aspects, an anti-TIGIT antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-TIGIT antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-TIGIT antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-TIM3 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-TIGIT antibody; and (h) about 2000 U/mL rHuPH20.

In some aspects, the antibody is a multispecific antibody, e.g., a bispecific antibody, that specifically (i) TIGIT and (ii) a second antigen. In some aspects, the antibody comprises a TIGIT bispecific antibody, which specifically binds (i) TIGIT; and (ii) an inhibitory receptor expressed on T cells, NK cells, or both T cells and NK cells. In some aspects, the antibody is a multispecific antibody, e.g., a bispecific antibody, that specifically (i) TIGIT and (ii) CD3.

III.G.11. Anti-IL-12 Antibodies

In some aspects, the second antibody comprises an anti-IL-12 antibody. In certain aspects, the pharmaceutical composition comprises: (a) an anti-IL-12 antibody; (b) about 20 mM histidine; (c) about 250 mM sucrose; (d) about 0.05% w/v polysorbate 80; (e) about 50 µM pentetic acid; and (f) about 5 mM methionine. In certain aspects, the pharmaceutical composition comprises: (a) an anti-IL-12 antibody; (b) about 20 mM histidine; (c) about 250 mM sucrose; (d) about 0.05% w/v polysorbate 80; (e) about 50 µM pentetic acid; (f) about 5 mM methionine; and (g) about 2000 U/mL rHuPH20.

In some aspects, an anti-IL-12 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-IL-12 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-IL-12 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-IL-12 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-IL-12 antibody; and (h) about 2000 U/mL rHuPH20.

In some aspects, the antibody is a multispecific antibody, e.g., a bispecific antibody, that specifically (i) IL-12 and (ii) a second antigen. In some aspects, the antibody is a multispecific antibody, e.g., a bispecific antibody, that specifically (i) IL-12 and (ii) CD3.

III.G.12. Anti-IL-13 Antibodies

In some aspects, the second antibody comprises an anti-IL-13 antibody. In certain aspects, the pharmaceutical composition comprises: (a) an anti-IL-13 antibody; (b) about 20 mM histidine; (c) about 250 mM sucrose; (d) about 0.05% w/v polysorbate 80; (e) about 50 µM pentetic acid; and (f) about 5 mM methionine. In certain aspects, the pharmaceutical composition comprises: (a) an anti-IL-13 antibody; (b)

about 20 mM histidine; (c) about 250 mM sucrose; (d) about 0.05% w/v polysorbate 80; (e) about 50 µM pentetic acid; (f) about 5 mM methionine; and (g) about 2000 U/mL rHuPH20.

In some aspects, an anti-IL-13 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-IL-13 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-IL-13 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-IL-13 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; (g) an anti-IL-13 antibody; and (h) about 2000 U/mL rHuPH20.

In some aspects, the antibody is a multispecific antibody, e.g., a bispecific antibody, that specifically (i) IL-13 and (ii) a second antigen. In some aspects, the antibody is a multispecific antibody, e.g., a bispecific antibody, that specifically (i) IL-13 and (ii) CD3.

III.G.13. Anti-IL-15 Antibodies

In some aspects, the second antibody comprises an anti-IL-15 antibody. In certain aspects, the pharmaceutical composition comprises: (a) an anti-IL-15 antibody; (b) about 20 mM histidine; (c) about 250 mM sucrose; (d) about 0.05% w/v polysorbate 80; (e) about 50 µM pentetic acid; and (f) about 5 mM methionine. In certain aspects, the pharmaceutical composition comprises: (a) an anti-IL-15 antibody; (b) about 20 mM histidine; (c) about 250 mM sucrose; (d) about 0.05% w/v polysorbate 80; (e) about 50 µM pentetic acid; (f) about 5 mM methionine; and (g) about 2000 U/mL rHuPH20.

In some aspects, an anti-IL-15 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; and (g) an anti-IL-15 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 µM pentetic acid; (f) about 5 mM methionine; (g) an anti-IL-15 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 µM pentetic acid; (f) about 5 mM methionine; and (g) an anti-IL-15 antibody. In certain aspects, the pharmaceutical composition comprises: (a) about 150 mg/mL of nivolumab; (b) about 20 mM histidine;

(c) about 250 mM sucrose; (d) about 0.05% w/v polysorbate 80; (e) about 50 μM pentetic acid; (f) about 5 mM methionine; (g) an anti-IL-15 antibody; and (h) about 2000 U/mL rHuPH20.

In some aspects, the antibody is a multispecific antibody, e.g., a bispecific antibody, that specifically (i) IL-15 and (ii) a second antigen. In some aspects, the antibody is a multispecific antibody, e.g., a bispecific antibody, that specifically (i) IL-15 and (ii) CD3.

III.G.14. Anti-SIRPalpha Antibodies

In some aspects, the second antibody comprises an anti-SIRPalpha antibody. In certain aspects, the pharmaceutical composition comprises: (a) an anti-SIRPalpha antibody; (b) about 20 mM histidine; (c) about 250 mM sucrose; (d) about 0.05% w/v polysorbate 80; (e) about 50 μM pentetic acid; and (f) about 5 mM methionine. In certain aspects, the pharmaceutical composition comprises: (a) an anti-SIRPalpha antibody; (b) about 20 nM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In some aspects, an anti-SIRPalpha antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) an anti-SIRPalpha antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; (g) an anti-SIRPalpha antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) an anti-SIRPalpha antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; (g) an anti-SIRPalpha antibody; and (h) about 2000 U/mL rHuPH20.

In some aspects, the antibody is a multispecific antibody, e.g., a bispecific antibody, that specifically (i) SIRPalpha and (ii) a second antigen. In some aspects, the antibody is a multispecific antibody, e.g., a bispecific antibody, that specifically (i) SIRPalpha and (ii) CD3.

III.G.15. Anti-CD47 Antibodies

In some aspects, the second antibody comprises an anti-CD47 antibody. In certain aspects, the pharmaceutical composition comprises: (a) an anti-CD47 antibody; (b) about 20 mM histidine; (c) about 250 mM sucrose; (d) about 0.05% w/v polysorbate 80; (e) about 50 μM pentetic acid; and (f) about 5 mM methionine. In certain aspects, the pharmaceutical composition comprises: (a) an anti-CD47 antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In some aspects, an anti-CD47 antibody can be formulated together with an anti-PD-1 antibody in any one of formulations disclosed herein as a single formulation. In certain aspects, the pharmaceutical composition comprises:

(a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) an anti-CD47 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; (g) an anti-CD47 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) an anti-CD47 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; (g) an anti-CD47 antibody; and (h) about 2000 U/mL rHuPH20.

In some aspects, the antibody is a multispecific antibody, e.g., a bispecific antibody, that specifically (i) CD47 and (ii) a second antigen. In some aspects, the antibody is a multispecific antibody, e.g., a bispecific antibody, that specifically (i) CD47 and (ii) CD3.

III.G.16. Anti-CCR8 Antibodies

In some aspects, the second antibody comprises an anti-CCR8 antibody. In certain aspects, the pharmaceutical composition comprises: (a) an anti-CCR8 antibody; (b) about 20 mM histidine; (c) about 250 mM sucrose; (d) about 0.05% w/v polysorbate 80; (e) about 50 μM pentetic acid; and (f) about 5 mM methionine. In certain aspects, the pharmaceutical composition comprises: (a) an anti-CCR8 antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In some aspects, an anti-CCR8 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) an anti-CCR8 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; (g) an anti-CCR8 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) an anti-CCR8 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; (g) an anti-CCR8 antibody; and (h) about 2000 U/mL rHuPH20.

In some aspects, the antibody is a multispecific antibody, e.g., a bispecific antibody, that specifically (i) CCR8 and (ii)

a second antigen. In some aspects, the antibody is a multi-specific antibody, e.g., a bispecific antibody, that specifically (i) CCR8 and (ii) CD3.

III.G.17. Anti-MICA Antibodies

In some aspects, the second antibody comprises an anti-MICA antibody. In certain aspects, the pharmaceutical composition comprises: (a) an anti-MICA antibody; (b) about 20 mM histidine; (c) about 250 mM sucrose; (d) about 0.05% w/v polysorbate 80; (e) about 50 μM pentetic acid; and (f) about 5 mM methionine. In certain aspects, the pharmaceutical composition comprises: (a) an anti-MICA antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In some aspects, an anti-MICA antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) an anti-MICA antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; (g) an anti-MICA antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) an anti-MICA antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; (g) an anti-MICA antibody; and (h) about 2000 U/mL rHuPH20.

In some aspects, the antibody is a multispecific antibody, e.g., a bispecific antibody, that specifically (i) MICA and (ii) a second antigen. In some aspects, the antibody is a multi-specific antibody, e.g., a bispecific antibody, that specifically (i) MICA and (ii) CD3.

III.G.18. Anti-ILT4 Antibodies

In some aspects, the second antibody comprises an anti-ILT4 antibody. In certain aspects, the pharmaceutical composition comprises: (a) an anti-ILT4 antibody; (b) about 20 mM histidine; (c) about 250 mM sucrose; (d) about 0.05% w/v polysorbate 80; (e) about 50 μM pentetic acid; and (f) about 5 mM methionine. In certain aspects, the pharmaceutical composition comprises: (a) an anti-ILT4 antibody; (b) about 20 mM histidine; (c) about 250 mM sucrose; (d) about 0.05% w/v polysorbate 80; (e) about 50 μM pentetic acid; (f) about 5 mM methionine; and (g) about 2000 U/mL rHuPH20.

In some aspects, an anti-ILT4 antibody can be formulated together with an anti-PD-1 antibody in any one of formulations disclosed herein as a single formulation. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; and (g) an anti-ILT4 antibody. In certain aspects, the pharmaceutical composition comprises: (a) about 150 mg/mL of the anti-PD-1 antibody; (b) about 20 mM histidine; (c) about 250 mM sucrose; (d) about 0.05% w/v polysorbate 80; (e) about 50 μM pentetic acid; (f) about 5 mM methionine; (g) an anti-ILT4 antibody; and (h) about 2000 U/mL rHuPH20.

In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; and (g) an anti-ILT4 antibody. In certain aspects, the pharmaceutical composition comprises: (a) about 150 mg/mL of nivolumab; (b) about 20 mM histidine; (c) about 250 mM sucrose; (d) about 0.05% w/v polysorbate 80; (e) about 50 μM pentetic acid; (f) about 5 mM methionine; (g) an anti-ILT4 antibody; and (h) about 2000 U/mL rHuPH20.

In some aspects, the antibody is a multispecific antibody, e.g., a bispecific antibody, that specifically (i) ILT4 and (ii) a second antigen. In some aspects, the antibody is a multi-specific antibody, e.g., a bispecific antibody, that specifically (i) ILT4 and (ii) CD3.

III.G.19. Additional Anti-Cancer Agents

In some aspects, the pharmaceutical composition disclosed herein comprises (i) an anti-PD-1 or an anti-PD-L1 antibody and (ii) an anti-IL-10 antibody. In some aspects, the pharmaceutical composition disclosed herein comprises (i) an anti-PD-1 or an anti-PD-L1 antibody and (ii) a long-acting IL-10 molecule. In some aspects, the long-acting IL-10 molecule comprises an IL-10-Fc fusion molecule. In some aspects, the long-acting IL-10 molecule comprises a Pegylated IL-10, such as AM0010 (ARMO BioSciences).

In some aspects, the pharmaceutical composition disclosed herein comprises (i) an anti-PD-1 or an anti-PD-L1 antibody and (ii) an anti-IL-2 antibody. In some aspects, the pharmaceutical composition disclosed herein comprises (i) an anti-PD-1 or an anti-PD-L1 antibody and (ii) a long-acting IL-2 molecule. In some aspects, the long-acting IL-2 comprises a Pegylated IL-2, such as NKTR-214 (Nektar; see U.S. Pat. No. 8,252,275, WO12/065086 and WO15/125159).

In some aspects, the pharmaceutical composition disclosed herein comprises (i) an anti-PD-1 or an anti-PD-L1 antibody and (ii) an anti-VISTA antibody.

In some aspects, the pharmaceutical composition disclosed herein comprises (i) an anti-PD-1 or an anti-PD-L1 antibody and (ii) an anti-CD96 antibody.

In some aspects, the pharmaceutical composition disclosed herein comprises (i) an anti-PD-1 or an anti-PD-L1 antibody and (ii) an anti-IL-8 antibody, e.g., with HuMax®-IL8.

In some aspects, the pharmaceutical composition disclosed herein comprises (i) an anti-PD-1 or an anti-PD-L1 antibody and (ii) an anti-TGFβ antibody.

In some aspects, the pharmaceutical composition disclosed herein comprises (i) an anti-PD-1 or an anti-PD-L1 antibody and (ii) an anti-B7-H4 antibody. In certain aspects, the anti-B7-H4 antibody is an anti-B7-H4 disclosed in Int'l Publ. No. WO/2009/073533.

In some aspects, the pharmaceutical composition disclosed herein comprises (i) an anti-PD-1 or an anti-PD-L1 antibody and (ii) an anti-Fas ligand antibody. In certain aspects, the anti-Fas ligand antibody is an anti-Fas ligand disclosed in Int'l Publ. No. WO/2009/073533.

In some aspects, the pharmaceutical composition disclosed herein comprises (i) an anti-PD-1 or an anti-PD-L1 antibody and (ii) an anti-CXCR4 antibody. In certain aspects, the anti-CXCR4 antibody is an anti-CXCR4 disclosed in U.S. Publ. No. 2014/0322208 (e.g., Ulocuplumab (BMS-936564)).

In some aspects, the pharmaceutical composition disclosed herein comprises (i) an anti-PD-1 or an anti-PD-L1 antibody and (ii) an anti-mesothelin antibody. In certain aspects, the anti-mesothelin antibody is an anti-mesothelin disclosed in U.S. Pat. No. 8,399,623.

In some aspects, the pharmaceutical composition disclosed herein comprises (i) an anti-PD-1 or an anti-PD-L1 antibody and (ii) an anti-HER2 antibody. In certain aspects, the anti-HER2 antibody is Herceptin (U.S. Pat. No. 5,821, 337), trastuzumab, or ado-trastuzumab emtansine (Kadcyla, e.g., WO/2001/000244).

In some aspects, the pharmaceutical composition disclosed herein comprises (i) an anti-PD-1 or an anti-PD-L1 antibody and (ii) an anti-CD27 antibody. In some aspects, the anti-CD-27 antibody is Varlilumab (also known as "CDX-1127" and "1F5"), which is a human IgG1 antibody that is an agonist for human CD27, as disclosed in, for example, U.S. Pat. No. 9,169,325.

In some aspects, the pharmaceutical composition disclosed herein comprises (i) an anti-PD-1 or an anti-PD-L1 antibody and (ii) an anti-CD73 antibody. In certain aspects, the anti-CD73 antibody is CD73.4.IgG2C219S.IgG1.1f.

In some aspects, the pharmaceutical composition disclosed herein comprises (i) an anti-PD-1 or an anti-PD-L1 antibody and (ii) an anti-MICA/B antibody. In certain aspects, the anti-MICA/B antibody is any antibody or antigen-binding portion thereof that specifically binds human MICA/B, including but not limited to, any anti-MICA/B antibody disclosed in International Publication No. WO 2019/183551, which is incorporated by reference herein in its entirety.

All of the references cited above, as well as all references cited herein, are incorporated herein by reference in their entireties.

The following examples are offered by way of illustration and not by way of limitation.

EXAMPLES

Example 1—Subcutaneous Injection Formulation Development

The present example discusses the development of a stable, robust subcutaneous (SC) formulation of nivolumab and a manufacturing process suitable for commercial scale production. As a part of the formulation studies, the effects of various different pharmaceutically acceptable excipients on the stability of nivolumab were evaluated. Studies were also undertaken to select processing and packaging components compatible with the selected formulation. In addition, use time studies were conducted to support administration of the drug product via subcutaneous injection.

The objectives of these studies conducted for the development of nivolumab SC injection include: 1. identification and development of a stable injectable formulation for nivolumab SC injection that would be suitable for clinical use and eventual commercialization; 2. identification of manufacturing equipment and packaging components that are compatible with nivolumab SC injection; 3. development and optimization of the process used for manufacture of the drug product; 4. manufacture of three batches of nivolumab SC injection for use in long-term stability studies and Phase 3 clinical trials; and 5. transfer of technology for product manufacture to a commercial production facility and manufacture PPQ batches.

Formulation Development

Selection of Buffer System and pH

Previous studies related to the development of an intravenous (IV) formulation for nivolumab evaluated protein stability as a function of solution pH using capillary differential scanning calorimetry (DSC), which measures the thermodynamics of protein unfolding; and further evaluated the physical stability of nivolumab in buffers that would be appropriate for formulation at pH 6.0 and 7.0. Based on the results of the two studies, 20 mM citrate buffer at pH 6.0 was selected for the IV formulation of nivolumab.

Although citrate proved to be a suitable buffer for the IV nivolumab drug product, citrate would not be a preferred buffer for a subcutaneously administered product as, citrate buffer is known to cause stinging and burning upon SC administration.

In an effort to identify other buffers with a target pH of 6.0 suitable for use in an SC formulation, a study was conducted to examine the stability of high concentration (100 mg/mL) nivolumab in a 20 mM histidine buffered formulation at pH values ranging from 5.5 to 6.5. Stability data for samples stored at the stress condition of 40° C. are presented in Table 2. Although rate of formation of high molecular weight species was relatively consistent across the pH range, after two months of storage at 40° C., the level of HMWS was lowest in the pH 6.0 samples. It was also observed that the main peak area by iCIEF was highest for the samples at pH 6.0. Based on the results of these studies, 20 mM histidine buffer at a target pH of 6.0, was selected for the formulation of nivolumab SC injection.

TABLE 2

Effect of Solution pH on the Stability Nivolumab SC Injection Stored for 2 Months at 40° C.

| pH | Time (Months) | pH | Protein Conc. (mg/mL) | HMWS Area % | LMWS Area % | Main Peak Area % by iCIEF | Subvisible Particulate Matter (Particles per Milliliter) | |
|----|----|----|----|----|----|----|----|----|
| | | | | | | | ≥10-μm | ≥25-μm |
| 5.5 | 0 | 5.51 | 102 | 0.65 | 0.00 | 67.0 | 1 | 0 |
| | 1 | 5.49 | 100 | 1.38 | 0.08 | 48.9 | 1 | 0 |
| | 2 | 5.51 | 99 | 2.49 | 0.17 | 27.7 | 5 | 0 |
| 5.7 | 0 | 5.72 | 101 | 0.68 | 0.00 | 66.6 | 3 | 0 |
| | 1 | 5.71 | 99 | 1.32 | 0.07 | 50.3 | 0 | 0 |
| | 2 | 5.73 | 97 | 2.29 | 0.15 | 29.6 | 1 | 0 |
| 6.0 | 0 | 5.96 | 101 | 0.72 | 0.00 | 66.1 | 3 | 0 |
| | 1 | 5.97 | 102 | 1.34 | 0.06 | 49.7 | 1 | 0 |
| | 2 | 5.96 | 103 | 2.16 | 0.12 | 31.8 | 8 | 0 |

TABLE 2-continued

Effect of Solution pH on the Stability Nivolumab SC Injection Stored for 2 Months at 40° C.

| pH | Time (Months) | pH | Protein Conc. (mg/mL) | HMWS Area % | LMWS Area % | Main Peak Area % by iCIEF | Subvisible Particulate Matter (Particles per Milliliter) ≥10-μm | ≥25-μm |
|---|---|---|---|---|---|---|---|---|
| 6.3 | 0 | 6.29 | 102 | 0.76 | 0.00 | 66.6 | 0 | 0 |
| | 1 | 6.29 | 100 | 1.44 | 0.05 | 49.0 | 0 | 0 |
| | 2 | 6.31 | 103 | 2.19 | 0.10 | 30.5 | 4 | 0 |
| 6.5 | 0 | 6.47 | 102 | 0.79 | 0.00 | 66.2 | 1 | 0 |
| | 1 | 6.49 | 101 | 1.53 | 0.05 | 48.4 | 1 | 0 |
| | 2 | 6.47 | 102 | 2.28 | 0.10 | 30.4 | 4 | 0 |

Selection of Formulation Buffer Concentration

A study was conducted to evaluate the effect of histidine buffer concentration on the solution stability of nivolumab. Solution samples were prepared with nivolumab concentrations of 100 mg/mL at pH 6.0. Histidine concentrations were adjusted to 10 mMv, 20 mM and 30 mMv. Each formulation also contained 250 mM sucrose, 0.05% w/w polysorbate 80 and 50 μM pentetic acid. Samples were filled into 3-cc glass vials which were stored at the accelerated storage condition of 25° C. for up to 6 months.

Throughout the study, the appearance of all samples was clear to slightly opalescent, colorless to pale-yellow. Additional stability results are presented in Table 3 and Table 4. Across the three histidine concentrations, there were no changes in solution pH or protein concentration. Levels of high and low molecular weight species increased with time at the same approximate rate during the 6 months of storage. Subvisible particulate levels were low, with no apparent trends.

TABLE 3

Effect of Histidine Concentration on the Stability of Nivolumab Stored for 6 Months at 25° C.

| Histidine Concentration (mM) | Time (Months) | pH | Protein Conc. (mg/mL) | HMWS (Area %) | LMWS (Area %) | Subvisible Particulate Matter (Particles per Milliliter) ≥10-μm | ≥25-μm |
|---|---|---|---|---|---|---|---|
| 10 mM | 0 | 6.14 | 101 | 0.98 | 0.07 | 8 | 0 |
| | 3 | 6.16 | 101 | 1.38 | 0.09 | 12 | 0 |
| | 6 | 6.09 | 100 | 1.42 | 0.08 | 40 | 0 |
| 20 mM | 0 | 6.10 | 102 | 0.94 | 0.07 | 10 | 0 |
| | 3 | 6.11 | 101 | 1.16 | 0.08 | 7 | 0 |
| | 6 | 6.13 | 102 | 1.31 | 0.10 | 25 | 0 |
| 30 mM | 0 | 6.12 | 100 | 0.91 | 0.07 | 7 | 0 |
| | 3 | 6.11 | 99 | 1.04 | 0.09 | 7 | 0 |
| | 6 | 6.14 | 101 | 1.30 | 0.08 | 32 | 2 |

Table 4 presents data for size variants by CE-SDS, both reduced and non-reduced. Over the 6 months of storage at the accelerated 25° C. condition, percent purity by both reduced and non-reduced CE-SDS was unchanged. Data for charge variants by iCIEF are also presented in Table 4. The level of acidic species for all 3 formulations increased by about 8% over the 6 months of storage at 25° C. The increase in acidic species was accompanied by an approximately equal decrease in main peak area. The level of basic species was little changed over the 6 month storage period. Based on the results of this study, a histidine buffer concentration of 20 mM was selected for the formulation of nivolumab SC injection.

TABLE 4

Effect of Histidine Concentration on the Stability of Nivolumab Stored for 6 Months at 25° C.

| Histidine Concentration (mM) | Time (Months) | Purity by CE-SDS Reduced (Area %) | Non-Reduced (Area %) | iCIEF Results Acidic Group (Area %) | Main Peak (Area %) | Basic Group (Area %) |
|---|---|---|---|---|---|---|
| 10 mM | 0 | 100.0 | 99.6 | 30.2 | 65.1 | 4.6 |
| | 3 | 100.0 | 99.8 | 34.9 | 60.3 | 4.8 |
| | 6 | 100.0 | 99.7 | 38.6 | 55.9 | 5.6 |

TABLE 4-continued

Effect of Histidine Concentration on the Stability of Nivolumab Stored for 6 Months at 25° C.

| Histidine | | Purity by CE-SDS | | iCIEF Results | | |
|---|---|---|---|---|---|---|
| Concentration (mM) | Time (Months) | Reduced (Area %) | Non-Reduced (Area %) | Acidic Group (Area %) | Main Peak (Area %) | Basic Group (Area %) |
| 20 mM | 0 | 100.0 | 99.6 | 30.5 | 64.8 | 4.7 |
| | 3 | 100.0 | 99.6 | 34.4 | 60.5 | 5.1 |
| | 6 | 100.0 | 99.7 | 37.9 | 57.5 | 4.6 |
| 30 mM | 0 | 100.0 | 99.6 | 30.4 | 64.8 | 4.8 |
| | 3 | 100.0 | 99.7 | 35.2 | 60.2 | 4.6 |
| | 6 | 100.0 | 99.8 | 38.1 | 57.5 | 4.5 |

Selection of Tonicity Adjusting Agent

A study was performed to evaluate the effect of sucrose on the stability of nivolumab in a high concentration protein formulation. Solutions were prepared with nivolumab concentrations of 100 mg/mL in 20 mM histidine buffer, pH 6.0, with sucrose concentrations ranging from 200 mM to 400 mM. Samples were monitored for up to 7 months at the accelerated condition of 25° C. The appearance of all samples remained clear to slightly opalescent, colorless to pale-yellow. Study results, presented in Table 5, show no changes in formulation pH or nivolumab concentration. The level of subvisible particulates for all samples was low, with no apparent trends. The rate of high and low molecular weight species formation was consistent across the range of sucrose concentrations evaluated in the study.

lations were prepared and then subjected to six freeze-thaw cycles (−60° C. to 25° C.). Formulations were also vigorously agitated on a wrist-action shaker for 60 minutes in room temperature/room light. Numerous visible particles were observed in the polysorbate 80-free samples when exposed to either freeze-thaw or agitation. Although reduced in number, visible particles were also observed in the 0.01% w/v/polysorbate 80 samples exposed to freeze-thaw or agitation. No visible particles were observed in the samples containing polysorbate 80 concentrations of 0.03% w/v, 0.05% w/v or 0.07% w/v. Thus, it was concluded that for nivolumab SC injection, a polysorbate 80 concentration below 0.01% w/v was insufficient to prevent the formulation of visible particles due to the stresses of freeze-thaw or vigorous agitation.

TABLE 5

Effect of Sucrose Concentration on the Stability Nivolumab SC Injection Stored for 7 Months at 25° C.

| Sucrose Concentration | Time | | Protein Conc. | HMWS | LMWS | Subvisible Particulate Matter (Particles per Milliliter) | |
|---|---|---|---|---|---|---|---|
| (mM) | (Months) | pH | (mg/mL) | Area % | Area % | ≥10-µm | ≥25-µm |
| 200 | 0 | 5.98 | 102 | 0.65 | 0.00 | 2 | 2 |
| | 3 | 6.00 | 101 | 0.92 | 0.00 | 10 | 1 |
| | 7 | 6.02 | 101 | 1.02 | 0.03 | 3 | 0 |
| 250 | 0 | 5.97 | 101 | 0.65 | 0.00 | 2 | 0 |
| | 3 | 6.01 | 99 | 0.92 | 0.01 | 0 | 0 |
| | 7 | 6.02 | 99 | 1.03 | 0.03 | 5 | 0 |
| 330 | 0 | 5.98 | 100 | 0.65 | 0.00 | 5 | 0 |
| | 3 | 6.04 | 101 | 0.90 | 0.00 | 1 | 0 |
| | 7 | 5.98 | 99 | 1.02 | 0.03 | 2 | 1 |
| 400 | 0 | 5.97 | 102 | 0.65 | 0.00 | 5 | 0 |
| | 3 | 5.99 | 101 | 0.90 | 0.00 | 0 | 0 |
| | 7 | 6.01 | 99 | 1.01 | 0.01 | 3 | 0 |

Figure 1:
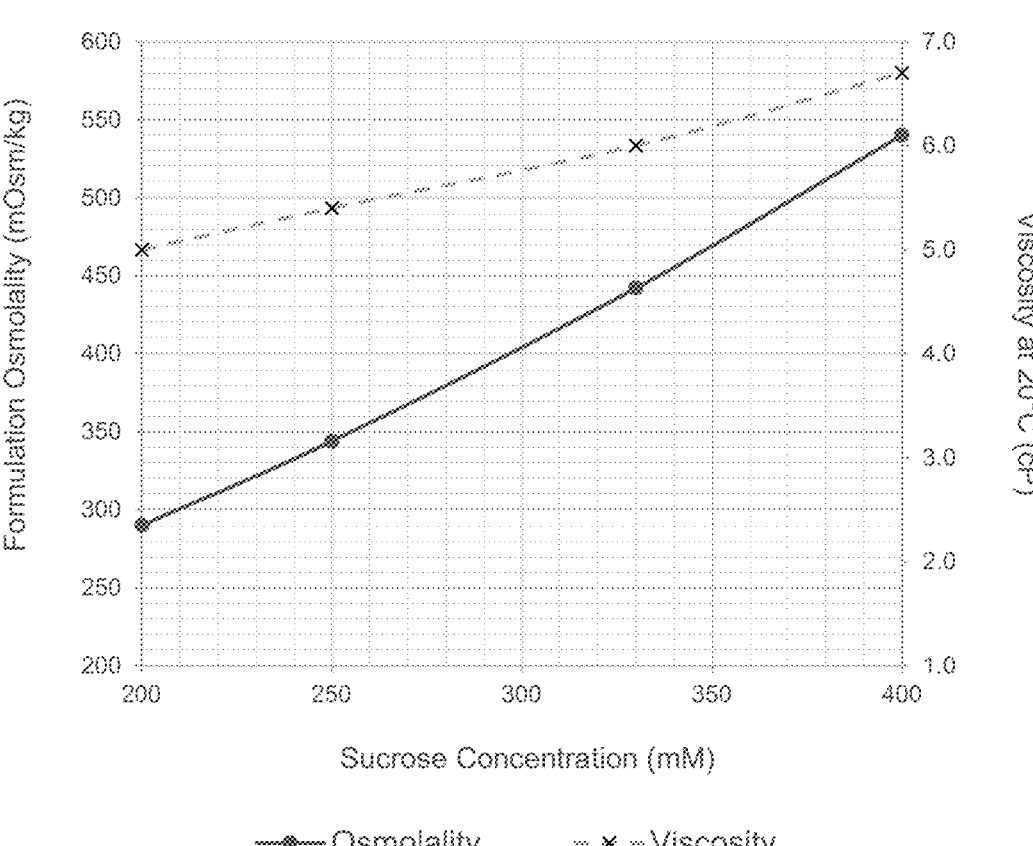
FIG. 1 presents a graphical representation of data related to the osmolality and viscosity of nivolumab subcutaneous (SC) injection formulations as a function of sucrose concentration in the formulation in accordance with Example 1. The X-axis represents sucrose concentration in mM, and the Y-axis represents formulation osmolality in mOsm/kg. The solid circles and solid line represent osmolality values, and the solid X and dashed line represent viscosity values.

Based on the results of the stability study, a sucrose concentration of 250 mM (85.6 g/L) was selected as the tonicity adjusting agent for the nivolumab SC injection formulation. As presented in FIG. 1, both formulation viscosity and osmolality increase with increasing sucrose concentration. But based on the results in Table 5, the increase in sucrose concentration was found to have little impact on the quality attributes of the formulation.

Selection of Surfactant Concentration

Polysorbate 80, a non-ionic surfactant, was evaluated for use in the formulation. Four different concentrations of polysorbate 80, 0.01% w/v, 0.03% w/v, 0.05% w/v and 0.07% w/v, along with a polysorbate 80-free sample, were evaluated for their effect on the stability of nivolumab SC injection. In the initial screening part of the study, formu- In the second part of this study, the effect of polysorbate 80 concentration on the stability of nivolumab SC injection was examined. Samples with polysorbate 80 concentrations of 0.03% w/v, 0.05% w/v and 0.07% w/v were stored at the stress condition of 40° C. and stability was monitored for two months. There were no changes in solution appearance throughout the study period and as presented in Table 6, there were no changes in pH or protein concentration. The rate of formation of high and low molecular weight species was relatively comparable across the three polysorbate 80 concentrations. Subvisible particulate levels for all samples were low, with no apparent trends. Based on the results of this study, a target polysorbate 80 concentration of 0.05% w/v was selected for the formulation of nivolumab SC injection.

TABLE 6

Effect of Polysorbate 80 Concentration on the Stability
Nivolumab SC Injection Stored for 2 Months at 40° C.

| Polysorbate 80 Concentration | Time | | Protein Conc. | HMWS | LMWS | Subvisible Particulate Matter (Particles per Milliliter) | |
|---|---|---|---|---|---|---|---|
| (% w/v) | (Months) | pH | (mg/mL) | Area % | Area % | ≥10-μm | ≥25-μm |
| 0.03 | 0 | 5.97 | 118 | 0.61 | 0.05 | 0 | 0 |
| | 1 | 5.99 | 119 | 2.09 | 0.12 | 5 | 0 |
| | 2 | 5.98 | 121 | 4.26 | 0.22 | 6 | 0 |
| 0.05 | 0 | 5.98 | 119 | 0.61 | 0.06 | 0 | 0 |
| | 1 | 6.01 | 120 | 2.14 | 0.13 | 6 | 0 |
| | 2 | 5.99 | 120 | 4.41 | 0.24 | 8 | 0 |
| 0.07 | 0 | 5.97 | 120 | 0.61 | 0.05 | 1 | 0 |
| | 1 | 5.99 | 120 | 2.27 | 0.13 | 6 | 0 |
| | 2 | 6.01 | 119 | 4.70 | 0.22 | 6 | 0 |

Addition of a Metal Ion Chelator

EDTA and DTPA (pentetic acid) were evaluated as potential metal chelators to be incorporated into the formulation for nivolumab SC injection. A preliminary screening study was performed to compare the performance of EDTA versus pentetic acid when nivolumab containing samples were spiked with metal. In this study, a solution was prepared containing nivolumab at 10 mg/mL in 20 mM histidine with 260 mM sucrose at pH 6.0. The samples were spiked with metal to a concentration of 500 ppb iron, 15 ppb chromium, 15 ppb nickel, 30 ppb copper, 10 ppb molybdenum and 10 ppb manganese. Unspiked samples were also prepared to serve as controls. The following six formulations were prepared: 1. Formulation A: no metal spike, no EDTA or pentetic acid; 2. Formulation B: no metal spike, 50 μM pentetic acid; 3. Formulation C: no metal spike, 50 μM EDTA; and 4. Formulation D: metal spike, no EDTA or pentetic acid; 5. Formulation E: metal spike, 50 μM pentetic acid; and 6. Formulation F: metal spike, 50 μM EDTA.

Samples were placed at the stress condition of 40° C. and levels of HMWS and LMWS were monitored for up to 4 weeks. The data presented in Table 7 show the benefit of added metal ion chelator. For formulation D, where the sample was spiked with metal, but no added chelator, the level of HMWS increased from 0.27% to 7.07% and the level of LMWS increased from 0.12% to 0.32% over the 4 weeks of storage at 40° C. EDTA, at a concentration of 50 μM (Formulation F) was able to limit the increase in levels of HMWS and LMWS to 3.75% and 0.18%, respectively, for the metal spiked samples. The best performance for metal spiked samples however was observed with the 50 μM pentetic acid where the level of HMWS increased to only 0.55% and there was no change in the level of LMWS over the 4 week study period. Even the unspiked formulations A, B and C, showed the benefit of added metal ion chelator. With no added chelator, the level of HMWS increased from 0.27% to 1.94% and the level of LMWS increased from 0.12% to 0.17% over the 4 weeks of storage at 40° C. When 50 μM pentetic acid or 50 p EDTA was included in the formulation, the increases in HMWS were reduced, from 0.26% to 0.48% for pentetic acid and from 0.26% to 0.52% for EDTA. The levels of LMWS for the samples containing metal ion chelator were unchanged over the 4 week storage period. Based on the results of this study, pentetic acid was selected as the metal ion chelator for the nivolumab SC injection formulation.

TABLE 7

Effect of EDTA vs Pentetic Acid on the Stability of Nivolumab
Stored for 4 Weeks at 40° C. After Spiking with Metal Ions

| Formulation | Time (Weeks) | HMWS Area % | LMWS Area % |
|---|---|---|---|
| Formulation A: No metal spike, no EDTA or pentetic acid | 0 | 0.27 | 0.12 |
| | 2 | 0.50 | 0.14 |
| | 4 | 1.94 | 0.17 |
| Formulation B: No metal spike, 50 μM pentetic acid | 0 | 0.26 | 0.12 |
| | 2 | 0.32 | 0.13 |
| | 4 | 0.48 | 0.12 |
| Formulation C: No metal spike, 50 μM EDTA | 0 | 0.26 | 0.12 |
| | 2 | 0.34 | 0.13 |
| | 4 | 0.52 | 0.12 |
| Formulation D: Metal spike, no EDTA or pentetic acid | 0 | 0.27 | 0.12 |
| | 2 | 4.66 | 0.33 |
| | 4 | 7.07 | 0.32 |
| Formulation E: Metal spike, 50 μM pentetic acid | 0 | 0.26 | 0.12 |
| | 2 | 0.34 | 0.13 |
| | 4 | 0.55 | 0.12 |
| Formulation F: Metal spike, 50 μM EDTA | 0 | 0.26 | 0.12 |
| | 2 | 1.23 | 0.22 |
| | 4 | 3.75 | 0.18 |

To further investigate the benefits of a metal ion chelator in preventing degradation that could potentially occur from the presence of trace metal ions, a second, more in-depth study was performed to evaluate the effect of pentetic acid on the stability of nivolumab SC injection. The formulation tested in this study was 120 mg/mL nivolumab in 20 mM histidine buffer, pH 6.0, with 250 mM sucrose and 0.05% w/v polysorbate 80. Solutions were spiked with a concentrated metal solution so that the total metal concentration in the metal spiked samples was 1.5 ppm (0.5 ppm each of iron, chromium and copper). As in the previous study, unspiked samples were also prepared to serve as controls. The following five formulations were prepared: 1. Formulation A: no metal spike, no pentetic acid; 2. Formulation B: no metal spike, 50 μM pentetic acid; 3. Formulation C: 1.5 ppm metal spike, no pentetic acid; 4. Formulation D: 1.5 ppm metal spike, 50 μM pentetic acid; and 5. Formulation E: 1.5 ppm metal spike, 100 μM pentetic acid.

Samples were filled into 3-cc glass vials that were stoppered and stored at the stress condition of 40° C. and stability was monitored for two months. There were no changes in solution appearance throughout the study period and as presented in Table 8, there were no changes in pH or protein concentration. Subvisible particulate levels for all samples were low, with no apparent trends. After 2 months of storage at 40° C., the level of HMWS and LMWS was the highest in Formulation C, the metal spiked solution without added pentetic acid. Lower and equal levels of HMWS and LMWS were observed in Formulations D and E, containing 50 µM and 100 µM pentetic acid, respectively. Results from the unspiked formulations A and B also showed the benefit of added pentetic acid. With no added chelator (formulation A), the level of HMWS increased from 0.61% to 4.34% and the level of LMWS increased from 0.05% to 0.25% over the 2 months of storage at 40° C. When 50 µM pentetic acid was included in the formulation (formulation B), the level of HMWS at the 2 month timepoint was only 2.97% and the level of LMWS at the 2 month timepoint was only 0.20%. Based on the results of this study, a target pentetic acid concentration of 50 µM was selected for the formulation of nivolumab SC injection.

140 mg/mL and solutions were prepared both with and without, 75 mM arginine. Typical stability data were generated for monitored quality attributes except that at the 3 month 40° C. timepoint, numerous small white visible particles were observed in the arginine containing formulations. No visible particles were observed in the formulations without arginine. Based on these stability results, it was decided that arginine would not be included in the formulation for nivolumab SC injection.

The target nivolumab concentration selected for nivolumab SC injection was 120 mg/mL. The formulation chosen for the FIH clinical trials was 20 mM histidine buffer at pH 6.0, with 250 mM sucrose, 0.05% w/v polysorbate 80 and 50 µM pentetic acid. Drug substance is provided in the

TABLE 8

Effect of Trace Metal Spiking and Pentetic Acid on the Stability Nivolumab SC Injection Stored for 2 Months at 40° C.

| Formulation | Time (Months) | pH | Protein Conc. (mg/mL) | HMWS Area % | LMWS Area % | Subvisible Particulate Matter (Particles per Milliliter) | |
|---|---|---|---|---|---|---|---|
| | | | | | | ≥10-µm | ≥25-µm |
| Formulation A: | 0 | 5.92 | 118 | 0.61 | 0.05 | 1 | 0 |
| No metal spike, | 1 | 5.92 | 117 | 2.11 | 0.12 | 5 | 0 |
| No pentetic acid | 2 | 5.91 | 118 | 4.34 | 0.25 | 11 | 0 |
| Formulation B: | 0 | 5.93 | 117 | 0.60 | 0.05 | 1 | 0 |
| No metal spike, | 1 | 5.92 | 117 | 1.67 | 0.10 | 9 | 0 |
| 50 µM pentetic acid | 2 | 5.90 | 117 | 2.97 | 0.20 | 2 | 0 |
| Formulation C: | 0 | 5.93 | 116 | 0.61 | 0.06 | 1 | 1 |
| 1.5 ppm metal spike, | 1 | 5.91 | 118 | 3.13 | 0.17 | 4 | 0 |
| No pentetic acid | 2 | 5.92 | 119 | 5.90 | 0.30 | 9 | 0 |
| Formulation D: | 0 | 5.93 | 116 | 0.61 | 0.06 | 0 | 1 |
| 1.5 ppm metal spike, | 1 | 5.90 | 119 | 1.86 | 0.11 | 9 | 0 |
| 50 µM pentetic acid | 2 | 5.91 | 118 | 3.39 | 0.20 | 7 | 0 |
| Formulation E: | 0 | 5.92 | 118 | 0.62 | 0.06 | 0 | 0 |
| 1.5 ppm metal spike, | 1 | 5.91 | 117 | 1.85 | 0.11 | 5 | 0 |
| 100 µM pentetic acid | 2 | 5.90 | 118 | 3.39 | 0.20 | 9 | 0 |

Selection of Protein Concentration

A number of experiments were conducted to aid in the selection of a target protein concentration for nivolumab SC injection. The formulation was found to be stable during handling, and ultrafiltration runs allowed for nivolumab concentrations as high as 200 mg/mL to be attained. However, it was found that viscosity increases rapidly at nivolumab concentrations greater than 150 mg/mL.

Figure 2:
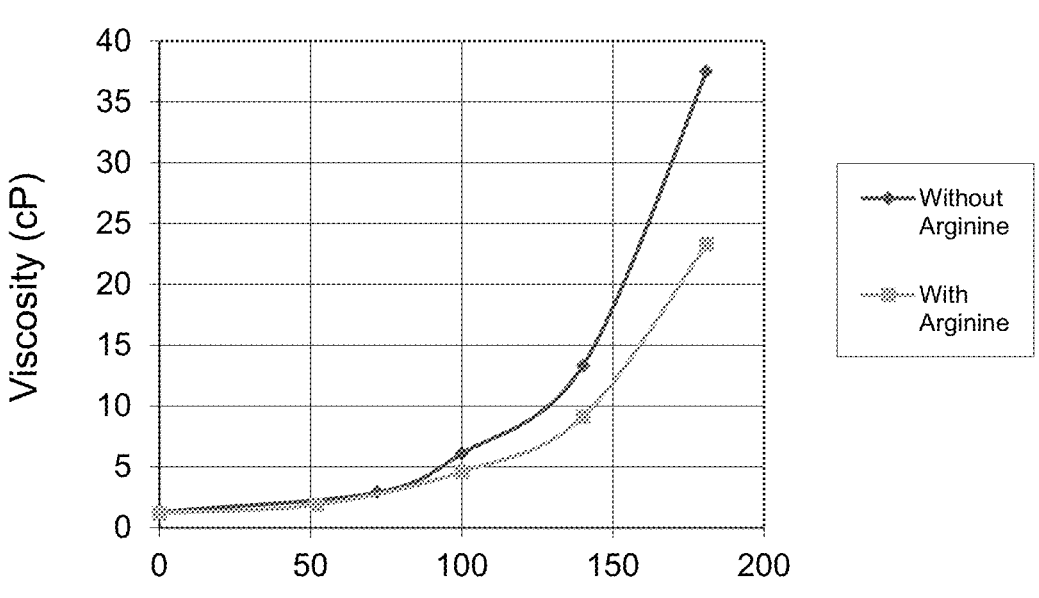
FIG. 2 presents a graphical representation of data related to the effect of 75 mM added arginine on Nivolumab subcutaneous (SC) injection formulation viscosity in accordance with Example 1. The X-axis represents protein concentration in mg/mL, and the Y-axis represents viscosity in cP at 20° C. The solid boxes represent samples comprising added arginine, and the solid diamonds represent samples without added arginine.

L-arginine is an amino acid that is known to lower solution viscosity. In order to evaluate the effect of arginine on formulation viscosity, a study was conducted where 75 mM arginine was added to a 140 mg/mL nivolumab SC formulation (in 20 mM histidine, 250 mM sucrose, 0.05% w/v polysorbate 80, 50 µM pentetic acid, pH 6.0) and then concentrated using a 10 kDa membrane and a centrifuge. The effect of added arginine on formulation viscosity is shown in FIG. 2. At nivolumab concentrations greater than 100 mg/mL, 75 mM arginine causes a lowering of solution viscosity. For example, the viscosity of a 140 mg/mL nivolumab formulation at 20° C. without arginine was 13.3 cP, but with 75 mM arginine it was 9.1 cP. Viscosity measurements were made at 20° C.

A study was then conducted to evaluate the effect of 75 mM arginine on the stability of nivolumab SC injection (ELN A0C6F-023, ELN A259D-007). Small batches of nivolumab were prepared in 20 mM histidine pH 6.0, with 250 mM sucrose, 0.05% w/v polysorbate and 50 µM pentetic acid. Nivolumab concentrations were either 100 mg/mL or same formulation, but at a target concentration of 150 mg/mL with storage at –60° C.

Stability Data for Laboratory Scale Batches of Nivolumab SC Injection

Two lab scale batches of nivolumab SC injection were prepared and placed on stability. Both batches used the selected FIH formulation, 20 mM histidine buffer at pH 6.0, 250 mM sucrose, 0.05% w/v polysorbate 80 and 50 µM pentetic acid. In order to bracket the 120 mg/mL protein concentration that was selected for the FIH formulation, the nivolumab concentration for one batch was 100 mg/mL and for the other batch it was 140 mg/mL. The formulations were prepared and small aliquots were aseptically filtered into 3-cc Type I glass vials. The vials were stoppered, sealed and placed on station at 5° C., 25° C. and 40° C. At specified timepoints, samples were pulled from the stability station and tested for appearance, pH, protein concentration, size homogeneity by SE-HPLC, subvisible particulate matter by HIAC, charge variants by iCIEF and molecular size variants by CE-SDS (R&NR).

The visual appearance for all samples at all timepoints was a clear to slightly opalescent, colorless to pale-yellow solution. Additional stability data are provided in Tables 9 to 11. As shown in Table 9, for both the 100 mg/mL and the 140 mg/mL samples, there were no changes observed in pH or protein concentration throughout the study. Over 12 months of storage at 5° C., the level of HMWS increased by 0.56% for the 100 mg/mL samples and by 0.73% for the 140 mg/mL samples. For the accelerated 25° C. condition, after 6 months of storage the level of HMWS increased by 0.88% for the 100 mg/mL samples and by 1.15% for the 140 mg/mL samples. At the 40° C. stress condition, the level of HMWS increased over 3 months of storage by 3.17% and 3.92% for the 100 mg/mL and the 140 mg/mL samples, respectively. The level of LMWS was little changed for samples stored at 5° C. and 25° C., but increased by about 0.2% for samples stored for 3 months at 40° C.

TABLE 9

| Stability Data for Nivolumab SC Injection, 100 mg/mL and 140 mg/mL | | | | | | | | | | | |
|---|---|---|---|---|---|---|---|---|---|---|---|
| | | pH | | Protein Concentration (mg/mL) | | SE-HPLC HMWS (Area %) | | SE-HPLC Monomer (Area %) | | SE-HPLC LMWS (Area %) | |
| Storage Cond. | Time (Months) | 100 mg/mL | 140 mg/mL | 100 mg/mL | 140 mg/mL | 100 mg/mL | 140 mg/mL | 100 mg/mL | 140 mg/mL | 100 mg/mL | 140 mg/mL |
| Initial | 0 | 6.14 | 6.20 | 100 | 141 | 0.69 | 0.75 | 99.19 | 99.14 | 0.12 | 0.11 |
| 5° C. | 3 | 6.20 | 6.21 | 102 | 139 | 0.89 | 1.04 | 99.00 | 98.85 | 0.12 | 0.11 |
| | 6 | 6.17 | 6.17 | 99 | 133 | 0.97 | 1.16 | 98.91 | 98.72 | 0.12 | 0.12 |
| | 9 | 6.14 | 6.16 | 101 | 137 | 1.19 | 1.41 | 98.69 | 98.47 | 0.12 | 0.12 |
| | 12 | 6.16 | 6.18 | 98 | 137 | 1.25 | 1.48 | 98.61 | 98.38 | 0.14 | 0.14 |
| 25° C. | 3 | 6.19 | 6.21 | 104 | 142 | 1.30 | 1.57 | 98.57 | 98.31 | 0.13 | 0.12 |
| | 6 | 6.18 | 6.19 | 101 | 135 | 1.57 | 1.90 | 98.29 | 97.97 | 0.14 | 0.13 |
| 40° C. | 1 | 6.18 | 6.22 | 98 | 141 | 1.29 | 1.60 | 98.59 | 98.29 | 0.12 | 0.11 |
| | 3 | 6.20 | 6.21 | 101 | 141 | 3.86 | 4.67 | 95.86 | 95.04 | 0.28 | 0.29 |

Table 10 presents results for subvisible particulates and charge variants. The level of subvisible particulates for all samples at all timepoints was low and there were no apparent trends. The level of acidic species increased with time at all storage conditions. Over 12 months of storage at 52C, acidic species increased by 6.3% for the 100 mg/mL samples and by 5.8% for the 140 mg/mL samples. At the accelerated 25C condition, acidic species increased by 26.0% for the 100 mg/mL samples and by 23.8% for the 140 mg/mL samples. At the 40° C. stress condition, the level of acidic species increased over 3 months of storage by 44.9% and 43.9% for the 100 mg/mL and the 140 mg/mL samples, respectively. The increase in acidic species was accompanied by an approximately equal decrease in main peak area. For all samples, the level of basic species was little changed throughout the study period.

Table 11 presents data for size variants by CE-SDS, both reduced and non-reduced. Over 12 months of storage at 5° C., percent purity by both reduced and non-reduced CE-SDS was unchanged for the 100 mg/mL and the 140 mg/mL samples. At the accelerated 25° C. condition, over 6 months of storage, percent purity by reduced CE-SDS was unchanged for the 100 mg/mL samples and decreased by 0.2% for the 140 mg/mL samples. At the 40° C. stress condition, the percent purity by reduced CE-SDS decreased over 3 months of storage by 1.0% for the 100 mg/mL samples and by 1.4% for the 140 mg/mL samples. For non-reduced CE-SDS, percent purity decreased by 2.2% over 6 months of storage at 25° C. for the 100 mg/mL samples. For the 140 mg/mL samples, the decrease in percent purity was 1.8%. At the 40° C. stress condition, the decrease in percent purity by non-reduced CE-SDS over 3

TABLE 10

| Stability Data for Nivolumab SC Injection, 100 mg/mL and 140 mg/mL | | | | | | | | | | | |
|---|---|---|---|---|---|---|---|---|---|---|---|
| | | Subvisible Particulates ≥10-μm (particles/mL) | | Subvisible Particulates ≥25-μm (particles/mL) | | iCIEF Acidic Group (Area %) | | iCIEF Main Peak (Area %) | | iCIEF Basic Group (Area %) | |
| Storage Cond. | Time (Months) | 100 mg/mL | 140 mg/mL | 100 mg/mL | 140 mg/mL | 100 mg/mL | 140 mg/mL | 100 mg/mL | 140 mg/mL | 100 mg/mL | 140 mg/mL |
| Initial | 0 | 2 | 3 | 0 | 0 | 27.7 | 29.1 | 67.8 | 65.9 | 4.4 | 5.0 |
| 5° C. | 3 | 4 | 7 | 0 | 3 | 29.7 | 31.0 | 66.4 | 64.7 | 3.9 | 4.4 |
| | 6 | 2 | 2 | 1 | 0 | 30.3 | 31.0 | 64.2 | 65.5 | 5.6 | 3.5 |
| | 9 | 13 | 5 | 1 | 5 | 31.2 | 31.3 | 63.7 | 63.8 | 5.1 | 4.8 |
| | 12 | 5 | 5 | 0 | 2 | 34.0 | 34.9 | 61.4 | 60.4 | 4.5 | 4.7 |
| 25° C. | 3 | 7 | 4 | 2 | 1 | 41.4 | 41.6 | 52.9 | 52.4 | 5.8 | 5.9 |
| | 6 | 8 | 0 | 0 | 0 | 53.7 | 52.9 | 39.9 | 40.6 | 6.5 | 6.4 |
| 40° C. | 1 | 5 | 1 | 0 | 0 | 48.3 | 48.1 | 46.1 | 45.3 | 5.6 | 6.6 |
| | 3 | 15 | 4 | 0 | 0 | 72.6 | 73.0 | 22.1 | 21.5 | 5.3 | 5.5 | months of storage was 2.6% and 3.1% for the 100 mg/mL and the 140 mg/mL samples, respectively.

TABLE 11

| | | Stability Data for Nivolumab SC Injection, 100 mg/mL and 140 mg/mL | | | |
| --- | --- | --- | --- | --- | --- |
| | | Purity by CE-SDS (Reduced) (Area %) | | Purity by CE-SDS (Non-Reduced) (Area %) | |
| Storage Cond. | Time (Months) | 100 mg/mL | 140 mg/mL | 100 mg/mL | 140 mg/mL |
| Initial | 0 | 99.5 | 99.8 | 99.3 | 99.2 |
| 5° C. | 3 | 100.0 | 100.0 | 99.5 | 99.5 |
| | 6 | 100.0 | 100.0 | 99.3 | 98.9 |
| | 9 | 100.0 | 100.0 | 99.3 | 99.2 |
| | 12 | 100.0 | 100.0 | 99.3 | 99.2 |
| 25° C. | 3 | 99.8 | 99.8 | 98.8 | 98.9 |
| | 6 | 99.6 | 99.6 | 97.1 | 97.4 |
| 40° C. | 1 | 99.9 | 99.9 | 98.4 | 98.2 |
| | 3 | 98.5 | 98.4 | 96.7 | 96.1 |

Description and Composition of Drug Product Selected for FIH Clinical Trials The drug product selected for FIH clinical trials was Nivolumab Injection, 960 mg/Vial (120 mg/mL). It is described as a sterile, non-pyrogenic, clear to very opalescent, colorless to yellow liquid. A few particulates, consistent in appearance to proteinaceous particles, may be present in some instances. The drug product is a single-use, preservative-free, isotonic aqueous solution for subcutaneous (SC) administration. Nivolumab SC injection is packaged in 10-cc Type 1 flint glass vials, stoppered with 20-mm Daikyo D21-7S Flurotec® coated butyl stoppers that are secured with 20-mm aluminum seals with flip-off caps. The composition of nivolumab SC injection, which includes the quality standard and function of each component, is presented in Table 12. An overfill of nivolumab SC injection is included in each vial to ensure that the labeled quantity of 8.0 mL can be administered to the patient. In determining the overfill for the drug product, the following were taken into account: 1. 0.5 mL for losses in the vial, needle and syringe (VNS) during use of the product (consistent with USP <1151> minimum recommended excess volume fill); 2. 0.2 mL for losses in a closed system transfer device (if used); 3. 0.5 mL for priming losses in winged infusion set (if used); and 4. 0.3 mL for filling machine variability.

Based on the amounts of nivolumab SC injection that can potentially be lost during dose preparation and administration, an overfill of 1.5 mL is included in each vial of drug product.

TABLE 12

| | Composition of Nivolumab Injection, 960 mg/vial (120 mg/mL) for FIH Clinical Studies | | |
| --- | --- | --- | --- |
| Component | Quality Standard | Function | Amount per Vial (mg)[a] |
| Nivolumab | BMS Specification | Active ingredient | 1,140 |
| L-Histidine | USP, Ph. Eur., JP | Buffering agent | 14.7 |
| L-Histidine HCl H2O | Ph. Eur., JP | Buffering agent | 20.0 |
| Sucrose | NF, Ph. Eur., JP | Tonicity modifier | 813 |
| Polysorbate 80 | NF, Ph. Eur., JP | Surfactant | 4.75 |
| Pentetic Acid | USP | Metal ion chelator | 0.187 |
| Water for Injection | USP, Ph. Eur., JP | Solvent | q.s. to 9.50 mL |

[a]Target fill includes a 1.5 mL overfill to account for vial, needle, and syringe (VNS) holdup, filling machine variability and administration component holdup
USP = United States Pharmacopoeia,
Ph. Eur. = European Pharmacopoeia,
NF = National Formulary,
JP = Japanese Pharmacopoeia,
q.s. = quantity sufficient

IND Enabling Stability Batch for FIH Formulation

A development laboratory batch of nivolumab SC injection (FIH formulation) was manufactured and placed on stability. The batch size was 3,000 mL in size and it yielded 291 vials after inspection. The drug product was filled (target fill of 9.5 mL) into Schott 10-cc Type I flint glass vials which were closed with 20-mm Daikyo D-21-7-S Flurotec coated butyl rubber stoppers. The vials were sealed with 20-mm West aluminum seals with flip-off caps. The drug product vials were placed on station at 5° C., 25° C. and 40° C. At specified timepoints, samples were pulled from the stability station and tested. Twelve months of stability data are presented in Table 13 to Table 16.

The visual appearance for all samples at all timepoints was a clear to slightly opalescent, colorless to pale-yellow solution. Additional stability data are provided in Tables 13 to 16. As shown in Table 13, there were no changes observed in pH or protein concentration throughout the study. Over 12 months of storage at 5° C., the level of HMWS increased by 0.3%. At the accelerated 25° C. condition, after 6 months of storage the level of HMWS increased by 0.6%. At the 40° C. stress condition, the level of HMWS increased over 3 months of storage by 3.3%. The level of LMWS was little changed for samples stored at 5° C. and 25° C., but increased by 1.1% for samples stored for 3 months at 40° C.

TABLE 13

| | | Stability Data for Nivolumab SC Injection, 960 mg/vial (120 mg/mL) | | | | | | |
| --- | --- | --- | --- | --- | --- | --- | --- |
| | | | | Nivolumab | | SE-HPLC | | |
| Storage Cond. | Time (Months) | Appearance | Solution pH | Concentration (mg/mL) | HMWS (Area %) | Monomer (Area %) | LMWS (Area %) |
| Initial | 0 | Complies[a] | 5.9 | 121.9 | 0.7 | 99.2 | 0.1 |
| 5° C. | 1 | Complies | 6.0 | 125.6 | 0.7 | 99.3 | <0.1 |
| | 3 | Complies | 5.9 | 126.5 | 0.8 | 99.1 | 0.1 |
| | 6 | Complies | 5.9 | 121.8 | 0.8 | 99.1 | <0.1 |
| | 9 | Complies | 5.8 | 122.6 | 1.0 | 98.9 | 0.1 |
| | 12 | Complies | 5.8 | 125.6 | 1.0 | 99.0 | <0.1 |
| 25° C./ | 1 | Complies | 5.9 | 125.6 | 0.9 | 99.0 | <0.1 |
| 60% RH | 3 | Complies | 6.0 | 126.3 | 1.1 | 98.8 | 0.1 |
| | 6 | Complies | 5.9 | 124.3 | 1.3 | 98.6 | <0.1 |
| 40° C./ | 0.5 | Complies | 5.9 | 123.8 | 1.2 | 98.7 | 0.1 |

TABLE 13-continued

| | | | | | SE-HPLC | | |
|---|---|---|---|---|---|---|---|
| Storage Cond. | Time (Months) | Appearance | Solution pH | Nivolumab Concentration (mg/mL) | HMWS (Area %) | Monomer (Area %) | LMWS (Area %) |
| 75% RH | 1 | Complies | 6.0 | 126.8 | 1.6 | 98.3 | 0.1 |
| | 3 | Complies | 5.9 | 125.9 | 4.0 | 94.8 | 1.2 |

Stability Data for Nivolumab SC Injection, 960 mg/vial (120 mg/mL)

[a]Complies = Clear to very opalescent, colorless to yellow liquid, light (few) particulates (consistent in appearance to protein particulates) may be present.

Table 14 presents data for size variants by CE-SDS, both reduced and non-reduced. Over 12 months of storage at 5° C., percent purity by both reduced and non-reduced CE-SDS was unchanged. At the accelerated 25° C. condition, over 6 months of storage, percent purity by reduced CE-SDS decreased by 0.2%. At the 40° C. stress condition, the percent purity by reduced CE-SDS decreased over 3 months of storage by 2.9%. For non-reduced CE-SDS, percent purity decreased by 1.2% over 6 months of storage at 25° C. and by 4.4% over 3 months of storage at the 40° C. stress condition.

TABLE 14

Stability Data for Nivolumab SC Injection, 960 mg/vial (120 mg/mL)

| | | CE-SDS (Reduced) | | CE-SDS (Non-Reduced) | |
|---|---|---|---|---|---|
| Storage Cond. | Time (Months) | Purity (Area %) | Sum of Minor Peaks ≥ LOQ (Area %) | Purity (Area %) | Sum of Minor Peaks ≥ LOQ (Area %) |
| Initial | 0 | 99.6 | <0.5 | 98.4 | 0.8 |
| 5° C. | 1 | 99.3 | 0.5 | 98.3 | 1.0 |
| | 3 | 99.7 | <0.5 | 99.3 | 0.7 |
| | 6 | 99.7 | <0.5 | 98.5 | 1.3 |
| | 9 | 99.7 | <0.5 | 98.5 | 0.9 |
| | 12 | 99.7 | <0.5 | 98.3 | 1.0 |
| 25° C./ | 1 | 99.3 | <0.5 | 98.1 | 1.0 |
| 60% RH | 3 | 99.5 | <0.5 | 98.9 | 0.8 |
| | 6 | 99.4 | <0.5 | 97.2 | 2.3 |
| 40° C./ | 0.5 | 99.0 | 0.5 | 98.2 | 0.9 |
| 75% RH | 1 | 98.8 | <0.5 | 96.8 | 2.4 |
| | 3 | 96.7 | 1.9 | 94.0 | 4.2 |

The level of acidic species increased with time at all storage conditions. Over 12 months of storage at 5° C., acidic species increased by 0.8%. At the accelerated 25° C. condition, acidic species increased by 11.3% over 6 months of storage. At the 40° C. stress condition, the level of acidic species increased over 3 months of storage by 38.8%. The level of basic species was little changed throughout the 12 months of storage at 5° C. At the 25° C. condition the level of basic species increased by 1.6% over 6 months and after 3 months of storage at 40° C., the level of basic species increased by 2.6%. The increases observed in acidic and basic species were accompanied by approximately equal decreases in main peak area.

TABLE 15

Stability Data for Nivolumab SC Injection, 960 mg/vial (120 mg/mL)

| | | iCIEF | | |
|---|---|---|---|---|
| Storage Cond. | Time (Months) | Acidic Group (Area %) | Main Peak (Area %) | Basic Group (Area %) |
| Initial | 0 | 31.4 | 63.8 | 4.8 |
| 5° C. | 1 | 31.2 | 63.8 | 5.0 |
| | 3 | 32.5 | 62.8 | 4.8 |
| | 6 | 33.3 | 62.2 | 4.5 |
| | 9 | 32.9 | 62.1 | 4.9 |
| | 12 | 32.2 | 62.9 | 4.9 |
| 25° C./ | 1 | 34.1 | 60.7 | 5.2 |
| 60% RH | 3 | 37.6 | 56.7 | 5.8 |
| | 6 | 42.7 | 50.9 | 6.4 |
| 40° C./ | 0.5 | 40.4 | 52.5 | 7.0 |
| 75% RH | 1 | 47.1 | 45.1 | 7.8 |
| | 3 | 70.2 | 22.4 | 7.4 |

Table 16 presents results for activity binding ELISA, cell-based bioassay and subvisible particulates. Across all temperatures and timepoints, results for activity binding ELISA range from 95% to 112% and for cell-based bioassay range from 79% to 105%. The level of subvisible particulates for all samples at all timepoints was low and there were no apparent trends.

TABLE 16

Stability Data for Nivolumab SC Injection, 960 mg/vial (120 mg/mL)

| | | | | Particulate Matter | |
|---|---|---|---|---|---|
| Storage Cond. | Time (Months) | Activity Binding ELISA % | Cell-Based Bioassay % | Particles/ Vial ≥10 microns | Particles/ Vial ≥25 microns |
| Initial | 0 | 109 | 79 | 43 | 0 |
| 5° C. | 1 | 103 | 101 | 56 | 0 |
| | 3 | 108 | 95 | 32 | 0 |
| | 6 | 97 | 89 | 56 | 0 |
| | 9 | 105 | 78 | 112 | 5 |
| | 12 | 102 | 96 | 40 | 5 |
| 25° C./ | 1 | 110 | 105 | 77 | 3 |
| 60% RH | 3 | 100 | 84 | 45 | 0 |
| | 6 | 96 | 88 | 45 | 0 |
| 40° C./ | 0.5 | 110 | 79 | 19 | 0 |
| 75% RH | 1 | 112 | 97 | 53 | 0 |
| | 3 | 95 | 94 | 27 | 3 |

Clinical Batch Manufacture (FIH Formulation)

Two clinical batches, BATCH 1 and BATCH 2, of nivolumab SC injection using the FIH formulation were manufactured. Both batches had a final batch scale of approximately 20 liters, which was filled into about 1,800 vials. Both batches passed all final testing and were released for clinical use. Release test results for these first two clinical batches of nivolumab SC injection are presented in Table 17.

A brief description of the manufacturing process is provided as follows. Nivolumab drug substance, 150 mg/mL in 20 mM histidine, 250 mM sucrose, 0.05% (w/v) polysorbate 80, and 50 µM pentetic acid at pH 6.0 was thawed at room temperature, protected from light, with sufficient space between the containers to ensure thawing efficiency. Once the drug substance was fully thawed, the bags were manually mixed for 2 to 3 minutes to ensure homogeneity. The formulation buffer solution (20 mM histidine, 250 mM sucrose, 0.05% (w/v) polysorbate 80, and 50 µM pentetic acid at pH 6.0) was prepared and then filtered through a 0.22-µm filter. A specific quantity of buffer solution was added to the drug substance to adjust the protein concentration to 120 mg/mL. Samples were removed for protein concentration determination, pH, and endotoxin testing. The 120 mg/mL drug product solution was filtered through a 0.45-µm pre-filter. A sample was removed for bioburden testing. The drug product solution was filtered through two 0.22-µm filters. Pre-filtration and post-filtration integrity tests were performed on the filters. The sterile filtered solution was then filled into washed, sterilized, depyrogenated vials. The vials were stoppered with sterilized stoppers and sealed with aluminum seals. During the filling process, fill weight checks were performed at regular intervals. The sealed vials were 100% visually inspected for defects. The inspected vials were labeled and packaged.

Formal Use-Time/Compatibility Study

A use-time study was performed to support the subcutaneous clinical administration of Nivolumab Injection, 960 mg/Vial (120 mg/mL). In the initial clinical studies, nivolumab was administered subcutaneously (SC) to patients using one of two methods. For Method 1, nivolumab was administered as a bolus subcutaneous injection at a rate between 2 and 4 milliliters per minute at doses of 480 mg, 720 mg and 960 mg, after addition of small aliquots of normal saline (NS) and rHuPH20 (ENHANZE Drug Product (EDP)) to adjust the nivolumab concentration in the vial to 109.1 mg/mL and the rHuPH20 concentration to 2,000 U/mL. At a concentration of 109.1 mg/mL, SC administered volumes of 4.4 mL, 6.6 mL and 8.8 mL provided nivolumab doses of 480 mg, 720 mg and 960 mg, respectively. For Method 2, the dose of 960 mg (8 mL of 120 mg/mL) was administered (without addition of NS and EDP) using a syringe pump over approximately 30 minutes (~0.27 mL/minute). To simulate worst case conditions in this use-time study, solution flow rates of as high as 4 milliliters per minute were qualified while passing through 27G ½" needles. Also, once the drug product was in the administration syringe, a hold period of up to 24 hours was qualified at 2°-8° C., with 4 hours of the 24 hours at room temperature/room light (RT/RL).

For Method 1, 0.76 mL NS and 0.19 mL EDP were added to vials of nivolumab SC injection which were then gently swirled and inverted to mix. The vial contents were pulled into separate 10-cc syringes. At the initial timepoint, the vial

TABLE 17

| Release Test Results for the First Two Clinical Batches of Nivolumab SC Injection, 120 mg/mL | | |
|---|---|---|
| Test | BATCH 1 | BATCH 2 |
| Appearance | Complies | Complies |
| pH | 5.9 | 5.8 |
| Identity: Peptide Map and | Sample identified as Nivolumab | Sample identified as Nivolumab |
| Concentration | 119.5 mg/mL | 120.6 mg/mL |
| Protein Concentration ($A_{280}$) | 119.5 mg/mL | 120.6 mg/mL |
| Activity Binding ELISA | 105% | 100% |
| Cell-Based Bioassay | 105% | 99% |
| SE-HPLC | Monomer: 99.2 Area % | Monomer: 99.3 Area % |
| | HMW: 0.6 Area % | HMW: 0.6 Area % |
| | LMW: 0.1 Area % | LMW: 0.1 Area % |
| CE-SDS (Non-Reduced) | 99 Area % | 99 Area % |
| | Sum of minor peaks ≥ | Sum of minor peaks ≥ |
| | LOQ: 1 Area % | LOQ: 1 Area % |
| CE-SDS (Reduced) | 100 Area % | 100 Area % |
| | Sum of minor peaks ≥ | Sum of minor peaks ≥ |
| | LOQ: <0.5 Area % | LOQ: <1 Area % |
| iCIEF | Main Peak: 62.2 Area % | Main Peak: 63.2 Area % |
| | Acidic Group: 33.1 Area % | Acidic Group: 32.0 Area % |
| | Basic Group: 4.6 Area % | Basic Group: 4.8 Area % |
| Endotoxin (LAL) | <0.01 EU/mg protein | <0.01 EU/mg protein |
| Particulate Matter | ≥10 µm: 32 particles/vial | ≥10 µm: 64 particles/vial |
| | ≥25 µm: 0 particles/vial | ≥25 µm: 5 particles/vial |
| Osmolality | 336 mOsm/kg | 323 mOsm/kg |
| Sterility | Complies | Complies |
| Extractable Volume in Container | 9.4 mL | 9.3 mL |
| Polysorbate 80 | 460 µg/mL | 0.05% w/v | contents were expelled through winged infusion sets (27G ½" needle) into sampling containers at a rate of 4 mL/minute. Tip caps were applied to the other group of filled syringes which were held at RT/RL for 4 hours, then at 2°-8° C., protected from light, for an additional 20 hours. At the 24 hour timepoint, the vial contents were again expelled through winged infusion sets into sampling containers at a rate of 4 mL/minute. For Method 2, vial contents (without added NS or EDP) were pulled into separate 10-cc syringes. Samples were collected, stored and sampled as described above for Method 1.

The results from the use-time study are presented in Tables 18-21. Table 18 shows results for protein concentration and size homogeneity by SE-HPLC. Throughout the study period, there were no changes in protein concentration or in the level of high or low molecular weight species.

TABLE 18

| | | | | | |
|---|---|---|---|---|---|
| Test Results for Protein Concentration and Size Homogeneity | | | | | |
| Preparation | Time | Protein Conc. (mg/mL) | Monomer Area % | HMWS Area % | LMWS Area % |
| Method 1: 0.76 mL NS and 0.19 mL EDP added to vial nivolumab SC injection and solution stored in syringe for 24 hours. | Initial | 109 | 0.7 | 98.7 | 0.6 |
| | 24 Hours | 110 | 0.7 | 98.7 | 0.6 |
| Method 2: nivolumab SC injection stored in syringe for 24 hours. | Initial | 120 | 0.7 | 98.7 | 0.6 |
| | 24 Hours | 119 | 0.7 | 98.7 | 0.6 |

Table 19 presents test results for solution appearance, pH, binding activity and subvisible particulate matter. Solution pH and activity binding were both little changed throughout the study period. Subvisible particulate levels in the samples were low and there were no apparent trends.

TABLE 19

| | | | | Activity Binding ELISA | Subvisible Particulate Matter, Particles per Milliliter | |
|---|---|---|---|---|---|---|
| Preparation | Time | Appearance | pH | (%) | ≥10-μm | ≥25-μm |
| Method 1: 0.76 mL NS and 0.19 mL EDP added to vial nivohunab SC injection and solution stored in syringe for 24 hours. | Initial | Complies(a) | 5.7 | 103 | 63 | 1 |
| | 24 Hours | Complies | 5.8 | 110 | 15 | 0 |
| Method 2: nivohunab SC injection stored in syringe for 24 hours. | Initial | Complies | 5.7 | 106 | 16 | 0 |
| | 24 Hours | Complies | 5.8 | 109 | 47 | 0 |

Test Results for Appearance, pH, Activity Binding ELISA and Subvisible Particulate Matter (a)Complies indicates a slightly yellow, very opalescent solution, essentially free from visible particles.

Table 20 shows data for percent purity by CE-SDS and the sum of all minor peaks (≥0.3%). The results show that for all samples, the level of size variants was unchanged throughout the study period.

TABLE 20

| | | CE-SDS-NR (%) | | CE-SDS-R (%) | |
|---|---|---|---|---|---|
| | | | Sum of All Minor Peaks | | Sum of All Minor Peaks |
| Preparation | Time | Purity | (≥0.3%) | Purity | (≥0.3%) |
| Method 1: 0.76 mL NS and 0.19 mL EDP added to vial nivolumab SC injection and solution stored in syringe for 24 hours | Initial | 98.1 | 1.2 | 98.9 | 0.8 |
| | 24 Hours | 98.0 | 1.5 | 98.9 | 0.9 |
| Method 2: nivolumab SC injection stored in syringe for 24 hours. | Initial | 98.0 | 1.2 | 98.8 | 0.9 |
| | 24 Hours | 98.1 | 1.2 | 98.9 | 0.9 |

Test Results for Size Variants

Table 21 presents data for enzyme activity and charge variants by iCIEF. The results show that enzyme activity was relatively unchanged throughout the study period. The level of acidic species, main peak and basic species was unchanged during the 24-hour study period.

TABLE 21

| Test Results for rHuPH20 Enzyme Activity and Charge Variants | | | | | |
|---|---|---|---|---|---|
| | | | Charge Variants by iCIEF | | |
| Preparation | Time | Enzyme Activity (Units/mL) | Acidic Species (%) | Main Peak (%) | Basic Species (%) |
| Method 1: 0.76 mL NS and 0.19 mL EDP added to vial nivolumab SC injection and solution stored in syringe for 24 hours. | Initial | 2,164 | 35.0 | 60.3 | 4.7 |
| | 24 Hours | 2,070 | 34.9 | 60.3 | 4.8 |
| Method 2: nivolumab SC injection stored in syringe for 24 hours. | Initial | Not Tested | 34.5 | 60.5 | 4.9 |
| | 24 Hours | Not Tested | 34.5 | 60.6 | 4.9 |

Based on the results of this use-time study, the following conclusions were made: 1. Nivolumab SC injection was stable when diluted with 0.76 mL 0.9% sodium chloride injection (NS) and 0.19 mL ENHANZE Drug Product (EDP) to a protein concentration of 109 mg/mL and stored in a plastic syringe for up to 24 hours at 2°-8° C., with 4 hours of the 24 hours at room temperature and room light; 2. Nivolumab SC injection, 120 mg/mL, was stable when stored in a plastic syringe for up to 24 hours at 2°-8° C., with 4 hours of the 24 hours at room temperature and room light; and 3. Nivolumab SC injection, diluted with NS and EDP to a protein concentration of 109 mg/mL and nivolumab SC injection, 120 mg/mL, was compatible with PVC administration components and was capable of being passed through syringe needles at flow rates as high as 4 milliliters per minute.

Commercial Formulation Development

In the initial clinical trials discussed supra, the rHuPH20 enzyme was added to the vial of nivolumab SC injection just prior to the subcutaneous administration of the dose to the patient. The present study evaluated addition of rHuPH20 to the formulation so that the dose could be prepared from a single vial for the commercial formulation of nivolumab SC injection.

In the initial clinical trials, ENHANZE® Drug Product (EDP, Halozyme Therapeutics) was added to the nivolumab and mixed, prior to being drawn up in the syringe. EDP is a sterile, non-pyrogenic, single-use, preservative-free, isotonic aqueous solution. The EDP provided 1 mg/mL rHuPH20 in a formulation containing 10 mM histidine, pH 6.5, 130 mM sodium chloride, 10 mM methionine, and 0.02% w/w polysorbate 80. EDP is packaged in 2-cc Type I flint glass vials, stoppered with chlorobutyl rubber stoppers, and sealed with aluminum seals.

For the co-formulated drug product, instead of EDP, rHuPH20 drug substance was be used in the formulation.

This drug substance provided a higher rHuPH20 concentration of 10 mg/mL and was formulated with 10 mM histidine and 130 mM sodium chloride, pH 6.5. The rHuPH20 drug substance was supplied as a frozen solution in a bottle, that was thawed and gently mixed prior to use. As with the FIH clinical studies, the enzyme concentration in the commercial co-formulated drug product remained at 2,000 U/mL.

Initial Feasibility Study

An initial feasibility study was conducted to evaluate the stability of 100 mg/mL nivolumab in the presence of 2,000 U/mL rHuPH20 at 5° C., 25° C. and 40° C. when packaged in glass vials. Formulations were prepared with and without 2,000 U/mL rHuPH20, filled into 3-cc glass vials, stoppered, sealed and placed on station. The samples were tested at the initial timepoint and again at 1 week, 2 weeks and 4 weeks for solution appearance, pH, protein concentration, size homogeneity by SE-HPLC and subvisible particulate matter by HIAC. In addition, charge variants were determined by iCIEF, molecular weight distribution by CE-SDS (R&NR) and enzyme activity using a plate based turbidimetric method.

The results generated in this study, presented in Table 22 to 26, showed that the presence of 2,000 U/mL of rHuPH20 in the formulation had no impact on the quality attributes of nivolumab. Through 4 weeks of storage at 5° C., 25° C. and 40° C., there were no differences in solution appearance, pH, protein concentration or subvisible particulate levels when results for the enzyme containing formulation are compared to results for the enzyme free control. There were also no differences observed in results for size homogeneity by SE-HPLC, charge variants by iCIEF or molecular weight variants by CE-SDS (R&NR). Comparable results for enzyme activity were observed at 5° C. and 25° C., but due to the relatively low Tm of the enzyme, there was a rapid decrease in activity when stored at the 40° C. condition.

TABLE 22

| Test Results for Solution Appearance, Protein Concentration and pH for Samples Stored at 5° C., 25° C. and 40° C. for Four Weeks | | | | | | | |
|---|---|---|---|---|---|---|---|
| | | Solution Appearance | | Protein Concentration (mg/mL) | | Solution pH | |
| Storage Cond. | Time (Weeks) | With rHuPH20 | Without rHuPH20 | With rHuPH20 | Without rHuPH20 | With rHuPH20 | Without rHuPH20 |
| Initial | 0 | Complies[a] | Complies | 101 | 102 | 6.15 | 6.15 |
| 5° C. | 1 | Complies | Complies | 101 | 102 | 6.15 | 6.18 |

TABLE 22-continued

Test Results for Solution Appearance, Protein Concentration and
pH for Samples Stored at 5° C., 25° C. and 40° C. for Four Weeks

| Storage Cond. | Time (Weeks) | Solution Appearance | | Protein Concentration (mg/mL) | | Solution pH | |
|---|---|---|---|---|---|---|---|
| | | With rHuPH20 | Without rHuPH20 | With rHuPH20 | Without rHuPH20 | With rHuPH20 | Without rHuPH20 |
| | 2 | Complies | Complies | 101 | 101 | 6.15 | 6.16 |
| | 4 | Complies | Complies | 101 | 101 | 6.17 | 6.18 |
| 25° C. | 1 | Complies | Complies | 102 | 101 | 6.17 | 6.16 |
| | 2 | Complies | Complies | 101 | 100 | 6.17 | 6.14 |
| | 4 | Complies | Complies | 99 | 102 | 6.17 | 6.17 |
| 40° C. | 1 | Complies | Complies | 101 | 102 | 6.16 | 6.15 |
| | 2 | Complies | Complies | 102 | 102 | 6.16 | 6.16 |
| | 4 | Complies | Complies | 101 | 101 | 6.18 | 6.18 |

[a]Clear to slightly opalescent, colorless to pale-yellow solution

TABLE 23

Test Results for High Molecular Weight Species, Low Molecular Weight Species
and Enzyme Activity Samples Stored at 5° C., 25° C. and 40° C. for Four Weeks

| Storage Cond. | Time (Weeks) | SE-HPLC HMWS (Area %) | | SE-HPLC LMWS (Area %) | | Enzyme Activity (Units/mL) | |
|---|---|---|---|---|---|---|---|
| | | With rHuPH20 | Without rHuPH20 | With rHuPH20 | Without rHuPH20 | With rHuPH20 | Without rHuPH20 |
| Initial | 0 | 0.54 | 0.56 | 0.05 | 0.05 | 2,209 | N/A [a] |
| 5° C. | 1 | 0.59 | 0.58 | 0.06 | 0.07 | 2,212 | N/A |
| | 2 | 0.61 | 0.60 | 0.07 | 0.07 | 2,288 | N/A |
| | 4 | 0.64 | 0.63 | 0.08 | 0.07 | 2,263 | N/A |
| 25° C. | 1 | 0.70 | 0.70 | 0.07 | 0.07 | 2,219 | N/A |
| | 2 | 0.78 | 0.77 | 0.07 | 0.07 | 2,236 | N/A |
| | 4 | 0.87 | 0.86 | 0.07 | 0.08 | 2,202 | N/A |
| 40° C. | 1 | 0.98 | 0.96 | 0.08 | 0.07 | 497 | N/A |
| | 2 | 1.18 | 1.16 | 0.08 | 0.09 | ND [b] | N/A |
| | 4 | 1.52 | 1.51 | 0.09 | 0.09 | ND | N/A |

[a] Not applicable,
[b] Not detected

TABLE 24

Test Results for Charge Variants by iCIEF for Samples Stored at 5°
C., 25° C. and 40° C. for Four Weeks

| Storage Cond. | Time (Weeks) | Acidic Group (Area %) | | Main Peak (Area %) | | Basic Group (Area %) | |
|---|---|---|---|---|---|---|---|
| | | With rHuPH20 | Without rHuPH20 | With rHuPH20 | Without rHuPH20 | With rHuPH20 | Without rHuPH20 |
| Initial | 0 | 31.4 | 31.5 | 64.3 | 64.8 | 4.3 | 3.7 |
| 5° C. | 1 | 31.3 | 31.6 | 64.8 | 65.3 | 3.9 | 3.1 |
| | 2 | 32.2 | 31.9 | 64.0 | 63.8 | 3.8 | 4.2 |
| | 4 | 32.2 | 32.3 | 63.6 | 63.6 | 4.3 | 4.1 |
| 25° C. | 1 | 31.5 | 31.1 | 64.8 | 65.2 | 3.7 | 3.7 |
| | 2 | 33.0 | 33.1 | 62.6 | 62.3 | 4.4 | 4.6 |
| | 4 | 33.8 | 33.6 | 61.5 | 61.8 | 4.7 | 4.7 |
| 40° C. | 1 | 34.7 | 33.9 | 60.6 | 61.2 | 4.7 | 5.0 |
| | 2 | 39.4 | 39.5 | 54.4 | 54.4 | 6.3 | 6.1 |
| | 4 | 47.0 | 47.4 | 45.8 | 45.7 | 7.2 | 6.9 |

TABLE 25

Test Results for Size Variants by CE-SDS (Reduced
and Non-Reduced) for Samples Stored at 5° C.,
25° C. and 40° C. for Four Weeks

| Storage Cond. | Time (Weeks) | Percent Purity, CE-SDS (R) (Area %) | | Percent Purity, CE-SDS (NR) (Area %) | |
|---|---|---|---|---|---|
| | | With rHuPH20 | Without rHuPH20 | With rHuPH20 | Without rHuPH20 |
| Initial | 0 | 100.0 | 100.0 | 98.4 | 98.5 |
| 5° C. | 1 | 100.0 | 100.0 | 98.4 | 98.5 |
| | 2 | 100.0 | 100.0 | 98.7 | 98.7 |
| | 4 | 100.0 | 100.0 | 99.3 | 99.3 |
| 25° C. | 1 | 100.0 | 100.0 | 98.4 | 98.4 |
| | 2 | 100.0 | 100.0 | 98.8 | 98.8 |
| | 4 | 100.0 | 100.0 | 99.3 | 99.4 |
| 40° C. | 1 | 100.0 | 100.0 | 98.4 | 98.4 |
| | 2 | 99.8 | 99.8 | 98.3 | 98.2 |
| | 4 | 99.8 | 99.8 | 98.9 | 98.9 |

TABLE 26

Test Results for Subvisible Particulate Matter
by HIAC for Samples Stored at 5° C.,
25° C. and 40° C. for Four Weeks

| Storage Cond. | Time (Weeks) | Particles per mL, ≥10-μm | | Particles per mL, ≥25-μm | |
|---|---|---|---|---|---|
| | | With rHuPH20 | Without rHuPH20 | With rHuPH20 | Without rHuPH20 |
| Initial | 0 | 3 | 3 | 0 | 0 |
| 5° C. | 1 | 4 | 3 | 3 | 1 |
| | 2 | 3 | 0 | 0 | 0 |
| | 4 | 1 | 4 | 0 | 0 |
| 25° C. | 1 | 0 | 4 | 0 | 2 |
| | 2 | 3 | 1 | 0 | 0 |
| | 4 | 5 | 0 | 0 | 0 |
| 40° C. | 1 | 6 | 9 | 0 | 0 |
| | 2 | 5 | 1 | 1 | 0 |
| | 4 | 1 | 5 | 0 | 0 |

Development of the Commercial Formulation—Addition of rHuPH20

The primary objective in the development of the commercial formulation for nivolumab SC injection was the addition of rHuPH20 to the FIH clinical formulation. As with FIH dosing, the target enzyme activity in the commercial drug product was 2,000 units per milliliter. The rHuPH20 drug substance has a target protein concentration of 10 mg/ml, a target enzyme activity of 110,000 units per milligram and a density of 1.010 g/mL at 20° C. Thus, for an enzyme activity of 2,000 units/mL, the theoretical amount of rHuPH20 drug substance needed per liter of finished drug product is: 2,000 kU/L of DP×1 mg rHuPH20/110 kU×1 mL/10 mg×1.010 g/mL=1.84 g/L.

The 1.84 g of rHuPH20 drug substance per liter of drug product results in a drug product enzyme concentration of 0.0182 mg/mL, from: 1.84 g/L×1 mL/1.010 g×10 mg/mL×1 L/1,000 mL=0.0182 mg rHuPh20/mL of drug product.

The actual amount of rHuPH20 drug substance added during manufacture of the drug product is determined based on the protein concentration and the enzyme activity of the rHuPH20 drug substance, which can range from 8.5 to 12.5 mg/mL and 80 to 140 kU/mg, respectively.

Addition of Methionine as a Sacrificial Antioxidant

To prevent oxidation of rHuPH20, a study was conducted where methionine was added to the formulation as a sacrificial antioxidant. To stress the formulation, peroxide was added at a concentration of 1 mM to formulations containing methionine at concentrations of 0 mM, 5 mM and 10 mM. The 1 mM level of peroxide was selected based on information in the literature stating that approximately 0.15 mM of peroxide can be formed in a solution containing 0.05% w/v polysorbate 80 when stored at 40° C. for up to 5 weeks.

In this experiment solutions were prepared with nivolumab concentrations of 120 mg/mL in 20 mM histidine buffer, pH 6.0, with 250 mM sucrose, 0.05% w/v polysorbate 80, 50 μM pentetic acid and 2,000 U/mL rHuPH20. Peroxide and methionine concentrations in each solution were adjusted as follows: 1. Formulation A: No peroxide, no methionine; 2. Formulation B: No peroxide, 10 mM methionine; 3. Formulation C: 1 mM peroxide, no methionine; 4. Formulation D: 1 mM peroxide, 5 mM methionine; and 5. Formulation E: 1 mM peroxide, 10 mM methionine Samples were placed on station at the accelerated condition of 25° C. and monitored for up to 6 months. The appearance of all samples remained clear to slightly opalescent, colorless to pale-yellow. Additional stability results are presented in Table 27. The data show essentially no differences in formulation pH, nivolumab concentration or level of high molecular weight and low molecular weight species were observed. Additionally, the level of subvisible particulates for all samples was low, with no apparent trends. The one difference observed was that the enzyme activity of Formulation C, which contained peroxide but no methionine, was significantly lower than that in the other 4 formulations. Even with 1 mM peroxide in the formulation, enzyme activity was completely preserved for both Formulations D and E. Based on the results of this stability study, a methionine concentration of 5 mM was selected for the commercial drug product.

TABLE 27

Effect of 1 mM Peroxide on the Stability Nivolumab SC Injection Stored
for 6 Months at 25° C. for Samples With and Without Added Methionine

| Formulation | Time (Months) | pH | Protein Conc. (mg/mL) | HMWS (Area %) | LMWS (Area %) | Enzyme Activity (U/mL) | Subvisible Particulate Matter (Particles per Milliliter) | |
|---|---|---|---|---|---|---|---|---|
| | | | | | | | ≥10-μm | ≥25-μm |
| Formulation A | 0 | 5.94 | 117 | 0.63 | 0.06 | 2,266 | 1 | 0 |
| (no peroxide, | 1 | 5.96 | 119 | 0.93 | 0.08 | 2,130 | 9 | 0 |
| no methionine) | 3 | 5.99 | 116 | 1.12 | 0.08 | 2,031 | 11 | 1 |
| | 6 | 5.94 | 118 | 1.21 | 0.12 | 2,015 | 14 | 0 |
| Formulation B | 0 | 5.93 | 118 | 0.62 | 0.06 | 2,292 | 0 | 0 |
| (no peroxide, | 1 | 5.95 | 118 | 0.90 | 0.07 | 2,262 | 3 | 0 |
| 10 mM methionine) | 3 | 5.97 | 119 | 1.09 | 0.08 | 2,055 | 9 | 0 |
| | 6 | 5.94 | 119 | 1.18 | 0.13 | 2,023 | 10 | 0 |

TABLE 27-continued

Effect of 1 mM Peroxide on the Stability Nivolumab SC Injection Stored
for 6 Months at 25° C. for Samples With and Without Added Methionine

| Formulation | Time (Months) | pH | Protein Conc. (mg/mL) | HMWS (Area %) | LMWS (Area %) | Enzyme Activity (U/mL) | Subvisible Particulate Matter (Particles per Milliliter) | |
|---|---|---|---|---|---|---|---|---|
| | | | | | | | ≥10-µm | ≥25-µm |
| Formulation C | 0 | 5.93 | 119 | 0.62 | 0.07 | 2,248 | 0 | 0 |
| (1 mM peroxide, | 1 | 5.94 | 117 | 0.89 | 0.08 | 2,038 | 6 | 0 |
| no methionine) | 3 | 5.96 | 118 | 1.08 | 0.09 | 1,856 | 13 | 0 |
| | 6 | 5.92 | 116 | 1.19 | 0.13 | 1,792 | 11 | 0 |
| Formulation D | 0 | 5.92 | 117 | 0.62 | 0.06 | 2,261 | 0 | 0 |
| (1 mM peroxide, | 1 | 5.94 | 119 | 0.92 | 0.09 | 2,239 | 5 | 0 |
| 5 mM methionine) | 3 | 5.99 | 120 | 1.10 | 0.08 | 2,081 | 24 | 0 |
| | 6 | 5.91 | 116 | 1.18 | 0.12 | 2,044 | 8 | 0 |
| Formulation E | 0 | 5.93 | 118 | 0.62 | 0.06 | 2,285 | 0 | 0 |
| (1 mM peroxide, | 1 | 5.94 | 119 | 0.90 | 0.08 | 2,211 | 10 | 0 |
| 10 mM methionine) | 3 | 5.97 | 117 | 1.08 | 0.08 | 2,036 | 9 | 0 |
| | 6 | 5.95 | 121 | 1.17 | 0.13 | 2,047 | 8 | 0 |

Stability of Nivolumab SC Injection when Formulation is Spiked with 1.5 ppm Metal—Assessing the Protective Effect of Pentetic Acid and Methionine As discussed previously, 50 µM pentetic acid was selected as a component of the formulation to prevent trace metal catalyzed degradation of nivolumab and 5 mM methionine was chosen as a sacrificial antioxidant to prevent peroxide induced oxidation of rHuPH20. A study was conducted to evaluate the impact on the stability of nivolumab SC injection when both of these excipients were included in the formulation. In this experiment, solutions were prepared with nivolumab concentrations of 120 mg/mL in 20 mM histidine buffer, pH 6.0, with 250 mM sucrose and 0.05% w/v polysorbate 80. Pentetic acid and methionine concentrations in each formulation were adjusted as follows: 1. Formulation A: No pentetic acid, no methionine; 2. Formulation B: 50 µM pentetic acid, no methionine; 3. Formulation C: No pentetic acid, 5 mM methionine; and 4. Formulation D: 50 µM pentetic acid, 5 mM methionine.

Each formulation was spiked with a concentrated metal solution such that the final formulation concentration of metal was 1.5 ppm (0.5 ppm each of iron, chromium and copper). Samples of each formulation were filled into vials, placed on station at the stressed condition of 40° C. and monitored for up to 2 months. The appearance of all samples remained clear to slightly opalescent, colorless to pale-yellow. Additional stability results presented in Table 28 show no differences in formulation pH, nivolumab concentration or level of subvisible particulates. After 2 months of storage at 40° C., the level of high molecular weight species was the greatest in Formulation A, which contained neither pentetic acid nor methionine and was lowest in Formulation D that contained both of these excipients. Comparing the level of HMWS in Formulation B vs C shows that 50 µM pentetic acid was more protective against HMWS formation than 5 mM methionine. The results of this study therefore support the inclusion of both 50 µM pentetic acid and 5 mM methionine in the commercial formulation for nivolumab SC injection.

TABLE 28

Effect of 1.5 ppm Metal on the Stability Nivolumab SC Injection Stored for 2 Months
at 40° C. for Samples With and Without 50 µM Pentetic Acid or 5 mM Methionine

| Formulation | Time (Months) | pH | Protein Conc. (mg/mL) | HMWS (Area %) | LMWS (Area %) | Subvisible Particulate Matter (Particles per Milliliter) | |
|---|---|---|---|---|---|---|---|
| | | | | | | ≥10-µm | ≥25-µm |
| Formulation A | 0 | 5.94 | 117 | 0.68 | 0.08 | 2 | 1 |
| (1.5 ppm metal spike, | 1 | 5.97 | 117 | 3.55 | 0.17 | 10 | 0 |
| no pentetic acid, | 2 | 5.93 | 118 | 6.01 | 0.28 | 9 | 2 |
| no methionine) | | | | | | | |
| Formulation B | 0 | 5.97 | 116 | 0.68 | 0.07 | 5 | 0 |
| (1.5 ppm metal spike, | 1 | 5.93 | 118 | 2.03 | 0.13 | 6 | 0 |
| 50 µM pentetic acid, | 2 | 5.95 | 116 | 3.37 | 0.18 | 10 | 0 |
| no methionine) | | | | | | | |
| Formulation C | 0 | 5.95 | 119 | 0.68 | 0.08 | 2 | 0 |
| (1.5 ppm metal spike, | 1 | 5.93 | 119 | 2.93 | 0.15 | 9 | 0 |
| no pentetic acid, | 2 | 5.96 | 118 | 5.18 | 0.25 | 10 | 1 |
| 5 mM methionine) | | | | | | | |
| Formulation D | 0 | 5.95 | 119 | 0.68 | 0.07 | 4 | 0 |
| (1.5 ppm metal spike, | 1 | 5.95 | 116 | 1.83 | 0.12 | 8 | 0 |
| 50 µM pentetic acid, | 2 | 5.92 | 119 | 2.87 | 0.18 | 5 | 0 |
| 5 mM methionine) | | | | | | | |

IND Enabling Stability Batch for Commercial Formulation

A laboratory batch of nivolumab SC injection, 120 mg/mL (commercial formulation) was manufactured and placed on stability. The formulation was 120 mg/mL nivolumab in 20 mM histidine buffer pH 6.0, with 250 mM sucrose, 0.05% w/v polysorbate 80, 50 μM pentetic acid, 5 mM methionine and 2,000 Units/mL rHuPH20. The batch size was 3,000 mL in size and it yielded 368 vials after inspection (800 mL from this batch were used for other development activities). The drug product was filled (target fill of 5.67 mL, label strength of 600 mg/vial) into Schott 10R Type I flint glass vials which were closed with 20-mm Daikyo D-21-7-S Flurotec coated butyl rubber stoppers. The vials were sealed with 20-mm West aluminum seals with flip-off caps. The drug product vials were placed on station at 5° C., 25° C. and 40° C. At specified timepoints, samples were pulled from the stability station and tested. Twelve months of IND stability data are presented in Table 29 to Table 32.

The visual appearance for all samples at all timepoints complied with specification (clear to very opalescent, colorless to yellow liquid, light (few) particulates (consistent in appearance to protein particulates) may be present). Additional stability data are provided in Tables 29 to 32. As shown in Table 29, there were no changes observed in pH or protein concentration throughout the study. Over 12 months of storage at 5° C., the level of HMWS increased by 1.X %. At the accelerated 25° C. condition, after 6 months of storage the level of HMWS increased by 0.6%. At the 40° C. stress condition, the level of HMWS increased over 3 months of storage by 3.3%. The level of LMWS was little changed for samples stored at 5° C. and 25° C., but increased by 1.1% for samples stored for 3 months at 40° C.

percent purity by reduced CE-SDS decreased over 3 months of storage by 2.9%. For non-reduced CE-SDS, percent purity decreased by 0.2 over 6 months of storage at 25° C. and by 4.4% at the 40C stress condition.

TABLE 30

| Stability Data for Nivolumab SC Injection, 600 mg/vial (120 mg/mL) | | | | | |
|---|---|---|---|---|---|
| | | CE-SDS (Reduced) | | CE-SDS (Non-Reduced) | |
| Storage Cond. | Time (Months) | Purity (Area %) | Sum of Minor Peaks ≥ LOQ (Area %) | Purity (Area %) | Sum of Minor Peaks ≥ LOQ (Area %) |
| Initial | 0 | 100.0 | <1 | 99.0 | 1.0 |
| 5° C. | 1 | 99.6 | <0.5 | 98.7 | 0.9 |
| | 3 | 99.7 | <0.5 | 98.6 | 0.9 |
| | 6 | 99.7 | <0.5 | 98.4 | 0.9 |
| | 9 | | | | |
| | 12 | | | | |
| 25° C./ | 1 | 99.6 | <0.5 | 99.3 | 0.7 |
| 60% RH | 3 | 99.4 | <0.5 | 97.9 | 1.5 |
| | 6 | 99.4 | <0.5 | 97.9 | 1.5 |
| 40° C./ | 0.5 | 99.2 | <0.5 | 98.3 | 0.5 |
| 75% RH | 1 | 99.2 | <0.5 | 97.0 | 2.2 |
| | 3 | 97.1 | 2.0 | 94.1 | 5.0 |

The level of acidic species increased with time at all storage conditions. Over 12 months of storage at 5° C., acidic species increased by 1.5%. At the accelerated 25° C. condition, acidic species increased by 11.3% over 6 months of storage. At the 40° C. stress condition, the level of acidic species increased over 3 months of storage by 38.8%. The level of basic species was little changed throughout the 12

TABLE 29

| Stability Data for Nivolumab SC Injection, 600 mg/vial (120 mg/mL) | | | | | | | |
|---|---|---|---|---|---|---|---|
| | | | | Nivolumab | SE-HPLC | | |
| Storage Cond. | Time (Months) | Appearance | Solution pH | Concentration (mg/mL) | HMWS (Area %) | Monomer (Area %) | LMWS (Area %) |
| Initial | 0 | Complies[a] | 5.8 | 123.3 | 0.6 | 99.3 | 0.1 |
| 5° C. | 1 | Complies | 5.8 | 124.5 | 0.9 | 99.0 | 0.1 |
| | 3 | Complies | 5.9 | 128.2 | 0.8 | 99.1 | <0.1 |
| | 6 | Complies | 5.8 | 130.9 | 0.8 | 99.0 | 0.2 |
| | 9 | Complies | 5.8 | 125.7 | 0.8 | | |
| | 12 | Complies | 5.9 | 121.6 | | | |
| 25° C./ | 1 | Complies | 5.8 | 127.2 | 1.0 | 98.9 | 0.1 |
| 60% RH | 3 | Complies | 5.9 | 127.5 | 1.1 | 98.7 | 0.1 |
| | 6 | Complies | 5.8 | 129.9 | 1.3 | 98.5 | 0.2 |
| 40° C./ | 0.5 | Complies | 5.9 | 123.0 | 1.0 | 98.9 | 0.1 |
| 75% RH | 1 | Complies | 5.8 | 124.7 | 1.6 | 98.3 | 0.1 |
| | 3 | Complies | 5.9 | 126.1 | 3.1 | 95.9 | 1.0 |

[a]Complies = Clear to very opalescent, colorless to yellow liquid, light (few) particulates (consistent in appearance to protein particulates) may be present.

Table 30 presents data for size variants by CE-SDS, both reduced and non-reduced. Over 12 months of storage at 5° C., percent purity by both reduced and non-reduced CE-SDS was unchanged. At the accelerated 25° C. condition, over 6 months of storage, percent purity by reduced CE-SDS decreased by 0.2%. At the 40° C. stress condition, the months of storage at 5° C. At the 25° C. condition the level of basic species increased by 1.6% over 6 months and after 3 months of storage at 40° C., the level of basic species increased by 2.6%. The increases in acidic and basic species were accompanied by an approximately equal decrease in main peak area.

TABLE 31

| Storage Cond. | Time (Months) | Acidic Group (Area %) | Main Peak (Area %) | Basic Group (Area %) | Polysorbate 80 (% w/v) | Enzyme Activity (Units/mL) |
|---|---|---|---|---|---|---|
| Initial | 0 | 31.9 | 63.5 | 4.6 | 0.04 | 2,110 |
| 5° C. | 1 | 33.5 | 61.7 | 4.8 | — | 2129 |
| | 3 | 33.2 | 61.8 | 4.9 | — | 2079 |
| | 6 | 35.6 | 60.0 | 4.4 | — | 1910 |
| | 9 | | | | | |
| | 12 | | | | | |
| 25° C./ | 1 | 35.2 | 59.2 | 5.6 | — | 2087 |
| 60% RH | 3 | 38.5 | 55.4 | 6.1 | — | 2105 |
| | 6 | 47.6 | 47.0 | 5.5 | 0.04 | 1870 |
| 40° C./ | 0.5 | 37.2 | 55.6 | 7.3 | — | 900 |
| 75% RH | 1 | 46.8 | 45.4 | 7.8 | — | 487 |
| | 3 | 66.7 | 25.5 | 7.8 | 0.04 | NR |

*Stability Data for Nivolumab SC Injection, 600 mg/vial (120 mg/mL)*
*iCIEF*

Table 32 presents results for activity binding ELISA, cell-based bioassay and subvisible particulates. Across all temperatures and timepoints, results for activity binding ELISA range from 95% to 112% and for cell-based bioassay range from 79% to 105%. The level of subvisible particulates for all samples at all timepoints was low and there were no apparent trends.

TABLE 32

| Storage Cond. | Time (Months) | Activity Binding ELISA % | Cell-based Bioassay % | Particles/ Vial ≥10 microns | Particles/ Vial ≥25 microns |
|---|---|---|---|---|---|
| Initial | 0 | 110 | 93 | 53 | 0 |
| 5° C. | 1 | 103 | 94 | 15 | 0 |
| | 3 | 102 | 88 | 33 | 0 |
| | 6 | 97 | 87 | 18 | 2 |
| | 9 | 102 | 91 | | |
| | 12 | 95 | 93 | | |
| 25° C./ | 1 | 95 | 86 | 35 | 2 |
| 60% RH | 3 | 92 | 77 | 48 | 0 |
| | 6 | 99 | 77 | 25 | 0 |

*Stability Data for Nivolumab SC Injection, 600 mg/vial (120 mg/mL)*
*Particluate Matter*

TABLE 32-continued

| Storage Cond. | Time (Months) | Activity Binding ELISA % | Cell-based Bioassay % | Particles/ Vial ≥10 microns | Particles/ Vial ≥25 microns |
|---|---|---|---|---|---|
| 40° C./ | 0.5 | 100 | 82 | 80 | 0 |
| 75% RH | 1 | 100 | 88 | 27 | 0 |
| | 3 | 97 | 89 | 32 | 0 |

*Stability Data for Nivolumab SC Injection, 600 mg/vial (120 mg/mL)*
*Particluate Matter*

Formulation Robustness

A study was performed to examine the robustness of the formulation selected for the commercial drug product. The study design called for the preparation of 13 different formulations. Nine formulations were prepared for main effects screening, two formulations were prepared at target and two axial runs were prepared to determine the effect of protein concentration. Extra vials were prepared for one of the target formulation and stored frozen at −60° C. These frozen samples were thawed and tested at each timepoint in order to assess analytical (between timepoint) variation. Five factors were varied in the prepared formulations and included protein concentration (105 mg/m to 135 mg/mL), pH (5.5 to 6.5), polysorbate 80 concentration (0.025% w/v to 0.075% w/v), pentetic acid concentration (25 µM to 75 µM and methionine concentration (2.5 mM to 7.5 mM). The formulations that were prepared for the robustness study are presented in Table 33.

TABLE 33

| Form. Number | Formulation Description | Protein Conc. (mg/mL) | pH | PS80 Conc. (% w/v) | Pentetic Acid Conc. (µM) | Methionine Conc. (mM) |
|---|---|---|---|---|---|---|
| 1 | Main Effects Screening | 135 | 6.5 | 0.075 | 75 | 7.5 |
| 2 | Main Effects Screening | 105 | 6.5 | 0.025 | 25 | 7.5 |
| 3 | Axial for Protein Conc. | 105 | 6.0 | 0.050 | 50 | 5.0 |
| 4 | Center Point | 120 | 6.0 | 0.050 | 50 | 5.0 |
| 5 | Main Effects Screening | 135 | 5.5 | 0.025 | 75 | 2.5 |
| 6 | Center Point | 120 | 6.0 | 0.050 | 50 | 5.0 |
| 7 | Main Effects Screening | 135 | 6.5 | 0.025 | 25 | 2.5 |
| 8 | Main Effects Screening | 135 | 5.5 | 0.075 | 25 | 7.5 |
| 9 | Main Effects Screening | 105 | 5.5 | 0.075 | 25 | 2.5 |
| 10 | Main Effects Screening | 105 | 5.5 | 0.025 | 25 | 2.5 |

*Formulations Prepared for Robustness Study*

TABLE 33-continued

| Formulations Prepared for Robustness Study | | | | | |
|---|---|---|---|---|---|
| Form. Number | Formulation Description | Protein Conc. (mg/mL) | pH | PS80 Conc. (% w/v) | Pentetic Acid Conc. (µM) | Methionine Conc. (mM) |
| 11 | Main Effects Screening | 105 | 5.5 | 0.025 | 75 | 7.5 |
| 12 | Main Effects Screening | 105 | 6.5 | 0.075 | 75 | 2.5 |
| 13 | Axial for Protein Conc. | 135 | 6.0 | 0.050 | 50 | 5.0 |
| 14 | Center Point (Stored at −60° C.) | 120 | 6.0 | 0.050 | 50 | 5.0 |

The formulations were prepared by first thawing approximately one liter of purified drug substance (150 g/L nivolumab in 20 mM histidine, 250 mM sucrose, pH 6.0). Tangential flow filtration was then used to exchange buffer and adjust one-half of the bulk to pH 5.5 and the other half to pH 6.5. For the middle target of pH 6.0, purified drug substance at pH 5.5 was added to purified drug substance at pH 6.5 until the target pH of 6.0 was reached. For each of the 14 formulations, a volume of 50 mL was prepared. The concentrations of polysorbate 80, pentetic acid and methionine in each formulation were adjusted by the addition of varying amounts of concentrated spike solutions. After preparation, each formulation was passed through a 0.22-µm sterilizing filter, then filled into 3-cc glass vials which were stoppered and sealed. The filled vials were then placed on station at the recommended storage condition of 5° C. and also at the accelerated stability condition of 25° C.

Samples from each group were tested at the initial timepoint for solution appearance, pH, protein concentration, size homogeneity by SE-HPLC and subvisible particulate matter by HIAC. In addition, charge variants were determined by iCIEF, molecular weight distribution by CE-SDS (R&NR) and enzyme activity using a plate based turbidimetric method. Samples were again tested after 1 month and 3 months of storage at the accelerated condition of 25° C. and after 6 months and 12 months of storage at 5° C. Stability results are presented in Table 34 to Table 39.

At the initial timepoint, across all four groups, there were no changes in solution appearance, pH or nivolumab concentration. Similar initial results were observed for size homogeneity by SE-HPLC, charge variants by iCIEF, size variants by CE-SDS (R&NR) and enzyme activity for Groups 1, 3 and 4. The level of HMWS for Group 2 samples (room temperature, room light and 30° C. storage) was 0.21% higher than the control and the level of acidic species for Group 2 samples was 1.4% higher than the control. Subvisible particulate matter by HIAC was very low for all samples. Enzyme activity for the Group 2 sample was 2.5% lower than that of the control at the initial timepoint.

After six months of storage at the accelerated condition of 25° C., across all four groups, there were no changes in solution appearance, pH or nivolumab concentration. The level of HMWS for Groups 1, 3 and 4 was similar and the level of HWWS for Group 2 was 0.15% higher than that of the control. The level of LMWS was identical at 0.13% for all four groups. For charge variants by iCIEF, the level of acidic species for Group 2 was 2.7% higher than that of the control and was similar to the control for Groups 1 and 3. Basic species across all four groups ranged from 5.9% to 6.0% at the six month timepoint. The level of molecular size variants across all four groups was in the range of 99.7% to 99.8% for reduced CE-SDS and in the range of 96.5% to 97.2% for non-reduced CE-SDS. At the six month timepoint, subvisible particulate mailer count by HIAC was very low for all samples, with no apparent trends and enzyme activity for all groups was determined to be within 99.2% and 105.6% of the control.

TABLE 34

| Stability Data for Nivolumab SC Injection-Stored at 25° C. | | | | | | | |
|---|---|---|---|---|---|---|---|
| | Time | | | Nivolumab | SE-HPLC | | |
| Formulation | (Months at 25° C.) | Appearance | Solution pH | Concentration (mg/mL) | HMWS (Area %) | Monomer (Area %) | LMWS (Area %) |
| 1 | 0 | Complies(a) | 6.46 | 127 | 0.72 | 99.17 | 0.10 |
| | 1 | Complies | | | | | |
| | 3 | Complies | | | | | |
| 2 | 0 | Complies | 6.41 | 102 | 0.66 | 99.22 | 0.12 |
| | 1 | Complies | | | | | |
| | 3 | Complies | | | | | |
| 3 | 0 | Complies | 5.99 | 102 | 0.62 | 99.27 | 0.11 |
| | 1 | Complies | | | | | |
| | 3 | Complies | | | | | |
| 4 | 0 | Complies | 5.97 | 117 | 0.62 | 99.28 | 0.09 |
| | 1 | Complies | | | | | |
| | 3 | Complies | | | | | |
| 5 | 0 | Complies | 5.49 | 133 | 0.59 | 99.32 | 0.09 |
| | 1 | Complies | | | | | |
| | 3 | Complies | | | | | |
| 6 | 0 | Complies | 5.96 | 118 | 0.62 | 99.28 | 0.10 |
| | 1 | Complies | | | | | |
| | 3 | Complies | | | | | |
| 7 | 0 | Complies | 6.46 | 132 | 0.73 | 99.15 | 0.12 |
| | 1 | Complies | | | | | |
| | 3 | Complies | | | | | |

TABLE 34-continued

Stability Data for Nivolumab SC Injection-Stored at 25° C.

| Formulation | Time (Months at 25° C.) | Appearance | Solution pH | Nivolumab Concentration (mg/mL) | HMWS (Area %) | Monomer (Area %) | LMWS (Area %) |
|---|---|---|---|---|---|---|---|
| 8 | 0 | Complies | 5.49 | 129 | 0.58 | 99.32 | 0.10 |
| | 1 | Complies | | | | | |
| | 3 | Complies | | | | | |
| 9 | 0 | Complies | 5.57 | 103 | 0.57 | 99.34 | 0.10 |
| | 1 | Complies | | | | | |
| | 3 | Complies | | | | | |
| 10 | 0 | Complies | 5.56 | 103 | 0.57 | 99.35 | 0.08 |
| | 1 | Complies | | | | | |
| | 3 | Complies | | | | | |
| 11 | 0 | Complies | 5.55 | 102 | 0.57 | 99.32 | 0.11 |
| | 1 | Complies | | | | | |
| | 3 | Complies | | | | | |
| 12 | 0 | Complies | 6.42 | 102 | 0.70 | 99.20 | 0.10 |
| | 1 | Complies | | | | | |
| | 3 | Complies | | | | | |
| 13 | 0 | Complies | 6.00 | 130 | 0.66 | 99.25 | 0.09 |
| | 1 | Complies | | | | | |
| | 3 | Complies | | | | | |
| 14 | 0 | Complies | 5.98 | 116 | 0.65 | 99.24 | 0.12 |
| | 1 | Complies | | | | | |
| | 3 | Complies | | | | | |

(a)Complies = Clear to slightly opalescent, colorless to pale-yellow solution

TABLE 35

Stability Data for Nivolumab SC Injection - Stored at 25° C.

| Formu-lation | Time (Months at 25° C.) | iCIEF Acidic Group (Area %) | Main Peak (Area %) | Basic Group (Area %) | Enzyme Activity (Units/mL) |
|---|---|---|---|---|---|
| 1 | 0 | 35.6 | 59.8 | 4.7 | 1,956 |
| | 1 | | | | |
| | 3 | | | | |
| 2 | 0 | 35.6 | 59.8 | 4.7 | 1,956 |
| | 1 | | | | |
| | 3 | | | | |
| 3 | 0 | 35.6 | 59.8 | 4.7 | 1,956 |
| | 1 | | | | |
| | 3 | | | | |
| 4 | 0 | 35.6 | 59.8 | 4.7 | 1,956 |
| | 1 | | | | |
| | 3 | | | | |
| 5 | 0 | 35.6 | 59.8 | 4.7 | 1,956 |
| | 1 | | | | |
| | 3 | | | | |
| 6 | 0 | 35.6 | 59.8 | 4.7 | 1,956 |
| | 1 | | | | |
| | 3 | | | | |
| 7 | 0 | 35.6 | 59.8 | 4.7 | 1,956 |
| | 1 | | | | |
| | 3 | | | | |
| 8 | 0 | 35.6 | 59.8 | 4.7 | 1,956 |
| | 1 | | | | |
| | 3 | | | | |
| 9 | 0 | 35.6 | 59.8 | 4.7 | 1,956 |
| | 1 | | | | |
| | 3 | | | | |
| 10 | 0 | 35.6 | 59.8 | 4.7 | 1,956 |
| | 1 | | | | |
| | 3 | | | | |
| 11 | 0 | 35.6 | 59.8 | 4.7 | 1,956 |
| | 1 | | | | |
| | 3 | | | | |
| 12 | 0 | 35.6 | 59.8 | 4.7 | 1,956 |
| | 1 | | | | |
| | 3 | | | | |

TABLE 35-continued

Stability Data for Nivolumab SC Injection - Stored at 25° C.

| Formu-lation | Time (Months at 25° C.) | iCIEF Acidic Group (Area %) | Main Peak (Area %) | Basic Group (Area %) | Enzyme Activity (Units/mL) |
|---|---|---|---|---|---|
| 13 | 0 | 35.6 | 59.8 | 4.7 | 1,956 |
| | 1 | | | | |
| | 3 | | | | |
| 14 | 0 | 35.6 | 59.8 | 4.7 | 1,956 |
| | 3 | | | | |
| | 6 | | | | |

TABLE 36

Stability Data for Nivolumab SC Injection - Stored at 25° C.

| Formu-lation | Time (Months at 25° C.) | CE-SDS (R) Purity (Area %) | CE-SDS (NR) Purity (Area %) | Particulate Matter Particles/ mL ≥10 microns | Particles/ mL ≥25 microns |
|---|---|---|---|---|---|
| 1 | 0 | 100.0 | 98.8 | 1 | 0 |
| | 1 | | | | |
| | 3 | | | | |
| 2 | 0 | 100.0 | 98.8 | 5 | 1 |
| | 1 | | | | |
| | 3 | | | | |
| 3 | 0 | 100.0 | 98.8 | 3 | 1 |
| | 1 | | | | |
| | 3 | | | | |
| 4 | 0 | 100.0 | 98.8 | 6 | 3 |
| | 1 | | | | |
| | 3 | | | | |
| 5 | 0 | 100.0 | 98.8 | 0 | 0 |
| | 1 | | | | |
| | 3 | | | | |
| 6 | 0 | 100.0 | 98.8 | 1 | 0 |
| | 1 | | | | |
| | 3 | | | | |

TABLE 36-continued

Stability Data for Nivolumab SC Injection - Stored at 25° C.

| Formu-lation | Time (Months at 25° C.) | CE-SDS (R) Purity (Area %) | CE-SDS (NR) Purity (Area %) | Particulate Matter Particles/ mL ≥10 microns | Particles/ mL ≥25 microns |
|---|---|---|---|---|---|
| 7 | 0 | 100.0 | 98.8 | 1 | 1 |
|  | 1 |  |  |  |  |
|  | 3 |  |  |  |  |
| 8 | 0 | 100.0 | 98.8 | 1 | 0 |
|  | 1 |  |  |  |  |
|  | 3 |  |  |  |  |
| 9 | 0 | 100.0 | 98.8 | 4 | 0 |
|  | 1 |  |  |  |  |
|  | 3 |  |  |  |  |
| 10 | 0 | 100.0 | 98.8 | 7 | 1 |
|  | 1 |  |  |  |  |
|  | 3 |  |  |  |  |

TABLE 36-continued

Stability Data for Nivolumab SC Injection - Stored at 25° C.

| Formu-lation | Time (Months at 25° C.) | CE-SDS (R) Purity (Area %) | CE-SDS (NR) Purity (Area %) | Particulate Matter Particles/ mL ≥10 microns | Particles/ mL ≥25 microns |
|---|---|---|---|---|---|
| 11 | 0 | 100.0 | 98.8 | 3 | 0 |
|  | 1 |  |  |  |  |
|  | 3 |  |  |  |  |
| 12 | 0 | 100.0 | 98.8 | 1 | 0 |
|  | 1 |  |  |  |  |
|  | 3 |  |  |  |  |
| 13 | 0 | 100.0 | 98.8 | 5 | 1 |
|  | 1 |  |  |  |  |
|  | 3 |  |  |  |  |
| 14 | 0 | 100.0 | 98.8 | 8 | 2 |
|  | 1 |  |  |  |  |
|  | 3 |  |  |  |  |

TABLE 37

Stability Data for Nivolumab SC Injection-Stored at 5° C.

| Formulation | Time (Months at 5° C.) | Appearance | Solution pH | Nivolumab Concentration (mg/mL) | SE-HPLC HMWS (Area %) | Monomer (Area %) | LMWS (Area %) |
|---|---|---|---|---|---|---|---|
| 1 | 0 | Complies(a) | 6.46 | 127 | 0.72 | 99.17 | 0.10 |
|  | 6 | Complies |  |  |  |  |  |
|  | 12 | Complies |  |  |  |  |  |
| 2 | 0 | Complies | 6.41 | 102 | 0.66 | 99.22 | 0.12 |
|  | 6 | Complies |  |  |  |  |  |
|  | 12 | Complies |  |  |  |  |  |
| 3 | 0 | Complies | 5.99 | 102 | 0.62 | 99.27 | 0.11 |
|  | 6 | Complies |  |  |  |  |  |
|  | 12 | Complies |  |  |  |  |  |
| 4 | 0 | Complies | 5.97 | 117 | 0.62 | 99.28 | 0.09 |
|  | 6 | Complies |  |  |  |  |  |
|  | 12 | Complies |  |  |  |  |  |
| 5 | 0 | Complies | 5.49 | 133 | 0.59 | 99.32 | 0.09 |
|  | 6 | Complies |  |  |  |  |  |
|  | 12 | Complies |  |  |  |  |  |
| 6 | 0 | Complies | 5.96 | 118 | 0.62 | 99.28 | 0.10 |
|  | 6 | Complies |  |  |  |  |  |
|  | 12 | Complies |  |  |  |  |  |
| 7 | 0 | Complies | 6.46 | 132 | 0.73 | 99.15 | 0.12 |
|  | 6 | Complies |  |  |  |  |  |
|  | 12 | Complies |  |  |  |  |  |
| 8 | 0 | Complies | 5.49 | 129 | 0.58 | 99.32 | 0.10 |
|  | 6 | Complies |  |  |  |  |  |
|  | 12 | Complies |  |  |  |  |  |
| 9 | 0 | Complies | 5.57 | 103 | 0.57 | 99.34 | 0.10 |
|  | 6 | Complies |  |  |  |  |  |
|  | 12 | Complies |  |  |  |  |  |
| 10 | 0 | Complies | 5.56 | 103 | 0.57 | 99.35 | 0.08 |
|  | 6 | Complies |  |  |  |  |  |
|  | 12 | Complies |  |  |  |  |  |
| 11 | 0 | Complies | 5.55 | 102 | 0.57 | 99.32 | 0.11 |
|  | 6 | Complies |  |  |  |  |  |
|  | 12 | Complies |  |  |  |  |  |
| 12 | 0 | Complies | 6.42 | 102 | 0.70 | 99.20 | 0.10 |
|  | 6 | Complies |  |  |  |  |  |
|  | 12 | Complies |  |  |  |  |  |
| 13 | 0 | Complies | 6.00 | 130 | 0.66 | 99.25 | 0.09 |
|  | 6 | Complies |  |  |  |  |  |
|  | 12 | Complies |  |  |  |  |  |
| 14 | 0 | Complies | 5.98 | 116 | 0.65 | 99.24 | 0.12 |
|  | 6 | Complies |  |  |  |  |  |
|  | 12 | Complies |  |  |  |  |  |

(a)Complies = Clear to slightly opalescent, colorless to pale-yellow solution

131

TABLE 38

Stability Data for Nivolumab SC Injection - Stored at 5° C.

| Formulation | Time (Months at 5° C.) | Acidic Group (Area %) | Main Peak (Area %) | Basic Group (Area %) | Enzyme Activity (Units/mL) |
|---|---|---|---|---|---|
| 1 | 0 | 35.6 | 59.8 | 4.7 | 1,956 |
|  | 6 |  |  |  |  |
|  | 12 |  |  |  |  |
| 2 | 0 | 35.6 | 59.8 | 4.7 | 1,956 |
|  | 6 |  |  |  |  |
|  | 12 |  |  |  |  |
| 3 | 0 | 35.6 | 59.8 | 4.7 | 1,956 |
|  | 6 |  |  |  |  |
|  | 12 |  |  |  |  |
| 4 | 0 | 35.6 | 59.8 | 4.7 | 1,956 |
|  | 6 |  |  |  |  |
|  | 12 |  |  |  |  |
| 5 | 0 | 35.6 | 59.8 | 4.7 | 1,956 |
|  | 6 |  |  |  |  |
|  | 12 |  |  |  |  |
| 6 | 0 | 35.6 | 59.8 | 4.7 | 1,956 |
|  | 6 |  |  |  |  |
|  | 12 |  |  |  |  |
| 7 | 0 | 35.6 | 59.8 | 4.7 | 1,956 |
|  | 6 |  |  |  |  |
|  | 12 |  |  |  |  |
| 8 | 0 | 35.6 | 59.8 | 4.7 | 1,956 |
|  | 6 |  |  |  |  |
|  | 12 |  |  |  |  |
| 9 | 0 | 35.6 | 59.8 | 4.7 | 1,956 |
|  | 6 |  |  |  |  |
|  | 12 |  |  |  |  |
| 10 | 0 | 35.6 | 59.8 | 4.7 | 1,956 |
|  | 6 |  |  |  |  |
|  | 12 |  |  |  |  |
| 11 | 0 | 35.6 | 59.8 | 4.7 | 1,956 |
|  | 6 |  |  |  |  |
|  | 12 |  |  |  |  |
| 12 | 0 | 35.6 | 59.8 | 4.7 | 1,956 |
|  | 6 |  |  |  |  |
|  | 12 |  |  |  |  |
| 13 | 0 | 35.6 | 59.8 | 4.7 | 1,956 |
|  | 6 |  |  |  |  |
|  | 12 |  |  |  |  |
| 14 | 0 | 35.6 | 59.8 | 4.7 | 1,956 |
|  | 6 |  |  |  |  |
|  | 12 |  |  |  |  |

TABLE 39

Stability Data for Nivolumab SC Injection - Stored at 5° C.

| Formulation | Time (Months at 5° C.) | CE-SDS (R) Purity (Area %) | CE-SDS (NR) Purity (Area %) | Particles/ mL ≥10 microns | Particles/ mL ≥25 microns |
|---|---|---|---|---|---|
| 1 | 0 | 100.0 | 98.8 | 1 | 0 |
|  | 6 |  |  |  |  |
|  | 12 |  |  |  |  |
| 2 | 0 | 100.0 | 98.8 | 5 | 1 |
|  | 6 |  |  |  |  |
|  | 12 |  |  |  |  |
| 3 | 0 | 100.0 | 98.8 | 3 | 1 |
|  | 6 |  |  |  |  |
|  | 12 |  |  |  |  |
| 4 | 0 | 100.0 | 98.8 | 6 | 3 |
|  | 6 |  |  |  |  |
|  | 12 |  |  |  |  |
| 5 | 0 | 100.0 | 98.8 | 0 | 0 |
|  | 6 |  |  |  |  |
|  | 12 |  |  |  |  |
| 6 | 0 | 100.0 | 98.8 | 1 | 0 |
|  | 6 |  |  |  |  |
|  | 12 |  |  |  |  |
| 7 | 0 | 100.0 | 98.8 | 1 | 1 |
|  | 6 |  |  |  |  |
|  | 12 |  |  |  |  |
| 8 | 0 | 100.0 | 98.8 | 1 | 0 |
|  | 6 |  |  |  |  |
|  | 12 |  |  |  |  |
| 9 | 0 | 100.0 | 98.8 | 4 | 0 |
|  | 6 |  |  |  |  |
|  | 12 |  |  |  |  |
| 10 | 0 | 100.0 | 98.8 | 7 | 1 |
|  | 6 |  |  |  |  |
|  | 12 |  |  |  |  |
| 11 | 0 | 100.0 | 98.8 | 3 | 0 |
|  | 6 |  |  |  |  |
|  | 12 |  |  |  |  |
| 12 | 0 | 100.0 | 98.8 | 1 | 0 |
|  | 6 |  |  |  |  |
|  | 12 |  |  |  |  |
| 13 | 0 | 100.0 | 98.8 | 5 | 1 |
|  | 6 |  |  |  |  |
|  | 12 |  |  |  |  |
| 14 | 0 | 100.0 | 98.8 | 8 | 2 |
|  | 6 |  |  |  |  |
|  | 12 |  |  |  |  |

132

Determination of Vial Target Fill Volume and Overfill

The labeled SC dose of nivolumab is 480 mg, which is a 4 mL injection of a drug product with a nivolumab concentration of 120 mg/mL. An overfill of nivolumab SC injection is included in each vial to account for losses in the vial, needle and syringe (VNS) during use of the product (consistent with USP <1151> minimum recommended excess volume fill) and to account for the variability in the filling machine. The overfill ensures that the label claim of nivolumab SC injection can be withdrawn from the vial.

A study was performed to determine the actual nivolumab SC injection holdup volume in the vial, needle and syringe. Vials were filled with exactly 4.50 mL of drug product, stoppered and sealed. Five participants used a 20G 1.5" needle to withdraw the vial contents using a 5-cc plastic syringe. The 20G 1.5" needle was replaced with a 25G ⅝" needle, and the syringe contents were expelled into a small beaker. The weight of expelled drug product was converted to volume and subtracted from the vial fill volume of 4.50 mL. The holdup volume across the 5 participants ranged from 0.29 mL to 0.35 mL, with an average of 0.32 mL. It was noted that this value is similar to the USP <1151> recommended excess of 0.34 mL (extrapolated value) for a 6-cc vial size.

Closed system transfer devices (CSTDs) are used at many facilities to protect the health care providers from exposure to drugs. The CSTD for direct SC injection generally is composed of 3 parts and includes a vial adapter, syringe adapter and a needle adapter. To determine the holdup volume in the CSTD, the same 5 participants repeated the study using 6 of the most commonly available CSTDs. Once the CSTD is attached to vial, it cannot be easily removed, thus this part of the study will determine the holdup volume in the vial plus the holdup volume in the CSTD and syringe.

As with the previous arm of the study, 6R vials were filled with exactly 4.50 mL of nivolumab injection, then stoppered and sealed. The five participants used a CSTD vial adapter and a CSTD syringe adapter to withdraw the vial contents into a 5-cc plastic syringe. The syringe was separated from the vial, the CSTD needle adapter and 25G ⅝" needle were added, and the syringe contents were expelled into a small beaker. The weight of expelled drug product was converted to volume and subtracted from the vial fill volume of 4.50 mL. The holdup volume across the 5 participants is presented in Table 40. Across the 30 results generated, the average vial plus CSTD holdup volume was 0.46 mL with a standard deviation of 0.06 mL. However, the highest holdup volume for each of the 6 different CSTDs ranged from 0.46 mL to 0.58 mL. The selected holdup volume is then 0.58 mL+0.06 mL=0.64 mL. With 3% filling machine variability the selected target fill is (4.00 mL+0.64 mL)/0.97=4.78 mL.

TABLE 40

| | Vial Plus CSTD Holdup Volumes for Nivolumab SC Injection | | | | | | |
|---|---|---|---|---|---|---|---|
| CSTD | Holdup Volume 1 (mL) | Holdup Volume 2 (mL) | Holdup Volume 3 (mL) | Holdup Volume 4 (mL) | Holdup Volume 5 (mL) | Average Holdup Volume (mL) | Highest Holdup Volume (mL) |
| PhaSeal | 0.41 | 0.50 | 0.51 | 0.51 | 0.43 | 0.47 | 0.51 |
| ChemoLock | 0.53 | 0.51 | 0.58 | 0.49 | 0.45 | 0.51 | 0.58 |
| ChemoClave | 0.44 | 0.40 | 0.45 | 0.51 | 0.41 | 0.44 | 0.51 |
| OnGuard | 0.42 | 0.46 | 0.34 | 0.52 | 0.43 | 0.43 | 0.52 |
| Equashield | 0.42 | 0.35 | 0.34 | 0.46 | 0.42 | 0.40 | 0.46 |
| CareFusion | 0.48 | 0.41 | 0.57 | 0.55 | 0.49 | 0.50 | 0.57 |

Description and Composition of a Commercial Formulation

A commercial formulation for Nivolumab SC Injection, 600 mg/Vial (120 mg/mL) is sterile, non-pyrogenic, clear to very opalescent, colorless to yellow liquid. A few particulates, consistent in appearance to proteinaceous particles, may be present. The drug product is a single-use, preservative-free, isotonic aqueous solution for subcutaneous (SC) administration. Nivolumab SC injection is packaged in 6R Type 1 flint glass vials, stoppered with 20-mm Daikyo D21-7S Flurotec® coated butyl stoppers that are secured with 20-mm aluminum seals with flip-off caps. The composition of nivolumab SC injection, which includes the quality standard and function of each component, is presented in Table 41. An overfill of nivolumab SC injection is included in each vial to ensure that the labeled quantity of 5.0 mL can be administered to the patient.

TABLE 41

| | Composition of Nivolumab SC Injection, 600 mg/vial (120 mg/mL) Commercial Formulation | | |
|---|---|---|---|
| Component | Quality Standard | Function | Amount per Vial (mg)[a] |
| Nivolumab | BMS Specification | Active ingredient | 780 |
| L-Histidine [b] | USP, Ph. Eur. | Buffering agent | 10.1 |

TABLE 41-continued

| | Composition of Nivolumab SC Injection, 600 mg/vial (120 mg/mL) Commercial Formulation | | |
|---|---|---|---|
| Component | Quality Standard | Function | Amount per Vial (mg)[a] |
| L-Histidine HCl H$_2$O | Ph. Eur. | Buffering agent | 13.7 |
| Sucrose | NF, Ph. Eur. | Tonicity modifier | 556 |
| Polysorbate 80 | NF, Ph. Eur. | Surfactant | 3.25 |
| Pentetic Acid | USP | Metal ion chelator | 0.128 |
| Methionine | USP, Ph. Eur. | Antioxidant | 4.85 |
| rHuPH20 | BMS/Halozyme | Endoglycosidase | 0.118 |
| Sodium Chloride [b] | NA | NA | NA |
| Water for Injection | USP, Ph. Eur. | Solvent | q.s. to 6.50 mL |

[a]Target fill includes a 1.5 mL overfill to account for vial, needle, and syringe (VNS) holdup, filling machine variability and administration component holdup.
[b] Sodium chloride and histidine are present in the rHuPH20 drug substance, but make insignificant contributions to the final composition.
USP = United States Pharmacopoeia,
Ph. Eur. = European Pharmacopoeia,
NF = National Formulary,
q.s. = quantity sufficient Selected Physical and Chemical Properties Selected physical and chemical properties of 150 mg/mL nivolumab drug substance, 120 mg/mL nivolumab drug product and dilution buffer are presented in Table 42.

TABLE 42

| | Selected Physical and Chemical Properties of 150 mg/mL Nivolumab Drug Substance, 120 mg/mL Nivolumab Drug Product and Dilution Buffer | | |
|---|---|---|---|
| Property | Drug Substance | Drug Product | Dilution Buffer |
| Nivolumab Concentration | 150 mg/mL (135-180 mg/mL) | 120 mg/mL (108-132 mg/mL) | 0 mg/mL |
| Formulation (Target Values) | 20 mM histidine, 250 mM sucrose, 0.05% w/v PS80, 50 μM pentetic acid | 20 mM histidine, 250 mM sucrose, 0.05% w/v PS80, 50 μM pentetic acid, | 20 mM histidine, 250 mM sucrose, 0.05% w/v PS80, 50 μM pentetic acid, |

TABLE 42-continued

Selected Physical and Chemical Properties of 150 mg/mL Nivolumab Drug
Substance, 120 mg/mL Nivolumab Drug Product and Dilution Buffer

| Property | Drug Substance | Drug Product | Dilution Buffer |
|---|---|---|---|
| | | 5 mM methionine, 2 kU/mL rHuPH20 | 25 mM methionine, 10 kU/mL rHuPH20[a] |
| Solution pH (at 18-22° C.) | 6.0 ± 0.5 | 6.0 ± 0.5 | 6.0 ± 0.5 |
| Density (at 15-25° C.) | 1.078 g/mL | 1.069 g/mL | 1.033 g/mL |
| Viscosity | 37 cP at 5° C. 17 cP 20° C. | 13 cP at 5° C. 7 cP 20° C. | 1.8 cP at 5° C. 1.6 cP 20° C. |
| Surface Tension (at 22° C.) | 46 mN/m | 45 mN/m | 42 mN/m |
| Osmolality (mOsm/kg) | TBD | 350 ± 20% | 330 ± 20% |
| Appearance | Colorless to yellow, clear to very opalescent liquid | Colorless to yellow, clear to very opal, liquid, light (few) particulates (consistent in appear. to protein part.) may be present | No appearance description since an in-process intermediate |
| Recommended Storage & Shipping Conditions | ≤−35° C., protected from light | 2-8° C., protected from light and freezing | 2-8° C., protected from light and freezing |

[a]Exact quantities of methionine and rHuPH20 in the dilution buffer will depend on the nivolumab concentration of the drug substance used to manufacture the batch. ref: ELN A0C6F-067, -079, -083, -085 -086.

Stress Studies

Short-Term Room Temperature and Room Light Study

The objective of this study was to evaluate the impact of short-term room temperature/room light (RT/RL) exposure on nivolumab SC injection. The data generated in this short term study helps inform about the length of exposure to be used in longer-term stress studies. The drug product formulation used in this study was 120 mg/mL nivolumab in 20 mM histidine buffer pH 6.0, with 250 mM sucrose, 0.05% w/v polysorbate 80, 50 μM pentetic acid, 5 mM methionine and 2,000 U/mL rHuPH20. The bulk solution (5.67 mL aliquots) was filled into 10-cc glass vials that were stoppered and sealed. The vials were then separately subjected to the following stresses. The vials were placed in the horizontal position for worst case light exposure: 25C/RL exposed—testing after 7 days, 14 days and 28 days at RT/RL; 25C/RL protected*-testing after 7 days, 14 days and 28 days at RT (*protected by wrapping vials in aluminum foil).

The light source was a halophosphate bulb encased in a plastic tube. The unlabeled vials were placed on white paper, in the horizontal position, on a plastic tray. UV meter readings at all four corners were 0 μW/cm² at every timepoint. Light meter readings at the four corners were taken at every timepoint and ranged from 933 lux to 1023 lux. After being pulled from exposure to the stress condition, the samples were stored at 5° C. All samples were tested together at the end of the study. Testing included appearance, pH, protein concentration, SE-HPLC, subvisible particulate levels by HIAC, CE-SDS (R&NR), iCIEF and enzyme activity.

Stability data from the study are presented in Tables 43 through 45. As presented in Table 43, the visual appearance for all samples at all timepoints was a clear to slightly opalescent, colorless to pale-yellow solution. There were no changes observed in pH or protein concentration for any of the samples over the 28 day study. The level of HMWS increased by 0.12% for samples stored at the accelerated 25° C. light protected condition, and by 1.00% for samples stored at 25° C. and 1,000 lux light. The level of LMWS was little changed for all samples through the 28 day timepoint.

TABLE 43

Stability Data for Nivolumab SC Injection

| Storage Cond. | Time (Days) | Appearance | Solution pH | Nivolumab Concentration (mg/mL) | SE-HPLC HMWS (Area %) | Monomer (Area %) | LMWS (Area %) |
|---|---|---|---|---|---|---|---|
| 25° C./ dark | 0 | Complies | 5.98 | 118 | 0.85 | 99.07 | 0.08 |
| | 7 | Complies | 5.99 | 117 | 0.89 | 99.03 | 0.08 |
| | 14 | Complies | 5.97 | 119 | 0.92 | 99.00 | 0.08 |
| | 28 | Complies | 6.00 | 121 | 0.97 | 98.94 | 0.09 |
| 25° C./ 1,000 lux | 0 | Complies | 5.98 | 118 | 0.85 | 99.07 | 0.08 |
| | 7 | Complies | 5.98 | 119 | 1.15 | 98.77 | 0.08 |
| | 14 | Complies | 6.01 | 118 | 1.35 | 98.57 | 0.08 |
| | 28 | Complies | 5.96 | 118 | 1.85 | 98.05 | 0.09 |

[a] Complies = Clear to slightly opalescent, colorless to pale-yellow solution.

Table 44 presents stability data for charge variants by iCIEF and enzyme activity. Over the 28 day storage period, the level of acidic species increased by 1.0% for samples stored in the dark at 25° C. and by 5.6% for samples stored at 25° C./1,000 lux. The level of basic species was little changed for both storage conditions. The increase observed in the level acidic species was accompanied by an approximately equal decrease in the main peak area. Enzyme activity was little changed for samples stored at 25° C. in the dark, but decreased by about 2% per day for samples stored at 25° C./1,000 lux.

TABLE 44

| Stability Data for Nivolumab SC Injection | | | | | |
|---|---|---|---|---|---|
| | | iCIEF | | | |
| Storage Cond. | Time (Days) | Acidic Group (Area %) | Main Peak (Area %) | Basic Group (Area %) | Enzyme Activity (Units/mL) |
| 25° C./ dark | 0 | 34.6 | 60.2 | 5.3 | 2,022 |
| | 7 | 34.3 | 60.2 | 5.5 | 1,996 |
| | 14 | 34.8 | 59.3 | 5.9 | 2,022 |
| | 28 | 35.6 | 58.5 | 5.9 | 2,000 |
| 25° C./ 1,000 lux | 0 | 34.6 | 60.2 | 5.3 | 2,022 |
| | 7 | 36.5 | 58.0 | 5.5 | 1,696 |
| | 14 | 37.1 | 57.2 | 5.7 | 1,362 |
| | 28 | 40.2 | 54.2 | 5.6 | 994 |

Table 45 presents data for CE-SDS reduced, CE-SDS non-reduced and subvisible particulate matter. Whether stored in the light or in the dark, percent purity by reduced CE-SDS was unchanged over the 28 day study period. The percent purity by non-reduced CE-SDS decreased by 0.4% over the 28 day storage period, both for samples exposed and protected from the room light. Subvisible particulate levels were low with no apparent trends.

TABLE 45

| Stability Data for Nivolumab SC Injection | | | | | |
|---|---|---|---|---|---|
| | | CE-SDS | CE-SDS | Particluate Matter | |
| Storage Cond. | Time (Days) | (R) Purity (Area %) | (NR) Purity (Area %) | Particles/ mL ≥10 microns | Particles/ mL ≥25 microns |
| 25° C./ dark | 0 | 100.0 | 99.5 | 5 | 2 |
| | 7 | 100.0 | 99.4 | 8 | 0 |
| | 14 | 100.0 | 99.2 | 5 | 0 |
| | 28 | 100.0 | 99.1 | 2 | 0 |

TABLE 45-continued

| Stability Data for Nivolumab SC Injection | | | | | |
|---|---|---|---|---|---|
| | | CE-SDS | CE-SDS | Particulate Matter | |
| Storage Cond. | Time (Days) | (R) Purity (Area %) | (NR) Purity (Area %) | Particles/ mL ≥10 microns | Particles/ mL ≥25 microns |
| 25° C./ 1,000 lux | 0 | 100.0 | 99.5 | 5 | 2 |
| | 7 | 100.0 | 99.3 | 8 | 0 |
| | 14 | 100.0 | 99.2 | 8 | 0 |
| | 28 | 100.0 | 99.1 | 8 | 0 |

Based on the results of this study, drug product exposure to room light is recommended to be limited.

Short-Term Stability of rHuPH20 in Nivolumab SC Injection Stored at 25-40° C.

A study was performed to evaluate the impact of storage temperature on rHuPH20 enzyme activity when nivolumab SC injection was stored for up to 24 hours at temperatures ranging from 25° C. to 40° C. Separate vials of drug product were stored at 25° C., 32° C., 36° C. and 40° C. in the dark for up to 24 hours. After the storage period the samples were tested for rHuPH20 activity. Each sample was tested in triplicate. A sample that had been stored continuously at 5° C. was also tested as a control. Results are presented in Table 46.

TABLE 46

| Effect of Storage Temperature on Enzyme Activity When Nivolumab SC Injection is Stored at Various Temperatures for 24 Hours in the Dark | | | | | |
|---|---|---|---|---|---|
| Storage Temperature | Analysis #1 (units/mL) | Analysis #2 (units/mL) | Analysis #3 (units/mL) | Average Enzyme Activity (units/mL) | Enzyme Activity as a % of 5° C. Stored Control |
| 5° C. (Control) | 2039 | 1982 | 1826 | 1949 | 100.0 |
| 25° C. | 2043 | 1937 | 1891 | 1957 | 100.4 |
| 32° C. | 2005 | 1797 | 1809 | 1870 | 95.9 |
| 36° C. | 2006 | 1916 | 1774 | 1899 | 97.4 |
| 40° C. | 1337 | 1565 | 1546 | 1483 | 76.1 |

Although the enzyme activity results show a considerable amount of variability, a trend of decreasing stability with increasing temperature is observed. Thus, drug product storage time above 25° C. must be limited.

Physical Stress Study

A study was performed to examine the impact of physical stresses on the stability of nivolumab SC injection. The physical stresses placed on the drug product were similar to those that might typically be experienced during manufacture, shipping or use. The stresses included freeze-thaw (Group 1), room temperature exposure, room light exposure, high temperature excursion (Group 2), shock and shaking (Group 3) and continuous storage at 5° C., protected from light (Group 4—control). A batch of nivolumab SC injection was prepared and 3.0 mL aliquots of the drug product were filled into 6-cc vials that were then stoppered and sealed. The filled vials were subjected to the various stresses, then placed on accelerated stability at 25° C.

For the freeze-thaw arm of the study (Group 1), the filled vials were cycled four times between –20° C. and 5° C., with a minimum freeze time at –20° C. of 16 hours and a minimum thaw time at 5° C. of 8 hours. It was observed that the solution in the vials completely froze after 2 to 3 hours of storage at –20° C. and completely thawed after 6 to 7 hours of storage at 5° C. For the room temperature, room light and high temperature excursion arm of the study (Group 2), the vials were stored for 22 days at 25° C., protected from light. The Group 2 vials also experienced two excursions from this 25° C./dark storage condition: 72 hours (3 days) at 25° C. in 1,000 lux light and 72 hours (3 days) at 30° C., protected from light. For the shock and shaking stress (Group 3), the vials were dropped five times from a height of 36 inches and then placed in the worst case horizontal position on an orbital shaker at 120 rpm for 24 hours. The dropping of vials and orbital shaking was performed at both 5° C. and ambient room temperature (approximately 22° C.). Samples of drug product Group 4, the control arm, remained in 5° C. storage, protected from light.

Samples from each group were tested at the initial timepoint for solution appearance, pH, protein concentration, size homogeneity by SE-HPLC and subvisible particulate matter by HIAC. In addition, charge variants were determined by iCIEF, molecular weight distribution by CE-SDS (R&NR) and enzyme activity using a plate based turbidimetric method. Samples were again tested after 3 months and 6 months of storage at the accelerated condition of 25° C. The stability results are presented in Table 47 to Table 49.

TABLE 48

Physical Stress Stability Study Data

| | | iCIEF | | | |
|---|---|---|---|---|---|
| Stress Condition | Time (Months at 25° C.) | Acidic Group (Area %) | Main Peak (Area %) | Basic Group (Area %) | Enzyme Activity (Units/mL) |
| Group 1 | 0 | 35.6 | 59.8 | 4.7 | 1,956 |
| 4 X F/T, | 3 | 40.1 | 54.0 | 5.9 | 1,936 |
| (–20° C. | 6 | 40.5 | 53.6 | 5.9 | 2,025 |
| to +5° C.) | | | | | |
| Group 2 | 0 | 37.0 | 57.8 | 5.3 | 1,855 |
| 25° C., | 3 | 40.9 | 53.2 | 5.9 | 1,816 |
| 30° C., | 6 | 44.0 | 49.9 | 6.0 | 1,901 |
| RT/RL | | | | | |
| Group 3 | 0 | 35.6 | 59.8 | 4.6 | 1,940 |
| Shock and | 3 | 39.4 | 55.0 | 5.6 | 1,936 |
| Shaking | 6 | 41.3 | 52.8 | 5.9 | 1,959 |
| Group 4 | 0 | 35.6 | 59.8 | 4.6 | 1,903 |
| 5° C./dark | 3 | 39.0 | 55.1 | 5.9 | 1,952 |
| stored | 6 | 41.3 | 52.8 | 6.0 | 1,917 |
| control | | | | | |

TABLE 49

Physical Stress Stability Study Data

| | | CE-SDS | CE-SDS | Subvisible Particulate Matter | |
|---|---|---|---|---|---|
| Stress Condition | Time (Months at 25° C.) | (R) Purity (Area %) | (NR) Purity (Area %) | Particles/ mL ≥10 microns | Particles/ mL ≥25 microns |
| Group 1 | 0 | 100.0 | 98.8 | 8 | 0 |
| 4 X F/T, | 3 | 99.9 | 99.4 | 8 | 3 |
| (–20° C. | 6 | 99.7 | 97.2 | 10 | 1 |
| to +5° C.) | | | | | |
| Group 2 | 0 | 100.0 | 98.5 | 8 | 0 |

TABLE 47

Physical Stress Stability Study Data

| | Time | | | Nivolumab | SE-HPLC | | |
|---|---|---|---|---|---|---|---|
| Stress Condition | (Months at 25° C.) | Appearance | Solution pH | Concentration (mg/mL) | HMWS (Area %) | Monomer (Area %) | LMWS (Area %) |
| Group 1 | 0 | Complies(a) | 5.96 | 121 | 0.86 | 99.07 | 0.07 |
| (4 X F/T, –20° C. | 3 | Complies | 6.01 | 119 | 1.00 | 98.88 | 0.12 |
| to +5° C.) | 6 | Complies | 5.97 | 123 | 1.29 | 98.58 | 0.13 |
| Group 2 | 0 | Complies | 5.93 | 119 | 1.06 | 98.86 | 0.08 |
| (25° C., 30° C., | 3 | Complies | 5.99 | 120 | 1.15 | 98.71 | 0.13 |
| RT/RL) | 6 | Complies | 5.92 | 121 | 1.45 | 98.42 | 0.13 |
| Group 3 | 0 | Complies | 5.94 | 119 | 0.87 | 99.06 | 0.08 |
| (Shock and | 3 | Complies | 5.98 | 118 | 1.00 | 98.90 | 0.10 |
| Shaking) | 6 | Complies | 5.93 | 121 | 1.30 | 98.56 | 0.13 |
| Group 4 | 0 | Complies | 5.95 | 121 | 0.85 | 99.06 | 0.08 |
| (5° C./Dark | 3 | Complies | 6.02 | 122 | 0.97 | 98.94 | 0.09 |
| Stored Control) | 6 | Complies | 5.94 | 120 | 1.30 | 98.58 | 0.13 |

(a)Complies = Clear to slightly opalescent, colorless to pale-yellow solution.

TABLE 49-continued

Physical Stress Stability Study Data

| Stress Condition | Time (Months at 25° C.) | CE-SDS (R) Purity (Area %) | CE-SDS (NR) Purity (Area %) | Subvisible Particulate Matter | |
|---|---|---|---|---|---|
| | | | | Particles/ mL ≥10 microns | Particles/ mL ≥25 microns |
| 25° C., | 3 | 99.9 | 99.2 | 5 | 1 |
| 30° C., | 6 | 99.7 | 96.5 | 6 | 0 |
| RT/RL | | | | | |
| Group 3 | 0 | 100.0 | 98.8 | 3 | 1 |
| Shock and | 3 | 99.9 | 99.3 | 7 | 0 |
| Shaking | 6 | 99.8 | 96.8 | 4 | 0 |
| Group 4 | 0 | 100.0 | 98.6 | 17 | 3 |
| 5° C./dark | 3 | 99.9 | 99.3 | 6 | 0 |
| stored | 6 | 99.8 | 96.8 | 14 | 2 |
| control | | | | | |

At the initial timepoint, across all four groups, there were no changes observed in solution appearance, pH or nivolumab concentration. Similar initial results were observed for size homogeneity by SE-HPLC, charge variants by iCIEF, size variants by CE-SDS (R&NR) and enzyme activity for Groups 1, 3 and 4. The level of HMWS for Group 2 samples (room temperature, room light and 30° C. storage) was 0.21% higher than the control and the level of acidic species for Group 2 samples was 1.4% higher than the control. Subvisible particulate matter by HIAC was very low for all samples. Enzyme activity for the Group 2 sample was 2.5% lower than that of the control at the initial timepoint.

After six months of storage at the accelerated condition of 25° C., across all four groups, there were no changes in solution appearance, pH or nivolumab concentration. The level of HMWS for Groups 1, 3 and 4 was similar and the level of HWWS for Group 2 was 0.15% higher than that of the control. The level of LMWS was identical at 0.13% for all four groups. For charge variants by iCIEF, the level of acidic species for Group 2 was 2.7% higher than that of the control and was similar to the control for Groups 1 and 3. Basic species across all four groups ranged from 5.9% to 6.0% at the six month timepoint. The level of molecular size variants across all four groups was in the range of 99.7% to 99.8% for reduced CE-SDS and in the range of 96.5% to 97.2% for non-reduced CE-SDS. At the six month timepoint, subvisible particulate matter count by HIAC was very low for all samples, with no apparent trends and enzyme activity for all groups was determined to be within 99.2% and 105.6% of the control.

Time Out Refrigeration and Time at Room Light

The recommended storage condition for nivolumab SC injection is 2-8° C., protected from light. Based on the data collected from the short-term room temperature/room light study, the short-term stability of rHuPH20 at 25-40° C. and the physical stress study, a time out of refrigeration and time at room light can be established for the drug product. The short-term RT/RL study showed the sensitivity to room light, the rHuPH20 study showed the sensitivity of the enzyme to higher temperatures and the physical stress study data showed minimal impact on quality attributes from stresses than might occur during drug product manufacture, shipping or use. Based on the results of these studies, a time out of refrigeration/time at room light (TOR/TARL) for the finished drug product can be recommended. This TOR/TARL covers the time period that begins with the application of the seal to the vial and ends with the start of preparation for administration to the patient and includes post-filling activities (vial handling, inspection, sampling, labeling, secondary packaging and shipping preparation) and temperature excursions during transport up to the start of preparation of the dose for patient administration.

The recommended storage condition for nivolumab SC injection is 2-8° C., protected from light. Excursions from the recommended storage condition for up to 28 days at up to 25° C. are permitted, including storage in room temperature and room light for up to 72 hours and storage at 30° C. for up to 72 hours.

Freezing Temperature for Drug Product in a Vial

As part of the physical stress evaluation, a study was conducted to determine the temperature at which nivolumab SC injection freezes when filled in a 6-cc glass vial and stored at sub-zero temperatures for relatively short periods of time. Six vials of nivolumab SC injection, 3 mL/vial, were placed in a temperature controlled water bath. The bath temperature was lowered to −8° C. (temperature confirmed with a calibrated thermocouple) and held for 9 hours. At the 9 hour timepoint, the vials were inspected to determine if the solution in the vials had frozen. The bath temperature was then lowered to −10° C. and held for another 15 hours. After 15 hours at −10° C., the vials were again inspected to determine if the solution in the vials had frozen. The bath temperature was then lowered to −12° C. and held for 9 hours. All 6 vials had frozen after 9 hours of storage at −12° C.

The results of the study are presented in the table below. After 9 hours at −8° C. followed by 15 hours at −10° C., all samples were still in the solution state. After 9 hours at −12° C., all six vials had frozen. Thus, the freezing temperature of nivolumab SC injection when filled in a glass vial is between −12° C. and −10° C. and the solution in the vials will not freeze when stored for up to 15 hours at temperatures as low as −10° C.

TABLE 50

Freezing Temperature Study Results

| Bath Temperature and Hold Period | Frozen (+) or Not-Frozen (−) at End of Hold Step | | | | | |
|---|---|---|---|---|---|---|
| | Vial 1 | Vial 2 | Vial 3 | Vial 4 | Vial 5 | Vial 6 |
| −8.0° C. for 9 Hours | − | − | − | − | − | − |
| −10.0° C. for 15 Hours | − | − | − | − | − | − |
| −12.0° C. for 9 Hours | + | + | + | + | + | + |

General Product Information

D05131 Some general information about the drug substance and drug product is provided as follows. Nivolumab drug substance is stored at ≤−35° C. in 12-L FFTp bags with protection from light. The storage condition for the drug product is 2-8° C., with protection from light. The compositions of the drug substance and drug product are listed in Table 51, the selected properties of drug substance, drug product and dilution buffer are presented in Table 52.

TABLE 51

| Description | Drug Substance | Drug Product 60 mg/vial & 600 mg/vial |
|---|---|---|
| Nivolumab (BMS-986298) | Target 150 mg/mL (135-180 mg/mL) | 120 mg/mL |

TABLE 51-continued

| Description | Drug Substance | Drug Product 60 mg/vial & 600 mg/vial |
|---|---|---|
| Histidine/Histidine HCl Monohydrate | 20 mM$^b$ | 20 mM$^b$ |
| Sucrose | 250 mM | 250 mM |
| Polysorbate 80 | 0.05% w/v | 0.05% w/v |
| Pentetic Acid | 50 µM | 50 µM |
| Methionine | N/A$^a$ | 5 mM |
| rHuPH20 | N/A$^a$ | 2,000 U/mL |
| Sodium Chloride | N/A$^b$ | N/A$^b$ |
| Target pH | 6.0 | 6.0 |

$^a$Methionine and rHuPH20 are added to the dilution buffer, which is then added to the drug substance to create the drug product.
$^b$Sodium chloride and histidine are present in the rHuPH20 drug substance, but make insignificant contributions to the final composition

TABLE 52

Selected Properties of Drug Substance, Drug Product and Dilution Buffer

| Property | Drug Substance | Drug Product | Dilution Buffer |
|---|---|---|---|
| Nivolumab Concentration | 150 mg/mL (135-180 mg/mL) | 120 mg/mL (108-132 mg/mL) | 0 mg/mL |
| Solution pH (at 18-22° C.) | 6.0 ± 0.5 | 6.0 ± 0.5 | 6.0 ± 0.5 |
| Density (at 15-25° C.) | 1.078 g/mL | 1.069 g/mL | 1.033 g/mL |
| Viscosity | 37 cP at 5° C., 17 cP 20° C. | 13 cP at 5° C., 7 cP 20° C. | 1.8 cP at 5° C., 1.6 cP 20° C. |
| Surface Tension (at 22° C.) | 46 mN/m | 45 mN/m | 42 mN/m |

Example 2—Subcutaneous Nivolumab with or without rHuPH20

In an ongoing Phase ½ study the PK, safety, efficacy, and tolerability was evaluated for nivolumab monotherapy administered subcutaneously (SC) with or without the hyaluronidase rHuPH20 in patients across solid tumors (metastatic melanoma, RCC, NSCLC, HCC, and CRC) where PK, efficacy, safety, and immunogenicity of nivolumab following IV administration have been well-characterized. Other solid tumors where PK of IV nivolumab was well-characterized (gastroesophageal junction [GEJ], gastric cancer (GC), metastatic urothelial carcinoma (mUC) and SCCHN were permitted).

The starting SC dose selected for Part A was 720 mg Q4W. Based on preliminary PK from Part A and subsequent modeling, this study proceeded as planned with a second dose of 960 mg Q4W for Part B.

For Parts A and B, PK of single dose SC nivolumab (with and without rHuPH20) was characterized, followed by IV nivolumab 480 mg Q4W at Week 4. These SC PK data were used to update existing IV PPK model. The combined SC/IV PPK model was then used to select SC nivolumab dosing regimen of 1200 mg Q4W for use in subsequent studies.

Parts C and D will provide additional PK and safety data following SC administration of 1200 mg Q4W in Part C (approximately 45 patients) and Part D (approximately 36 patients). Part C was designed to characterize the PK and study safety of continuous dosing of SC nivolumab 1200 mg Q4W in the context of switching from IV (transition from Parts A and B). Part D includes PK and safety of continuous dosing of SC nivolumab 1200 mg Q4W from initiation of therapy. An interim analysis will be performed including evaluation of pre-dose Cycle 2 Day 1 PK and early safety in approximately 10 subjects with the 1200 mg dose.

The primary objective of Parts A-D is to describe the PK of SC nivolumab with or without rHuPH20 as assessed by multiple measures including Cavgd28, Cmind28, and Cmax1.

Parts A-D study primary objectives are to describe the pharmacokinetics of nivolumab administered subcutaneously, with or without rHuPH20, and the endpoints are Cmax, Tmax, AUC(TAU), and Ctau (Parts A, B, and D), and Ctau (Part C). Secondary objectives include (i) to assess the safety profile of SC nivolumab; (ii) to evaluate incidence of AEs in the broad standardized MedDRA query (SMQ) of Anaphylactic Reaction and the select AE hypersensitivity/infusion reaction category; and (iii) to assess the immunogenicity of nivolumab. Secondary endpoints include (i) incidences of AEs, SAEs, AEs leading to discontinuation, deaths, and laboratory abnormalities; (ii) incidence of AEs in the broad SMQ of Anaphylactic Reaction occurring within 2 days after study drug administration; (iii) incidence of events within the hypersensitivity/infusion reaction select AE category occurring within 2 days after study drug administration; and (iv) incidence of anti-nivolumab antibodies and neutralizing antibodies, if applicable. Exploratory objectives include (i) to evaluate preliminary efficacy in all participants; (ii) to characterize biomarker measures of immune function and tumor genetics and genomics; (iii) to assess the immunogenicity of rHuPH20; and (iv) to assess the preliminary participant experience and preference for SC or IV administration of nivolumab. Exploratory endpoints include (i) ORR, PFS, and OS; (ii) summary measures of change (or % change) from baseline in various biomarkers and molecular characteristics of the tumor; (iii) incidence of anti-rHuPH20 antibodies and neutralizing antibodies, if applicable; and (iv) patient experience/preference questionnaire and qualitative patient interviews.

Results

Thirty-two subjects have been treated with a single dose of nivolumab (either 720 mg or 960 mg) administered via SC injection co-administered with rHuPH20, followed by IV nivolumab. An interim analysis was conducted after all subjects in Part B (Group 3) completed 1 cycle of SC nivolumab. 22 subjects in Part A—Group 1 (720 mg+rHuPH20) and 10 subjects in Part B—Group 3 (960 mg+rHuPH20) were analyzed for PK and early safety data. No formal outputs for efficacy are available at the time of the lock due to the short follow-up.

As of the DBL (minimum pre-dose Cycle 2 Day 1 on all Part B Group 3), the median follow-up for Part A—Group 1 (N=22) was 4.4 months (range: 2.4-8.8 months) and in Part B—Group 3 (N=10) was 2.5 months (range: 2.1-3.5 months).

The baseline disease characteristics of the study participants are shown in Table 53. There were 14 males and 18 females. Median (range) age of all patients was 66.5 (48-90) years. The 32 subjects represent a diverse patient population, including subjects with a range of ages, weights, and tumors (NSCLC, CRC, RCC, HCC, melanoma, and SCCHN) in the advanced/metastatic setting.

TABLE 53A

| Baseline Characteristics | | | |
|---|---|---|---|
| | Number of Subjects (%) | | |
| | PART A—GRP 1 N = 22 | PART B—GRP 3 N = 10 | Total N = 32 |
| TUMOR TYPE | | | |
| COLORECTAL CANCER | 6 (27.3) | 3 (30.0) | 9 (28.1) |
| HEPATOCELLULAR CARCINOMA | 2 (9.1) | 0 | 2 (6.3) |
| MELANOMA | 2 (9.1) | 0 | 2 (6.3) |
| NON-SMALL CELL LUNG CARCINOMA | 7 (31.8) | 3 (30.0) | 10 (31.3) |
| RENAL CELL CARCINOMA | 5 (22.7) | 3 (30.0) | 8 (25.0) |
| NOT REPORTED* | 0 | 1 (10.0) | 1 (3.1) |
| SUBJECTS WITH PD-L1 CERTIFIABLE AT BASELINE (N(%)) | 18 (81.8) | 3 (30.0) | 21 (65.6) |
| SUBJECTS WITH BASELINE PD-L1 EXPRESSION >= 1% | 9 (50.0) | 3 (100.0) | 12 (57.1) |
| SUBJECTS WITH BASELINE PD-L1 EXPRESSION < 1% | 9 (50.0) | 0 | 9 (42.9) |
| SUBJECTS WITH BASELINE PD-L1 EXPRESSION >= 5% | 7 (38.9) | 2 (66.7) | 9 (42.9) |
| SUBJECTS WITH BASELINE PD-L1 EXPRESSION < 5% | 11 (61.1) | 1 (33.3) | 12 (57.1) |
| SUBJECTS WITH BASELINE PD-L1 EXPRESSION >= 50% | 3 (16.7) | 0 | 3 (14.3) |
| SUBJECTS WITH BASELINE PD-L1 EXPRESSION < 50% | 15 (83.3) | 3 (100.0) | 18 (85.7) |
| PRIOR LINES OF THERAPIES | | | |
| 0 | 2 (9.1) | 2 (20.0) | 4 (12.5) |
| 1 | 0 | 0 | 0 |
| 2 | 13 (59.1) | 4 (40.0) | 17 (53.1) |
| >=3 | 5 (22.7) | 4 (40.0) | 9 (28.1) |
| NOT REPORTED | 2 (9.1) | 0 | 2 (6.3) |
| PERFORMANCE STATUS (ECOG) [%] | | | |
| 0 | 9 (40.9) | 3 (30.0) | 12 (37.5) |
| 1 | 13 (59.1) | 7 (70.0) | 20 (62.5) |

Preliminary Safety Data

Group 1 (720 mg+rHuPH20 SC dose followed by IV): Any-grade treatment-related AEs (TRAEs) were reported in 10 (45.5%) subjects and were generally known AEs within nivolumab IV program (Table 54B). Low-grade erythema, irritation, and swelling at the SC injection site were reported in 3 (14%) subjects.

Group 3 (960 mg+rHuPH20 SC dose followed by IV): Any grade TRAEs were reported in 3 (30%) subjects, which included Grade 1-2 immune-mediated skin rash, livedo reticularis, and local site reactions. Low grade erythema, pruritis and swelling at the SC injection site were reported in 2 (20%) subjects. At time of the DBL, there were no treatment-related SAEs (TRSAE) reported in Group 3.

Early safety analyses of subjects receiving SC nivolumab 720 mg+rHuPH20 (Group 1) and 960 mg SC+rHuPH20 (Group 3) are descriptive (and not intended for comparison across groups). The clinical safety profile of single dose SC nivolumab followed by IV (Cycle 2+) reflect treatment-related AEs and SAEs previously reported within the nivolumab IV IB, with the exception of SC local reactions. With respect to local AEs with SC injection, there were no unexpected local site reactions and all reported events were low grade and manageable. All 32 subjects in Group 1 and 3 had Cycle 1 Day 1 SC nivolumab (720 mg or 960 mg)+rHuPH20 doses administered in a single manual injection of either 6 mL or 8 mL, respectively.

Two deaths occurred on study due to progressive disease (neither was attributed to study drug).

Summaries of AEs, TRAEs, and TRSAEs are provided in Tables 2A-2C, respectively.

TABLE 54A

| Adverse Events Summary-All Treated Subjects, Group 1 and Group 3-Interim Analysis | | | | | | |
|---|---|---|---|---|---|---|
| | PART A-GRP 1, N = 22 | | | PART B-GRP 3, N = 10 | | |
| | Any Grade (%) | Grade 3-4 (%) | Grade 5 (%) | Any Grade (%) | Grade 3-4 (%) | Grade 5 (%) |
| Any AE | 21 (95.5) | 4 (18.2) | 2 (9.1)[a] | 10 (100) | 2 (20) | 0 |
| Drug-Related AEs | 10 (45.5) | 1 (4.5) | 0 | 3 (30) | 0 | 0 |
| Drug-Related AEs leading to DC | 1 (4.5) | 1 (4.5) | 0 | 0 | 0 | 0 |

TABLE 54A-continued

Adverse Events Summary-All Treated Subjects,
Group 1 and Group 3-Interim Analysis

| | PART A-GRP 1, N = 22 | | | PART B-GRP 3, N = 10 | | |
|---|---|---|---|---|---|---|
| | Any Grade (%) | Grade 3-4 (%) | Grade 5 (%) | Any Grade (%) | Grade 3-4 (%) | Grade 5 (%) |
| SAEs | 5 (22.7) | 5 (22.7) | 2 (9.1)[a] | 3 (30) | 3 (30) | 0 |
| Drug-Related SAEs | 1 (4.5) | 1 (4.5) | 0 | 0 | 0 | 0 |

[a]Grade 5: Death due to Malignant Neoplasm Progression 50 year-old male, RCC with pulmonary metastases; and Death due to Malignant Neoplasm Progression 76 year-old male CRC

TABLE 54B

Drug-Related Adverse Events Summary by Worst CTC Grade-All
Treated Subjects, Group 1 and Group 3-Interim Analysis

| System Organ Class (%) | PART A-GRP 1 N = 22 | | | PART B-GRP 3 N = 10 | | |
|---|---|---|---|---|---|---|
| Preferred Term (%) | Any Grade | Grade 3-4 | Grade 5 | Any Grade | Grade 3-4 | Grade 5 |
| TOTAL SUBJECTS WITH AN EVENT | 10 (45.5) | 1 (4.5) | 0 | 3 (30.0) | 0 | 0 |
| General disorders and administration site conditions | 4 (18.2) | 0 | 0 | 2 (20.0) | 0 | 0 |
| Fatigue | 2 (9.1) | 0 | 0 | 0 | 0 | 0 |
| Injection site erythema | 2 (9.1) | 0 | 0 | 1 (10.0) | 0 | 0 |
| Administration site erythema | 0 | 0 | 0 | 1 (10.0) | 0 | 0 |
| Injection site irritation | 1 (4.5) | 0 | 0 | 0 | 0 | 0 |
| Injection site pruritus | 0 | 0 | 0 | 1 (10.0) | 0 | 0 |
| Injection site swelling | 1 (4.5) | 0 | 0 | 1 (10.0) | 0 | 0 |
| Musculoskeletal and connective tissue disorders | 3 (13.6) | 0 | 0 | 0 | 0 | 0 |
| Arthralgia | 2 (9.1) | 0 | 0 | 0 | 0 | 0 |
| Arthritis | 1 (4.5) | 0 | 0 | 0 | 0 | 0 |
| Psoriatic arthropathy | 1 (4.5) | 0 | 0 | 0 | 0 | 0 |
| Endocrine disorders | 2 (9.1) | 0 | 0 | 0 | 0 | 0 |
| Hyperthyroidism | 2 (9.1) | 0 | 0 | 0 | 0 | 0 |
| Skin and subcutaneous tissue disorders | 2 (9.1) | 0 | 0 | 2 (20.0) | 0 | 0 |
| Pruritus | 2 (9.1) | 0 | 0 | 0 | 0 | 0 |
| Livedo reticularis | 0 | 0 | 0 | 1 (10.0) | 0 | 0 |
| Rash macular | 0 | 0 | 0 | 1 (10.0) | 0 | 0 |
| Cardiac disorders | 1 (4.5) | 1 (4.5) | 0 | 0 | 0 | 0 |
| Cardiac failure congestive | 1 (4.5) | 1 (4.5) | 0 | 0 | 0 | 0 |
| Gastrointestinal disorders | 1 (4.5) | 0 | 0 | 0 | 0 | 0 |
| Diarrhoea | 1 (4.5) | 0 | 0 | 0 | 0 | 0 |
| Injury, poisoning and procedural complications | 1 (4.5) | 0 | 0 | 0 | 0 | 0 |
| Infusion related reaction | 1 (4.5) | 0 | 0 | 0 | 0 | 0 |
| Renal and urinary disorders | 1 (4.5) | 1 (4.5) | 0 | 0 | 0 | 0 |
| Tubulointerstitial nephritis | 1 (4.5) | 1 (4.5) | 0 | 0 | 0 | 0 |

TABLE 54C

Drug-Related Serious Adverse Events Summary-All Treated
Subjects, Group 1 and Group 3-Interim Analysis

| System Organ Class (%) | PART A-GRP 1 N = 22 | | | PART B-GRP 3 N = 10 | | |
|---|---|---|---|---|---|---|
| Preferred Term (%) | Any Grade | Grade 3-4 | Grade 5 | Any Grade | Grade 3-4 | Grade 5 |
| TOTAL SUBJECTS WITH AN EVENT | 1 (4.5) | 1 (4.5) | 0 | 0 | 0 | 0 |
| Cardiac disorders | 1 (4.5) | 1 (4.5) | 0 | 0 | 0 | 0 |
| Cardiac failure congestive | 1 (4.5) | 1 (4.5) | 0 | 0 | 0 | 0 |
| Renal and urinary disorders | 1 (4.5) | 1 (4.5) | 0 | 0 | 0 | 0 |
| Tubulointerstitial nephritis | 1 (4.5) | 1 (4.5) | 0 | 0 | 0 | 0 |

Population Pharmacokinetic Analysis of Combined Nivolumab SC/IV Data

A population pharmacokinetic (PPK) modeling and simulation approach was employed to characterize SC nivolumab PK and optimize dose selection for SC nivolumab. The objective of this modeling based analysis was to build a PPK model that describes nivolumab concentration data when administered by both SC and IV routes of administration. Nivolumab concentration data following first dose SC administration from the ongoing trial Parts A and B were available from 29 subjects across 2 dose levels including 720 mg SC nivolumab+rHuPH20 (Part A—Group 1) and 960 mg SC nivolumab+rHuPH20 (Part B—Group 3). These SC data were pooled with the existing IV concentration data in order to develop a combined SC/IV PPK model for nivolumab. An extravascular absorption component was added to the existing established IV PPK model and subsequently the appropriate parameters for absorption including BA (F1) and absorption rate constant (ka) were estimated. Estimates of PK parameters from the combined SC/IV model are summarized in Table 55.

TABLE 55

| Estimates of PK Parameters from the Combined SC/IV PPK Model of Nivolumab | | | |
| --- | --- | --- | --- |
| Parameters[a, b] [Units] | Estimate[c] | Standard Error (RSE %)[d] | 95% Confidence Interval[e, BS] |
| Fixed Effects | | | |
| CL [L/h] | 0.0109 | 3.17E–04 (2.90) | 0.0105-0.0114 |
| VC [L] | 4.26 | 0.0398 (0.936) | 4.19-4.32 |
| Q [L/h] | 0.0335 | 0.00203 (6.07) | 0.0305-0.0377 |
| VP [L] | 2.61 | 0.0831 (3.18) | 2.46-2.73 |
| $CL_{BBWT}$ | 0.588 | 0.0315 (5.36) | 0.532-0.639 |
| $CL_{GFR}$ | 0.147 | 0.0230 (15.6) | 0.111-0.184 |
| $CL_{SEX}$ | −0.163 | 0.0161 (9.83) | −0.191--0.137 |
| $CL_{PS}$ | 0.165 | 0.0137 (8.32) | 0.141-0.187 |
| $CL_{OTH}$ | 0.0243 | 0.0184 (76.0) | −0.005-0.0537 |
| $VC_{BBWT}$ | 0.628 | 0.0358 (5.70) | 0.570-0.685 |
| $VC_{SEX}$ | −0.136 | 0.0180 (13.2) | −0.167--0.107 |
| $CL_{GC}$ | 0.185 | 0.0489 (26.5) | 0.101-0.267 |
| $CL_{EMAX}$ | −0.316 | 0.0321 (10.2) | −0.377--0.275 |
| $CL_{T50}$ | 1.40E+03 | 73.7 (5.27) | 1.27E+03-1.52E+03 |
| $CL_{HILL}$ | 2.78 | 0.512 (18.4) | 2.06-3.78 |
| $CL_{RAAA}$ | 0.0573 | 0.0396 (69.1) | −0.0066-0.122 |
| $CL_{RAAS}$ | −0.0766 | 0.0258 (33.7) | −0.121--0.0356 |
| $CL_{CHL}$ | −0.321 | 0.0272 (8.47) | −0.366--0.275 |
| KA | 0.0127 | 0.00121 (9.52) | 0.0108-0.0151 |
| F1 | 0.676 | 0.0430 (6.36) | 0.60-0.75 |
| Random Effects | | | |
| ω2CL [-] | 0.112 (0.335) | 0.00560 (5.00) | 0.102-0.120 |
| ω2VC [-] | 0.127 (0.356) | 0.0138 (10.9) | 0.102-0.150 |
| ω2VP [-] | 0.231 (0.480) | 0.0245 (10.6) | 0.194-0.282 |
| ω2EMAX [h] | 0.0504 (0.224) | 0.00893 (17.7) | 0.0379-0.0664 |
| ω2KA | 0.172 (0.414) | 0.0634 (36.9) | 0.070-0.262 |
| ω2F1 | 0.625 (0.791) | 0.239 (38.2) | 0.230-1.046 |
| ω2CL:ω2VC | 0.0354 (0.297) | 0.00347 (9.80) | 0.0294-0.0419 |
| ω2KA:F1 | 0.253 (0.773) | 0.0684 (27.0) | 0.127-0.360 |
| Residual Error | | | |
| Proportional Error[f] | 0.205 | 0.00512 (2.50) | 0.196-0.213 |

[a]Parameters with fixed values (not estimated) are denoted with a superscript 'f' after the names, with the fixed value given in the Estimate column.
[b]Random Effects and Residual Error parameter names containing a colon (:) denote correlated parameters.
[c]Random Effects and Residual Error parameter estimates are shown as Variance (Standard Deviation) for diagonal elements ($\omega$i, i or $\sigma$i, i)) and Covariance (Correlation) for off-diagonal elements ($\omega$i, i or $\sigma$i, i).
[d]RSE % is the relative standard error (Standard Error as a percentage of Estimate).
[e]Confidence intervals of Random Effects and Residual Error parameters are for Variance or Covariance.
[BS]Confidence Interval values are taken from bootstrap calculations (934 successful out of a total of 1000).

The structural PK model consisted of 2 compartments: zero-order absorption for IV administration and first-order absorption for SC administration. The model-determined BA of nivolumab was 67% with high precision (95% CI:

60%-75%). PPK modeling and simulation approach was employed to characterize SC nivolumab PK and optimize dose selection for SC nivolumab. The objective of this modeling based analysis was to build a PPK model that describes nivolumab concentration data when administered by both SC and IV routes of administration. Nivolumab concentration data following first dose SC administration from the ongoing trial (Parts A and B) were available from 29 subjects across 2 dose levels including 720 mg SC nivolumab+rHuPH20 (Part A—Group 1) and 960 mg SC nivolumab+rHuPH20 (Part B—Group 3). These SC data were pooled with the existing IV concentration data in order to develop a combined SC/IV PPK model for nivolumab. An extravascular absorption component was added to the existing established IV PPK model and subsequently the appropriate parameters for absorption including BA (F1) and absorption rate constant (ka) were estimated. Estimates of PK parameters from the combined SC/IV model are summarized in Table 55.

The structural PK model consisted of 2 compartments: zero-order absorption for IV administration and first-order absorption for SC administration. The model-determined BA of nivolumab was 67% with high precision (95% CI: 60%-75%). PPK modeling and simulation approach was employed to characterize SC nivolumab PK and optimize dose selection for SC nivolumab. The objective of this modeling based analysis was to build a PPK model that describes nivolumab concentration data when administered by both SC and IV routes of administration. Nivolumab concentration data following first dose SC administration from the ongoing CA2098KX (Parts A and B) were available from 29 subjects across 2 dose levels including 720 mg SC nivolumab+rHuPH20 (Part A—Group 1) and 960 mg SC nivolumab+rHuPH20 (Part B—Group 3). These SC data were pooled with the existing IV concentration data in order to develop a combined SC/IV PPK model for nivolumab. An extravascular absorption component was added to the existing established IV PPK model and subsequently the appropriate parameters for absorption including BA (F1) and absorption rate constant (ka) were estimated. Estimates of PK parameters from the combined SC/IV model are summarized in Table 55.

The structural PK model consisted of 2 compartments: zero-order absorption for IV administration and first-order absorption for SC administration. The model-determined BA of nivolumab was 67% with high precision (95% CI: 60%-75%).

Figure 4:
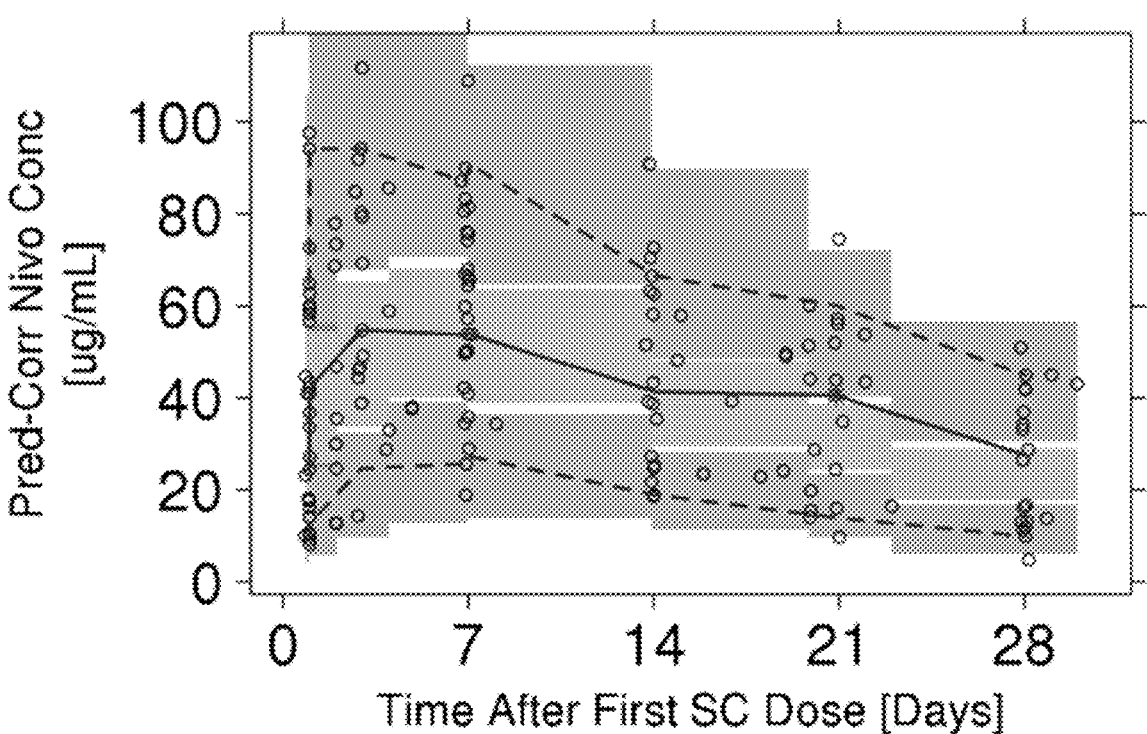
FIG. 4 is a line graph illustration of a predictive check of a combined SC/IV PPK model for administration of nivolumab. Individual dots represent observed data. The lines represent the 5th, 50th, and 95th percentiles of observed data, respectively. Shaded areas represent the simulation-based 90% CIs for the 5th (lowest trend line), 50th (middle trend line), and 95th (highest trend line) percentiles of the predicted data. Conc=concentration; Nivo=nivolumab; Pred-Corr=prediction corrected.

The combined SC/IV PPK model underwent an internal validation exercise to ensure that the model was able to predict the observed concentration values following SC administration. Visual predictive checks (FIG. 4) suggested that the combined SC/IV model adequately captured and described the observed SC nivolumab concentration data.

Using the model described above, deterministic simulations were conducted to generate exposure measures for the subjects treated with available PK data in CA2098KX. Summary of the exposure measures by dose level are provided in Table 56.

TABLE 56

Summary of Predicted Exposures in Treated Subjects by Dose Level

| Dose SC Q4W | Cavgd28 (ug/ml) GeoMean(% CV) | Cmind28 (ug/ml) GeoMean(% CV) | Cmax1 (ug/ml) GeoMean(% CV) | Tmax1 (hours) Mean (SD) |
|---|---|---|---|---|
| 720 mg (N = 22) | 36.9 (44.2) | 22 (56.8) | 51.3 (24.7) | 141 (63.8) |
| 960 mg (N = 9) | 61.8 (27.2) | 40.6 (24.3) | 83.5 (31.3) | 136 (48) |

Abbreviations:
Cavgd28 = average concentration at day 28;
Cmax1 = maximum concentration after the first dose;
Cmind28 = minimum concentration at day 28;
CV = coefficient of variation;
GeoMean = geoetric mean;
Q4W = every 4 weeks;
SC = subcutaneous;
SD = standard deviation;
Tmax1 = time to maximum plasma concentration after the first dose.

Single Arm Expansion Cohort of RCC Subjects

Figure 3:
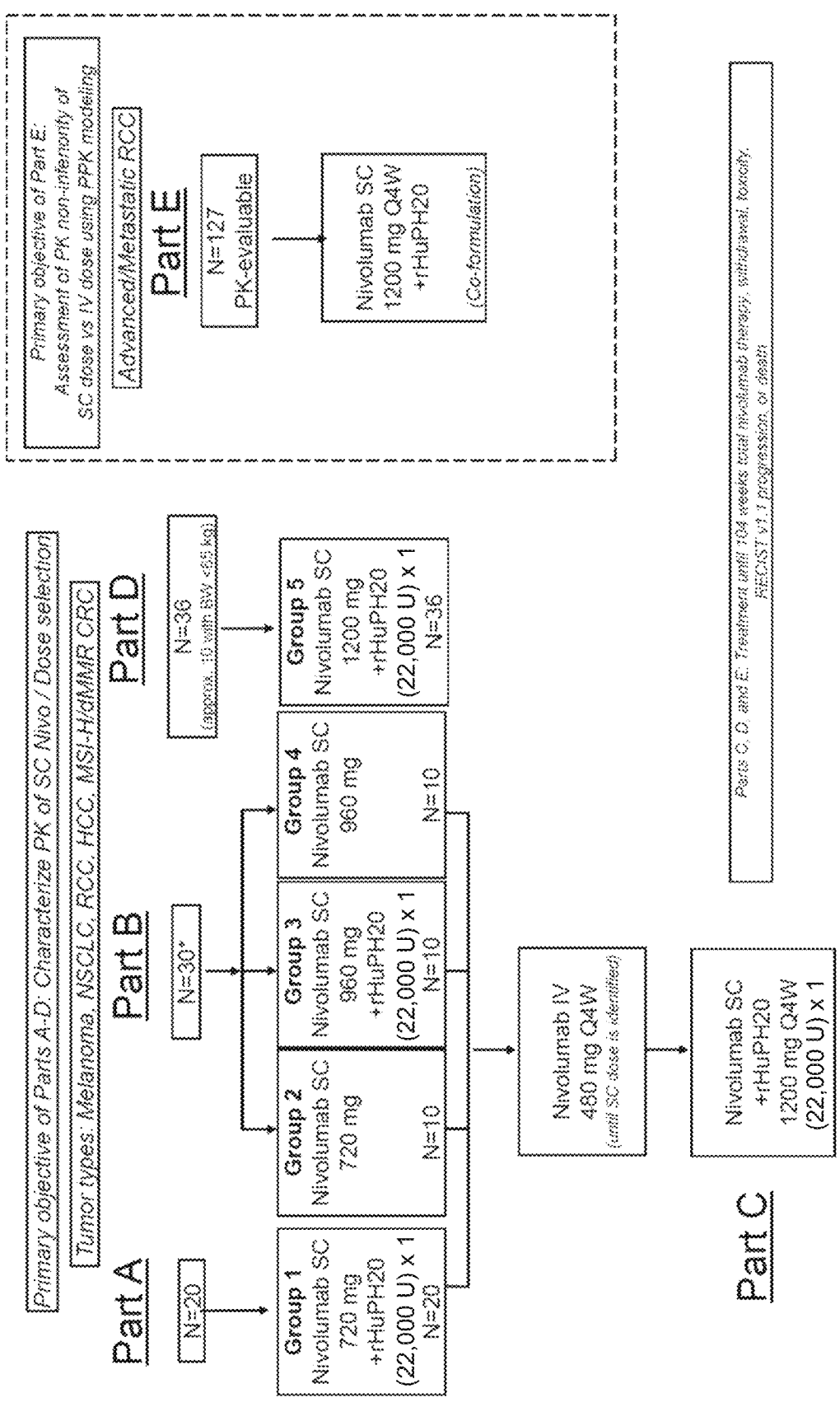
FIG. 3 is a schematic of a study directed to assessing the safety and efficacy of various doses of a subcutaneously administered anti-PD-1 antibody (e.g., nivolumab) alone or in combination with a hyaluronidase (e.g., rHuPH20).

The trial will be expanded to include a single-arm, single-tumor, expansion cohort (Part E) with advanced/metastatic RCC (FIG. 3). The primary objective of Part E is to demonstrate PK non-inferiority of SC nivolumab 1200 mg+rHuPH20 (co-formulation) Q4W versus IV dosing (3 mg/kg Q2W) by comparing the model-predicted SC and IV exposures. Non-inferiority is defined as the lower limit of the two-sided 90% CI of the geometric mean ratio of at least 0.8 for the measure of exposure (co-primary endpoints: Cavgd28; Cmind28). Demonstration of Cavgd28 and Cmind28 non-inferiority will ensure that efficacy of SC nivolumab Q4W will be maintained at a level comparable to IV nivolumab 3 mg/kg Q2W.

Secondary objections of Part E are (i) to evaluate PK of SC nivolumab co-formulated with rHuPH20; (ii) to evaluate the safety profile of SC nivolumab co-formulated with rHuPH20; (iii) to evaluate the immunogenicity of nivolumab; and (iv) to evaluate investigator-assessed response. Secondary endpoints include (i) Cmax1, AUC (TAU), Cavg(ss), and Cmin(ss); (ii) incidences of AEs, SAEs, AEs leading to discontinuation, deaths, and laboratory abnormalities; (iii) incidence of anti-nivolumab antibodies and neutralizing antibodies, if applicable; and (iv) ORR. Exploratory objectives include (i) to explore efficacy in all participants; (ii) to explore biomarker measures of immune function and tumor genetics and genomics; (iii) to explore the immunogenicity of rHuPH20; and (iv) to explore participant experience with SC nivolumab. Exploratory endpoints include (i) PFS, OS, time to response, and duration of response; (ii) change from baseline in different biomarkers and molecular characteristics of the tumor/blood; (iii) incidence of anti-rHuPH20 antibodies and neutralizing antibodies, if applicable; and (iv) patient experience/preference questionnaire and qualitative patient interviews.

Selection of RCC as the tumor type for Part E is supported by extensive historical PK data and well-established PPK and E-R models for IV nivolumab in tumor type. Nivolumab E-R curves for efficacy and safety in RCC were flat in the dose range of 1 mg/kg to 10 mg/kg (data not shown). Given the well-established flat E-R relationship in RCC and melanoma across a wide range of tested doses, the benefit/risk assessment of SC nivolumab in Part E can reasonably support extrapolation to all tumor types where IV nivolumab has proven to be safe and efficacious. Selection of 3 mg/kg IV Q2W as the virtual IV treatment arm is based on: robust data on exposure, efficacy, and safety for 3 mg/kg IV Q2W. Most studies, including pivotal studies for all approved indications, evaluated nivolumab at a dose of 3 mg/kg IV Q2W. Well-characterized efficacy, safety, and PK profiles are, therefore, available for this dose. Well-established E-R in RCC and melanoma that spans the 3 mg/kg IV Q2W regimen showed no significant association of exposure and safety/efficacy. Demonstration of PK non-inferiority of SC dose versus the 3 mg/kg Q2W IV dose is sufficient to conclude that the benefit-risk profile of SC nivolumab would be comparable to IV nivolumab in advanced/metastatic RCC and by extrapolation to other tumor types for the following reasons:

Efficacy of 3 mg/kg IV Q2W has been demonstrated in dose ranging and pivotal studies conducted across tumor types. Therefore, if similar or greater Cavgd28 and Cmind28 are achieved with the SC dosing regimen of 1200 mg Q4W, then it is expected that the safety and efficacy profile of SC nivolumab would be comparable to IV nivolumab.

Inclusion/Exclusion Criteria/Patient Characteristics

Key inclusion criteria include: (i) PD-L1 treatment naïve; (ii) histological confirmation of RCC with a clear cell component (must have received at least 1, and no more than 2, lines of prior systemic treatment regimens in the advanced or metastatic setting, and must have evidence of progression on or after the last treatment regimen received and within 6 months prior to study enrollment); (iii) a formalin-fixed, paraffin-embedded tumor tissue block or unstained slides of tumor sample (archival or recent) for biomarker evaluation is requested for subjects at study entry; (iv) male and female participants must be ≥12 years old or age at the time of informed consent; (v) participants must be assessed for tumor PD-L1 expression by immunohistochemistry (IHC); (vi) measurable disease as per Response Evaluation Criteria In Solid Tumors (RECIST) version 1.1 criteria; (vii) participants must have an ECOG performance status of 0 or 1; and (viii) all participants must have the ability to comply with treatment, patient-reported outcomes, PK, pharmacodynamic sample collection, and study follow-up requirements.

Key exclusion criteria include (i) treatment with botanical preparations (eg, herbal supplements or traditional Chinese medicines) to treat the disease under study within 2 weeks prior to randomization/treatment; (ii) participants with an active autoimmune disease or any other condition requiring systemic treatment with either corticosteroids within 14 days (>10 mg daily prednisone equivalent) or other immunosuppressive medications within 30 days of randomization (inhaled or topical steroids, and adrenal replacement steroid doses >10 mg daily prednisone equivalent, are permitted in the absence of active autoimmune disease); (iii) participants with type I diabetes mellitus, hypothyroidism only requiring hormone replacement, skin disorders (such as vitiligo, psoriasis, or alopecia) not requiring systemic treatment, or conditions not expected to recur in the absence of an external trigger are permitted to enroll; (iv) untreated symptomatic central nervous system (CNS) metastases (patients are eligible if CNS metastases are asymptomatic and do not require immediate treatment, or have been treated and patients have neurologically returned to baseline (except for residual signs or symptoms related to the CNS treatment); in addition, patients must have been either off corticosteroids, or on a stable or decreasing dose of ≤10 mg daily prednisone (or equivalent) for at least 2 weeks prior to enrollment); (v) patients with known human immunodeficiency virus (HIV) who have had an acquired immunodeficiency syndrome (AIDS) defining opportunistic infection within the last year, or a current cluster of differentiation 4 (CD4) count <350 cells/uL; (vi) inadequate organ function based on baseline laboratory assessment; (vii) patients with a concurrent malignancy requiring treatment (patients with a previously treated malignancy are eligible if treatment was completed at least 2 years before registration and the patient has no evidence of disease; and patients who have a concurrent malignancy that is clinically stable and does not require tumor-directed treatment are also eligible); (viii) patients with serious or uncontrolled medical disorders; (ix) serologic evidence of chronic hepatitis B virus (HBV) infection with an HBV viral load above the limit of quantification. Participants with chronic HBV infection must be on concurrent viral suppressive therapy; (x) serologic evidence of current hepatitis C virus (HCV) infection with an HCV viral load above the limit of quantification; (xi) participants who have received a live/attenuated vaccine within 30 days of first treatment; (xii) history of allergy or hypersensitivity to study drug components; and (xiii) prior treatment with an anti-PD-1, anti-PD-L1, anti-cytotoxic T-lymphocyte associated antigen-4 (CTLA-4) antibody, or any other antibody or drug specifically targeting T-cell co-stimulation or checkpoint pathways.

Rationale for Selection of SC Dose

A PPK modeling and simulation approach was employed for dose selection for SC nivolumab. Nivolumab concentration data following first dose SC administration from Parts A and B were collected across 2 dose levels co-administered with rHuPH20 (720 mg and 960 mg). These data were pooled with the existing IV concentration data in order to develop a combined SC and IV PPK model for nivolumab. An extravascular absorption component was added to the existing established IV PPK model and subsequently the appropriate parameters for absorption including BA and ka were estimated. Simulations were performed using this combined SC/IV PPK model to predict systemic exposures following administration of a range of doses across the range of body weights. Under the various scenarios that accounted for the potential uncertainty in BA tested, it was determined that a SC nivolumab 1200 mg Q4W regimen would elicit a comparable benefit-risk profile to IV nivolumab 3 mg/kg Q2W. This was based on the rationale that this dosing regimen is capable of delivering Cavgd28 and Cmin28 exposures that are similar to or greater than those associated with the IV nivolumab 3 mg/kg Q2W while maintaining all measures of exposures below those associated with IV nivolumab 10 mg/kg Q2W for all body weights. Additionally, clinical trial simulations under the most conservative scenario considered (low bioavailability, in an RCC population that tends to have higher body weights) suggest that SC nivolumab 1200 mg Q4W has a relatively higher probability than 960 mg Q4W of achieving the non-inferiority criteria in a SC versus IV trial.

With regards to the anticipated safety profile with the 1200 mg SC dose, predicted exposures are not expected to exceed those produced by nivolumab 10 mg/kg Q2W IV, a dose where safety has been well-characterized and shown to be similar to 3 mg/kg Q2W IV. Given that there were no clinically meaningful differences in incidence of AEs between IV exposures of 3 mg/kg and 10 mg/kg Q2W IV, 1200 mg+rHuPH20 Q4W SC is an appropriate dose, which will provide exposures equal to or greater than 3 mg/kg Q2W IV and within those produced by 10 mg/kg Q2W IV. This will be assessed as part of the amendment underway to characterize actual PK of the 1200 mg SC dose (Parts C and D) and preliminary results will be reviewed prior to the initiation of Part E.

Figures 5A, 5B, 5C:
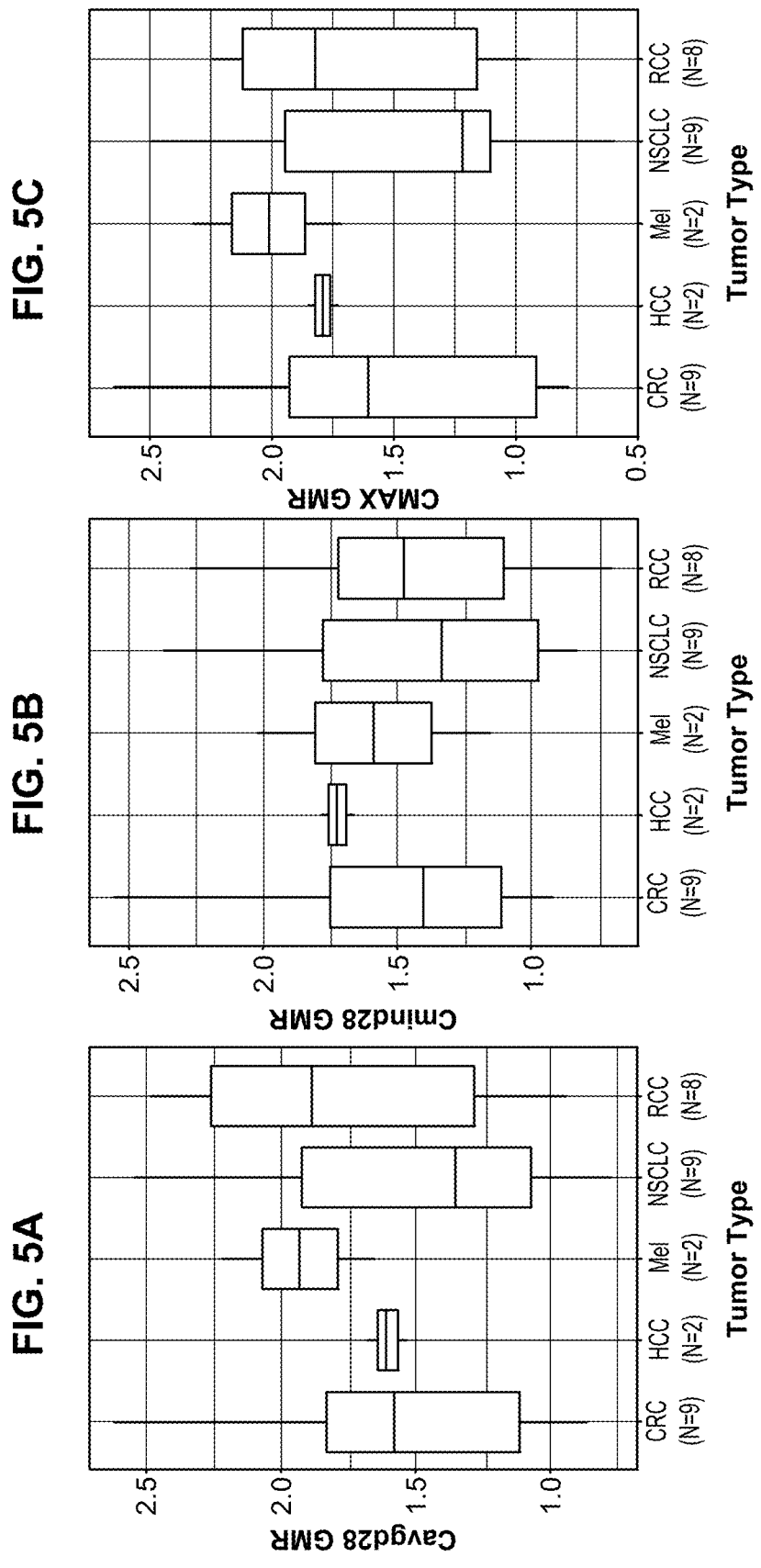
FIGS. 5A-5C are box plots illustrating the predicted geometric mean ratios (SC/IV) for Cavgd28 (FIG. 5A), Cmind28 (FIG. 5B), and Cmax1 (FIG. 5C) exposures, by tumor type. CRC=colorectal cancer; HCC=hepatocellular cancer; Mel=melanoma; NSCLC=non-small cell lung cancer; and RCC=renal cell carcinoma.

Further comparisons of the exposures from deterministic simulations for patients in Arms A and B were conducted to ascertain whether there were any differences in exposures of SC nivolumab 1200 mg Q4W relative to 3 mg/kg Q2W based on tumor type. These simulations accounted for individual parameters of absorption, bioavailability, systemic PK parameters and individual covariate information. Across the tumor types collected in this study, there were no apparent trends or differences in geometric mean ratios (GMRs) for all measures of exposures. All GMRs being equal or greater than 1, indicated that tumor type is unlikely to impact the interpretation of non-inferior exposures, and body weight would continue to remain the major contributor to any differences in exposures from SC 1200 Q4W and 3 mg/kg Q2W IV dosing (FIGS. 5A-5C).

Example 3—Subcutaneous Nivolumab with or without rHuPH20

In support of the clinical studies with subcutaneous (SC) nivolumab administration, nonclinical study was conducted in cynomolgus monkeys to evaluate local tolerance and systemic exposures to nivolumab when administered twice (3 weeks apart) as a SC formulation with and without rHuPH20. SC nivolumab was supplied at 154.57 mg/mL and was administered by SC injection at doses of 0 mg/kg (vehicle), 50 mg/kg (no rHuPH20), or 50 mg/kg (with rHuPH20, 2000 U/mL), twice (Days 1 and 22/20 [males/females]), to groups of 3 monkeys per sex. All doses were administered at 0.5 mL/kg in a vehicle/carrier consisting of 20 mM histidine, 250 mM sucrose, 0.05% polysorbate-80, and 50 µM pentetic acid (histidine buffer). Samples for toxicokinetic analysis were collected following dosing on Day 1 and scheduled necropsies were conducted at 72 hours following dosing on Day 22/21 (males/females).

Mean nivolumab systemic exposures (AUC[0-T]) at 50 mg/kg with rHuPH20 were generally similar to those without rHuPH20 (Table 57). Mean time to maximum plasma concentration (Tmax) was 32 hours or 68 hours post-dose with or without rHuPH20, respectively. These results demonstrate that, despite an earlier Tmax with rHuPH20 co-administration, rHuPH20 had no substantial impact on the overall nivolumab systemic exposure in this non-clinical study.

TABLE 57

| Toxicokinetic Summary—Mean Sex-combined Values | | |
|---|---|---|
| | All Monkeys/Exclusion of Monkeys with Detectable Treatment-emergent Anti-nivolumab Antibodies[a] | |
| Parameter | Nivolumab 50 mg/kg (no rHuPH20) | Nivolumab 50 mg/kg (with rHuPH20) |
| AUC(0-T) ($\mu g \cdot$ h/mL) | 187,000/166,000 | 184,000/182,000 |
| Cmax ($\mu g$/mL) | 537/454 | 647/647 |
| Tmax (h) | 68/60 | 32/24 |

Abbreviations:
AUC = area under the concentration-time curve;
Cmax = maximum concentration;
Tmax = time to maximum plasma concentration.
[a]Values were calculated with all/exclusion of monkeys with detectable treatment-emergent anti-nivolumab antibodies.

Treatment-emergent nivolumab anti-drug antibodies (ADAs) were detected in 1 of 6 monkeys either with or without rHuPH20. However, in general, the presence of treatment-emergent ADAs had no substantial impact on nivolumab exposure.

Nivolumab, administered at 50 mg/kg with and without rHuPH20 (2000 U/mL), was well-tolerated with no clinical observations and no local tolerance issues at the SC injection sites and there were no meaningful differences in exposure to nivolumab in the presence or absence of rHuPH20 in this non-clinical study.

Example 3 Subcutaneous Nivolumab in Combination with Recombinant Human Hyaluronidase in Previously Treated Advanced, Recurrent, or Metastatic Non-Small Cell Lung Cancer A phase 3 study will be performed to evaluate the administration of subcutaneous (SC) nivolumab coformulated with recombinant human PH20 (rHuPH20) versus intravenous (IV) nivolumab in participants with previously treated advanced, recurrent, or metastatic non-small cell lung cancer (NSCLC). This study seeks to establish pharmacokinetic (PK) and efficacy non-inferiority of 1200 mg of nivolumab coformulated with 20,000 Units of rHuPH20 administered SC every 4 weeks (Q4W) compared with 3 mg/kg nivolumab administered IV every 2 weeks (Q2W). Throughout the protocol, the coformulation of nivolumab and rHuPH20 will be referred to as SC nivolumab and the IV formulation of nivolumab will be referred to as IV nivolumab.

Males or females 18 years of age or older (or local age of majority) with histologically confirmed Stage IIIB/IIIC/IV NSCLC (squamous or non-squamous) who have experienced disease recurrence or progression during or after 1 prior systemic therapy for advanced or metastatic disease. Objectives and endpoints are presented in Table 58.

TABLE 58

| Objectives and Endpoints | |
|---|---|
| Objective | Endpoint |
| Co-Primary | |
| To demonstrate PK non-inferiority of SC nivolumab 1200 mg Q4W versus IV nivolumab 3 mg/kg Q2W. | Cmind28 |

TABLE 58-continued

| Objectives and Endpoints | |
|---|---|
| Objective | Endpoint |
| To demonstrate ORR non-inferiority of SC nivolumab 1200 mg Q4W versus IV nivolumab 3 mg/kg Q2W . . . | ORR by BICR with a minimum of 6 months follow-up |
| Secondary | |
| To evaluate the PK of SC nivolumab 1200 mg Q4W and IV nivolumab 3 mg/kg Q2W. | Cavgd28, Cmax1, Tmax, Cminss, Cavgss |
| To evaluate the efficacy of SC nivolumab 1200 mg Q4W and IV nivolumab 3 mg/kg Q2W. | 1) ORR by BICR with a minimum of 12 of months follow-up and at end of study<br>2) DCR by BICR with a minimum of 6 and 12 months of follow-up and at end of study<br>3) PFS with a minimum of 6 and 12 months of follow-up and at end of study<br>4) OS with a minimum of 6 and 12 months of follow-up and at end of study<br>5) DoR with a minimum of 6 and 12 months of follow-up and at end of study<br>6) TTR with a minimum of 6 and 12 months of follow-up and at end of study |
| To evaluate the safety profile of SC nivolumab and IV nivolumab. | 7) Incidences of AEs, SAEs, AEs leading to discontinuation, deaths, and laboratory abnormalities |
| To evaluate AEs in the broad standardized MedDRA query (SMQ) of Anaphylactic Reaction, in SC nivolumab arm and in IV nivolumab arms | Incidence of anaphylactic, hypersensitivity, and systemic infusion reactions. Incidence of injection and local infusion site reactions occurring within 2 days of study drug administration |
| To evaluate the immunogenicity of SC nivolumab and IV nivolumab | Percentage of participants who develop anti-nivolumab antibodies and neutralizing antibodies, if applicable |
| Exploratory | |
| To explore translational biomarkers for SC nivolumab and IV nivolumab clinical activity | Summary measures of change (or % change) from baseline in intratumoral markers of tumor inflammation Summary measures of change (or % change) from baseline in peripheral markers of immune activation Summary measures of baseline levels of intratumoral and peripheral biomarkers in both treatment arms to identify potential imbalances |
| To explore the immunogenicity of rHuPH20 | Percentage of participants who develop anti-rHuPH20 antibodies and neutralizing antibodies, if applicable and the impact of anti-rHuPH20 antibodies on AEs, administration related reactions, and events within MedDRA SMQ anaphylactic reactions |
| To explore the impact of immunogenicity of SC nivolumab and IV nivolumab | Percentage of participants who develop anti-nivolumab antibodies and neutralizing antibodies, if applicable, the impact of anti-nivolumab antibodies on AEs, administration-related reactions, and events within MedDRA SMQ anaphylactic reactions |
| To explore the participant experience and preference with SC nivolumab | Percentage of participants who prefer SC and the percentage of participants who prefer IV treatment through PEPQ (Arm A only, SC nivolumab) |

TABLE 58-continued

Objectives and Endpoints

| Objective | Endpoint |
|---|---|
| To explore changes in disease-related symptoms and impacts on health-related quality of life in the IV and SC arms | Mean NSCLC-SAQ scores at baseline and post-baseline score changes |
| To explore changes in health status and health-related quality of life in the IV and SC arms | Mean EQ-5D-5L utility and visual analogue scale scores and post-baseline score changes |

Abbreviations:
AE = adverse event;
BICR = blinded independent central review;
CminD28 = minimum serum concentration over 28 days;
Cavgd28 = average serum concentration at day 28;
Cmax1 = maximum serum concentration after the first dose;
Cminss = steady state trough concentration;
Cavgss = steady state average serum concentration;
DCR = disease control rate;
DoR = duration of response;
IV = intravenous;
MedDRA = Medical Dictionary for Regulatory Activities;
ORR = objective response rate;
OS = overall survival;
PFS = progression-free survival;
PK = pharmacokinetic;
Q2W = every 2 weeks;
Q4W = every 4 weeks;
rHuPH20 = recombinant human hyaluronidase PH20;
SAE = serious adverse event;
SC = subcutaneous;
SMQ = standardized MedDRA queries;
Tmax = time at which Cmax1 is attained;
TTR = time to response.

Overall Design

The present study is a multicenter, randomized, open-label, Phase 3 study that will evaluate PK and efficacy non-inferiority of SC nivolumab versus IV nivolumab and safety and tolerability of SC nivolumab in participants with advanced, recurrent, or metastatic NSCLC.

Arm A (n=257): SC nivolumab coformulation of 1200 mg of nivolumab with 20,000 units of rHuPH20 Q4W±7 days; and Arm B (n=257): IV nivolumab 3 mg/kg Q2W±3 days (FIG. 6).

Figure 6:
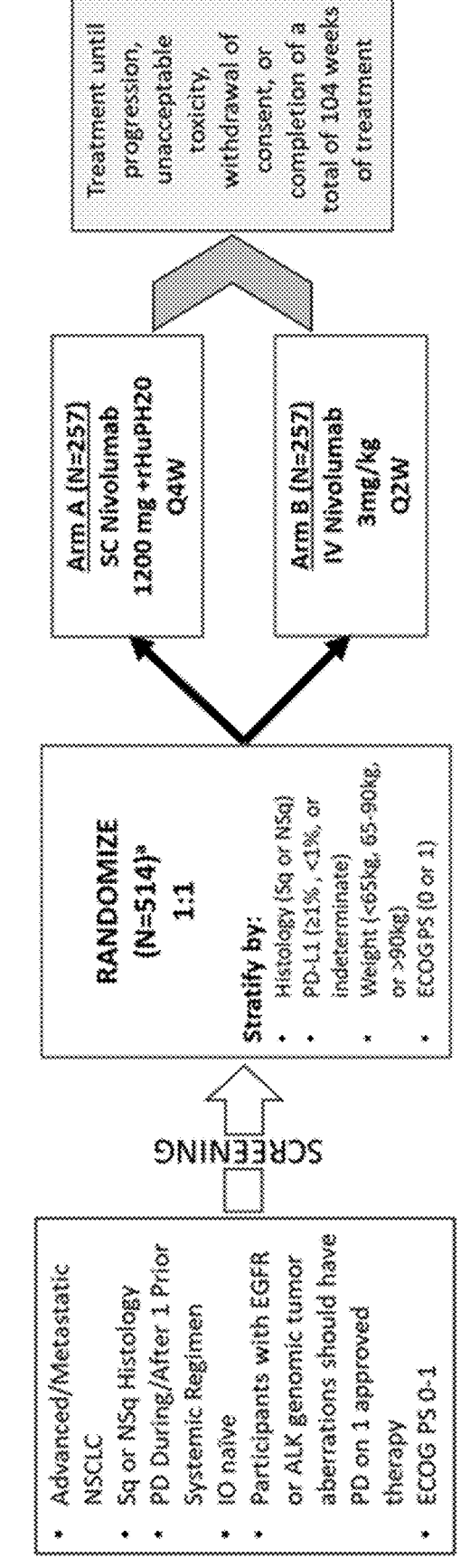
FIG. 6 is a schematic of a study directed to assessing the safety and efficacy of a 1200 mg nivolumab in combination with a hyaluronidase (e.g., rHuPH20) administered subcutaneously once every 4 weeks, as compared to 3 mg/kg nivolumab administered IV once every 2 weeks.

Approximately 514 total participants will be randomized in a 1:1 fashion into the following treatment groups: randomization into treatment groups will be stratified by histology (squamous versus nonsquamous), PD-L1 score (≥1% versus <100 versus indeterminate), weight (<65 kg versus 65-90 kg versus >90 kg), and Eastern Cooperative Oncology Group performance status ECOG-PS (0 versus 1) (FIG. 6). ECOG PS must be assessed within 14 days prior to randomization. Dosing in this study will continue until disease progression per Response Evaluation Criteria in Solid Tumors (RECIST) v.1.1, unacceptable toxicity, withdrawal of consent, completion of 104 weeks of treatment, death, or study termination by the Sponsor, whichever occurs first.

On study tumor assessments should consist of contrast enhanced CT of the chest, CT/MRI of the abdomen, pelvis, and all other known and/or suspected sites of disease should occur every 8 weeks (±7 days) starting from randomization for 2 years (104 weeks), then every 12 weeks (±7 days) until disease progression and treatment discontinuation (including treatment beyond progression), whichever occurs later. Partial response (PR) and complete response (CR) must be assessed and confirmed at least 4 weeks following initial assessment. Tumor response will be assessed using RECIST 1.1.

Serial blood samples will be collected during Cycle 1 in Arm A and during Cycles 1 and 2 in Arm B, followed by predose PK samples throughout the treatment period in both Arms A and B to characterize the PK and immunogenicity of nivolumab.

Safety monitoring will consist of physical examinations, vital sign measurements, and clinical laboratory evaluations at selected times throughout the dosing interval. Participants will be closely monitored for AEs throughout the study. Collection of AEs and severity per National Cancer Institute Common Terminology Criteria for Adverse Events (NCI CTCAE) v.5 criteria will also include local injection-site reactions after SC administration and IV infusion related reactions.

Justification for Dose

Figure 7:
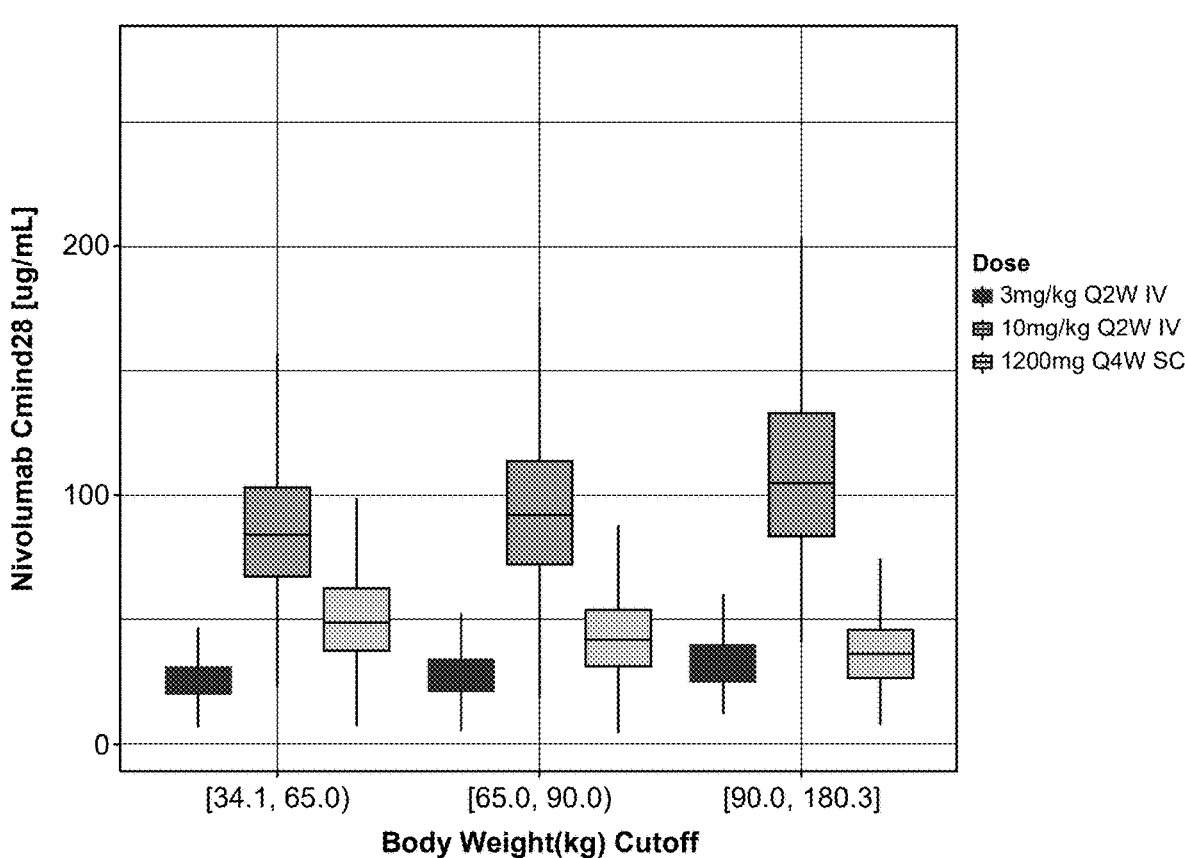
FIG. 7 is a box plot illustrating the distribution of nivolumab Cmind28 across dose and body weight at 3 mg/kg nivolumab IV once every 2 weeks, 10 mg/kg nivolumab IV once every 2 weeks, and 1200 mg nivolumab subcutaneously once every 4 weeks.

PK data from participants enrolled in the study, where nivolumab (720 mg, 960 mg, and 1200 mg) was administered SC with or without rHuPH20, and historical IV data across several tumor types (data from approximately 3000 patients) were used to characterize the absorption profile of nivolumab when given subcutaneously. Population PK (PPK) analysis estimated the mean (90% CI) bioavailability to be 70% (66-74%) and first order rate of absorption to be 0.250 (90% CI: 0.225-0.274) $day^{-1}$. All other PK parameters and effects of covariates on these parameters were consistent with those estimated previously with the IV PPK model. The model estimated exposures with SC nivolumab 1200 mg Q4W and IV nivolumab 3 mg/kg Q2W are presented in Table 59. Based on these results, the SC nivolumab dose of 1200 mg Q4W nivolumab is expected to provide similar or higher exposures across all body weight ranges as compared to IV nivolumab 3 mg/kg Q2W. Also the geometric mean exposures with nivolumab administered SC 1200 mg Q4W are lower than the exposure from the highest tolerated IV dose of 10 mg/kg Q2W and are considered safe (FIG. 7).

TABLE 59

| Model Estimated Exposures for SC Nivolumab (with rHUPH20) and IV Nivolumab Geometric Mean (% CV) | | | |
|---|---|---|---|
| Dose | Cavgd28 (µg/mL) | Cmind28 (µg/mL) | Cmax1 (µg/mL) |
| 1200 mg Q4W SC | 65.50 (35.10) | 40.40 (41.50%) | 93.00 (38.10%) |
| 3 mg/kg Q2W IV | 40.20 (29.40%) | 27.40 (35.20%) | 57.80 (37.70%) |

Abbreviations:
Cavgd28 = average serum concentration on Day 28;
Cmax1 = maxiumum serum concentration after the first dose;
Cmind28 = minimum serum concenration on Day 28;
CV = coefficient of variation;
IV = intravenous;
Q4W = every 4 weeks;
Q2W = every 2 weeks;
SC = subcutaneous.

Inclusion Criteria

Participants must have histologically confirmed NSCLC (squamous or non-squamous) and present with Stage IIIB/IIIC/IV disease (according to version 8 of the International Association for the Study of Lung Cancer Staging Manual in Thoracic Oncology) or with recurrent or progressive disease (according to RECIST 1.1 criteria) following multimodal therapy (radiation therapy, surgical resection, or definitive chemo radiotherapy for locally advanced disease). Participants must have measurable disease by CT or MRI per RECIST 1.1 criteria within 28 days prior to first treatment dose. Participants must have an ECOG performance status of 0 or 1 assessed within 14 days of randomization. Participants must have experienced disease recurrence or progression during or after 1 prior systemic therapy for advanced or metastatic disease.

Maintenance therapy following platinum doublet-based chemotherapy is not considered as a separate regimen of therapy. Participants who received pemetrexed, bevacizumab, or erlotinib as maintenance therapy (non-progressors with platinum-based doublet chemotherapy) and progressed are eligible. Participants who have received adjuvant or neoadjuvant platinum-doublet chemotherapy (after surgery and/or radiation therapy) and developed recurrent or metastatic disease within 6 months of completing therapy are eligible. Participants with recurrent disease >6 months after adjuvant or neoadjuvant platinum-based chemotherapy, who also subsequently progressed during or after a platinum-doublet regimen given to treat the recurrences, are eligible.

All participants with non-squamous histology must have been tested for EGFR mutation status (including, but not limited to, deletions in exon 19 and exon 21 [L858R] substitution); the use of regulatory-approved test is strongly encouraged. Participants who are positive on sensitizing EGFR mutations should have progressive disease after receiving one prior approved EGFR inhibitor. Participants with non-squamous histology who have a known ALK translocation should have progressive disease after receiving one prior approved ALK inhibitor. ALK mutation testing is not required for this study.

Participants with symptomatic tumor lesions at baseline who may require palliative radiotherapy within 4 weeks of the first dose of study treatment are strongly encouraged to receive palliative radiotherapy prior to enrollment. Palliative radiotherapy should be completed 2 weeks prior to the first dose. Target lesions may be located in a previously irradiated field if there is documented (radiographic) disease progression (following RECIST 1.1 criteria) in that site.

Participants with chronic obstructive pulmonary disorder (COPD) that is controlled at study entry are eligible.

A formalin fixed, paraffin-embedded (FFPE) tumor tissue block or a minimum of 20 unstained slides of tumor tissue obtained from core biopsy, punch biopsy, excisional biopsy, or surgical specimen prior to enrollment (within 12 weeks of enrollment) with no intervening systemic anti-cancer treatment between time of acquisition and treatment randomization in IRT. If despite efforts, a minimum of 20 slides are not obtainable, submission of fewer slides may be acceptable in some circumstances following discussion with the Medical Monitor or designee. If tumor tissue obtained within 12 weeks of enrollment is not available, an archival tissue block (within approximately 12 months of enrollment) with no intervening systemic anti-cancer treatment between time of acquisition and treatment randomization in IRT may be submitted. Fine needle aspirates and other cytology samples are not acceptable. Assessment of tumor-cell PD-L1 expression by IHC must be performed by analyzing lab using pre-treatment tissue sample. Analyzing lab must provide IRT with PD-L1 results prior to randomization.

Exclusion Criteria

Participants with an active autoimmune disease or any other condition requiring systemic treatment with either corticosteroids within 14 days (>10 mg daily prednisone equivalent) or other immunosuppressive medications within 30 days of randomization. Inhaled or topical steroids, and adrenal replacement steroid doses >10 mg daily prednisone equivalent, are permitted in the absence of active autoimmune disease. Known history of positive test for human immunodeficiency virus (HIV) or known acquired immunodeficiency syndrome (AIDS).

Participants with type I diabetes mellitus, hypothyroidism only requiring hormone replacement, skin disorders (such as vitiligo, psoriasis, or alopecia) not requiring systemic treatment, or conditions not expected to recur in the absence of an external trigger are permitted to enroll.

Participants with untreated symptomatic CNS metastases. Participants are eligible if CNS metastases are asymptomatic and do not require immediate treatment, or have been treated and patients have neurologically returned to baseline (except for residual signs or symptoms related to the CNS treatment). In addition, participants must have been either off corticosteroids, or on a stable or decreasing dose of ≤10 mg daily prednisone (or equivalent) for at least 2 weeks prior to enrollment.

Participants with a concurrent malignancy requiring treatment. Participants with a previously treated malignancy are eligible if treatment was completed at least 2 years before randomization and the patient has no evidence of disease. Patients who have a concurrent malignancy that is clinically stable and does not require tumor-directed treatment are also eligible.

Participants with interstitial lung disease that is symptomatic or may interfere with the detection or management of suspected drug-related pulmonary toxicity.

Participants who have received treatment with botanical preparations (e.g. herbal supplements or traditional Chinese medicines) to treat the disease under study within 2 weeks prior to randomization/treatment. Participants who have received a live/attenuated vaccine within 30 days of first treatment. Participants who have received prior treatment with an anti-PD-1, anti-PD-L1, anti-CTLA 4 antibody, or any other antibody or drug specifically targeting T-cell co-stimulation or checkpoint pathways.

Inadequate organ function based on baseline laboratory assessments include (i) white blood cell (WBC) <2000/μL; (ii) neutrophils <1500/μL; (iii) platelets <100×103/μL; (iv) hemoglobin <9.0 g/dL; (v) serum creatinine >1.5×upper limit of normal (ULN), unless creatinine clearance ≥40 mL/min (measured or calculated using the Cockroft-Gault formula); (vi) aspartate aminotransferase (AST)/alanine aminotransferase (ALT): >3.0×ULN; (vii) total bilirubin >1.5×ULN (except participants with Gilbert Syndrome who must have a total bilirubin level of <3.0×ULN); and (viii) any positive test result for HBV or HCV virus indicating presence of virus, eg, Hepatitis B surface antigen (HBsAg, Australia antigen) positive, or Hepatitis C antibody (anti-HCV) positive (except if HCV-RNA negative).

Subcutaneous Administration of Nivolumab with rHuPH20 (Arm A)

SC nivolumab should be administered on Day 1 of each treatment cycle every 4 weeks±7 days, until progression, unacceptable toxicity, withdrawal of consent, completion of 104 weeks (2 years) of treatment, death, or the study ends, whichever occurs first. Participants should begin study treatment within 3 calendar days of randomization.

There will be no dose escalations or reductions of nivolumab allowed. Participants may be dosed no less than 25 days from the previous dose for Q4W cycles. Premedications are not recommended for the first dose of nivolumab.

Doses of nivolumab may be interrupted, delayed, or discontinued depending on how well the participant tolerates the treatment. Dosing visits are not skipped, only delayed SC Nivolumab will be administrated via manual injection in one of the quadrants of the abdomen for the first cycle. For subsequent cycles, one of the four quadrants of the abdomen and either thigh are options, and injection sites should be alternated. SC administration should occur as steadily as possible (i.e., no start or stop, and at a steady rate) over a period of approximately 3-5 minutes. Participants will be monitored for approximately 360 minutes following the Cycle 1 Day 1 and Cycle 2 Day 1 SC manual injections of SC nivolumab. Participants receiving subsequent SC injections may be monitored for approximately 30 minutes post injection as clinically warranted and at the discretion of the investigator. In addition, all participants will be contacted approximately 24 hours after each SC injection for reporting of any injection-site reactions. The injection site will be also be evaluated at the next study visit. The site of SC injection, duration, and needle type must be recorded in the electronic case report form (eCRF). Instructions for preparation of the SC nivolumab dose are provided in the Pharmacy Manual.

Example 4—Subcutaneous Nivolumab with or without rHuPH20

In an ongoing phase ½ study, checkpoint inhibitor-naïve patients (pts) who were ≥18 years of age, ECOG PS 0-1, with metastatic/unresectable solid tumors and measurable disease were administered varying doses of nivolumab, with our without rHuPH20. The primary objective was to describe subcutaneous nivolumab pharmacokinetics (PK); and secondary objectives were safety and immunogenicity. Additional analyses compared exposures to historical IV nivolumab. In cycle 1, patients in Part A received subcutaneous nivolumab 720 mg+rHuPH20, and patients in Part B received subcutaneous nivolumab 720 mg, subcutaneous nivolumab 960 mg+rHuPH20, or subcutaneous nivolumab 960 mg. For cycles 2+, patients in Parts A and B received IV nivolumab 480 mg every 4 weeks (Q4W). Patients still on study switched to Part C, subcutaneous nivolumab 1200 mg+rHuPH20 until end of therapy. In Part D, patients received de novo subcutaneous nivolumab 1200 mg+rHuPH20 Q4W. Subcutaneous injection was a single injection into the abdomen or thigh.

Patient characteristics varied by age, weight, tumor type, and prior treatment. Baseline demographics and disease characteristics for Parts C and D are shown in Table 60. Tumor types in Part A included non-small cell lung cancer (NSCLC), renal cell carcinoma (RCC), melanoma (Mel), hepatocellular carcinoma (HCC), and microsatellite instability-high/mismatch repair deficient colorectal cancer (MSI-H/dMMR CRC).

TABLE 60

| Baseline demographics/disease characteristics for Parts C and D | | | | | |
|---|---|---|---|---|---|
| | Part C patients who transitioned to SC (1200 mg + rHuPH20 by initial treatment assignment | | | | Part D (1200 mg + |
| | Group 1 n = 9 | Group 2 n = 6 | Group 3 n = 5 | Group 4 n = 8 | Total N = 28 | rHuPH20) N = 36 |
| Age, years | | | | | | |
| Mean | 70.7 | 65.3 | 65.2 | 69.3 | 68.1 | 64.6 |
| Median (range) | 71.0 (52-90) | 64.0 (53-80) | 66.0 (60-70) | 69.0 (58-80) | 67.5 (52-90) | 69.0 (24-93) |
| Age category, n (%) | | | | | | |
| <65 | 2 (22.2) | 3 (50.0) | 2 (40.0) | 2 (25.0) | 9 (32.1) | 14 (38.9) |
| ≥65 to < 75 | 4 (44.4) | 1 (16.7) | 3 (60.0) | 4 (50.0) | 12 (42.9) | 17 (47.2) |
| ≥75 | 3 (33.3) | 2 (33.3) | 0 | 2 (25.0) | 7 (25.0) | 5 (13.9) |
| Sex, n (%) | | | | | | |
| Male | 3 (33.3) | 5 (83.3) | 2 (40.0) | 6 (75.0) | 16 (57.1) | 26 (72.2) |
| Female | 6 (66.7) | 1 (16.7) | 3 (60.0) | 2 (25.0) | 12 (42.9) | 10 (27.8) |
| ECOG PS, n (%) | | | | | | |
| 0 | 6 (66.7) | 5 (83.3) | 2 (40.0) | 2 (25.0) | 15 (53.6) | 12 (33.3) |
| 1 | 3 (33.3) | 1 (16.7) | 3 (60.0) | 6 (75.0) | 13 (46.4) | 24 (66.7) |
| Weight, Kg[a] | | | | | | |
| Mean | 77.1 | 70.2 | 60.6 | 75.9 | 72.3 | 80.4 |
| Median (range) | 72.7 (66-97) | 69.5 (63-78) | 60.0 (50-71) | 73.3 (66-94) | 71.6 (50-97) | 80.7 (48-133) |
| Tumor types, n (%) | | | | | | |
| NSCLC | 3 (33.3) | 0 | 2 (40.0) | 2 (25.0) | 7 (25.0) | 11 (30.6) |
| RCC | 2 (22.2) | 0 | 2 (40.0) | 1 (12.5) | 5 (17.9) | 9 (25.0) |
| MSI-H/dMMR CRC | 2 (22.2) | 3 (50.0) | 1 (20.0) | 2 (25.0) | 8 (28.6) | 7 (19.4) |
| HCC | 1 (11.1) | 3 (50.0) | 0 | 3 (37.5) | 7 (25.0) | 6 (16.7) |
| Melanoma | 1 (11.1) | 0 | 0 | 0 | 1 (3.6) | 3 (8.3) |
| Region, n (%) | | | | | | |
| EU | 1 (11.1) | 5 (83.3) | 3 (60.0) | 6 (75.0) | 15 (53.6) | 14 (38.9) |
| New Zealand | 5 (55.6) | 1 (16.7) | 2 (40.0) | 1 (12.5) | 9 (32.1) | 15 (41.7) |
| South America | 0 | 0 | 0 | 1 (12.5) | 1 (3.6) | 7 (19.4) |
| United States | 3 (33.3) | 0 | 0 | 0 | 3 (10.7) | 0 |
| Lines of prior therapy, n (%) | | | | | | |
| 0 | 2 (22.2) | 0 | 1 (20.0) | 1 (12.5) | 4 (14.3) | 8 (22.2) |
| 1 | 5 (55.6) | 3 (50.0) | 2 (40.0) | 5 (62.5) | 15 (53.6) | 26 (72.2) |
| 2 | 2 (22.2) | 2 (33.3) | 0 | 2 (25.0) | 6 (21.4) | 1 (2.8) |
| ≥3 | 0 | 1 (16.7) | 2 (40.0) | 0 | 3 (10.7) | 1 (2.8) |

Figures 8A, 8B, 8C:
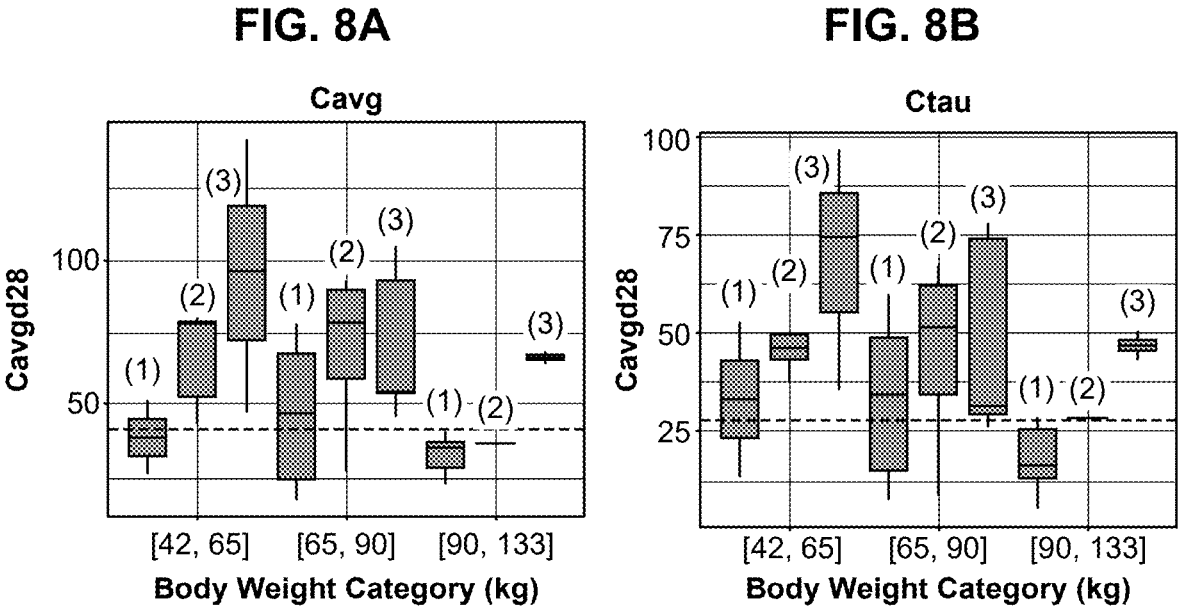
FIGS. 8A-8C are box plots illustrating observed distribution of $C_{avg}$ (FIG. 8A), $C_{tau}$ (FIG. 8B), and $C_{max}$ (FIG. 8C) by weight observed following subcutaneous delivery of nivolumab at 720 mg, 960 mg, or 1200 mg with rHuPH20. The dashed line shows the geometric mean $C_{avg}$ (FIG. 8A) and $C_{tau}$ (FIG. 8B) for nivolumab 3 mg/kg IV Q2W (historical) and the geometric mean $C_{max}$ (FIG. 8C) for nivolumab 10 mg/kg IV Q2W (historical).

Nivolumab exposures increased with increasing subcutaneous dose (Table 61; FIGS. 8A-8C). For 960 mg and 1200 mg nivolumab+rHuPH20, $C_{avg}$ and $C_{tau}$ were above geometric mean exposures for IV nivolumab 3 mg/kg every 2 weeks (Q2W), and $C_{max}$ was below IV nivolumab 10 mg/kg Q2W. In Part C (n=28), 13 (46.4%) patients experienced any-grade TRAEs with no new/worsening grade 3+ TRAEs or TRAEs leading to discontinuation/death; 7 (25.0%) reported grade 1 local site reactions. In Part D (n=36), 27 (75.0%) patients experienced any-grade TRAEs, 4 (11.1%) grade ¾ TRAEs, 2 (5.6%) serious grade ¾ TRAEs with 1 leading to discontinuation, and no treatment-related deaths; 10 (27.8%) reported grade 1 local site reactions. Anti-nivolumab antibodies (Ab) were observed with subcutaneous nivolumab but not associated with altered PK/safety, or neutralizing antibodies. One (4.5%) patient from Part A was considered persistent anti-drug antibody (ADA) positive (Table 62). In Part D, only 1 (3.8%) patient had positive ADA titers of 8 titer units. No neutralizing ADAs were detected, and there was no evidence of altered PK profile with ADA development. There was also no association of anti-nivolumab antibody development with select AEs (ie, bronchospasm, hypersensitivity, infusion-related reactions). Exploratory biomarker data found increased CD8+ tumor-infiltrating lymphocytes and PD-L1 tumor expression in post-treatment biopsies, similar to IV nivolumab.

TABLE 61

Nivolumab exposures by dose with rHuPH20

| | Geometric mean nivolumab concentration, µg/mL (range) | | | |
|---|---|---|---|---|
| | $C_{tau}$ | $C_{avg}$ | $C_{max}$ | $T_{max}$ |
| Nivolumab 720 mg subcutaneous (n = 20[a]) | 22.2 (4.76-59.6) | 36.6 (16.5-76.3) | 54.8 (19.9-114) | 144 (47.0-357) |
| Nivolumab 960 mg subcutaneous (n = 9) | 39.5 (8.06-67.6) | 62.2 (26.8-93.3) | 84.8 (42.7-128) | 104 (47.2-168) |
| Nivolumab 1200 mg subcutaneous (n = 25[b]) | 51.3 (18.4-96.5) | 77.5 (39.1-141) | 105 (40.0-245) | 118 (48.1-192) |

[a] n = 22 for $C_{max}$;
[b] n = 26 for $C_{max}$;
$C_{tau}$ = concentration at the end of the dosing interval

TABLE 62

NIVO ADA assessments: Parts A, B, and D

| | Part A 720 mg + rHuPH20 | Part B | | | Part D 1200 mg + rHuPH20 |
|---|---|---|---|---|---|
| | | 720 mg without rHuPH20 | 960 mg + rHuPH20 | 960 mg without rHuPH20 | |
| Patient ADA Status, n (%) | n = 22 | n = 18 | n = 10 | n = 17 | n = 26 |
| Baseline ADA positive[a] | 2 (9.1) | 0 | 2 (20.0) | 0 | 1 (3.8) |
| ADA positive | 7 (31.8) | 5 (27.8) | 3 (30.0) | 0 | 1 (3.8) |
| Persistent positive | 1 (4.5) | 0 | 0 | 0 | 0 |
| Not persistent positive— last sample positive | 0 | 3 (16.7) | 0 | 0 | 0 |
| Other positive | 6 (27.3) | 2 (11.1) | 3 (30.0) | 0 | 1 (3.8) |
| Neutralizing positive | 0 | 0 | 0 | 0 | 0 |
| ADA negative | 15 (68.2) | 13 (72.2) | 7 (70.0) | 17 (100.0) | 25 (96.2) |

Exposures associated with subcutaneous nivolumab+rHuPH20 doses investigated in the present study were well tolerated, with a safety profile consistent with IV nivolumab. Data support evaluation of subcutaneous nivolumab+rHuPH20 in a phase 3 study.

Mean duration of subcutaneous nivolumab injection was less than 5 minutes across treatment groups. All patients in Parts C and D received the full subcutaneous dose of nivolumab 1200 mg+rHuPH20 (22,000 U) via single injection.

Pre- and on-treatment (C1D15) paired biopsies were assessed for CD8 (n=23) expression on tumor-infiltrating lymphocytes (TILs) (FIG. 9A) and tumor PD-L1 (n=25) (FIG. 9B) expression by immunohistochemistry (IHC). Immunohistochemistry results for subcutaneously delivered nivolumab demonstrate a mean change of 5.0% in CD8 TIL expression and 2.8% in PD-L1 tumor expression, suggesting similar pharmacodynamics effects in the tumor microenvironment compared with historical intravenously delivered nivolumab.

Example 5—Analysis of Oxidative Stress

In this report, we assess the factors that contribute to increased stability for both Nivolumab and rHuPH20-two very different proteins at very different levels in their stable and active state with one formulation. There were three studies conducted to fully understand the formulation composition impact.

Study 1—Investigating multiple oxidation stress conditions with regard to different combination of metal, peroxide and light in addition to accelerated stability. Study 2—Investigating the concentration ranges where formulation protection is observed. Study 3—Investigating additional primary packaging components relevant to a pre-filled syringe and wearable device. This study also carefully examined formulation impact with-out rHuPH20.

To assess the stability of Nivolumab size exclusion chromatography (SEC) was primarily used and to assess the stability of rHuPH20 enzyme activity was measured. PS80 levels and particulates will be measured at select time points. In this report it is shown that addition of DTPA and Met minimizes the risk of oxidation of rHuPH20 and maximizes the stability of Nivolumab.

Study Design

Study 1: Stress Conditions

Study 1 was set-up to determine the effect of different oxidative stresses in combination with each-other. The three oxidation stresses studied were: light [L](1000 lux at room temperature), metal stress [M] (1.5 ppm total, 0.5 ppm each of iron, chromium, and copper) and peroxide [P] (1 mM peroxide). The three stresses were assessed individually and in combination with each other. Preliminary data showed that enzyme activity decreases with RT/RL storage, so the light exposure in combination with other stresses [LP, LM, MPL] was kept to 3 days (3D) at 1000 lux at RT. Note: the light exposure arm of this study [L] is the only condition exposed to 1000 lux at RT for the full duration of the time point. Nivo shows minimal HMW increase under 25° C. exposure so the standard storage condition temperature was increased to 30° C. Due to light combination stress conditions having a 3 day exposure to light at room temperature (RT) all conditions start with either 3 days at RT/Dark or 3 days at 1000 lux at RT. The 8 stress conditions in the study are Light/RT (1000 Lux) [L]; Metal Stress (1.5 ppm iron, chromium and copper) @ RT/Dark 3D+30° C./Dark [M]; 1 mM peroxide @ RT/Dark 3D+30° C./Dark [P]; Light/RT 3D+Peroxide+30° C./Dark [PL]; Light/RT 3D+Metal+30° C./Dark [ML]; Peroxide+Metal @ RT/Dark 3D+30° C./Dark [MP]; Light/RT 3D+Metal+peroxide+30° C./Dark [MPL]; RT/Dark 3D+30° C./Dark [Control].

The center point formulation composition was: 120 mg/mL Nivo, 20 mM histidine at pH 6.0, 250 mM sucrose, 0.05% w/v polysorbate 80 with 2000 U/mL rHuPH20. In this study the impact of headspace, chelating agent (DTPA/EDTA) and sacrificial oxidizing agent (Met) were studied as shown in Table 63. Table 64 shows the storage conditions and planned time points for this study.

TABLE 63

Study 1—Experimental Conditions
for Oxidation Study of BMS-986298

| Formulation | Headspace | DTPA (μM) | EDTA (μM) | Met (mM) |
|---|---|---|---|---|
| 1 | Air | 50 | 0 | 5.0 |
| 2 | Air | 0 | 0 | 0.0 |
| 3 | Air | 0 | 0 | 5.0 |
| 4 | Air | 50 | 0 | 0 |
| 5 | Air | 0 | 100 | 5.0 |
| 6 | Nitrogen | 50 | 0 | 5.0 |
| 7 | Nitrogen | 0 | 0 | 0 |

(Present in all formulations equally are 120 mg/mL BMS-986298 in 20 mM histidine at pH 6.0, 250 mM sucrose. 0.05% (w/v) polysorbate 80, and 2,000 U/mL rHuPH20)

TABLE 64

Study 1—Oxidation Study Time Points

| Temperature | T0 | 3 days | 14 days | 1 month | 3 months |
|---|---|---|---|---|---|
| Light [L] (1000 Lux @ RT) | abcd | X | ab | ac | ac |
| Metal [M] (3 D RT/Dart + 30° C./Dark) | | X | ab | a | a |
| Peroxide [P] (3 D RT/Dart + 30° C./Dark) | | X | ab | a | a |
| Light + Peroxide [PL] (3 D RT/RL + 30° C./Dark) | | X | ab | a | a |
| Light + Metal [ML] (3 D RT/RL + 30° C./Dark) | | X | ab | a | a |
| Metal + Peroxide [MP] (3 D RT/Dart + 30° C./Dark) | | X | ab | a | a |
| Metal + Peroxide + Light [MPL] (3 D RT/RL + 30° C./Dark) | | X | abc | acd | ac |
| Control [RT30] (3 D RT/Dark + 30° C.) | | X | ab | ac | ac |

X pulled but not tested. Sample analysis defined in Table 65

In this report, we focused on how different parameters affect stability of Nivolumab (Nivo) by size exclusion chromatography (SEC). Evaluation of the stability of rHuPH20 was conducted only at selected time points due to low throughput of the method. In addition select samples were chosen for evaluation of the stability of PS80—a key excipient added to provide stability of the drug product. These results were used to predict how the selected conditions affect both stability of Nivo and rHuPH20 under different oxidation stress conditions.

TABLE 65

Study 1—Analysis Volumes

| Code | Measurement | Volume (mL) |
|---|---|---|
| a | Appearance | 0.6 |
| | SEC | 0.1 |
| b | MFI* | 1.1 |
| c | Enzyme Activity* | 0.2 |
| d | PS80* | 0.1 |

*performed for select samples

Study 2: Formulation Composition Variation

Study 2 was set-up to determine the ranges where the benefits of the formulation composition are observed. Study 1 defined the condition to include from an oxidation stress perspective to be MPL and RT/RL. These two stress conditions along with a control were studied for oxidation stress. Formulation conditions expected to have oxidation benefits were studied under both oxidation and thermal stress (5, 25, and 35° C.) conditions. All formulations were studied using thermal stress conditions to assess stability.

Oxidation Stress conditions:

MPL: Combination of all three stresses: 3 days at room temperature/room light [L](1000 lux), with spiked metal [M] (1.5 ppm total, 0.5 ppm each of iron, chromium, and copper) and spiked peroxide [P] (1 mM peroxide). Metal and peroxide are spiked at TO (initial time point). After the 3 days at room temperature/room light samples are moved and stored at 30° C./protected from light for the remainder of that time point.

RT30: Control to the MPL stress condition. Room temperature/dark for 3 days followed by 30° C./protected from light for the remainder of that time point RT/RL: Room temperature/room light (1000 lux) for the full duration of the study.

Thermal Stress conditions included (i) 5° C./protected from light; (ii) 25° C./protected from light (also used as a control to the RT/RL condition); and (iii) 35° C./protected from light.

Formulations were selected to show that the formulation is stable across the following formulation compositions: (i) pH: 5.2-6.8 His; (ii) Histidine: 10-100 mM (Alt: Succinate); (iii) DTPA 10-200 μM (Alt: 100 μM EDTA); (iv) Met: 1-20 mM (Alt: 10 mM Trp); (v) rHuPH20: 0-5,000 U/mL; (vi) PS80: 0.01-0.1% w/v (Alt: PS20 0.05% w/v and Poloxamer 0.2 mg/mL); (vii) Sugar: 10-400 mM sucrose (Alt: 10% sorbitol and trehalose); and (viii) Protein: 100-175 mg/mL. For all these conditions the center point formulation composition was: 120 mg/mL Nivo, 20 mM histidine at pH 6.0, 250 mM sucrose, 50 μM DTPA, 5 mM Met, 0.05% polysorbate 80 with 2,000 U/mL rHuPH20 and tested in a vial.

Conditions that were studied for both thermal and oxidation stress conditions are shown in Table 66. Note there are duplicate independent formulation preparations in the design for the center point condition and the condition with 50 μM DTPA and no Met. The screen included a small excipient characterization DOE investigating if there are any combined effects between pH, DTPA, and Met concentration. Variations in DTPA, Met, and enzyme levels, in addition to having a nitrogen head space was studied under these conditions where oxidation is more likely to be impacted by these formulation changes. Alternate excipients were added to understand how they behave relative to the proposed excipient. As an alternate to Met Trp was added and as an alternate to DTPA, EDTA was studied. Higher levels of these alternate excipients were studied to ensure there is no question about the performance of the alternate excipient relative to the proposed excipient. Independent replicates for select formulations are included in the study (formulation 21 and 29 with DTPA only and formulation 15 and 28—center point).

Formulation conditions that have been investigated for thermal stress alone are listed in Table 67. Factors that are less likely to impact oxidation were varied here. These factors were: protein concentration, use of an alternate buffer and buffer strength, alternate sugar and sugar concentration, and alternate surfactant and varied surfactant levels. Extremes of the buffer pH were also studied here. For all these conditions the formulation included 50 μM DTPA, 5 mM Met with 2,000 U/mL rHuPH20.

The stress and time points corresponding to the oxidation stress conditions are tabulated in Table 68. The time points corresponding to the thermal stress condition are tabulated in Table 69.

TABLE 66

Study 2—Experimental Conditions for Oxidation and Thermal Stress of BMS-986298

| Formulation | pH | DTPA (uM) | Met (mM) | rHuPH20 (U/mL) | Headspace |
|---|---|---|---|---|---|
| 1 | 5.5 | 10 | 1 | 2000 | Air |
| 2 | 5.5 | 10 | 10 | 2000 | Air |

TABLE 66-continued

Study 2—Experimental Conditions for Oxidation and Thermal Stress of BMS-986298

| Formulation | pH | DTPA (uM) | Met (mM) | rHuPH20 (U/mL) | Headspace |
|---|---|---|---|---|---|
| 3 | 5.5 | 100 | 1 | 2000 | Air |
| 4 | 5.5 | 100 | 10 | 2000 | Air |
| 5 | 6.5 | 10 | 1 | 2000 | Air |
| 6 | 6.5 | 10 | 10 | 2000 | Air |
| 7 | 6.5 | 100 | 1 | 2000 | Air |
| 8 | 6.5 | 100 | 10 | 2000 | Air |
| 9 | 5.5 | 50 | 5 | 2000 | Air |
| 10 | 6.5 | 50 | 5 | 2000 | Air |
| 11 | 6 | 10 | 5 | 2000 | Air |
| 12 | 6 | 100 | 5 | 2000 | Air |
| 13 | 6 | 50 | 1 | 2000 | Air |
| 14 | 6 | 50 | 10 | 2000 | Air |
| 15* | 6 | 50 | 5 | 2000 | Air |
| 16 | 6 | 0 | 0 | 2000 | Air |
| 17 | 6 | 200 | 5 | 2000 | Air |
| 18 | 6 | 100—EDTA | 0 | 2000 | Air |
| 19 | 6 | 100—EDTA | 5 | 2000 | Air |
| 20 | 6 | 0 | 5 | 2000 | Air |
| 21* | 6 | 50 | 0 | 2000 | Air |
| 22 | 6 | 50 | 5 | 2000 | Nitrogen |
| 23 | 6 | 0 | 0 | 2000 | Nitrogen |
| 24 | 6 | 50 | 5 | 0 | Air |
| 25 | 6 | 50 | 5 | 500 | Air |
| 26 | 6 | 50 | 5 | 5000 | Air |
| 27 | 6 | 50 | Trp (10 mM) | 2000 | Air |
| 28* | 6 | 50 | 5 | 2000 | Air |
| 29* | 6 | 50 | 0 | 2000 | Air |
| 30 | 6 | 50 | 20 | 2000 | Air |

*duplicate independent formulations preparations.
(Present in all formulations equally are 120 mg/mL BMS-986298 in 20 mM histidine, 250 mM sucrose, and 0.05% (w/v) polysorbate 80)

TABLE 67

Study 2-Experimental Conditions for Thermal Stress only for BMS-986298

| Formulation | Protein Conc (mg/mL) | pH | Buffer | Buffer (mM) | Sugar | Sugar (mM) | PS80 (wt %) |
|---|---|---|---|---|---|---|---|
| 31 | 100 | 6.0 | his | 20 | Sucrose | 250 | 0.05 |
| 32 | 175 | 6.0 | his | 20 | Sucrose | 250 | 0.05 |
| 33 | 120 | 5.2 | his | 20 | Sucrose | 250 | 0.05 |
| 34 | 120 | 6.8 | his | 20 | Sucrose | 250 | 0.05 |
| 35 | 120 | 6.0 | his | 10 | Sucrose | 250 | 0.05 |
| 36 | 120 | 6.0 | his | 50 | Sucrose | 250 | 0.05 |
| 37 | 120 | 6.0 | his | 100 | Sucrose | 250 | 0.05 |
| 38† | 120 | 6.0 | his | 20 | sugar free | 0 | 0.05 |
| 39† | 120 | 6.0 | his | 20 | Sucrose | 10 | 0.05 |
| 40† | 120 | 6.0 | his | 20 | Sucrose | 400 | 0.05 |
| 41 | 120 | 6.0 | his | 20 | Sucrose | 250 | 0.05-PS20 |
| 42 | 120 | 6.0 | his | 20 | Sucrose | 250 | Poloxamer-0.2 mg/mL |
| 43†† | 120 | 6.0 | his | 20 | Sorbitol | 10% | 0.05 |
| 44†† | 120 | 6.0 | his | 20 | Trehalose | 10% | 0.05 |
| 45 | 120 | 6.0 | succinate | 20 | Sucrose | 250 | 0.05 |
| 46 | 120 | 6 | his | 20 | Sucrose | 250 | 0 |
| 47 | 120 | 6 | his | 20 | Sucrose | 250 | 0.01 |
| 48 | 120 | 6 | his | 20 | Sucrose | 250 | 0.1 |
| 49†* | 120 | 6 | his | 20 | Sucrose | 250 | 0.05 |

*Duplicate independent formulation preparations to formulation 15 and 28 in Table 66 above (also tested for thermal stress). This formulation also confirms comparable performance of the two DS sources.
†Formulated using a different DS source without sugar.
‡ for this formulation it was later discovered that the sugars were not added. These results were omitted here but these two sugars were covered in study 3.
(Present in all formulations equally are 50 μM DTPA, 5 mM Met with 2,000 U/mL rHuPH20)

TABLE 68

| Study 2—Oxidation Study Time Points | | | |
| --- | --- | --- | --- |
| | Temperature | | |
| | Light 25° C./ 1000 Lux@ RT [25RT] | Light (3 D) 25° C. + Metal + peroxide + 30° C./Dark [MPL] | 25 C./Dark (3 D) + 30° C./Dark [RT30] |
| T0 | abcde | — | — |
| 2 W | a* | a* | a* |
| 1 M | a | a | a |
| 3 M | — | acde | a |

Sample analysis defined in Table 70.
Note.
1 M and 3 M samples for MFI where planned but could not be run due to staffing constraints during COVID.
*Optional testing

TABLE 69

| Study 2—Thermal Study Time Points | | | |
| --- | --- | --- | --- |
| | Temperature | | |
| | 5° C. | 25° C. | 35° C. |
| T0 | abcde | — | — |
| 2 W | — | a* | a* |
| 1 M | — | a | a |
| 3 M | a | a | acde |
| 6 M | a | a | a |

Sample analysis defined in Table 70.
Note.
6 M samples for MFI where planned but could not be run due to staffing constraints during COVID.
*Optional testing In this study, we focused on how different parameters affect stability of BMS-986298 or Nivolumab primarily by size exclusion chromatography (SEC). Evaluation of the stability of rHuPH20 was performed only at selected time points, due to the low throughput of the enzyme activity method. In addition, select samples were chosen to evaluate the stability of PS80—a key excipient added to provide stability of the drug product. CE-SDS and iCE were tested on select samples to understand formation of low molecular weight species and charge variants. These results were used to predict how the selected conditions affect both stability of Nivo and rHuPH20 under different oxidation stress conditions.

TABLE 70

| Study 2-Analysis Volumes | | |
| --- | --- | --- |
| Code | Measurement | Volume (mL) |
| a | Appearance | 0.5 |
| | SEC | 0.1 |
| b | MFI* | 1.1 |
| c | Enzyme Activity* | 0.2 |
| d | PS80* | 0.1 |
| e | CE-SDS* | 0.1* |
| | iCIEF* | |

*run for select samples

Study 3: Formulation Composition Variation of PFS and Wearable Devices

Study 3 was set-up similar to Study 2 but had conditions focused on the use of the pre-filled syringe and wearable devices. Similar to Study 2, the worst-case condition from Study 1 (MPL) was included from an oxidation stress condition. The room temperature/room light condition was taken out, since it is unlikely to be encountered in real life, and the high stress it imparts on both protein and enzyme. Similar to Study 2 the standard thermal stress conditions were studied in addition to oxidation stress. Formulation conditions likely to impact oxidation were studied for both oxidation and thermal stress conditions. All formulations were tested under standard thermal stability conditions.

Oxidation Stress conditions included:

MPL: Combination of all three stresses: 3 days at room temperature/room light [L](1000 lux), with spiked metal [M] (1.5 ppm total, 0.5 ppm each of iron, chromium, and copper) and spiked peroxide [P] (1 mM Peroxide). Metal and peroxide are spiked at T0 (initial time point). After the 3 days at room temperature/room light samples are moved and stored at 30° C./protected from light for the remainder of that time point.

RT30: Control to the MPL stress condition. Room temperature/dark for 3 days followed by 30° C./protected from light for the remainder of that time point.

Thermal Stress conditions included (i) 5° C./protected from light; (ii) 25° C./protected from light; and (iii) 35° C./protected from light.

Using the data from Study 2 the formulation concentration ranges that was desired to investigate was narrowed to try to find the optimum range for stabilization. Formulations were selected to show that the formulation is stable across these formulation compositions: (i) pH: 5.2-6.5 His; (ii) Histidine: 15-100 mM; (iii) DTPA 10-200 μM (Alt: 100 μM EDTA); (iv) Met: 1-20 mM (Alt: 10 mM Trp); (v) rHuPH20: 0-10,000 U/mL; (vi) PS80: 0.01-0.1% w/v (Alt: PS20 and Poloxamer 0.2 mg/mL); (vii) Sugar: 10-400 mM sucrose (Alt: 10% sorbitol and trehalose); (viii) Protein: 100-200 mg/mL; and (ix) Vial and PFS and Patch pump.

For all these conditions the center point formulation composition was: 20 mM histidine at pH 6.0, 250 mM sucrose, 50 μM DTPA, 5 mM Met, 0.05% w/v polysorbate 80 with 2,000 U/mL rHuPH20. The protein concentration for samples in the vial was at 120 mg/mL. Samples in the PFS had a nivolumab protein concentration of 150 mg/mL. This study included multiple conditions studied in study 2 but with no enzyme. Minimal impact due to enzyme is expected so a confirmatory study was done and with one-off conditions tested at the center point.

Conditions that were studied for both thermal and oxidation stress and oxidation stress conditions are shown in Table 71. Conditions added to cover PFS were included here as well as conditions that pertain to the use of a PFS (silicone oil and tungsten spike). DTPA, Met, and enzyme levels were also studied here where oxidation is more likely to be impacted by these formulation composition differences.

Formulation conditions that have been investigated for thermal stress alone are listed in Table 72. Factors that are less likely to impact oxidation were varied here. These factors were: protein concentration, buffer strength, and enzyme levels. For all these conditions the formulation included 50 μM DTPA and 5 mM Met.

The stress and time points corresponding to the oxidation stress conditions are tabulated in Table 73. The time points corresponding to the thermal stress condition are tabulated in Table 74.

TABLE 71

Study 3-Experimental Conditions for Oxidation
and Thermal Stress of BMS-986298

| Formu-lation | BMS-986298 (mg/mL) | DTPA (uM) | Met (mM) | rHPH20 (U/mL) | Notes |
|---|---|---|---|---|---|
| 1 | 150 | 50 | 5 | 2000 | Silicone oil-2X PFS |
| 2 | 120 | 50 | 5 | 2000 | PFS |
| 3 | 150 | 50 | 5 | 2000 | PFS |
| 4 | 165 | 50 | 5 | 2000 | PFS |
| 5 | 120 | 50 | 5 | 2000 | center point connectivity to study 2 |
| 6 | 150 | 50 | 5 | 2000 | Tungsten 1.0 ppm spike |
| 7 | 120 | 50 | 5 | 10,000 | |
| 10 | 120 | 50 | 5 | 0 | N = 1 |
| 11 | 120 | 50 | 5 | 0 | N = 2 |
| 12 | 120 | 50 | 0 | 0 | N = 1 |
| 13 | 120 | 50 | 0 | 0 | N = 2 |
| 14 | 120 | 0 | 0 | 0 | |
| 15 | 120 | 0 | 5 | 0 | |
| 16 | 120 | 10 | 5 | 0 | |
| 17 | 120 | 200 | 5 | 0 | |
| 18 | 120 | 50 | 1 | 0 | |
| 19 | 120 | 50 | 20 | 0 | |
| 20 | 120 | EDTA (100) | 5 | 0 | |
| 21 | 120 | 50 | Trp (10) | 0 | Trp (10) |
| 22 | 150 | 50 | 5 | 0 | Tungsten 1.0 ppm spike |
| 38 | 150 | 50 | 5 | 0 | Silicone oil -2X |
| 39 | 120 | 50 | 5 | 0 | PFS |
| 40 | 150 | 50 | 5 | 0 | PFS |
| 41 | 165 | 50 | 5 | 0 | PFS |
| 42 | 200 | 50 | 5 | 0 | PFS |
| 43 | 200 | 50 | 5 | 2000 | PFS |
| 44 | 120 | 50 | 5 | 2000 | patch pump |
| 45 | 120 | 50 | 5 | 0 | patch pump |
| 46 | 120 | 50 | 5 | 2000 | patch pump control |

Present in all formulations equally are 20 mM histidine pH 6.0, 250 mM sucrose, and 0.05% (w/v) polysorbate 80.

TABLE 72

Study 3-Experimental Conditions for Thermal Stress only for BMS-986298

| Formulation | Protein Conc (mg/mL) | pH | Buffer | Buffer (mM) | Sugar (mM) | PS80 (wt %) | rHuPH20 (U/mL) |
|---|---|---|---|---|---|---|---|
| 8 | 200 | 6 | Histidine | 20 | 250 | 0.05 | 2000 |
| 9 | 120 | 6 | Histidine | 15 | 250 | 0.05 | 2000 |
| 23 | 120 | 5.2 | Histidine | 20 | 250 | 0.05 | 0 |
| 24 | 120 | 6.5 | Histidine | 20 | 250 | 0.05 | 0 |
| 25 | 120 | 6.0 | Succinate | 20 | 250 | 0.05 | 0 |
| 26 | 120 | 6 | Histidine | 20 | Sorbitol (10%) | 0.05 | 0 |
| 27 | 120 | 6 | Histidine | 20 | 10 | 0.05 | 0 |
| 28 | 120 | 6 | Histidine | 20 | 400 | 0.05 | 0 |
| 29 | 120 | 6 | Histidine | 20 | Trehalose(10%) | 0.05 | 0 |
| 30 | 120 | 6 | Histidine | 20 | 250 | 0.01 | 0 |
| 31 | 120 | 6 | Histidine | 20 | 250 | 0.1 | 0 |
| 32 | 120 | 6 | Histidine | 20 | 250 | 0.05 (PS-20) | 0 |
| 33 | 120 | 6 | Histidine | 20 | 250 | Poloxamer (0.2 mg/mL) | 0 |
| 34 | 120 | 6 | Histidine | 15 | 250 | 0.05 | 0 |
| 35 | 120 | 6 | Histidine | 100 | 250 | 0.05 | 0 |
| 36 | 100 | 6 | Histidine | 20 | 250 | 0.05 | 0 |
| 37 | 200 | 6 | Histidine | 20 | 250 | 0.05 | 0 |

(Present in all formulations equally are 50 uM DTPA and 2 mM Met. All filled in vials)

TABLE 73

Study 3-Oxidation Study Time Points

| | Temperature | |
|---|---|---|
| | Light (3 D) 25° C. + Metal + peroxide + 30° C./Dark [MPL] | 25 C./Dark (3 D) + 30° C./Dark [RT30] |
| T0 | — | — |
| 2 W | a* | a* |
| 1 M | a | a |
| 3 M | abcde | ab |

Sample analysis defined in Table 75.
*Optional testing.

TABLE 74

Study 3-Thermal Study Time Points

| Temperature | 5° C. | 25° C. | 35° C. |
|---|---|---|---|
| T0 | ab | — | — |
| 2 W | — | a* | a* |
| 1 M | — | a | a |
| 3 M | a | a | a |
| 6 M | ab | ab | a |

Sample analysis defined in Table 75.
*Optional testing.

In this study, we focused on how different parameters affect stability of BMS-986298 or Nivo primarily by size exclusion chromatography (SEC). Confirmatory MFI samples are run only for the 5 and 25° C. 6M samples.

TABLE 75

| Study 3-Analysis Volumes | | |
| --- | --- | --- |
| Code | Measurement | Volume (mL) |
| a | Appearance | 0.5 |
| | SEC | 0.1 |
| b | MFI* | 1.1 |

*run for select samples

Materials and Methods

Materials

Details for materials used in the studies are provided in Table 76.

TABLE 76

| Material Information | | | | |
| --- | --- | --- | --- | --- |
| | Material Number | Study 1 Lot Number | Study 2 Lot Number | Study 3 Lot Number |
| Nivo DS (170 mg/mL) | 1274255 | | A1A8A-036 | ABP4182-01 |
| Nivo DS-sugar free (10 mg/mL) | N/A | | VF Pool CRU 20 Aug. 2018 | VF Pool CRU 20 Aug. 2018 |
| rHuPH20 (10 mg/mL) | 1405640 | 104-003-16-290016S | 2HUN1803CA | 2HUN1803CA |
| Neopack 2.25 mL Syringes | RFS 27G1/25BSTW RNSBD260HS | | — | 6299337 |
| 2X Si syringes | Pilot 0T002 Fleming SCF | | — | 18B331YL . . . 0204 |
| Vial | 1325008 | | AAK2742 | AAR0679 |
| Stoppers | 1292715 | | AAL9676 | AAL9676 |
| Crimps | 1221911 | | AAC2886 | 3K78805 |
| Patch pump-Smart Dose 10 mL | West: 26018026 | | — | SC00013392 |
| Patch Pump Stopper | D 21-7HW SD2 10 mL piston FR2RUV | | — | 905004 |
| Patch Pump West cartridge | 26017493 | | — | SC00004318 |
| Histidine | 1274255 | | AAM9761 | ABJ4908 |
| His HCl H2O | 1275346 | | AAM9523 | ABJ5012 |
| Sucrose | 1244359 | | AAS9949 | AAX0304 |
| PS80 | 1353220 | | ABE4589 | NOF 707361Z2 |
| DTPA | 05GD11.HQ00003 | | LG16.360 | ABT3852 |
| EDTA | 1372205 (Hovione) | | AAL6226 | AAN9782 |
| Methionine | M9625-1KG (Sigma-Aldrich) | | SLBZ1683 | SLBZ1683 |
| Peroxide | BDH7690-1 (VWR) | | 18C065005 | 18C065005 |
| Chromium(III)Chloride hexahydrate | 27096-1000G-F (Sigma-Aldrich) | | BCBC0518V | BCBC0518V |
| Copper (II) Nitrate trihydrate | 61194 (Fluka) | 1272598 | 42807279 | — |
| Copper(II) Chloride, anhydrous, 98% | #12457 (Alfa Aesar) | | — | A28Q06 |
| Ammonium Iron (II) sulfate | 13448 (Alfa Aesar) | | J23N13 | J23N13 |

Sample Preparation

Thaw

Drug substance (DS) BMS-986298 and rHuPH20 are stored frozen. These DS bottles were thawed at room temperature protected from light. Once thawed the DS bottles were gently mixed to ensure homogeneity. The DS was stored at 5° C. until use and any remaining portion was re-frozen after the use. DS used in the formulation studies are all DTPA and PS80 free.

For the Study 1 formulation, the DP samples were prepared using bulk DS material BMS-986298 (at 170 mg/mL) by adding the following stock solutions: (i) 10 mg/mL rHuPH20 DS (112 kU/mg rHuPh20); (ii) 5% Polysorbate 80 (100×); (iii) 2.5 mM DTPA (50×); (iv) 5 mM EDTA (50×);

(v) 250 mM Methionine (50×); (vi) 20 mM Histidine 250 mM Sucrose pH 6.0; (vii) 50 mM hydrogen peroxide (50×); (viii) 50 ppm Chromium(III)Chloride hexahydrate, 50 ppm Copper (II) Nitrate trihydrate, and 50 ppm Ammonium Iron (II) sulfate (100×). The DS starting composition comprised 20 mM Histidine, and 250 mM Sucrose, at pH 6.0.

For each formulation a sample was prepared with no spike, spiked with peroxide only, metal only, and metal and peroxide. Metal cocktail was prepared immediately before spiking. All formulations were filtered using an Acrodisc syringe filter with 0.2 µm Supor membrane after gentle mixing. Experiments are documented in notebook A0F7F-090.

For the Study 2 formulation, the DP samples were prepared by 4 methods. First, by direct addition using bulk DS material BMS-986298 (at 170 mg/mL) with no further preparation—no buffer exchange. Formulated by adding 0.2 µm filtered stock solutions to target concentration. Stock solutions included: 2 M Sucrose; 495 mM Histidine pH 6.0; 500 mM Histidine pH 5.2; 500 mM Histidine pH 5.5; 211 mM Histidine pH 6.5; 262.5 mM Histidine pH 6.8; 5% PS80; 5 mM EDTA; 2.5 mM DTPA; 250 mM Met; 5% PS80; 20 mg/mL Poloxamer; 1400 mM Succinate; 80% Sorbitol; 40% Trehalose; 54 mM Tryptophan; and Water.

This approach was taken for formulation compositions where the DS pH was 6.0 with sucrose at 250 mM level. DS starting composition was: 20 mM Histidine, 250 mM Sucrose, pH 6.0.

CM3: Buffer was exchanged using automation equipment where a 10 kDa filter was used with pressure to concentrate and addition of target buffer to the target buffer exchange composition. Two input DS streams were used: (i) DS at 170 mg/mL Nivo stock (this was used directly as-is; DS starting composition is: 20 mM Histidine, 250 mM Sucrose, pH 6.0); and (ii) DS at 10 mg/mL Nivo stock (this material is harvested during the viral filtration step prior to the addition of sugars; samples where sugar composition is varied was used this DS stock; appropriate sugars were added to the DS to the target composition then concentrated using a centric on filter; a 30 kDa filter was used for the concentration).

The formulations where this type of buffer exchange was needed had small sample requirement (used for only 1 formulation with a unique pH or sugar level was needed). After buffer exchange same stocks that are used to formulate as noted above. Tangential flow filtration (TFF) using a 30 kDa filter with 8 diavolumes of buffer exchange. Two TFFs were run one with pH 5.5 and one at pH 6.5. This was needed due to the number of formulations at these two pH values. After buffer exchange same stocks that are used to formulate as in step 1 above. Dialysis was used to prepare formulation 38—a sugar free formulation. The solution was a sugar free formulation initially and was then buffer exchanged to the target buffer pH/composition. The concentration was adjusted subsequently by centrifugation through a 10 kDa membrane. After buffer exchange, the same stocks were used to formulate as in step 1 above.

For MPL conditions metal was spiked by creating a stock solution of 50 ppm chromium(III) chloride hexahydrate, 50 ppm copper (II) nitrate trihydrate, and 50 ppm ammonium iron (II) sulfate. Similarly a 50 mM hydrogen peroxide solution was made to spike in peroxide.

All formulations were filtered using an Acrodisc syringe filter with 0.2 μm Supor membrane after gentle mixing.

Excipient analysis was run on the TFF buffers to confirm excipient levels. The analysis found that the CM3 buffer exchange with sorbitol did not have sorbitol added and trehalose was also inadvertently missed. Due to this the results from these two samples (formulation 43 and 44) are omitted from the analysis. These conditions are included in Study 3 but with-out enzyme.

For the Study 3 formulation, the DP samples were prepared by direct addition, buffer exchange by the CM3, or buffer exchanged with TFF. The preparation methods mirror that of study 2. The main differences between study 2 and 3 was that the DS stock is a different lot of material and one of the metals used for spiking for study 3 was copper(II) chloride vs. in study 2 was copper (II) nitrate trihydrate.

Patch pump cartridges were filled using a needle and placed on stability along with the vials and syringes. Samples were pulled at the appropriate pull time and frozen until the Smart Dose patch pumps arrived. The patch pump was used to deliver the solution from the cartridge. The liquid was removed for the control samples using a needle.

Fill

Formulated and filtered DP was filled into depyrogenated 3-cc vials (Schott Type 1 glass) or BD Neopack 2.25 mL syringes and stoppered with autoclaved 13-mm Daikyo stoppers (D-21-75, Fluorotec-coated serum) or BD1-3 mL plunger stoppers. Vials were crimped and placed on stability upright in a vertical position. The exception to that is when exposed to light where the vials are placed horizontally. Syringes were stored in a horizontal position.

Analysis

Samples were pulled and then immediately frozen until time of analysis with the exception of particulate analysis (MFI); which was held at 5° C. until analysis.

SEC

DP samples were analyzed by SEC-HPLC (MTD-10789) for quantitative analysis of HMW and LMW species. Samples were analyzed using a TSK gel Super SW 3000 column (TOSOH 1875) with a flow rate of 0.5 m/min and a run time of 35 min. Mobile phase was 100 mM phosphate and 100 mM sodium sulfate pH 6.8. A load of 50 pg of Nivo sample was injected for each run. The peaks were detected by UV-absorbance at 280 nm, and the area and retention time were measured for each peak. The area percentage for the monomer, HMW, and LMW species were calculated and reported.

Enzyme Activity rHuPH20 activity was measured using a plate-based turbidity assay, method CTL-10028 in DCA. The hyaluronidase potency assay is based on the formation of an insoluble precipitate when hyaluronic acid (HA) binds with acidified serum. The precipitate results in a turbid solution that can be measured at 640 nm. Potency (or activity) of hyaluronidase is directly measured by incubating the enzyme with HA substrate for 30 minutes, precipitating out the undigested HA with acidified serum, and comparing the turbidity against a reference standard curve. PS80 Analysis PS80 levels were measured using a Waters Oasis Max column at a flow rate of 1 mL/minute with 0.1% formic acid with 5 mM ammonium formate/0.1% formic acid in acetonitrile at 30° C. with a mass spectrometer.

Particulates

Particulate levels were tested using Micro flow imaging (MFI). 1.1 mL of each sample were filled into separate glass vials for MFI analysis. Samples were tested with a water sample run between analysis. Sample is tested with 0.15 mL purge and 0.43 mL analysis volume.

Charge Variants by Imaged Capillary Isoelectric Focusing (iCIEF)

Charge variants were analyzed by iCIEF using an imaged isoelectric focusing system, known as iCE3 (MTD-10788). Samples mixed with appropriate pI markers, ampholytes and other additives were injected by an auto-sampler into a fluorocarbon (FC) coated capillary cartridge. After high voltage of pre-focusing and focusing, sample migration was captured by a UV detector, and UV light absorption images were taken by a CCD camera. The area percentages for the main peak, acidic variants, and basic variants were calculated and reported.

CE-SDS

Relative percent purity of Nivo was determined by CE-SDS using the LabChip GX II Caliper system under non-reducing conditions. The samples were denatured and prepared in the presence of sodium dodecyl sulfate (SDS), a detergent that coats the protein providing a negative charge effectively masking its native charge. Each sample was aspirated onto the chip, mixed with a dye and electrophoretically separated. A separate de-staining step was then performed on the chip. Optics within the instrument detected the florescent signal for each sample. Protein species were separated based on size and electrophoretic mobility. Relative percent area was calculated for each peak and relative percent purity (% main peak) was reported.

Results—Study 1

Size Exclusion Chromatography

Size exclusion chromatography was the primary tool used to monitor the stability of Nivolumab under the various stress conditions studied.

Figure 10:
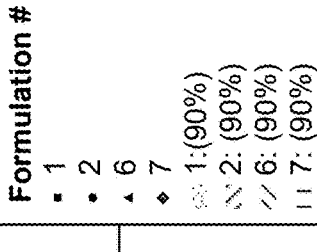
FIG. 10 is a graphical representation of impact of headspace nitrogen and air on % HMW species for Nivo by SEC after combination of metal, peroxide and light stress with a thermal stress of 30° C., in study 1. RT/Light is continuous light stress, other light stress conditions are for a 3 day duration. Formulation 1 (Air) and 6 (Nitrogen) have: 50 μm DTPA 5 mM Met; Formulation 2 (Air) and 7 (Nitrogen) have: 0 μM DTPA, 0 mM Met. All formulations also contain 120 mg/mL Nivo, 20 mM Histidine, 250 mM Sucrose, 0.05% w/v PS80 at pH 6.0 with 2,000 U/mL rHuPH20.

To investigate the impact of nitrogen head space, two formulations with nitrogen headspace were investigated. A formulation with both 50 μm DTPA and 5 mM Met (Formulation 1—Air, Formulation 6—Nitrogen) and a formulation without DTPA nor Met (Formulation 2—Air, Formulation 7—Nitrogen). The HMW change is plotted in FIG. 10. For the formulation with both DTPA and Met the headspace impact is minimal for all conditions other than the RT/Light condition with continuous light exposure (FIG. 10). In the formulations with no DTPA and no met there is a benefit in having a nitrogen headspace (FIG. 10). With the addition of both DTPA and Met, the oxidation is well controlled and thus a nitrogen headspace is unnecessary.

Figure 11:
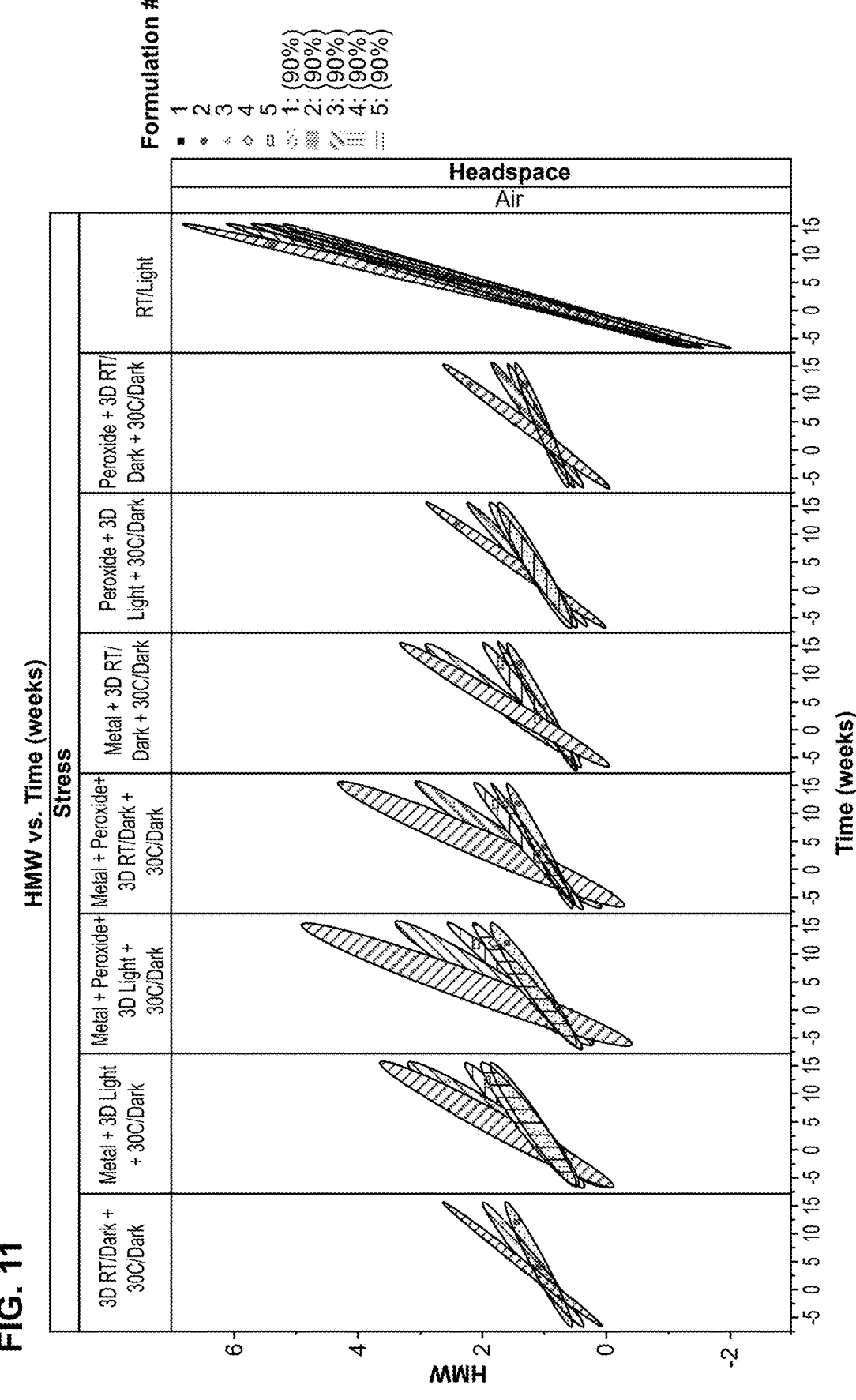
FIG. 11 is a graphical representation of the impact for various stress conditions on % HMW species for Nivo by SEC after combination of metal, peroxide and light stress with a thermal stress of 30° C., in study 1. RT/Light is continuous light stress, other light stress conditions are for a 3 day duration. Formulation 1: 50 μm DTPA 5 mM Met; Formulation 2: 0 μM DTPA, 0 mM Met; Formulation 3: 0 μM DTPA, 5 mM Met; Formulation 4: 50 μM DTPA, 0 mM Met; and Formulation 5:100 μM EDTA, 5 mM Met. All formulations also contain 120 mg/mL Nivo, 20 mM Histidine, 250 mM Sucrose, 0.05% w/v PS80 at pH 6.0 with 2,000 U/mL rHuPH20.

The impact of the various formulations on HMW species formation of Nivo after exposure to various stress conditions are shown in FIG. 11. The stress conditions include (from left to right): 1.) a control-exposure to 3 days at room temperature/dark (control for 3 days light exposure for L conditions)+30° C. thermal stress (thermal stress for all conditions other than the RT/Light); 2.) metal-0.5 ppm each of iron, chromium, and copper (M condition)+light (3 days at 1000 lux at room temperature –L condition)+30° C. thermal stress; 3.) M+1 mM peroxide (P condition)+L+30° C. thermal stress; 4.) M+L+30° C. thermal stress; 5.) M+30° C. thermal stress; 6.) P+L+30° C. thermal stress; 7.) P+30° C. thermal stress; 8.) Room temperature/room light (no extra thermal stress).

Across all stress conditions formulation 2: with no DTPA and no Met had the highest rate of HMW formation, followed by formulation 3: with no DTPA and 5 mM Met. Formulation 5: with 100 mM EDTA and 5 mM Met followed by Formulation 4: 50 μM DTPA with no Met. The best formulation was Formulation 1 with both 50 μm DTPA and 5 mM Met. This behavior is observed across all stress conditions but the differences are best observed by looking at the MPL (combined stress condition with thermal stress of 30° C.). The plot of this MPL stress condition against all formulation conditions is shown in FIG. 12.

Figure 12:
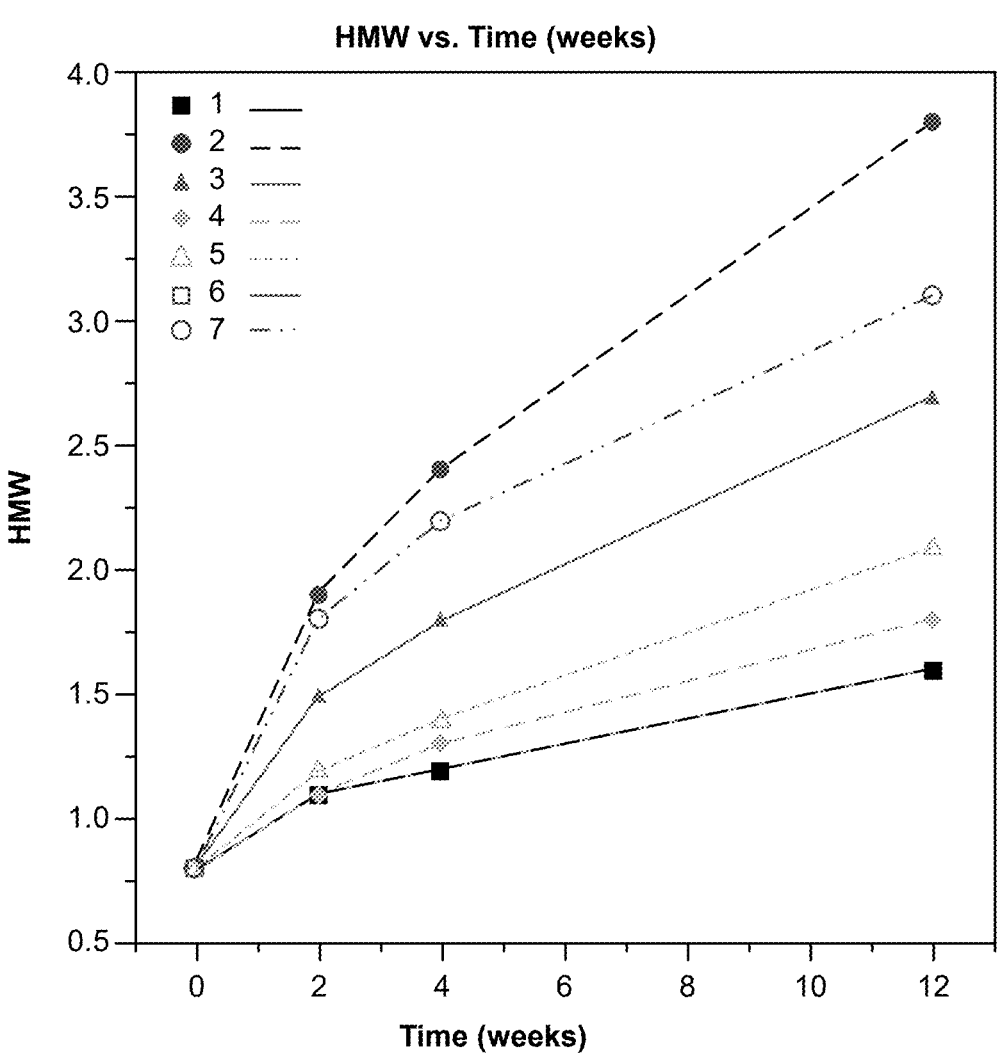
FIG. 12 is a graphical representation of HMW formation under Metal−0.5 ppm each of iron, chromium, and copper+light (3 days at 1000 lux at room temperature+1 mM peroxide+30° C. thermal stress), in study 1. Note: Formulation 1 (air) and 6 (nitrogen) overlay on top of each other completely and has the least HMW formation with the same formulation composition. Formulation 1 (air) and 6 (nitrogen): 50 μm DTPA 5 mM Met; Formulation 2 (air) and 7 (nitrogen): 0 μM DTPA, 0 mM Met; Formulation 3: 0 μM DTPA, 5 mM Met; Formulation 4: 50 μM DTPA, 0 mM Met; and Formulation 5:100 μM EDTA, 5 mM Met. All formulations also contain 120 mg/mL Nivo, 20 mM Histidine, 250 mM Sucrose, 0.05% w/v PS80 at pH 6.0 with 2,000 U/mL rHuPH20.

Careful examination of the MPL stress condition in FIG. 12 shows the benefit of having both 50 μM DTPA and 5 mM Met (formulation 1-air and 6-nitrogen). Having both anti-oxidants in the formulation stabilizes Nivo such that exchanging the headspace with nitrogen does not show an improved stabilization (formulation 1 overlays completely with 6). Having DTPA alone (Formulation 4: 50 μM DTPA with 0 mM Met) outperforms higher amounts of EDTA with Met (Formulation 5: 100 μM EDTA with 5 mM Met). The highest HMW formation is observed with no DTPA and no Met under air headspace (Formulation 2: 0 μM DTPA with 0 mM Met) followed by the same formulation but under nitrogen headspace (Formulation 7) and having Met alone (Formulation 3: 0 μM DTPA with 5 mM Met).

Figure 13:
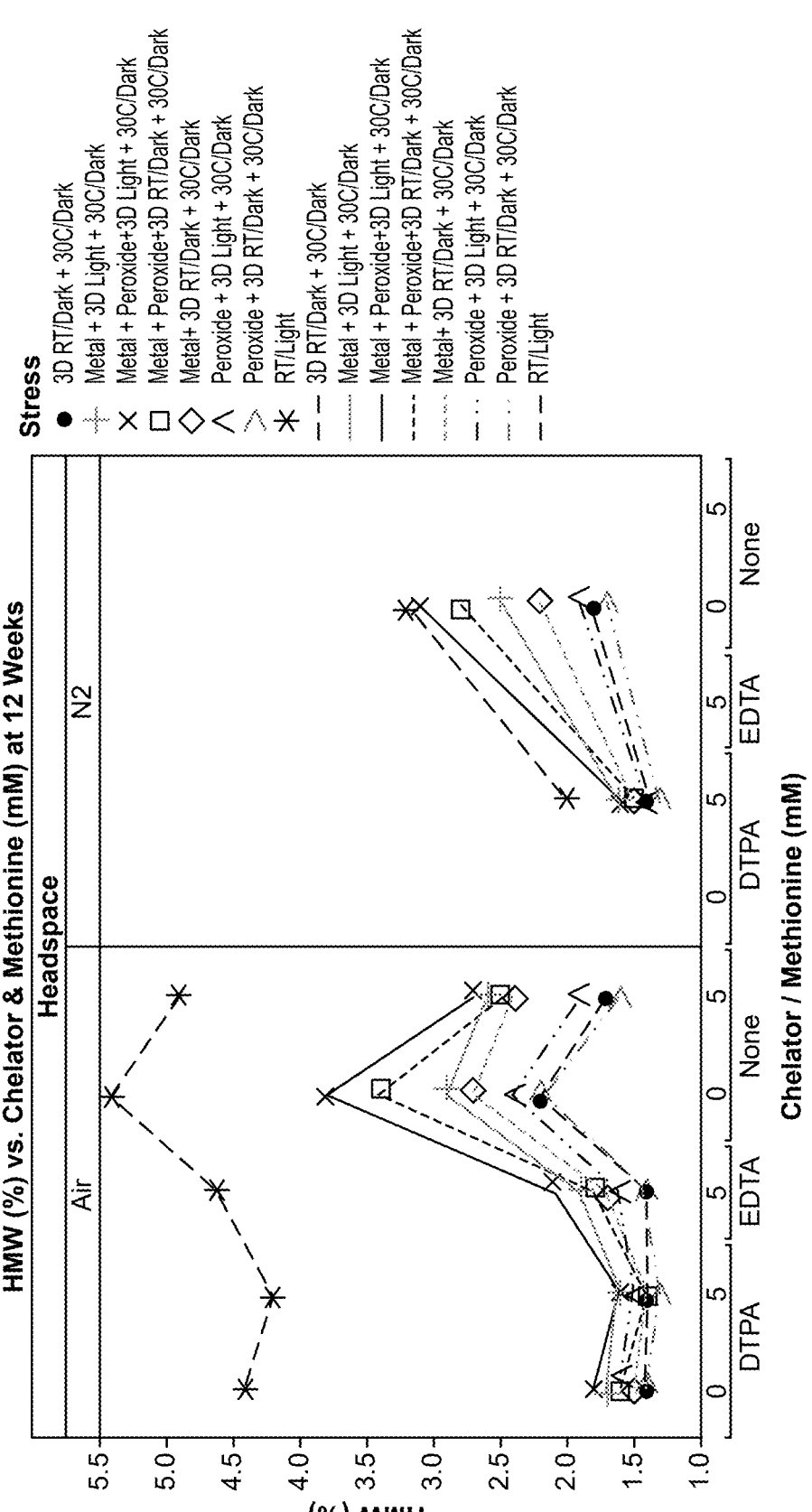
FIG. 13 is a graphical representation of the % HMW in Study 1 after 3 months under various combinations of metal (0.5 ppm each of iron, chromium, and copper), light (3 days at 1000 lux at room temperature), and peroxide (1 mM peroxide) with 30° C. thermal stress by formulation composition with/without 5 mM Met and 50 μM DTPA and 100 μm EDTA. All formulations also contain 120 mg/mL Nivo, 20 mM Histidine, 250 mM Sucrose, 0.05% w/v PS80 at pH 6.0 with 2,000 U/mL rHuPH20.

Another way to examine these data is by looking at the formulation compositions and how they perform by stress condition as shown in FIG. 13. The benefits of having both DTPA and Met can be observed. This way of examining the data shows that the RT/Light condition to be the worst case and from an individual stress perspective 3 days light and/or metal results in the highest % HMW formation and the effect of peroxide is muted. The benefit of a nitrogen headspace is very apparent for the RT/Light condition. For the no DTPA, no Met samples nitrogen headspace decreases % HMW by approximately 0.5% across all stress conditions. No significant improvement due to nitrogen headspace is observed for the formulations with both DTPA and Met. % HMW for 100 μM EDTA with 5 mM Met is greater than 50 μM DTPA with 5 mM Met but the size of the effect could be dependent on the precise stressor.

Figure 14:
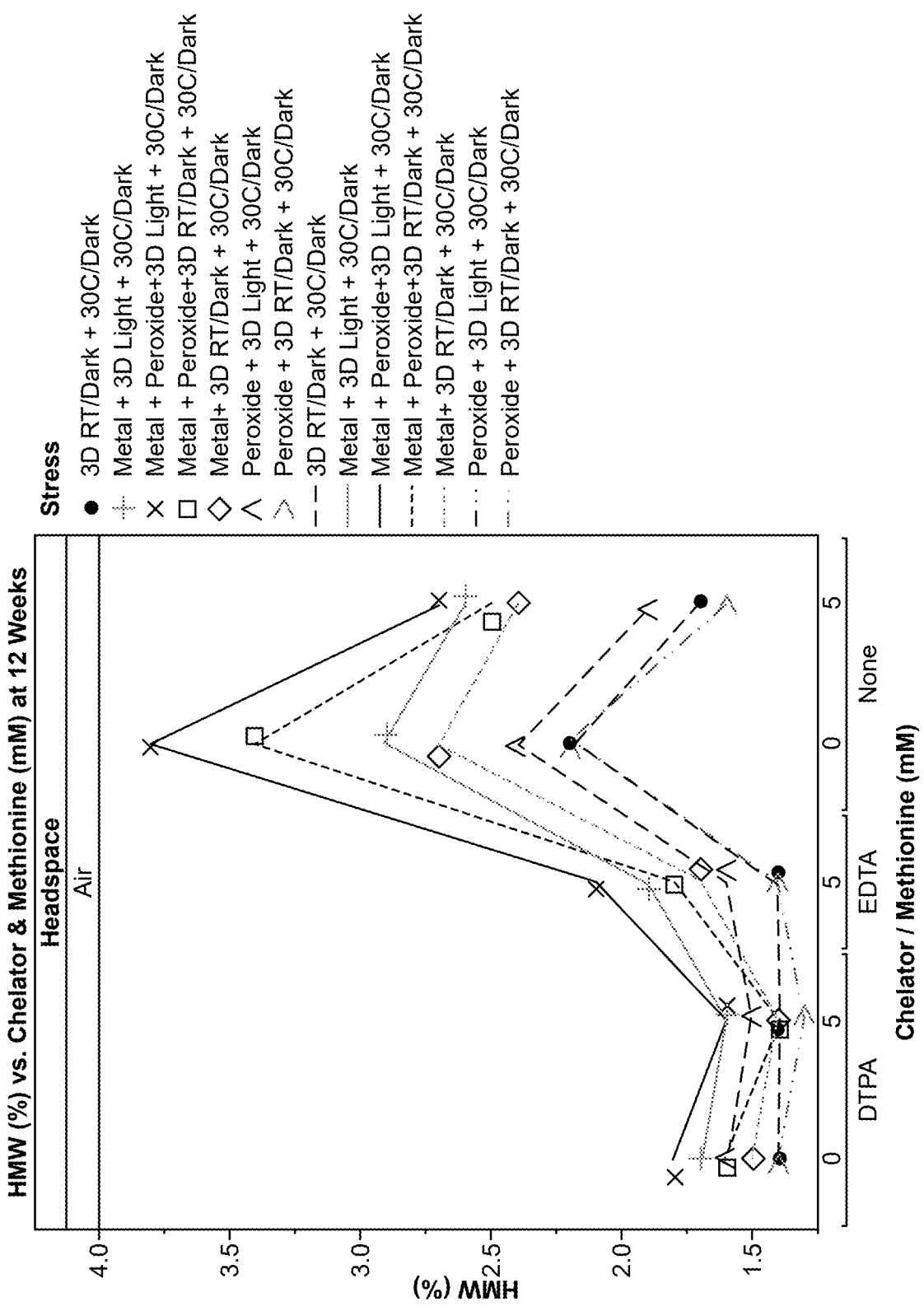
FIG. 14 is a graphical representation of % HMW in Study 1 after 3 months under various combinations of metal (0.5 ppm each of iron, chromium, and copper), light (3 days at 1000 lux at room temperature), and peroxide (1 mM peroxide) with 30° C. thermal stress included in the main effects statistical model. The graph is divided by formulation composition with/without 5 mM Met and 50 μM DTPA. All formulations also contain 120 mg/mL Nivo, 20 mM Histidine, 250 mM Sucrose, 0.05% w/v PS80 at pH 6.0 with 2,000 U/mL rHuPH20.

To provide a statistical assessment various linear models were explored. The absence of an estimate for pure error, design imbalance, and complicated formulation-stress dynamics obviated attempts at a single combined model incorporating all factors. The nitrogen and EDTA samples were excluded from analysis. The remaining chelator-methionine observations are shown in FIG. 14 and provide a pictorial motivation for the analyses described below. The RT/room Light condition, while included in the statistical model, has been removed from the graph below since this extreme stress condition was less relevant to the intended usage case.

For this reduced dataset the potential for a chelator-stress interaction is evident. But, within the DTPA-only samples the stress effect appears additive. This suggests a main effect statistical model is estimable and could be used to compare DTPA with/without methionine. Residual variance differences are possible based on the presence or absence of DTPA.

Based on the analysis presented, comparison of DTPA with or without 5 mM methionine with an air headspace was carefully examined. Using DTPA-only samples under air, a main effect linear model incorporating methionine and stress estimates a marginally significant average benefit with the addition of methionine in % HMW (difference 0.0375%, p ~ 0.0796) at 4 weeks and a statistically significant average improvement in % HMW (difference 0.125%, p~0.0016) at 12 weeks across all stress conditions (data not shown).

Polysorbate 80

A subset of samples were tested to understand the stability of polysorbate—a surfactant critical to protect Nivo from forming particulates. Levels of PS80 for samples tested are shown in Table 77. PS80 does get oxidized by metal, peroxide, and light. Degradation is mitigated by the addition of a chelating agent (DTPA or EDTA). Conditions without chelator have a significant drop in PS80 levels upon storage. This drop can be observed even at 5° C. storage after 2 months. After 1 month of storage at 30° C. with metal and peroxide stress of which 3 days where at room temperature/ room light, the samples without chelator drop to less than 0.1 mg/mL (from starting 0.5 mg/mL target). Headspace of nitrogen slightly protects the PS80 (0.08 mg/mL under nitrogen vs. 0.02 mg/mL under air).

TABLE 77

| Study 1-PS80 levels after 2 months at 5° C. and 1 month after 3 days at Light + Metal + Peroxide + 30° C./Dark [MPL] starting from 0.5 mg/mL initial PS80. | | | | | |
|---|---|---|---|---|---|
| Formulation # (Headspace) | DTPA (uM) | EDTA (uM) | Met (mM) | PS80 MP 5 C. 2 M (mg/mL) | PS80 MPL 30 C. 1 M (mg/mL) |
| 1 | 50 | 0 | 5 | 0.49 | 0.49 |
| 2 | 0 | 0 | 0 | 0.45 | 0.02 |

TABLE 77-continued

Study 1-PS80 levels after 2 months at 5° C. and
1 month after 3 days at Light + Metal + Peroxide +
30° C./Dark [MPL] starting from 0.5 mg/mL initial PS80.

| Formulation # (Headspace) | DTPA (uM) | EDTA (uM) | Met (mM) | PS80 MP 5 C. 2 M (mg/mL) | PS80 MPL 30 C. 1 M (mg/mL) |
|---|---|---|---|---|---|
| 3 | 0 | 0 | 5 | 0.34 | 0.03 |
| 4 | 50 | 0 | 0 | 0.49 | 0.51 |
| 5 | 0 | 100 | 5 | 0.49 | 0.48 |
| 6 (N2) | 50 | 0 | 5 | 0.51 | 0.49 |
| 7 (N2) | 0 | 0 | 0 | 0.46 | 0.08 | rHuPH20 Enzyme Activity

Figure 15:
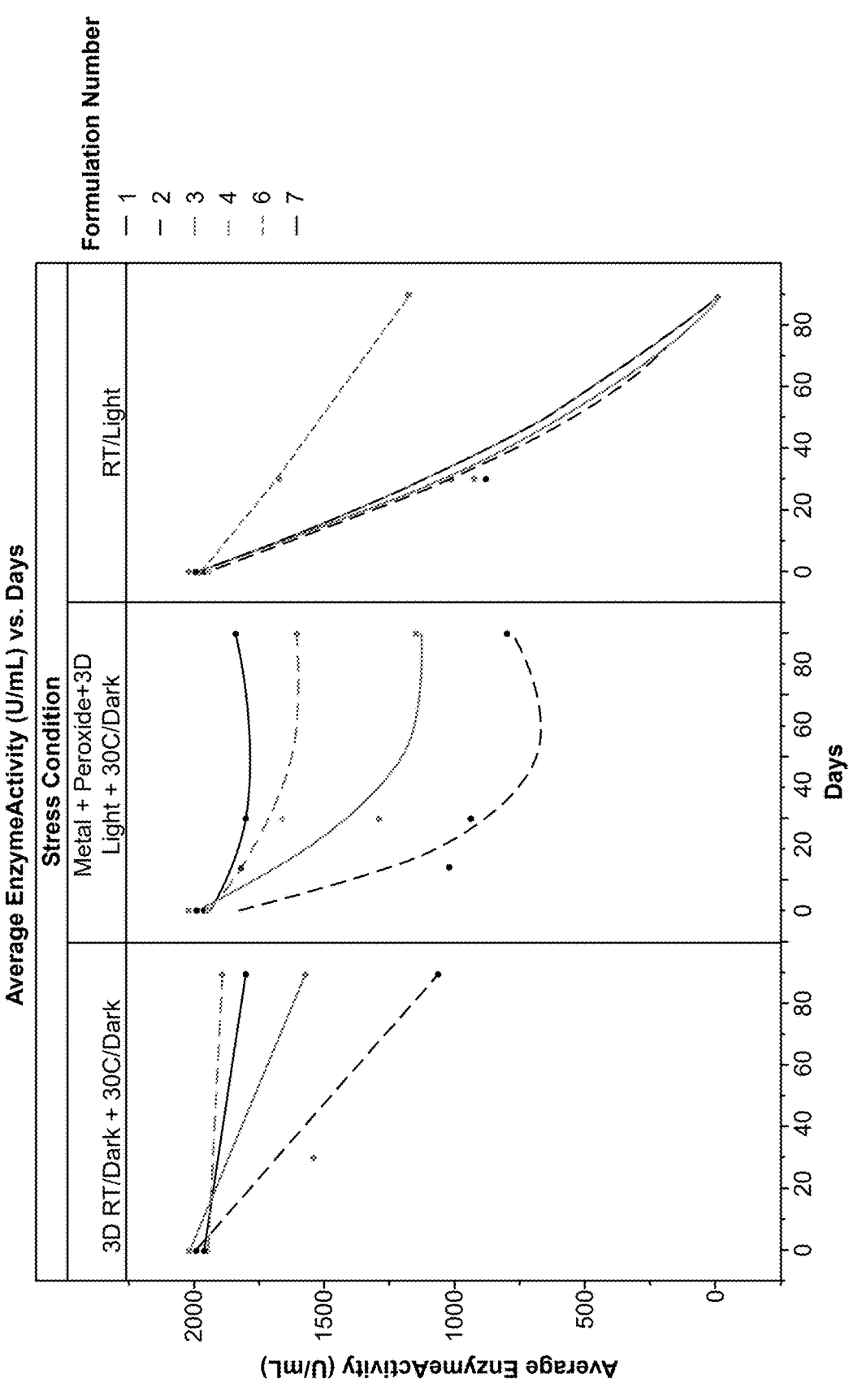
FIG. 15 is a graphical representation of rHuPH20 enzyme activity in Study 1 upon storage at 3 days RT/Dark followed by 30° C./Dark [Control—Left], RT/RL for 3 days followed by 30° C./Dark with Metal Spike and Peroxide Spike [MPL—Middle], and Room temperature/room light [RT/Light—Right]. Formulation 1 (air) and 6 (nitrogen): 50 μm DTPA 5 mM Met; Formulation 2 (air) and 7 (nitrogen): 0 μM DTPA, 0 mM Met; Formulation 3: 0 μM DTPA, 5 mM Met; Formulation 4: 50 μM DTPA, 0 mM Met. All formulations also contain 120 mg/mL Nivo, 20 mM Histidine, 250 mM Sucrose, 0.05% w/v PS80 at pH 6.0 with 2,000 U/mL rHuPH20.

To assess the stability of rHuPH20, the enzyme activity was measured for a limited set of samples. Results from the enzyme activity assay are shown in FIG. 15. Enzyme levels for samples stored at 30° C./dark with MPL stress (metal and peroxide stress where the first 3 days where at room temperature/room light) are tabulated in FIG. 15 (middle). Formulations with both DTPA and Met (Formulation 1) out performs formulations with DTPA alone which out performs formulations with Met alone. Formulations with none (neither DTPA nor Methionine) had the largest enzyme activity drop.

Samples exposed to 3 days RT/dark followed by 30° C./dark FIG. 15 (left) show similar behavior where formulations with DTPA and Met and formulations with DTPA alone outperforms formulations with Met alone and formulations with neither DPTA nor Met.

The rHuH20 enzyme activity showed a different behavior for samples exposed to RT/RL FIG. 15 (right). For these conditions all formulation had non-reportable (low) levels of rHuPH20 activity for all 3 M sample except for the sample that was held under nitrogen headspace with DTPA and Met. The formulation differences are not observed after continuous exposure to room light with a headspace of air. These results suggest that headspace nitrogen in combination with DTPA and Met help protect the enzyme under continuous exposure to room temperature/room light.

Particulate Formation

Particulate formation was evaluated at the two-week time point for all stress conditions and formulations. Levels of large particulates ≥25 μm particles are low (less than 32 particles/mL) for all samples. The particulates ≥10 am particles are all below 164 particles/mL for all samples. Samples with the highest particulate counts were conditions under room temperature/room light but the number of particles are well below the USP <788> specifications. No particulate issues are observed during this study.

the stability of the formulation was monitored by three key components: stability of Nivo by SEC, stability of rHuPH20 by monitoring enzyme activity, and stability of PS80 by measuring PS80 levels. For each of these quality attributes the formulation performance and rank ordering the best formulation to the worst (top to bottom) formulation is tabulated in Table 78.

Nivo stability by SEC shows HMW increase in response to oxidation stresses. Across the various combination of stresses (metal, peroxide, and light) the increase of HMW is protected by the presence of antioxidants. Combination of Met and DTPA demonstrate better stability over DTPA alone, which outperformed Met, which out performed formulations with neither DTPA nor Met.

rHuPH20 enzyme activity decreases in response to oxidation stresses. In particular the drop is significant due to light stress. The formulation composition benefits can be observed for a combination of metal, peroxide and light stress (3 days) conditions. The enzyme activity is best preserved with the presence of both Met and DTPA. There is a measurable drop in enzyme activity relative to DTPA alone, which has a measurable drop relative to Met alone, which has a measurable drop in activity relative to having no Met nor DTPA.

PS80 protection was observed for conditions that had a chelating agent (DTPA). Met did not protect PS80 from degrading.

TABLE 78

Study 1-Quality attributes studied that were able to distinguish
formulations and the ranking of these formulations

| Quality Attribute | Nivo SEC-HMW | rHuPH20 Enzyme activity | PS80 stability |
|---|---|---|---|
| (best) | Met + DTPA | Met + DTPA | Met + DTPA = DTPA |
| Rank | DTPA | DTPA | Met = None |
| Ordering | Met | Met | |
| (worst) | None | None | |

Key results from investigating various combinations of peroxide, metal, and light with the addition of thermal stress at 30° C. with various formulations indicate that there is a benefit in the formulation having both 50 μM DTPA and 5 mM Met. The stability with just one of these anti-oxidants is less superior to having both the chelating agent and sacrificial antioxidant.

Results—Study 2

The formulations tabulated in Tables 68 and 69 were analyzed. In this study, the aim was to understand the factors and ranges where the benefits of this formulation can be observed. Factors and ranges explored were: pH: 5.2-6.8 His; Histidine: 10-100 mM (Alt: Succinate); DTPA 10-200 μM (Alt: 100 μM EDTA); Met: 1-20 mM (Alt: 10 mM Trp); rHuPH20: 0-5,000 U/mL; PS80: 0.01-0.1% w/v (Alt: PS20 and Poloxamer 0.2 mg/mL); Sugar: 10-400 mM sucrose; and Protein: 100-175 mg/mL. This resulted in 49 different formulations to be studied here. pH, DTPA and Met levels where co-varied. Formulations at the max and min of the excipient ranges were varied one-variable at a time with all other factors at the target composition. The target composition is: 120 mg/mL Nivo in 20 mM Histidine, 250 mM Sucrose, 50 μM DTPA, 5 mM Met, 2,000 U/mL rHuPH20, 0.05% w/v PS80 at pH 6.0 with air headspace. Note there were duplicate independent formulation preparations in the design for the center point condition and the condition with 50 μM DTPA and no Met. The distribution of the formulation studied is shown in FIGS. 16A-16F.

Similar to the formulation ranges studied at the target composition alternate excipients: succinate, 100 μM EDTA, 10 mM Trp, 0.05% w/v PS20, poloxamer 0.2 mg/mL, 10% sorbitol and trehalose, were also studied with other excipients at the target composition.

Size Exclusion Chromatography

Size exclusion chromatography was the primary tool used to monitor the stability of Nivolumab.

Reproducibility

The duplicate and independent formulation preparations were included in the design for the center point condition and the condition with 50 µM DTPA and no Met. The final HMW by SEC by stress and time point for these formulations are tabulated in Table 79.

TABLE 79

Study 2 - High molecular weight species by SEC for the last time point in each of the stress condition studied for the duplicate samples - center and 0 Met formulations. Center formulation composition: 120 mg/mL Nivo, 20 mM Histidine, 250 mM Sucrose, 50 µM DTPA, 5 mM Met, 0.05% w/v PS80 at pH 6.0. 0 Met composition: 120 mg/mL Nivo, 20 mM Histidine, 250 mM Sucrose, 50 µM DTPA, 0.05% w/v PS80 at pH 6.0.

| | | | % HMW by SEC | | | | | |
| | | | --- | --- | --- | --- | --- | --- |
| Formulation | Descriptor | DS Source | 5° C. 6 M | 25° C. 6 M | 35° C. 3 M | RT/30 3 M | RT/RL 1 M | MPL 3 M |
| 15 | Center | Nivo DS | 0.9 | 1.4 | 1.7 | 1.2 | 1.9 | 1.5 |
| 28 | Center | Nivo DS | 0.9 | 1.4 | 1.8 | 1.3 | 1.8 | 1.6 |
| 49 | Center | Sugar-free DS | 0.8 | 1.3 | 1.6 | — | — | — |
| 21 | 0 Met | Nivo DS | 0.9 | 1.5 | 1.8 | 1.3 | 1.9 | 1.8 |
| 29 | 0 Met | Nivo DS | 0.9 | 1.5 | 1.8 | 1.3 | 1.9 | 1.8 |

Enzyme Level

In this study a range of enzyme levels was studied between 0 to 5,000 U/mL. The final HMW by SEC for varied enzyme levels is tabulated for the final time point for that stress condition in Tale 80. The formulation composition had varied level of enzyme with 120 mg/mL Nivo, 20 mM histidine, 250 mM sucrose, 50 µM DTPA, 5 mM Met, 0.05% w/v PS80 at pH 6.0. Enzyme level had no impact on the formation of HMW species across all stress conditions studied.

TABLE 80

Study 2- High molecular weight species by SEC for the last time point in each of the stress condition studied for varied enzyme level. Formulation composition: 120 mg/mL Nivo, 20 mM Histidine, 250 mM Sucrose, 50 µM DTPA, 5 mM Met, 0.05% PS80 at pH 6.0.

| | % HMW by SEC | | | | | |
| --- | --- | --- | --- | --- | --- | --- |
| Enzyme (U/mL) | 5° C. 6 M | 25° C. 6 M | 35° C. 3 M | RT/30 3 M | RT/RL 1 M | MPL 3 M |
| 0 | 0.9 | 1.4 | 1.8 | 1.2 | 1.9 | 1.6 |
| 500 | 1.0 | 1.4 | 1.8 | 1.2 | 1.9 | 1.6 |
| 2000 | 0.9 | 1.4 | 1.7 | 1.2 | 1.9 | 1.5 |
| 2000 | 0.9 | 1.4 | 1.8 | 1.3 | 1.8 | 1.6 |
| 5000 | 0.9 | 1.4 | 1.8 | 1.2 | 1.9 | 1.6 |

Alternate Excipients

In this study alternate excipients were studied with the center point composition for all other excipients. As an alternate surfactant to PS80 at 0.05% w/v, 0.05% w/v PS20 and 0.2 mg/mL poloxamer were studied. As an alternate buffer to 20 mM histidine 20 mM succinate was studied. Surfactant and buffer alternatives were unlikely to have a large impact protection against oxidation so performance for these alternatives were studied under thermal stress conditions. The final HMW by SEC using these alternate excipients is tabulated for the final time point for that stress condition next to the center point conditions (with the target formulation composition of 120 mg/mL Nivo, 20 mM histidine, 250 mM sucrose, 50 µM DTPA, 5 mM Met, 2,000 U/mL rHuPH20, 0.05% w/v PS80 at pH 6.0) in Table 81. As an alternate excipient PS80 can be replaced by PS20 or poloxamer with minimal impact to stability. The formulation with histidine as a buffering agent is critical for Nivo stability and cannot be replaced with succinate. There is a substantial increase in HMW species with succinate buffer across all thermal stress conditions studied (5° C. 25° C. and 35° C.).

TABLE 81

Study 2-High molecular weight species by SEC for the last time point in each of the stress condition studied for alternate excipients. Center point composition: 120 mg/mL Nivo, 20 mM Histidine, 250 mM Sucrose, 50 µM DTPA, 5 mM Met, 0.05% w/v PS80, 2000 U/mL rHuPH20 at pH 6.0.

| | % HMW by SEC | | |
| --- | --- | --- | --- |
| Alternate Excipient | 5° C. 6 M | 25° C. 6 M | 35° C. 3 M |
| Center | 0.9 | 1.4 | 1.7 |
| Center | 0.9 | 1.4 | 1.8 |
| PS20 | 0.9 | 1.3 | 1.7 |
| Poloxamer | 0.9 | 1.3 | 1.7 |
| Succinate | 1.3 | 3.2 | 6.8 |

As an alternate chelator to 50 µM DTPA, 100 µM EDTA was studied. DTPA is a better chelating agent so a higher level of EDTA was studied here. Similarly, as an alternate sacrificial agent to 5 mM methionine, 10 mM tryptophan was studied. Since addition of chelator and sacrificial oxidizing agent can impact protection against oxidation these were studied under both thermal and oxidation stress conditions. The final HMW by SEC using these alternate excipients is tabulated for the final time point for that stress condition next to the center point condition and the corresponding controls (with the center point formulation composition of 120 mg/mL Nivo, 20 mM histidine, 250 mM sucrose, 50 µM DTPA, 5 mM Met, 2,000 U/mL rHuPH20, 0.05% PS80 at pH 6.0) in Table 82.

TABLE 82

Study 2 High molecular weight species by SEC for the
last time point in each of the stress condition studied
for alternate excipients to DTPA and Met. Composition
includes: 120 mg/mL Nivo, 20 mM Histidine, 250 mM Sucrose,
0.05% w/v PS80, 2000 U/mL rHuPH20 at pH 6.0.

| | % HMW by SEC | | | | | |
|---|---|---|---|---|---|---|
| Formulation | 5° C. 6 M | 25° C. 6 M | 35° C. 3 M | RT/30 3 M | RT/RL 1 M | MPL 3 M |
| 5 mM Met 50 µm DTPA | 0.9 | 1.4 | 1.7 | 1.2 | 1.9 | 1.5 |
| 5 mM Met 50 µm DTPA | 0.9 | 1.4 | 1.8 | 1.3 | 1.8 | 1.6 |
| 10 mM Trp 50 µm DTPA | 0.9 | 1.4 | 1.8 | 1.2 | 2.4 | 1.9 |
| 5 mM Met 100 µM EDTA | 0.9 | 1.5 | 1.8 | 1.3 | 1.8 | 2.1 |
| 0 mM Met 100 µM EDTA | 1 | 1.7 | 2.1 | 1.3 | 1.9 | 3.7 |
| 0 mM Met 50 µM DTPA | 0.9 | 1.5 | 1.8 | 1.3 | 1.9 | 1.8 |
| 0 mM Met 50 µM DTPA | 0.9 | 1.5 | 1.8 | 1.3 | 1.9 | 1.8 |

The tabulated % HMW values after 3 months with MPL stress clearly shows the unique benefit of having DTPA, and that it is a superior chelator, compared to EDTA. The % HMW observed was 1.6% vs. 2.1% HMW after 3 months with MPL stress. Evaluation of the chelator alone (with no Met) further illustrates the benefit of DTPA over EDTA (1.8% HMW for DTPA vs. 3.7% HMW for EDTA after 3M of MPL stress). Similarly, the data shows that Met is superior to Trp. The HMW observed was 1.9% for Met vs. 2.4% for Trp after 1M at RT/RL and 1.5% for Met vs. 1.9% HMW for Trp after 3M MPL. % HMW increase is best controlled when formulated with 5 mM Met and 50 µM DTPA. These results are in agreement with Study 1.

Levels of DTPA

Figure 17:
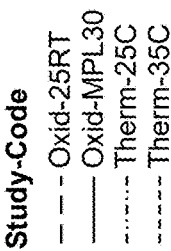
FIG. 17 is a graphical representation of high molecular weight species by SEC at various time points up to 6 months for 25° C., 35° C., and MPL, and RT/RL stress conditions for 0-200 μM DTPA, for Study 2. Composition includes: 120 mg/mL Nivo, 20 mM Histidine, 250 mM Sucrose, 5 mM Met, 0.05% w/v PS80, 2000 U/mL rHuPH20 at pH 6.0.

A range of DTPA levels were studied from 0-200 µM with the center point formulation composition of 120 mg/mL Nivo, 20 mM histidine, 250 mM sucrose, 5 mM Met, 2,000 U/mL rHuPH20, 0.05% w/v PS80 at pH 6.0. The final HMW by SEC at various Met levels is tabulated for the final time point for that stress condition in Table 83. Across accelerated thermal conditions (25° C., and 35° C.) and the MPL oxidation conditions there is an impact of having 0 µM DTPA; however, between the concentrations of 10-200 µM no compelling evidence of a concentrate dependent DTPA effect is observed. This behavior is consistent across stress conditions across time as shown in FIG. 17.

TABLE 83

Study 2 High molecular weight species by SEC for the
last time point in each of the stress condition studied
for various DTPA levels. Composition includes: 120
mg/mL Nivo, 20 mM Histidine, 250 mM Sucrose, 5 mM Met,
0.05% w/v PS80, 2000 U/mL rHuPH20 at pH 6.0.

| | % HMW by SEC | | | | | |
|---|---|---|---|---|---|---|
| DTPA (µM) | 5° C. 6 M | 25° C. 6 M | 35° C. 3 M | RT/30 3 M | RT/RL 1 M | MPL 3 M |
| 0 | 1.0 | 1.8 | 2.2 | 1.4 | 2.0 | 2.4 |
| 10 | 0.9 | 1.4 | 1.7 | 1.2 | 1.8 | 1.5 |
| 50 | 0.9 | 1.4 | 1.7 | 1.2 | 1.9 | 1.5 |
| 50 | 0.9 | 1.4 | 1.8 | 1.3 | 1.8 | 1.6 |

TABLE 83-continued

Study 2 High molecular weight species by SEC for the
last time point in each of the stress condition studied
for various DTPA levels. Composition includes: 120
mg/mL Nivo, 20 mM Histidine, 250 mM Sucrose, 5 mM Met,
0.05% w/v PS80, 2000 U/mL rHuPH20 at pH 6.0.

| | % HMW by SEC | | | | | |
|---|---|---|---|---|---|---|
| DTPA (µM) | 5° C. 6 M | 25° C. 6 M | 35° C. 3 M | RT/30 3 M | RT/RL 1 M | MPL 3 M |
| 100 | 0.9 | 1.4 | 1.7 | 1.2 | 1.8 | 1.6 |
| 200 | 0.9 | 1.4 | 1.7 | 1.2 | 2.0 | 1.5 |

Levels of Methionine

A range of methionine (Met) levels were studied from 0-20 mM Met with the center point formulation composition of 120 mg/mL Nivo, 20 mM histidine, 250 mM sucrose, 50 µM DTPA, 2,000 U/mL rHuPH20, 0.05% w/v PS80 at pH 6.0. The final HMW by SEC at various Met levels is tabulated for the final time point for that stress condition in Table 84. For the thermal conditions (5° C., 25° C., 35° C., and RT/30° C. control) there is no major impact due to changes in Met levels. The benefit of higher levels of Met is observed in combination with DTPA under oxidation stress conditions of RT/RL over 1 month and MPL for 3 months. The benefits are minimal due to the larger impact adding DTPA has on HMW formation in all these formulations.

TABLE 84

Study 2 High molecular weight species by SEC for the
last time point in each of the stress condition studied
for various Met levels. Composition includes: 120 mg/mL
Nivo, 20 mM Histidine, 250 mM Sucrose, 50 µM DTPA,
0.05% w/v PS80, 2000 U/mL rHuPH20 at pH 6.0.

| Met Level (mM) | % HMW by SEC | | | | | |
|---|---|---|---|---|---|---|
| | 5° C. 6 M | 25° C. 6 M | 35° C. 3 M | RT/30 3 M | RT/RL 1 M | MPL 3 M |
| 0 | 0.9 | 1.5 | 1.8 | 1.3 | 1.9 | 1.8 |
| 0 | 0.9 | 1.5 | 1.8 | 1.3 | 1.9 | 1.8 |
| 1 | 0.9 | 1.5 | 1.7 | 1.3 | 1.9 | 1.7 |
| 5 | 0.9 | 1.4 | 1.7 | 1.2 | 1.9 | 1.5 |
| 5 | 0.9 | 1.4 | 1.8 | 1.3 | 1.8 | 1.6 |
| 10 | 0.9 | 1.4 | 1.6 | 1.2 | 1.8 | 1.5 |
| 20 | 0.9 | 1.4 | 1.7 | 1.2 | 1.6 | 1.4 |

Figure 18:
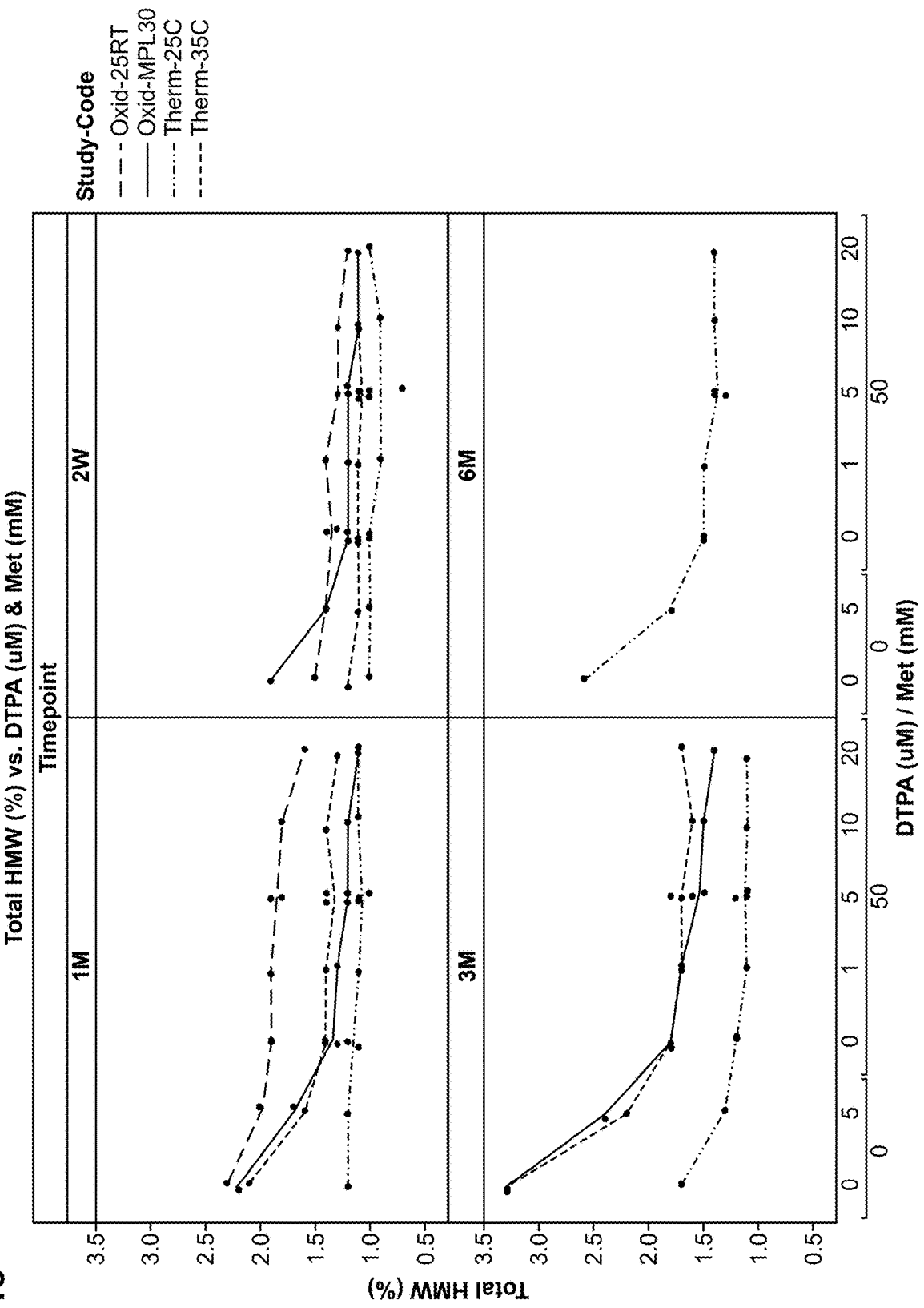
FIG. 18 is a graphical representation of high molecular weight species by SEC at various time points up to 6 months for 25° C., 35° C., and MPL, and RT/RL stress conditions separated by formulation DTPA and Met concentrations, for Study 2. Composition includes: 120 mg/mL Nivo, 20 mM Histidine, 250 mM Sucrose, 0.05% w/v PS80, 2000 U/mL rHuPH20 at pH 6.0.

The time course change in % HMW under each condition is shown in FIG. 18. Across stress conditions 0 µM DTPA with 0 mM Met has the highest HMW level. Differentiation between 0 and 5 mM methionine formulations at the 0 µM DTPA level is clear-addition of Met is beneficial to the stability of Nivo. At the target 50 µM DTPA concentration the effect of Met levels at various stresses at 2 weeks and 1 month timepoints are harder to differentiate. However, at the 3 month and 6 month timepoints careful evaluation is needed.

Figure 19:
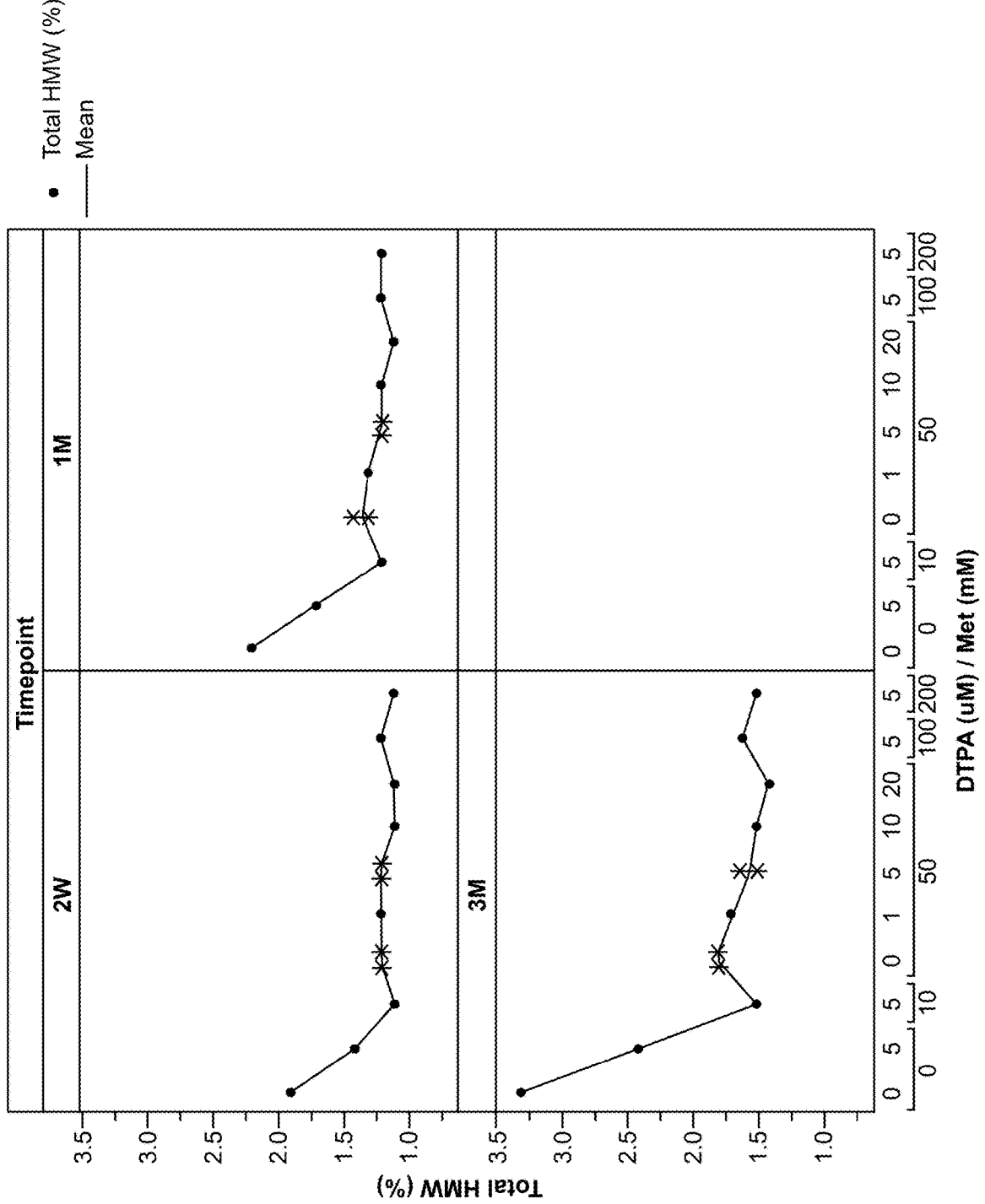
FIG. 19 is a graphical representation of high molecular weight species by SEC at various time points up to 6 months separated by formulation DTPA and Met concentrations, for Study 2. Composition includes: 120 mg/mL Nivo, 20 mM Histidine, 250 mM Sucrose, 0.05% w/v PS80, 2000 U/mL rHuPH20 at pH 6.0.

Careful evaluation of the MPL (Metal+Peroxide+3D of light followed by 30° C./Dark stress condition) is shown in FIG. 19. Note: for the formulation with 0 mM Met with 50 µM DTPA and the formulation with 5 mM Met with 50 µM DTPA there are duplicate independent formulations marked by two and three * marks. The 0 and 5 mM Met formulations at 0 µM DTPA differentiate at all three time points. At 50 µM DTPA concentration the % HMW formation appears to be a function of methionine concentration at both 1 and 3 month timepoints under these MPL conditions. In particular, for the MPL stress condition at the 3 month timepoint, the benefits of having higher level of Met is clearly observed. The HWM formation at the 100 and 200 µM DTPA with 5 mM Met concentration is similar to the 50 µM DTPA with 5 mM Met level. This is due to the binary effect of having DTPA but no compelling evidence of a concentration dependent DTPA effect as discussed above.

pH

A range of pH levels were studied from 5.2 to 6.8 with the center point formulation composition of 120 mg/mL Nivo, 20 mM Histidine, 250 mM Sucrose, 50 µM DTPA, 5 mM Met, 2,000 U/mL rHuPH20, 0.05% w/v PS80. The final HMW by SEC at various pH levels is tabulated for the final time point for that stress condition in Table 85. Across all thermal conditions (5° C., 25° C., and 35° C.) and the oxidation conditions (RT/RL, MPL, and RT/30° C. control), there is an impact of having higher pH. Between the pH range of 5.2 to 6.5 the formulation has good stability.

TABLE 85

Study 2 High molecular weight species by SEC for the last time point in each of the stress condition studied for various pH levels. Composition includes: 120 mg/mL Nivo, 20 mM Histidine, 250 mM Sucrose, 50 µM DTPA, 5 mM Met, 0.05% w/v PS80, and 2000 U/mL rHuPH20.

| | % HMW by SEC | | | | | |
|---|---|---|---|---|---|---|
| pH | 5° C. 6 M | 25° C. 6 M | 35° C. 3 M | RT/30 3 M | RT/RL 1 M | MPL 3 M |
| 5.2 | 1.0 | 1.4 | 1.9 | — | — | — |
| 5.5 | 0.9 | 1.5 | 1.8 | 1.2 | 1.8 | 1.5 |
| 6.0 | 0.9 | 1.4 | 1.7 | 1.2 | 1.9 | 1.5 |
| 6.0 | 0.9 | 1.4 | 1.8 | 1.3 | 1.8 | 1.6 |
| 6.5 | 1.1 | 1.8 | 2.0 | 1.5 | 2.7 | 2.1 |
| 6.8 | 1.2 | 2.6 | 4.1 | — | — | — |

DOE Evaluation of pH, Met, and DTPA Levels

There was a small excipient characterization DOE run on the combination of pH, Met, and DTPA levels. The formulations in the DOE are tabulated in Table 86 with all formulations containing 120 mg/mL Nivo, 20 mM Histidine, 250 mM Sucrose, 2,000 U/mL rHuPH20, and 0.05% PS80. The final HMW by SEC at various Met levels is tabulated for the final time point for that stress condition. Examination of the results show the clear pH effect across all stress conditions. The results in this part of the study are consistent with the univariant study results described above. For the MPL condition the dominant effect is pH, with higher pH resulting in higher HMW values. There is a protective effect with higher levels of Met, and DTPA levels studied here (10-100 µM) do not impact the HMW.

TABLE 86

Study 2 High molecular weight species by SEC for the last time point in each of the stress condition studied for the DOE that investigated impact of pH, Met, and DTPA levels. Composition includes: 120 mg/mL Nivo, 20 mM Histidine, 250 mM Sucrose, 0.05% w/v PS80, and 2000 U/mL rHuPH20.

| pH | DTPA (uM) | Met (mM) | 5° C. 6 M | 25° C. 6 M | 35° C. 3 M | RT/30 3 M | RT/RL 1 M | MPL 3 M |
|---|---|---|---|---|---|---|---|---|
| 5.2 | 50 | 5 | 1 | 1.4 | 1.9 | — | — | — |
| 5.5 | 10 | 1 | 0.9 | 1.5 | 1.9 | 1.3 | 1.7 | 1.5 |
| 5.5 | 10 | 10 | 0.9 | 1.4 | 1.8 | 1.2 | 1.6 | 1.4 |
| 5.5 | 100 | 1 | 0.9 | 1.5 | 1.9 | 1.3 | 1.8 | 1.6 |
| 5.5 | 100 | 10 | 0.9 | 1.4 | 1.8 | 1.2 | 1.6 | 1.4 |
| 5.5 | 50 | 5 | 0.9 | 1.5 | 1.8 | 1.2 | 1.8 | 1.5 |
| 6 | 10 | 5 | 0.9 | 1.4 | 1.7 | 1.2 | 1.8 | 1.5 |
| 6 | 100 | 5 | 0.9 | 1.4 | 1.7 | 1.2 | 1.8 | 1.6 |
| 6 | 50 | 1 | 0.9 | 1.5 | 1.7 | 1.3 | 1.9 | 1.7 |

TABLE 86-continued

Study 2 High molecular weight species by SEC for the last time point in each of the stress condition studied for the DOE that investigated impact of pH, Met, and DTPA levels. Composition includes: 120 mg/mL Nivo, 20 mM Histidine, 250 mM Sucrose, 0.05% w/v PS80, and 2000 U/mL rHuPH20.

| pH | DTPA (uM) | Met (mM) | 5° C. 6 M | 25° C. 6 M | 35° C. 3 M | RT/30 3 M | RT/RL 1 M | MPL 3 M |
|---|---|---|---|---|---|---|---|---|
| 6 | 50 | 10 | 0.9 | 1.4 | 1.6 | 1.2 | 1.8 | 1.5 |
| 6 | 50 | 5 | 0.9 | 1.4 | 1.7 | 1.2 | 1.9 | 1.5 |
| 6 | 50 | 5 | 0.9 | 1.4 | 1.8 | 1.3 | 1.8 | 1.6 |
| 6 | 50 | 5 | 0.8 | 1.3 | 1.6 | — | — | — |
| 6.5 | 10 | 1 | 1.1 | 1.8 | 2.1 | 1.6 | 2.8 | 2.2 |
| 6.5 | 10 | 10 | 1.1 | 1.8 | 1.9 | 1.5 | 2.7 | 1.9 |
| 6.5 | 100 | 1 | 1.1 | 1.8 | 2 | 1.6 | 2.8 | 2.4 |
| 6.5 | 100 | 10 | 1.1 | 1.7 | 1.9 | 1.5 | 2.6 | 1.9 |
| 6.5 | 50 | 5 | 1.1 | 1.8 | 2 | 1.5 | 2.7 | 2.1 |
| 6.8 | 50 | 5 | 1.2 | 2.6 | 4.1 | — | — | — |

Impact of Histidine Levels

A range of histidine levels was studied from 10 to 100 mM with the center point formulation composition of 120 mg/mL Nivo, 250 mM Sucrose, 50 µM DTPA, 5 mM Met, 2,000 U/mL rHuPH20, 0.05% w/v PS80 at a pH of 6.0. The final HMW by SEC at various histidine levels are tabulated for the final time point for that stress condition in Table 87. The data suggest that histidine is not only the buffering agent in the formulation, but also has protective properties with higher histidine levels increasing the stability of the protein. At low histidine concentrations the protective behavior is minimized especially below 20 mM Histidine. The data here suggest a cliff below this 20 mM histidine level. The exact location of this cliff is unknown. A histidine concentration range of 15 mM-100 mM is expected to have comparable and good stability.

TABLE 87

Study 2 High molecular weight species by SEC for the last time point in each of the stress condition studied for various histidine levels. Composition includes: 120 mg/mL Nivo, 250 mM Sucrose, 50 µM DTPA, 5 mM Met, 0.05% w/v PS80, and 2000 U/mL rHuPH20 at a pH of 6.0

| | % HMW by SEC | | |
|---|---|---|---|
| His (mM) | 5° C. 6 M | 25° C. 6 M | 35° C. 3 M |
| 10 mM | 1.1 | 2.1 | 4.1 |
| 20 mM | 0.9 | 1.4 | 1.7 |
| 20 mM | 0.9 | 1.4 | 1.8 |
| 50 mM | 0.9 | 1.1 | 1.5 |
| 100 mM | 0.8 | 0.9 | 1.3 |

Impact of Protein Concentration

The range of protein concentration studied was from 100 to 175 mg/mL, with the center point formulation composition of 20 mM Histidine, 250 mM Sucrose, 50 µM DTPA, 5 mM Met, 2,000 U/mL rHuPH20, 0.05% w/v PS80 at a pH of 6.0. The final HMW by SEC at various protein concentrations are tabulated for the final time point for that stress condition in Table 88. Higher protein concentrations have shown higher HMW formation and is consistent with other studies at higher protein concentration.

TABLE 88

Study 2 High molecular weight species by SEC for the last
time point in each of the stress condition studied for
various protein concentrations. Composition includes:
20 mM Histidine, 250 mM Sucrose, 50 μM DTPA, 5 mM Met,
0.05% w/v PS80, and 2000 U/mL rHuPH20 at a pH of 6.0

| Protein | % HMW by SEC | | |
|---|---|---|---|
| Conc (mg/mL) | 5° C. 6 M | 25° C. 6 M | 35° C. 3 M |
| 100 | 0.9 | 1.3 | 1.6 |
| 120 | 0.9 | 1.4 | 1.7 |
| 120 | 0.9 | 1.4 | 1.8 |
| 175 | 1.2 | 3 | 6.3 |

Impact of Sucrose Concentration PUP-115,11

The range of sucrose concentration studied was from 0 to 400 mM with the center point formulation composition of 120 mg/mL Nivo, 20 mM histidine, 50 μM DTPA, 5 mM Met, 2,000 U/mL rHuPH20, 0.05% w/v PS80 at a pH of 6.0. The final HMW by SEC at various sucrose concentrations are tabulated for the final time point for that stress condition in Table 89. Low sucrose levels have lower stability. The elevated HMW values are not concerning in the range of 10-400 mM sucrose.

TABLE 89

Study 2 High molecular weight species by SEC for the last
time point in each of the stress condition studied for
various sucrose concentrations. Composition includes:
120 mg/mL Nivo, 20 mM Histidine, 50 μM DTPA, 5 mM Met,
0.05% w/v PS80, and 2000 U/mL rHuPH20 at a pH of 6.0

| Sucrose (mM) | % HMW by SEC | | |
|---|---|---|---|
| | 5° C. 6 M | 25° C. 6 M | 35° C. 3 M |
| 0 | 1 | 1.9 | 2.3 |
| 10 | 1 | 1.7 | 2.2 |
| 250 | 0.9 | 1.4 | 1.7 |
| 250 | 0.9 | 1.4 | 1.8 |
| 400 | 0.9 | 1.2 | 1.6 |

Impact of PS80 Concentration

The range of PS80 concentration studied was from 0 to 0.10 w/v PS80 with the center point formulation composition of 120 mg/mL Nivo, 20 mM histidine, 250 mM sucrose, 50 μM DTPA, 5 mM Met, 2,000 U/mL rHuPH20, at a pH of 6.0. The final HMW by SEC at various PS80 concentrations were tabulated for the final time point for that stress condition in Table 90. The HMW values observed are constant in the range of the formulation compositions studied.

TABLE 90

Study 2 High molecular weight species by SEC for the last
time point in each of the stress conditions studied for
various PS80 concentrations. Composition includes: 120
mg/mL Nivo, 20 mM histidine, 250 mM sucrose 50 μM
DTPA, 5 mM Met, and 2000 U/mL rHuPH20 at a pH of 6.0

| PS80 (%) | % HMW by SEC | | |
|---|---|---|---|
| | 5° C. 6 M | 25° C. 6 M | 35° C. 3 M |
| 0 | 0.9 | 1.4 | 1.7 |
| 0.01 | 0.9 | 1.4 | 1.7 |
| 0.05 | 0.9 | 1.4 | 1.7 |

TABLE 90-continued

Study 2 High molecular weight species by SEC for the last
time point in each of the stress conditions studied for
various PS80 concentrations. Composition includes: 120
mg/mL Nivo, 20 mM histidine, 250 mM sucrose 50 μM
DTPA, 5 mM Met, and 2000 U/mL rHuPH20 at a pH of 6.0

| PS80 (%) | % HMW by SEC | | |
|---|---|---|---|
| | 5° C. 6 M | 25° C. 6 M | 35° C. 3 M |
| 0.05 | 0.9 | 1.4 | 1.8 |
| 0.10 | 0.9 | 1.4 | 1.7 |

Impact of Nitrogen Headspace

To understand the benefits of the formulation—nitrogen headspace was used to determine its impact on HMW during oxidation stress, as well as thermal stress. The two formulations studied are the target center point formulation condition of: 120 mg/mL Nivo, 20 mM histidine, 250 mM sucrose, 50 μM DTPA, 5 mM Met, 2,000 U/mL rHuPH20, 0.05% w/v PS80 at a pH of 6.0 and the condition with no DTPA nor Met: 120 mg/mL Nivo, 20 mM Histidine, 250 mM Sucrose, 2,000 U/mL rHuPH20, 0.05% w/v PS80 at a pH of 6.0. The final HMW by SEC for these two formulations with nitrogen and air head space are tabulated in Table 91 for the final time point for that stress condition.

TABLE 91

Study 2 High molecular weight species by SEC for the last time
point in each of the stress condition studied for 2 formulations
with and with-out nitrogen headspace. Center composition is
120 mg/mL Nivo, 20 mM histidine, 250 mM sucrose 50 μM DTPA,
5 mM Met, 0.05% w/v PS80 and 2000 U/mL rHuPH20 at a pH of
6.0. 0 DTPA 0 Met refer to the removal of both anti-oxidants
(DTPA and Met) from the center point formulation.

| Formulation - Headspace | % HMW by SEC | | | | | |
|---|---|---|---|---|---|---|
| | 5° C. 6 M | 25° C. 6 M | 35° C. 3 M | RT/30 3 M | RT/RL 1 M | MPL 3 M |
| Center-Air | 0.9 | 1.4 | 1.7 | 1.2 | 1.9 | 1.5 |
| Center - N₂ | 1 | 1.4 | 1.7 | 1.2 | 1.5 | 1.5 |
| 0 DTPA 0 Met - Air | 1 | 2.6 | 3.3 | 1.6 | 2.3 | 3.3 |
| 0 DTPA 0 Met - N₂ | 1 | 1.7 | 2.4 | 1.4 | 1.7 | 3 |

The data show the clear benefit of the center point formulation with both DTPA and Met relative to the composition with no DPTA nor Met. In the cases where no anti-oxidant (sacrificial agent and chelator) are added there is a benefit of having nitrogen headspace. The interesting behavior is the slight difference in behavior of the center point formulation under RT/RL condition. Here, the nitrogen headspace helps reduce the HMW formation. However, under the MPL condition the nitrogen headspace doesn't impact the HMW formation when both chelating agent and sacrificial agent are present. The formulation containing both sacrificial agent and chelator is able to protect against HMW formation from oxidation stresses coming from minor light (3 days), peroxide and metals compared to having neither sacrificial nor chelating agents.

Statistical Model: Final Time Point for pH 6 50 μM DTPA Concentration Formulations Statistical models were evaluated for the total % HMW. Due to small/negligible effects observed across most stress conditions statistical models were only developed for a subset of the stress conditions. Various mixed models were also explored (not shown) assuming a linear model for %

HMW versus time (days). Due to design constraints, a limited number of degrees of freedom for estimating inter- and intra-formulation variability and % HMW root-mean-square-error (RMSE) of approximately 0.15 to 0.25% average confidence intervals for key comparisons substantially overlapped for the stress conditions at 12 weeks. Results from the first study estimated an average % HMW difference of 0.125% for the two key formulation comparisons (above). All analyses were performed using JMP 15.2.0.

Close evaluation of the 25° C., 35° C. and MPL conditions provides weak to pronounced evidence of a no-yes DTPA beneficial effect for these three stress conditions for at least the longest time point at pH 6. Moreover, a 0-5 mM no-yes methionine effect was observed for the no-DTPA pH 6 formulations. To simplify the presentation of results, statistical models were developed for each of these three stress conditions at only the last measured time point. % HMW RMSE's of approximately 0.15 to 0.25% under various statistical models were observed even when restricted to the pH 6-only formulations. To further lessen the need for potentially inadequate empirical models only statistical results at 50 µM DTPA are outlined. Model complexity and/or nonlinearity, e.g., due to the inclusion of the no-DTPA samples, may increase the residual variance for mis- or underspecified models.

Figure 20:
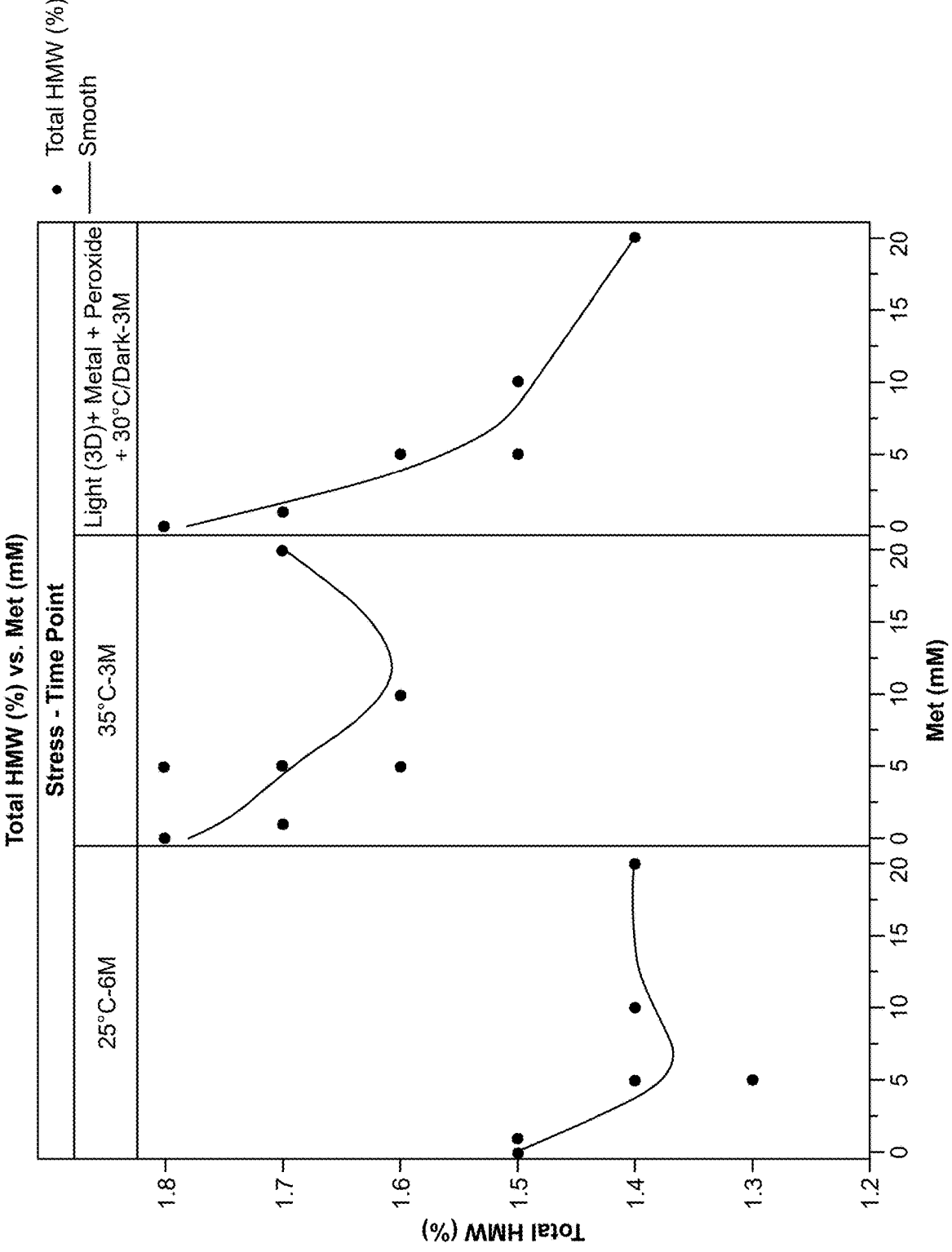
FIG. 20 is a graphical representation of SEC % HMW versus methionine concentration at the three last-sampled stress conditions with a smooth curve trend estimate at 120 mg/mL Nivo, 20 mM histidine, 250 mM sucrose, 50 μM DTPA, 0.05% w/v PS80, 2000 U/mL rHuPH20 at pH 6.0.

FIG. 20 shows a graph of SEC % HMW versus methionine concentration at the three last-sampled stress conditions with a smooth curve trend estimate.

For the 35° C. 3 month samples the replicate variability is large relative to the remaining signal. Only three distinct values were obtained for the 25° C.-6 month measurements. Little-or-no trend is evident for these two thermal stress conditions. A near-linear trend is most evident for the combined oxidation stress—MPL condition at 3 months.

A simple linear regression was estimated for each condition to evaluate the strength of the observed relationship (FIGS. 21A-21C).

Only the combined oxidation stress condition (MPL) linear regression was significant (p~0.0088). These data suggest a clear benefit of increasing methionine concentration in the presence of 50 µM DTPA for this oxidative stress condition. Model lack of fit was not detected (a curvilinear model was also estimated with improved fit, not shown) and the average % HMW RMSE was approximately 0.06 to 0.08% across all three regressions. The predicted average % HMW at 3 months for the 50 µM DTPA-0 mM methionine formulation is 1.73% (95% confidence interval 1.62-1.83); the corresponding 50 µM DTPA-5 mM methionine estimate is 1.63% (95% confidence interval 1.55-1.71). The average difference between these estimates is approximately equal to the 0.125% average difference observed in the first study (above) between the same two formulations under the MPL oxidative stress conditions at 3 months.

Charge Variants

Charge variants were assessed using iCIEF. A sub-set of samples focused on the benefits of having two anti-oxidants was studied in detail to evaluate the impact of charge variants on Nivo. Samples tested were for the 3 M time point for the MPL oxidation stress condition and the 3 M time point for the 35° C. thermal stress. The results are graphed in FIGS. 22A-22B.

The % acidic species is highest for conditions with no anti-oxidants (None). Methionine alone has less protection than having both just DTPA or having both DTPA and Methionine. There is no difference between formulations with DTPA alone vs. formulations with both DTPA and Met when stored at the 35° C. condition. A slight benefit can be observed in the 3 month timepoint under MPL stress for 3 months.

CE-SDS

CE-SDS was used to measure the clipped species of Nivo. A sub-set of samples focused on the benefits of having two antioxidants was studied in detail to evaluate the impact of the formulation on protecting Nivo from oxidation. Samples tested were for the 3 M time point for the MPL oxidation stress condition and the 35° C. 3 M time point. The results for the main peak area % are tabulated in Table 92. No major difference in main peak area is detected across the samples relative to the initial (T0) samples. No changes in LMW species formation over the study conditions studied were detected across the formulations studied.

TABLE 92

Study 2 CE-SDS main peak area percent as a function of time under MPL condition and 35° C. stress. Duplicate samples were prepared for formulations with DTPA and Met as well as for samples with DTPA alone. Formulations had DTPA at 50 µM and Met at 5 mM concentrations. All formulations also contain 120 mg/mL Nivo, 20 mM histidine, 250 mM sucrose, 0.05% w/v PS80, 2,000 U/mLrHuPH20 at pH 6.0

| | | CE-SDS Main peak (%) | |
| Formulation | T0 | 35 C. T 3 M | MPL 3 M |
| --- | --- | --- | --- |
| DTPA and Met | 97.0 | 97.2 | 98.5 |
| DTPA and Met | 97.0 | 97.6 | 97.6 |
| DTPA | 97.0 | 96.7 | 98.2 |
| DTPA | 96.9 | 98.2 | 97.9 |
| Met | 96.7 | 96.7 | 98.0 |
| None | 96.3 | 96.8 | 98.0 |

Enzyme Activity

Enzyme activity was measured to determine stability of the rHuPH20 enzyme. A sub-set of samples focused on the benefits of having two antioxidants was studied in detail to evaluate the impact of the formulation on protecting the enzyme from oxidation—the primary degradation mechanism. Samples tested were for the 3 M time point for the MPL oxidation stress condition and the 35° C. 3 M time point. The results are graphed in FIGS. 23A-23B.

The enzyme degradation was highest for conditions with no anti-oxidants (None). Methionine alone has less protection than having just DTPA. Having both DTPA and Methionine offers the best protection. The benefits were more pronounced looking at the MPL stress condition but consistent trend was observed between both 35° C. and MPL conditions. These results are consistent with what was observed in Study 1, above.

PS80 Stability

PS80 stability was measured to determine stability of the key excipient, PS80. A sub-set of samples focused on the benefits of having two antioxidants was studied in detail to evaluate the impact of the formulation on protecting the PS80 from oxidation. Samples tested were for the 3 M time point for the MPL oxidation stress condition and the 35° C. 3 M time point. The results are graphed in FIGS. 24A-24B.

The PS80 degradation was high and PS80 levels drop to zero for the condition without DTPA (data not shown) under the MPL stress condition. The distinction between None and Met alone can be observed for the 35° C. condition at the 3 M time point. The PS80 degradation kinetics are fastest for the conditions with no antioxidants (None) followed by the methionine alone condition. Both MPL and 35° C. stress conditions show comparable protection to PS80 between formulation having just DTPA and formulation having both DTPA and Methionine. The key feature from a PS80 stability perspective was the inclusion of DTPA. These results are consistent with what was observed in Study 1.

Formulation Ranges and Alternate Excipients

Study 2 was set-up to determine the impact and ranges where the benefits of the formulation composition is observed primarily by SEC. Formulations were stressed with thermal stress (5, 25, 35° C.) alone or with thermal and oxidation stress (MPL, RT/RL).

Based on this study the formulation composition ranges where stability is best maintained are as follows: pH: 5.2-6.5 His; Histidine: 15-100 mM; DTPA 10-200 µM (Alt: 100 µM EDTA); Met: 1-20 mM (Alt: 10 mM Trp); rHuPH20: 0-5,000 U/mL; PS80: 0.01-0.1% w/v (Alt: PS20 0.05% w/v and Poloxamer 0.2 mg/mL); Sugar: 10-400 mM sucrose; and Protein: 100-175 mg/mL The center point formulation is: 120 mg/mL Nivo, 20 mM histidine, 250 mM sucrose, 5 mM Met, 50 µM DTPA, 0.05% w/v polysorbate 80 at pH 6.0 with 2,000 U/mL rHuPH20.

The histidine buffer is critical in the formulation-formulations at the same pH using succinate as the buffer did not demonstrate sufficient stability (Table 91). Histidine has a stabilizing effect that shows increasing stability at higher concentrations. In this study up to 100 mM histidine was RT/RL conditions but shows higher HMW species formation under accelerated thermal conditions and under MPL stress condition. The combined formulation has oxidation protection that doesn't need nitrogen headspace to protect against MPL stresses (Table 91).

The DTPA levels between 10-200 µM have demonstrated comparable stability (Table 83). Having DTPA at a minimum concentration of 10 µM is critical but higher levels of DTPA do not increase the stability of Nivo.

Increase in Met has demonstrated acceptable stability within the range of 1-20 mM levels (Table 84). For the case of Met a statistical model was built and for the MPL stress condition a linear regression was found to be significant (above). This shows that there is a clear benefit of having Met and higher concentrations of Met being favorable against the MPL stress.

Rank Order

The benefit of having both anti-oxidants was demonstrated by monitoring: stability of Nivo by SEC and iCIEF, stability of rHuPH20 by looking at enzyme activity, and stability of PS80 by looking at PS80 levels. This part of the study focused on a sub-set of samples focused on the need for both anti-oxidants (both, vs. just one vs. none). For each of these quality attributes, the formulation performance and rank ordering the best formulation to the worst (top to bottom) formulations is tabulated in Table 93.

TABLE 93

| Study 2-Quality attributes studied that were able to distinguish formulations and the ranking of these formulations | | | |
|---|---|---|---|
| Quality Attribute | Nivo SEC % HMW | Nivo iCE % Acidic | rHuPH20 Enzyme activity | PS80 stability |
| (best) Rank Ordering (worst) | Met + DTPA DTPA Met None | Met + DTPA DTPA Met None | Met + DTPA DTPA Met None | Met + DTPA = DTPA Met None | studied (Table 87) but higher histidine concentrations are expected to be stable as well. At low histidine concentrations the stability drops. In particular, at histidine concentrations less than 10 mM the % HMW increases. The range between 15-100 mM is critical in minimizing HMW species formation.

The pH range is also critical—higher pH past pH of 6.5 shows an increase in HMW on stability (Table 85).

Nivo in the absence of sucrose results in slightly higher levels of HMW formation (Table 89). Sucrose between 10-400 mM demonstrates good stability.

PS80 levels studied here between 0-0.1% protected Nivo from HMW formation (Table 90). Alternate surfactants: PS20 (0.05% w/v) and poloxamer (0.2 mg/mL) demonstrated good protection for Nivo against HMW formation (Table 81).

Addition of enzyme in the range between 0 to 5,000 U/mL does not impact the stability of Nivo (Table 80).

This report demonstrates the need for two anti-oxidants. One sacrificial agent (Met) is needed in addition to a chelating agent (DTPA). In particular these two anti-oxidants perform better than their alternative excipients (Table 82). To confirm the superiority of the chosen excipient the performance of alternative oxidation agents has been tested at higher concentrations. Replacing 5 mM Met with 10 mM Trp results in higher HMW under both RT/RL conditions as well as under the MPL stress condition. Replacement of 50 µM DTPA with 100 µM EDTA behaves comparably under Nivo stability by SEC shows HMW increase in response to oxidation stress (MPL). The increase of HMW is minimized by the presence of anti-oxidants. Combination of Met and DTPA demonstrate better stability over DTPA alone, which outperformed Met, which outperformed formulations with neither DTPA nor Met. These results are consistent with Study 1.

Charge variants (above) show % acidic species increase to be highest with no DTPA nor Met. Having Met alone shows a slightly slower rate of increase for both thermal (35° C.) and oxidation (MPL) stress conditions. Having DTPA alone is comparable to having both DTPA and Met under thermal stress condition; but, under MPL condition a slight benefit is observed with both vs. DTPA alone.

rHuPH20 enzyme activity decreases in response to both thermal and oxidation stresses. The formulation composition benefit can be best observed for the oxidation stress (MPL). The enzyme activity was best preserved with the presence of both Met and DTPA. There was a measurable drop in enzyme activity relative to DTPA alone, which had a measurable drop relative to Met alone, which had a measurable drop relative to having no Met nor DTPA. This behavior was consistent for the thermal stress (35° C.) condition but the difference between DTPA alone and both (DTPA and Met) was smaller.

PS80 protection was observed for conditions that had a chelating agent (DTPA). Met did not protect PS80 from degrading.

Key results from investigating oxidation stress (MPL—combination of metal, peroxide, and 3 days of light in addition to thermal stress at 30° C.) with various combinations of formulations indicate that there was a benefit in the formulation having both 50 μM DTPA and 5 mM Met. The stability with just one of these antioxidants was less superior to having both chelating agent and sacrificial antioxidant. These results were consistent with Study 1 results.

Results—Study 3

In this study the aim was to understand the behavior of the molecule in different packaging components (the pre-filled syringe and the patch pump). In addition, there were a few formulation composition variations to the original to determine the ranges where benefits of this formulation can be observed. These include:

i. Histidine range of 15-100 mM. Study 2 showed increase in HMW at a low histidine concentration of 10 mM.

ii. Wider enzyme level from 0-10,000 U/mL vs. Study 2 only covered up to 5,000 U/mL.

iii. Wider protein concentration from 100-200 mg/mL. Study 2 covered up to 150 mg/mL.

This study also used these confirm formulation ranges in the case when enzyme is not present the formulation: pH: 5.2-6.5 His; Histidine: 15-100 mM; DTPA: 10-200 μM (Alt: 100 μM EDTA); Met: 1-20 mM (Alt: 10 mM Tryp); PS80: 0.01-0.1% w/v (Alt: PS20 and Poloxamer 0.2 mg/mL); Sugar: 10-400 mM Sucrose (Alt: 10% sorbitol and trehalose); Protein: 100-200 mg/mL; and Primary packaging: Vial, PFS and Patch pump.

Note that in this study the sorbitol and trehalose was correctly added in the TFF buffer which was missed in study 2. Due to the enzyme having no impact on HMW formation these results will be leveraged to understand the behavior with these alternate sugars with enzyme as well.

This resulted in 46 formulations where similar to study 2 formulations are studied one-variable at a time with all other factors at the target composition. In this study vials and patch pumps were studied primarily at 120 mg/mL and PFS were at 150 mg/mL Nivo target concentration. Target formulation composition was: 20 mM histidine, 250 mM sucrose, 50 μM DTPA, 5 mM Met, 2,000 U/mL rHuPH20, 0.05% w/v PS80 at pH 6.0 with air headspace. Note there were duplicate independent formulation preparations in the design for the center point condition and the condition with 50 μM DTPA and no Met.

In this study stability of Nivo was investigated using SEC and due to lack of particulate data from study 3 particulate analysis was done for select time points (MPL 3M, RT30 3M, 5C 6M and 25C 6M).

Size Exclusion Chromatography

Size exclusion chromatography was the primary tool used to monitor the stability of nivolumab.

Reproducibility and Enzyme Impact

Duplicate and independent formulation preparations were included in the design for the center point condition and 0 Met conditions as was done for study 2; but for study 3, the formulation did not include enzyme. The final HMW by SEC by stress and time point for the two formulations are tabulated for both study 2 and 3 in Table 94. This data shows the reproducibility across study 2 and 3 as well as across independent preparations with-in a study. The data are consistently within 0.1% HMW of each other.

TABLE 94

Study 2 and 3 - High molecular weight species by SEC for the last time point in each of the stress condition studied for the duplicate samples - center and 0 Met formulations. Center formulation composition: 120 mg/mL Nivo, 20 mM Histidine, 250 mM Sucrose, 50 μM DTPA, 5 mM Met, 0.05% w/v PS80 at pH 6.0. 0 Met composition: 120 mg/mL Nivo, 20 mM Histidine, 250 mM Sucrose, 50 μM DTPA, 0.05% w/v PS80 at pH 6.0.

| Study - Form | De- scriptor | Enzyme (U/mL) | % HMW by SEC | | | | |
|---|---|---|---|---|---|---|---|
| | | | 5° C. 6 M | 25° C. 6 M | 35° C. 3 M | RT30 3 M | MPL 3 M |
| Study 3 - 12 | 0 Met | 0 | 1.0 | 1.5 | 1.8 | 1.3 | 1.9 |
| Study 3 - 13 | 0 Met | 0 | 1.0 | 1.5 | 1.8 | 1.3 | 1.8 |
| Study 2 - 21 | 0 Met | 2000 | 0.9 | 1.5 | 1.8 | 1.3 | 1.8 |
| Study 2 - 29 | 0 Met | 2000 | 0.9 | 1.5 | 1.8 | 1.3 | 1.8 |
| Study 3 - 10 | Center | 0 | 1.0 | 1.5 | 1.7 | 1.2 | 1.5 |
| Study 3 - 11 | Center | 0 | 1.0 | 1.4 | 1.7 | 1.2 | 1.5 |
| Study 3 - 5 | Center | 2000 | 1.0 | 1.5 | 1.7 | 1.2 | 1.5 |
| Study 2 - 15 | Center | 2000 | 0.9 | 1.4 | 1.7 | 1.2 | 1.5 |
| Study 2 - 28 | Center | 2000 | 0.9 | 1.4 | 1.8 | 1.3 | 1.6 |

This study as well as study 2 (Table 80) shows that there is no impact to Nivo stability with or with-out enzyme (Table 95) across the full enzyme level studied (0-10,000 U/mL). Throughout study 3 there are duplicate compositions tested with and with-out enzyme. These results have been very consistent (Table 95, Table 96, Table 97, Table 98, Table 99, Table 100, FIG. 25A, and FIG. 25B) and allow us to confidently translate learnings across condition with and with-out enzyme.

TABLE 95

Study 3 - High molecular weight species by SEC for the last time point in each of the stress condition studied for varied enzyme level. Formulation composition: 120 mg/mL Nivo, 20 mM Histidine, 250 mM Sucrose, 50 μM DTPA, 5 mM Met, 0.05% w/v PS80 at pH 6.0.

| Enzyme (U/mL) | T0 | % HMW by SEC | | | | |
|---|---|---|---|---|---|---|
| | | 5° C. 6 M | 25° C. 6 M | 35° C. 3 M | RT30 3 M | MPL 3 M |
| 0 | 0.8 | 1.0 | 1.5 | 1.7 | 1.2 | 1.5 |
| 0 | 0.8 | 1.0 | 1.4 | 1.7 | 1.2 | 1.5 |
| 2000 | 0.8 | 1.0 | 1.5 | 1.7 | 1.2 | 1.5 |
| 10000 | 0.8 | 1.0 | 1.5 | 1.7 | 1.2 | 1.5 |
| 10000 | 0.8 | 1.0 | 1.5 | 1.7 | 1.2 | 1.5 |

Primary Packaging

This study evaluated three different types of primary packaging: Vial, pre-filled syringe, and patch pump. The data for the various primary packaging is shown in Table 96 for a protein concentration of 120 mg/mL in the center point formulation composition: 20 mM Histidine, 250 mM Sucrose, 50 μM DTPA, 5 mM Met, 0.05% w/v PS80 at a pH of 6.0. There was no difference in HMW formation due to primary packaging differences.

TABLE 96

Study 3 - High molecular weight species by SEC for the last time point in each of the stress condition studied for the varied primary packaging at 120 mg/mL Nivo, Formulation composition: 20 mM Histidine, 250 mM Sucrose, 50 μM DTPA, 5 mM Met, 0.05% w/v PS80 at pH 6.0

| | | | | % HMW by SEC | | | |
|---|---|---|---|---|---|---|---|
| Primary Packaging | Enzyme (U/mL) | T0 | 5° C. 6 M | 25° C. 6 M | 35° C. 3 M | RT30 3 M | MPL 3 M |
| Vial | 0 | 0.8 | 1.0 | 1.5 | 1.7 | 1.2 | 1.5 |
| Vial | 0 | 0.8 | 1.0 | 1.4 | 1.7 | 1.2 | 1.5 |
| Vial | 2000 | 0.8 | 1.0 | 1.5 | 1.7 | 1.2 | 1.5 |
| PFS | 0 | 0.7 | 1.0 | 1.5 | 1.7 | 1.2 | 1.5 |
| PFS | 2000 | 0.8 | 1.0 | 1.5 | 1.7 | 1.2 | 1.5 |
| Patch Pump | 0 | 0.8 | 0.9 | 1.4 | N/A* | 1.2 | 1.4 |
| Patch Pump | 2000 | 0.8 | 0.9 | 1.4 | N/A* | 1.2 | 1.4 |

*Due to limited number of patch pumps limited data is available for the patch pump.

To understand if there are any liabilities due to the PFS components, two extra conditions were tested: one with a 1 ppm tungsten (W) spike and fill into a BD Neopack syringe with two times the silicone oil found in standard BD Neopack syringes. The high molecular weight values at the last time point for that stress condition are tabulated in Table 97 at the 150 mg/mL concentration again with 20 mM Histidine, 250 mM Sucrose, 50 μM DTPA, 5 mM Met, 0.05% w/v PS80 at a pH of 6.0. No increase in HMW was detected due to tungsten or silicone oil.

TABLE 97

Study 3 - High molecular weight species by SEC for the last time point in each of the stress condition studied for the use of PFS components at 150 mg/mL Nivo. Formulation composition: 20 mM Histidine, 250 mM Sucrose, 50 μM DTPA, 5 mM Met, 0.05% w/v PS80 at pH 6.0

| | | | | % HMW by SEC | | | |
|---|---|---|---|---|---|---|---|
| Descriptor | Enzyme (U/mL) | T0 | 5° C. 6 M | 25° C. 6 M | 35° C. 3 M | RT30 3 M | MPL 3 M |
| 0 | W spike PFS | 0.8 | 1.1 | 1.7 | 1.9 | 1.4 | 1.6 |
| 0 | 2X Si Oil PFS | 0.8 | 1.1 | 1.7 | 1.9 | 1.4 | 1.7 |
| 0 | PFS | 0.8 | 1.1 | 1.7 | 2.0 | 1.4 | 1.7 |
| 2000 | W spike PFS | 0.8 | 1.1 | 1.7 | 1.9 | 1.4 | 1.7 |
| 2000 | 2X Si Oil PFS | 0.8 | 1.1 | 1.7 | 1.9 | 1.4 | 1.7 |
| 2000 | PFS | 0.8 | 1.1 | 1.7 | 1.9 | 1.4 | 1.7 |

Protein Concentration

Primary packaging and enzyme levels do not impact HMW formation as discussed above. HMW formation across packaging and enzyme levels at the center point formulation composition at a range of protein concentrations from 100 to 200 mg/mL was tabulated together in Table 98. The center point formulation composition includes 20 mM Histidine, 250 mM Sucrose, 50 μM DTPA, 5 mM Met, 0.05% w/v PS80 at a pH of 6.0. Higher protein concentrations have shown higher HMW formation, and the was consistent with other studies at higher protein concentration and data from study 2 (Table 88).

TABLE 98

Study 3 - High molecular weight species by SEC for the last time point in each of the stress condition studied for various protein concentrations. Formulation composition: 20 mM Histidine, 250 mM Sucrose, 50 μM DTPA, 5 mM Met, 0.05% w/v PS80 at pH 6.0

| Primary Packaging Primary | En-zyme (U/mL) | Protein Conc (mg/mL) | T0 | 5° C. 6 M | 25° C. 6 M | 35° C. 3 M | RT30 3 M | MPL 3 M |
|---|---|---|---|---|---|---|---|---|
| Vial | 0 | 100 | 0.7 | 0.9 | 1.3 | 1.5 | | |
| Vial | 0 | 120 | 0.8 | 1.0 | 1.5 | 1.7 | 1.2 | 1.5 |
| Vial | 0 | 120 | 0.8 | 1.0 | 1.4 | 1.7 | 1.2 | 1.5 |
| Vial | 2000 | 120 | 0.8 | 1.0 | 1.5 | 1.7 | 1.2 | 1.5 |
| PFS | 0 | 120 | 0.7 | 1.0 | 1.5 | 1.7 | 1.2 | 1.5 |
| PFS | 2000 | 120 | 0.8 | 1.0 | 1.5 | 1.7 | 1.2 | 1.5 |
| PFS | 0 | 150 | 0.8 | 1.1 | 1.7 | 2.0 | 1.4 | 1.7 |
| PFS | 2000 | 150 | 0.8 | 1.1 | 1.7 | 1.9 | 1.4 | 1.7 |
| PFS | 0 | 165 | 0.8 | 1.1 | 1.8 | 2.1 | 1.5 | 1.8 |
| PFS | 2000 | 165 | 0.9 | 1.1 | 1.8 | 2.0 | 1.4 | 1.8 |
| Vial | 0 | 200 | 1.0 | 1.3 | 2.1 | 2.5 | | |
| PFS | 0 | 200 | 1.0 | 1.3 | 2.2 | 2.5 | | |
| PFS | 2000 | 200 | 1.0 | 1.3 | 2.2 | 2.5 | | |
| Vial | 2000 | 200 | 1.0 | 1.3 | 2.1 | 2.5 | | |

Alternate Excipients

In study 3 as an alternate sugar to 250 mM (8.6%) sucrose two alternate sugars: 10% sorbitol and 10% trehalose were studied. The results along with the results from use of the alternate surfactant to PS80 at 0.05% w/v, 0.05% w/v PS20 and 0.2 mg/mL poloxamer were studied and are tabulated in Table 99. These results tabulated against study 2 vs. study 3 where the difference here is study 2 had 2,000 U/mL of rHuPH20 and study 3 had no rHuPH20. The other excipients were at target composition: with the target formulation composition of 120 mg/mL Nivo, 20 mM Histidine, 250 mM Sucrose, 50 μM DTPA, 5 mM Met, 0.05% w/v PS80 at pH 6.0. There was an error during the preparation of the samples in study 2 for the formulations with trehalose and sorbitol for the alternate excipient so data with enzyme is not presented.

TABLE 99

Study 2 and 3 - High molecular weight species by SEC for the last time point in each of the stress condition studied for alternate excipients. Study 2 conditions have 2,000 U/mL of rHuPH20, study 3 have 0 U/mL of rHuPH20. Center point composition: 120 mg/mL Nivo, 20 mM Histidine, 250 mM Sucrose, 50 μM DTPA, 5 mM Met, 0.05% w/v PS80, at pH 6.0.

| | % HMW by SEC | | | | | |
|---|---|---|---|---|---|---|
| Alternate | 5° C. 6 M | | 25° C. 6 M | | 35° C. 3 M | |
| Excipient | Study 2 | Study 3 | Study 2 | Study 3 | Study 2 | Study 3 |
| Center | 0.9 | 1.0 | 1.4 | 1.5 | 1.7 | 1.7 |
| Center | 0.9 | 1.0 | 1.4 | 1.4 | 1.8 | 1.7 |
| PS20 | 0.9 | 0.9 | 1.3 | 1.4 | 1.7 | 1.7 |
| Poloxamer | 0.9 | 1.0 | 1.3 | 1.5 | 1.7 | 1.7 |
| Sorbitol | | 1.3 | | 1.9 | | 2.1 |
| Trehalose | | 1.6 | | 2.2 | | 2.5 |
| Succinate | 1.3 | 1.5 | 3.2 | 3.2 | 6.8 | 5.7 |

As an alternate excipient, PS80 can be replaced by PS20 or poloxamer with minimal impact to stability. These results are consistent across the two studies.

Having histidine as the buffering agent was critical for Nivo stability and cannot be replaced with succinate. There was a substantial increase of HMW species with succinate buffer across all thermal stress conditions studied (5° C. 6M, 25° C. 6M, and 35° C. 3M), and this was again consistent across the two studies.

The sugar data suggest that sucrose had a superior stabilizing effect relative to sorbitol or trehalose.

As an alternate chelator to 50 μM DTPA, 100 μM EDTA was studied as was done in study 2. DTPA is a better chelating agent so a higher level of EDTA was studied here. Similarly, as an alternate sacrificial agent to 5 mM methionine, 10 mM tryptophan was studied. Since addition of a chelator and a sacrificial oxidizing agent can impact protection against oxidation these were studied under both thermal and oxidation stress conditions. The final HMW by SEC using these alternate excipients is tabulated in Table 100 for the final time point for that stress condition for both studies 2 and 3, where the difference here is study 2 had 2,000 U/mL of rHuPH20 and study 3 had no rHuPH20. The formulation composition included 120 mg/mL Nivo, 20 mM histidine, 250 mM sucrose, 0.05% w/v PS80 at pH 6.0.

Results from the two studies were comparable to each other. The exception is the condition with 0 DTPA and 0 Met—where there was a higher variability in how quickly this auto-catalytic HWM increase occurs. The tabulated % HMW values after 3 months with MPL stress clearly showed the unique benefit of having DTPA across the two studies, and that it was a superior chelator, compared to EDTA. Similarly, the data showed that Met is superior to Trp. % HMW increase was best controlled when formulated with 5 mM Met and 50 μM DTPA. These results were in agreement across the three studies.

These studies showed the unique and beneficial effect of histidine and sucrose, in combination with both Met and DTPA to Nivo stability.

In studies 2 and 3 the formulation composition ranges where stability was best maintained were as follows: pH: 5.2-6.5 His; Histidine: 15-100 mM; DTPA: 10-200 μM (Alt: 100 μM EDTA); Met: 1-20 mM (Alt: 10 mM Trp); rHuPH20: 0-5,000 U/mL; PS80: 0.01-0.1% w/v (Alt: PS20 0.05% w/v and Poloxamer 0.2 mg/mL); Sugar: 10-400 mM sucrose; Protein: 100-175 mg/mL; and Primary packaging: Vial, PFS, patch pump.

The center point formulation was: 120 mg/mL Nivo, 20 mM histidine, 250 mM sucrose, 5 mM Met, 50 μM DTPA, 0.05% w/v polysorbate 80 at pH 6.0 with 2,000 U/mL rHuPH20.

The pH range for this formulation was critical. Past a pH of 6.5, an increase in HMW was observed, and this was consistent across both studies 2 and 3. Formulating closer to pH 6 was advised based on the data.

Histidine as a buffer was critical in the formulation and had a stabilizing effect. Data from studies 2 and 3 were consistent. Succinate as a buffer did not demonstrate sufficient stability. Lower histidine concentrations led to higher HMW formation. Close to the 15 mM histidine level there was a cliff where stability decreases. In this study, up to 100 mM Histidine was studied but higher concentrations are expected to be stable.

An enzyme range between 0 to 10,000 U/mL has been studied and did not impact the stability of Nivo. This was consistent across studies 2 and 3.

PS80 levels between 0-0.1% w/v protected Nivo from HMW formation. Alternate surfactants PS20 (0.05% w/v)

TABLE 100

Study 2 and 3 - High molecular weight species by SEC for the last time point in each of the stress condition studied for alternate excipients to DTPA and Met. Composition includes: 120 mg/mL Nivo, 20 mM Histidine, 250 mM Sucrose, 0.05% w/v PS80, at pH 6.0. Study 2 conditions have 2,000 U/mL of rHuPH20, study 3 have 0 U/mL of rHuPH20.

| | % HMW by SEC | | | | | | | | | |
| Alternate | 5° C. 6 M | | 25° C. 6 M | | 35° C. 3 M | | RT30 3 M | | MPL 3 M | |
| Excipient | Study 2 | Study 3 | Study 2 | Study 3 | Study 2 | Study 3 | Study 2 | Study 3 | Study 2 | Study 3 |
|---|---|---|---|---|---|---|---|---|---|---|
| 5 mM Met 50 μm DTPA | 0.9 | 1.0? | 1.4 | 1.5 | 1.7 | 1.7 | 1.2 | 1.2 | 1.5 | 1.5 |
| 5 mM Met 50 μm DTPA | 0.9 | 1.0? | 1.4 | 1.4 | 1.8 | 1.7 | 1.3 | 1.2 | 1.6 | 1.5 |
| 10 mM Trp 50 μm DTPA | 0.9 | 0.9 | 1.4 | 1.4 | 1.8 | 1.7 | 1.2 | 1.2 | 1.9 | 1.9 |
| 5 mM Met 100 μM EDTA | 0.9 | 1.0? | 1.5 | 1.5 | 1.8 | 1.8 | 1.3 | 1.3 | 2.1 | 2 |
| 0 mM Met 0 μM DTPA | 1.0? | 1.0? | 1.7 | 2.6 | 2.1 | 3.2 | 1.3 | 1.6 | 3.7 | 4 |
| 0 mM Met 50 μM DTPA | 0.9 | 1.0? | 1.5 | 1.5 | 1.8 | 1.8 | 1.3 | 1.3 | 1.8 | 1.8 |
| 0 mM Met 50 μM DTPA | 0.9 | 1.0? | 1.5 | 1.5 | 1.8 | 1.7 | 1.3 | 1.3 | 1.8 | 1.7 |

Excipient Ranges

Similar to study 2, various excipient ranges were studied in study 3. These results were consistent and in agreement with study 2 results, as was demonstrated by the key finding in study 2 where the impact of Met concentration had beneficial effects with increased concentration. The results across all three studies are shown in FIG. 25. Study 1 only evaluated 0 and 5 mM Met values, and study 2 focused on conditions with enzyme and study 3 focused on conditions with-out enzyme. Throughout this example, it has been demonstrated that the enzyme does not impact Nivo stability, and this finding was again demonstrated here.

A regression plot with all 3 studies is shown in FIG. 26. The three studies overlayed very well with each other. The linear approximation for 0 to 5 mM Methionine effect was 0.19% HMW at the center point composition: 120 mg/mL Nivo, 20 mM Histidine, 50 μM DTPA, 250 mM Sucrose, 0.05% w/v PS80 at pH 6.0.

and poloxamer (0.2 mg/mL) demonstrated good protection for Nivo against HMW formation.

Nivo with sucrose levels between 10-400 mM demonstrated good stability. As an alternate excipient, trehalose and sorbitol showed higher HMW formation as compared to sucrose upon storage.

No impact to stability due to primary packaging was observed across the vial, PFS and patch pumps tested.

DTPA at a concentration range between 10-200 μM DTPA showed the same stability. Presence even at the low 10 μM level was sufficient to protect Nivo. No concentration dependence was observed across both studies 2 and 3.

Increased Met levels demonstrated acceptable stability within the range of 1-20 mM Met. The results were consistent across the studies (FIG. 26). For the case of Met, a statistical model was built. For the MPL stress condition, a linear regression was found to be significant for both studies 2 and 3. This showed that there was a clear benefit of having Met, and higher concentrations of Met were favorable against the MPL stress.

Particulates

Study 2 did not include particulate analysis. In study 3 particulate analysis was done for select timepoints (MPL 3M, RT30 3M, 5° C. 6M and 25° C. 6M). One sample had elevated particulate counts: a sample that had replaced histidine as a buffer with succinate-formulation 25. The HMW at 25C for 6 months showed 6527 particles/mL ≥10 μm. The remaining samples had less than 130 particles/mL ≥10 μm, well below the USP <788> particle specification limits. These data showed concerns with switching to succinate as the buffering agent, even with all other formulation components are present.

Conclusions—Study 3

In study 3 different packaging components (pre-filled syringe and patch pump) were studied in addition to the vial and confirmed to perform well with the formulation.

The study also aimed at understanding the full range where stability was best maintained. The range found (from a combination of studies 2 and 3) are as follows: pH: 5.2-6.5 His; Histidine: 15-100 mM; DTPA: 10-200 μM (Alt: 100 μM EDTA); Met: 1-20 mM (Alt: 10 mM Trp); rHuPH20: 0-5,000 U/mL; PS80: 0.01-0.1% w/v (Alt: PS20 0.05% w/v and Poloxamer 0.2 mg/mL); Sugar: 10-400 mM sucrose; Protein: 100-175 mg/mL; and Primary packaging: Vial, PFS, patch pump. These ranges were the same for samples without enzyme.

The center point formulation was: 120 mg/mL Nivo for the vial and 150 mg/mL Nivo for the PFS, both contain 20 mM histidine, 250 mM sucrose, 5 mM Met, 50 μM DTPA, 0.05% w/v polysorbate 80 at pH 6.0 with 2,000 U/mL rHuPH20.

The pH range for this formulation was critical. Past a pH of 6.5, an increase in HMW was observed. Histidine as a buffer was critical in the formulation and had a stabilizing effect. Lower histidine concentrations led to higher HMW formation. Close to the 15 mM histidine level there was a cliff where stability decreases. In this study up to 100 mM Histidine was studied but higher concentrations are expected to be stable. DTPA presence was important in maintaining Nivo stability but no concentration dependence was observed. Increase in Met demonstrated higher protection for Nivo. There was a clear benefit of having Met, and higher concentrations of Met were favorable against the MPL stress.

Succinate as a buffer did not demonstrate sufficient stability for Nivo, forming both soluble aggregates (increase in HMW by SEC) and insoluble aggregates (particles by MFI). As an alternate stabilizing agent to sucrose, trehalose and sorbitol showed higher HMW formation upon storage. EDTA was less superior to DTPA, and Tryp was less superior to Met, even at higher concentrations. These studies showed the unique and beneficial effect of histidine and sucrose, in combination with both Met and DTPA to improve Nivo stability.

Example 6—Probing Nivolumab-Excipient Interactions Using Nuclear Magnetic Resonance (NMR) Spectroscopy and Molecular Dynamics (MD)

NMR experiments and computational modeling have been performed to study Nivolumab-excipient interactions.

Both approaches confirm there to be preferential protein-sugar interactions and show a stronger binding behavior for sucrose over mannitol, trehalose, glycine, sorbitol or succinate. The results may indicate a key molecular mechanism for the role of sugars in protein formulation.

Sugars are used to stabilize protein formulations and prevent the formation of protein aggregates. The goal of this example is better understand the mechanism for stabilization, determine why some sugars work better than others, and help guide formulation selection using a combination of nuclear magnetic resonance (NMR) and molecular dynamic (MD) methods. STD (Saturation Transfer Difference) NMR experiments were adopted to measure protein-ligand interactions and binding (see Angulo J. et al., Chem. Eur. J., 16:7803-7812 (2010), which is incorporated herein by reference in its entirety).

STD NMR experiments were performed on a NEO 700 Bruker NMR spectrometer using NMR data acquisition in ICONNMR at 283 K using the pulse sequence stddiff. A recycle delay of 3-4.5 seconds was used. The NMR experiments were performed on Nivolumab samples (21.3 mg/ml concentration) with excipients glycine, mannitol, sucrose, trehalose, sorbitol, and succinate to access binding efficiency of each sugar with Nivolumab. The experiments were done at a series of excipient concentrations and fit the intensities of integrated peaks in the difference spectra to the Michaelis-Menten equation in order to assess whether the interactions between the excipient and the protein are specific or not. A specific interaction produces a saturation effect of the signal in the difference spectra.

Molecular Dynamics (MD) is an in silico approach to simulate the interactions between molecules at an atomistic level. Here, simulations were setup containing one Nivolumab Fab group, histidine buffer (15 mM equivalent) and excipient molecules (approx. 190 mM equivalent). Each excipient molecule was studied in a separate simulation. The simulation cells were setup using the MOE 2019.0101 software (Molecular Operating Environment 2019.0101; Chemical Computing Group Inc., Montreal, Canada, 2017) and the simulations were run using NAMD 2.12 (Phillips, J. C. et al., J. Comp. Chem, 26:1781-1802 (2005)).

The MD results were analyzed by first counting how many of the excipient molecules were within hydrogen bonding distance (<2A) from any atom of the Fab group. To distinguish tightly bound interaction poses of the excipients from more lightly bound ones, a clustering analysis was performed to group similar binding poses of each separate excipient and rank how frequently those poses were occupied in the simulation.

STD NMR results show that sucrose has the smallest Kd (dissociation constant) value, showing the strongest interaction to Nivolumab mAb with respect to trehalose, glycine and mannitol, sorbitol and succinate (FIG. 26).

FIG. 27 shows the average number of sugar molecules within 2 Å of the Nivolumab Fab group during the final 8 ns of the MD simulations. There is a significant difference seen between the different excipients, with the sucrose molecules interacting the most, and glycine the least. The overall trend for the number of interactions is sucrose>mannitol=trehalose>glycine. Sucrose molecules interact more than five-times more frequently than glycine, and around 50% more than mannitol, which has the next-most number of interactions. Qualitatively these results agree with the NMR results but because the STD-NMR experiments are sensitive to the strength of binding, not just the number of interactions, we further explored the strength of the interactions in the MD using a clustering analysis.

Figures 28A, 28B, 28C, 28D, 28E:

FIGS. 28A-28C show the locations of unique binding sites identified for each excipient by the clustering analysis. Visually, the difference between the excipients is clear, with far greater numbers of binding sites for mannitol (FIG. 28C), trehalose (FIG. 28E), and sucrose (FIG. 28D) than for sorbitol (FIG. 28B) and glycine (FIG. 28A), matching the trends in FIG. 27. FIGS. 29A-29B show the number of unique sites identified for each excipient, with FIG. 29A being weak-medium bound, and FIG. 29B strongly bound sites. Only sucrose, trehalose and sorbitol have strongly bound sites in the simulation, with trehalose and sorbitol having 1 such site, and sucrose 7. Further analysis of these sites has shown that in these strongly bound poses, there are 3-4 hydrogen bonds formed between the protein and excipient molecule, verifying that these poses are highly favorable and may be good candidates for the exchange sites identified by the STD-NMR results. It is of note that the strongly bound trehalose and sorbitol sites are in the constant domain of the Fab and close to the hinge region where there may be additional steric interactions that would prevent binding in the full mAb.

NMR results suggest that only sucrose strongly interacts/binds with Nivolumab in comparison to glycine, mannitol, sucrose, trehalose, sorbitol and succinate. MD results suggest that all the sugars studied interact to some extent, with preference for: sucrose>mannitol≥trehalose>glycine>sorbitol. MD Cluster analysis shows that only sucrose and trehalose have strong binding interactions that are stabilized by non-specific and specific interactions with exposed residues on the Fab. The observation of strong binding sites only for sucrose correlates the NMR observations and MD results, and therefore the differential behavior of sucrose (Kamerzell, T. J. et al., Advanced Drug Delivery Reviews, 63:1118-1159 (2011)) making it a better excipient to stabilize proteins. The larger overall number of sucrose binding sites may explain why sucrose shows the best aggregation inhibition of the molecules tested.

Example 7—Analysis of Additional Hyaluronidase Enzymes with Nivolumab

Nivolumab subcutaneous formulation includes hyaluronidase enzyme (rHuPH20). In the current study, compatibility of nivolumab and an alternate analog of rHuPH20 will be evaluated. The alternate enzyme variant will be placed on stability (e.g., at 5° C., 25° C., or 35° C.) in the current formulation composition: 120 mg/mL nivolumab in 20 mM histidine (pH 6.0), 250 mM sucrose, 0.05% polysorbate 80, 5 mM methionine, 50 µM pentetic acid and 2000 U/mL rHuPH20.

Various alternate analogs of rHuPH20 will be evaluated for combination with nivolumab subcutaneous formulation. Example alternate analoges that will be considered include, but are not limited to, enzymes having an amino acid sequence selected from the amino acid sequences set forth in SEQ ID NOs: 5-263. For example, the alternate analog of rHuPH20 having the amino acid sequence set forth in SEQ ID NO: 92 will be placed on stability in the current formulation composition: 120 mg/mL nivolumab in 20 mM histidine (pH 6.0), 250 mM sucrose, 0.05% polysorbate 80, 5 mM methionine, 50 µM pentetic acid and rHuPH20 (e.g., 2000 U/mL); wherein the rHuPH20 has the amino acid sequence set forth in SEQ ID NO: 92.

The following will be measured for each time point: pH, protein concentration, and SEC. Select samples will be tested for particulate matter (using HIAC) and enzyme activity. Sufficient sample will be kept for PS-80 analysis and analysis by CD-SDS and iCiEF, and will be tested if necessary. For each time point, 6 mL will be prepared for analysis.

A total of 22 vials will be filled with 3 mL per sample to cover the 11 time points. This will be done by preparing samples with 80 mL of formulation to account for losses during filtration using a 0.22 µM PES filter. The filtered drug product will be filled into depyrogenated 3-cc vials (Schott Type 1 glass) and stoppered with autoclaved 13-mm Daikyo stoppers (D-21-7S, Fluorotec-coated serum). Vials will be crimped and placed on stability in an upright position.

---

What is claimed is:

1. A method of treating renal cell carcinoma in a human subject in need thereof, comprising subcutaneously administering to the subject a pharmaceutical composition comprising (i) nivolumab and (ii) a hyaluronidase;

(1) wherein 1200 mg of nivolumab and 20,000 units of the hyaluronidase are administered in a single unit flat dose every four weeks; or (2) wherein 600 mg of nivolumab and 10,000 units of the hyaluronidase are administered in a single unit flat dose every two weeks.

2. The method of claim 1, wherein the hyaluronidase comprises the amino acid sequence as set forth in SEQ ID NO: 5.

3. The method of claim 1, wherein the pharmaceutical composition is administered:

(i) using a syringe, an auto-injector, or a wearable pump;

(ii) by subcutaneous infusion for less than 10 minutes; or (iii) both (i) and (ii).

4. The method of claim 1, wherein the subject has a body weight from 48 kg to 133 kg.

5. The method of claim 1, wherein the pharmaceutical composition is subcutaneously administered by infusion in a period between 3 minutes and 5 minutes.

6. The method of claim 1, wherein the pharmaceutical composition has 120 mg/ml of nivolumab.

7. The method of claim 1, wherein 1200 mg of nivolumab and 20,000 units of the hyaluronidase are administered to the subject in a single unit flat dose every four weeks.

8. The method of claim 7, wherein the hyaluronidase comprises the amino acid sequence as set forth in SEQ ID NO: 5.

9. The method of claim 7, wherein the pharmaceutical composition is administered by subcutaneous infusion for less than 10 minutes.

10. The method of claim 7, wherein the pharmaceutical composition is administered by using a syringe, an auto-injector, or a wearable pump.

11. The method of claim 7, wherein the subject has a body weight from 48 kg to 133 kg.

12. The method of claim 7, wherein the pharmaceutical composition has 120 mg/mL of nivolumab.

13. A method of treating renal cell carcinoma in a human subject in need thereof, comprising subcutaneously administering to the subject in a period between 3 minutes and 5 minutes a pharmaceutical composition comprising (i) nivolumab at 120 mg/ml and (ii) a hyaluronidase comprising the amino acid sequence as set forth in SEQ ID NO: 5; wherein 1200 mg of nivolumab and 20,000 units of the hyaluronidase are administered in a single unit flat dose once every four weeks.

14. The method of claim 1, wherein 600 mg of nivolumab and 10,000 units of the hyaluronidase are administered to the subject in a single unit flat dose every two weeks.

15. The method of claim 14, wherein the hyaluronidase comprises the amino acid sequence as set forth in SEQ ID NO: 5.

16. The method of claim 14, wherein the pharmaceutical composition is administered by subcutaneous infusion for less than 10 minutes.

17. The method of claim 14, wherein the pharmaceutical composition is administered by using, a syringe, an auto-injector, or a wearable pump.

18. The method of claim 14, wherein the subject has a body weight from 48 kg to 133 kg.

19. The method of claim 14, wherein the pharmaceutical composition has a total administered volume of 5 mL.

20. The method of claim 14, further comprising administering a chemotherapy.

21. The method of claim 20, wherein the chemotherapy comprises a platinum based chemotherapy.

22. The method of claim 20, wherein the chemotherapy comprises cabozantinib.

23. The method of claim 20, wherein the chemotherapy comprises a platinum-containing chemotherapy.

24. A method of treating renal cell carcinoma in a human subject in need thereof, comprising subcutaneously administering to the subject in a period between 3 minutes and 5 minutes a pharmaceutical composition comprising (i) nivolumab and (ii) a hyaluronidase comprising the amino acid sequence as set forth in SEQ ID NO: 5; wherein 600 mg of nivolumab and 10,000 units of the hyaluronidase are administered in a total administered volume of 5 mL in a single unit flat dose once every two weeks.

25. A method of treating renal cell carcinoma in a human subject in need thereof, comprising subcutaneously administering to the subject a pharmaceutical composition comprising (i) nivolumab and (ii) a hyaluronidase comprising the amino acid sequence as set forth in SEQ ID NO: 5; wherein 900 mg of nivolumab and 15,000 units of the hyaluronidase are administered in a single unit flat dose every three weeks.

26. The method of claim 25, further comprising administering a platinum-based therapy to the human subject.

27. The method of claim 25, further comprising administering a platinum-based doublet chemotherapy.

28. The method of claim 25, further comprising administering an anti-CTLA-4 antibody.

29. The method of claim 28, wherein the anti-CTLA-4 antibody comprises ipilimumab or tremelimumab.

30. A method of treating renal cell carcinoma in a human subject in need thereof, comprising subcutaneously administering to the subject a pharmaceutical composition comprising (i) nivolumab and (ii) a hyaluronidase; (1) wherein 1200 mg of nivolumab and 20,000 units of the hyaluronidase are administered in a single unit flat dose once every four weeks; (2) wherein 900 mg of nivolumab and 15,000 units of the hyaluronidase are administered in a single unit flat dose once every three weeks; or (3) wherein 600 mg of nivolumab and 10,000 units of the hyaluronidase are administered in a single unit flat dose once every two weeks.

* * * * *

SEQUENCE LISTING

```
Sequence total quantity: 264
SEQ ID NO: 1              moltype = AA  length = 509
FEATURE                  Location/Qualifiers
REGION                   1..509
                         note = rHuPH20
source                   1..509
                         mol_type = protein
                         organism = synthetic construct
SEQUENCE: 1
MGVLKFKHIF FRSFVKSSGV SQIVFTFLLI PCCLTLNFRA PPVIPNVPFL WAWNAPSEFC   60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDAFLK PPMETEEPQI  480
FYNASPSTLS ATMFIVSILF LIISSVASL                                    509

SEQ ID NO: 2              moltype = AA  length = 113
FEATURE                  Location/Qualifiers
REGION                   1..113
                         note = Anti-PD-1 Antibody Heavy Chain Variable Region
```

```
source                  1..113
                        mol_type = protein
                        organism = synthetic construct
SEQUENCE: 2
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS          113

SEQ ID NO: 3           moltype = AA  length = 107
FEATURE                Location/Qualifiers
REGION                 1..107
                       note = Anti-PD-1 Antibody Light Chain Variable Region
source                 1..107
                       mol_type = protein
                       organism = synthetic construct
SEQUENCE: 3
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK              107

SEQ ID NO: 4           moltype = AA  length = 509
FEATURE                Location/Qualifiers
REGION                 1..509
                       note = rHuPH20
source                 1..509
                       mol_type = protein
                       organism = synthetic construct
SEQUENCE: 4
MGVLKFKHIF FRSFVKSSGV SQIVFTFLLI PCCLTLNFRA PPVIPNVPFL WAWNAPSEFC  60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDAFLK PPMETEEPQI  480
FYNASPSTLS ATMFIVSILF LIISSVASL                                   509

SEQ ID NO: 5           moltype = AA  length = 447
FEATURE                Location/Qualifiers
REGION                 1..447
                       note = Hyaluronidase Variant
source                 1..447
                       mol_type = protein
                       organism = synthetic construct
SEQUENCE: 5
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFY                                    447

SEQ ID NO: 6           moltype = AA  length = 446
FEATURE                Location/Qualifiers
REGION                 1..446
                       note = Hyaluronidase Variant
source                 1..446
                       mol_type = protein
                       organism = synthetic construct
SEQUENCE: 6
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIF                                     446

SEQ ID NO: 7           moltype = AA  length = 445
FEATURE                Location/Qualifiers
REGION                 1..445
                       note = Hyaluronidase Variant
source                 1..445
                       mol_type = protein
                       organism = synthetic construct
```

```
SEQUENCE: 7
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTAV    420
DVCIADGVCI DAFLKPPMET EEPQI                                        445

SEQ ID NO: 8              moltype = AA   length = 444
FEATURE                   Location/Qualifiers
REGION                    1..444
                          note = Hyaluronidase Variant
source                    1..444
                          mol_type = protein
                          organism = synthetic construct
SEQUENCE: 8
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTAV    420
DVCIADGVCI DAFLKPPMET EEPQ                                         444

SEQ ID NO: 9              moltype = AA   length = 443
FEATURE                   Location/Qualifiers
REGION                    1..443
                          note = Hyaluronidase Variant
source                    1..443
                          mol_type = protein
                          organism = synthetic construct
SEQUENCE: 9
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTAV    420
DVCIADGVCI DAFLKPPMET EEP                                          443

SEQ ID NO: 10             moltype = AA   length = 442
FEATURE                   Location/Qualifiers
REGION                    1..442
                          note = Hyaluronidase Variant
source                    1..442
                          mol_type = protein
                          organism = synthetic construct
SEQUENCE: 10
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTAV    420
DVCIADGVCI DAFLKPPMET EE                                           442

SEQ ID NO: 11             moltype = AA   length = 483
FEATURE                   Location/Qualifiers
REGION                    1..483
                          note = Hyaluronidase Variant
source                    1..483
                          mol_type = protein
                          organism = synthetic construct
SEQUENCE: 11
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FYN                                                                483
```

-continued

---

```
SEQ ID NO: 12              moltype = AA   length = 432
FEATURE                    Location/Qualifiers
REGION                     1..432
                           note = Hyaluronidase Variant
source                     1..432
                           mol_type = protein
                           organism = synthetic construct
SEQUENCE: 12
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DA                                                      432

SEQ ID NO: 13              moltype = AA   length = 448
FEATURE                    Location/Qualifiers
REGION                     1..448
                           note = Hyaluronidase Variant
source                     1..448
                           mol_type = protein
                           organism = synthetic construct
SEQUENCE: 13
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYN                                     448

SEQ ID NO: 14              moltype = AA   length = 462
FEATURE                    Location/Qualifiers
REGION                     1..462
                           note = Hyaluronidase Variant
source                     1..462
                           mol_type = protein
                           organism = synthetic construct
SEQUENCE: 14
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLSATMFI VS                     462

SEQ ID NO: 15              moltype = AA   length = 460
FEATURE                    Location/Qualifiers
REGION                     1..460
                           note = Hyaluronidase Variant
source                     1..460
                           mol_type = protein
                           organism = synthetic construct
SEQUENCE: 15
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLSATMFI                        460

SEQ ID NO: 16              moltype = AA   length = 458
FEATURE                    Location/Qualifiers
REGION                     1..458
                           note = Hyaluronidase Variant
source                     1..458
                           mol_type = protein
                           organism = synthetic construct
SEQUENCE: 16
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
```

-continued

```
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLSATM                          458

SEQ ID NO: 17              moltype = AA   length = 456
FEATURE                    Location/Qualifiers
REGION                     1..456
                           note = Hyaluronidase Variant
source                     1..456
                           mol_type = protein
                           organism = synthetic construct
SEQUENCE: 17
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLSA                            456

SEQ ID NO: 18              moltype = AA   length = 461
FEATURE                    Location/Qualifiers
REGION                     1..461
                           note = Hyaluronidase Variant
source                     1..461
                           mol_type = protein
                           organism = synthetic construct
SEQUENCE: 18
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLSATMFI V                      461

SEQ ID NO: 19              moltype = AA   length = 459
FEATURE                    Location/Qualifiers
REGION                     1..459
                           note = Hyaluronidase Variant
source                     1..459
                           mol_type = protein
                           organism = synthetic construct
SEQUENCE: 19
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLSATMF                         459

SEQ ID NO: 20              moltype = AA   length = 457
FEATURE                    Location/Qualifiers
REGION                     1..457
                           note = Hyaluronidase Variant
source                     1..457
                           mol_type = protein
                           organism = synthetic construct
SEQUENCE: 20
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLSAT                           457

SEQ ID NO: 21              moltype = AA   length = 474
FEATURE                    Location/Qualifiers
REGION                     1..474
                           note = Hyaluronidase Variant
```

-continued

```
source                     1..474
                           mol_type = protein
                           organism = synthetic construct
SEQUENCE: 21
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLSATMFI VSILFLIISS VASL        474

SEQ ID NO: 22               moltype = AA   length = 474
FEATURE                     Location/Qualifiers
REGION                      1..474
                            note = Hyaluronidase Variant
source                      1..474
                            mol_type = protein
                            organism = synthetic construct
SEQUENCE: 22
LNFRAPPVIP NVPFLWAWNA PSEFCLGKFD EPLDMSLFSF IGSPRINVTG QDVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVQEA IRVSKIPDAK SPLPVFVYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EESQIFYNAS PSTLSATMFI VSILFLIISS VASL        474

SEQ ID NO: 23               moltype = AA   length = 477
FEATURE                     Location/Qualifiers
REGION                      1..477
                            note = Hyaluronidase Variant
source                      1..477
                            mol_type = protein
                            organism = synthetic construct
SEQUENCE: 23
LNFRAPPIIP NVPFLWAWNA PSEFCLGKFN EPLDMSLFTL MGSPRINITG QGVTIFYVDR  60
LGYYPYIDLT TGVTVHGGIP QKVSLQDHLD KSKQDILFYM PVDNLGMAVI DWEEWRPTWA  120
RNWKPKDVYK NRSIELVQQQ NVQLSLPQAT DKAKQEFEKA GKDFMLETIK LGRSLRPNHL  180
WGYYLFPDCY NHHYRKPGYN GSCFDVEIKR NDDLSWLWNE STALYPSIYL NTQQSVVVAT  240
LYVRNRVREA IRVSKIPDAK NPLPVFVYAR LVFTDQVLKF LSREELVSTL GETVALGASG  300
IVIWGSLSIT RSMKSCLLLD TYMETILNPY IINVTLAAKM CSQVLCQEQG VCIRKDWNSS  360
DYLHLNPDNF DIRLEKGGKF TVHGKPTVED LEEFSEKFYC SCYTNLSCKE KADVKDTDAV  420
DVCIADGVCI DASLKPPVET EGSPPIFYNT SSSTVSTTMF IWRLEVWDQG ISRIGFF     477

SEQ ID NO: 24               moltype = AA   length = 475
FEATURE                     Location/Qualifiers
REGION                      1..475
                            note = Hyaluronidase Variant
source                      1..475
                            mol_type = protein
                            organism = synthetic construct
SEQUENCE: 24
LNFRAPPIIP NVPFLWAWNA PSEFCLGKFN EPLDMSLFTL MGSPRINVTG QGVTIFYVDR  60
LGYYPYIDLT TGVTVHGGIP QKVSLQDHLD KSKQDILFYM PVDNLGMAVI DWEEWRPTWA  120
RNWKPKDVYK NRSIELVQQQ NVQLSLPQAT DKAKQEFEKA GKDFMLETIK LGRSLRPNHL  180
WGYYLFPDCY NHHYRKPGYN GSCFDVEIKR NDDLSWLWNE STALYPSIYL NTQQSVVVAT  240
LYVRNRVREA IRVSKIPDAK NPLPVFVYAR LVFTDQVLKF LSREELVSTL GETVALGASG  300
IVIWGSLSIT RSMKSCLLLD TYMETILNPY IINVTLAAKM CSQVLCQEQG VCIRKDWNSS  360
DYLHLNPDNF DIRLEKGGKF TVHGKPTVED LEEFSEKFYC SCYTNLSCKE KADVKDTDAV  420
DVCIADGVCI DASLKPPVET EGSPPIFYNT SSSTVSTTMF IVNILFLIIS SVASL       475

SEQ ID NO: 25               moltype = AA   length = 510
FEATURE                     Location/Qualifiers
REGION                      1..510
                            note = Hyaluronidase Variant
source                      1..510
                            mol_type = protein
                            organism = synthetic construct
SEQUENCE: 25
ANFRAPPVIP NVPFLWAWNA PTEFCLGKSG EPLDMSLFSL FGSPRKNKTG QGITIFYVDR  60
LGYYPYIDPH TGAIVHGRIP QLGPLQQHLT KLRQEILYYM PKDNVGLAVI DWEEWLPTWL  120
RNWKPKDIYR IKSIELVKSQ HPQYNHSYAT EKAKRDFEKA GKDFMEETLK LGRLLRPNHL  180
WGYYLFPDCY NHHYDKPNLY KGSCFDIEKK RNDDLSWLWK ESTALFPSVY LTSRARSATA  240
LSKLYVVRNR VHEAIRVSKI PDDKSPLPNF VYTRLVFTDQ IFQFLSHHDL VYTIGEIVAL  300
GASGIVVWGS QSLARSMKSC LHLDNYMKTI LNPYLINVTL AAKMCNQVLC QEQGVCTRKN  360
WNPNDYLHLN PGNFAIQLGS NGTYKVDGKP TLTDLEQFSK NFQCSCYTNL NCKERTDMNN  420
```

```
VRTVNVCAVE NVCIDTNVGP QAVTYAPKEK KDVAHILSNT TSINSSTTMS LPFPRKHVSG   480
CLLVLCMYSQ YLNICYRLVA IGIQHGYYLK                                    510

SEQ ID NO: 26          moltype = AA  length = 430
FEATURE                Location/Qualifiers
REGION                 1..430
                       note = Hyaluronidase Variant
source                 1..430
                       mol_type = protein
                       organism = synthetic construct
SEQUENCE: 26
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI                                                         430

SEQ ID NO: 27          moltype = AA  length = 431
FEATURE                Location/Qualifiers
REGION                 1..431
                       note = Hyaluronidase Variant
source                 1..431
                       mol_type = protein
                       organism = synthetic construct
SEQUENCE: 27
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI D                                                       431

SEQ ID NO: 28          moltype = AA  length = 433
FEATURE                Location/Qualifiers
REGION                 1..433
                       note = Hyaluronidase Variant
source                 1..433
                       mol_type = protein
                       organism = synthetic construct
SEQUENCE: 28
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAF                                                     433

SEQ ID NO: 29          moltype = AA  length = 434
FEATURE                Location/Qualifiers
REGION                 1..434
                       note = Hyaluronidase Variant
source                 1..434
                       mol_type = protein
                       organism = synthetic construct
SEQUENCE: 29
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFL                                                    434

SEQ ID NO: 30          moltype = AA  length = 435
FEATURE                Location/Qualifiers
REGION                 1..435
                       note = Hyaluronidase Variant
source                 1..435
                       mol_type = protein
                       organism = synthetic construct
```

```
SEQUENCE: 30
LNFRAPPVIP NVPFLWAWNA PSEFCLGKFD EPLDMSLFSF IGSPRINATG QGVTIFYVDR 60
LGYYPYIDSI TGVTVNGGIP QKISLQDHLD KAKKDITFYM PVDNLGMAVI DWEEWRPTWA 120
RNWKPKDVYK NRSIELVQQQ NVQLSLTEAT EKAKQEFEKA GKDFLVETIK LGKLLRPNHL 180
WGYYLFPDCY NHHYKKPGYN GSCFNVEIKR NDDLSWLWNE STALYPSIYL NTQQSPVAAT 240
LYVRNRVREA IRVSKIPDAK SPLPVFAYTR IVFTDQVLKF LSQDELVYTF GETVALGASG 300
IVIWGTLSIM RSMKSCLLLD NYMETILNPY IINVTLAAKM CSQVLCQEQG VCIRKNWNSS 360
DYLHLNPDNF AIQLEKGGKF TVRGKPTLED LEQFSEKFYC SCYSTLSCKE KADVKDTDAV 420
DVCIADGVCI DAFLK                                                 435

SEQ ID NO: 31           moltype = AA  length = 436
FEATURE                 Location/Qualifiers
REGION                  1..436
                        note = Hyaluronidase Variant
source                  1..436
                        mol_type = protein
                        organism = synthetic construct
SEQUENCE: 31
LNFRAPPVIP NVPFLWAWNA PSEFCLGKFD EPLDMSLFSF IGSPRINATG QGVTIFYVDR 60
LGYYPYIDSI TGVTVNGGIP QKISLQDHLD KAKKDITFYM PVDNLGMAVI DWEEWRPTWA 120
RNWKPKDVYK NRSIELVQQQ NVQLSLTEAT EKAKQEFEKA GKDFLVETIK LGKLLRPNHL 180
WGYYLFPDCY NHHYKKPGYN GSCFNVEIKR NDDLSWLWNE STALYPSIYL NTQQSPVAAT 240
LYVRNRVREA IRVSKIPDAK SPLPVFAYTR IVFTDQVLKF LSQDELVYTF GETVALGASG 300
IVIWGTLSIM RSMKSCLLLD NYMETILNPY IINVTLAAKM CSQVLCQEQG VCIRKNWNSS 360
DYLHLNPDNF AIQLEKGGKF TVRGKPTLED LEQFSEKFYC SCYSTLSCKE KADVKDTDAV 420
DVCIADGVCI DAFLKP                                                436

SEQ ID NO: 32           moltype = AA  length = 437
FEATURE                 Location/Qualifiers
REGION                  1..437
                        note = Hyaluronidase Variant
source                  1..437
                        mol_type = protein
                        organism = synthetic construct
SEQUENCE: 32
LNFRAPPVIP NVPFLWAWNA PSEFCLGKFD EPLDMSLFSF IGSPRINATG QGVTIFYVDR 60
LGYYPYIDSI TGVTVNGGIP QKISLQDHLD KAKKDITFYM PVDNLGMAVI DWEEWRPTWA 120
RNWKPKDVYK NRSIELVQQQ NVQLSLTEAT EKAKQEFEKA GKDFLVETIK LGKLLRPNHL 180
WGYYLFPDCY NHHYKKPGYN GSCFNVEIKR NDDLSWLWNE STALYPSIYL NTQQSPVAAT 240
LYVRNRVREA IRVSKIPDAK SPLPVFAYTR IVFTDQVLKF LSQDELVYTF GETVALGASG 300
IVIWGTLSIM RSMKSCLLLD NYMETILNPY IINVTLAAKM CSQVLCQEQG VCIRKNWNSS 360
DYLHLNPDNF AIQLEKGGKF TVRGKPTLED LEQFSEKFYC SCYSTLSCKE KADVKDTDAV 420
DVCIADGVCI DAFLKPP                                               437

SEQ ID NO: 33           moltype = AA  length = 438
FEATURE                 Location/Qualifiers
REGION                  1..438
                        note = Hyaluronidase Variant
source                  1..438
                        mol_type = protein
                        organism = synthetic construct
SEQUENCE: 33
LNFRAPPVIP NVPFLWAWNA PSEFCLGKFD EPLDMSLFSF IGSPRINATG QGVTIFYVDR 60
LGYYPYIDSI TGVTVNGGIP QKISLQDHLD KAKKDITFYM PVDNLGMAVI DWEEWRPTWA 120
RNWKPKDVYK NRSIELVQQQ NVQLSLTEAT EKAKQEFEKA GKDFLVETIK LGKLLRPNHL 180
WGYYLFPDCY NHHYKKPGYN GSCFNVEIKR NDDLSWLWNE STALYPSIYL NTQQSPVAAT 240
LYVRNRVREA IRVSKIPDAK SPLPVFAYTR IVFTDQVLKF LSQDELVYTF GETVALGASG 300
IVIWGTLSIM RSMKSCLLLD NYMETILNPY IINVTLAAKM CSQVLCQEQG VCIRKNWNSS 360
DYLHLNPDNF AIQLEKGGKF TVRGKPTLED LEQFSEKFYC SCYSTLSCKE KADVKDTDAV 420
DVCIADGVCI DAFLKPPM                                              438

SEQ ID NO: 34           moltype = AA  length = 439
FEATURE                 Location/Qualifiers
REGION                  1..439
                        note = Hyaluronidase Variant
source                  1..439
                        mol_type = protein
                        organism = synthetic construct
SEQUENCE: 34
LNFRAPPVIP NVPFLWAWNA PSEFCLGKFD EPLDMSLFSF IGSPRINATG QGVTIFYVDR 60
LGYYPYIDSI TGVTVNGGIP QKISLQDHLD KAKKDITFYM PVDNLGMAVI DWEEWRPTWA 120
RNWKPKDVYK NRSIELVQQQ NVQLSLTEAT EKAKQEFEKA GKDFLVETIK LGKLLRPNHL 180
WGYYLFPDCY NHHYKKPGYN GSCFNVEIKR NDDLSWLWNE STALYPSIYL NTQQSPVAAT 240
LYVRNRVREA IRVSKIPDAK SPLPVFAYTR IVFTDQVLKF LSQDELVYTF GETVALGASG 300
IVIWGTLSIM RSMKSCLLLD NYMETILNPY IINVTLAAKM CSQVLCQEQG VCIRKNWNSS 360
DYLHLNPDNF AIQLEKGGKF TVRGKPTLED LEQFSEKFYC SCYSTLSCKE KADVKDTDAV 420
DVCIADGVCI DAFLKPPME                                             439

SEQ ID NO: 35           moltype = AA  length = 440
```

```
FEATURE              Location/Qualifiers
REGION               1..440
                     note = Hyaluronidase Variant
source               1..440
                     mol_type = protein
                     organism = synthetic construct
SEQUENCE: 35
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET                                               440

SEQ ID NO: 36       moltype = AA   length = 441
FEATURE              Location/Qualifiers
REGION               1..441
                     note = Hyaluronidase Variant
source               1..441
                     mol_type = protein
                     organism = synthetic construct
SEQUENCE: 36
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET E                                             441

SEQ ID NO: 37       moltype = AA   length = 449
FEATURE              Location/Qualifiers
REGION               1..449
                     note = Hyaluronidase Variant
source               1..449
                     mol_type = protein
                     organism = synthetic construct
SEQUENCE: 37
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNA                                     449

SEQ ID NO: 38       moltype = AA   length = 450
FEATURE              Location/Qualifiers
REGION               1..450
                     note = Hyaluronidase Variant
source               1..450
                     mol_type = protein
                     organism = synthetic construct
SEQUENCE: 38
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS                                    450

SEQ ID NO: 39       moltype = AA   length = 451
FEATURE              Location/Qualifiers
REGION               1..451
                     note = Hyaluronidase Variant
source               1..451
                     mol_type = protein
                     organism = synthetic construct
SEQUENCE: 39
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
```

-continued

```
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS P                                  451

SEQ ID NO: 40           moltype = AA  length = 452
FEATURE                 Location/Qualifiers
REGION                  1..452
                        note = Hyaluronidase Variant
source                  1..452
                        mol_type = protein
                        organism = synthetic construct
SEQUENCE: 40
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PS                                 452

SEQ ID NO: 41           moltype = AA  length = 453
FEATURE                 Location/Qualifiers
REGION                  1..453
                        note = Hyaluronidase Variant
source                  1..453
                        mol_type = protein
                        organism = synthetic construct
SEQUENCE: 41
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PST                                453

SEQ ID NO: 42           moltype = AA  length = 454
FEATURE                 Location/Qualifiers
REGION                  1..454
                        note = Hyaluronidase Variant
source                  1..454
                        mol_type = protein
                        organism = synthetic construct
SEQUENCE: 42
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTL                               454

SEQ ID NO: 43           moltype = AA  length = 455
FEATURE                 Location/Qualifiers
REGION                  1..455
                        note = Hyaluronidase Variant
source                  1..455
                        mol_type = protein
                        organism = synthetic construct
SEQUENCE: 43
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLS                              455

SEQ ID NO: 44           moltype = AA  length = 463
FEATURE                 Location/Qualifiers
REGION                  1..463
                        note = Hyaluronidase Variant
```

-continued

```
source                  1..463
                        mol_type = protein
                        organism = synthetic construct
SEQUENCE: 44
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLSATMFI VSI                   463

SEQ ID NO: 45          moltype = AA  length = 464
FEATURE                Location/Qualifiers
REGION                 1..464
                       note = Hyaluronidase Variant
source                 1..464
                       mol_type = protein
                       organism = synthetic construct
SEQUENCE: 45
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLSATMFI VSIL                  464

SEQ ID NO: 46          moltype = AA  length = 465
FEATURE                Location/Qualifiers
REGION                 1..465
                       note = Hyaluronidase Variant
source                 1..465
                       mol_type = protein
                       organism = synthetic construct
SEQUENCE: 46
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLSATMFI VSILF                 465

SEQ ID NO: 47          moltype = AA  length = 474
FEATURE                Location/Qualifiers
REGION                 1..474
                       note = Hyaluronidase Variant
source                 1..474
                       mol_type = protein
                       organism = synthetic construct
SEQUENCE: 47
LNFRAPPVIP NVAFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLSATMFI VSIWFLIISS VASL       474

SEQ ID NO: 48          moltype = AA  length = 474
FEATURE                Location/Qualifiers
REGION                 1..474
                       note = Hyaluronidase Variant
source                 1..474
                       mol_type = protein
                       organism = synthetic construct
SEQUENCE: 48
LNFRAPPVIP NAPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
```

```
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLSATMFI VSILFLIISS VASL          474

SEQ ID NO: 49           moltype = AA  length = 474
FEATURE                 Location/Qualifiers
REGION                  1..474
                        note = Hyaluronidase Variant
source                  1..474
                        mol_type = protein
                        organism = synthetic construct
SEQUENCE: 49
LNFRAPPVIP NVPFLWAWNA PSEFCLGKFD EPLDMSLFSL TGSPRINVTG QGVTIFYVDR    60
LGYYPYIDSI TGVTVNGGIP QKISLQDHLD KAKQDITFYM PVDNLGMAVI DWEEWRPTWA    120
RNWKPKDVYK NRSIELVQQQ NVQLSLAEAT EKAKQEFEKA GKDFMVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFVYAR IVFTDQVLKF LSRDELVYTL GETVALGASG    300
IVIWGSLSIV RSMKSCLLLD NYMETILNPY IINVTLAAKM CSQVLCQEQG VCIRKDWNSS    360
DYLHLNPDNF AIQLEKGGKF TVRGKPTPED LEQFSEKFYC SCYSTLSCKE KADVKDTDAV    420
DVCIADGVCI DAFLKPPKET EESQIFYNAS PSTLSATMFI VSILFLIISS VVSL          474

SEQ ID NO: 50           moltype = AA  length = 474
FEATURE                 Location/Qualifiers
REGION                  1..474
                        note = Hyaluronidase Variant
source                  1..474
                        mol_type = protein
                        organism = synthetic construct
SEQUENCE: 50
LNFRAPPIIP NVPFLWAWNA PSEFCLGKFD EPLDMSLFSL IGSPRINVTG QGVTIFYVDR    60
LGYYPYIDPT TGAVVNGGIP QKIALQDHLD KVRKDIIFYM PVDNLGMGVI DWEEWRPTWA    120
RNWKPKDIYK NKSIEMVQQR NVQLNLTQAT DIAKQEFEKA AKDFMLETIK LGKALRPNHL    180
WGYYLFPDCY NHHYKKPDYN GSCFNIEIKR NNDLSWLWNE STALYPSIYL NTQQSAVAAM    240
LYVRNRVQEA IRVSKTPNAN SPLPVFVYAR LVFTDQVLKF LVFTDQVLTL GETVALGASG    300
IVIWGSLSIM RSMKSCLLLD TYMETVLNPY IINTTLAAKM CSQVLCQEQG VCIRKDWNSS    360
DYLHLNPDNF AIETEKGGKF TVRGKPTYED LEQFSEKFYC SCYTSLSCKV KADVKDTDAV    420
DVCIADGVCI DASLKPPKET EESSQIFYNP SSSTPSAAIF IVAILFFISC VVSL          474

SEQ ID NO: 51           moltype = AA  length = 476
FEATURE                 Location/Qualifiers
REGION                  1..476
                        note = Hyaluronidase Variant
source                  1..476
                        mol_type = protein
                        organism = synthetic construct
SEQUENCE: 51
LNFRAPPIIP NMPFLWAWNA PSEFCLGKFD EPLDMSLFSL IGSPRINVTG QAVTIFYVDR    60
LGYYPYIDSI TGVTVNGGIP QKISLQDHLD KAKKDILFYM PVDNLGMAVI DWEEWRPTWA    120
RNWKPKDVYK NRSIELVQQQ NVQLNLTEAT EKAKQEFEKA GKDFMVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFVYAR IVFTDQVLKF LSQDELVYTF GETVALGASG    300
IVIWGSLSIM RSMKSCLLLD NYMETILNPY IINVTLAAKM CSQVLCQEQG VCIRKDWNSS    360
DYLHLNPDNF AIQLEKGGKF TVRGKPTLED LEQFSEKFYC SCYSTLSCKE KADVKDTDAV    420
DVCIADGVCI DAFLKPPMET EESQIFYNAS PSTLSATMFI WRLEVWDQGI SRMGFF        476

SEQ ID NO: 52           moltype = AA  length = 474
FEATURE                 Location/Qualifiers
REGION                  1..474
                        note = Hyaluronidase Variant
source                  1..474
                        mol_type = protein
                        organism = synthetic construct
SEQUENCE: 52
LNFRAPPVIP NVPFLWAWNA PSEFCLGKFD EPLDTSLFSF IGSPRINVTG QDVTIFYVDR    60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYARNRVQEA IRVSKIPDAK SPLPVFVYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVYI DAFLKPPMET EESQIFYNAS PSTLSATMFI VSILFLIISS VASL          474

SEQ ID NO: 53           moltype = AA  length = 455
FEATURE                 Location/Qualifiers
REGION                  1..455
                        note = Hyaluronidase Variant
source                  1..455
                        mol_type = protein
                        organism = synthetic construct
```

```
SEQUENCE: 53
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIT RTKESCQAIK EYMDTTLGPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLS                            455

SEQ ID NO: 54             moltype = AA  length = 455
FEATURE                   Location/Qualifiers
REGION                    1..455
                          note = Hyaluronidase Variant
source                    1..455
                          mol_type = protein
                          organism = synthetic construct
SEQUENCE: 54
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIT RTKESCQAIK EYMDTTLNPF ILNVTSGALL CSQALCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLS                            455

SEQ ID NO: 55             moltype = AA  length = 455
FEATURE                   Location/Qualifiers
REGION                    1..455
                          note = Hyaluronidase Variant
source                    1..455
                          mol_type = protein
                          organism = synthetic construct
SEQUENCE: 55
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIT RTKESCQAIK EYMDTTLGPF ILNVTSGALL CSQALCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLS                            455

SEQ ID NO: 56             moltype = AA  length = 455
FEATURE                   Location/Qualifiers
REGION                    1..455
                          note = Hyaluronidase Variant
source                    1..455
                          mol_type = protein
                          organism = synthetic construct
SEQUENCE: 56
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWVSWENT RTKESCQAIK EYMDTTLGPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLS                            455

SEQ ID NO: 57             moltype = AA  length = 455
FEATURE                   Location/Qualifiers
REGION                    1..455
                          note = Hyaluronidase Variant
source                    1..455
                          mol_type = protein
                          organism = synthetic construct
SEQUENCE: 57
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLS                            455

SEQ ID NO: 58             moltype = AA  length = 455
```

```
FEATURE            Location/Qualifiers
REGION             1..455
                   note = Hyaluronidase Variant
source             1..455
                   mol_type = protein
                   organism = synthetic construct
SEQUENCE: 58
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWVSWENT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLS                            455

SEQ ID NO: 59          moltype = AA  length = 455
FEATURE            Location/Qualifiers
REGION             1..455
                   note = Hyaluronidase Variant
source             1..455
                   mol_type = protein
                   organism = synthetic construct
SEQUENCE: 59
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSNT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLS                            455

SEQ ID NO: 60          moltype = AA  length = 455
FEATURE            Location/Qualifiers
REGION             1..455
                   note = Hyaluronidase Variant
source             1..455
                   mol_type = protein
                   organism = synthetic construct
SEQUENCE: 60
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLENT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLS                            455

SEQ ID NO: 61          moltype = AA  length = 455
FEATURE            Location/Qualifiers
REGION             1..455
                   note = Hyaluronidase Variant
source             1..455
                   mol_type = protein
                   organism = synthetic construct
SEQUENCE: 61
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTWENT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV   420
DVCIADGVCI DAFLKPPMET EEPQIFYNAS PSTLS                            455

SEQ ID NO: 62          moltype = AA  length = 455
FEATURE            Location/Qualifiers
REGION             1..455
                   note = Hyaluronidase Variant
source             1..455
                   mol_type = protein
                   organism = synthetic construct
SEQUENCE: 62
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
```

```
LYVRNRVREA IRVSKIPDAK SPLPVFAYTR IVFTDQVLKF LSQDELVYTF GETVALGASG   300
IVIWGTLSIT RTKESCQAIK EYMDTTLNPF ILNVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLS                              455

SEQ ID NO: 63             moltype = AA  length = 455
FEATURE                   Location/Qualifiers
REGION                    1..455
                          note = Hyaluronidase Variant
source                    1..455
                          mol_type = protein
                          organism = synthetic construct
SEQUENCE: 63
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIT RTKESCQAIK EYMDTTLNPF ILNVTSGAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLS                              455

SEQ ID NO: 64             moltype = AA  length = 453
FEATURE                   Location/Qualifiers
REGION                    1..453
                          note = Hyaluronidase Variant
source                    1..453
                          mol_type = protein
                          organism = synthetic construct
SEQUENCE: 64
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGTLSITRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA FLKPPMETEE PQIFYNASPS TLS                                453

SEQ ID NO: 65             moltype = AA  length = 430
FEATURE                   Location/Qualifiers
REGION                    1..430
                          note = Hyaluronidase Variant
source                    1..430
                          mol_type = protein
                          organism = synthetic construct
SEQUENCE: 65
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIT RTKESCQAIK EYMDTTLNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI                                                          430

SEQ ID NO: 66             moltype = AA  length = 433
FEATURE                   Location/Qualifiers
REGION                    1..433
                          note = Hyaluronidase Variant
source                    1..433
                          mol_type = protein
                          organism = synthetic construct
SEQUENCE: 66
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIT RTKESCQAIK EYMDTTLNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAF                                                      433

SEQ ID NO: 67             moltype = AA  length = 436
FEATURE                   Location/Qualifiers
REGION                    1..436
                          note = Hyaluronidase Variant
```

-continued

```
source                    1..436
                          mol_type = protein
                          organism = synthetic construct
SEQUENCE: 67
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKP                                                  436

SEQ ID NO: 68              moltype = AA   length = 452
FEATURE                    Location/Qualifiers
REGION                     1..452
                           note = Hyaluronidase Variant
source                     1..452
                           mol_type = protein
                           organism = synthetic construct
SEQUENCE: 68
FRGPLLPNRP FLWAWNAPSE FCLGKFDEPL DMSLFSFIGS PRINATGQGV TIFYVDRLGY  60
YPYIDSITGV TVNGGIPQKI SLQDHLDKAK KDITFYMPVD NLGMAVIDWE EWRPTWARNW  120
KPKDVYKNRS IELVQQQNVQ LSLTEATEKA KQEFEKAGKD FLVETIKLGK LLRPNHLWGY  180
YLFPDCYNHH YKKPGYNGSC FNVEIKRNDD LSWLWNESTA LYPSIYLNTQ QSPVAATLYV  240
RNRVREAIRV SKIPDAKSPL PVFAYTRIVF TDQVLKFLSQ DELVYTFGET VALGASGIVI  300
WGTLSITRTK ESCQAIKEYM DTTLNPYIIN VTLAAKMCSQ VLCQEQGVCI RKNWNSSDYL  360
HLNPDNFAIQ LEKGGKFTVR GKPTLEDLEQ FSEKFYCSCY STLSCKEKAD VKDTDAVDVC  420
IADGVCIDAF LKPPMETEEP QIFYNASPST LS                                452

SEQ ID NO: 69              moltype = AA   length = 452
FEATURE                    Location/Qualifiers
REGION                     1..452
                           note = Hyaluronidase Variant
source                     1..452
                           mol_type = protein
                           organism = synthetic construct
SEQUENCE: 69
FRGPLLPNRP FTTVWNAPSE FCLGKFDEPL DMSLFSFIGS PRINATGQGV TIFYVDRLGY  60
YPYIDSITGV TVNGGIPQKI SLQDHLDKAK KDITFYMPVD NLGMAVIDWE EWRPTWARNW  120
KPKDVYKNRS IELVQQQNVQ LSLTEATEKA KQEFEKAGKD FLVETIKLGK LLRPNHLWGY  180
YLFPDCYNHH YKKPGYNGSC FNVEIKRNDD LSWLWNESTA LYPSIYLNTQ QSPVAATLYV  240
RNRVREAIRV SKIPDAKSPL PVFAYTRIVF TDQVLKFLSQ DELVYTFGET VALGASGIVI  300
WGTLSITRTK ESCQAIKEYM DTTLNPYIIN VTLAAKMCSQ VLCQEQGVCI RKNWNSSDYL  360
HLNPDNFAIQ LEKGGKFTVR GKPTLEDLEQ FSEKFYCSCY STLSCKEKAD VKDTDAVDVC  420
IADGVCIDAF LKPPMETEEP QIFYNASPST LS                                452

SEQ ID NO: 70              moltype = AA   length = 433
FEATURE                    Location/Qualifiers
REGION                     1..433
                           note = Hyaluronidase Variant
source                     1..433
                           mol_type = protein
                           organism = synthetic construct
SEQUENCE: 70
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLK                                                     433

SEQ ID NO: 71              moltype = AA   length = 431
FEATURE                    Location/Qualifiers
REGION                     1..431
                           note = Hyaluronidase Variant
source                     1..431
                           mol_type = protein
                           organism = synthetic construct
SEQUENCE: 71
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
```

-continued

```
IWGTWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 72            moltype = AA   length = 455
FEATURE                  Location/Qualifiers
REGION                   1..455
                         note = Hyaluronidase Variant
source                   1..455
                         mol_type = protein
                         organism = synthetic construct
SEQUENCE: 72
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGSWENT RTKESCQAIK EYMDTTLNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYNAS PSTLS                              455

SEQ ID NO: 73            moltype = AA   length = 451
FEATURE                  Location/Qualifiers
REGION                   1..451
                         note = Hyaluronidase Variant
source                   1..451
                         mol_type = protein
                         organism = synthetic construct
SEQUENCE: 73
APPVIPNVPF LWAWNAPSEF CLGKFDEPLD MSLFSFIGSP RINATGQGVT IFYVDRLGYY   60
PYIDSITGVT VNGGIPQKIS LQDHLDKAKK DITFYMPVDN LGMAVIDWEE WRPTWARNWK   120
PKDVYKNRSI ELVQQQNVQL SLTEATEKAK QEFEKAGKDF LVETIKLGKL LRPNHLWGYY   180
LFPDCYNHHY KKPGYNGSCF NVEIKRNDDL SWLWNESTAL YPSIYLNTQQ SPVAATLYVR   240
NRVREAIRVS KIPDAKSPLP VFAYTRIVFT DQVLKFLSQD ELVYTFGETV ALGASGIVIW   300
GTLSITRTKE SCQAIKEYMD TTLNPYIINV TLAAKMCSQV LCQEQGVCIR KNWNSSDYLH   360
LNPDNFAIQL EKGGKFTVRG KPTLEDLEQF SEKFYCSCYS TLSCKEKADV KDTDAVDVCI   420
ADGVCIDAFL KPPMETEEPQ IFYNASPSTL S                                  451

SEQ ID NO: 74            moltype = AA   length = 449
FEATURE                  Location/Qualifiers
REGION                   1..449
                         note = Hyaluronidase Variant
source                   1..449
                         mol_type = protein
                         organism = synthetic construct
SEQUENCE: 74
PVIPNVPFLW AWNAPSEFCL GKFDEPLDMS LFSFIGSPRI NATGQGVTIF YVDRLGYYPY   60
IDSITGVTVN GGIPQKISLQ DHLDKAKKDI TFYMPVDNLG MAVIDWEEWR PTWARNWKPK   120
DVYKNRSIEL VQQQNVQLSL TEATEKAKQE FEKAGKDFLV ETIKLGKLLR PNHLWGYYLF   180
PDCYNHHYKK PGYNGSCFNV EIKRNDDLSW LWNESTALYP SIYLNTQQSP VAATLYVRNR   240
VREAIRVSKI PDAKSPLPVF AYTRIVFTDQ VLKFLSQDEL VYTFGETVAL GASGIVIWGT   300
LSITRTKESC QAIKEYMDTT LNPYIINVTL AAKMCSQVLC QEQGVCIRKN WNSSDYLHLN   360
PDNFAIQLEK GGKFTVRGKP TLEDLEQFSE KFYCSCYSTL SCKEKADVKD TDAVDVCIAD   420
GVCIDAFLKP PMETEEPQIF YNASPSTLS                                     449

SEQ ID NO: 75            moltype = AA   length = 432
FEATURE                  Location/Qualifiers
REGION                   1..432
                         note = Hyaluronidase Variant
source                   1..432
                         mol_type = protein
                         organism = synthetic construct
SEQUENCE: 75
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTWENT RTKESCQAIK EYMDTTLNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DA                                                       432

SEQ ID NO: 76            moltype = AA   length = 429
FEATURE                  Location/Qualifiers
REGION                   1..429
                         note = Hyaluronidase Variant
source                   1..429
                         mol_type = protein
                         organism = synthetic construct
```

```
SEQUENCE: 76
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTWENT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV  420
DVCIADGVC                                                           429

SEQ ID NO: 77          moltype = AA  length = 426
FEATURE                Location/Qualifiers
REGION                 1..426
                       note = Hyaluronidase Variant
source                 1..426
                       mol_type = protein
                       organism = synthetic construct
SEQUENCE: 77
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTWENT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV  420
DVCIAD                                                              426

SEQ ID NO: 78          moltype = AA  length = 423
FEATURE                Location/Qualifiers
REGION                 1..423
                       note = Hyaluronidase Variant
source                 1..423
                       mol_type = protein
                       organism = synthetic construct
SEQUENCE: 78
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTWENT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV  420
DVC                                                                 423

SEQ ID NO: 79          moltype = AA  length = 420
FEATURE                Location/Qualifiers
REGION                 1..420
                       note = Hyaluronidase Variant
source                 1..420
                       mol_type = protein
                       organism = synthetic construct
SEQUENCE: 79
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTWENT RTKESCQAIK EYMDTTLNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTAV  420

SEQ ID NO: 80          moltype = AA  length = 433
FEATURE                Location/Qualifiers
REGION                 1..433
                       note = Hyaluronidase Variant
source                 1..433
                       mol_type = protein
                       organism = synthetic construct
SEQUENCE: 80
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTAVDV  420
CIADGVCIDA FLK                                                       433

SEQ ID NO: 81          moltype = AA  length = 435
FEATURE                Location/Qualifiers
```

```
REGION                   1..435
                         note = Hyaluronidase Variant
source                   1..435
                         mol_type = protein
                         organism = synthetic construct
SEQUENCE: 81
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPP                                                  435

SEQ ID NO: 82            moltype = AA  length = 436
FEATURE                  Location/Qualifiers
REGION                   1..436
                         note = Hyaluronidase Variant
source                   1..436
                         mol_type = protein
                         organism = synthetic construct
SEQUENCE: 82
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPM                                                 436

SEQ ID NO: 83            moltype = AA  length = 437
FEATURE                  Location/Qualifiers
REGION                   1..437
                         note = Hyaluronidase Variant
source                   1..437
                         mol_type = protein
                         organism = synthetic construct
SEQUENCE: 83
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPME                                                437

SEQ ID NO: 84            moltype = AA  length = 438
FEATURE                  Location/Qualifiers
REGION                   1..438
                         note = Hyaluronidase Variant
source                   1..438
                         mol_type = protein
                         organism = synthetic construct
SEQUENCE: 84
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPMET                                               438

SEQ ID NO: 85            moltype = AA  length = 439
FEATURE                  Location/Qualifiers
REGION                   1..439
                         note = Hyaluronidase Variant
source                   1..439
                         mol_type = protein
                         organism = synthetic construct
SEQUENCE: 85
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
```

```
IWGTWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA FLKPPMETE                                                439

SEQ ID NO: 86           moltype = AA  length = 454
FEATURE                 Location/Qualifiers
REGION                  1..454
                        note = Hyaluronidase Variant
source                  1..454
                        mol_type = protein
                        organism = synthetic construct
SEQUENCE: 86
NFRAPPVIPN VPFLWAWNAP SEFCLGKFDE PLDMSLFSFI GSPRINATGQ GVTIFYVDRL   60
GYYPYIDSIT GVTVNGGIPQ KISLQDHLDK AKKDITFYMP VDNLGMAVID WEEWRPTWAR   120
NWKPKDVYKN RSIELVQQQN VQLSLTEATE KAKQEFEKAG KDFLVETIKL GKLLRPNHLW   180
GYYLFPDCYN HHYKKPGYNG SCFNVEIKRN DDLSWLWNES TALYPSIYLN TQQSPVAATL   240
YVRNRVREAI RVSKIPDAKS PLPVFAYTRI VFTDQVLKFL SQDELVYTFG ETVALGASGI   300
VIWGTLSITR TKESCQAIKE YMDTTLNPYI INVTLAAKMC SQVLCQEQGV CIRKNWNSSD   360
YLHLNPDNFA IQLEKGGKFT VRGKPTLEDL EQFSEKFYCS CYSTLSCKEK ADVKDTDAVD   420
VCIADGVCID AFLKPPMETE EPQIFYNASP STLS                              454

SEQ ID NO: 87           moltype = AA  length = 452
FEATURE                 Location/Qualifiers
REGION                  1..452
                        note = Hyaluronidase Variant
source                  1..452
                        mol_type = protein
                        organism = synthetic construct
SEQUENCE: 87
RAPPVIPNVP FLWAWNAPSE FCLGKFDEPL DMSLFSFIGS PRINATGQGV TIFYVDRLGY   60
YPYIDSITGV TVNGGIPQKI SLQDHLDKAK KDITFYMPVD NLGMAVIDWE EWRPTWARNW   120
KPKDVYKNRS IELVQQQNVQ LSLTEATEKA KQEFEKAGKD FLVETIKLGK LLRPNHLWGY   180
YLFPDCYNHH YKKPGYNGSC FNVEIKRNDD LSWLWNESTA LYPSIYLNTQ QSPVAATLYV   240
RNRVREAIRV SKIPDAKSPL PVFAYTRIVF TDQVLKFLSQ DELVYTFGET VALGASGIVI   300
WGTLSITRTK ESCQAIKEYM DTTLNPYIIN VTLAAKMCSQ VLCQEQGVCI RKNWNSSDYL   360
HLNPDNFAIQ LEKGGKFTVR GKPTLEDLEQ FSEKFYCSCY STLSCKEKAD VKDTDAVDVC   420
IADGVCIDAF LKPPMETEEP QIFYNASPST LS                                452

SEQ ID NO: 88           moltype = AA  length = 450
FEATURE                 Location/Qualifiers
REGION                  1..450
                        note = Hyaluronidase Variant
source                  1..450
                        mol_type = protein
                        organism = synthetic construct
SEQUENCE: 88
PPVIPNVPFL WAWNAPSEFC LGKFDEPLDM SLFSFIGSPR INATGQGVTI FYVDRLGYYP   60
YIDSITGVTV NGGIPQKISL QDHLDKAKKD ITFYMPVDNL GMAVIDWEEW RPTWARNWKP   120
KDVYKNRSIE LVQQQNVQLS LTEATEKAKQ EFEKAGKDFL VETIKLGKLL RPNHLWGYYL   180
FPDCYNHHYK PGYNGSCFN  VEIKRNDDLS WLWNESTALY PSIYLNTQQS PVAATLYVRN   240
RVREAIRVSK IPDAKSPLPV FAYTRIVFTD QVLKFLSQDE LVYTFGETVA LGASGIVIWG   300
TLSITRTKES CQAIKEYMDT TLNPYIINVT LAAKMCSQVL CQEQGVCIRK NWNSSDYLHL   360
NPDNFAIQLE KGGKFTVRGK PTLEDLEQFS EKFYCSCYST LSCKEKADVK DTDAVDVCIA   420
DGVCIDAFLK PPMETEEPQI FYNASPSTLS                                   450

SEQ ID NO: 89           moltype = AA  length = 428
FEATURE                 Location/Qualifiers
REGION                  1..428
                        note = Hyaluronidase Variant
source                  1..428
                        mol_type = protein
                        organism = synthetic construct
SEQUENCE: 89
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCI                                                           428

SEQ ID NO: 90           moltype = AA  length = 429
FEATURE                 Location/Qualifiers
REGION                  1..429
                        note = Hyaluronidase Variant
source                  1..429
                        mol_type = protein
                        organism = synthetic construct
```

```
SEQUENCE: 90
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCID                                                          429

SEQ ID NO: 91          moltype = AA  length = 430
FEATURE                Location/Qualifiers
REGION                 1..430
                       note = Hyaluronidase Variant
source                 1..430
                       mol_type = protein
                       organism = synthetic construct
SEQUENCE: 91
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA                                                         430

SEQ ID NO: 92          moltype = AA  length = 431
FEATURE                Location/Qualifiers
REGION                 1..431
                       note = Hyaluronidase Variant
source                 1..431
                       mol_type = protein
                       organism = synthetic construct
SEQUENCE: 92
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 93          moltype = AA  length = 441
FEATURE                Location/Qualifiers
REGION                 1..441
                       note = Hyaluronidase Variant
source                 1..441
                       mol_type = protein
                       organism = synthetic construct
SEQUENCE: 93
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPMETEE P                                            441

SEQ ID NO: 94          moltype = AA  length = 443
FEATURE                Location/Qualifiers
REGION                 1..443
                       note = Hyaluronidase Variant
source                 1..443
                       mol_type = protein
                       organism = synthetic construct
SEQUENCE: 94
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPMETEE PQI                                          443

SEQ ID NO: 95          moltype = AA  length = 445
```

-continued

```
FEATURE              Location/Qualifiers
REGION               1..445
                     note = Hyaluronidase Variant
source               1..445
                     mol_type = protein
                     organism = synthetic construct
SEQUENCE: 95
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPMETEE PQIFY                                        445

SEQ ID NO: 96          moltype = AA  length = 447
FEATURE              Location/Qualifiers
REGION               1..447
                     note = Hyaluronidase Variant
source               1..447
                     mol_type = protein
                     organism = synthetic construct
SEQUENCE: 96
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPMETEE PQIFYNA                                      447

SEQ ID NO: 97          moltype = AA  length = 449
FEATURE              Location/Qualifiers
REGION               1..449
                     note = Hyaluronidase Variant
source               1..449
                     mol_type = protein
                     organism = synthetic construct
SEQUENCE: 97
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPMETEE PQIFYNASP                                    449

SEQ ID NO: 98          moltype = AA  length = 451
FEATURE              Location/Qualifiers
REGION               1..451
                     note = Hyaluronidase Variant
source               1..451
                     mol_type = protein
                     organism = synthetic construct
SEQUENCE: 98
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGTWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA FLKPPMETEE PQIFYNASPS T                                 451

SEQ ID NO: 99          moltype = AA  length = 455
FEATURE              Location/Qualifiers
REGION               1..455
                     note = Hyaluronidase Variant
source               1..455
                     mol_type = protein
                     organism = synthetic construct
SEQUENCE: 99
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
```

```
LYVRNRVREA IRVSKIPDAK SPLPVFAYTR IVFTDQVLKF LSQDELVYTF GETVALGASG    300
IVIWGGWENT RTKESCQAIK EYMDTTLNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLS                               455

SEQ ID NO: 100               moltype = AA  length = 455
FEATURE                      Location/Qualifiers
REGION                       1..455
                             note = Hyaluronidase Variant
source                       1..455
                             mol_type = protein
                             organism = synthetic construct
SEQUENCE: 100
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGAWENT RTKESCQAIK EYMDTTLNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLS                               455

SEQ ID NO: 101               moltype = AA  length = 455
FEATURE                      Location/Qualifiers
REGION                       1..455
                             note = Hyaluronidase Variant
source                       1..455
                             mol_type = protein
                             organism = synthetic construct
SEQUENCE: 101
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGCWENT RTKESCQAIK EYMDTTLNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLS                               455

SEQ ID NO: 102               moltype = AA  length = 455
FEATURE                      Location/Qualifiers
REGION                       1..455
                             note = Hyaluronidase Variant
source                       1..455
                             mol_type = protein
                             organism = synthetic construct
SEQUENCE: 102
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGDWENT RTKESCQAIK EYMDTTLNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFYNAS PSTLS                               455

SEQ ID NO: 103               moltype = AA  length = 431
FEATURE                      Location/Qualifiers
REGION                       1..431
                             note = Hyaluronidase Variant
source                       1..431
                             mol_type = protein
                             organism = synthetic construct
SEQUENCE: 103
FRAPPVIPNV PFLWAWNAPS EFCLGKFDEP LDMSLFSFIG SPRINATGQG VTIFYVDRLG     60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGTLSNTRT KESCQAIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                         431

SEQ ID NO: 104               moltype = AA  length = 431
FEATURE                      Location/Qualifiers
REGION                       1..431
                             note = Hyaluronidase Variant
```

```
source                          1..431
                                mol_type = protein
                                organism = synthetic construct
SEQUENCE: 104
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGTLENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 105              moltype = AA   length = 431
FEATURE                     Location/Qualifiers
REGION                      1..431
                            note = Hyaluronidase Variant
source                      1..431
                            mol_type = protein
                            organism = synthetic construct
SEQUENCE: 105
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGAWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 106              moltype = AA   length = 431
FEATURE                     Location/Qualifiers
REGION                      1..431
                            note = Hyaluronidase Variant
source                      1..431
                            mol_type = protein
                            organism = synthetic construct
SEQUENCE: 106
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGGWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 107              moltype = AA   length = 431
FEATURE                     Location/Qualifiers
REGION                      1..431
                            note = Hyaluronidase Variant
source                      1..431
                            mol_type = protein
                            organism = synthetic construct
SEQUENCE: 107
FRGPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 108              moltype = AA   length = 400
FEATURE                     Location/Qualifiers
REGION                      1..400
                            note = Hyaluronidase Variant
source                      1..400
                            mol_type = protein
                            organism = synthetic construct
SEQUENCE: 108
FRGPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC                         400
```

```
SEQ ID NO: 109           moltype = AA  length = 482
FEATURE                  Location/Qualifiers
REGION                   1..482
                         note = Hyaluronidase Variant
source                   1..482
                         mol_type = protein
                         organism = synthetic construct
SEQUENCE: 109
FRAPPVIPNV PFLWAWNAPS EFCLGKFDEP LDMSLFSFIG SPRINATGQG VTIFYVDRLG     60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGTWENTRT KESCQAIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA FLKPPMETEE PQIFYNASPS TYSTLSCKEK ADVKDTDAVD VCIADGVCID    480
AF                                                                   482

SEQ ID NO: 110           moltype = AA  length = 455
FEATURE                  Location/Qualifiers
REGION                   1..455
                         note = Hyaluronidase Variant
source                   1..455
                         mol_type = protein
                         organism = synthetic construct
SEQUENCE: 110
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIT TSTETCQYLK DYLTRLLNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTAV    420
DVCIADGVCI DAFLKPPMET EEPQIFYNAS PSTLS                               455

SEQ ID NO: 111           moltype = AA  length = 455
FEATURE                  Location/Qualifiers
REGION                   1..455
                         note = Hyaluronidase Variant
source                   1..455
                         mol_type = protein
                         organism = synthetic construct
SEQUENCE: 111
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIS SSEEECWHLH DYLVDTLNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTAV    420
DVCIADGVCI DAFLKPPMET EEPQIFYNAS PSTLS                               455

SEQ ID NO: 112           moltype = AA  length = 455
FEATURE                  Location/Qualifiers
REGION                   1..455
                         note = Hyaluronidase Variant
source                   1..455
                         mol_type = protein
                         organism = synthetic construct
SEQUENCE: 112
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIT ASKANCTKVK QFVSSDLNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTAV    420
DVCIADGVCI DAFLKPPMET EEPQIFYNAS PSTLS                               455

SEQ ID NO: 113           moltype = AA  length = 431
FEATURE                  Location/Qualifiers
REGION                   1..431
                         note = Hyaluronidase Variant
source                   1..431
                         mol_type = protein
                         organism = synthetic construct
```

```
SEQUENCE: 113
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTMT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 114          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 114
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRQ KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 115          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 115
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT QESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 116          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 116
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KEQCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 117          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 117
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIQEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 118          moltype = AA  length = 431
```

```
FEATURE            Location/Qualifiers
REGION             1..431
                   note = Hyaluronidase Variant
source             1..431
                   mol_type = protein
                   organism = synthetic construct
SEQUENCE: 118
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY VDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 119        moltype = AA  length = 431
FEATURE            Location/Qualifiers
REGION             1..431
                   note = Hyaluronidase Variant
source             1..431
                   mol_type = protein
                   organism = synthetic construct
SEQUENCE: 119
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTANPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 120        moltype = AA  length = 431
FEATURE            Location/Qualifiers
REGION             1..431
                   note = Hyaluronidase Variant
source             1..431
                   mol_type = protein
                   organism = synthetic construct
SEQUENCE: 120
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWVNTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 121        moltype = AA  length = 431
FEATURE            Location/Qualifiers
REGION             1..431
                   note = Hyaluronidase Variant
source             1..431
                   mol_type = protein
                   organism = synthetic construct
SEQUENCE: 121
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWEFTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 122        moltype = AA  length = 431
FEATURE            Location/Qualifiers
REGION             1..431
                   note = Hyaluronidase Variant
source             1..431
                   mol_type = protein
                   organism = synthetic construct
SEQUENCE: 122
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
```

-continued

```
VRNRVREAIR VSKIPDAKSP LPVFAYTRIV FTDQVLKFLS QDELVYTFGE TVALGASGIV    300
IWGSWENTRT KESCQAIKEY MKTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                        431

SEQ ID NO: 123          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 123
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGSWENTRT KESCQAIKEY MDYTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                        431

SEQ ID NO: 124          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 124
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGSWENTRT KESCQAIKEY MDTMLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                        431

SEQ ID NO: 125          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 125
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGSWENTRT KESCEAIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                        431

SEQ ID NO: 126          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 126
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGSWENTRT KESCQAIKEY MDTTLMPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                        431

SEQ ID NO: 127          moltype = AA  length = 431
FEATURE                 Location/Qualifiers
REGION                  1..431
                        note = Hyaluronidase Variant
```

-continued

```
source                   1..431
                         mol_type = protein
                         organism = synthetic construct
SEQUENCE: 127
FRAPPVIPNV PFLWAWNAPS EFCLGKFDEP LDMSLFSFIG SPRINANGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 128          moltype = AA   length = 431
FEATURE                 Location/Qualifiers
REGION                  1..431
                        note = Hyaluronidase Variant
source                  1..431
                        mol_type = protein
                        organism = synthetic construct
SEQUENCE: 128
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKKR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 129          moltype = AA   length = 431
FEATURE                 Location/Qualifiers
REGION                  1..431
                        note = Hyaluronidase Variant
source                  1..431
                        mol_type = protein
                        organism = synthetic construct
SEQUENCE: 129
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAEKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 130          moltype = AA   length = 431
FEATURE                 Location/Qualifiers
REGION                  1..431
                        note = Hyaluronidase Variant
source                  1..431
                        mol_type = protein
                        organism = synthetic construct
SEQUENCE: 130
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAQKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 131          moltype = AA   length = 431
FEATURE                 Location/Qualifiers
REGION                  1..431
                        note = Hyaluronidase Variant
source                  1..431
                        mol_type = protein
                        organism = synthetic construct
SEQUENCE: 131
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
```

-continued

```
IWGSWENTRT KESCQASKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 132              moltype = AA  length = 431
FEATURE                     Location/Qualifiers
REGION                      1..431
                            note = Hyaluronidase Variant
source                      1..431
                            mol_type = protein
                            organism = synthetic construct
SEQUENCE: 132
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAVKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 133              moltype = AA  length = 431
FEATURE                     Location/Qualifiers
REGION                      1..431
                            note = Hyaluronidase Variant
source                      1..431
                            mol_type = protein
                            organism = synthetic construct
SEQUENCE: 133
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAAKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 134              moltype = AA  length = 431
FEATURE                     Location/Qualifiers
REGION                      1..431
                            note = Hyaluronidase Variant
source                      1..431
                            mol_type = protein
                            organism = synthetic construct
SEQUENCE: 134
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQANKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 135              moltype = AA  length = 431
FEATURE                     Location/Qualifiers
REGION                      1..431
                            note = Hyaluronidase Variant
source                      1..431
                            mol_type = protein
                            organism = synthetic construct
SEQUENCE: 135
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQATKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 136              moltype = AA  length = 431
FEATURE                     Location/Qualifiers
REGION                      1..431
                            note = Hyaluronidase Variant
source                      1..431
                            mol_type = protein
                            organism = synthetic construct
```

-continued

```
SEQUENCE: 136
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKMY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                     431

SEQ ID NO: 137         moltype = AA  length = 431
FEATURE                Location/Qualifiers
REGION                 1..431
                       note = Hyaluronidase Variant
source                 1..431
                       mol_type = protein
                       organism = synthetic construct
SEQUENCE: 137
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKFY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                     431

SEQ ID NO: 138         moltype = AA  length = 431
FEATURE                Location/Qualifiers
REGION                 1..431
                       note = Hyaluronidase Variant
source                 1..431
                       mol_type = protein
                       organism = synthetic construct
SEQUENCE: 138
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKIY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                     431

SEQ ID NO: 139         moltype = AA  length = 431
FEATURE                Location/Qualifiers
REGION                 1..431
                       note = Hyaluronidase Variant
source                 1..431
                       mol_type = protein
                       organism = synthetic construct
SEQUENCE: 139
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKLY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                     431

SEQ ID NO: 140         moltype = AA  length = 431
FEATURE                Location/Qualifiers
REGION                 1..431
                       note = Hyaluronidase Variant
source                 1..431
                       mol_type = protein
                       organism = synthetic construct
SEQUENCE: 140
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKQY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                     431

SEQ ID NO: 141         moltype = AA  length = 431
```

-continued

```
FEATURE              Location/Qualifiers
REGION               1..431
                     note = Hyaluronidase Variant
source               1..431
                     mol_type = protein
                     organism = synthetic construct
SEQUENCE: 141
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKVY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 142         moltype = AA  length = 431
FEATURE              Location/Qualifiers
REGION               1..431
                     note = Hyaluronidase Variant
source               1..431
                     mol_type = protein
                     organism = synthetic construct
SEQUENCE: 142
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKKR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWVNTRT KESCQAIKEY MDTMLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 143         moltype = AA  length = 431
FEATURE              Location/Qualifiers
REGION               1..431
                     note = Hyaluronidase Variant
source               1..431
                     mol_type = protein
                     organism = synthetic construct
SEQUENCE: 143
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWQSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 144         moltype = AA  length = 431
FEATURE              Location/Qualifiers
REGION               1..431
                     note = Hyaluronidase Variant
source               1..431
                     mol_type = protein
                     organism = synthetic construct
SEQUENCE: 144
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGHWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 145         moltype = AA  length = 431
FEATURE              Location/Qualifiers
REGION               1..431
                     note = Hyaluronidase Variant
source               1..431
                     mol_type = protein
                     organism = synthetic construct
SEQUENCE: 145
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
```

```
VRNRVREAIR VSKIPDAKSP LPVFAYTRIV FTDQVLKFLS QDELVYTFGE TVALGASGIV   300
IWGSIENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                      431

SEQ ID NO: 146          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 146
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWYNTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                      431

SEQ ID NO: 147          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 147
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENERT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                      431

SEQ ID NO: 148          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 148
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTFT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                      431

SEQ ID NO: 149          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 149
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRE KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                      431

SEQ ID NO: 150          moltype = AA  length = 431
FEATURE                 Location/Qualifiers
REGION                  1..431
                        note = Hyaluronidase Variant
```

-continued

```
source                    1..431
                          mol_type = protein
                          organism = synthetic construct
SEQUENCE: 150
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KLSCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 151          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 151
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KEICQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 152          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 152
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCGAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 153          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 153
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQARKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 154          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 154
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
```

```
IWGSWENTRT KESCQAIKEY RDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 155           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 155
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MVTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 156           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 156
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDRTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 157           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 157
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENKRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 158           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 158
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTLT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 159           moltype = AA  length = 431
FEATURE                  Location/Qualifiers
REGION                   1..431
                         note = Hyaluronidase Variant
source                   1..431
                         mol_type = protein
                         organism = synthetic construct
```

```
SEQUENCE: 159
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRV KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 160          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 160
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KWSCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 161          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 161
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAWKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 162          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 162
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MYTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 163          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 163
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRW KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 164          moltype = AA  length = 431
```

-continued

```
FEATURE              Location/Qualifiers
REGION               1..431
                     note = Hyaluronidase Variant
source               1..431
                     mol_type = protein
                     organism = synthetic construct
SEQUENCE: 164
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEW MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 165       moltype = AA   length = 431
FEATURE              Location/Qualifiers
REGION               1..431
                     note = Hyaluronidase Variant
source               1..431
                     mol_type = protein
                     organism = synthetic construct
SEQUENCE: 165
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSDENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 166       moltype = AA   length = 431
FEATURE              Location/Qualifiers
REGION               1..431
                     note = Hyaluronidase Variant
source               1..431
                     mol_type = protein
                     organism = synthetic construct
SEQUENCE: 166
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWQNTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 167       moltype = AA   length = 431
FEATURE              Location/Qualifiers
REGION               1..431
                     note = Hyaluronidase Variant
source               1..431
                     mol_type = protein
                     organism = synthetic construct
SEQUENCE: 167
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRH KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 168       moltype = AA   length = 431
FEATURE              Location/Qualifiers
REGION               1..431
                     note = Hyaluronidase Variant
source               1..431
                     mol_type = protein
                     organism = synthetic construct
SEQUENCE: 168
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
```

-continued

```
VRNRVREAIR VSKIPDAKSP LPVFAYTRIV FTDQVLKFLS QDELVYTFGE TVALGASGIV    300
IWGSWENTRT FESCQAIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                         431

SEQ ID NO: 169            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 169
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGSWENTRT KEDCQAIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                         431

SEQ ID NO: 170            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 170
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGSWENTRT KESCYAIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                         431

SEQ ID NO: 171            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 171
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGSWENTRT KESCQEIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                         431

SEQ ID NO: 172            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 172
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN    120
WKPKDVYKNR SIELVQQQNV QLSLTEATEK AKQEFEKAGK DFLVETIKLG KLLRPNHLWG    180
YYLFPDCYNH HYKKPGYNGS CFNVEIKRND DLSWLWNEST ALYPSIYLNT QQSPVAATLY    240
VRNRVREAIR VSKIPDAKSP LPVFAYTRIV FTDQVLKFLS QDELVYTFGE TVALGASGIV    300
IWGSWENTRT KESCQAIKEY YDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                         431

SEQ ID NO: 173            moltype = AA   length = 431
FEATURE                   Location/Qualifiers
REGION                    1..431
                          note = Hyaluronidase Variant
```

```
source                  1..431
                        mol_type = protein
                        organism = synthetic construct
SEQUENCE: 173
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MQTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 174          moltype = AA   length = 431
FEATURE                 Location/Qualifiers
REGION                  1..431
                        note = Hyaluronidase Variant
source                  1..431
                        mol_type = protein
                        organism = synthetic construct
SEQUENCE: 174
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDLTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 175          moltype = AA   length = 431
FEATURE                 Location/Qualifiers
REGION                  1..431
                        note = Hyaluronidase Variant
source                  1..431
                        mol_type = protein
                        organism = synthetic construct
SEQUENCE: 175
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTELNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 176          moltype = AA   length = 431
FEATURE                 Location/Qualifiers
REGION                  1..431
                        note = Hyaluronidase Variant
source                  1..431
                        mol_type = protein
                        organism = synthetic construct
SEQUENCE: 176
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLEPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 177          moltype = AA   length = 431
FEATURE                 Location/Qualifiers
REGION                  1..431
                        note = Hyaluronidase Variant
source                  1..431
                        mol_type = protein
                        organism = synthetic construct
SEQUENCE: 177
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
```

```
IWGSHENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 178           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 178
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT DESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 179           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 179
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTHLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 180           moltype = AA  length = 430
FEATURE                  Location/Qualifiers
REGION                   1..430
                         note = Hyaluronidase Variant
source                   1..430
                         mol_type = protein
                         organism = synthetic construct
SEQUENCE: 180
RAPPVIPNVP FLWAWNAPSE FCLGKFDEPL DMSLFSFIGS PRINATGQGV TIFYVDRLGY  60
YPYIDSITGV TVNGGIPQKI SLQDHLDKAK KDITFYMPVD NLGMAVIDWE EWRPTWARNW  120
KPKDVYKNRS IELVQQQNVQ LSLTEATEKA KQEFEKAGKD FLVETIKLGK LLRPNHLWGY  180
YLFPDCYNHH YKKPGYNGSC FNVEIKRNDD LSWLWNESTA LYPSIYLNTQ QSPVAATLYV  240
RNRVREAIRV SKIPDAKSPL PVFAYTRIVF TDQVLKFLSQ DELVYTFGET VALGASGIVI  300
WGSWENTRTK ESCQAIKEYM DTTLNPYIIN VTLAAKMCSQ VLCQEQGVCI RKNWNSSDYL  360
HLNPDNFAIQ LEKGGKFTVR GKPTLEDLEQ FSEKFYCSCY STLSCKEKAD VKDTDAVDVC  420
IADGVCIDAF                                                         430

SEQ ID NO: 181           moltype = AA  length = 429
FEATURE                  Location/Qualifiers
REGION                   1..429
                         note = Hyaluronidase Variant
source                   1..429
                         mol_type = protein
                         organism = synthetic construct
SEQUENCE: 181
APPVIPNVPF LWAWNAPSEF CLGKFDEPLD MSLFSFIGSP RINATGQGVT IFYVDRLGYY  60
PYIDSITGVT VNGGIPQKIS LQDHLDKAKK DITFYMPVDN LGMAVIDWEE WRPTWARNWK  120
PKDVYKNRSI ELVQQQNVQL SLTEATEKAK QEFEKAGKDF LVETIKLGKL LRPNHLWGYY  180
LFPDCYNHHY KKPGYNGSCF NVEIKRNDDL SWLWNESTAL YPSIYLNTQQ SPVAATLYVR  240
NRVREAIRVS KIPDAKSPLP VFAYTRIVFT DQVLKFLSQD ELVYTFGETV ALGASGIVIW  300
GSWENTRTKE SCQAIKEYMD TTLNPYIINV TLAAKMCSQV LCQEQGVCIR KNWNSSDYLH  360
LNPDNFAIQL EKGGKFTVRG KPTLEDLEQF SEKFYCSCYS TLSCKEKADV KDTDAVDVCI  420
ADGVCIDAF                                                          429

SEQ ID NO: 182           moltype = AA  length = 419
FEATURE                  Location/Qualifiers
REGION                   1..419
                         note = Hyaluronidase Variant
source                   1..419
                         mol_type = protein
                         organism = synthetic construct
```

```
SEQUENCE: 182
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVD   419

SEQ ID NO: 183           moltype = AA  length = 430
FEATURE                  Location/Qualifiers
REGION                   1..430
                         note = Hyaluronidase Variant
source                   1..430
                         mol_type = protein
                         organism = synthetic construct
SEQUENCE: 183
RAPPVIPNVP FLWAWNAPSE FCLGKFDEPL DMSLFSFIGS PRINATGQGV TIFYVDRLGY   60
YPYIDSITGV TVNGGIPQKI SLQDHLDKAK KDITFYMPVD NLGMAVIDWE EWRPTWARNW  120
KPKDVYKNRS IELVQQQNVQ LSLTEATEKA KQEFEKAGKD FLVETIKLGK LLRPNHLWGY  180
YLFPDCYNHH YKKPGYNGSC FNVEIKRNDD LSWLWNESTA LYPSIYLNTQ QSPVAATLYV  240
RNRVREAIRV SKIPDAKSPL PVFAYTRIVF TDQVLKFLSQ DELVYTFGET VALGASGIVI  300
WGSWENTRTK EQCQAIKEYM DRTLNPYIIN VTLAAKMCSQ VLCQEQGVCI RKNWNSSDYL  360
HLNPDNFAIQ LEKGGKFTVR GKPTLEDLEQ FSEKFYCSCY STLSCKEKAD VKDTDAVDVC  420
IADGVCIDAF                                                         430

SEQ ID NO: 184           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 184
FRAPPVIPNV PFLWAWNAPS EFCLGKFAEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 185           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 185
FRAPPVIPNV PFLWAWNAPS EFCLGKFDAP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 186           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 186
FRAPPVIPNV PFLWAWNAPS EFCLGKFDEA LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 187           moltype = AA  length = 431
FEATURE                  Location/Qualifiers
```

-continued

```
REGION                   1..431
                         note = Hyaluronidase Variant
source                   1..431
                         mol_type = protein
                         organism = synthetic construct
SEQUENCE: 187
FRAPPVIPNV PFLWAWNAPS EFCLGKFDEP ADMSLFSFIG SPRINATGQG VTIFYVDRLG      60
YYPYIDSITG VTVNGGIPQK ISLQDHLDKA KKDITFYMPV DNLGMAVIDW EEWRPTWARN     120
WKPKDVYKNR SIELVQQQNV QLSLTEATEK AKQEFEKAGK DFLVETIKLG KLLRPNHLWG     180
YYLFPDCYNH HYKKPGYNGS CFNVEIKRND DLSWLWNEST ALYPSIYLNT QQSPVAATLY     240
VRNRVREAIR VSKIPDAKSP LPVFAYTRIV FTDQVLKFLS QDELVYTFGE TVALGASGIV     300
IWGSWENTRT KESCQAIKEY MDTTLNPYII NVTLAAKMCS QVLCQEQGVC IRKNWNSSDY     360
LHLNPDNFAI QLEKGGKFTV RGKPTLEDLE QFSEKFYCSC YSTLSCKEKA DVKDTDAVDV     420
CIADGVCIDA F                                                         431

SEQ ID NO: 188          moltype = AA   length = 431
FEATURE                 Location/Qualifiers
REGION                   1..431
                         note = Hyaluronidase Variant
source                   1..431
                         mol_type = protein
                         organism = synthetic construct
SEQUENCE: 188
FRAPPVIPNV PFLWAWNAPS EFCLGKFDEP LDMSLFSFIG SPRINATGQG VTIFYVDRLG      60
YYPYIDSITG VTVNGGIPQK ISLQDHLDKA KKDITFYMPV DNLGMAVIDW EEWRPTWARN     120
WKPKDVYKNR SIELVQQQNV QLSLTEATEK AKQEFEKAGK DFLVETIKLG KLLRPNHLWG     180
YYLFPDCYNH HYKKPGYNGS CFNVEIKRND DLSWLWNEST ALYPSIYLNT QQSPVAATLY     240
VRNRVREAIR VSKIPDAKSP LPVFAYTRIV FTDAVLKFLS QDELVYTFGE TVALGASGIV     300
IWGSWENTRT KESCQAIKEY MDTTLNPYII NVTLAAKMCS QVLCQEQGVC IRKNWNSSDY     360
LHLNPDNFAI QLEKGGKFTV RGKPTLEDLE QFSEKFYCSC YSTLSCKEKA DVKDTDAVDV     420
CIADGVCIDA F                                                         431

SEQ ID NO: 189          moltype = AA   length = 431
FEATURE                 Location/Qualifiers
REGION                   1..431
                         note = Hyaluronidase Variant
source                   1..431
                         mol_type = protein
                         organism = synthetic construct
SEQUENCE: 189
FRAPPVIPNV PFLWAWNAPS EFCLGKFDEP LDMSLFSFIG SPRINATGQG VTIFYVDRLG      60
YYPYIDSITG VTVNGGIPQK ISLQDHLDKA KKDITFYMPV DNLGMAVIDW EEWRPTWARN     120
WKPKDVYKNR SIELVQQQNV QLSLTEATEK AKQEFEKAGK DFLVETIKLG KLLRPNHLWG     180
YYLFPDCYNH HYKKPGYNGS CFNVEIKRND DLSWLWNEST ALYPSIYLNT QQSPVAATLY     240
VRNRVREAIR VSKIPDAKSP LPVFAYTRIV FTDQALKFLS QDELVYTFGE TVALGASGIV     300
IWGSWENTRT KESCQAIKEY MDTTLNPYII NVTLAAKMCS QVLCQEQGVC IRKNWNSSDY     360
LHLNPDNFAI QLEKGGKFTV RGKPTLEDLE QFSEKFYCSC YSTLSCKEKA DVKDTDAVDV     420
CIADGVCIDA F                                                         431

SEQ ID NO: 190          moltype = AA   length = 431
FEATURE                 Location/Qualifiers
REGION                   1..431
                         note = Hyaluronidase Variant
source                   1..431
                         mol_type = protein
                         organism = synthetic construct
SEQUENCE: 190
FRAPPVIPNV PFLWAWNAPS EFCLGKFDEP LDMSLFSFIG SPRINATGQG VTIFYVDRLG      60
YYPYIDSITG VTVNGGIPQK ISLQDHLDKA KKDITFYMPV DNLGMAVIDW EEWRPTWARN     120
WKPKDVYKNR SIELVQQQNV QLSLTEATEK AKQEFEKAGK DFLVETIKLG KLLRPNHLWG     180
YYLFPDCYNH HYKKPGYNGS CFNVEIKRND DLSWLWNEST ALYPSIYLNT QQSPVAATLY     240
VRNRVREAIR VSKIPDAKSP LPVFAYTRIV FTDQVAKFLS QDELVYTFGE TVALGASGIV     300
IWGSWENTRT KESCQAIKEY MDTTLNPYII NVTLAAKMCS QVLCQEQGVC IRKNWNSSDY     360
LHLNPDNFAI QLEKGGKFTV RGKPTLEDLE QFSEKFYCSC YSTLSCKEKA DVKDTDAVDV     420
CIADGVCIDA F                                                         431

SEQ ID NO: 191          moltype = AA   length = 431
FEATURE                 Location/Qualifiers
REGION                   1..431
                         note = Hyaluronidase Variant
source                   1..431
                         mol_type = protein
                         organism = synthetic construct
SEQUENCE: 191
FRAPPVIPNV PFLWAWNAPS EFCLGKFDEP LDMSLFSFIG SPRINATGQG VTIFYVDRLG      60
YYPYIDSITG VTVNGGIPQK ISLQDHLDKA KKDITFYMPV DNLGMAVIDW EEWRPTWARN     120
WKPKDVYKNR SIELVQQQNV QLSLTEATEK AKQEFEKAGK DFLVETIKLG KLLRPNHLWG     180
YYLFPDCYNH HYKKPGYNGS CFNVEIKRND DLSWLWNEST ALYPSIYLNT QQSPVAATLY     240
VRNRVREAIR VSKIPDAKSP LPVFAYTRIV FTDQVLAFLS QDELVYTFGE TVALGASGIV     300
```

-continued

```
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 192            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 192
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLAT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 193            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 193
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNA QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 194            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 194
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT AQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 195            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 195
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QASPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 196            moltype = AA   length = 431
FEATURE                   Location/Qualifiers
REGION                    1..431
                          note = Hyaluronidase Variant
source                    1..431
                          mol_type = protein
                          organism = synthetic construct
```

```
SEQUENCE: 196
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSAVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 197           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 197
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPAAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 198           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 198
FRAPPVIPNV PFLWAWNAPS EFCLGKFDEP LDMSLFSFIG SPRINATGQG VTIFYVDRLG  60
YYPYADSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 199           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 199
FRAPPVIPNV PFLWAWNAPS EFCLGKFDEP LDMSLFSFIG SPRINATGQG VTIFYVDRLG  60
YYPYIASITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 200           moltype = AA  length = 431
FEATURE                  Location/Qualifiers
REGION                   1..431
                         note = Hyaluronidase Variant
source                   1..431
                         mol_type = protein
                         organism = synthetic construct
SEQUENCE: 200
FRAPPVIPNV PFLWAWNAPS EFCLGKFDEP LDMSLFSFIG SPRINATGQG VTIFYVDRLG  60
YYPYIDAITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 201           moltype = AA  length = 431
```

-continued

```
FEATURE            Location/Qualifiers
REGION             1..431
                   note = Hyaluronidase Variant
source             1..431
                   mol_type = protein
                   organism = synthetic construct
SEQUENCE: 201
FRAPPVIPNV PFLWAWNAPS EFCLGKFDEP LDMSLFSFIG SPRINATGQG VTIFYVDRLG   60
YYPYIDSATG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 202         moltype = AA   length = 431
FEATURE            Location/Qualifiers
REGION             1..431
                   note = Hyaluronidase Variant
source             1..431
                   mol_type = protein
                   organism = synthetic construct
SEQUENCE: 202
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDIAFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 203         moltype = AA   length = 431
FEATURE            Location/Qualifiers
REGION             1..431
                   note = Hyaluronidase Variant
source             1..431
                   mol_type = protein
                   organism = synthetic construct
SEQUENCE: 203
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITAYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 204         moltype = AA   length = 431
FEATURE            Location/Qualifiers
REGION             1..431
                   note = Hyaluronidase Variant
source             1..431
                   mol_type = protein
                   organism = synthetic construct
SEQUENCE: 204
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFAMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 205         moltype = AA   length = 431
FEATURE            Location/Qualifiers
REGION             1..431
                   note = Hyaluronidase Variant
source             1..431
                   mol_type = protein
                   organism = synthetic construct
SEQUENCE: 205
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNAEIKRND DLSWLWNEST ALYPSIYLNT QQSPVAATLY  240
```

```
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 206              moltype = AA   length = 431
FEATURE                    Location/Qualifiers
REGION                     1..431
                           note = Hyaluronidase Variant
source                     1..431
                           mol_type = protein
                           organism = synthetic construct
SEQUENCE: 206
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVAIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 207              moltype = AA   length = 431
FEATURE                    Location/Qualifiers
REGION                     1..431
                           note = Hyaluronidase Variant
source                     1..431
                           mol_type = protein
                           organism = synthetic construct
SEQUENCE: 207
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEAKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 208              moltype = AA   length = 431
FEATURE                    Location/Qualifiers
REGION                     1..431
                           note = Hyaluronidase Variant
source                     1..431
                           mol_type = protein
                           organism = synthetic construct
SEQUENCE: 208
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIARND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 209              moltype = AA   length = 431
FEATURE                    Location/Qualifiers
REGION                     1..431
                           note = Hyaluronidase Variant
source                     1..431
                           mol_type = protein
                           organism = synthetic construct
SEQUENCE: 209
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QASLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                       431

SEQ ID NO: 210              moltype = AA   length = 431
FEATURE                    Location/Qualifiers
REGION                     1..431
                           note = Hyaluronidase Variant
```

```
source                    1..431
                          mol_type = protein
                          organism = synthetic construct
SEQUENCE: 210
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLALTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 211            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 211
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSATEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 212            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 212
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLAEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 213            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 213
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEAAEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 214            moltype = AA   length = 431
FEATURE                   Location/Qualifiers
REGION                    1..431
                          note = Hyaluronidase Variant
source                    1..431
                          mol_type = protein
                          organism = synthetic construct
SEQUENCE: 214
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATAK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
```

-continued

```
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 215           moltype = AA   length = 431
FEATURE                  Location/Qualifiers
REGION                   1..431
                         note = Hyaluronidase Variant
source                   1..431
                         mol_type = protein
                         organism = synthetic construct
SEQUENCE: 215
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEA AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 216           moltype = AA   length = 431
FEATURE                  Location/Qualifiers
REGION                   1..431
                         note = Hyaluronidase Variant
source                   1..431
                         mol_type = protein
                         organism = synthetic construct
SEQUENCE: 216
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSAIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 217           moltype = AA   length = 431
FEATURE                  Location/Qualifiers
REGION                   1..431
                         note = Hyaluronidase Variant
source                   1..431
                         mol_type = protein
                         organism = synthetic construct
SEQUENCE: 217
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKAPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 218           moltype = AA   length = 431
FEATURE                  Location/Qualifiers
REGION                   1..431
                         note = Hyaluronidase Variant
source                   1..431
                         mol_type = protein
                         organism = synthetic construct
SEQUENCE: 218
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIADAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 219           moltype = AA   length = 431
FEATURE                  Location/Qualifiers
REGION                   1..431
                         note = Hyaluronidase Variant
source                   1..431
                         mol_type = protein
                         organism = synthetic construct
```

```
SEQUENCE: 219
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTASCKEKA DVKDTDAVDV   420
CIADGVCIDA F                                                        431

SEQ ID NO: 220          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 220
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLACKEKA DVKDTDAVDV   420
CIADGVCIDA F                                                        431

SEQ ID NO: 221          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 221
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKATDAVDV   420
CIADGVCIDA F                                                        431

SEQ ID NO: 222          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 222
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDADAVDV   420
CIADGVCIDA F                                                        431

SEQ ID NO: 223          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 223
FRAPPVIPNV PFLWAWNAPS EFCLGKFDEP LDMSLFSFIG SPRINATGQG VTIFYVDRLG    60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTAAVDV   420
CIADGVCIDA F                                                        431

SEQ ID NO: 224          moltype = AA  length = 431
```

```
FEATURE              Location/Qualifiers
REGION               1..431
                     note = Hyaluronidase Variant
source               1..431
                     mol_type = protein
                     organism = synthetic construct
SEQUENCE: 224
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIAAGVCIDA F                                                      431

SEQ ID NO: 225         moltype = AA  length = 431
FEATURE              Location/Qualifiers
REGION               1..431
                     note = Hyaluronidase Variant
source               1..431
                     mol_type = protein
                     organism = synthetic construct
SEQUENCE: 225
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADAVCIDA F                                                      431

SEQ ID NO: 226         moltype = AA  length = 431
FEATURE              Location/Qualifiers
REGION               1..431
                     note = Hyaluronidase Variant
source               1..431
                     mol_type = protein
                     organism = synthetic construct
SEQUENCE: 226
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGACIDA F                                                      431

SEQ ID NO: 227         moltype = AA  length = 431
FEATURE              Location/Qualifiers
REGION               1..431
                     note = Hyaluronidase Variant
source               1..431
                     mol_type = protein
                     organism = synthetic construct
SEQUENCE: 227
FRAPPVIPNV PFLWAWNAPS EFCLGKFDEP LDMSLFSFIG SPRIAATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 228         moltype = AA  length = 431
FEATURE              Location/Qualifiers
REGION               1..431
                     note = Hyaluronidase Variant
source               1..431
                     mol_type = protein
                     organism = synthetic construct
SEQUENCE: 228
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKAR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
```

```
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 229            moltype = AA  length = 431
FEATURE                   Location/Qualifiers
REGION                    1..431
                          note = Hyaluronidase Variant
source                    1..431
                          mol_type = protein
                          organism = synthetic construct
SEQUENCE: 229
FRAPPVIPNV PFLWAWNAPS EFCLGKFDEP LDMSLFSFIG SPRINATGQG VTIFYVDRLG   60
YYPYIDNITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 230            moltype = AA  length = 431
FEATURE                   Location/Qualifiers
REGION                    1..431
                          note = Hyaluronidase Variant
source                    1..431
                          mol_type = protein
                          organism = synthetic construct
SEQUENCE: 230
FRAPPVIPNV PFLWAWNAPS EFCLGKFDEP LDMSLFSFIG SPRINATGQG VTIFYVDRLG   60
YYPYIDSQTG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT QQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 231            moltype = AA  length = 431
FEATURE                   Location/Qualifiers
REGION                    1..431
                          note = Hyaluronidase Variant
source                    1..431
                          mol_type = protein
                          organism = synthetic construct
SEQUENCE: 231
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT DQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 232            moltype = AA  length = 431
FEATURE                   Location/Qualifiers
REGION                    1..431
                          note = Hyaluronidase Variant
source                    1..431
                          mol_type = protein
                          organism = synthetic construct
SEQUENCE: 232
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN   120
WKPKDVYKNR SIELVQQQNV QLSLTEATEK AKQEFEKAGK DFLVETIKLG KLLRPNHLWG   180
YYLFPDCYNH HYKKPGYNGS CFNVEIKRND DLSWLWNEST ALYPSIYLNT IQSPVAATLY   240
VRNRVREAIR VSKIPDAKSP LPVFAYTRIV FTDQVLKFLS QDELVYTFGE TVALGASGIV   300
IWGSWENTRT KESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDTDAVDV   420
CIADGVCIDA F                                                        431

SEQ ID NO: 233            moltype = AA  length = 431
FEATURE                   Location/Qualifiers
REGION                    1..431
                          note = Hyaluronidase Variant
```

-continued

```
source                  1..431
                        mol_type = protein
                        organism = synthetic construct
SEQUENCE: 233
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKGPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 234          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 234
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIDDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 235          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 235
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDDDAVDV  420
CIADGVCIDA F                                                      431

SEQ ID NO: 236          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 236
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDHDAVDV  420
CIADGVCIDA F                                                      431

SEQ ID NO: 237          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 237
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
```

```
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDKDAVDV  420
CIADGVCIDA F                                                      431

SEQ ID NO: 238            moltype = AA  length = 431
FEATURE                   Location/Qualifiers
REGION                    1..431
                          note = Hyaluronidase Variant
source                    1..431
                          mol_type = protein
                          organism = synthetic construct
SEQUENCE: 238
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDGDAVDV  420
CIADGVCIDA F                                                      431

SEQ ID NO: 239            moltype = AA  length = 431
FEATURE                   Location/Qualifiers
REGION                    1..431
                          note = Hyaluronidase Variant
source                    1..431
                          mol_type = protein
                          organism = synthetic construct
SEQUENCE: 239
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDPDAVDV  420
CIADGVCIDA F                                                      431

SEQ ID NO: 240            moltype = AA  length = 431
FEATURE                   Location/Qualifiers
REGION                    1..431
                          note = Hyaluronidase Variant
source                    1..431
                          mol_type = protein
                          organism = synthetic construct
SEQUENCE: 240
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDMDAVDV  420
CIADGVCIDA F                                                      431

SEQ ID NO: 241            moltype = AA  length = 431
FEATURE                   Location/Qualifiers
REGION                    1..431
                          note = Hyaluronidase Variant
source                    1..431
                          mol_type = protein
                          organism = synthetic construct
SEQUENCE: 241
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDFDAVDV  420
CIADGVCIDA F                                                      431

SEQ ID NO: 242            moltype = AA  length = 431
FEATURE                   Location/Qualifiers
REGION                    1..431
                          note = Hyaluronidase Variant
source                    1..431
                          mol_type = protein
                          organism = synthetic construct
```

```
SEQUENCE: 242
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIARGVCIDA F                                                       431

SEQ ID NO: 243          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 243
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGYCIDA F                                                       431

SEQ ID NO: 244          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 244
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLTLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 245          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 245
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKSTDAVDV  420
CIADGVCIDA F                                                       431

SEQ ID NO: 246          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 246
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVPKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 247          moltype = AA  length = 431
```

-continued

```
FEATURE          Location/Qualifiers
REGION           1..431
                 note = Hyaluronidase Variant
source           1..431
                 mol_type = protein
                 organism = synthetic construct
SEQUENCE: 247
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVMKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 248          moltype = AA   length = 431
FEATURE          Location/Qualifiers
REGION           1..431
                 note = Hyaluronidase Variant
source           1..431
                 mol_type = protein
                 organism = synthetic construct
SEQUENCE: 248
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QSSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 249          moltype = AA   length = 431
FEATURE          Location/Qualifiers
REGION           1..431
                 note = Hyaluronidase Variant
source           1..431
                 mol_type = protein
                 organism = synthetic construct
SEQUENCE: 249
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QISLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 250          moltype = AA   length = 431
FEATURE          Location/Qualifiers
REGION           1..431
                 note = Hyaluronidase Variant
source           1..431
                 mol_type = protein
                 organism = synthetic construct
SEQUENCE: 250
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QFSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                       431

SEQ ID NO: 251          moltype = AA   length = 431
FEATURE          Location/Qualifiers
REGION           1..431
                 note = Hyaluronidase Variant
source           1..431
                 mol_type = protein
                 organism = synthetic construct
SEQUENCE: 251
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
```

```
VRNRVREAIR VSKIPDAKSP LPVFAYTRIV FTDQVLKFLS QDELVYTFGE TVALGASGIV    300
IWGSWEFTRT QESCQAIQEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDTDAVDV    420
CIADGVCIDA F                                                         431

SEQ ID NO: 252              moltype = AA  length = 431
FEATURE                     Location/Qualifiers
REGION                      1..431
                            note = Hyaluronidase Variant
source                      1..431
                            mol_type = protein
                            organism = synthetic construct
SEQUENCE: 252
FRAPPVIPNV PFLWAWNAPS EFCLGKFDEP LDMSLFSFIG SPRINATGQG VTIFYVDRLG     60
YYPYIDSITG VTVNGGIPQK ISLQDHLDKA KKDISFYMPV DNLGMAVIDW EEWRPTWARN    120
WKPKDVYKNR SIELVQQQNV QLSATEATDK AKQEFEKAGK DFLVETIKLG KLLRPNHLWG    180
YYLFPDCYNH HYKKPGYNGS CFNVEIKRND DLSWLWNEST ALYPSIYLNT NQSPVAATLY    240
VRNRVREAIR VSKLPDAKSP LPVFAYTRIV FTDQALKFLS QDELVYTFGE TVALGASGIV    300
IWGSWENTRT KESCQAIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDDDAVDV    420
CIADGVCIDA F                                                         431

SEQ ID NO: 253              moltype = AA  length = 432
FEATURE                     Location/Qualifiers
REGION                      1..432
                            note = Hyaluronidase Variant
source                      1..432
                            mol_type = protein
                            organism = synthetic construct
SEQUENCE: 253
NFRAPPVIPN VPFLWAWNAP SEFCLGKFDE PLDMSLFSFI GSPRINATGQ GVTIFYVDRL     60
GYYPYIDSIT GVTVNGGIPQ KISLQDHLDK AKKDITFYMP VDNLGMAVID WEEWRPTWAR    120
NWKPKDVYKN RSIELVQQQN VQLSLTEATE KAKQEFEKAG KDFLVETIKL GKLLRPNHLW    180
GYYLFPDCYN HHYKKPGYNG SCFNVEIKRN DDLSWLWNES TALYPSIYLN TQQSPVAATL    240
YVRNRVREAI RVSKIPDAKS PLPVFAYTRI VFTDQVLKF SQDELVYTFG ETVALGASGI    300
VIWGSWENTR TKESCQAIKE YMDTTLNPYI INVTLAAKMC SQVLCQEQGV CIRKNWNSSD    360
YLHLNPDNFA IQLEKGGKFT VRGKPTLEDL EQFSEKFYCS CYSTLSCKEK ADVKDTDAVD    420
VCIADGVCID AF                                                        432

SEQ ID NO: 254              moltype = AA  length = 433
FEATURE                     Location/Qualifiers
REGION                      1..433
                            note = Hyaluronidase Variant
source                      1..433
                            mol_type = protein
                            organism = synthetic construct
SEQUENCE: 254
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGSWENT RTKESCQAIK EYMDTTLNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAF                                                       433

SEQ ID NO: 255              moltype = AA  length = 431
FEATURE                     Location/Qualifiers
REGION                      1..431
                            note = Hyaluronidase Variant
source                      1..431
                            mol_type = protein
                            organism = synthetic construct
SEQUENCE: 255
FKAPPVIPNV PFLWAWNAPS EFCLGKFDEP LDMSLFSFIG SPRINATGQG VTIFYVDRLG     60
YYPYIDSATG VTVNGGIPQK ISLQDHLDKA KKDISFYMPV DNLGMAVIDW EEWRPTWARN    120
WKPKDVYKNR SIELVQQQNV QLSMTEATDK AKQEFEKAGK DFLVETIKLG KLLRPNHLWG    180
YYLFPDCYNH HYKKPGYNGS CFNVEIKRND DLSWLWNEST ALYPSIYLNT AQSPVAATLY    240
VRNRVREAIR VSKLPDAKSP LPVFAYTRIV FTDQALKFLS QDELVYTFGE TVALGASGIV    300
IWGSWENTRT KESCQAIKEY MDTTLNPYII NVTLAAKMCS QVLCQEQGVC IRKNWNSSDY    360
LHLNPDNFAI QLEKGGKFTV RGKPTLEDLE QFSEKFYCSC YSTLSCKEKA DVKDDDAVDV    420
CIADGVCIDA F                                                         431

SEQ ID NO: 256              moltype = AA  length = 431
FEATURE                     Location/Qualifiers
REGION                      1..431
                            note = Hyaluronidase Variant
```

-continued

```
source                1..431
                      mol_type = protein
                      organism = synthetic construct
SEQUENCE: 256
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDIAFYMPV DNLGMAVIDW EEWRPTWARN  120
WKPKDVYKNR SIELVQQQNV QLSATEATAK AKQEFEKAGK DFLVETIKLG KLLRPNHLWG  180
YYLFPDCYNH HYKKPGYNGS CFNVEIKRND DLSWLWNEST ALYPSIYLNT AQSPVAATLY  240
VRNRVREAIR VSKLPDAKSP LPVFAYTRIV FTDQALKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDDDAVDV  420
CIADGVCIDA F                                                      431

SEQ ID NO: 257        moltype = AA  length = 431
FEATURE               Location/Qualifiers
REGION                1..431
                      note = Hyaluronidase Variant
source                1..431
                      mol_type = protein
                      organism = synthetic construct
SEQUENCE: 257
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWEITRT MESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 258        moltype = AA  length = 431
FEATURE               Location/Qualifiers
REGION                1..431
                      note = Hyaluronidase Variant
source                1..431
                      mol_type = protein
                      organism = synthetic construct
SEQUENCE: 258
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGDLSISST MESCQAIDEY METILNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 259        moltype = AA  length = 431
FEATURE               Location/Qualifiers
REGION                1..431
                      note = Hyaluronidase Variant
source                1..431
                      mol_type = protein
                      organism = synthetic construct
SEQUENCE: 259
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGDLSISRT MESCQAIDEY METILNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431

SEQ ID NO: 260        moltype = AA  length = 431
FEATURE               Location/Qualifiers
REGION                1..431
                      note = Hyaluronidase Variant
source                1..431
                      mol_type = protein
                      organism = synthetic construct
SEQUENCE: 260
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDISFYMPV DNLGMAVIDW EEWRPTWARN  120
WKPKDVYKNR SIELVQQQNV QLSATEATDK AKQEFEKAGK DFLVETIKLG KLLRPNHLWG  180
YYLFPDCYNH HYKKPGYNGS CFNVEIKRND DLSWLWNEST ALYPSIYLNT NQSPVAATLY  240
```

-continued

```
VRNRVREAIR VSKLPDAKSP LPVFAYTRIV FTDQALKFLS QDELVYTFGE TVALGASGIV   300
IWGSWENTRT MESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDDDAVDV   420
CIADGVCIDA F                                                        431

SEQ ID NO: 261          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 261
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDISFYMPV DNLGMAVIDW EEWRPTWARN   120
WKPKDVYKNR SIELVQQQNV QLSATEATDK AKQEFEKAGK DFLVETIKLG KLLRPNHLWG   180
YYLFPDCYNH HYKKPGYNGS CFNVEIKRND DLSWLWNEST ALYPSIYLNT NQSPVAATLY   240
VRNRVREAIR VSKLPDAKSP LPVFAYTRIV FTDQALKFLS QDELVYTFGE TVALGASGIV   300
IWGSWEITRT MESCQAIKEY MDTTLNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDDDAVDV   420
CIADGVCIDA F                                                        431

SEQ ID NO: 262          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 262
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDIAFYMPV DNLGMAVIDW EEWRPTWARN   120
WKPKDVYKNR SIELVQQQNV QLSATEATAK AKQEFEKAGK DFLVETIKLG KLLRPNHLWG   180
YYLFPDCYNH HYKKPGYNGS CFNVEIKRND DLSWLWNEST ALYPSIYLNT AQSPVAATLY   240
VRNRVREAIR VSKLPDAKSP LPVFAYTRIV FTDQALKFLS QDELVYTFGE TVALGASGIV   300
IWGDLSISST MESCQAIDEY METILNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDDDAVDV   420
CIADGVCIDA F                                                        431

SEQ ID NO: 263          moltype = AA  length = 431
FEATURE                 Location/Qualifiers
REGION                  1..431
                        note = Hyaluronidase Variant
source                  1..431
                        mol_type = protein
                        organism = synthetic construct
SEQUENCE: 263
FRAPPVIPNV PFLWAWNAPS EFCLGKFDEP LDMSLFSFIG SPRINATGQG VTIFYVDRLG   60
YYPYIDSITG VTVNGGIPQK ISLQDHLDKA KKDIAFYMPV DNLGMAVIDW EEWRPTWARN   120
WKPKDVYKNR SIELVQQQNV QLSATEATAK AKQEFEKAGK DFLVETIKLG KLLRPNHLWG   180
YYLFPDCYNH HYKKPGYNGS CFNVEIKRND DLSWLWNEST ALYPSIYLNT AQSPVAATLY   240
VRNRVREAIR VSKLPDAKSP LPVFAYTRIV FTDQALKFLS QDELVYTFGE TVALGASGIV   300
IWGDLSISRT MESCQAIDEY METILNPYII NVTLAAKMCS QVLCQEQGVC IRKNWNSSDY   360
LHLNPDNFAI QLEKGGKFTV RGKPTLEDLE QFSEKFYCSC YSTLSCKEKA DVKDDDAVDV   420
CIADGVCIDA F                                                        431

SEQ ID NO: 264          moltype = AA  length = 447
FEATURE                 Location/Qualifiers
REGION                  1..447
                        note = Hyaluronidase Variant - PH20v
source                  1..447
                        mol_type = protein
                        organism = synthetic construct
SEQUENCE: 264
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCPNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFY                                       447
```